(12) United States Patent
Van de Water et al.

(10) Patent No.: US 9,695,481 B2
(45) Date of Patent: Jul. 4, 2017

(54) POLYNUCLEOTIDES COMPRISING A REPORTER SEQUENCE OPERATIVELY LINKED TO A REGULATORY ELEMENT

(75) Inventors: Bob Van de Water, Leiden (NL); Harm Vrieling, Leiden (NL)

(73) Assignees: UNIVERSITEIT LEIDEN, Leiden (NL); ACADEMISCH ZIEKENHUIS LEIDEN, Leiden (NL)

( * ) Notice: Subject to any disclaimer, the term of this patent is extended or adjusted under 35 U.S.C. 154(b) by 0 days.

(21) Appl. No.: 13/823,661

(22) PCT Filed: Sep. 15, 2011

(86) PCT No.: PCT/EP2011/066050
§ 371 (c)(1),
(2), (4) Date: Jul. 17, 2013

(87) PCT Pub. No.: WO2012/035120
PCT Pub. Date: Mar. 22, 2012

(65) Prior Publication Data
US 2013/0302815 A1    Nov. 14, 2013

(30) Foreign Application Priority Data

Sep. 15, 2010 (GB) .................................. 1015416.9
Sep. 15, 2010 (GB) .................................. 1015419.3
Apr. 1, 2011 (GB) .................................. 1105572.0

(51) Int. Cl.
*C12N 15/85* (2006.01)
*C12Q 1/68* (2006.01)
*C07K 14/47* (2006.01)
*C12N 15/10* (2006.01)

(52) U.S. Cl.
CPC ........ *C12Q 1/6897* (2013.01); *C07K 14/4738* (2013.01); *C12N 15/1086* (2013.01); *C12N 15/85* (2013.01); *A01K 2207/12* (2013.01); *A01K 2267/0393* (2013.01); *C12Q 2600/142* (2013.01)

(58) Field of Classification Search
None
See application file for complete search history.

(56) References Cited

FOREIGN PATENT DOCUMENTS

| EP | 1 769 085 | 4/2012 |
|---|---|---|
| WO | WO 01/88188 | 11/2001 |
| WO | WO 02/080849 | 10/2002 |
| WO | WO 2006008484 A2 * | 1/2006 |
| WO | WO 2006/025879 | 3/2006 |

OTHER PUBLICATIONS

Windpassinger et al., Nature Genetics, 2004, vol. 36, pp. 271-276.*
BAC clone RP24-458M20, genbank AC129217.3, 2003, accessed Dec. 24, 2014 from: http://www.ncbi.nlm.nih.gov/nucleotide/28436304?report=genbank&log$=nuclalign&blast_rank=2&RID=9NTGT0VY015.*
Clonetech, pDsRed-Express2-1, 2008, vector information.*
Adiseshaiah et al., The Journal of Biological Chemistry, 2003, vol. 278, pp. 47423-47433.*
Jin et al., Free Radical Biology & Medicine, 2000, vol. 29, pp. 736-746.*
BAC clone, RP23-389K5, downloaded May 31, 2016 from: http://www.ncbi.nlm.nih.gov/nucleotide/40539144?report=genbank&log$=nuclalign&blast_rank=2&RID=MV40CJ6N01R.*
Chung, et al. "Human Embryonic Stem Cell Lines Generated without Embryo Destruction," Cell Stem Cell (2008).
Agarwal and Garg (2004) Trends in Molecular Medicine. 9, 440-444.
Altschul, et al., (1996) Methods in Enzymology. 266:460-480.
Ashino, et al., (2003) The Journal of Toxicological Sciences. 28(3): 181-189.
Attardi, et al., (2000) Genes & Development. 14(6): 704-718.
Aubrecht, et al., (2007) Mutagenesis. 22(5): 335-42.
Beggs (1978) Nature. 275, 104-109.
Bergmeyer (1974) Methods of Enzymatic Analysis (vol. 2).
Bevis and Glick (2002) Nat. Biotechnol. 20(1): 83-87.
Birrell, et al. (2010) Mutation Research. 1-2, 87-95.
Brennan and Schiestl (2004) Methods Mol. Biol. 262: 111-24.
Cahill, et al. (2004) Mutagenesis. 19(2): 105-19.
Chang, et al. (2004) J Biochem. 49, 50994-51001.
Chowers, et al., (2004) Investigative Ophthalmology & Visual Science. 45(7). 2098-2106.
Clement, et al., (2007) Toxicology. 240: 111-124.
Cohen (1996) PNAS USA. 93: 11242-11247.
Cohen, et al., (1972) Proc. Natl. Acad. Sci. USA. 69, 2110.
Corbet, et al., Oncogene (1999) 18(8): p. 1537-44.
Corn and El-Deiry (2007) Cancer Biol Ther. 6(12): 1858-66.
Cortes, et al., (2000) Molecular Carcinogenesis. 27: 57-64.
Cotter (2009) Nat. Rev. Cancer. 9(7): 501-507.
Cuaz-Pérlin, et al., (2004). Arterioscler. Thromb. Vasc. Biol. 24: 1830-1835.

(Continued)

*Primary Examiner* — Anne Gussow
*Assistant Examiner* — Mindy G Brown
(74) *Attorney, Agent, or Firm* — Norton Rose Fulbright US LLP

(57) ABSTRACT

The invention provides a polynucleotide comprising a reporter sequence operatively linked to a regulatory element of a gene selected from Bscl2, Srxnl, Cbr3, Ephxl, Nope, Cdknla, Perp, Pltp, Cgrefl, Ltb4r1, Btg2, Gpx2, Ltb4r2, Ddit4l, Fosl1, and Egr1, which regulatory element stimulates expression of the reporter sequence in response to a genotoxic agent or to an oxidative stress-inducing agent. The invention also provides a method of detecting a genotoxic or oxidative stress-inducing agent comprising subjecting a cell containing the polynucleotide of the invention to a test agent; and assessing the expression of the reporter sequence. The invention provides a method of detecting a genotoxic or oxidative stress-inducing agent comprising subjecting one or more cells that comprise a reporter sequence operatively linked to a regulatory element of a gene, which regulatory element stimulates expression of the reporter sequence in response to a genotoxic agent or to an oxidative stress-inducing agent, to a test agent, and assessing the expression of the one or more reporter sequences; wherein at least one cell subjected to a test agent comprises a polynucleotide comprising a reporter sequence operatively linked to a regulatory element of the Bscl2 gene.

16 Claims, 91 Drawing Sheets

(56) References Cited

OTHER PUBLICATIONS de Waard, et al., (2008) DNA Repair. 7(10): 1659-1669.
Decker, et al., (2009) Archives of Toxicology. 83(4): 297-318.
Downes, et al., (1998) Genomics. 53: 220-230.
Elkon, et al., (2005) Genome Biology. 6(5): R43.
Ellinger-Ziegelbauer, et al., (2005) Mutation Research. 575: 61-84.
Ellisen, et al., (2002) Molecular Cell. 10: 995-1005.
Francis and Rainbow, (2000) Photochemistry and Photobiology. 72(4): 554-561.
Hastwell, et al., (2006) Mutat. Res., 607(2): 160-75.
Hayes and McLellan (1999) Free radical research. 4, 273-300 51001.
Hendriks, et al., (2008) DNA Repair (Amst). 7(8): 1330-9.
Hendriks, et al., (2011) Mutation Research. 10;709-710:49-59.
Hendriks, et al., (2010) EMS Conference. Sep. 15-18.
Hendriks, et al., (2010b) Current Biology. 20: 170-175.
Hernández, et al., (2009) Mutation Research/Reviews in Mutation Research. 682(2-3): 94-109.
Hickson, et al., (2004) Cancer Res. 24, 9152-9159.
Ihrie and Attardi, (2004) Cell Cycle. 3(3): 267-9.
Ihrie, et al., (2003) Current Biol. 13(22): 1985-1990.
Imen, et al., (2009) Free Radical Biology & Medicine. 46: 1404-1410.
Jing, et al., (2007) Biochemistry and cell biology = Biochimie et biologie cellulaire. 2, 265-271.
Kaspar, et al., (2009) Free Radical Biology & Medicine. 9, 1304-1309.
Kho, et al., (2004) JCB—papers in press.
Kim, et al., (2010) J. Biol. Chem. 285, 34419-34428.
Kirkland, et al., (2008) Mutation Research. 1-2, 99-108.
Kirkland, et al., (2011) Mutation Research. 721(1):27-73.
Knight, et al., (2002) Journal of Biochemical and Biophysical Methods. 51(2): 165-177.
Knight, et al., (2007) Mutagenesis. 22(6): 409-16.
Knight, et al., (2009) Regul Toxicol Pharmacol. 55(2):188-99.
Kruse, et al., (2007) Mutat. Res. 617(1-2): 58-70.
Lou and Chen (2005) Advances in Experimental Medicine and Biology vol. 570: 425-455.
Lu, et al., (2009) Genomics. 93(4): 332-342.
Magkoufopoulou, et al., (2012) Carcinogenesis. 33. 1421-1429.
Magré, et al., BSCL Working Group (2001). Nat. Genet. 4: 365-370.
Meek (2009) Nat. Rev. Cancer. 10: 714-723.
Meireles, et al., (2010) Cancer Prev. Res. 3: 707-717.
Mizumoto, et al., (1993) Biochemical Pharmacology. 46(10):1811-1818.
Mouse Genome Sequencing Consortium, et al., Nature. 2002, 420(6915):520-62.
Nishida, et al., (2009) Nucleic Acids Res. 17: 5678-5689.
Niture, et al., (2010) Toxicol. Appl. Pharmacol. 1, 37-42.
Olaharski, et al., (2009) Mutation Research/Genetic Toxicology and Environmental Mutagenesis. 672(1): 10-16.
Paulsen and Cimprich (2007) DNA Repair (Amst). 7: 953-966.
Pilka, et al., (2009) PLoS One. 4(10): e7113.
Poser, et al, (2008) Nature Methods. 5: 409-415.
Quinones, et al., (2003) Life Sciences. 72: 2975-2992.
Reifferscheid, et al., (1991) Mutat Res 253(3): 215-22.
Reinhardt and Yaffe (2009). Curr. Opin. Cell Biol. 2, 245-255.
Riley, et al., (2008) Nat. Rev. Mol. Cell Biol. 9(5): 402-412.
Ritter and Knebel (2009) Toxicol. In Vitro. 23(8):1570-5.
Rouault, et al., (1996) Nat. Genet. 1996. 14(4): p. 482-486.
Sabapathy, et al., (1997) EMBO. J., 16(20): 6217-6229.
Sambrook, et al. (2001) Molecular Cloning, A Laboratory Manual, 3$^{rd}$ Ed. Cold Spring Harbor Laboratory, Cold Spring Harbor, NY.
Sancar, et al., (2004). Annu Rev Biochem. 39-85.
Schiestl, et al., (1989) Carcinogenesis. 10(8): p. 1445-55.
Sherman, et al., (1986) Methods in Yeast Genetics, A Laboratory Manual, Cold Spring Harbor, NY.
Sherman, et al., (2011) Trends Cell Biol. 5, 312-319.
Singh, et al., (2009) Free Radical Biology & Medicine. 3, 376-386.
Strack, et al., (2008) Nat. Methods. 5(11): 955-7.
Szymanski, et al., (2007) Proc. Nat'l. Acad. Sci. U S A. 52, 20890-20895.
Tolentino, et al., (2008) Nucleic Acids Res. 4, 1300-1308.
van Delft, et al., (2004) Carcinogenesis. 25(7): 1265-1276.
van der Lelie, et al., (1997) Mutat. Res. 389(2-3): 279-90.
Wada, et al., (2008) Biotechnology and Bioengineering. 102(5): 1460-1465.
Wakabayashi, et al., (2010) Antioxidants & Redox Signaling. 11: 1649-1663.
Walmsey et al., (2008) Expert Opin. Drug Metab. Toxicol., 4(6): 827-835.
Watanabe, et al., (2006) Anticancer Res. 26: 3421-3428.
Watters, et al., (2009) Mutat. Res. 679(1-2):50-8.
Westerink, et al., (2009) Mutat. Res. 676(1-2): 113-30.
Westerink, et al., (2010) Mutat. Res. 696(1):21-40.
Wilhelm, et al., (1997) Mol. Cell. Biol., 17(8): 4792-4800.
Yan and Chen (2006) The Journal of Biological Chemistry. 281 (12): 7856-7862.
Yu, et al., (2002) Cancer Res. 20, 5743-5748.
Zacal, et al., (2005) Biochemical and Biophysical Research Communications, 332(2): 441-449.
Zager, et al., (2010) Radiol. Oncol. 44(1): 42-51.
Zhan (2005) Mutat. Res. 569(1-2): 133-43.
Zhang, et al., (1999) Am. J. Physiol. 276: F786-F793.
Zhou, et al., (2006) Mutat. Res. 604(1-2): 8-18.
Gen Bank Accession No. NC_000078.5, GI:149292731, Region: complement (77893323 . . . 77896492) (Mus Musculus)(Accessed May 6, 2015).
Gen Bank Accession No. NC_000080.5, GI:149292735, Region: 56380760 . . . 56381842 (Mus Musculus) (Accessed May 6, 2015).
Gen Bank Accession No. NC_000069.5, GI:149352351, Region: 137286699 . . . 137291295 (Mus Musculus) (Accessed May 6, 2015).
Gen Bank Accession No. NC_000085.5, GI:149323268, Region: 5447697 . . . 5455937 (Mus Musculus) (Accessed May 6, 2015).
Gen Bank Accession No. NC_000084.5, GI:149321426, Region: 35020860 . . . 35024609 (Mus Musculus) (Accessed May 6, 2015).
Gen Bank Accession No. NC_000082.5, GI:149304713, Region: 93683463 . . . 93691231 (Mus Musculus) (Accessed May 6, 2015).
Gen Bank Accession No. NC_000067.5. GI:149288852, Region: complement (182919686 . . . 182947625) (Mus Musculus) (Accessed May 6, 2015).
Gen Bank Accession No. NC_000075.5, GI:149361524, Region: 64949341 . . . 64985748 (Mus Musculus) (Accessed May 6, 2015).
Gen Bank Accession No. NC_000083.5, GI:149313536, Region: 29230719 . . . 29237666 (Mus Musculus) (Accessed May 6, 2015).
Gen Bank Accession No. NC_000076.5, GI:149288869, Region: 18564876 . . . 18576878 (Mus Musculus) (Accessed May 6, 2015).
Gen Bank Accession No. NC_000068.6, GI:149338249, Region: complement (164665017 . . . 164683207) (Mus Musculus) (Accessed May 6, 2015).
Gen Bank Accession No. NC_000068.6, GI:149338249, Region: 151931465 . . . 151937088 (Mus Musculus) (Accessed May 6, 2015).
Gen Bank Accession No. NC_000071.5, GI:149354224, Region: complement (31235515 . . . 31247963) (Mus Musculus) (Accessed May 6, 2015).
Gen Bank Accession No. NC_000080.5, GI:149292735, Region: 56384852 . . . 56387325 (Mus Musculus) (Accessed May 6, 2015).
Gen Bank Accession No. NC_000085.5, GI:149323268, Region: 8913992 . . . 8923156 (Mus Musculus) (Accessed May 6, 2015).
Gen Bank Accession No. NC_000067.5, GI:149288852, Region: complement (135971441 . . . 135975731) (Mus Musculus) (Accessed May 6, 2015).
Alberts, et al., "Figure 7-24 The differences between cDNA clones and genomic DNA clones" from *Molecular Biology of the Cell, Third Edition*, 1994, p. 311.
Zubay, et al., "Figure 28.11" *Principles of Biochemistry*, 1995.
https://en.wikipedia.org/wiki/CDNA_library Accessed Sep. 30, 2015.
Verhoeven, et al., "Mutations in the Small GTP-ase Late Endosomal Protein RAB7 Cause Charcot-Marie-Tooth Type 2B Neuropathy" *Am. H. Hum. Genet.*, 72:722-727, 2003.

(56) References Cited

OTHER PUBLICATIONS

Casali and Preston, *Methods in Molecular Biology*, vol. 235: *E coli Plasmid Vectors*, p. 19-21, 2003.
http://www.ncbi.nlm.nih.gov.nuccore/NG_008461.1) Gen Bank Accession No. NG_008461.1, GI:197927417, (*Homo sapiens* (human)) (Accessed Oct. 10, 2015).

* cited by examiner

Figure 1

A Bsc12:

```
      GTAAGC AGGCAGGGAT TATAACAAGG ATCCTTCCTG GGGTTTTCAC AAGAAAGAAG
1561  GAGCAAAGGT TATAAAATAC TGAAGTCTGC GTGTGTGCGC ATGCACGCGC TCTAGAGAGA
1621  GAGTGTGCAG GGTACTCTTG TGGAGTCAGA AAAACTCTTG AGTTCTCCCC CACCACCTTG
1681  ATGGTTGAAA CTCACTGGGC CTGCAGTCAA ACACCTGTAC CTGTTCAGCC ATTTGGTTAT
1741  GACACCCAGG GAATAGTTAG ACCTTCCTAC CCAGAACGAT TTGTCACCTA AACTAGAAC
1801  AGCCGGGCAT GGTGGCGCAC GCCTTTAATC CCAGCATTCA GGGAGGCAGA GGCAGGCGGA
1861  TCTCTGAGTT TGAGGCCAGC CTGGTCTACA AAGTGAGTTC CAGGACAGCC AGGGCTATAC
1921  AGAGAAACCC TGTCTCGAAA AACCAAAAAG AATAAAACA AAAACAAAAC AACTAGGACA
1981  TTTAAATGTA GCCCAGGATC CAAAACATAT ATGTACGTTC ACTCAGACCA AAAAGCTTCT
2041  AGGCGGTGGC CTGGATCCCC TAACCCTTTG CCGGGATCTC ACTCTAGGAG GCATTCTTGA
2101  GACATGGTTT CCAGTCAGAC GACATTCTGA ACCCTTGTGA TGTTTTCAGT TACCTTGAGG
2161  AGAAAATAAA AAAGCCCCAA TTCAACAAGA AACAAATTT ATTACTTATT TAGATCCCAC
2221  AGAGACCAAG GAACAGGGTG CTCCAAGATG GCCTGTTTAA CACATTTGTG TTATTACATA
2281  CACCTCAAAG GGAACCTCTA CTCAGGCGAG ATTCTTATGC AAAACTCACT CTGGGCTTCT
2341  TGGGTCCCAG TCCTAGTGAC TGGTTGTTTT AAGTCAGGAT TTCATTGTGT ATTGTGTGTC
2401  GTCGTGGCTG GCTTGGAACT CAGAGATCCA TCTGCCTCTG TGTGTGTCCA ACACCTCCGG
2461  AGTGTTGGTC ACCACACTGA ACTTAAGAAC CCATGACTGC TTTAGGTGTC TCCCCATCCC
2521  CACTCCCCGT GATTGGTCTC CAAAGCATGT CTAGTTCCAG ATTCTATGGG ACAGAGAACC
2581  TGACTCTGAC TTTGAGAGGG CAGGGGCAGC CATTTTAAGA CCAGAGGATC GCATAAGGGA
2641  TCGTTCCCTA TTGGGAACGC TGGGGACCGC CATTTTAAGA GCACCCTCGG CGCGTGCCTC
2701  CATGCGGGTA CGAACAGGCA GCCGCCATCT TGGGCATTGG CTGCCGCGCC GAGTCGCCCT
2761  GTCCCGCCCC ACGGCCTCTC GGGCCACCTC CCCCGGGGC TGCTGTCCCT GGGCCTGCGG
2821  AAACCCACCC TGCTCGCCCT TGTGTGGTTC TCGCCGCTTA CGTTGCGCGC TCGTGTGAAT
2881  GCTCCGCGGC TTCTGAGCGC TCGTTTTAAC AACCCCCCAC TGGGGGCGCT CGGGCACCTT
2941  ATACTTTGCG ATCTCCAATC CTTACA
```

For: CGC GCG AGA CTC GTA AGC AGG CAG GGA TTA TAA CAAG
Rev: CTG GGG GTC GAC TGT AAG GAT TGG AGA TCG CAA AGT ATA AG

B Ephx1

```
      ACA CACCAGAAGA
601   GGGCATCAGA TCCCATTACA GATGGTTGTG AGCCACCATG TGGTTGCTGG GATTTGAACT
661   CAGGACCTTC CGAAGAGCAG TCGGTGCTCT TAACCTCTGA GCCATCTCAC CAGCCCCTTT
721   CTTTCTTTTT CAAGACAGGG TTTCTCTGTG TGACCCTGGC TGTCCTGGAA CTTTCTCTGT
781   AGACCAGGCT GGCATCATAG TCAAAGATCT GCCTGCCTCT GGCTCCTACT CAAGGAATGC
841   TGGGAATAAA GGTGTAGCCA CCATTGCCCA GCACATTAGA ATGTTTCCAT CTACACTTTG
901   TTAAGAACAA TACGTTACT GCTTTGCTGA ATGGCTGGAG GCAGCGCTCC TGTGGGAACA
961   GTTTAGACGG CGCTATGAAA CAAGCCTGGA CTATACACTC CAGAGGAGGA CGGCAGGTGT
1021  GCAAACGGTG TGCTGGGGAG GGGAAGGAGC TGCAGTACCT GGAAATCCCA GGTTCCCAGA
1081  GAGGATTGAG GACACACTAT CCAGGAGTTC CACGGAGGCA GGAATGAGTT GAATGTGTTC
1141  ACTGAGAGA AACCGGCTCT CCGTTAGAAC GGAGAGGGTT TGGGCCATGA TGAGCAGCGA
1201  AGGAGGCTGG AGATCAGAGG TGAGAGGTGA AAATAGGATC CCTACGCTTC ACATGTGTGT
1261  AGGATGATAA ACCTGGACCC CGCGGCAGGC ACTGCTAGGC CCTCACAGTG GTGTGCCTGG
1321  TCATCTTGTC TGTGTGGCTG CTGAAGCCTG AGAAGGTTCT AGGCGAGTCT TAGGAGGGCC
1381  GCGGGGTAA AGACAGGGCA CTGGGCAGGC TGGCTAATGG AGAGCAGGTT AGCCCCAAGG
1441  GTGCCAGGAA CTGTGGTTGT CCTACTCCTG CTTGCTGGCT AGGCAGCGCT CTCTCCCTCC
1501  TCCCTGTGCT GGCCTCTGCT TGGTGTCCAT GCCTCCTGGG CTTCAGATCA GCCAGCCTCA
1561  CAGGGTGCAC TTAACGACAA ACTTCAGGTT TGTGTGTTCA TTCCACACTT CACTATTTTA
1621  TTTGTGGTTC TGGGAATGAA CTCCAGCGCC TTGCCCACGC GAGACACTCT ACCCTCAAGC
1681  TTTATCCCCA GATGTTTGCT CACTGACTGG TTCGCTTATA AATGGTTAC AACGAACTGC
1741  TAGGAAGGTG AGAGGAAGGC TGTAGCACCA GGCCAGCTTG GGCTCTTGTG TGTAGAGTCC
1801  ACAGACTGCA GAGTTTAAAC TGCCAATACC CTGTTCAGAA CAGCAGACTT TGCCAGAATA
1861  GGTGAAACAC CTTAGCTAGA TGCTCAGCTA GCCTTGGCCA ACCAGCCAAC TCGGGGGTGG
1921  GGCCAAGGCC TGGGCGGGGC TAGTGGGGGC GGGGCTAACA GGCAGCTGGT GTCACCAGCT
1981  CAGCAGCAGG CAAAGAGGCT CAAGAGGAGT TGAGAGTGG AGGAACTGCA CACCAGCCGC
2041  CGCGGGAGTA GGAACCCGAG AGCGAC
```

For: CG GAA TTC ACA CAC CAG AAG AGG GCA TC
Rev: GG GGT ACC GTC GCT CTC GGG TTC CTA CT

Figure 1 (continued)

C Nope

```
         GAGGAGCC CTGGTTTCAG AGCCCCGCTA TCATTAACAG GGCCTGGGGG TGCATACTGG
  361    TCATCCCAGC ACTCCAGAGG CAGAGGCCAG AGGATCAAAG GCTCAAGGAC ATCTTTGACT
  421    ACATAATGGG TTTGAGGGTA CAGGAACTTC TTCCTCCCCA AAAGGGATAG AACTTACTGG
  481    CAGCATGTGA GCCGGAATGG AAATGATTCT AAATCATGGG GATGCCAATG GATACAAGAA
  541    AAGGAAGAAT GTAGCATTTT TCCTTTAAAA AAAAATTTTT TTTTATGTGT ATGTGTGTAC
  601    TTGCATGAGT TTATGTGCAC CATGTGCAGG AAAGTGCCTA CAAAGCCCAG AAGAGGGCAT
  661    CAGATTCATT GGAAATGGAA TTACAGATGG TTATGGCTGT CATATGGGTG CTGGGAGCAG
  721    AACCCAGGTC CTTTGTTAGG GCAGGAAGCA CTCTAGCCAC TGGGCCACCT CTCTAGCCTC
  781    AAAATCCGGA TATATATATA TAATTTTTAT TTATTTTAAA TTGTATCTAA TTGTGTGTCT
  841    GCTTGTAGGT GCAGATGCCA CAGAGCCCAG TGGTATCAGA CCTCCTGGAG CTAGAGTTAC
  901    AGACTGATGT GAGTCGCCTG GGTGGGTACC GGAACCAAAT CTAGGTCCTC TGCAAATGCA
  961    ATAAGCACTC TAACCGCTGA GCCATCTCTC CCATCACAAA CGCATCATTT TAAATAGACG
 1021    TTTAGTATGT TTTTCTCTCC CCAACCCAAC CTGACATTTG ATTCCCCCAG CTTTAGACAC
 1081    ACTGAGGCAA CTAACCTGGC CAGCTCAGTT GGAAAAGAGG CAGTTCTGAA AAAGAGAGTG
 1141    GACCGGTGGA GGCTCAACAC CATTAGCAGG CCCTGCACCT GCTGCTTTAA GCCTCCTGTC
 1201    CTTAGGGAGT CCCCACTACA AACCCAAATA TTCCCAGTAT GCAGGTATGT AAAATGGTGG
 1261    TAAGCAAGTC TTCGTTGTCC CTCACAGAGG TGGAACACAG TACAGACTGG GTTGGCTACT
 1321    GAGGAGGAAG GAAGGAAGCC AAGAGAATCC CTCAGCTTGG CATGGAAGAG GTAGCGGGGA
 1381    CAAGGAATTG TAGTGTCCTC AGAGAGTCTG TTGGTGCAGC CTGTGGAGAG GCTAAACAGG
 1441    ATTCAGGTCA GGCTGTGAGT TGGAAAAGGA CAGGTCTCAG TGAACTGAGC CTGGAACAGA
 1501    GGTGGAGGCG ACCCTGAAGG TAGAGTCATG GTAGGGTTAG GGAACAGAGA TCCAGAGGCT
 1561    CAGGTAAAAA GATGAACAGA AAGGAGCCTG AGGTGACCCG AGGAGCGGGA GGCTCCCGCG
 1621    TGCTGAGTGA GCCGCAGGAG CAGGCTGGTG GCGCGCGGGC GCGTGTCCCC TGTGGTGCAG
 1681    GGTGGCCACA CTGGCGGGGC GCCCCCGCGT GGGCCGCTAG CCCAAGATGG CGATGGAGGG
 1741    GCGGGCGAGC TGGCCGCGGC CCCGGCCCCC GCGCCGGCCC CCGCTCGGGC CCCGGCCCCG
 1801    GAGGCCGCGC CCCCGCCCGC GGCGCCGCGC CTCCCGGAGC CACTGACGCC CGGCGCGCCC
 1861    TCCCCCGGCG GCGGCCCAGG CGCCCGGACG CGGCGGCAGC GGCCCGAGCC CGGCCCTATG
```

For: CGG AAT TCG AGG AGC CCT GGT TTC AGA G
Rev: ACG CGT CGA CCA TCG CCA TCT TGG GCT A
Rev2: AGG GCC GGG CTC GGG CCG CTG

The PCR with For and Rev2 primers did not produce a product, probably because of the high GC content right upstream of the TSS, therefore a more upstream promoter fragment (lacking the TSS of Nope) was PCR-ed and used for reporter construction.

Figure 1 (continued)

D Cdkn1a

```
           TCAGCAGGCC TGGGTCTGTT CAGTCCTGGG TGGGGACTAG CTTTCTGGCC TTCAGGAACA
 661       TGTCTTGACA TGTTCAGCCC TGGAATTGAA GAGGTGGGGC TGCTTCAGTG CAGGGTGGTG
 721       GAGACCTGAT GATACCCAAC TACCAGCTGT GGGGTGAGGA GGAGCATGAA TGGAGACAGA
 781       GACCCCAGAT AATTAAGGAC GTCCCACTTT GCCAGCAGAA TAAAAGGTGG TATGTATCTT
 841       GTGACATGTA TCAGGTGAAG GATGCTTTTG TGCATCTGTG TGTGTGTGCC TGGGGTGTGT
 901       ATGTGTCAGG TACTGTATGT AGTCATTTTG TCACTTTGTC ATTTTGGGGT CTGGAGGGCT
 961       CCTCCAACCA TGTTTCTGAG TATACATTCA CGTGCAATGG TGTGCCTGAC TATACATTCA
1021       AGTGCAAGGC CAAGAATGTT TGTTAGAAAG ACTGAGTAGT CCCAGACTTA ATAAATATTT
1081       GTTGAGTACT TTTGTGGTGC TCTGGGAAGC CAGAAGTTGT TTAAAATAAA TCTCTCCAAC
1141       ACCAGTAGGG TAAAGGCACA GGAGGTCACA GCACTCAGCA GTTCAGTATA AGCCTTTATT
1201       CAAGCTGTTT TCTCCCAAAG TAAACAGACA GACAATGTCA CTTCTATCTG AGAAGCCTGG
1261       AGGCCAAGGG GATTTGGGCA GTTTTGACAT CCTGTCCTGG CCCCTGACAG CCCAGCCCTG
1321       GGATGGACGA CTTGGATGCA GGGACTGGAC CGTTCAGGAG CTGGGGCATT GTGGGAGTGG
1381       CCATTATGTC TGTCCTGGTT TGGGGGTCTG AAGGGGGTCC TTCAACTGTG TTTCTGAACA
1441       GGATGAGGCT TTTGAGGGGG GTTGGGAAGG TGGCCAAGCC CTTCCCAGAC TTCCACCCCC
1501       CATCACAGAA GAGGAGGCCT GTCTAGGTCA GCTAAATCCG AGGAGGAAGA CTGGGCATGT
1561       CTGGGCAGCG ATCTCTAGAC ATCGGAGAGC AGATGTCAGA ACTCACAGCT TCTCCAAAGC
1621       AGGATTTTGA TCTTTTAACT AAAGATATCC GTTCAAACTA AGACTCCAGT CTCTGCTTTA
1681       TTTAAAATTT TTGTTTGTGT TTGTTTGAG AGAGAGGA ATTTGTTTTT GTTTTAGAGG
1741       CAGGATGTCA TGTAACCTTG ATGAATTATT GGTCCTCCTG TTTCTGTCTC CTGAGTGCCG
1801       GGATTACAGA TGTATGCCGC TATCATCTAG ATGATGCCTT ACTAGGGATC CAACTCCTGG
1861       CTTCATACAT GTTAGGCAAG CGCTATATTA ACGGAGCTAC ATCCCTTTTT GGATGCATGG
1921       TGATCTCAGA TAGCTCAGGC TAGCCTTGAG CTCCAAATCC CCCTGCCTC CCAAGTACCG
1981       TGATTTCAGG CATGTACCTC TATGCTTAGC TGAGATGGTG GTCTTGCTAT GTAGCCCATG
2041       TGACCAGGCT GGATCGTGTA ACAAGACTGA AGAAACCCC CTTCTGCTGG GTGTGATGGC
2101       TCAGACCTGT AGTCTTAACT CTAAGCAAGG AAGTTAAGGC AGGAAGATTG CCTTGAATAT
2161       GAGGGCCACC CTGGGCTACA TAGCGAGGCC TCGTCTCAAA AGACCCCAAA CAGAAGGAAA
2221       TAAAACTGAC TAGAGACATG GAGGAAGGTG GGAACGGAGA ATGTCTTACT GCTATGTCTG
2281       TCAGGAACAT CCGTAGATGT TTCTAGAATT GTCCTTTATC AATGTCATTT TAGTGGACTG
2341       TCTGGATCTT GGGAGGGGGA GTATTAGACA TTTCCCTCAT TTTGGACCCA GAGAAAGAAA
2401       TCTGCAAGCA GAGTACTCTG GGCAGCTTGC CAGAGGTCAG CAGGTAGCCA TTAGTGTGGT
2461       CCCAGTCAGG TCTTGATGCT CTCACTTGCA GGATGTATTA TGGTGTGAGA AATGTTCACA
2521       TGCTGGCTTC TGAAGAGGGG AGAGGGGAGG TAAGGAGCCT GGCGGCTGTT TTTCTTGGTA
2581       GTCCGTGGTC TGAGAACTGG ACTCAATCTC CCCGATTTCT GAGGCGGTTG ACAGCATCCT
2641       TTCCTTCTGT GGAACTGCTT TCCTCGTCTG TGAGACAGGG AGGAAATGAT CGCGTTCTGG
2701       ACCCGATGTC CGAGGGGCTT CTGGGAGGAG GGGAAAAAA ATCTCCAGAC ATAGTGGGAC
2761       TTCTTGGGAT TTTAAACTAT TTTTTATTAT TTATGGGTCT GTTTTGTTTT TGAGAGGGTC
2821       TCAATGGATA GCCCAGGCTG GTCTTGAACC TGTAACGCCC CTCGTGCCTC AATCTCCCAA
2881       GTATAGGATT CCAGGCTTTT GCTATCATAC TCAAATGATC AATTTATTTA TATTTGAAAC
2941       AGTGTCACAT ATTTCAAGTT GGTCTCCATC GGAATAGGTA GCTGTCAAAA CGACCTTGAA
3001       TGCCTATTTC CCCCTCCTCA CCCCCCACTG GGCGCTGTTA TTACAGACGT GACCCCGCAT
3061       GCCCAGTTTA TGGGGCCCTG GAGCTCCAAC CCAGGGCTTC ACTTCCAGCA AGTTAGGCAA
3121       ACACTGTACC AACAGACCCA CCTCCCGAAA CCCAGGATTT TATTTACTAA TATCAGTGAT
3181       CTGGAAAAGA GTTAGTCCTT CCCACAGTTG GTCAGGACA GACCCATAAA CACTCACTCA
3241       GCTCTAACTG TACTGTTGTT CATAGATGTA TGTGGCTCTG CTGGTGCGCT GCGTGACAAG
3301       AGAATAGCCC AGGTGTGGGG GAGGGGAGGG CGCGCCCTCT TAACGCGGCC CGGTTCTAGC
3361       TGTCTGGCGC GGGCTTAGAT TCCCAGAGGG GAGGGCGGCC CAGCGAGTCC CCGGGATCGG
3421       TGAAGGAGTG GGTTGGTCCT GCCTCTGAGG GGGCGGGGCC TGGGCCGACG CTATAAGGAG
3481       GCAGCTCGAC GCCAACTGCA GCAG
```

```
For(2900 bp): CGG AAT TCT TTC TGG CCT TCA GGA ACA T
For(2364 bp): CGG AAT TCA GGG TAA AGG CAC AGG AGG T
Rev: GGG TCA CCT CGA GCT GCC TCC TTA TAG C
```

Two different promoter constructs were made for CDKN1A. One with For (2900 bp) and Rev, the other with For(2394 bp) and Rev. Rev is located just upstream of the TSS.

Figure 1 (continued)

E Perp

```
1     ATTGCCTGGT GTTATGGTTT ATGCCGGTCA CGTGGTGTCT TGGCTTTAGG CATCAATTAG
61    TTTAGCTTTT GTTATTTTTA CCTTGAGAAA TAAACTATAT CTTATTCCCC TTTGAGCCGA
121   CAGAACCAAT TAATTACTAT AGTCTCTTTC AGAGATTCTG AACAGTCAAA ATTACCTTTG
181   ACCAGATTGA TATTAAGGAG TCCCTCTCCA CAAAACTGTG GAAATTGTAT CACAAGAATG
241   AGGACATAAT ATAAACATAT ATATATATGC GTGTGTGTGT GTGTATTCCA AAATTATTCA
301   TTAAGACACC AGTGGAAACT CATTTGATTG GTAAAAATAC GACTTTTCCA CACAGGACAT
361   AGCTAGCTAA AATATTTTCA TTACGTTTGA AAGCCTTTAG GTCCTAACGT TTAGGGCATA
421   CGCACCGCAC TTGTCCTGTG GGCAATGAAC CTTGCTCAAC GTGTATGTGC CTCTGCGGTT
481   TTCAGGACTG AAATGCTTAC TGGTTTCTGC TAAGTGAAGG CTGGGTAGTG ATATTCTTTG
541   GACTCTGAGA CAGATCTTCT CAGTGTTCTT AGTCTATGCG TCCTAGTAAC TACTTCTGTT
601   GCGAGCGTCT TGTGTAAGAA GGAAATACCA CTGAGTGCTT TCCATATCTT TAAACTGACA
661   TGAGGTGTCA GAAGATTTCG GGCACGGGG  TAAAAGTGA  ATGCTCTGGT TGATCTCTCC
721   CTGGCCACCA TTGACCTGGC ACTGGGAATT TGTTTCTCTC AGCGCCACTC CTGGCTGATG
781   CCCCACCCTC CCTGCTACAA GTGAAGATTC TTAGGGACAG AAGCTAGCTC AGGATTTGGG
841   GAGGATTTCA GTTGCTTGTG CATGCTGACA CGTGCTTATA TTTGAAAAAA CAAAAACTGT
901   GTAAAGTAGA TAGAAAGGGT AGATGTGTGG GGAACACACT AACTGGGGCA AAGGGAACTG
961   AAGTTATCAA CACCAAAGCT ACCCGGATTA AGAGACAGCC TCCGCAACCT AGAGTGAGCC
1021  ACTGGGACCT GCTGGTCACC CAGCCTGAAC CACCAGAGCA CAGAACATTT GCGTGTCTAT
1081  GGCAGCAAGA GCCAAGGTCC AAAGGTAGAT CCGGGCAGGA AGTGTAGGAT CTGCCTGTGG
1141  AAGCCAGGGA CAGACGCTCC CAGGTTTGAA CCCACAAGTC CTTACATTTT AGGGCCCATC
1201  ATTTATTTCA CAGGCTATTG GGATGTCCTG GGCACGGTGC TTGGAGCTCA AGTGTAGCCT
1261  TAGCCATGCT CCTTACACTG TGTTAATTTA GGGCAGAGCA CAGGCTGGCG CTGGAGTGTC
1321  CACAGGTGTG TGCGCTGGGC TGGCGGCAAT CTGGTGGGAC TGCAGGCGGC TGGAGGCACA
1381  GGCACGCCCA CCCTGGCGAC GAGCCCGGGG CGAGCCTGAG CTCTGCCGCC CGGGTGACCC
1441  AGCAGGTCGG GGCGGTGCGC TCTGAGTCAC CGGAATCAAG GTGTGGCTGG AGCGCCGCTC
1501  CCCCGCCGCC AGCCCGGGGG CCGCGTCTTC GGGGGAGCCG CCTCTTCCTT TAGTCGCGGT
1561  GTCAGCGCTC GCAGGACCAC TCTTGGCCGC TGCTCCTGCC CGGCGTTCCT CCGCTCCGCG
1621  CCCGCCGCCA CCGACGACAT GCTGCGCTGC
```

For: CGG AAT TCT TTG AGC CGA CAG AAC CAA T
Rev: ACG CGT CGA CGC GGA GCG GAG GAA CGC CG

Figure 1 (continued)

F Pltp

```
 421      ATAA TATGTAATGT ATTATACATA ATACATATAA TATTTTATAT
 481 GTATATGTAT CACTAGGGAT ATGGCAGGA ATCTACACAG CACTTAAACC ATCTATGTTT
 541 ACAATAACCT TACACTAAAC CTGGGGGATG TAGCTCACTT GGTAGAGTGC CTAACATGCA
 601 CAGGTCCTGT ATGCAGTATC CCCAGCACCA GACAGACCAG GAGTGATGCT GTACATCTGT
 661 AATCCCAGCA TTCTGGCGAT GGAGGCAGGA GAAGCCAAAG TTCAAGACCA CCCTTAGTTG
 721 CATAGAGAAT TCAGAGCCAG CCTGGGCTAC ATGAGAACCT TTCTCAACCC TCCCTCCCCT
 781 CCAAAACAAA AACAAAACCC CACTCCCTCC CCAAACCTTT AATATATACT ATTTTAGATA
 841 CGATTTAGAA GGAGAAAATC GCCTGAGCTA TTTATACAAT AAGTGTCCTG AGGCTGACAT
 901 CCTAGGATGT AAGCGCTGGT CCCTCAGAGA GAAGGCTTCT TGAGCTACCA ATCCTACCTC
 961 ACACTGTTTT GGAACAATCC TTGAATTCTG CATTTACAGT CACAGAATTG TCTCAACCTC
1021 AACCTCCAGT TTCCTGCCAG AGAGCCAGCC TCACAGACTA TAAGAAGGTA AAACCAGATC
1081 TAGAGTGATT AGCCATTCTG GTTCGCTTGG GACTGAGTGG ATTCCCGTGG GTAGTTCTGA
1141 ATCCAGGAAG GTCCTGGACA AAACAAGACT ATTGGGTCAG CTGAGCTGGC TGAGTGCTGA
1201 GTGTTAAGTA TATGCTCAGC AAACATCTTT ATCAGTTCCC CCTTTCCATT TCGCCCGCAT
1261 GGCTACAAAA AGAAAGCAAG CATCTACTGT CTGTTTTCCA CTGTGATGCT CGGAACTGTG
1321 CGGGGCGGTG CACGGGGTGA GGGGGACTGT GCAAAGCAGC CACCTCCAAG TCCTCACTAA
1381 AGAATTCAGA GTTCCTCAGG AAGGCCAAAC CTCCCTCTGG GATGATCGCT TTTCCAATAG
1441 GGGAAGGTCC CTGGGGCCCT AAAAGCCAAT CAAGTAGGTT GGGGTCTCAT AACAAAGCCA
1501 GCGGGAGACG GTTGTGAGAG AAAAGAAAGG GGAATGACCG TAGGGCATTG GCTTTCGCTG
1561 GCCTAGCGTG GAAGCCGAGT GGGAGTTCCC ATAAGGAGGC ACTCGGTGCT GGGTGAGGAA
1621 ACTGAGGCTC CGCAGCCAAG TGAAGGAGTT TGTTTAGGAG CGTGCAGGAA TTGCTGTGTG
1681 ATTGGAATTC CACAGCAGTG GTTTGGCAAG CCGCTTTCTT CACTTTTCTC GCTCTTTTAG
1741 GAGCGAGTCC CCCACTTGTC CAGACAGCAG CTAGGCTTGT CACAGGCTCC GTACTGCCCT
1801 ATCCACCCTC CCAACTGCCA GCGTCCCGCC CCGTCCCCTC CCAGCCCCCA AGGAGGAGGG
1861 AAGAACCGCG GCGAGGAGGG GCGGCGGAGG CCCAGACTTA TAAAGGCTGC TGGACCCGCG
1921 CTACCCGCCA GACCCC[G]CCG CCCGGATCCC CCGCGCTGCC TGTCGCCCCA CGTGACCACA
1981 CTACTAAGTG AGTTGGGGCG CGTCCCCATC GCATCCCCAG ACCCTCGTGA GTTGTGTGGC
2041 TCACTAAATC CAGGTGGGGA GGAGAGCGGA TGAAGGAGGG CTCCGGGATG GGGCACCAGA
2101 CAGAATGCGT TATAGCGGAG TCTTAGGAGC TAGGGGAGCG GAGGGACTCA GGGGATAGCG
2161 CTCAGTCGGG CCATCCCCGC GCGCGGCCTG GGAGACCTCA AG**CTACTCAG CAGGAATGCG
2221 CTT**GTGGTCG TCGCC

For: CCG CTC GAG AGC CTG GGC TAC ATG AGA AC
Rev: CCC AAG CTT AAG CGC CAT TCC TGC TGA GTA
```

G Srxn1

```
          GGGAAC CAGAGAAACC CTCTAGAAGG ATTAGGTAAT CTAAAATTTC
 481 ATTAGTAGAT GCTAAGGGGT CATAGGTGGT CAGTGGTCTG CATTCCTATG TCAGAAGCGG
 541 TCAACCATGT GATGAGATAG GGCTGCCCAG GACAGTGGC CTATTCTGAG ATAAGGAATT
 601 TTCCCATTTT TGTGGTTATT TCAGTCTGTT CTTTGGGAGG TGGTTTTATG ATCTTGTTCT
 661 GAATTTTATG GTATGTTCCT AGAGCTGGTG TCTTATGCCT TGGTTTCTGG GACTTATGGT
 721 CTATTCCTGA AGTTGGTTCC TTATAGCCTT TAAAAAAAAA AAAAAAGCAA GCCGGGGGGG
 781 GGGGGGGGGG CGTGGTGGCG CAAGCCTTTA ATCCCAGCAG AGGAGGCAGA GGCAGGTGGA
 841 TTTCTGAGTT CGAGGCCAGC CTGGTCTACA AAGTGAGTTC CAGGACAGCC AGGGCTTCAG
 901 AGAAACCCTG TCTTGAAAAA CAAAAACCAA AACAAACAAA AAAGGCTGGT TCTTCAAATG
 961 GAGCCAAATG GGGTTTATAC TGTCCTTTCA ACATCAGCTT CTCGAATGGA ATATTACAGA
1021 GACGATGATG TACAGGATCC AGGTTGACTT GGAAGTGGCT CAGCCTCTCT AGGGACACTC
1081 ATTGTTGGAA ACCACGCACC AGGCTAGGAG GAAGCACAAG TCACAGGAGC GGGCTTGTAC
1141 AGCTGTTCAT GCTGGATACT TGCTGTGTAG TCAGGTGACC TGTCTTTCAG CGGTTTTTTA
1201 TTGTTTTGTT TCCCTGGAGT GGACCTACTT TGGGGAGGCC CTTCAGTAAC CATACCTATT
1261 TCTATTTCCT GGATATGTTT AAGATGATTG CGACACCGGA AACTTCAGGA CAGAACCATA
1321 AAGAATCAGC ACAACTCAAG CCACTGTGGG GAGTTCCTGA CGCTGAGCCT AGATGAGAGA
1381 CAGCGCTGGG ATCCAAAGCG ATCTATGGAG CGGTGTTGCC CGGATTTGGG CCTCGGCTCA
1441 CTCACTCATT AGCTCCATAC CTTGTGAGTG TGTGTGTGTG TGGGGGGGGG CGGTCATAAC
1501 TTTTCTGTGC CTCAGTTTCC TTCACTGTAA AATGAATTG GCATCGTGCT CAGCTAGCAG
1561 GGTCGCTCTG AAATGTGAGT AGGTCATCAC ACTTGGCTTT ACTTCGTGGA GGCCACTGTT
1621 CCCAGCTTCT ACTGAGAGCC GACTCATCCT CTCTGGGCAG ATCTGACCGC CCGCGTCCTC
1681 GCCTCGGAGG GCCTGAGTCA CCACGCTGTG CGTCACCCGC GCCTCTGCTC CGCGACCTGC
1741 AAATTCACCC TGAGTCAGCG GCCGGGCGCG TCCATTGAGC GCATC[G]CGAG GGGCGGCAG
1801 AGCGCCACGG CGGGCAGTGG GCAGCTAGGT CAGAGTGAGA CACGCAGGGA GGGAGGGGCG
1861 GCGAGTCAAG CGGCTCGGGG ACAGGTAGGA TCACAGCG

For: CGG AAT CGG GAA CCA GAG AAA CCC TC T
Rev: CGG GGT ACC GCT GTG ATC CTA CCT GT CC
```

Figure 1 (continued)

H Cgref1:

```
         C ACTGAGCCAA GCCAGCCGTG CCCAAAAGTG CCTCGTCCCC CACAAACGAA
1141     GGCCAGTCTG AGGGGCTTGT GGCTGTGATG GCTGCTGACT GAAGGTCCCG AGGCATGAAA
1201     GTTTTATTTG AAGGGTTTTT TGTTTGTTTG TTTTTGTTTT TGTTTTGTTT TGTTTGTTTT
1261     TTTTGAGACA GGGTTTCTCT GTATAGCCCT GGCTGTCCTG GAACTCCCTC TGTAGACCAG
1321     GCTGGCCTCG AACTCAGAAA TCCACCTGCC TCTGCCTCCC AAGTGCTGGG ATTAAAGGCG
1381     TACGCCACCA CGCCCAGCTT ATTTGAAGGT TTTATTTATT TATTATTTAT ATGAGTACAC
1441     CGTAGCTGTC TTCTGACACA CCAGAAGAGG GCATCAGATC CCATTACAGG TGGTTGTGAG
1501     CCACCACATG GTTGCTGGGA ATTGAACTCA GGACCTCTGG AAGAGCAGTC AGTGCTCTTA
1561     ACCATTGACC CATCTCTCTA GCCCCCATGA AGTTATTTAA AAACAAAAAA TCTAAGTCCA
1621     TGGGCCAGTG GGCAAGGAGG TAGCCTAGGA CTCAGGCAGA GGGACTTACT ACTGGGATAA
1681     AAGTAGGTGT GTGACACTCC GTCTTGATCA TAAAGCCGTG GTCCTAGAGC TGCAGCATTT
1741     GCACTGGAAA ACTTGTTCCT GTGGCTGTGG TCTCGTCTAG CACACAGCCC CATCACCTCT
1801     CCCTGCACAC ACGCCTCTCC CCGTACATGA AGCCTCCTCT TCTTACTGCT TATGCTCCCC
1861     GGGACCTGAT CCCTTCCCTG GAATCTCAGC TCCATCAACT TGAGAGGACT TTGTTCCCAT
1921     GTCGTGATAC CTATAACCTG CTCGATACTG TCACATTCTT AGATAATCGG CCAGGTATGG
1981     GCCACACTGC TCTTTCCAGT TGAAGGCCAC AATCACACAT ACTAACAGTA AGTCATTCTT
2041     TTTAGTCACT AACGAGTTTC TCAGATAAAG CCAGTGACAC CCACACAGCA TAATCAAAGG
2101     CACTTTTTAA TGAGCACCAG CCTCACATCT GTCTAGTTTT AATTATTTCT GTCTCTCTCA
2161     TACCACACCC CTGCCTCATC AATACATGTC TATGTGTCTA ATACACACAT GCACATCAGA
2221     CTCACCATTC TGTGACTCTG TATACACAGA ACCGACTCAC TACTCTGTTT CTTGAATACA
2281     TGCCTCATAT AGATGTTTCA CCAGCCGCCC ACACTCACAA ATCCTTCCCA GCCTGTCATA
2341     CGCACATACA TACTCAGCCA CACCAGCTCG TCACACTCAA AATCACAAAC CAGTCTGCCT
2401     CCATCTGAGT CACAGTGACA CACACTGAGG ACTCCATCCA TCTTCTCTCA GATCCACATG
2461     GAACAAGGCC AGGTGGAGGC GCTGCGGGAC AGGTCTGCCC AAGGAGGGGC GGTGGCCCTC
2521     CCGTGGCTGT CGCTCGCTCC GGACTCTGCC CGGGCCTGGG CGGCGGCTGC AGCCGGGAGG
2581     GCGACGTGGA
```

For: CCC TGA GAT TCT CAC TGA GCC AAG CCA GC
Rev: CCC TGG TCG ACT CCA CGT CGC CCT CCC

I Ltb4r1:

```
601      CC TTCCTCTGCT GTCTACTCTC CACCTTACAC ACCCCATGTG GTCAGAGAGA
661      TCCTTCCTCA ACTCTGCCCT CTGTTTTTGC TGTGGTTTCA GCTCCCCTTT TCATCATATC
721      CTCTGCTTGA CAGTTACTGG GCCAATGCTG ATCGGCTTT TCTCAACTGA CAGCAGGTGA
781      GGGCACTGGG GGACAAAAGG GACATCAGTG ATCACCATTA TGCTGCTTTG CCTAAGAAGT
841      GACAGAGTGA AAGACAAACA GAAAGGCCCG TGCAGACTGG AGGGCTGTGT TCTTGGTGCT
901      ACGGGACACT TCAAAGAGAG CCAGCATCCT TTCTTTTGTC GAGGGGAGTA GAAGGCTGTG
961      GTGGCTTTAC AAATTCTTAG ATGCTCTTGT GGTAGGGCTG GAGGGAGGTA GGGCTGCTGG
1021     CCCTGAGCCA TCCTGTCTCT TCTTCATTCT CAGTATCCCC TAGCTTAGCC CACATTCTCC
1081     CTGTCAGAGT TGAAACCAGA CGGTACAAGG CTGTAGGGAT ACAGGAAAGA AGTGTGGATT
1141     CTTGCCTAGA TCCCAGAAGG AAAGTCCACC AGGGCTGCTA AATGGCCTGG GTAAGGTAAG
1201     GGGAAGACAT CCGTATTTTG TGTCATGAAG GAGATCAATT AGACTTTGAT GTCTCTCATA
1261     AAGAATGGAG AATTGGTTAA CCTGGAACGG GCAGTGCTGG ATGTGGCTTG TCTCTTATAG
1321     CCACACCACA GTTGTGGTCT GACCTGCCTG AAGTCAAGAT TAGGTTGTGG TTCTCTTCTT
1381     TCATTTTTTC ACATTCTCAT TGATATTCTT TCTCTTTGTA ACCCTCCTCC TCCTCTCTCT
1441     CTCTCTCTCT CTCTCTCTCT CTCTCTCTCT CTCTCTCTCC TCTCTCCCAT ATAGCCTAGG
1501     GTGGCCTTGA CCCCAATATG CTGTTTTTAA TACCATGATA CCCTAACTCA CAACAATACA
1561     CAGAACATAG GCGGTCAACC TAATCTAAAA GCGCATTAAT CAAAAAACTA CAGCATGTGC
1621     AGGTTGTTAA TGTGAAGTAC AAAGATAATA TTTTAAAAAT CAGCAGTCTC AATCTTAGCC
1681     TTCTCCCTTG CTTCCTTCTC CTACAATTCA ATCCGTAACT TGCTCACTC CTCCTGTCTA
1741     GACCTGCACT TTTAGACCAC ACCCCAAGCC AAGTCACTCC TGGCACCCCT CTTTCCTACT
1801     TCACTGCCCC TTTCTGGCTA CTACTCACTT AGCCCCACCC AAAGAGTCTT CCTCTCTTTT
1861     GGACTGCGTT GGAACACAGA CTGTCCCACC CCAACAGTGA AGGGAGGTGT GGGGGTTTTC
1921     AGCCTCACCC TCAGGAAGAT GCTCCCCCGC CCCGCCTCCT TTGCTCTGCT CTGTGGTACT
1981     TCCTCTCTG CTGACTTAGC TGACAGACCT AGAAGTGGGA CCAGGACCCT GGCACTAAGA
2041     CAGATTCAAG GATTGTATAT CCAACAACTA GACAAGACAT TACCTTCTGA TCAGCATCAG
2101     GGAAACCCT
```

For: GAC TAG ATC TCC TTC CTC TGC TGT CTA CTC
Rev: GCT AGT CGA CAG GGT TTC CCT GAT GCT GAT

Figure 1 (continued)

J Cbr3

```
        CAT
1       TGCTGCCTTG ATCACATAAC CAAAGAAAAA GCGATTTAAG AGCGGGTTTA TCCTGGCTCA
61      CAGTTCGAGA GTCCAACACT GTGGGGTCCT AACCACATGA GCATAAGACA GATGGTCAAA
121     CTGTGTGTGG GGGTTGGGAG GAAGGGGGCG GGGTTCCCGT GTATGCAGAG GTCAGAGGTT
181     GACAAATGTC TTCTGCTATT CATCTCTTCC TGATTCTTTG AGGCAGGGTC TCTCACTTGA
241     ACCAGACCTT GCAGACTTGG CTAATCAGCT CGCCTCCGGA AATCCTGCTT CTGGGGTCAC
301     ACAGCAGCCA CACTGCCCCA CGTTGTGTGG AGCGGGGATT TGAACTCTAG TCCTCATAAC
361     CTTCACCCAC GGAGCCAGCT CCACAGCCTT GGCCCAGCTC ACTTCTCCG TTTCATTCAG
421     TCCAGCATCC CAGTCCCTGG AACGGTACTG AGCTTAGGGT GGGCCTCCTA CCCCAGTCAG
481     CCTAACTGAG AAACTCCCTC AGAGACAGGC TGAGAGAGAG GTCTGTCTCC TAGATCCTCT
541     CAAGTTAACA TCACAGGCAG GCTAGGCCCC CACAGACCTC ACCTTCCTCA CCTCATTTGA
601     AACAGAAGGT GGAGTCCGTA ATAAGAGGCT AAGGCAGTTT GGCCGGATCA GCTCGGGAAA
661     CGCTGAATCA CTGTGAGTGA GGACTTAATT GTCCTTCAGC ATCACAATCC CTAGCCAAGT
721     AGGATCAGCA CAGAGTCGAT TCCACCCAAG AAGGGAGGAG GTCTGATTGC GTGCCCACAT
781     TTAGACACGC CTGGAATTTT GTTAGTAGGT TCAGCATCTC CTTGGGAGAT GACTCGCATA
841     GACTGAGACC AATGCAGATG TATTTGCATA CCCAGTACAC TTGGAATAAA CCAAAGACCG
901     GCACTGAGGA CTCCCGTACT ACTCAAAACA GTTCGATAAA CATGAGCCTT CTCTCTCCAC
961     CGTGGGGGCG CACTCGAGAC CTCCAGCCGA GAGGGCTCGC CCACACCTGT TCAGTCTACT
1021    CCCAGGCACT GTTCCCTGAA GTCCCTGAGC AAACCGCGGG GTGTGTTAAG TAATCTCAGA
1081    GCGAGTTCCG CAGAAGCAAA CATTTGCATT CTGCAGAGAA CGACGGGTTC TCGCCCAAGA
1141    AAATTACGGA GCATTTGTTT TCCTCCTTTT GAAGTTTCCC CAAAATAGTT GTTTCAATCC
1201    GACTGCCACG AGTCCTGCTG ACCCCTTCCT TTGGGAGCAG CGCTTGTCCC TGACCACTGC
1261    TTAGCTCGGA ACCAGGATCT CTACACTGGC CGGCGGGCGG GCGGGCAGGC GAGCGGCAGG
1321    AGGCGGACCC TTCGGGAACA GACGGCTCCT CCTCAGAGGG GAGGGACAGG CTTCTCAAGG
1381    CCTTGCTCTC [T]AGCAGTCGC AGCGCCGGGT CCCAGAATCT AGTCCTACGC CACGGTTTTG
1441    ACCACGCGTG ACCCGCTGCC CAGCCGGCCC GGCCATCAGG TGGTCCGTGT GTCCCTCTGA
1501    C

For: CGG AAT TCC ATT GCT GCC TTG ATC ACA TAA C
Rev: ACG CGT CGA CGA CAC ACG GAC CAC CTG ATG
```

K Btg2

```
        GATG
1021    AAATGTCTTG CTGGTCAGGC AAATGAGTCC AGGCAACCTG GCAAGGGGGG GAGGGGTTGT
1081    CTCAGATGGT TGAGCAAGG CAAGAGCAAG CAGATGGACA CTTTAGAAAA AGACTCTTTC
1141    CGGGAAGGTG CTTTGGGCAT GGGAGGGGAA GGAACCCACT GAGATTATTT AGGGATGAAG
1201    AAGCCAACAG TCTTGGGACC AGGTCTGAGG AAGCAAAAAG AGGGTCTGGG TGCTATAGGG
1261    ACAGTGATCA GTAGCTTTGT CTGAAAGGGG GAACAGGGAG GGAGGTAGCT TTAGAGGGAG
1321    CACTAGACAT TTAGAGGGAG GGATAGAGCA TGTGGGAAAA GGGACAGAAG TATTGATGGG
1381    AAGTCCACTG AAGAAAAACA AGCAGCAAAA CAGACAGTGG AGAGAAAAGG GAAGAGGGAA
1441    ATGGGTAGG GTGGATACAG AGGATCCAGG TAGGGAAGCT GGTGGCTCAG ACCAGGGATA
1501    CAGGGAGAGA AGCCTGGCTT AGAACTCAGG GAAAACAGGA TTTTACACAA GCCATGGCGC
1561    TAAATTCAGG CCCCATCCTG TGCAGGGCTC AGAGATGTGG GTGACAAGTT GCCCCACTCA
1621    GTAGTCTGCC TAGCTTCCTG GCACCAGTCC CTGAGCCCT GCGTGTAGAC AAGCCAGACC
1681    TGAAGCCTTT CCTCTGGGGA GCTAGTGTTT ACAAAAGCCT CAGTGCACAA AAGGAAGGA
1741    AAACAATCAG GAAGAGGGA GGGGCAGGGA ACTGATGGAA AACTTTGTAC AATTCACACC
1801    AGATTACTTA AACACACACA CACACACACA CACACACACA CACACACACA CACACACACA
1861    CACACACACA GACACTGCCA TTTAAAGGAA AGTGAGTGCT GGAAAATAA CCCTACGGAC
1921    AGAAAATACT CTCCTCGACA CTCCTCCCAC CAAACAGTGA GAGCTGATTA CTTTTAGGCA
1981    ATTACAGAAG AGGAAGAGCA GAATTTGTTG GGGGAGGTGG AATTATTATG GAAGCAAAAA
2041    GAATACAATC CCCATTGCTG AAAACACGAG GAACCCGTTT TGATCAGCTG GGGGGATGAG
2101    TGGCAGAGAT GTTCAGGTAG GGGGGTGAAC GGCTCTGTCA GTGTCTGTCA GGAGACATGG
2161    GAGAAATAAC ATCGGCGAGG GCATCCTGGA GGAGGCAGCA GGCAACCTGG GTTTTGGCGC
2221    TGTGCAGAGA CGACGTCCGG GCATGCCCGG TGTAGCGCGC TTCCTCTGCC CAGGTCCAAG
2281    GCCCTCTCCC GCCTGCCTCC CACAGCACGG GAGTCCGGTG CTTGTTCCCA ATAATGACGT
2341    CAGTGAGCGA TGACCTCAGC GCCTGGGAGG CGCGGGCGAG CTGGCGGGCG GGCGGAGAG
2401    GGGCGGGCGC AGGCGGAGGG GAGAGGCGAG ACACCGGAGG GGCACGCCCC CATCCGCCAG
2461    CGTCGGCCAA TGGGCGCCAC CGACGGCTCC CCGCC[T]CCCC GAGTGGT

For: CGGGAGATCTGATGAAATGTCTTGCTG
Rev: GATAAGTCGACACCACTCGGGGAG
```

Figure 2

A Gpx2

```
        GCCTAGGGAT TCTGTCATGC CCTCAGAAGA ATTAAGTTCT
 781    TGCCACCATT TATGGCATCG AAAGACTCCA TTCCCACTTG GATAATGGAA ACTTGTTCTT
 841    AGGGAGCTGT CAGACAATGA GCTCCACACC CTTAAACAAG CTATGCAGCA GAAGTGAAGG
 901    CACTCCCGGG AAGTAGTTTC TTTGTCTCCC AACAAATCAG ATCCGGAAGG CTGGGTGCCA
 961    CTCTTGCTGA CTCTCTTCTA GGAGACAGCT CTCACTGGAT AGGAAAACAT TTGCCTTATT
1021    AAAATAGCCA GGATAAACCC AATGGTTAGT TTACTGATG GGGGAAATCA AGGGTTTCTG
1081    AAAAGTTCCT GATTCAGTTA GCTCATGCTT GGACCGTGGA GTGGCATTAT GGTCTTTTCA
1141    GCTGCTGAGC TCCCAAGAGT GGGCTCCGAT GACAGCCCTC AGCAGGCCAG AGATCGCCCA
1201    TCATACATGG CTGGCTTTGA GGATGTCTTA GTGGCCTACC TGGAACCGCA GCTGCTTTGC
1261    CTTCCTGCAT GTCACCTCCT GTGAGGAGAG GGTCACACAT TCACACAAGC CTCCTCCAAA
1321    AAGTCTCAGA GACTGAACCT GTCTGAGAGG GAGATAGGTA CAGTTGTCTA CCCAGAATTT
1381    TACCATCCAT TCTGAGGGTC CTGATCACTA AGTCAGCAAG GACTCCATCC TCATGACTGG
1441    CTTGGGAATG GAGAGCGGAG GTGGATGTCC TAATGTAGGA CATGCTACAG TACAGGGACA
1501    AAGACCCCAG TGTTCTCCAG GACAAGGAAC ATCATTCACT AAAAGGCTTC CTAAGACAAA
1561    CACATCTTCG TCCCTCTGCC TGGTGCAAAC TGAGGCGCTG GAAAACAACA CACTCTCCTC
1621    CCAAGGGTCC CTTTGATTCC ACTTGAGAAT TCAGACCCAA GCATATCTTG TCTCCCACAA
1681    CTCAGAGACT GATGCTCTAA TAAATGTGTT GAGACAGATG TCTGTGCCAG GCAAAATCAA
1741    CTTGCTGGGG CAAGCAGAAG TCAATCTTGC ATCCTCCCTC CCTTCTTTCC TCCCCACTTG
1801    ACCTTTATGG CTCTGGTTTC CAGCAAGGAG TGAATTATTC ACATCGCTC ACAGATATCA
1861    AATTGGCCCT TTCCAGGTTG CCAGTGGGGT GGGGCAGAAG GTGGCTTTGT TCAGTGGCAG
1921    TAAGTGGGAG GAGCTACAGC CTTGTTCAAA CAGTTCACAG GTGGGTACCT GTTTTTTGCT
1981    AAGTCATCCC GGGAATGCTC AAAGGCCCTT TGTGAAGTCC TTTCGGTCTT CTCCGGCTCC
2041    TCCTTTCTTC CCACCGGTCT AAAGGACTTA AGGAGGCTCA CAGAGCAGGG CAGGGCTCAC
2101    TGCTCTTCAG CATGGCTTAC ATTGCCAAGT CGTTCTACGA TCTCAGTGCC GTTGGCCTGG
2161    ATGGGGAGAA GATAGACTTC AATACGTTCA GAGGCAGGGC TGTGCTGATT GAGAATGTGG
2221    CGTCACTCTG AGGAACAACT ACCCGG
```

For: CCG CTC GAG GCC TAG GGA TTC TGT CAT GC
Rev: CCC AAG CTT CCG GGT AGT TGT TCC TCA GAG

B Ltb4r2:

```
        GGAT AATTGCACAG AAACTGAGAT TTACTGTTAG
 541    TAAACCCCTT AACTGAGCAC AGTCCCTGTT CTCCTGACTG GGAGCCTCCA AGGCTCTCCT
 601    AGTTCCCTAG CTTCTTGAGT CCTGAGTATC CCGAGCTTAT CCCCGTCCCG CGGGAAATAA
 661    ACACAGGACA CACCAGGTTC TTCCACGGTT AACTTTTACT TCTTAAACAT AGTGAGGTAG
 721    ACAAAGAAGG CTCAGAAAGT GTGTGGCTTA ATACTTTTG GTGACGTGTC TAAACTAGGA
 781    CTGGTAGCAA CACCCATGAT CCTCATGCAC CCTGGGGATA GGTTAAAGCC CCCAGGGGTT
 841    GGGCAAAAGC CCCGGAGACG GACTGGTGGC TTTGGCTGGC TGTGTTCTCG CAGCTGCGCA
 901    CAAAGAGGTT TAGCACCATC TAGTGGCGGC ACATATATTG CAGCCCTTTA CACCTGAGAA
 961    ACACAAGGTG CCTGGACAGC TTTGTGACCT AGCCAGCTTC ATTTCTCATG CCAGCTGGAG
1021    CCCCAGCCAG GGCCACTTCA GGCACCAATC AAGGGCAAAT TATAGGGGTA TAACACCTCT
1081    AGGGCAATCC TCCCTCAATG GGCATGCCCT AGTTTTATTC TGCCTTAGGT ATTCTGTATA
1141    CCTCAGGGTC CTGATGGCTA GTCATGGGA GCAATGCATT GGATTGTTCT CCTCTTCCTG
1201    GTGTGTGTGA CACACACACA CACACACACA CACACACACA CACACACACA CACACAGAGA
1261    GAGAGAGAGA GAGAGAGAGA GAGGTGGAGG TCAGAGTCAG TGTTAGAATC TATTGAGCTA
1321    GAATTCCAAA TAGTTATGAG CTGCCTAACA CGGTGCTGGA AAACAAACCC AGGTCCTCTG
1381    GCTGAGCAGC AAATGTTCTT AGCCACTGAG CCATTTCTTC AGCCTTCTTC CTGATCTTTT
1441    TTTTTTTTTC TTCCTGATCT TAATATGTTC CGTCCCTCCC CAGTGTTATG ATCTCCACCC
1501    CTAAACCAGG TTGTAAGCTC TTATTACCCA AATGCATAGC CTTAGGCCTG AGCATCATGT
1561    ATTACACTGA AATGTCACCG GCAACTGAGT AATAGCTGTA GGGTGGAGGG CTCTGACAG
1621    GCCCCAAAG AAACTGAAGC AGAAGAGGAC ACTCCGCAGG AACGGAAGGT TGAAACAAGC
1681    AAAAGGAGAG CAGCTGGGAG AGCGCCTTGT TGGGTTACT TCTCTGTTGC CTGCAAGCCA
1741    TGGAGGCTAG ATAGAACATA AACATTGCAG GAGGTGGGCT GAAAGGACTG GGGCCAGAGG
1801    TGGGGAGATG TGGGAGCAGT CGTTAGCAGG TACAACTGCT CTTCTCCGCA GGCTGAGCCT
1861    TCTCTGCACC TCAGCCTTAT CCTGCTTCCT GGGGAGGCTG GCCTCCACAT GCCTGGGCCT
1921    GTCAGTGATG GGAAGGAGTA GGATGAAGGA GGGCCCAGGG TGAGCACCAT CTTGTCCCTC
1981    TCCATTCTTG ACTCATCCTC TCCGC
```

For: GCG GGA GGA GAT CTG GAT AAT TGC ACA GAA ACT GAG
Rev: GGT CGT CGA CGC GGA GAG GAT GAG TCA AGA

Figure 2 (continued)

C Ddit4l:

```
1     AAAATGGACC TTCAAGCTGG CTTTAGTTTC TGTTGCTCTG CCTGCAAGTG TCCTCCCACT
61    GATCTGTTTA TCACACTCTC TTTACCACTT TTGTTGTTGT TTTTCCTTCT GAGAGTTTTT
121   TTAGCCTGGA CAGCGGATCC TACTTCTCAA GGCCCTAACC TGCAGGTCCT TCCTTGCACG
181   TGGGGACCCA AAGTGTGCGG GAGTGGTGCT GGAACCTGGC CTTGAATGAG GTTCACCCTC
241   ACCCCAAGTA TCTCGGTCTC TTCCTTTTCT GATCCACCTC AACCATCTCA GCAACCTCAG
301   CAACCTCGCT GGGAACGCCC ACCCATTGCA AACCCTGTGC CACTGGCGCA GGGCAGCAGG
361   AAGGGTGGCT TAGTAAAGTT AGAAGAAAAC GTTTGGCATC GTGCTTTTAG TGGTGTCCCA
421   GACCCTCTGT TCCCTCTTGC TCAAGACTCC CCGGAAAGAG TCGCAGAGCT TATCCTAGCA
481   GGACAACTCT TTATTCTCAT GCCCCACAAG CTTTTTAAAG ACCACTAAAG CTTAAACTTC
541   TTCCCAAACA AGCCCACCGG GAACTTTTGC TTCTGGGAAT GGCAATTGCT CCTAACTATC
601   CTGCGGCTGG AGCAGGCAAC TGAGATCCTG TTAGTGGTTT TGTTTAGTTT CTTGGCACTG
661   GCCCTCTTCA ATTCAAGTTC TGTGCCTTTC GAAGCCAGGT CTTAGAACAG GGCCAGGCTC
721   GCCCTGGCCG CGGAGAAAAA CGGTTTAGTC ACAGATGTAG TATCCCCAAA GATGCCCCAT
781   TGATTCCTGA GTGCAGCTGA AGCTAGAGAG CCCTTACCAC ATCCCGACCA CCTGCGGGGA
841   GACTGGGTGC GGACTGGAGC TGATGGGTTA GAGTCAGAAC ATGGGCATAA AGGATGCTCA
901   CAGAGCACAG TGTCAACTAA GCCAAATACT TATTCAGAAT GACACAGCAA AGTTTTGGGT
961   CATGCCTAAC AGGACCTGGA GCTTCTAGCT GCTTGAAAAG TTCCATAGCC AAAACCTGAG
1021  CAGTCTGAGC CTGGAAGCAG GCAAGCTGTG GGCAGGGGCT CACGCCAAAG AATCTAGGTT
1081  AGTGGCCGAA GGGAGATGCT CTTTAGGAGG GTGACCAGTG GCCAACTCAG GGTGACCAGT
1141  GGCCAACTCA GGAAGCAGCA GGTGTCCGCC CAAGGCGAGG CTGATCACCA ACTCCCAGGG
1201  GCTTGCCTGG GCCCCTGCCT GGGAAGGAAC TGAAAGGTGA CCTGACCCTG CAGGGCGGG
1261  CCGGGGCACG GGCCCGAGCC AGTGGCGCAG GTGGGCGTGC CGGCCAGGAG GAGAGGCGGG
1321  ACCTATAAAG CGCTCTCCAT TCGGGAGGC[G] GAGCGGCCGG GTGCAGCCTG TGCTGGTGGG
1381  CGCGGTGGCC CGCAGCCTTC GGCTTGCTGC AGGACTGTGC AGGGGACCAC TGTCCAAGCT
1441  TCGGACTACT GAGGGGCGCC TGCCTCGGTT TACCCTTCAG CGTCTGGTGA AATCCGGCAG
```

For: GCC AGA TCT AAA ATG GAC CTT CAA GCT GG
Rev: GCT GTC GAC CTG CCG GAT TTC ACC AGA CG

D Fosl1:

```
1     CCTGAGGACA AGTTTCTTCA GTCTCCATTG AGATGGAAGA AATCAGAGAA AGAGTTTTGG
61    GACCCATGCT CTCCCAGTCT GCCATTCTTC GTGTACGTAC AATGTAAAGG CTTGAAGCTC
121   ATGGCCTGAC TTGGTCACCA GACTCAGCCA CTTACTCAGT GGCCTTGAGC AACTCATTTC
181   AATACCTGTC AGCCTCAGTT TTTCCCATCT GAGAAGTGGG GGTTATGATG GCATTTACCT
241   CCTCAGCACA CCTGGTCAGG ACCTCACCCG TATCAAGGCC TTTCACATAC TTCCAAAGTG
301   GGCTGGTGAC ACACATAGTA CTGGAGGAGT GCCTCCAGTC AGACCTTCAG TCAAGAAGCC
361   TTACTGACTG TGTCTCAGGA CACCTATGTC CTTCTGTAGG CGCTCTCTGC CTGTAGAGGC
421   CTGGATTAAA GCTTGTGATA GCTCCAGAGA CGGTCTCAAA CATGTAGCGC CTTCTATCTG
481   TGGGTACACT AAATGCCACT TCACGTAGTA TTCAAATATA CAACATTTC ATAACCCTGG
541   TTTGTCAATA ACCTTTCAGT CTATCAAAAA CCTTGACAAC AGTTGAAACT GGGTGTGGAG
601   GGGCACATTT GTAATGTCTG CCCTCCACTT GAGAAGTGAA AGCAGGTTAT TCTAAGCTAC
661   ATAAGGAGTT CAAGGCCAAC CTGCACAACA AGAGACCCTA TCTACAAAAG CCAGGTGTGA
721   TGGTGGCACA GTCCAACACT TGAGAGGTGA CGGAAGGATC AGGAGTTCAA GGGCAGCCTC
781   AACTAGATAC CTGAGACCCT GTCTCAACCA ACCTCCCTCC ACAAACCACA AGCAAAGCAA
841   ACTCAACTAA AGAAACTTCT CACCCCACTT GAGAGGAGCG TCTTAAGTC AGGACTGCAG
901   ACTTGGGTGA CAGTTGGAAT GATTCTCTCC AGGTAAATAA TGATGATGAT AATAATAACC
961   CATATTTATA ATTCACTTCC CAGCTTTCAG ACACTCTCCC CGTTCTTCTT TCTAAGTCTT
1021  GGCGCGAGGC CAGGCGGCCA CAGGATTTTG TTTCGCCCTG TGTTGGGAAC CTTGGCTAGT
1081  CTGAACGGGG CGGGGCGCAG TTGCAAGCCC CAACTTCGGC AAGGTGCGTC AGGGGGAATC
1141  CTCGGTGCAC CTGGGCGCGG CAAGGAAATT GCACCGTGTA TGGGCAGCTG CGTCAGAGGG
1201  GGGCGTGCC GCCGCGGATG CTAGGGGACG CCAAGTCGGT CGCTTTCTGT CTGTAGAGGC
1261  GGCTTGCCAC CCGAGCAGAG GGTCGTGAAG TTCCGAGCGG ACCGGTCCAC AGAGGTTCAT
1321  CTGGAGAGGT GGGTCCCCTG CGAGGTGAAA GGCGCCGCTG AGACACGCCC CACCCCCCG
1381  TGGTGCAAGT GGTTCAGCCC AAGAACTTTT CATTCATAAA AAGACCAGA CTCCGAGAGG
1441  CGC[G]AGTGAG TCAGAACCGC AGCCGCCAAC GCGGACCCTA CCGAACATCC AGCCCAGGGC
```

For: GCC AGA TCT CCT GAG GAC AAG TTT CTT CAG
Rev: GCT GTC GAC GCC CTG GGC TGG ATG TTC GG

Figure 2 (continued)

E Egr1:

```
1     TGGGGCTCCC GAAATACAAC CAGAGACCTA CAGAGGGCAG CACCGAGCCG TAAACGGGTC
61    CTCCGCACTG CAAGCTTGGG GTCGCCAGAC TGCCCAAAGC CAAGTCCCCC TCTTTAGGAC
121   AGGGCAGGGT TCGTGCCCGA CCAGTCCCTG GCCTGGATAA AAGTCAGGAA GTGTCTAACC
181   ATCACAAGAA CCAACAGATC CTGGCGGGGA CTTAGGACTG ACCTAGAACA ATCAGGGTTC
241   CGCAATCCAG GTCCCCAAAG GTGGGATCCT CAACCGCAGG ACGGAGGGAA TAGCCTTTCG
301   ATTCTGGGTG GTGCATTGGA AGCCCCAGGC TCTAAAACCC CCAACCTACT GACTGGTGGC
361   CGAGTATGCA CCCGACTGCT AGCTAGGCAG TGTCCCAAGA ACCAGTAGCC AAATGTCTTG
421   GCCTCAGTTT TCCCGGTGAC ACCTGGAAAG TGACCCTGCC ATTAGTAGAG GCTCAGGTCA
481   GGGCCCCGCC TCTCCTGGGC GGCCTCTGCC CTAGCCCGCC CTGCCGCTCC TCCTCTCCGC
541   AGGCTCGCTC CCACGGTCCC CGAGGTGGGC GGGTGAGCCC AGGATGACGG CTGTAGAACC
601   CCGGCCTGAC TCGCCCTCGC CCCCGCGCCG GGCCTGGGCT TCCCTAGCCC AGCTCGCACC
661   CGGGGGCCGT CGGAGCCGCC GCGCGCCCAG CTCTACGCGC CTGGCGCCCT CCCCACGCGG
721   GCGTCCCCGA CTCCCGCGCG CGCTCAGGCT CCCAGTTGGG AACCAAGGAG GGGGAGGATG
781   GGGGGGGGGG GTGTGCGCCG ACCCGGAAAC GCCATATAAG GAGCAGGAAG GATCCCCCGC
841   CGGAACAGAC CTTATTTGGG CAGCGCCTTA TATGGAGTGG CCCAATATGG CCCTGCCGCT
901   TCCGGCTCTG GGAGGAGGGG CGAGCGGGGG TTGGGGCGGG GGCAAGCTGG GAACTCCAGG
961   CGCCTGGCCC GGGAGGCCAC TGCTGCTGTT CCAATACTAG GCTTTCCAGG AGCCTGAGCG
1021  CTCGCGATGC CGGAGCGGGT CGCAGGGTGG AGGTGCCCAC CACTCTTGGA TGGGAGGGCT
1081  TCACGTCACT CCGGGTCCTC CCGGCCGGTC CTTCCATATT AGGGCTTCCT GCTTCCCATA
1141  TATGGCCATG TACGTCACGG CGGAGGCGGG CCCGTGCTGT TCCAGACCCT TGAAATAGAG
1201  GCCGATTCGG GGAGTCGCGA GAGATCCCAG CGCGCAGAAC TTGGGGAGCC GCCGCCGCGA
1261  TTCGCCGCCG CCGCCAGCTT CCGCCGCCGC AAGATCGGCC CCTGCCCCAG CCTCCGCGGC
1321  AGCCCTGCGT CCACCACGGG CCGCGGCTAC CGCCAGCCTG GGGCCCACC TACACTCCCC
1381  GCAGTGTGCC CCTGCACCCC GCATGTAACC CGGCCAACCC CCGGCGAGTG TGCCCTCAGT
1441  AGCTTCGGCC CCGGGCTGCG CCCACCACCC AACATCAGTT CTCCAGCTCG CTGGTCCGGG
```

For: GCC AGA TCT TGG GGC TCC CGA AAT ACA AC
Rev: GCT GTC GAC CCC GGA CCA GCG AGC TGG AG

Figure 3

A Bsc12:
```
   1 gctgggctgc tgctccccca ccccccacccc caccctgaca cagcacttag cacctgaatc
  61 ttggtttctt tcagtgaccc accgttcttc agagctagga aaatgtaaca ctctacaggt
 121 gatcagcttc tagatcacca ctttctacca cgtgagtgac gcgagctggg agacccagag
 181 gtaacccatc aggaagatag ctaaagaaat gatacatcaa agaagagaag ctgggcaag
 241 agagacatgc agagaccaga tcaaaggatc agacaaagac gaggtaaggc accttgccac
 301 gagagttagt gtgaatgttg tgaacacagg tgggcttctc ggagtgggga gtagggtggc
 361 aagagttggc actgggaaa tagggaatcg attggaaatt tttcatgtaa tttgagtgga
 421 ttactactat tcaaaaagat gtgcattggc cttgcctcct ggaggacgtt atccagacga
 481 tgccaccatc agaaatctag tctcatggtt ttttgtaggg attttgaggt tggctgcatc
 541 acgtgggtca cagaaggtca atcacgcagc ataaaaactg gagactgaaa ggggttgaaa
 601 tgccgccacg cttgactagc ggacggcacc atctgcgcac acaacacaca agattcagat
 661 tctggcaggg tgcaaggctc tctgagctcc agttggactc ctacaggccc aaggaactct
 721 actgaattta caaaaaacaa acaaacaaaa caaaacaaaa caaaatcagc atttatttca
 781 cacctccatt caatcacact gaaaagacag gtggtaaagg tatgggcaga gggttgtggt
 841 tgaggcctgg aaaggaggac caaggagtcc cagactgcgt tggagattat aatgggtcct
 901 ttggtcactt aactaaagtg taatgggcag agacactggg gagcaaagca ttttacaggc
 961 tctgccctct atgcaaggct cagcccctgt aggcgattga cagttgggcg gggcttcctc
1021 ggcagccgga actgccttct gtatattgcc tgggcagcga gaggccggtg agtctgcctc
1081 gccgcggtgg cgatctggtg tacaccgcat taccccaggg gtgggcgccg cagcgtcggc
1141 cacagggtgc tgtgcggggg taggggtcac ttcctccgtg agcgagcaca ggtccaggca
1201 gaggaaagaa actcttggga ggcaattttg actgctctaa ggctgctggc tttgagccag
1261 actggccggc tgtgcaacct taggcaagtc actcacctcc ttgcaaacct ctggcatttt
1321 ggatccatgt catctgggtt tcgagagaga tttaaaggcc tcgttctctg tacgttatac
1381 ttctgtgaat gtatcaagga ggtttgtccc aggctcccga aactggagga agaggctgga
1441 agcacactca gtggagggag gtgaaggagt aattggaaga gaagcgcatg tgaagcaatg
1501 actttgcttt gccctgctac ctctagtttt caaagccagt tgaataagct tttttgtctc
1561 cagctaccct ggaaaagaaa ctgtcttttc ccttctcttt ctccaggaac cttcagctgc
1621 cctatcccat ggccaaggt atcgtccctg tggaagacca gccaggaact caaagcctga
1681 ggctgggcc agaccccctg ctgtccccat catggtcaat gacccaccag tccccgcctt
1741 actgtgggcc caggaagtgg gccacgtctt ggcaggccgt gcccgcaggc tgatgctgca
1801 gtttggggtg ctcttctgca ccatccttct tttgctttgg gtgtctgtgt tcctctatgg
1861 ctccttctac tactcctaca tgccgacggt cagccacctc agccctgtgc acttccacta
1921 caggtgagaa ggctgctcca ttcaagtaga tggatcttaa cttgaaaatt acttcaggga
1981 cttgtggagt ctctcctctg ttgaatccca gtattgaccg agggtgaaat cttattctag
2041 tgtgctatca ggacttctgc cctcctgagc caaggcttga gcaggtctgg gctggtaggg
2101 ctttagggtt ctaggtctgc ctctgctgga aattgtggtt aagaactgag aaaaagagcc
2161 tggtcacgtg tgtaatacca gtctggggag gctgagttgg gagaattagc atgagttcca
2221 ggccagcctg gaagacaggt tgagaactttg tctcaaaggg gtctaaaaaa aaaaaaaaga
2281 ctaggaaaag aaagtcactt ttagccgggc agtggtggtg catgcctgta atcccagcac
2341 ttgggaggca gaggcaggtg gatttctgag ttcgaggcca gcctggtcta cagagtgagt
2401 tccaggacag ccaggactgc acagagaaac cctgtctcga aaaaaaaaaa aaatcacttt
2461 tagaccaagt agggctcagc gtctgttctg ttgaggttgc atgaaaccTt tgagccaatt
2521 caactgccat ggcatctaag aattacactg gctttattaa cacgtgagct attaggaaat
2581 acctcctttg cctttagtg tactgccact cacccccaat ggtacattca gtaacccaag
2641 gcagtcctac tgctaaccta gccttcgagt tcatatccat tttactcaca ctgccaaagt
2701 ctctgtatgt ctcccagcaa tggctatgag acaaattaac atatacagaa aacgcttta
2761 tgatcattgg tttaaaacct ttttttcccc tgtcccaaat ccctaatctt gtgttgtcat
2821 ttctaaggta gacccatgta aacactagg gaacatgaat cctttttaa taattatttt
2881 tgtttcatgt gcattggtgt tttgcctgcc cgtgtggttg tgtgaaggtg tcagatcccc
2941 tgcaactgga gttacaggcg gtcgtgagct gccacgtggt tgctgggaat tgaactcagg
3001 tcctctgcaa gagtaaccag tgctcttgac caatgggcca tctctccagc cccaagggag
3061 cacgagtctt acatacatgg ggtatatgta tgtatactga ggtaggagct gtgtaccata
3121 tactactgc agttttgcgt ataatttatc tttaaaagac atatccatag gtcctttagg
3181 atgaatttct ttttccaacc tagtccagaa ctgctgaatc agactcttta ggagagggac
3241 cctaaaatcc acatgccctg agatcttcaa gggagcctat agaaaccctg agtgtccttc
3301 ggctcctccc tatgggttct gttctcatga ggaagagaat gaaagtctta ttaggatctc
```

Figure 3 (continued)

```
3361 ctgactctag tgtccacttc tgttctccat ttcctgtaat ggggaaaagg gatgagtgag
3421 gggaggggcc ctagagacta ggtgtgtgag caggtaggct gggcaggctg gcacctcaca
3481 aagcattgtt catcccttct catttaggac agactgtgat tcctccaccg cctctctctg
3541 ctctttccct gttgccaatg tctcactggc taagagtgga cgtgatcggg tgagtatgag
3601 aactagacag aggctttgat tgcttgagga agatggggag agcagggatt gagcaaccga
3661 gattgaagag aaaggctctg acgcaaacgg gtggaaaaga aaatctggaa gttggtccca
3721 gtcactgtga tacatatctg taatgccagc actaggagga aaaagacaca gggagattat
3781 tccaaatctg atatcagctt gggcttcata gccagaccct atctctctag aggctctgat
3841 aaaaaataga attacaagct taaaatgtcc cttgatatca aaaaataaaa caaaaaagga
3901 ctttgagaat taatgtcatt ttttattaaa tgaggttttt ctagttgtca gtcttaactt
3961 gaacattttt ttaaagtggt atttaagaag aaactgactt tatagtagaa tatcagctct
4021 ggcacagtgg cacacatcta taatcacaat acttaacata gaaggatgct gcccaggctg
4081 gcctcgcacg ctgagatcca cttgcctttg cctcctaagt gtggccatca ccacgcaagg
4141 gaggatatct tgagtttagg agttaagagc atcctgaata agttagttca aggcctctca
4201 ttaaaaaaaa aacaaaggag cttgggaggt agaggcagaa aggctagcct ggactattta
4261 aaaaataaaa agtagtttac cttaaagtta tggtcactat gtctccgcct cctatgtgct
4321 ggagttaaag gtacgccatg taccaatcca gactggaagt gagtaacctc agacgtgctc
4381 ggcttcctaa gcgttgggat tgttaggaag tgggcaccac cgtgccaggc ttggatttct
4441 ttttttcttt tttttttctt acacaccaga agagggcttg ggatcccatt acagatggtt
4501 gtgagtcacc atgtgattgc tgggaattga actcaggacc tctggaagag tagtcagtgc
4561 tcttaactgc tgagccatct ctccagaccc tcttaatagg tttattaagt taaaatttat
4621 atgagataca gtttacctct taaggtatac agtcgtcgtc atatcattcg atgcatgtat
4681 ttgggacaga gtttcactat gtagccttgg ctggcctgga actggccatt tcaaccaggt
4741 tggccttgaa tccacagctc tcctcctccc tttggcctct tgtgtgctgg gattaaaacc
4801 atgcactgcc gccccaggca gttctattgt ttttaataag ttcagtgttg cacgcatact
4861 gatataaata gacaaactta atcttttttt taaattaata agcactctgc ctttaaaaat
4921 gaagaaagac caggataaca agatgatctg ccactgcagt gattgtgcaa gagctgacta
4981 gggaggcaga gcagcacttg cttaattagc aagtgagggc agactaggcc caggggaca
5041 gctccggcgg cacacaggcc tgaatcacag atgcccagt tggcaatgtg actgttcact
5101 tttggaaaag aaatgcaaca gggcacttct cgtaaacata gtagtccaag acagacctaa
5161 gagctcacag ggtgaatgtg gtggtgcaag cctaaaatgt cagcgccaga ggctgaggca
5221 agtgaagttc tatgaatttg aggctttgta gtcagtgctt ggctagccag agatatgtag
5281 caagacccac ttaaaacaca gggttctcta cctgacaacc caaccccctag gccccaaata
5341 aaatcaaacc agcaaacaaa atagaagtct ggaaagccag ggtgtccagt gaccagcagg
5401 gggcagcatc aaatcatgat taaacaatga gaagaccaaa gggattttgt tgagttctta
5461 agcagagaca gtacatttta aaaaaaaaaa aaatagatta agacatacca ggcacggtgg
5521 cacatacctt taatcacagc actggggagg cagaggcaag cagctctctg aatttgaggc
5581 caacctgatc tacagagtga gttccaggcc agtctcaaaa caccacaatt tttttttttt
5641 tttaacaaga tgtgtgttac cttgggcagg tactgatgta tggacagcca tatcgagtca
5701 ccttagagct tgaactgccc gaatcccctg tgaatcaaga cttgggcatg ttcttagtca
5761 ctgtttcatg ttataccaga ggtggccgaa tcatctccac ttcttcacgc tcagtaagtg
5821 tttatggaca atactggaat gtttgaacaa tgatgggaga atcagaatat cgggctagtg
5881 tttcaaaaga agacctcctt ggctctgaga tcaggcctaa accagataag tgaagaagct
5941 gtttaataag cttaacattt gccaaacact ggtatcctat ggtgtgccca aattcagggt
6001 aaataataca ggtatccttt tttaaattat tcatttattg tatgtatgta agtacactgt
6061 cgctgtcttc agacacacaa gaagagtgca tcagatccca ttacagatgg ttgtgagcca
6121 ccatgtggtt gaactcagga cctctggaag agcagtcagt gctcttaacc actgagccat
6181 ctccccagcc caatacagct gttcttaaaa caagcagaca ccagaaacat accagctttg
6241 agataactga cttaattgct agagtttag agtaacttct tcctaacaag actaggaaga
6301 aatgctgggt tcttactagc atgtgttgaa cactcattca acactgagcc ccattggtaa
6361 actgtcaaca gagtcaccac atttgaggaa agctttaggt gggatgctgg gacacagatc
6421 ccagcccaga aggcagacca cgtgcaagca gactgcttac ctcagggagg taattttga
6481 gagggctttt ctctgtgttg gaattaggaa atggggtcag gaagtaggga gtgttactag
6541 aacaggtgga aaggttgggt aggtggtgac tggaagttag agagagaaag tgaaggagca
6601 gggagcctgg aatgagcgag cgagcgtgtt gcttagcatg ggcagatgga cccagcgcct
6661 gtccccaatc tgtcctctcg gccgtcaggt gatgctgcat taccgctcgc agctgctcca
```

Figure 3 (continued)

```
6721 ggtgctcgac acgctgctgt tctccagcct cctgctgttt ggcttcgctg aacagaagca
6781 gctcctggaa gtagaactct actctgacta tagggagaat tcggtaagtg gctgacagag
6841 ttaggagaca actcttcaac gagcccaaga ttgtacctga gaagcccatg gacagtcaac
6901 tgcaagagcc acagactgga agtagacctc atactgactc tgctctcacc ttgcaccctc
6961 gcagtatgtg ccaacaactg gagcaattat tgagatccac agcaagcgca tccagatgta
7021 tggagcctac ctccggatcc atgcccactt cactgggctc aggtaaaaaa gccacggaag
7081 gaaacatcga cagctttcct atacccctgcc ctaaaatgaa gagagttcca ggcagaggtg
7141 accagtaaca atcacatcat attttacaaa ggccagaggt ggttctccct ggcttcactg
7201 tgcttgtcac ctttcaagag agcttcttaa aaatgccatg tgaagggggc ttggagagat
7261 ggctcagggt ttaagagcac ccacaaggtt agttccagga gatctcattt attcttctgg
7321 ggacaccagg catccatgtg atatgtgtac gtacatccag gcaaatactc agacatatac
7381 agatgtgaat atcctgtagg agatgacaga ccccttcgtt ccagcactgg atgggcctga
7441 ggcaagaaat cttgaactac aaagcaagac tctcaacata aataatgaaa agggaaaacg
7501 aaaagtatcc gatgagccgg gtgtagtccc gtgtctagcc cctggttctc agacaacaaa
7561 gtgagatccg tatacacaca caaccactct ggcccaataa aatctccgtg caatccactg
7621 ccttgttgga ctggctcaga aagtattgga gtgactagag gagttacagt cgaagccatt
7681 gaaatgctgt ggccttgtga ttctgagatg gcctggaatc cttggccttt attagaacct
7741 ggtgcagggt ggtctggaac ctgggcaggg gagtgggtgc cacagtggca gaaggcagct
7801 ccagccatcc tcactcaggc tgtcctacaa atcttcttgg agtgatagtg tcgagtgcta
7861 tccagtaacc gctgttccct tcctgaccct gtttctcacc tcaggtacct gctgtacaac
7921 ttccccatga cctgcgcctt cgtgggtgtg gccagcaact tcacgttcct cagcgtcatc
7981 gtgctcttca gctatatgca gtgggtgtgg ggtgctgtct ggccccgcca ccgcttctct
8041 ctgcaggtct caaggggcaa aggccccgtt tttcttccct tggtggtcag gggcatgtta
8101 gggctagggt atgattgctg cggaggggag tcaggcctca ctgctcagtg gttactgctc
8161 cacaggttaa tatccgacaa agggataact cacaccacgg ggccccgcgt cggatctcgc
8221 gccatcagcc aggtaacctg gttggttgac agtatccttg aagggtaggc tggctgggtt
8281 agagggttgg cctgcctcca ctatgaagta tgcagtactc tggaactaag gattcgagga
8341 agaggtagag ttggcactgc aagccaagga taaccactga ccctagctgt cctctgtttg
8401 tggaacctga aggtcaggaa tctacccagc agtcggatgt gacggaggat ggtgagagcc
8461 ctgaagatcc ctcaggaaca ggtatgttca gttcctcttc ctcgctcctc atccccagca
8521 ctcacctgca gtgcctggct ctcaccttct gtctcacctc tgtttccctt tggctgaaga
8581 gggccagctg tctgaggaag agaaaccaga gaagcggccc tgaatggag aggaggagca
8641 agagccagag gctagtgatg gtgagggcac tgtgtgatgg ggagggcact gtgtgatggg
8701 gagggcactg tgtgatgggg agggcactgt gtgatgggga gggtactgtg tgatggggag
8761 ggcactgtgt gatgggagg gcactgtgtg atgggagggg cactgtgtga tggggagggc
8821 actgtgtgat ggggagggca ctgtgtgatg ggtgatggt ggtggggatg tgtgatggag
8881 tgatggtggt ggggatgcta tcccacccct cctagcctgt ctcactcaca ttttgtttgg
8941 ccctttctg gctctgcttc aggctcctgg gaagatgcag ctttgctgac agaggccaac
9001 ccacctacct ctgcctcagc atctgccctt gccctgaga ctctgggtag cctcaggcaa
9061 cgcccgacct gctccagttc ctgaacaaag ggtgaattcc tcacattcca gcgctttccc
9121 atcatacacc tttccccttg ctcccttaat aaactatttt gtggc
```

Figure 3 (continued)

B Ephx1:

```
   1 ggagtttgag agtggaggaa ctgcacacca gccgccgcgg gagtaggaac ccgagagcga
  61 ccctgacagt aagctccggg gacagcagcg gcactccagc gtgagagttg cgagggcttc
 121 gcgtatctcc cgcagctaaa tgcgcttccc cttatcctaa gaccgatcca ggcgtgcaat
 181 aggccatgct tcttagtcct gcatctgatg ctccatcctc ttccagggc gtcaacccct
 241 tgcttgcgct tcggaagcaa ggggtgggtg ctgcgcctga cagcgatgct ggctcctcag
 301 cccctggtt tccccgcccg cccgccccc catgcatgtt tgtcccttgg gttccaggct
 361 tgctacttgc ccaggcacct gagccaatcc aggtagctga gggcgccgtc caagtgactc
 421 ttaattttaa cttctccagt ctgcacctcc cgtcatttaa acttccggcg gccagaagtc
 481 tggatagcct ttctggcatc tggttggcgg gatcaggagg gaggtggagg gatccggtat
 541 gtatgcatgc gcgttgacag tagggctgtg cctttgctgg cattctgtgc tgctggcagg
 601 attgtagaga tggacatctg cgacatttgc ttctctgcct ccgatttcgg cctgatcttt
 661 tttttaaagt cgcagagccc cagaggctca cattgttttt actgtgacag tgacttcctc
 721 cctcaagtgg aggctttcac tggctgtgcg tggtctgact tcacacaaga cttgaagctg
 781 aggggctgg ggaagggt ggaacaaaaa cgtgggcgtg ttcagcaaag actttccatt
 841 ccctaatacc cacaccaggc gggccacgtg agggcttcct gtgtccctaa agaagtatgt
 901 tcagtgcaac cgtgctcaac gacacggact gactgttcag acactgcccc ccacccaccc
 961 accctgggga tagcagggaa tgtgttctca tgggctctgg gagcttttga atgcagacaa
1021 caaacaaaat tcaaggtcct gggtcagatc cccaacacca cataataaat aaacatatct
1081 ttgtaaaata taaattatat ttgtgagctg taggaaatag gaggtcataa agagggagca
1141 ggactgttga ctagagagga agaggccaca ctttcacact ccagagggtc aggagggtca
1201 ggagtgcgcc tcactactca gtatccagct gcacaaggct gaggagaaca tgcaaaggcc
1261 ctgaggcaga ggtgcgcctg ctgtgggtgg cttttatgtc ctcagttgcc ctctggaaga
1321 gagaccagag tcagtgagga ggctccaagc tttcagctgc ccctccgacc aagaaaacaa
1381 gatttcccta gaccctcggg tgctcctgga gtcagctggg tgaccttcag caccatccct
1441 aatccccatg ttatctggtg tgactgcacc agcctttggc tgtgccttac acacctgctg
1501 cccagatgaa ctgagaggga aatgcatggg gaacagaggg agggattttt agtgaaaggg
1561 tgagagcctc caccagaccc ctgggtcca gtttctgccc agagcccaac tagagcacag
1621 tggtacccac aaaaagccct gtaaggatga gtagtgtctc tcctccatgc ccagcagctc
1681 cagcatgccc aggcatagcc ctactgatct ggtgcctcca cccttttgt tttttgtttc
1741 ccctgggatc ctggccctgg atcaagtatt tgaagggcag aggcccaagt tccacttcct
1801 ggttcttgtt ttaagacctc agagtatggg aacacagcct ggctggaggg atgagggaca
1861 acagagaata agattggagg caggagagcc actagtcagt gccactggcc ttttggggtt
1921 acctgcaggg ggtcttcagg ccaagctagt atcatggtgg agtcaccagg gagctgtgtt
1981 gataagactg ggaaaggatg tccaagaggg agcccagcct cagccaggaa ccttctcctg
2041 catggtggtc cccagggaat gggggggggg gggaggcgtc tggctctcca tcctcagaca
2101 taatcaattt cacaaactgg ttcaaaggag caaagtgccc tgctaccagg gcttattgat
2161 ttactgagga aaaccacagt tcatgctttc tccccagaga gcaactgttt tccctctcag
2221 agtgtctagc gtgctccttc caccattaca ggcctggggt gacatctgac tcctggccca
2281 gtgcctgcct tcccttgact gctacttggc catcctcact ttcctgtgga gccaagccac
2341 ggtgcagagc cacacctatg cgctcttcca aggctgaggg gttcacttta ggggacagt
2401 gttgtttcag ctgtgttact aaaatgtctt tacagaaaac tcctcttgac caactgcaa
2461 acaagcctta tttgtgctta agaaggtgga gtctttgctg cctctagcag tgcagaggct
2521 gaggcgcagt gatgcagtgt gggtgtctct ttggctcttc tgctcagatt ctcttcactg
2581 aacttcctct ctgaactcta agtgctcttt aaacacaggg caatgccctt tagttcttag
2641 ggttgtgatt ttacatgtgg tgataaattc aagagccagg ccttcctcag ctgcaaggac
2701 agagctctgc actatggctg tgtggcccgt ggctttccct gttaacatcc agtcaggtgc
2761 agctaggatc ttaacctcgg gtgcagaaag ggatttcagg gttagtcagt atgaagtaga
2821 attggagatt attaagaaaa gatttttagta tagacgttaa aagagcaaca tgaacacgta
2881 tctattcgtc tcagataggc agcaatgaca agtgattcca cagaagaaca acttgatgaa
2941 cccttgaatg gactgtgctt acaggaacat aagtgaggga gtctttacag cattgtgggt
3001 gacttggggc agtttcatca ctgataagtc ccaatttatc accaagagct ctaccctccc
3061 ttcaggtaac tgtagttacc ctacctcctg catactctac cagcccacc ctagcccagc
3121 ctgggccac ttatactgat agcaaactag tggtgggcag ctgaggtggt tgaaagaaa
3181 atgaactccc cataggttca tagggagtgg tcctattagg aggtgtggac ttgttggaga
3241 agcggccttg ttggagacag tgtgtcactg gggcgggcct tgaggtgtca gatgctcagg
3301 ctgtacttgt ggttctgtct cttcctgctg tctacagacc cagatgtaga actctcagct
3361 tcctctccag caccatgtct gcctgcatgc cgccatgctt cccaccatga tgacaatgga
3421 ctaaacttct ctactataag tcagccccaa ttaaatcttt ccttctaaga cttgctgagt
3481 tgtggtctct cttcacagca atagaaatcc tcactaaggc agtgggaaag ggtaagtgac
```

Figure 3 (continued)

```
3541 tgatggccct cagttctgct ccatctaggg tgtgttagga tctccattgc cctaggccta
3601 gttatcactc ccttgcctta atgttatctc tgctccttga tggtgatagg atggagaaag
3661 ttgccacagt gccacactgg tgcccacctc agggtgagtg ccattccgag agggtcccac
3721 tgaggtaggt gctttggtgg cttttgaagt ctccctgttc aaaggattga gaagattgaa
3781 aatgttttag cattcacgtt tttatctaca ctttatttag caactaggat tatgctgagg
3841 tttgtggggt tcattgtaca cgtgtttgct gataagagag aagtatgggg tttttttttt
3901 ttaagcaggt caaaggaact cttactacac gtcgcaagga gttggaggca tgtgctttga
3961 ctgctaagca cggttaagtc ttatttgtgg gcttctctca aaggattatg gtcccttgcc
4021 agccatttga aagttccttg aagagactta aacagatcct ggggttgagg gctcctctat
4081 ctccctgtct ttctgtaagt actaccacaa tgttacaaca gtccagggcc tctctgaact
4141 tcctctagac agtggatgcc tgacacatga gtgttcctgc catggacaca tctggctggc
4201 tttaatctgc ctgcagtttt cttcatgacc tgggaaggct gtgggatgcc atggtcaggg
4261 ttaggaggtc ccagagcctc catgtggcat cacagggaca cagtgaaact tctataaact
4321 gaggacatgg ccactccaag gcatggttaa ctggaaagtt tttattgtgt atatgagaga
4381 gtgccgctag aggtatcctg atgggtttgg aacagagaga gagaaagtca taaactgagc
4441 atggccagca gactgcatgg gccacgagag aaggcttgat tctaaaatcc atctctagag
4501 agatgagagc agaggtactt ggcactggga aaagacagat tagcctgtct ccctgtcaca
4561 tacaaatgaa aggccatttc cccaaatgct ggtgactaga caaacgccgg cattgctcta
4621 gaacttggga agctggcttc cctctactaa aggagccatt tccttaacac tggcagaagg
4681 gacaaacggc taactctggt gcctgatagc acgacaaagc ccatgctggc ctccaggtcc
4741 ctcagtatta caagggccta gctctttcta cctcctccag gaccccaagc ttctccagct
4801 catggccttc ctccccagct gtccatttct tccaaccctg ctaattctgc tgtgtacact
4861 ctgggtcttc ccttgatctt catccctcca tcccccaacc cccaccccac gctgttctct
4921 tgcttctctc atggccaggt ccagtctact ggccttgttc aatctactgc tccctgtctc
4981 tgctctggac tcttccaagg cctctggctg ttctctccct catatctaca atgaaaacct
5041 tcctcttcac catgtcatgg aacaatcaca tcaccagctc acacactcac aggtaaattt
5101 acccatgttt taccttggtt ccatggcttt ctataaactg taagaggatg ctgtctggag
5161 aaacttagag accctccctt gtctaaattg taagcaaatc cgctctcctt ggagagtttg
5221 tttcttaaat cttttttagaa tataaggcag tcagactgca ggtttctgga cctaagtccc
5281 cggggaatgt cagggcagtt tagggggagct ggtcttccct gcttactcag ggaattatgc
5341 cttccttctt gcttgcctct ggcagaccta ctgcccaacc agcttgtctc tcagaggaaa
5401 cagaaccacc cagaaaatgg aaaggaactc atctcccgct gcaaggtggc tctgttctct
5461 ccccattgtg caccctactg tgggaggcct cccagcccct gttaggatcc tgacttctga
5521 gaacctgtgt tcaaagagat gatactgggg cagagcatct taaagtcaga gaagatgatg
5581 gctccggcat ctgaacctct gcagctacct ggggagtttc cttttctttt caccgtggat
5641 tgaccccagg gcctcataaa tgctaggcac ggtgctctgc tattgagcta cacccagttc
5701 cctccacagg cttttgaact ccttacttgt agcccctgga gacctgacgc tctcttgaga
5761 cctaggcatt gctacaggca aattcaacac tctcccagcc tccaatgaaa acccagaga
5821 gcagtgctgg aaggctagcc aggcctcacg gggcagccag gaagttcttc ctgtacccac
5881 acagcaagga gggtggattg gactactcaa aagccttgca ggttctgttg caggctatcg
5941 aggacacttt caggctatga aggttccagg ccacaggtta taatctctga ggatccgctg
6001 ggtatggtgt ggacaatgca cggcacagag tggcttgtgg agggaggata gtgcatgctg
6061 gacagtctac tcctgctact ccagcctggg catccatcaa cccagctcaa cagcaggcat
6121 gggctagcct tcctccttaa aggaggtgag atgcacttct agacatttaa agccagtgga
6181 aaacttgaca gatcctattt ggatcatcag agctggagat gggaaaggc acagggacct
6241 aacagtgcag ctcccctgcc cttctctcct tataggactt aaaaacctgt gtcacagcat
6301 tgagggaat agtgaatcca tgctggctga cagcatagtg ggaaaggatg tgcccacatg
6361 agggaggctc taaaagccat cccaagttca tgcatgcaca cacacacaca cacttaat
6421 ggagcatgtt tgtttgagag cccatgaagt agagtcaaga ggccattgtc aatgagatct
6481 cagacacatc tgcactagaa tctgcctgag accgtgtaaa acaatcattt ctaactaatt
6541 aacgagctag ctttcacaga ctccttaagt ttaaagctta taaacacagg cttaagtcaa
6601 tacatttaag tggcttttcc acaccggaag tatcctccct ctctaaaggc atccagggcc
6661 tgccctccca cccgtactat ccccgccctc cctagttaac tcctctgtgg ggtgaccag
6721 actaaggcct ggagaagcag tccctgtcct taggaggggt caggggcagc actgaaggcc
6781 tggcctccag ctgggctggc cctggcctct ggtgtgcttc agcagtgcac cctccagatg
6841 gtgaagtctc tgctgacacc acactgggct ctcctcacct tgccctgctt atcctctttc
6901 ctatattgcc ttgaaatgca cccaaaacct tctcttgctg gttgactcta gccttctctc
6961 cttagctcac atccaaggct gtgccaccta ggcaccggca cagagggcac accacagctg
7021 agccaccaca gcacagggac agtggcactg agggagaaca gactggccct tagccatctg
7081 tgtggtccaa ggaagcctct gcttagccat cactgaccag cctgaaacct ggagtggtga
```

Figure 3 (continued)

```
 7141 gcaggctgca ctgtcagaag gaaggcctgg ggggttgtcag caaagacatt tgcacccctt
 7201 ccttttgtgg caggctgact ggaacacaag aggggccaaa tgcctccctt ccccctgctta
 7261 gagtttcctc acttccctag gaagggagat ggagttgctg ggccagtcag atccagggtc
 7321 aaaaggaggt cacacctctc tctctccctc tgacacctga aggcagcagg tacttcccct
 7381 cagctcccac agtcaccaag gcaaagtgta gatgccagga tctctggtca ccaccaggcg
 7441 atctcacata gcctctctga gggagcgtgc cttatgtcca gtcagatcca gggcctgctg
 7501 ccaacagtgg caaggctctc tgcacttact cttggccgtt gttctggaaa agccctgagt
 7561 ttccaggcct gtgatctgcc ctacagagac cacatctgct gagtcactat tagctggtat
 7621 tagagggcaa tctcagggag catgcctctc tctctctctc tctctctctc tctctctctc
 7681 tctctctctc tctctctggg taaagagaac aggtttctct ccaagggcag ttggctgacc
 7741 ccaactatga ggcttgcagt gactgcctct gaccccacac ttatctctag tcttgctcca
 7801 cacttaacaa taatcctcaa tccattagct ccgcagacta gactgagaaa taagctgtat
 7861 gctattactt aagaaaaatt taaaatcttc ttcaatcaaa acttctagtg tctacgttat
 7921 gatccagaga acttatctca ttcagtcagt gttgaattat tattcagtaa gtgccagggt
 7981 ctgagaatac agagggaacc aagggtgctt gcctatagtg agaggggcac aggccctggt
 8041 gtaacagcta agcccaggca gaactgaagg ccatgggaat aaacagccac ctcagagctc
 8101 tggaacaaga gaggttgctg ggcataggaa ctgaacaaag atggttaggg tctgtggctc
 8161 aagcgagtac aggggagat gggtcatcag acttggaacc atggtaaatt cctgaggtg
 8221 tgtgtgtgtg tgtgtgtgtg ttggagatgt ggactgggaa tggaatcccc atcctctgaa
 8281 agactagcga agctcttctg agtcatcttc ccagcctggg gttacaatgt tgtaacatat
 8341 gtatccagct gtttgttttg gttttttggt ttttttggt gttttgtttt gttttgtttt
 8401 gttttgtttt gttttgtttt gtttgacagt tattatattt atatgaagtg ttggttttag
 8461 tttggttttg ttgttgtcgt tttaagatt ttatttattt atcttatgta tgtgggtaca
 8521 ctgtaactga acagatggtt gtgagctttc atgtagttgt tgggtttaag attttattta
 8581 ttaattttat gtatgtgggt acactgtagc tgaacagatg gttgtgagct ttcatgtggt
 8641 tgttgggaat tgatttttag gacctctgct cgctctggtc aaccccactc actcagtccc
 8701 tgctcgctct ggcccaaaga tttatttatg attatacata agtacactgt agctgtcttc
 8761 agatgcacca gaagggatg tcagatctca ttacgggtgg ttgtgagcca ccttatagtt
 8821 gctggggattt gaactcagga ccttcggaag agcagtctta actgctgagc catctcatca
 8881 gcccctggtt ttggttttc aacacatctt ctttactaag caaccaatcc tttccttggg
 8941 gagaatacct taactctaag aaaaaatgg tttccttttg cttttgtaac actaggcatc
 9001 aaacatctca catgagctag gagccatgcc aacagcccg ccctccaata gaatggcttc
 9061 ctcttcaact gcaattctct gggcacaggt cttcttcatt ggaaaattgg gttacaaagc
 9121 aaatgaaaag actactggaa gaatgaaacc tttggtacaa gataaattga ccttcagttt
 9181 ccagtgctag catgtcaaaa aggaacttgg gacttgttat ttttgtttcc agagtctttc
 9241 ctgatatcct ctaactttgg tgttttgaag aggttagaat gttctctgct gcaaaagaaa
 9301 tagaccacac agaagacttt gttgcaactg ttcactacag ggtagagcct cagcagacag
 9361 cagtgagacc cctgacaatg agaacaggac ttctctgagc taatagcaca gacatgcacc
 9421 ccctaggaca tggtttacag aacgtggatg gtcacgggcc tatctggact gagcttggct
 9481 taaccgtct ggatcacagc ttcggtgagg gcacatgggc aggacagtgg gcatcccagg
 9541 acataggtgt ctccactctc tcaccttcag cctggttctg tgcacatatg ctgctgtaga
 9601 cggcttggat atgagagtcc cacatagtga attaggggaa aggaaaggac acccacgttg
 9661 gtggagcacc tgctcagggc cattcattcg tcatcggtag cctgataggt tgatgatccc
 9721 cacactctag ataacaaagg ctcaagggt tttataactt atccagagtc tcgaagctgc
 9781 tgtgatagaa ctgcaaatgg atccagcaaa ggaagaaaac atactagaac cccccttact
 9841 gtgcctccaa gatctcctgc ccctaaagcc agatgcatcc aagcttctaa ttgtggcacc
 9901 atggctcaga agctctggag gacaacagca ggcagcatcc tcactgtccc tccaaatgtg
 9961 ctaccatgct actcagatca cagacactgc atggtacatc catgactgct aatggcacta
10021 gcatgtcaca tcctccagga gactcatggt tgggtcttcc ctctgaacca actctttcag
10081 gaactgggct atctggagtt gacctctcct aaaaggtcta tgaaaagtg agagtccagg
10141 tgaacttttc atgaccacct gaactgaaga tggcatctcc ctgtgagact ttcactgagg
10201 tgaactgtgt cagcattctt atctttacta gattcataca gacctttatt ctttatccaa
10261 tgacctccaa tatctttgta gttatgcttt ggaagaaatg ctgtggaact tatagatgtg
10321 tcgatgggat aagaaagggt gctagaacca ccttttctgt agactctgaa tgaagccaga
10381 cccaagtcta tcctgctctg aattgtgggc atctcaatgc ttagtctagg ggaagggtta
10441 tgtgggcaaa gatataccca tagacagcag gcaccagctc tgactggtca gactccaggc
10501 tctatgtttt ccaggtggca ctacctactc atgttcagag aaaggcattg catattatcc
10561 ttccaggagg agggaggaaa gactcacagt ctaggaggtt cctgggggc cacagtacct
10621 gggctcgtca gtgagtgttc tgaggtccca gggctggtat gaaagtttca gactgtaaac
10681 acatactgag aaagcaggct agagaggggg catgcagcac atgtgagcaa atgtacataa
```

Figure 3 (continued)

```
10741 caacagatat attcttcagc catgaattgt aattctcaaa agcacggagc tatgcatttc
10801 ctgtttccag ttcttacctt aagtaagtgt tgggataggt tggttggttg gtgggctgct
10861 tggttggctg gttgacaggc tggttggttg gttggttgat tggttcgttg gttggttggc
10921 tagttggttg gttggttgac tggctggctg gctagttggt tggctggttg attttttaaag
10981 gtccatgaag agtggatttg cctttactgt tgattggcaa atgcagcaaa cccaacctgc
11041 agcaggacaa tgccagtggc tatttgaggc taatcagaaa taacatttct gtgcacctt
11101 cttacctgct cttaagtaat gactgttggt caggtggggt gaactgaggc attgcagcca
11161 atcctgcttt gtagtctgag acccagtgac tccaaggccc atcaacttac acttgagcaa
11221 agtacaccac cattttacat agtggataat acttatattc tcctacctgg attattctaa
11281 gaaacaaagc ctttacatta ctctttagct ttgtcacttt gtgccccac tgtatgcttg
11341 agttttttgg agaacaatac tttccaagac accacataga tgcagtggta actgcatctg
11401 agtgacatag ggttacctga cttcaggctc accattgtga tcactagggt gccctatat
11461 aattaatgga tacatagtat atccatcata gatacattga acaaaagaat catttacaac
11521 ctgggcagga tggagccggg aagtgggaga tgccactatt tgtgatcaca cctttgggga
11581 tttgttgtct acttggagtc ttttggggag gaagagacta tgaagaggaa aataagaact
11641 ttgcagagtt ggttctttcc attcatcatg tcgctccctg agagcaaaca tagcctgtca
11701 ggcttagcag caagtacttt tactccctga gccttcttgc agaccaacac acagttttaa
11761 actaggaatt acttctaaaa tgtctgttta cactttcagg ccacggtcac ccatgggtaa
11821 acaaaacctc ctaagggttg ggctctgggg caagctgggc aagaggcatc ctagtgccct
11881 tttgcctgga tcctggtgtt ttggttttt tccgatggag ctccagcact gaaccctcag
11941 cactgatcct ccgggtactg gtgactgtca ctgtcactgt ggttcagttt gctgtctgaa
12001 gtccaggtga taactgctct gtgcacacag tggatcagct gagtcatcgg ggctatgaaa
12061 ttatataaag tcagggctgg tagggactcc acgcagccac cctcaccggc atgctgtgac
12121 cagggaggaa tcacgagcc cccacttagc cctggtgaac agcggagcat gctggaataa
12181 ttctgcccag aaaaagacaa gcaggcacct ctgttccag ggaaaacagg ggcactttgg
12241 gcctccctgc tgcagtcagg caggggctga ctgtcaagtt ccctgggcag actggccagc
12301 tttcccactt ggctcttctt gtagctctcg tggtaacatc atacaaaatt ggtcttctct
12361 cagtggccct cgggcgacag gtgacagtat tccatcttct ccaagaagag gactttatag
12421 taggaacaga gagtctctag aaatgaaaaa caacaacaac aacaacaaca aagtccctgt
12481 ttaaattcag gactcatcct cagtcgtttc taacttgttt tgattcaagt tggtctcacc
12541 acctgacgga tcagggatct gaagacaagg actgaaggag agacaaaaag gcttggtctg
12601 ggggcctggg aatggaatgg tgggatgtac accatacgtt tacagataga cagacagaca
12661 gacagacaga cagacagaca cacacacaca cacacacaca cacacataca cacacaccaa
12721 tatcctctca ctaggatggg caagactttc tctctggcac ccagactctt gggaaacatt
12781 ctcacagaga ctcagagaca ttgagccaca cagatgttac agcccagaga gggagatggg
12841 aaggaagtag aagattgtat tcacaggaca tggcctttat ggagggctgt actgggatct
12901 caatgctccca gtgactttgc ctgatggtgc ctaggttacc tctcttgaga tctgtggcag
12961 tattcgatgt gggtgataag gtctctggtc agagaggggc tggccatggg ggaggttata
13021 tctgtgtggc accagttcct gatgatggat gggtatggag gaagacacag aggtggctct
13081 gggactgaca gtaggtcggg gaagatcagt atggtccctg ccagacagaa gcagtttcca
13141 cttgagattt gttccacatc agggtgtaag tactcccacc ccattatcca catctctgtg
13201 gaagccccac agctggcttt ctgtgtggct tggtatcact ggaaatggca tgtagtggac
13261 cagttcttag cttaaatggg cagctttccg caggaacaaa cctgggccct ctacaaacat
13321 tgatgggcct gaccatctga ttttagcagg tggagtgtgc acatatgttt ttctaacagg
13381 ttttatcctg ccttgagatt ccacgatctg ctctgtcaac ccagactagt cctgactata
13441 tagagtgacc agtgaaacct ctcttcctt gctccaaggg tagttcatgt tcctgccaag
13501 ctgggcgctg tcctaggagg atggaagctg aggagcctgg ccacaatgct gggctgggat
13561 ctctctggta ttggcttgca gagacctggt tcttcttcct tcctcctgag agaaaagaca
13621 aaagattcag acccatgggt gttaacatac agcttggatt ttctgaaaca taatagcaca
13681 tgcctacaga aactggagac acagttacag aggggccagg ataggttgag gactagagaa
13741 gcaacatgtt cagggtgtaa ggtttctctt tgttgagatg acaatatcct aacatcatct
13801 gtgccagcgg ttgcctgtgt ccatgagtac actccaaaca attgcattgt acacttgaaa
13861 cgggcacacg gtagggtgtg tatatcctct ttcaaaaaaa ctatttaaaa tacccagaga
13921 tggcagccat agttgagggt cagctcctga acattgtccc attctcagct ggactcaggg
13981 tcccaggacc tctgacctcc cacttttccct gtgcccatg aaccctcctt ccaggaccac
14041 acatagaatg taccccctct tttcacacat cagggtatag agagtgcctc ctgagaagcc
14101 tcaggaacag aaagcccctc agaagcccca aaccccccaa tgcagccccc accctgcact
14161 gttgaagccg ccatctacag ttcccagggg ttgggcaatt ctcactacct agtaaagtta
14221 tgattgggct cgtctctctt aacattatgc agatgtttat attggatacc attagcattg
14281 ttggcctaaa taagaaaatt attggccaga catgatgcct agaaaacctg aggcaggaag
```

Figure 3 (continued)

```
14341 atggctgtgg ttcatggcca acctggatgc cattgccaac ctccatctca aacatcatta
14401 aaacttttaa aagaaggacc agtgtttctc cgagtattac tattgatttg ggaacagtgg
14461 agcaaggcaa acagaataca ctgagaaggg ctggagagat ggctccgcca tttcagatga
14521 gattcacaac taaaagcata agagaataca caggccatta aagtatgccc tcattagaaa
14581 agatggaaac aaagggagtt gtttaaaggc aaaaacaagg agtatggaac ttagccatga
14641 tatagacctt gcctataata cttgagacca gggattattt cccagtgacc agaatattaa
14701 taatattaaa cacagataaa tttaaaacaa agatgcagta aattagtact ttgaaacagt
14761 aactttggcc actgtcatta ataaggaaag tggatttgga gtgaggcaga agacactggc
14821 caaacagttg ttcttgcaga agtgctattg tgtgggctgt ggcagccact gggcaaacat
14881 agggcatggc aaaggcttct ccagtggctg tcagtcatgt agaacaatcc attgctcaga
14941 aacggtcctt gtgggtctga cacaagaaac tccatttca ttctggctgt attgactttt
15001 ttcacaaggc aaacatgaat aggtccggga gtggatcata cagtagttat tttctggttg
15061 gtgtgacaaa atacacccaa ggagctactt aatggatgga gactttgctt gatctgttct
15121 tgactagtca atcctggcag ggcaggcgtg gcctctgagg agctgctggt gactggtcac
15181 attgtatcca cagtcagaga gagctgaaca ctgaagctca gatctcttgg ttctttatt
15241 cagcatgggg ctctagtgct tggagaggca ccaaccaaat tcaaagtggc tcttcccacc
15301 gcagatcagc tcctctggag gcactgtcac agttatacct gcaaccttgt ctcctgaggg
15361 gctctaagtt ccatcaggt gacagctgag atgaaccctc acatttggga atgagctggg
15421 gaagagcctt tctgataact tgcatcccta gcaagccagg caccaggcca ggttgtccct
15481 cttgctgatg tgtcctctca tctcccagga gtcatgtggc tggaactcat cctggcttct
15541 gtgctgggct ttgtcatcta ctggtttgtc tcccgggaca aggaggagac cttaccactt
15601 gaagatgggt ggtggggccc agggtcaaag ccatcagcca aagaagatga gagcatccgg
15661 cccttcaagg tggaaacatc agatgaggag atcaaggtga gacacccctt cccaggcagg
15721 gcagaaccaa agggacggtc ctgctgtgtt ccctgggac cagagtgggg acatgactga
15781 ggaaggagct ttggaaatgg aacatcctga ggtttccctg gccactcttc tcctgaggt
15841 catgtgcatt ttgctcctaa aaggacttct ctccttccta tccccatttc tctagctact
15901 tctcctcccc ctcaccaggc ccaggaagct gctggtagaa ccattgtgtg caccatagac
15961 tgaagaaagc tcccatcccc ccacctccct gtctgcccac ttgatgctgg tacagtttaa
16021 gagacagagt gagcaggtgt cccgggctga catggaagtc acagctacag aagggagtgg
16081 cgctcagggc atgtagtagc atggagacca cacggtcagc cttagacaag cccttactgt
16141 gtattgacca ctcctgggcc catcatgtcc ctataacaag tctgcccatt gtcacctgtt
16201 gtggcatctc tcaaaggttg gccctgatgc tgagaatagt acagcagagg gtcccaggtg
16261 ctggagggca cagactgagg attgtaagtc tcagggccct ggcctttcca cacagagctg
16321 gagtcagaaa ggatgggctg gtgggtaggg gatgggagaa ggaagtctcc tgagggagcc
16381 agtcagtcac aagggatcag accttacatg gcccatcctt cctttcaccc tgtgatcctt
16441 gggcagctac tgtgtcaggt gctctgtgga gtgctgggaa gtcagagacc cttccctcac
16501 acagcccagc gtttagcatc cacacatggt aaggtaatga aaacatcaag agatacagtg
16561 acccacacgt cagtggagat taatgtcact ggggcactaa caaaaggtca ccgaagttcc
16621 caggaggaag ggattgagag cagggtctgg actgaagcca agggcgagca gctgaggttc
16681 atgtgcgggg catgctgggc tctagctgct gagggtgaag ctgagctctg aggatcagct
16741 ctggatggag tctaaggttt ccaaacctgt tcggggagg ccaggggaca tgaaaatctc
16801 tgtgaataat gacactgagc ccctccaaga ggcaccaggc acgtccctca gctggaatgc
16861 tgaactttga tctgcatcca gtgtgtttgg agcctgtgcc ctgggcaggc catttgtctg
16921 tgttaggatc gtttgatgct gtacagcaag ggcgggcacg ccatggctca agggcaagta
16981 tagcctgcct gttgttcatt aactgcccct taatagctta tttgtctgta aagggtgtg
17041 gggggaaaat aaatacatta attaatgctc ctgcagggt cacccgtgtc cacggcctct
17101 ctgctcctgc aggggtcacc cgtgtccaca gtctctctgc tcctgcaggg gtcatctata
17161 gccgctcctt tgttgctggg agaaagtgga accttgcat cttctgtaca atcttgctat
17221 ttacaaagtt tgccaattct acaactatag gtggtttggt gatttaagtg agtgttgatc
17281 acacacctaa gaaatgagaa gatgactggg gtcgactaa gcgggaggac acatcatgtg
17341 tggcatgtgc aaagccttcc attctctccc tgaatgtccc ccaccctacc ccagcacaag
17401 agagatagat gaaaggggaa acctgaagcc tgcaggagag accaccttgg ccctctagg
17461 atccagtgac atgcatgggt gccctgtgtg gcttctccat ggtgaccatc tatagcttgg
17521 agggtttcct ctgagttgtg cacacaagcc ctctcctgtc tctgccaccc accctgactt
17581 cttcactgca ggacttgcac cagaggatag ataggttccg ggcatcccca cctttggagg
17641 gcagtcgctt ccactatggc ttcaactcca gctacctgaa gaaagtggtg tccttctgga
17701 ggaatgagtt tgactggagg aagcaggtgg agatcctcaa ccaataccca cactttaaga
17761 ccaagattga aggtgagatt ccagaacacc aggcaggatg ggggaagcag ggatgggtgt
17821 gaactcagga gcagccttcc tgcatatgtc aaccgtactg tgcacctcag ggtcaagtgg
17881 tagatcactg agatgtcatg gttcaccatc ttgccaggat gtaccaatga tgctgagtca
```

Figure 3 (continued)

```
17941 gtaagctgtt agtctgtagc gctaaactaa agagcagagc agtggttgtg caacctgaga
18001 cctgcaaact ccagtcagca gtgtagagag gcccttgagc agcgtctata caggaagcct
18061 ggaggctgga catgacctgc ctaggctcag ccccgataga attgcaggtt agacagttct
18121 ataggggttct tagtggtcca tcctatgata aactgtcctg tccaccatgg ccctcaacct
18181 cacagcccag cccctcacct gctgtcactc agactaacca tgaagacagg aagttaacac
18241 tttaattcca gggagggtga ccccaggatc attttatcta aactcatatt ttccttagta
18301 gaacgcaaat ttttaactac ccacagactc agaatgaagc agagtatgtt taatgctgtt
18361 aattttttta accctcttat ttttcttgtg gtaaaataca tgtaacataa cattctccaa
18421 ccagtggctc agtggcaata ggtgtgacgt tctgtggcat taagaagggt cactgttggg
18481 caggctctag ctctaattta ataagaatta acaatgataa cagtaacctt aaatttctct
18541 attctaagaa ttgcaagggt acccctgtca gtgtgtctcc aacctagacg caagtctgct
18601 gaccttacat gagctaccgg ggagagcccg tgagcatgag agcatggatg tggattcgtt
18661 tctaacttta taatcagatg atgtggcact aaaatttgaa ttaaaaataa cttcacttca
18721 acaaataacc acttaaatta acttgaatat ggcagtaagt ttagcaacag aggagaaccc
18781 tgggagatat gtagtgagaa aatttaggtt ccaaaatagc acaaacatag acttttagtt
18841 ttgttaaaag ggagttatgt actggaagtg tttcttgaaa atgtggacta tattaaagaa
18901 aacctaagat cacaggtcag gcagggtcct gggaaagacc ctgaaaagtg aagtcagatt
18961 aaagcccaga acccagaatc acacagccct ggatgtgtat tatcagtgtc acacgctgtt
19021 gaaaagggac acagtgaagc tgtgtggttg tctgttgtcc tagcccttgg aaggcagagg
19081 caggaggatc acaactgaga gtcgaactag gacctgatta taggtttcaa aaagaaaata
19141 taaattttc agtgtgacac catgagcaaa ccttaaggat attgtattgt cctgggtgtc
19201 gagtgtcact cacaaagagc agactcatga tgccacctat gtgtctgaaa cagagaaaca
19261 tggagaaaga gactcagtgg gctgggggaca tgctaaccat gtgcaggatg gtgtggtggg
19321 gagatgctgc ctgtgtatgg gatgctgtcg tgggagatg ctgactgtgt gcaggatcct
19381 gtggtgggga gatgctgact gtgtgcagga tgctgtcgtg gggagatgct gactgtgtgc
19441 aggatgctgt ggtggggaga tgctgactgt gtgcaggatg ctgtggtggg gagatgctga
19501 ctgtgtgcag gatgctgtgg tggggagatg ctgcctgtgt gcaggatgct gtagtgggga
19561 gatgctgact gtgtgcagga tgctgtagtg gggagatgct gactatgtgc agggtgctgt
19621 ggtggggaga tgctgactgt gtgcaggatg ctgtggtggg gagatgctga ctgtgtgcag
19681 gatgctgtgg tgatggcaga tgactgagct ctagggattg atctgctttt acagccatag
19741 tgacagacaa tgcaggtgag ggctgtggct catatggacc atttgcctcg agtgtgcagg
19801 gccttggatc cagctccagc accacaaact gaatggagga aattttttaat gaataatttt
19861 gagaaggtaa aaggtttagt ttggggatgg agcgaaggct tggcagttaa gagcactttg
19921 taggcttgta gagaaccagg cttcctagca ccaatgtgat ggcccacacc agttccagga
19981 caccagatgc cctcttttga cctctgcaag cgccatgcat tcctgtgaca tacagacata
20041 catgcaacag aacactcata tgcatacaat aaaataaatc ttaaaaagtt tggttttata
20101 attagaaaat ggtaacaaat gcttcagtcc aaacctgtgg aaaacttaca cattttgtat
20161 ctgttatag tagaaaaatt aaatatatat accacaaaaa caaattaaa gtactcggtt
20221 atactttaat cctcctggag gattactttg tacagttttg tcatttatac ttgagaactt
20281 caaacctctg cctacagaat tgcataaagt cttggccctc ggtgctgtag cccatggttt
20341 actatggtgt gaagtcaatg tgcgctctgc agaaaccaca cttgggcttt tcctgggctt
20401 ctgacactca ctttaggcac aactctcact cagccccagt accacagagg aaacaagcta
20461 ctctgtaggg aactggggag ctaagctttc ttgtttgaca aattaggtat gtgaaatgca
20521 cttgtgtgcg tgtgcatgtg cgtgtgtgag tgtgtgtgt tgtgtgagtg tgtgtgtgtg
20581 tgtgtgtgtg ttgctgagca ctgaacatgg ggcctcctgt gtactaggca agtgatctgc
20641 caatctattg aatcattgaa taagtgggta tttaaagcat tttaacttct aacttttca
20701 cgtcaggcag gttcatcaga atgaaagctg cacgtgactg ctgcgtttat gcacacggtc
20761 aatacagtca gcaattccag catggcttcc cctcgatgag aagctgctgg ctgctggtgg
20821 ttgctgaggg aggggaaatc cttttctct ggggaggcag ctgattctag gttggccagg
20881 gccatgcaga cagcactacc tggacttagt gggttagaaa acagacaac aagaacacgg
20941 gaggggagtc ctgaggagta gggtgctacc aagatacata tatgtgtatt ctgtgtatgt
21001 atatattagt gtattataga tactgtgtac tatatatatt atgcacatgt aaaaattatg
21061 cacatgaaga ataagttaaa ctactgcatt tttacaagaa tacagcccca tgtaagtaaa
21121 tatacagtgc ctagagctgt ctgtaaagct gagctatacc acggccatgg caaggacatt
21181 taatttgatg gctatgagct cttctctatg tcagctgagc acgtggatga tagttgctcc
21241 acaggactgt cctgcagtgg gacctccttc cctcagcctg aatgctctgt ccctcaccct
21301 gaccgtctct gtccccaggg ctggacatcc acttcatcca cgtgaaacct ccccagctgc
21361 cctcaggccg cactccaaag cccttgctga tggtgcacgg ctggcctggc tccttctatg
21421 agttctacaa gattatccca ctgctgacag accccaagac ccacggcctg agtgatgagc
21481 acgtgtttga agtcatctgt cctcaattc ctggctatgg cttctcagag gcatccagca
```

Figure 3 (continued)

```
21541 agaaaggtac agggtcctga agggacatcc agactgtcat cacagtgcct gctagggaca
21601 gcaccactct aagtcctatt atgctgtgtg gctcacaggc ccattggtgg cttcaatgtt
21661 ctaaggaaga cataaccagg ctcattgcac tgtgatctgg gtcttcttta gggcaccaaa
21721 gttccgtctg tctggtcccc tttgagctac tgtctcctta gtctggagaa agagaggtct
21781 gttgaatttc atgactcccc gttcagtgct cattgcactg gtacgttgtc atgtgatttt
21841 ggagttcagt gaagcaggct ctggaggcaa ggatgctaac accccacttc aagtccctat
21901 ttgagacgca agcatgttta tctgcaagtg ttcttcagga cacacagtcc tgggtcaggc
21961 tggccctgac tctgcaatgg ggagagggaa aaacagcaag cagctcagag tatttaaaat
22021 gttgcatccc tgggctagag agatggctca gcaattaaga gcactgactg gccaggcagt
22081 ggtggcgcat gcctttaatc ccagcacttt gcaggcagag gcaggcagat ttctgagttc
22141 aaggccagcc tggtctacag agtgagttcc agcaggacag ccagggctac acagagaaac
22201 tttgtctcca aaaaaaaaaa aaaaaaaaaa gcactgactg ctcttccaga agtcatgagt
22261 tcaatcccca acaactacac tgtggctcac agccatctat gatgggatct gatacctct
22321 tctagtgtgt ctgaaaacag tgactctggt gtgtttgaag acagtgatgg tgtacttaga
22381 tacataaaat gaataaataa atctttaaaa aagaagaaa aaaccttgca tcccaaagac
22441 agctgagaag acaaacttat ttccagcaga cgctgctatt gtttagccca acagtggagt
22501 ctcatccacg gggagaaact cctccgccag tctcccccctc tccccgttgc ttgctttctc
22561 agggaggtgc cttactcacc tctgcaggcg aatgtacact tatggtttgg tgaggtttg
22621 ctattttatc tgctgctgct gctgtactca ataaactcat tcgaagccca aagtacagca
22681 accatagacc tttcggccaa ccgtttagaa cagtctctct gctcccttct cactcaggtt
22741 taaattcggt ggccactgcg aggatcttct acaagctgat gtcacggctg ggcttccaga
22801 agttctacat tcaaggcggc gactggggt ctctcatctg caccaacata gcccagatgg
22861 tgcccaagtg agtttgcatg gcgcagcctc accaggctct gtgggtgggt ggaatccaca
22921 caggacgcgg gactgttcac cccaagccct cttcagcagt tctgagact tgggacttcc
22981 ttggccaggt ctcccaggcc cagaggcttg cggacctgag acagaggaaa cagatcttcc
23041 cccattgggt ggaaaaggcc gtgttgaccc ttgggatagc tgtggcagct gtctaagcag
23101 aggaaagaga ctctaataaa tcatgtggga caaggtctag agcagccctg gcaagaacac
23161 tctagaacac tttcttcttc cccagccaca ggttcaaccc agtggatgcc ccagagggaa
23221 ggggctaaag ggggccggct tgtgttcttc tgtcctgctg cctctcctct cctctcctct
23281 cctctcctct cctctcctct cctctcctct cctctcctct cctctcctct cctctccctc
23341 cttctccctc tcctctcctg tccttcccag cagctgagct cacctgtgcc tgttcctctg
23401 cctacagcca cgtgaaaggt ttgcacttga atatgtcttt catttcaaga aacatttatt
23461 ccctgacccc tctcctgggc caacgttttg ggagatttct tggctacaca gagaaggatc
23521 tggagctctt gtacccattc aaggaaaagg ttttctacaa catcatgagg gagagtggct
23581 acttacacat ccaggccacc aagccggaca ctgtgggtaa gcacaccggg gcagtggagc
23641 ccagagggaa tctcactgcc cctgagcgca cagcttacag caagaaaccc ctgacaagga
23701 agcagaaatc tctgttttct ctactgagaa ctgaaccaag gcatcacact gtgtgacaag
23761 tgatctgtca tttaccacag ctagagttcc acatatgaga gacagaggct atgggaaccc
23821 cacaagtttt aggctagcct agtctacaca gcgagtttca agccatcctg ggctacatag
23881 caagacactt tactagagag gggtggttgt aaagaaaaaa gaaagaaac taaaaattgt
23941 agtttataaa gaaaattata aatgctcaaa caatagtttg ttcaaaggta tggagaatac
24001 aaatcatttt gtagtttata caaggctcat taccacccag agtaaccaag cctgatgata
24061 cacggaggcc tggtgcctca gcaaggtctg taacccagct gctctggagg ctgcagcaag
24121 aggatcaaga aagtcaaggc ctgcccatgt gccttagacc ctatttcaga atagacaaac
24181 gtgttgggag gcagctgagt ggaagaatcc ttacttcaaa cctgttaagt ccctaggtcc
24241 aaccccagt ccagaaggaa aaatagcact gaaaaaaatg tgtttcttct tgataggcca
24301 gaatcatttg aactctcctg gttttctatc tttgacagag ctgtgaagaa gctaaaaggc
24361 agagctaggt gggaccaccc tagtacagtg gttctcagcc ttcctaatgc ttcaatcctt
24421 tcaaacagtt cctcatgttg tgactcccaa ccgtaaagtt atttctcttg ttatttcata
24481 gctataattt tgttactgct atgaatcgtc atgtaaatat ctgatatgca ggatatcaga
24541 tatgcaaccc ctgtgaaagg gtcatgggac cctaaaggga tcacaaccca cagtttgaca
24601 attgatgccc tagaagatgc aaggactgtc aggtgtcctc tggatgtccc ctgagtccac
24661 tcagaggaca cctgggagtc agtttgccca ctgtggagcc tcccacaacg cccatggtag
24721 ctccacgccc acagcaagga cacctcctga tcacaatagc actttataaa gtcaggctgt
24781 cttcccgtt gcgatgcaga tgttcgtgct atgactggga atgtaaaaaa tccaaaatac
24841 agcagaaaga agtcagtctc tggctctcct tccagccaca ctccccagaa gagctcacca
24901 gcattgtccc ttatgcatgt tgtaaacgca ggtccacatg tcccagactc agtcaatggc
24961 ctctttggtc agtccccctt gctcccctaa ctaggggtcc tagagcactg ttgcctctac
25021 ttatcctcag ggactgaagt cacacagcga ggactccgtg ttcttgctcc tttggctcac
25081 cgtgacccctt gtgagtgtct gtactgctat ctctgccatg atgtttaaag ctggtcatgg
```

Figure 3 (continued)

```
25141 tacctagggc ctcaggaatg ctatgcatat actgccccct gctggttcaa tgactggaat
25201 tgtattttaa ctagtgggta tattaagatt tatttgtaat taactatcaa ttttatacca
25261 agatacagcc catatcttct gtgaatctca tgagattgta gagaatattg atctcctctt
25321 gctatatgag gctactcagg ccagggtgca cagctagacc tgccacccct ctgtggcacc
25381 cacataccte tetectggag tcacatactc tctggggcca ggcttgaacc cctcccttgc
25441 tcctcccatc caggctgtgc tctgaatgac tctcctgtgg gcctggctgc ctacatctta
25501 gagaagttct ccacctggac caagtcagaa taccgtgaac tggaggatgg aggcctggag
25561 aggtgaggcc ccaccttttc tgtcagaact catccccagg ctctgcctct ctcggcctga
25621 cattctaccc ctgtctccag acaccccata gggaagccag caagcttctt ctctgtttgg
25681 cttgtgcacc tcctactcta tgccctcatt aggaatgggg aggtagacac aagaaagggc
25741 ctgtgacttg tgaagcacca tagttggggg tcagacaaaa tatgcgtgcc aggaagtccc
25801 cacagcagca aatacccttg tggaagaata gctgaagcct gtcacttggg ccctatacat
25861 ccatgagctc tgtggagagc gatgggaggg gacagagctg tgagattgca tgggtgtgag
25921 ggtaactgct gtgtcctctg acacagtgct ctgtcacagg agcttggcct gatgccaagc
25981 tccttttgg cactgtcaca ctgaggggca gagactgcaa gacatcccag tggggtgtcc
26041 actcggagcc tgggtccaca aaggtagcgc ttggataaaa tatggtactg aagagagagt
26101 tccatgtggt ctgcttgatc cttggtagat atcacagaac atgtgagtag cagcatctaa
26161 ggatgctagg aagtcttatt gactacagag aagagacagg aaggacaga gggacagaca
26221 gactaagagg acagagccct ataagtgcct cactcctaca gacccaagca atatacacag
26281 ttacagggtg caggactgag agagaatagg agtggaagtt gggttgggga aggcagctgg
26341 tagaaagggg taacatgaga ccagatagtg cagttaccac agggaagagg cgctaacatg
26401 gccaagaagg cagatggagg taacttacct gcagatcaca attcctgtgg ggcagaaaaa
26461 ccttgaaact ctagccccag acacagtgga cactggtgtc ttctagacta agatgttctc
26521 atggcaagga agcttgggct gtggtagact catggccatc agaacacatg caatgttgaa
26581 acttttggag gagtcagcag ccgggattga ttgggtcacc agggttaaga ggccacgtgg
26641 agctacagct agtcacagtt aagactcaga agactgtagg cctgaaacac tgatgtcagc
26701 gagtgtcatg gaggggatga gagccctctg cagtgggcaa tctaaagcta acacagagg
26761 ctcttctaca gcacagacag ctaccaggga aggctggagt tgttccctgt ggaaggccac
26821 accctgagt gcaggttta agtcattagt cctgccctgg gctcccagca tgtgagaggt
26881 aggcattgtc tgttgtggtg accctgaaga gggcagccct ttattcttga cagccatagc
26941 tttcactgag cctgggcatc ctgtgtgttt tccaggaag ttctccctgg aagatctgct
27001 gactaacatc atgatctact ggacgacagg aaccattgtc tcctcccagc gcttctacaa
27061 ggaaaacttg ggccagggtg tcatggtcca tagacatgag gggtaagcct ggctgagcag
27121 gaggcagggc tggggctagg ggatggttac catctgtcct ttaactcaga gaaggcttga
27181 tggacaggtg agaaagatac cagacatcct gagtatccac ttcttcataa ttgtcaggta
27241 ctttgggatt cacaggccta tgtagagacc ctcaggtgag agcaaagaga tggtccagta
27301 aggtgggcat cagaggttgc ccatttcctg cttgggtgac cctccctggc agacaaggtc
27361 cctaatgaat gaaaatggcg gtctataatg agagggtagt ggaagccctt gccattatgg
27421 ctccatctga cctagccaag tcctccccag gccctgggag tcctctctgg gaacaggaga
27481 acacagcccc tcacctcatc tctcttcccc acaggatgaa ggtcttttgtg cccactggct
27541 attcagcctt cccttctgag atcctgcatg cccagaaaaa gtgggtgaag gtcaagtacc
27601 ccaaactcat ctcctattcc tacatggaac gtgggggcca ctttgctgcc ttcgaagagc
27661 ccaagcttct ggcccaggac atccgcaagt tcgtgtccct ggctgagctg cagtgatgac
27721 gctacacacc aaccatggct ttagcagcag ccctggttcc ttcccagtca tacttatgga
27781 agatgtgccc ttccagagga ataagtttgt tccctgacca cactggggga cccagacttc
27841 aaccccacag agtcctctct taccaccccc atatgcttcg ccccactgca tagctgtgtt
27901 aagctacatg gctttaatga taaatgggtt tatttctaag
```

Figure 3 (continued)

C Nope:
```
   1 tatggcgcgg gcggacacgg gccgcgggct cctggtgctg accttctgcc tgctgtccgc
  61 gcgcggtaag ggcccgggtg gccgcagtcg cgagtgggcg tccccggcgc ccgcgatgct
 121 tgcgcgccgg gggctgtggg gacttgcccc caggggggtgt gtgtccttgc tgtgcacagc
 181 ctggcaccgt gcgtgtcccc ctgcgcgtgg cccttgtgca tgtgaggttt gcatgtgtgt
 241 gtcctgcggg ggtgggggtg tcctgcgggg aacgtgtcc acagcgcgtg cctaaggcgc
 301 cgggtagcat cgccagcgcg cgggtggctg caagcgggac atgattctgc cctgcccgca
 361 agcgtctcgc ggtcgcgagt gtgcctgaga gagcgggcgg ggaggggagtg tacacttaca
 421 cctccatttg tgtcgggtgc gtgtgtaact ggatgggact gagctaatat ttggccttgg
 481 cttttgggga gtgtccttgc tcttgatggg ggcggcggtg agaaaaacca cactcaactt
 541 tgcccaatgg gtgtggcccc tgggccagc tagggaggtt ggggaatgt ggaggtgttg
 601 tggacccaaa cccagggttc ggagtggggc tggggaagg gcaggaaacc agttgctttg
 661 ccgaacgcgt ccaacactcg ctctctggat gggacgcgtg tcactcctgc cccaccccca
 721 agggcggacc agggaagcgt ggacgagatc agcaaggccc cctccagtgc caggtcta
 781 gtgttgggta ggtcaaggg taaggatcac aactgtccac accaaagaaa ggactggggg
 841 cggggggaga cgaagtgtcc aagtgtgtat gccaaagctg ttttaccac ccccggccct
 901 ctcactctca gtgggggtgtg cgttgggg acagcccaaa ggaggttagg tggtagggcc
 961 tggaggggga tgggctgccc gctttgttcg attacttctt gccttcctg ccgagggggg
1021 agttaaggat gtgtccgggg cgagtcgggg agggacttgg cagtgggggt ggggagggggg
1081 atttttctcc agctgctgcg gctttccaga gagactgggc caggccacgt gggagggaga
1141 caggagggga ggcggggggt ggtggaaagg agcctccgct gggccaaccc caggcccatc
1201 tccaggaaaa cagcgggtgg gagagtgctg gaaacagctc ggacccttgc tctccccgca
1261 agacacgccc ctttccctcc gagaccctga accggctgg gagcccatag aagctcggtg
1321 cgtggggctg ggccgcagaa gcgggagggc ccggagttgt caggtgaacg cggcgccagg
1381 gaaatgtcag agaggtgtct tgtctgtctt tgcggagccc aaaggattaa ggaatagttg
1441 cacttcccct cctcctcttc ctcctcctcc tcctccctcc tgttcttccc aaagctccag
1501 gaacgcggga tcctggctgg caaccgcacc cgcgctttat taaatacttc tgaggcttca
1561 ggccgggaca ccgggtagag tgttgggaga ctggactctt cttcccagtg aactgactga
1621 ggagcgggca ttgggattct ccctgtctgc tacctgactg gctactgcaa ctactattct
1681 taccctggtt taacctcctt tgagtgtgta aacctctgca gtctgcagac accctacag
1741 agtggaggtc ttcccttctt ttcacagtat ttgctgagca ctctttatag gttaacatgt
1801 gcctgatgcc cagaacgtgg tgaataaggc cctagaccca gactgtccgt catagggtca
1861 ggacaaggag ccaggactag caaggtactg cagaagagag gctcctcctg gggagacctg
1921 gaaaggttct gaagaaaacg atggagagag gaaaagccag ccctgcagag ggaggagtct
1981 tccagatcaa gcaggggtg ccaacgctgg gaggcgattt aattcacatc attgcatcaa
2041 gctaaatctg gctggagttt agaatatggc ggtgggagtt gggcaggtgg gggaggggtg
2101 ggcctcatat ccagagagga ggcgaaggag gaagtcccag ctcacaaagt gcagtgccag
2161 tctcactgaa gtttctggcc tgagaccctc ctgcccccact gagggaagcg cccctgtcct
2221 ggggaagagg tggccatcca agagagagtg gtggcagcca gtggaatagt agcttgggtg
2281 gctggattct aaagatactg agcaagtgga atcagtaggg tgtgagcata gactgacgac
2341 ttttttgtttg ttatttatt atatgtgttc gtctatgcac catgtatgtg tgcccagtgc
2401 ctgtggaagc cagctgatag tgtcagatcc actggaactg cagttacatg gttgggagcc
2461 accatgtggg tgctggaaac tggacccagg tggtcatgac gcgtagccag tgcttttgac
2521 cactgaggca tccctccagg ccctgtagtg gggtttttaa ggagtgagga aagtcaaacg
2581 taacagtctt cccagcaaag ccaacatgag cagaatgaag ggcagtacca gggataggta
2641 caatggcagt ggttggctag tccccgaca ttgcccttgg gtcaaagatt gggtctgtga
2701 gctcatagga gtgagacctc catctgaggt caatggtagg aaactgagct ctttcactat
2761 aagaaaaagt ggggctcccc ctttccctta gaatttggag ctctgagaac acaggggaact
2821 cttcctcacc cgtgaagccc ctctctacca tccctttctc agccttgata ctcaggggcc
2881 catcttagag atttgccacc agagccaaca ctagaaccctt tttaaaaat gctatatgtt
2941 aatatatgta tgtatgtgta tatatatata tatatataga gagagagaga gagagagaga
3001 gagagaaaga gagagagaga gattgagagc atgtacattg attggtgttt tgcctacatg
3061 tatatcaggg tgaaggtgtc agatttctct ggaactggag ttataagcag ctgcaaacgg
3121 ctatgtgggt gggtttcgaa aattgaactc tggtcctcta aaagagccat ctcttcaact
3181 cttgacccctt cttttaatag tgactctttt tgggggggggg gaggggttga aaacaaggtt
3241 tctctgtgta gtcctggctg tcctggaact cactctgtag accagactgt cctggaactc
3301 aaagacccat ctgcttctgc ctcctgagtg ctgaaagtgt gccaccatca ctcggttttta
```

Figure 3 (continued)

```
3361 atagtgactc tgctgtaatt tacctgtgag cttgtgagta ttttcgtgac ctcattaacc
3421 ctatatttat agataaattt ttttcctaaa gataccttct tcaagctaaa gaatctcatc
3481 atataatgtc agcactcaaa gaaacatagg aagctaggct tcatgatgcc tatctgtaac
3541 cccagtactt gaaagactga ggcaggagga ttgctatgag ttcagtgcca gtctaaacta
3601 tataataacc taactaactc acttcaaaaa aagagaacga aatttgctat gagtccattt
3661 tacagatgag aaacctgagc aactgcctag agttatgcaa ataggaactg atctggagct
3721 agaccggtcg cctgactctt ctttgtaagg cagaccagcc actcttccca ggaatttggt
3781 gcacacatac caagttcctt gtctctgtac ttctgccttc cataagagaa gttagcagct
3841 ttaggtcgga gtcttctctc tggttggccc aaggctatgg aatccttttt cacctacctc
3901 ctacttgctc caaaggctct gaggtacagc aaccagatgc agaacagatg tcactgccag
3961 gcgtgtctgg ggcgcccagg agcccggggg gggggtgggg ggggagaga atctgtggag
4021 aagatcccag cttgatcagg gaaagaaagt gagggttgag taaggggaac cagaaaggaa
4081 gccctgaagc ccagcatgct cccttctggg ccaggccagc tgtagctcct cctgtatcct
4141 ggcaagagct ccagcctgtg gatatggagg gacactgggg acattgggat caaggaggct
4201 aagggccaat gagctttccc ctggagtaca aatcggtatt ctccaacaca cggtaagaaa
4261 cgtattactt tgtggtaacc ttgttacgta gttttaagga cagagcgcta ggctatctga
4321 gacccaggtg ggctctgaag aaagataact gtaagcatgt gaactgtaga gcagagccca
4381 caggctcccc acccttagga tgtgcagact aaggttcaca atgaccttac tcttctgctt
4441 ccatgtgctt tttgtttgcc tgttccaaac aggtccaatg tagcccaggc tagccttgaa
4501 ctcactatat aaccttgacc tttgattctt ctgcctctac cctctaagtg ttgggctcac
4561 aggattcccc gccacacagt ttatgcagtg ctgggaacca tcccagggtt tcacatattc
4621 taaataagca tactaccaac tgagactatc ctgagttccc aatttcagtg ttattcagc
4681 attttattcg gtgtctagta gaagctacat agtatgccat gaaatttctt cctgtattat
4741 tcagatcatt cttagccctg aagagactta ctatattttt acagataaca aagaggaggc
4801 ttggaaaggc ataagggatt ctatgatatt atttgagagg gtctgcatgt ctacacggcc
4861 atttgaggaa tttgtgttgg atatctattc tacacaacat ggtgttttag atgccaaagc
4921 ctaaaggcca actaggataa aatcctaaga gattattaag gacagaccaa aaacaggacc
4981 agggttatag ctcacttggt agagtgcttt gcccagcatg caagtggccc tatggcctag
5041 ccagtcatcc tagtacttgg gacttagaag caagagaatc agaagttcaa ggtcattctc
5101 agctgcacat agagttcagg accagcctgg gttacatggg actttgtctc aaaaaaacag
5161 tctagactgg tcactgcagc aatccagcat ccagtttccc caaggcagga agaggaggga
5221 caagtatcta agtcagactg gttcaaagcc tttctaagaa gtagcaaggg agcccacaag
5281 gcactctcaa gagactttca gtgacttgtt agggataggt aggtgggcaa ggatattagg
5341 gggcccagat ggaagcaagc catgttgtat gtggctttgc gtcaccctag aggacactga
5401 gcctccttct caggattgta gatagaggga cggttgaggc cctccttgtg tccttggcag
5461 ccatctggac tctccttcca gctgttggag ggagggacgt agtgtgtggt aaggaaggtg
5521 gccaagattc tagaagaaat tgacttgtgc ctcttgagaa gaaagagtgg cctatggtgt
5581 caggaaggat cgcccttcct gagaacaagc cataaatctg tgcagagggt gagggaatct
5641 ctgccatttg tggcaagtcc ttggccttgc tcccctcccc cacctacaca tcctgtcctt
5701 cctgaacatt cctttgaaaa tggaaccgaa ctcaggttcc tgataacttc accaaatagc
5761 tccaatgaga ccctgaact ctcagcaaa ttgcctttat gactaggttt tcataggtgt
5821 cataaaatct aatttatcct cttaagtgag caaagggct tctcatagcc catgatggca
5881 caatctgtaa aagaagtaga ggcaggttga tcaagaacaa acagcctgag ctgaatagtg
5941 aggccgtgtc tcaaaaaaac agaaagaaaa aacaaaacaa aacaaaacaa aacaaagaaa
6001 gaaaacacct gtttgaaaac taagattggg gggcaagccc agtggcagaa gcctttaatc
6061 tcagtactca gggcagaagt aggtagactc tctgtgagtt caaggctaga ctttcagatt
6121 gagttctagg atagactggg ctatgtagaa agaccttgtc tcgaaagaa aagaaaagaa
6181 aagaaaagaa aagaaaagaa aggaaaagaa aagaaaagaa aagaaaagaa aagaaaagaa
6241 aaaagaaaag attgagaaat ggctgggaga cccccaaaac agaacttctg catctctgat
6301 ggactctcac gaaaaaaaga aagaggagga gaaggaggaa gaagaagaag agaattgagg
6361 gaagcctctg tcctgtaggg aaaagactgg tgatcagcag gtctcctggt acctgctgcg
6421 tgcttccttc atatcagtct aaggaagaat ggaaataaat gcttgtgcaa agtggaagtc
6481 agccatgcag tgggttgggg gagcaagagg ccttggacaa gaaaggtcta ctctctttca
6541 gatatgacta ctatggactt ggcagtggag agatcatacc atgttaaagt aaacattgct
6601 atttaaacat tgcagagtac aaggaagttt aaaaataaag gtagaggtta gggagacagc
6661 tcagtgatta agagcatgtg ttgttcttgc agaggacccc agtttggttc ccagcatgga
```

Figure 3 (continued)

```
6721  agttcagatc cttcagagga tctgaagcct tcttttgacc tccacaggca tcatgcatgc
6781  atatggtgca catacatata ttcaggcaaa acacataaca ataaatgttt gtggttttgt
6841  tttgttttgt ttttttttta attaaatagc atttcaggct atctgttaat ggaagaattt
6901  agtttggttt tctgtgtgtg tgtgtgtgtg tgtgtgtgtg tgtgtgtgtg caagcacgcg
6961  cacacacaca cacacacaca cactccattt gcatgtattc ctgcatgaca gatgagggca
7021  tcaatcctgt tatagagagt tgtgaaccac catgtgggtg ctgggaattg aactcagccc
7081  ctggtttgat tttcttgaaa caaggtttca tgtagtccag gctggacttg aatccctata
7141  ttgtggagga tgacctagaa ctttgtgagt gtgatgctgg gaattgaact tagggcctca
7201  agcatgccag gcaagcgctc ttaatcactg agcacttgaa cttctggccc tcctgcctcc
7261  acctccttag tgctgctatt ttcttttttcg ggtgtgtact gctaagcact aattatccag
7321  agctagagga tcaaccctag ggcctgctag cctgagctac atccctagcc ccgaagaag
7381  ttcgatggaa atatttgagt ttgaatctcc ttgtttaagg ttggagaaac tgagacagaa
7441  gggtgtgtgg gatgagctaa tccaagatgg tgcaagaaag gactggacct agagtcctgg
7501  cgacggggac caatgatggt agagaggcac aaagttcggt tcacctctag gtgagaggaa
7561  aaattcttag gagacttcca gatggcgttt gaaaatcttc cctggaggaa ggcggagaag
7621  tctcctgaag agcggctggt gtctgggcaa agtttcctgg aaaacctctt tttcaggagc
7681  aactgcaccc ccttttcctca tcccccagtt gcgggttcag cccctgaaag tcagattccc
7741  ccacaccacc gctctctcct gtcgctagct tcctcatcgg tagaatggac cttgaacttc
7801  tgagaagttg ccactgaaat gagtctgcta gggctcatgg cgcagacctg cttctctcag
7861  aggcggatcc ctgttctttc tgcatcttcg tccctgtggc tttcccagat tccgccttgt
7921  tgggctcctc tgaggtggcg aagttagaca tctgctgatc catgaatatt caggaaggga
7981  actggagctc ctggggcccc gctgccagcc accagcccct ctggcggctg tcctgcccgc
8041  cagagcccag gctgctgaca tcccagcag ctgctcgggc cccaactgtt cacattgttt
8101  gttctgcacg gcagggatt tttcaagccc cggacatgct ttagggggtg gggagctgc
8161  cagaggactc gaagattcgt gttctgtggg gcttttctcc cctgaaatcc aagcctccag
8221  ttctgcctct ggaccggagc atttgaagct gctgggctgg gagcccaggc ttgccttcca
8281  caactctgaa tttgaatcat ggaatctggg gctttagaag agaaaggact gaatgctaag
8341  ggcagcaaag agcgtttgtg tagctcctta ccgtatgccc agggtcttac agaatgaggc
8401  tttgggcata gttgtgtagt gagctttcgc ctgacctgca caaaaactgt ggttctgttc
8461  ccagtaccga accaaaaaaa aggtggagtt tctctacttc ttgagtgatg ttcttcaggg
8521  tctggcctga acccctgaca ggctcagtag catcttcatt ttaaatatgt ggaaaccgag
8581  taccagagag gacacctggc tgtcacagct ggcaggcgaa atggcaagac tgggaccttg
8641  gtgtgtgtgt gtgtgtgtgt gtgtgtgtgt gtgtgtgtgt gtgtgtgtgt gtgtgtgccc
8701  atgagaatgt ataggtgttt atgaggaggt cagagatcat cgttcttttt ttaaggtgag
8761  ggcatggatg agatggagtt tcctgaggct accagcaaca cgaaacaccct ggtgtcctgt
8821  atacacctgg ttcactacag ctgaggagga gggagacttt gaggaggagg aagtggcctg
8881  gagctgtctc agcagctaaa acattggagc aaagtgatgg cttattcac tcagagtctg
8941  tctgctggcc ataacggctg cgcaaatgct gtcttaccct gacatcactt gtacagacag
9001  aaaccaccac aaaagcaact tcacagtaat aatataagtt agattgcaat aattataata
9061  aactacattt taataataaa tatattaaaa taagtagagg aaaattattt tagatttatt
9121  tctttttattt gatgcgtatg agtgtttttgc tgtggatatg tgtgtgcagc tgcctgggcc
9181  tcagatccct cagaactgga gctacacatg accgtgaact cctatgcgga tgctaggaac
9241  tgaaccctag tactccgcaa gagtagcaaa tacccttcct tagtggctga gccacttatc
9301  cagtccccat cttaatttca gaaacagggt ctcttactga actcagagat tgactttcag
9361  attggcaaaa ctggctccag ggactctcct gtctccacct tcccagctct gtgattgcag
9421  ctgttagtgt gagaatccaa agtcggatcg gcacagccgt gtggaaaaca ctttccacct
9481  gggccatgtc tccagcccct ggaaccttga ctgggagggg actgccttct tccctagccc
9541  tgtgtatctc tcagggcagc catgagccag aactgtccag cagagctctg ctgaaggagt
9601  ggaagggtgg tgatctggtc aggccctttc tgacccttta tccttcacat ttcttcccag
9661  attccctccc ctcagccagc taggacttta ttattactat tattattatt attattatta
9721  ttattattaa ttttatgtgt atatgtattt tgcctgcatg tatgcctctg tgtaccatgt
9781  gtgtgcctgc tgcctgcaga ggccatcaga gaggatcaga gttccctgga actggagttg
9841  tggatggttg tgagctgatg gggtgctgag cctgagtccc agtcctctga caaacagct
9901  agtactttt ttttttttt tttttgag acagggtttc tctgtgtagc cctggctgtc
9961  ctggagctca ctttgtagac caggctggcc ttgaactcag aaatctgcct gcctctgcct
10021 cctgagtgct gggattaaag gcacgtactc ccggcacagc tagtactctt aacccctgaa
```

Figure 3 (continued)

```
10081 ccatctctcc agttcctggg ctgtcttatt ctgctttgaa tgctgtagga aggaaacatg
10141 ggcacacaga ggggtcgagt gtgttgacca gtgtagcaga cagaggaaca tgtgtatagg
10201 ggaccatagt tggaacactg tgggttgttc gtggcatggt actgtatttg ctctggaaca
10261 gagatctttg tatcagtgga taaactgaga ctcagaagaa gagcccagtc caaggccgta
10321 catcttcccg actgccaacc tttcctgctt tgtccctcca gccttgctgg agaccttggc
10381 ttgggtgact gagttcttat gggacaggga gggagcagga caactgtgac aaagcactcc
10441 aatgggaagc tattgccccg tgacaatgag caggcccgt tgaagcattg attatgataa
10501 gaaatatttt ccctttgtga ttattgccct gagatgggat agtgtatgct ctattctaat
10561 cctccttctc ttcccttcat ggcaggggca gtgttagggt ctatgggcag catacgtgta
10621 cacacacaca cacacacaca cacactcatg ccttacacac atagtacatt tctcagagtt
10681 ttccagctac aacatttttc aagcttgagg tatgagcaac agtggtgggg atgagacatt
10741 ggattcctgg aggactaaaa ccactaagcc accacacagt gccaggcaat gctacaccac
10801 gtacacatca cccagcgacc attcataaca gccctaaaag gacagaactg ctctgtattt
10861 ttaaaaccaa gaaacaactc acaatttata tagaatttac cacgtatata ggttaaaaaa
10921 aaaatttttt ttgagacaga ctttcatgta gtccagactg gcttccaatt tctacatagc
10981 tgaagaatga ggaagaccct gaactattga tcatcctgcc tccttctctg tagtgttggg
11041 attacaggtg tgcactaccc cactcagtta cccactcggt gctaggggcc aaactcaggc
11101 cttaaggcat gctatgcaaa tgctctacca tctgagccat agcccccccc accaccacca
11161 tccactctac cctgtggttt tgaatctact aataaggtta tgttgccttg gccactgtct
11221 aattctagaa cctttccata aaaagaaac gtcatactcc ttagtggtca ttccccattc
11281 ctctctgctc aagactcctg gtaaccatta ctctactttc tgacttatgg acattccaca
11341 gaaatgggt cccaaagtgt gtggtggctg gtggctggtg gctttcactt ggcatgaagt
11401 ttccagggtt tttctatgca ctagcatgcg gaatgtttca tcccttctgc tgactgagta
11461 aaatattagt tacttatcag gcgaagagca aacatttggg tcaagtctac cttctggctg
11521 ttgtaataaa gctgctgtga gttgggtctt tcgtgggcaa agaagttaaa ccatggggag
11581 atgggccttg agaagtaagg ggctgttggc aaagaaaatg gatgcagatg gtcacagggt
11641 ctttccttaa gtgattgaca ctgggtggtg catcagggac caggaggcca cacaccacag
11701 ccctggtgtc tcttccttct cacaggggag ctgccattgc cccaggagac aactgtcaag
11761 ctgagctgtg atgagggacc cctgcaagtg atcctgggcc ctgagcaggc tgtggtgctg
11821 gactgcactt tgggggctac agctgctggg cctccgacca gggtgacatg gagcaaggat
11881 ggagacactg tactagagca tgagaacctg cacctgctac ccaatggctc cctgtggctg
11941 tcctcacccc tagagcaaga agacagcgat gatgaggaag ctcttaggat ctggaaggtc
12001 actgagggca gctattcctg tctggcccac agcccgctag gagtggtggc cagccaggtt
12061 gctgtggtca agcttgccag taagtgcttg catctctggg gtgagggtgg agatttggag
12121 accaaggggg acagaaggga tagggagaag gatctaaagt tagttacctg catcagaacc
12181 gggagcccag cccaggttcc ctgcctcctg tcctgtccca ctcactgggt ccctcttgc
12241 tgttagctac tcttgctgct cggtgttcca tcagccaggt cttcactcca tcaacctcct
12301 ttctcaccct ttgagttcta gtgtatagga ctggcttgtc tgccaggaag aggtcaggag
12361 cccaaaggtt tctcttcctg tttcctaccc acacaccaca gtgtacaagg atataaccat
12421 gacctatcct ggcactggct ccttagggct ctctagaggt accagaaat actgtgatgg
12481 taatgttgga catgggtaca acatgctttg gattacacac tgccagtacc atctgaccag
12541 caatcctttc ttagcccttg gctaccactg tgctctccct cactgtgggt ttgctcagct
12601 gtgtgtccat gactctgcgt tctgtgccac tgtgctgaca gcaatctctc ttctcttctc
12661 ttctcttctc ttctcttctc ttctcttctc ttctcttctc ttctcttctc tttctctctc
12721 tctctctctc tctctctctc tctctctcca ccatgttcat ccccagcact cgaagacttc
12781 tctctgcacc ccgagtccca gattgtggag gagaacggga cagcacgctt tgaatgccac
12841 accaagggcc ttccagcccc catcattact tgggaaaagg accaggtgac cgtgcctgag
12901 gagtcccggt gagtgaccct cagggagtct gccccagtgt gcaggacata gggttctggg
12961 acatgcttag aactgggatt cttacagcca aggtgctcca tttgcctaaa ctcacccaag
13021 agccaaccac tagcccgact cctggcccag tgagaaggtt tcctctctgg aagagaagct
13081 acccaccagg ctgaggtgca tagaactagg ggacagtcta gagctcttcc aagcactgct
13141 ggtccacact tgctttatca agggctctaa gagccagaca gcagctatga tctattcaag
13201 accacatcag gggccacggg cagaagactg gcttctgctc tgctcttttcc aaggttcctc
13261 tggagtttct ccatggactc ctacttctct tcctatctct gctctaccct gtcaggcaca
13321 ggcatctctg accagcaggc tacagggtct attttggtcc attcacttct ctttttataa
13381 agatagtatt ggtggaacaa tcctggggaa ggttctaggt tgaatgccaa gcagaggaca
```

Figure 3 (continued)

```
13441 accaggattt ggcccctgct gtggcctcct gatgcacaca cagcagacca gaacccagag
13501 gctcactgcc tctggggctt ctgggttggc ttcacatctt ggtcctcacc ccatggatcc
13561 ttacacatct ttgggaaatg cgcctccaaa ggtctctccc aggcattctg caaccctctg
13621 ctgcatggaa atgcgatccc caccccgaca cacacttaga aacattggct tgcacatcac
13681 tcccaagtac atccaactcc gtcttgactg ttgggctgcc tcatcattgc tgactttga
13741 cccagtggtg ggagtagaag gtgtagaaaa gtcacagaac acctttgatc aggtaaagtc
13801 aacagatagc atccttgttg acagagtgca gtttggtctc cactcatcct tggcacatcc
13861 agttcagctc ttgtctccct atatctgtga aatgaaatgt gaagggcatt cggctaaatt
13921 gtaattttcc aaatgtgacc tctgtagcat gtttgttttg tgtttgtttt gtcttagata
13981 aggtcttatt gtagctcagg ctagcctcaa actctcagca ttagtcaggg atgatcttga
14041 actcatgatc ttcctctctg cttggtactg aaatatcagt ttatgtggta ttggggatgg
14101 aacccagagc ttcaggcatg ctaagcaagt attcttagca actgagctac atccccagcc
14161 cgaagacata ttttaaaat acatataaac aaaaaggag gaaaaaatta tctcattgcc
14221 caaccactgt tatttagaca ggatggtcaa ttgtttcctg acacagggtc ttgctaggta
14281 gcccaggctg gccttctgcc tcagcttccg cagtcctgga attacaggcc tgtgccaaca
14341 tctctggccc cttttattat tgtggttttg tttttctctc attgttaggt ttctgcattg
14401 ttttgaacag ggtctccctg tgaacaccag gcttgtctag acctcagtgt gtagacgagg
14461 ctgtcctcct caaaacagtg ggaatcagac ttcccttccc cgcatctaat tcaggccaca
14521 gacctcaccc attaggtggg gctgccagct tccaggcccc agaagtgctt gccaccaagt
14581 cctctgaaaa ttgatcctgg cctataaata gaccaggctc acatgtccca gcacattgtg
14641 tcagggaata agaaatgtc taaagcagca actagattat ggccaaggta tgtatttttg
14701 catgtgccca gatatacaga tattctaatg acaaactcag ctcagtggtc acaagagatc
14761 gcattcctta gagttggctg tgagcatttg cagctcaaat acactctgtc aggggaaagg
14821 cacatacttt tgtaacagat gacaaaggct aaacactaag gcagttccct ggtatttatg
14881 atttacccat ctatctgtct gtccgtccga tcatccacca tccatctgtc tgtctgtctg
14941 tgtctgtcta tcaatttcaa ggcagggtct gatgtggcct aggctgactt tgaattccta
15001 actctccatc cattcgtcca cccaccatcc accatccacc atccatccat ccatccatct
15061 gtctatctgt ctatctattt aaaggcagaa aggtagggtc ccatgtggcc taggctggct
15121 ttcagcgcct agttctcttg cttctacctc ctaagtgcta caattgcagg caagtgctac
15181 cacaccatga ggtgttgagc ttaggaccca gcacgtccag agttttgtgt atgctagaca
15241 atccactctc ccacctgaac tccaccctag cctcacttac attcatctct agtaatagga
15301 gatacctttt ttttccatgg gagccagcca tgaatgaaac taaaaaaaga atttatatta
15361 aaatgccaaa atgcagccgg gcgtggtggc acacaccttt aatcccagca cttgggaggc
15421 agaggcaggc ggatttctga gttcagggcc agcctggtct acagagtgag ttctaggaca
15481 gcgagggcta cacagagaaa ccctgtctca aaaaccaaa aaaaaaaaa gaaaaaaaga
15541 aaaaaaagc caaaatgcac attatagaat gaaagggaa gcccctcctg actgaacgca
15601 ggccttacca ttttgagtat tccaccatcc tcatcctcac tccagaccag cctaactcaa
15661 aaacaaaaag gttttcattt tgtaaaattc aacaataag agtgctcaac aatcccctc
15721 acaagggaa ccccaagcac tacaaaagct ttgccaacca tgtgcctcaa cctgtcattt
15781 atctgtttcc ccaaaccaga attgcttcct ttttgtttgt tttaaatatt tttgtgccca
15841 tacatgtttt tttttttcatt tattttatgt atatgagtac actgcaagct gtcttcagac
15901 acaccagaag agggccatta cagatggttg tgagccacca cgtggttgct gggacttgaa
15961 ctcaggacct ctggaagagc agtcagtgct cttaactgct gagccatctc accagcccca
16021 gaattgtttc ttaagcacta ttttgtaact tctcccctac tagccaatac atttcagtca
16081 tcttcagaa gccagagttt ctaaaccac attgtaacaa aaccagaaca ggtttagaca
16141 gccctgggga ggcagggcag caccttgcct ctggctgcag ctacagctct gtcccgagg
16201 aaaggagcag gcagatccat tcctgcacac aaagtgaagg aaatgctatt gctcaaggaa
16261 caggtttgct cttagcactt ggtgctccct ttcctggca ccaagattcg aaagtggagg
16321 taatcccta ggggaactgg ctggatggag gatggagggg aagaaaaagc cacagattgc
16381 agcatgtgaa gtagagtcgg ccgtgagggg tggtctttct catctgattt ctcatggcag
16441 tagattgggt actgcccag atgtctccct acatgtttct cctgcttccc cgccccatc
16501 tctctactgt agcacatctg tgagtgcatc tggagctgag gtgagaggtt gggtgtggga
16561 caaaggctca cctgggcaga tgagggaagg actggtccca ccatattccc aagaatgtct
16621 cccaatacc ttcttcagtc ccttggccat ctcaccgctc ccatacttag gtttccttag
16681 cccctgcttt tccaggaaca aagagcttc cccagcaccc aatgccctgt cgccctatgg
16741 ttccacccag tctgtacact taagattctc actacctgga gctgaccccc gtagaaggcc
```

Figure 3 (continued)

```
16801 tcatcacctc ctgactggtt gaacatactc agtgcccacc atccccaac ctccctgccc
16861 caagtttctc aagcaaggtc tcctggcttt ctcaaccttc tctcctgcag gtctggtaag
16921 aaggccccgt cttcctggtc ttctaaattg ctttgtggat tgctgggtag aaactattgg
16981 aaaccacacc catccctccc acagccacac ctagctatga gcagggggct gaacttggcc
17041 tctaggacca gaagacctgg cctcaagatg tcttgtagca tagtgtcaca tcatctacaa
17101 tggcctccaa cgcactgtgt ggcacaggat gaccttcagc ttctgattct cctgcctcca
17161 cctccctaac gctgtcatta caggcgtgga gcgttactga ttcacacagt gctgaagatg
17221 gaagtggggt ctggtgcaag ctagacaagc cttctactca tggaaccata tcccagccc
17281 ctggttttgg gctgtaactg ctccagcatg aagacctgg gtgaatgcac taccctgagc
17341 ttcaattttg ttaccataaa atggaggttg tgattctcct gcctcttggg attcctttga
17401 gggtcagagg agatgaggga ataagggaat ttttgttagg aagagggaaa ggaaatgcag
17461 gtaagaggtt aataaaggtg gagcaagcag agatgacg gcttggcagt tgtaaatgcg
17521 agctactcct ctggagttag ctcccagcac cacatcaggc cgctcgccac tgccagtaac
17581 tgcagctcca tctgcaacgc cagcccttc ctcaacttgg caggcacctg cgctaaggca
17641 cacacacaca aacgctgttt ctgttgttgg ttttaatct tccagggtg aaaaaaaaag
17701 gtttaaaaca tccaaaatct tttttgttt gtttgcttgt ttgggttttt tcgagacag
17761 ggtttctctg tgtagtcttg gctgtcctgg aactcactct gtagaccagg ctggcctcga
17821 actcagaaat ctgcctgcct ctgcctccca agtgctggga tcaaaggcgt gcaccaccac
17881 gcctggctaa aacattcaaa ttcttaaaat ggtatatgtg tgtaataaaa agttaggctt
17941 cgggctggtg agatggctca atgggtaaga gcactgactg ctcttctgaa ggtccagagt
18001 tcaaatccta gcaaccacat ggtaggtcac aaccacctgt aatgagatct gatgccctct
18061 tctggtgtgt ctgaagtcgg ctacattgta cttacatata ataaataaa aatctttaa
18121 aaaaaaaaaa agttaggctt ctcacacctc cagcttccag gctaccaggc ccctcctca
18181 gaaacaactt ccttttctgg ggacattcag tacatataca atctagtaag aatttggctc
18241 tgagtgtgtt atcctgcggc accaaagcac acagtgcgga gggcgcctgg acctgccgcg
18301 ttccattgca ggaggtgccc acctgtga ggccaggata cacccaacag tttccagcct
18361 ctgcacaggg ctgcagtaaa cactgacatg caggtgctgt gtgtgtctga ctgactgtga
18421 tagagtccca gaagtcccag ggctagatga acagctcctt gctgttggat catgctacca
18481 gcttgtccag aaaagagcat gtcctgggtg atgcctgctg gacagatgtg ccttctgtga
18541 tttccttacc cacccgcctg agctgttagt aaaccatttg gtctttgcca gtctgttagg
18601 tgagggttgg catttctgtc cctcagggcc accctctct atcgccttcc cacacctcac
18661 aggctccctc tgctccttcc caaggctcat cactcttccc aatggcgtcc tccagatcct
18721 agatgtccag gacagtgatg caggctccta ccgctgcgtg gccaccaatt cagcccgcca
18781 acgattcagc caggaggcct cgctcactgt ggccctcaga ggtaagggga tttctgggga
18841 cagctatact gggaatgaaa gtgactagac ccgggtcttt ggaaagctga ttgagtagta
18901 attctacatg ggatagacct agggttggg actccaactg gcagggggtg ggggtggggg
18961 tggggttcgt tccttatggg gtgtctgtgt ttcctacggt tgcacaagaa ctggtgaaca
19021 ggcaaggtat ccaaatgccc tgcagcctct ggtcccttct gcccttccag gtgccttaaa
19081 ggctttgggc tagaggttca cccaatctcc ttatgtatgc caaactggct cctcacctgt
19141 actctggtcc ttttctgcct ttctttttcc cattttttt aaacatttat tttgtgtgtt
19201 catacacaag tcccatagca ctcatgaaca gagaaggat tgtggaagtc ggttgtcttc
19261 ttccacttag tgggttcctg ggatccgtca gacttggcag caagcatctg tagctagaag
19321 tctcttttct gcctctcttt gaaaagcccc tgccaggatt aggtagtaac aagggcactg
19381 gtttgggggg tcacgaagac ctgttttgaa tcctgactct cctcaccatc tgtgtgaccc
19441 tgagatggga atggaaagtg cttggcattc agcagctgct ccacagatct cactgcaagc
19501 ctcccccaag gttgctcact tgtctcatcc ctcctcttca ctggttccat cctctagtcc
19561 ctaggctgag gctccagcc atccttgcgc gctctccagc actaggtcta tgcttccccc
19621 tgctggacaa atcaggtgtt caatgttgtg ccacaaggag agagagttgg acacagaaac
19681 acatcgtgaa gcttctttgc taaaaacaac agcccacctt tttttttggg gggggtgtt
19741 ttttgagac agggtttctc tgtatagccc tggctgtcct ggaactcact tgtagacca
19801 ggctggcctc gaactcagaa atccgcctgc ttctacctcc tgagtgctgg gattaaagtt
19861 gtgcgccacc aggcccggct aacagcccca ccttttgctt gtagaactct gaggtactt
19921 ggaaaggcat ctgcctgact cacacaacaa cttatagaca gtcttagaac tagagctggg
19981 tgctgagtct aaggcagatg ccatgggagc tggatttggg cggggaaata tgggggaggt
20041 atggtctacc cagtaacttg tggggtttca cttgtgtcgg agagcattct tctggctcca
20101 agagaaagaa ctccaaggcc tacgccagct ctgcttgaca gttgctttcc ccttctgaca
```

Figure 3 (continued)

```
20161 gaaagaacca tgacgcccca ggcccctgc tttgggcatt cagaagcagt aattggcaag
20221 ctaaccctgt cctatcttca ctacagggtc tttggaggct accaggggc aggatgtggt
20281 cattgtggca gccccagaga acaccacggt agtgtctgga cagagtgtag tgatggagtg
20341 cgtggcctct gctgacccca ccccttttgt gtcctgggtc cgacagggtg agtgctgagg
20401 aaagaggagg aggagactgg ggaagtgggc aagatggtac agtatttcac aggctccaag
20461 tcaggagctt ctgcctaaag atagaaggag agaattgact ccttagagtt gtcctttgac
20521 ttccatagcc catgcaagca agctcacatg tacacacatt catgcagtaa taaagtctaa
20581 agaaggttgt attaaagccc agtggtggtg gcacacatcc ttaatcccag cactggggag
20641 gcagaggcag gcggggctct gagtttgagg ccagcctggt ctacagagca agttcagggt
20701 aaccagggct actcagagga aaccctactt tggaaaattc tggggtggg aggagagaga
20761 gacacagaga gacagagaga gcgagggaca gagagacaga gacaggcaga cacacacaca
20821 cacacacaca cacacacaca cacacacaga gagagagaga gagagagaga gagagagaga
20881 gagagagaga gagagattgt attaaatatc tgctccgccc accagagacc atttagccat
20941 cgtttaccca cctcccttct gcttttccac ctagggatca gagtaagaag gaactgggat
21001 tcaaaccagc ggctgtgatg cagctttgca gggatgtagt gggaacctcg tagttggaga
21061 gggtgtagag ggacagttcc agcgtccccc tccagcctgc tccttctctg tcaccagatg
21121 gaaagcctat ctccacggat gtcatcgttc tgggccggac caatctactc atcgccagcg
21181 cgcagcctcg gcactctgga gtctatgtct gccgagccaa caagccccgc acgcgtgatt
21241 tcgccactgc ggctgctgag ctccgagtgc ttggtaagga agggctggtg ctggggacg
21301 ttaaggatgg gtgtgtgtta gagggagaag gggcggtcct agaagactaa atgtgagggg
21361 gaccacatgg gaggagtctg aattttctga ttggtggtga ttgttggagg actggattcc
21421 gtagctgggg gggggggggg agggaatggg gcgatttgag acgggggtg gggggcgga
21481 tttaaagcct ggtttgggtc atgaggagtg agagtgcagg cgagcaggag tggggtgagg
21541 ttatggaagg agatagtgga atggtctagg ggggtgtgtg aagcccagaa tctgtacgtg
21601 gtagcactca gaaaactgtg gcaggagcgt gagttcgata ccagccctag ctacagagtt
21661 gagaccagct acagagtgaa aagtctatct caaaacaaa attattaaac aatgacaatg
21721 tcttaggcta ttaagtccct atgagtgtgt gcaggccatg gtgagtgtat tgcggtcaca
21781 gactgagttg agacaaggtt tcttgttcac ttcatactcc aggctagctg gcccggggaa
21841 ttctggggaa tctcctgtct ctgtctccta ggaatgctgg gattaatcag ttggggtgat
21901 gctgaggcgg gcagatcaga aattcaaggc caacctgggc tataaaagag cttttctcaat
21961 acaacagaaa actgggggac caggcttgct gaaagctgga gtaactgctg gtataagaa
22021 gccacgggga ggagaaagtg aagttacagc ctagagctca aaagctggaa atctgctggg
22081 cttgggagaa aggaggacta gcccaggagg ggtcgagtct agtggaccag agctgggccc
22141 gtatgactag gggagaggac ctcagggtga ggcttgggcg cggtgttggg acacttggag
22201 aggggtaggc cctcttgtca gagtctccct tctgccctc agctgcccca gccatctcgc
22261 aggcgccga ggcgctctcg cggacgcggg ccagcaccgc gcgcttcgtg tgccgggcgt
22321 ccggggagcc acggcccgcg ctgcactggc tgcacgacgg gatcccgttg cgacccaatg
22381 ggcgcgtcaa ggtgcaggc ggtggcggca gcttggtcat cactcagatc ggccttcagg
22441 acgctggcta ctaccagtgc gtagcagaaa acagcgcggg aactgcctgt gccgctgcgc
22501 ccctggcggt agtggtgcgc gagggctgc ccagcgcccc gactcgggtc acagccacgc
22561 cgctgagcag ctcctctgtg ctggtggcct gggagcggcc tgagttgcac agcgagcaaa
22621 tcattggctt ctctcttcac taccaaaagg caagggtat gtctactctt gaccgcggga
22681 atcccagtta gggcaagtat gggatggata attaaagatg agaggaaggg atggggagca
22741 atactgctgg gaagtgatct agtattagag aatggagtgt acacgcactc cttgacggag
22801 agaatgcttc tctttccagg gttaaaggag ccatcttcca cccccagcta actaactgca
22861 ggacgggctc cttcaattag cacggggagc ttcctggcct attatggaat caatgcaata
22921 agtagactag atggcagagg catttctatc cttcacccta gattgtctgt aacaatttag
22981 ctatacatag accagtagga tccccagaca gtctccagct agtcagacat ggagtgggct
23041 gtgacagtcc ctttgtcccc cccgtgctac cacctcagga gtggacaatg tggagtacca
23101 gtttgcagta aacaatgaca ccacagagct gcaggttcgg gacctggaac ccaacacgga
23161 ttatgagttc tacgtggtgg cctactccca gctggggcc agccgaacct ccagcccagc
23221 cctggtgcat acactggacg atggtaggac ctctgaacct gcagtgacct gggacccaga
23281 gacactccca ctcagggaca gtgtgcccca aggccctctt ccctgccttg tgatgtctgt
23341 tgtgccctat aaagcagtgg gcagaggttc ttcttccag tgtaaaatgg gaaactggg
23401 gctcagaaaa tgaaaatgac ttgccaagct cagcagggca gctgggactt gagcccagct
23461 ctgagccccc ataccatgca gcccttcttc ctaacataca tttactaccc agccattgga
```

Figure 3 (continued)

```
23521 tatgaaagct tctggcccac actgtccact agccttggga tagaaaggat gtctccgcat
23581 cctccagcgt agggctcccc tgagaggctc cctccctccc tccctcagat cctgggcctg
23641 ggcctacttc tgacttgctg tgtgacctgg gcaagtctct gatcactcct gactgtgtct
23701 tatcttccct gttggtggag cggagctcac gccaatgttc ttctgtctca gtccccagcg
23761 cagcacccca gcttaccttg tccagcccca acccctcgga catcagggtg gcatggctgc
23821 ccctgccctc cagcctgagc aatggacagg tgctgaagta caagatagag tacggtttgg
23881 ggaaggaagg tgagtggggc cggggaggta cagagatgtc agtgggaatg gggtcctcc
23941 cctagatgag ggacgttgtc agtggaagtg gagcctaatt gggcatggg atgagaaagc
24001 tctggaaaag agcattggga gactagatag cccaatgtgt aaagtatgtg tgcaagccca
24061 aaggcctgag ttcaatctca gacttcatgt taaaaaaaaa aaagcctggc acagtggtag
24121 gtgcctgctt gtaatcccag agcaggggag gtggagacac ggggacacct tgagctcact
24181 gggctaaacc agtgagttcc aggccagcga gagtccctgt gcagaagaga aggtggacaa
24241 taccagagaa atgacaacag aggttgtcat ctgacctcca catgtatgtg tacacacacc
24301 tgcacatagg tgaacactca cactcatgga cacacacgga cacagggttt cggggcagtt
24361 gaggaaaagg gaaagcaaag agggtcagta gcctgcgcac agataaggag ggtgatcagt
24421 gggaccttgg actgttccct ttctgtgaag ggagcaattt acccagtgga tccttggaac
24481 ccttctaggt ttttgtgttt gtttattttt taagatgtat ttatttattt tatgtatatg
24541 agttctctat ctgcacgccc acctgcatgc cagaagaggg aatcagatcc cagtacagat
24601 ggttgtgagc cacagtgtgg ttgctgggaa ttgaactcag gacctctgga agagcagtca
24661 gtgctcctaa caattgagcc atctctccag cccagaaac cttctggttt acacaccaga
24721 gaagatgtgg gaggctgcag gagtgcacat gagacatggg ctgctcctac tggggagatg
24781 atgctggtct gggggaggtg atgtggttgg gaaaggaatg gagagtgagg aaaagaaaag
24841 tggtgagggt cagggtaaag ctaaagagag aggcaggagg ctgatgggag acagcagtca
24901 gggctcctga caccagggac tgcttagtgt ccttagccag ccatcaagcc tgtgtaagag
24961 gtgtgtactg gctgttgctg ttggttcaca gggaggaaaa gttcatgcct tggtttctcc
25021 atatggaacg gaggccaatg ggcttcagca gcgataggta gaagcccagg gtcaacctgg
25081 aggcatgaaa cctgcctccg tgctgagggg tcagtgccca gaggaccctg gggacctgaa
25141 atggaaaagt caatgtgata aatttaaaga ttgatggtcc cccaatgaag gacacccagc
25201 agcctatcct ttttgtccca gaagatcagg ttttctccac cgaggtgcct ggaaatgaga
25261 cacaacttac gttaaactca cttcagccaa acaaagtgta ccgagtccgg atttcagctg
25321 gcactggcgc tggctatgga gtcccttctc agtggatgca gcacaggaca cctggtgtgc
25381 acaaccagag ccatgtatg gacctacacg ggcagactgg acagcgggga caggtgctct
25441 gtggccttag atattgcccc tgttattgcc tgttattgcc accccccccc cccacaaac
25501 acacacttga tgcacccgga aggcctggt gtaggagtga agggctgggc tcaaatatct
25561 ccttgttcac tctgtgactt tgacaagcca ctcgcatctc cagagcttcg gtactaccaa
25621 ggatgatagc aggactagtc attgtaatta tacacagagt ggtcggcata gaacaggagc
25681 tccttgggtt gagaccacgg ctcacttgac agagtgcttg cctagcatgt acaaagcact
25741 aaattcaatc cccaggacca cataaaccca gcatacctct gatcctggca gttcaaggtc
25801 tgcctcacct acctagtgag ttggggacca gctaggagg tatgaaactc tgtatcaaag
25861 aaaggaagga acccattaaa agctagctgg ctttgccaag aggcccaaac agtagagtgg
25921 ttaaatggct acaaagtctc caggcaggtg ctagtggagg ctcatgcctt taatcccagc
25981 actcgagagg tggaggcagg cagatttctg aatttgaaga cagcctggtc tacaccaagg
26041 ttacacagag aaaccctgtc tcaaaaaacc agaaaagaaa aaagactaca aagtcagcta
26101 ccatattcag acattagaca agctatagct taaaaaaaaa aaaaaaaaaa aaagctggat
26161 tatggaatta taagaatggg ccgggcgcgg tggcgcacgc atgcctttga tcccagtact
26221 cgggaggcag aggcaggcgg atttctgagt tcgagcctgg tctacaaagt gagttccagg
26281 acagccaggg ctacacagaa aaccctgtc tcgaaaaaag aaaagaaaaa agaaaaaaaa
26341 atgaatgaag taaaaatata caaaggctgc caaggtcgcc cagctaataa aggggcttgc
26401 tccatttttct ggggatctga cttccaatgt ctccccagaa tttatatgat gagtgagtct
26461 acagcttgcg gcctctgacc gccaccagca cgcacataaa ttaaataaat actttaaatt
26521 ttttaaaata catatacaaa atgtttgaaa tggggtctga cacacagcca acctctact
26581 cttgggctcc gagtgttgct cgtcgtgttg atggtcccaa atctccctca tgatctcagc
26641 agccccttga ccatactaac tcttttcaaga gacctgcaga agcccctctg cccctgaccg
26701 cgggcctgcg cagacacgcc ccctgctgtc tcttgtgcgt gcccggcaga cgcgcctgcg
26761 cagctaacat gcagagctca aacccaccgg gaagtggcag agtggagcag ttagggaaag
26821 cccaggcaca gctctatgct gtgctccgcc cctgcctgc accggctcac ctccctgacc
```

Figure 3 (continued)

```
26881 acttcactcc tcattctctt cccttgtcc ccatcatctt cctctgcccc ccagttccct
26941 ttgcccctgc agaattgaag gtgagggcaa agatggagtc cctggtggtg tcatggcagc
27001 cgcccctca ccccacccag atctctggat acaaactcta ctggagagag gtgggaacag
27061 aggaggaggc agatggtgac cgcccccag ggggtcgtgg agatcaagct tgggacgtcg
27121 ggcccgtgcg gctgaagaag aaagtgaagc agtatgaact gacccagtta ggtgagtagg
27181 cttggcttg ggagggtcat gggcaagcta agcacacgga gagtgacact catggccttt
27241 ccccagtccc tggcaggctg tacgaggtga agctcgtagc tttcaacaaa cacgaggacg
27301 gctacgctgc tgtgtggaag ggcaagacgg agaaggcgcc cacgccaggt gagggggagg
27361 caggcggggg tcttggagcc ttctttcct ttttcttat cagccagcaa gccgtgtgca
27421 tgccacagcc acccggccca ccctcctggg cagaaatcct cctgctctag acatgcccct
27481 cattctcaag ctaagcagag cgaacgggag agattggaaa gagaaactcc gtgtccgatg
27541 cgtgattcct ggctcaagct ttaaccttta aacagctttt tagatcgcat ccacgtatac
27601 cacatggtcc gtcagattat cccataattc ttttttttaa agacttactt acttatttta
27661 tgtatatgag tacactgtag ctgtcttcag acacaccaga agagggcacc agatcccatt
27721 acagatggtt gtggcttctg ggaattgaac tccagacctc tagaaagca gtcagtgctc
27781 tcaaccactg agccatctct ccagccccac cccataattc ttaagcaggg gcaagcacaa
27841 cacagtggtt tgtcaccctg acgatccagc ctgacagtca gaagaaacct gggttctaat
27901 tccagcgagt tcagttttt cattgagcaa atatttacc taagtatcta ccacatgaca
27961 gctctgttct ggaaacttag taatgaacaa catgaataag gtatctgctc tcttggagct
28021 tattttatgc ttatctaata aacatttgtc atcaccaaat agtatacact gtcccacagt
28081 cttctacctg ctttgtaagc agcctcctaa ggacactcat gaggggacag tgagatggtt
28141 cagcagggaa ggtgattgct acaagccaca tgacctgagc ttggtttctg cacccccccc
28201 caaattgtcc tctgctcccc cacatgcaca cagcagcaca ctccctccct tcctccaca
28261 caataaatgt gtgactgaga agatgcagga gttaagaatt ttaaatatgt tttaaagatg
28321 tatttatgta tttatatgtg tgagtacact gtcactgttg ctatcttcag acacagcaga
28381 agaggtcact agatcccatt atagatggtt gtgagccacc atgtggttgc tgggaattga
28441 actcagggac tctggaagag cagtcagtgc ttaaccgctg agccctctct tcagccccca
28501 gaatttaaa tatttaaag aagtaaatat aaagaaaaga agaaaatgt caagatgtag
28561 gtattgtcat cagatcctta taagaataga aaatgatggc acagagaggt taaacaactt
28621 ctctaaagcc acatacatag ctaggaagtg gcagcaatgg agcctggctc cagagtcagg
28681 gcatgctttc tctgtcacat tctcatcagc catgggatat gtcacagtca ctctatgtgt
28741 gacctaagca aaaaaaatc acttccattc ttgggagcct cagctgcagt aggaataatg
28801 tcacccaact cacaggatca caagagaggc ccggtgccag ctgtggtatc acacagctgt
28861 aacccctgtg ctaaaggacc agaggcacaa ggatggagaa ttacaggcca gcctaggcta
28921 ctacataatg agattctgcc tcaaaataa gaggggaaa ggccaaatga aacctactga
28981 gaccatgtac gtccacctac tctctgcaca cttgggtttc cccctctaga cctgcctatc
29041 cagagggggc caccgctgcc tcctgcccat gtccacgcag agtcaaacag ctccacttcc
29101 atttggcttc ggtggaagaa gccagacttt accactgtca agattgtcaa ctacactgta
29161 cgcttcggcc cctgggggct caggaatgct tccctggtca cctactatac caggtatcag
29221 tgagggggga gtgtagctgg ggtggtagac tagcgggttc agctgtggtg aggccacacc
29281 caggatctac acagatgtct tttccgtgac tgctgacctg ggggtaata atgagggatg
29341 ggattccccc atccctcagt ggcagaatgt gtggtcagcc tttggtgaga gtggatgcaa
29401 gactagaggc ttccatccgt tggctggcac cctgccggcc catcattcgg aagatagctt
29461 aaggagctgc tgttctgatt gggaagacac cctgtgaaag ccaacagaga gagaaactaa
29521 gctgaggata gacacttcag gagcgattgg tcccccaggt gcagaataac ttagattaat
29581 tcgggaaagc gtcccagagg agagaagggc ttgctttgga gatgagacat ggaataacat
29641 atgtccggcc tttctgtggt ttgcctgtc gtgtgtggga ggggaggttg tgggcccaac
29701 aagcagctcc ctccaggggtg gggcctggct ggaggcaggg gcttctgtct ggggttctgc
29761 ctggcttgag gcctgtctga gggcactagt cctatccctt tcctggaag tctggagaa
29821 gacattctca ttggcggcct gaaaccattt accaagtacg agtttgcggt acagtcccac
29881 ggagtggata tggatgggcc ctttggctcc gtcgtagaac gctccaccct gcctgaccgt
29941 gagtatccac tgcccgctcc ccacctgtgc caccatttgc tgggtctgag aaggaagaa
30001 gaagaggagg ctgtgccctc atccccttag ttagggctgt gtctctgact ctccacccct
30061 tccctgtgc tgcagggcct tcaacacctc cttctgacct gcgcctgagc ccctgacac
30121 catccaccgt tcggttacac tggtgtcccc ccacggagcc caatggtgag attgtggagt
30181 atctaattct ctacagcaac aaccacaccc agcccgaaca ccagtggaca ctgctcacca
```

Figure 3 (continued)

```
30241 cagagggtaa ggacgcccac ccctgcctcc ttgccctttt gttccaaggg tctctgggat
30301 tggaggctga agctactgtc tgggtgcaaa gttggtttgc ccatggtgct ttggcctcct
30361 gccaccctgt ctcctcccac ttcccaccac aggaaacatc ttcagtgcag aggtccatgg
30421 cctagagagt gacactcggt atttcttcaa gatgggagcc cgcacagagg tggggcctgg
30481 gcccttttcc cgcttgcagg atgtgattac tctgcaaaag acattctcag gtaccaggca
30541 ggagggagaa ggcccttggg acaactggag gccccaagac ccctggattg gctcccaagg
30601 ccctgccttc tggaaattac attttcttta ctttggaacc ctaaggtgtg ggggatggag
30661 aagcagtgac agcttgatag agggactgtc atagctttga ggggtctttt attattttat
30721 tctctctgtg tgtgtttggc acagtgcata tgcgaaggtc agaggacatc agagagttgg
30781 ttttgtgggg atcttgcttt gcctggaggg ttgggtgagc tcctgagttc tgtgaagaag
30841 tggtcaatag gctggataga cactcacaag ggctcaatta agatacaaaa tgagatccca
30901 gggctcctta ttgtaaatta ttgaagatgt gaagatgagc cagtgggcca ttagccacac
30961 ataggactga ggagcatgaa gccctgagtc caaatgcaca cacacacaca cacacacaca
31021 cacacacaca cacaccgtaa aacttggctg tggctgctgt aatccttgct gaggatgcag
31081 agacaggata tttctgggc tgagagggac tggggaagtc acgtgatgta gacctctgat
31141 ctccacacta catatacatg cccttagatg aacatataca gacatgacac acacatgtgt
31201 gcacctagag cccaccttgg ttatacatat ataccatg agagcccttg ttgccaggag
31261 gaaaacaact tcactgaaga gctgattcta tagagtccag ttttgtgagg agtggcaggt
31321 tctgtacagc agggaagacc gtggtggact cagtatgagg cccagtaaga tcccgtggct
31381 ctctctattc caatcagaag ggagtgagct tccaaaccag gtgtgaacca ggtgtggtac
31441 tgcacacctt tgatctccgt cctggtttat gagcactgct tccttctgac ctggagtcac
31501 actgttctcc cccgcagact ccttggatgt gcacgccgtc acgggcatca tcgtgggtgt
31561 ctgcctgggc cttctctgcc tcctggcctg catgtgtgct ggcctacgac gaagctccca
31621 caggtgaacc ggggaaccac tgagaccact gagttaccag gaagggctgc agagtggaca
31681 aaggagcgtg tccttccctg ctgccccgga agcccagta tagatagggc tatggagctg
31741 gagtgaagtt cagtgctaca tgtgccccca tgtgaggccc tgggcgtcat cctcagtagc
31801 acaaaacaag tggataattt atttattagg attctgagat gaaggattga ggtgttgttc
31861 tcatgagaat gtagaataaa cttagggaag ccccaggact ccccacctca gtaacagcgg
31921 gctgagctac ctgtgggctt ccctcatggc ttaaatggaa atggcccatc tcgccataca
31981 aggaagcgtg ccatctgagg ggtcaggccg agtggacttg tattccttcc ttctgttttg
32041 attgcaccac accaggaaac caaatccact cttgtccgac ccataacttt gttctgttga
32101 tcacagggaa gccctgcccg gattgtcctc ctcaggcacc ccaggaaacc cagcgctcta
32161 cacaagagct cgacttgggc ccccagtgt ccctgctgcc catgagttgg agtccctcgt
32221 gcatcctcgt ccccaggatt ggtccccacc accctcagat gtggaagaca aggctgaagt
32281 acacagcctt atgggtggca gtgtttcaga ttgccggggc cactccaaga gaaaggtgag
32341 actggagtct cttcaggtca gggactcaca cgaacccatt cccaaatcaa acaccagggg
32401 gcaccagagc acaacttctg acggtgagat gcgctcgcgc gcacacacac acacacacac
32461 acacacacac acacacacac acacacaggc actgaaccat acagagaaag cctgtccata
32521 ccacctggga ggatcccaga gctgtgtttt cgagagcacc catacttctc ttcacttacc
32581 taatatggag aaaagaggct ggtcacttttt gctgtggcca agtagggctg gccccagaat
32641 aaggtgaaac cccataggcc aggtgttctg ggggcacacc ctgaccaagt ggacagtcag
32701 tcttcccatc tcttcacttt cctctgcaat tagaaagagt ccagcaagct gggagcttt
32761 ggattttgca catcaactgt tgttaggctt atgggtccgc ccttcccatt ctccctacct
32821 cagttctcac ctctgtcccg gggtggggct ttagtgtgga gtttagtgtt atctggagat
32881 aacaggggtc cacaggtctg gaccctgcat gccatactg tcttcttcct tctctgcaga
32941 tctcctgggc tcaggcaggg ggaccaaact gggcaggctc ctgggcaggc tgtgagctgc
33001 cccagggtag tggtccaagg ccggctctga cccgtgctct gctgcctcca gcgggaaccg
33061 ggcagacact gctgctgcaa gccctggtat atgacgccat aaaggttggt tggtgctgtt
33121 tgagagggag ggagaggcag gatggggagg caggagggaa agtccccct ccatgcactt
33181 ccagggacag aagtgtattt gaaagacctt gtagcttcca aggggagtg ggtgacagga
33241 agccagtgtg gagcttcttt acctggtcct aagtgactta cagtagactt acagagtatc
33301 tgaaggtggc cttagccct tagatacggc cagcgcctcc ttgtcttcgt ggaggttctg
33361 ggtctagtac tttctggtag cctgagtgag ggcaaacgtg tgacattctg cgtttctcat
33421 ctctgccaga gcctgagcgt cgtctcttct taggtggaac agtgcttgta tcatctaatg
33481 gggagtcagc ctctcccccc gcccccaat atgttggtca ttttctgaag accattctca
33541 gtggtgctca cctagccttt tgttctccac tctgccagag caacgggaga aagaagccgt
```

Figure 3 (continued)

```
33601 ccccagcctg caggaatcag gtggaagctg aggtcattgt ccactccgac ttcggtgcat
33661 ccaaaggatg tcctgacctc cacctccaag acctggagcc agaggaacca ctgactgcag
33721 agactctgcc ttccacgtct ggagctgtgg atctgtctca aggagcagac tggctgggca
33781 gggagctggg agggtgccaa ccaacaacca gtgggccaga gaggctcacc tgcttgccag
33841 aagcagccag tgcctcctgc tcctgctcag acctccagcc cagcactgct atagaggagg
33901 cccctgggaa aagctgccag cccaaagccc tgtgtcctct aacagtcagc ccaagccttc
33961 ccagggcccc tgtctcctct gctcaggtcc cctgagcaga aggcagatat ggctcaggaa
34021 catgccatgc atggctacac atgtgtgtac tagagatatc cataagtcct tggagcctct
34081 tagggtcctt tggctggggt tgggagaac tttactctcc ctcatattct gcatcacata
34141 caggagggac ttgagacaca gctctgtgta atggacacgt gtgaagtcgt gtgtgtgtgt
34201 gtgtgtgtgt gtgctggttg agctaggaaa cctctcccta tgtagcactc actgtggcct
34261 agttgaccct ccgtggcagg atggtgtaac agtgatcagt gccagctctt tgagctttta
34321 gccttgtcac ctagcctttt attacactct gagagtgtct ccagtgctgt gtctacaaag
34381 acagcgccag ccctcttct gtcagctgtg ctgagcagag tgccagtcaa ctccacgggc
34441 ctatgacacc gcagcctacc acagcatggc tgtcatcccc ctggcctcct aaggtccaga
34501 tgtctgggtg aacccagctc agctcccctc tcctttgagc atctctgtac ctaattttgt
34561 aatctgggaa gtgcctggtt tgggaaatct tctttcgcac cctgtccctc tctgcccctt
34621 ccttcatttg ttctggtgat ctgtctcatg tcatcttgct cgattatcct ggggcccttc
34681 tctttcccat gatgcccctg atttcctcac tgctgttttc atttctgtct gccatgcttg
34741 tctttatgtc gtgtgtttct cgtccctgag ttcaacctat gcacccttc ctaacaacat
34801 gactacctca tgtctgcttc agaccatagt gtgaccctg ggtccccaca gctccctgc
34861 caaccgcctt cctgggcaga tgacccactc caagtagatc tggaaaagac cttgtggctt
34921 gtctggctgc cctcccttg tgttgagat gagaaggttt tctatggaag agatgagtcc
34981 aggctgcaca ggggaacccc caagaagggg tagggagtga aaccaagagg ctgaaaaaaa
35041 atggctgcca cccatctgca cagagagatg ggtgtgtgct tttgacgtgc agtcctggct
35101 gaaactgaag gggtgaggag aggggagcta ctgggctgc catggctcag ttccctgacc
35161 ctggagccct gaacctggct tcagagtagc aaagagtttc ctccaagatg ctgtaaggga
35221 agtctttgca taggaaaagg gcggctggct catttatt tatctttctt tacactgaat
35281 cccaaaatca tcttaccaca aagggccaag cctgactggt atttcctgag tcacaagagc
35341 catgccatct ctctggtttc tcacctcagt catgtcccag aattgtcaga tccagtggca
35401 tctgtgctct tgctgcacat cttttctattt caactggctg gcacatcaag tgttaactct
35461 ggcttctggg ccaagttaga aataaccagt ctattttccc tttattttat tttattttat
35521 tttattttat gtctttcagt ggagttgtag cttctgaaag cgtctgtgtt tattagcctt
35581 gtgtgtcact catgtttgac cccaccaca tttccttctc ctcccctctt cagccagcct
35641 atgataacac taaagattat taatgctggc ttcgtatctc attaaagaca ggattgtcac
35701 ttgaactact tctatagcat tcaaagtggc cacggccaac accaccgtat gtttcttcat
35761 tgctctgaag gtcaagagcc tcattttgtt ttcctggtta gattttttc ctccttgcct
35821 tgaatgaaat aaccgtttta acagtaggct cttagcatca caccacatag tcattcctca
35881 tgttcttgtt taacaagcac tgaggttctg gtttaaatta aatagctgca aatgagacaa
35941 tttataaccc attaggctgg gtggaaaatt gtttctcaaa agcaaataag taataaatct
36001 ggtatctgcc tataactcac agttgataag aaagtagcca gaactcacta gcattatata
36061 tgatttgggt tctgagtaac tggggagtgt tagctttgtg actttgtagc agcaggtctt
36121 attaggaaag tctgttggcc ttttacaggg cattagtccc tttgtcgttt gccatggatg
36181 ccttaagttc tttggagtct catttaagaa tttcttttct cgaagcatga caagtgtatg
36241 caatacttac atgctcactc gtttacctgt gcttagtttg tgctgggtta tttaattgca
36301 ctttccagca tcatgcttcc tccttacaaa tatgatattc tttattgtta cactaaggtg
36361 ttgatcatgt atctgtccct gtaaagaatt aataaactat tttccaga
```

Figure 3 (continued)

D Cdkn1a:

```
   1 cagccgagag gtgtgagccg ccgcggtgtc agagtctagg ggaattggag tcaggcgcag
  61 atccacagcg atatccagac attcagaggt gagagcttcg tggcagggaa caatagttct
 121 tccccgtagc aatgcgctga gcccagtggg tgtccccaga agtgtgtgtg tgtgtgtgtg
 181 tgtgtgtgtg tggtgatgag tggatcacct gtgtgtgtat atgtgtattt gtgcgtgccc
 241 gccagagtca caggtgtgtc cgcggcaggt ggatgacggg tgtgggtctg agcgtccgtg
 301 gtggctgaag gcttcgtttg ttggagtgtg acgagggtca ggctatgtcg cggactcggc
 361 atacagagtc tgaactccag gaccacggat ggcagccact cttccagtcc ttggagaccg
 421 ggtccgagcg atggctggcg gggatcggct accgggagct cgcttctggt tgccaatgtt
 481 tctagggatt ccaggtgcgg ctcgcccaaa gcgtgagaat gaagctcacg gtgccccgag
 541 atgggtcctg ggtggcggtt gtgacaagct tcggcgagtc tatctagagc ttagcgcaga
 601 gcggttctcc gatccatgg gtgccgccgg atccccggtc cttgtgaacc aagtgccctg
 661 tttcgcggta gccaccaccc cactgggctc tgaggtcagc gcgagctgtg tcctccgccc
 721 tcgggatcgt gcctgggcac gtcctagagg acaggcgagg aggtgactca ttgtgacaag
 781 gagacccgg gcactggatt gagaccagaa tcgcgccaca actggggatg ggtcagtggc
 841 agcccagaag ccccttccc tgcccgggta cagcctcgtt cctgccccgt cccctccccc
 901 gcgcggcaca gtgacctatt tggcgggcac agtatgttcc cagggaaccc gggacacggg
 961 gaggtccagg acgcggtgtc cggtccccgc tcggcggcgc gccctcgggg acagggagtc
1021 tgggcgggtc ctgtccaccc tgccagcccg ggaagcgcaa agggtcccac ccaccgcgcc
1081 caccacgacc cggaccagtg accgtggggc gcgagaggag cccgcactgt agagcggccg
1141 gtatcctcgc ggagtgaggc ttacgggtgc cgtacatcag acgccccggg gctgggccc
1201 tcgacccagt ccacacccag tgtaggaagg tgaccaggct gagtgcgccc actagggcac
1261 atccattcca ctcggaacct ccggggacaa gggctacact tgcaccctgg tcgtgcggga
1321 aatactttgg gcttgggttt ggcatttggg ggcgcgctgg cagcttcctc tgtccctac
1381 gtcgcgtttc agagaggaca ctcaggcggt tttttgttgt cctcgccctc atctattttt
1441 attttccagg gatctgactc atcgcgtgct ttgggcgtgg agatcaaggt ggaggggcc
1501 agagctaaga gcactttctt tgctctcgag tgtccgtgcg tgcgtgtgtg cgtgcgtgcg
1561 tatgtgtgtg tgtgtgtgtg tctgtgtacg tgcgtgtgtg tgtgtgtgtg tatgcgtgcg
1621 cgcgcgcgcg ctcagtctgg tttcccaaca taggcgggaa tttaggaagc ctgggctcat
1681 cgtgacgtgt tttgtggccc ggggtccccc tcctttcctc tcctctctcc accccagggt
1741 gacgcgcagc tccggtgccc aagcagtttt ggcgggcggg cagcgccggg caggaaactg
1801 actcaccact ccttgctcgg cctacgcgcc gcctaccgag cgccatttcc tgagtgcaca
1861 gcgccccta ccggcatcag tgaggactgc aaggccggct aggcgcgggt ggcaccacgg
1921 gcttctgcca ccccaccgc ggcttaaagg gaattaaaat atgcctgatg gccagataca
1981 agtgatttta gcagggtgtg ctagcggact attagggagg cgtggcccctt gagagacaag
2041 gtggagatcg tgccctctt gggttcctgg tcttatcttc agctatgaaa aactggggac
2101 tatccagcct tagccgagtc cattggtgtc ttcccttcct tcctctgcc cctgtgagct
2161 accgtctggg aagggcacc aaacttgttt tcggctcag tttgtctggg gaaatgagcc
2221 aatctatatt tctatatcta tatagatctc tctctctgtc tctgtgtgtg tgtgaaagag
2281 agacagagac agagagacaa gcttacaaaa tggcccagc taccagtact atatagacag
2341 gctggcccag tggcctggaa ctcataagga tcacgtgcct ctggtggagt gctgggatta
2401 aagactctcc ccataacatg gagctcagtc tatatttaat aaaaaagctt ttccagctga
2461 ttttaatgga gtcctctggt catgcccctc aaggtgagaa gacgagagaa tgatcaatac
2521 tagaccaaaa gggtctgaat tcaaacccg cttgtgagcc ctgtgccttt ggacacacat
2581 tctgaacctg gattagctct gccgtaaaag aatgtgatat tgccatctat taacgatagc
2641 ttttggtggc ttacaactgc aatcccagca cactagaggc agaggcagga ggatgactga
2701 gttgtactaa aggatgtgaa taggccccaa gctctacctg taggcagagg ccatctgagg
2761 tcctttaggc ctctgaggtc tgcaccttga gaatccttt gcgggcagtg ggaatccttg
2821 ttagaccgt gtttcggttg gttggtgttt agccaggctc tcactatgca caccaggatg
2881 gccttcaact cacagacatt ttgcctctgc ctcccgagtg ctgtgttttg ggaattggct
2941 gttttactta tttatggaag ccacaatgct ggccacgttc cctatgtagt agccaaggta
3001 gaccctgaac ttctttccct acctctgcct ccagcgatta caggtgtgtg ccgccacacc
3061 cagttttata gagagctcct tgcttagcac aaggcccagg ctttaccatc ggggccccag
3121 acgcttcatc tcttctggct tcctaccttg aatcatagtc tgggtacccc cttctctctt
3181 ccagctgtgg gcaaactcac cctgaggtct taaggagctg ggcgtgtgta tgtgtgtggt
3241 agtgtatgtg gtaagagccc aggggtcgtt gcctcaggaa gccactgggg ctcaccttgc
3301 aagctcaaag gccctcctta gaagctgcat cccctagtct tggagtcagg atgggccact
```

Figure 3 (continued)

```
3361 caggtatccc tctttcctgg agaggagcca ggtaaaccaa cacctttaac ttttttttttt
3421 ttttcagtgc ctgtaaaacg ggttccttgg gcacaggcta taggcacgtc tggggctggg
3481 aggtgtctag actccagatt acctgatctg cctggcagga tgtggctcag cctgggagag
3541 agccttaacc ccgctccacc ccttcagact ctcctctccc ccaggctact gcctccccccc
3601 aggctgctgc ctcccccccag gctactgcct ccccccaggc tgctgcctcc tcccaggcta
3661 ctgcctcctc ccaggctgct gcctcctccc aggctactgc ctgccagcgt cctttggaaa
3721 ggcctccagc ctggagcacc tgtcagtgac agtgggaggg agggaggggc agggaggagg
3781 ctctgtcaga attaggggca gagaggcacg ctcatggctt ctgtttctca ggattgccta
3841 tgttaactta gttcattctc aaatagggag cccagagatg ttagggtact tattcggggt
3901 cacccagcaa agccttgatt ctgatctggg cagtctagct ccggcattct cgcgcctctc
3961 tcccagccac catgccagcc tcgcgagtat gctgccacaa ccacactggc taagaaacag
4021 aggctggaga catggagtca cttttttaaaa ctggtgccaa gtagcagcac taatgctata
4081 cagtttatgt gtagtatccc aaagtccagg gcactttttt tttttttttt tttttttttt
4141 tttttttttt ttgagacagg atgtctctgt atagccctgg ctgtcctgga actcactttg
4201 tagaccaggc tggcctcgaa ctcagaaatc cgcctgcctc tgcctcccga gtgctgggat
4261 taaaggcgtg tgccaccacg cccggctgtc cagggtactt tgattggcc tgatggagtt
4321 aatcaccaag acagcagggt agggagacca ctggacctag caattcacac gtatttggga
4381 tgttcacacc catgaagaac acgttagcac attgattttg gctaatagaa ttcctggggt
4441 aaacaggacg gtgactccta cttctgtgga catcacccgt gaccttgggg tgcagggctg
4501 gctgaactca acacccacct tagtctcatg gtgtggtgga aaagcacctg caaggaccag
4561 agggagcctg aagactgtga tggggtagtt tccatagtga cccgggtcct tcttgtgttt
4621 cagccacagg caccatgtcc aatcctggtg atgtccgacc tgttccgcac aggagcaaag
4681 tgtgccgttg tctcttcggt cccgtggaca gtgagcagtt gcgccgtgat tgcgatgcgc
4741 tcatggcggg ctgtctccag gaggcccgag aacggtggaa ctttgactt c gtcacggaga
4801 cgccgctgga gggcaacttc gtctgggagc gcgttcggag cctagggctg cccaaggtct
4861 acctgagccc tgggtcccgc agccgtgacg acctgggagg ggacaagagg cccagtactt
4921 cctctgccct gctgcagggg ccagctccgg aggaccacgt ggccttgtcg ctgtcttgca
4981 ctctggtgtc tgagcggcct gaagattccc cgggtgggcc cggaacatct cagggccgaa
5041 aacggaggca gaccagcctg acaggtaagg acaggagcag agaaggagaa agatcctgca
5101 agaggcctgg agaggagagg ccaccatttg aggatggcct ttacagagaa cattccagcc
5161 cttccccacc accaagccat tccataggcg tgggacctcg tggggctcag aggaacagtt
5221 gatgttcata tgatccaggc attttttctct gcagtgaccg aaatgcccag gatagtgtgg
5281 tgattggcag tagagctcta agaagggagc cgggctgaag agatggctca gcagatgagg
5341 gcacttactc ttgctgaggg cctgattccc agcaccggaa atgacaactt cctataacta
5401 actctgggcg ttggggatc taccctctct agagccctgt ccctctgacc aggaggtgtt
5461 gtgccctgtg gctgtggctt ttccccacga tgagccacat gtcccttaga ctctggggaa
5521 tgatgtcctt ccccttggca tctggcctga catctgttct ctctccacag atttctatca
5581 ctccaagcgc agattggtct tctgcaagag aaaaccctga agtgccacg ggagccccgc
5641 cctcttctgc tgtgggtcag gaggcctctt ccccatcttc ggccttagcc ctcactctgt
5701 gtgtcttaat tattatttgt gttttaattt aaacgtctcc tgtatatacg ctgcctgccc
5761 tctcccagtc tccaaactta aagttattta aaaaagaac aaaacaaaac aaaaaaaacc
5821 aaaacaaaac aaacctaaat tagtaggacg gtagggccct tagtgtgggg gatttctatt
5881 atgtagatta ttattattta agcccctccc aacccaagct ctgtgtttcc tataccggag
5941 gaacagtcct actgatatca acccatctgc atccgtttca cccaaccccc ctcccccat
6001 tccctgcctg gttccttgcc acttcttacc tgggggtgat cctcagacct gaatagcact
6061 ttggaaaaat gagtaggact ttggggtctc cttgtcacct ctaaggccag ctaggatgac
6121 agtgaagcag tcacagccta gaacagggat ggcagttagg actcaacagt aatatcccga
6181 ctcttgacat tgctcagacc tgtgaagaca ggaatggtcc ccactctgga tcccctttgc
6241 cactcctggg gagcccacct ctcctgtggg tctctgccag ctgccctct attttggagg
6301 gttaatctgg tgatctgctg ctcttttccc ccacccccata cttccccttc tgcaggtcgg
6361 caggaggcat atctaggcac ttgcccccaca gctcagtgga ctggaaggga atgtatatgc
6421 aggtacact aagtgggatt ccctggtctt accttaggca gctccagtgg caacccctg
6481 cattgtgggt ctagggtggg tccttggtgg tgagacaggc ctcccagagc attctatggt
6541 gtgtggtggt ggggtgggc ttatctggga tggggacccc agttggggtt ctcagtgact
6601 tctcccattt cttagtagca gttgtacaag gagccaggcc aagatggtgt cttggggggct
6661 aagggagctc acaggacact gagcaatggc tgatcctttc tcagtgttga ataccgtggg
```

Figure 3 (continued)

```
6721 tgtcaaagca cttagtgggt ctgactccag ccccaaacat ccctgtttct gtaacatcct
6781 ggtctggact gtctacccTT agcccgcacc ccaagaacat gtattgtggc tccctccctg
6841 tctccactca gattgtaagc gtctcacgag aagggacagc accctgcatt gtcccgagtc
6901 ctcacacccg accccaaagc tggtgctcaa taaatacttc tcgatgat
```

E Perp:
```
   1 gggggccgcg tcttcggggg agccgcctct tcctttagtc gcggtgtcag cgctcgcagg
  61 accactcttg gccgctgctc ctgcccggcg ttcctccgct ccgcgcccgc cgccaccgac
 121 gacatgctgc gctgcggcct ggcctgcgag cgctgcaggt ggatcctgcc cctgctgctg
 181 ctcagcgcca tcgccttcga catcatcgcg ctggccggcc gcggctggct gcagtctagc
 241 aaccacatcc agacatcgtc gctttggtgg aggtgtttcg acgagggcgg cggcagcggc
 301 tcctacgacg atggctgcca gagcctcatg gagtacggtg agtggccgcc gcctccggga
 361 agcccttggg ggcctgagct gtggtagcag ctggagctga tcttttaaaag gtcagggta
 421 gtgggtgttt caaagtccgc ttagagttca aacttcagaa gcagcagttt tgggtgaccc
 481 gaatcaggct caaccctgaa agactccaac tcatttaaaa gtaaagtttc tcagttacca
 541 gtgcaaactg atgccagtca ttgcaaagta cgtataaaaa taaataatat gccagggtga
 601 attcatttca tttcatctaa cttaaacttt tttttttaa tcttatgaga aagtcctttc
 661 aggccaagta ggagcattta tgatttagat agatatttca gtatcttagc tgtggagctg
 721 tttcatgttc attcttgttc tggggagtgg ccttcgttga aaagtgaatg ttaaggaagt
 781 ttatctgagt ctgatttaaa atcggagaag taaacacttc actgaagttg agttgccact
 841 tttaacacat cgcaggaaa ctctgtacac atcgcagggg aactctgttt gcctctgcca
 901 gggaaaggcc ccaagtactt gatttacaag ttagtagtag tctttgaaaa aacaaaacca
 961 agaaaagcct tttctccctc aagcaagtgt ccctcctgtt taggatggag acagtagtga
1021 ccagcagtgt gtagggagca gtgtgcaggc tttacgggtc agtttgcccc ctttaaagga
1081 agcaagttac tttttttgtt ttcattcatt ttctagatta accataactt gattcttttc
1141 ctaaagcacc caggacttct gccagacgct gtttggtttg ggtctggcc cttatcagct
1201 ttttctccct ggaagaactt cctcagacag ggaggcaggc aataaaagga gaagactaca
1261 gatattcctg cttgttttaa aaggcctttg ctctacctaa aaacaggcat aaatgcttgg
1321 cttacaggac tttctattgc ttcgaatctt ttagttctta caggcattgt gctgccttgg
1381 aataacctag ctgtttctta aaatgaattc aaactcaagt ctttcagggg ctataagagg
1441 tatgcttgta ggtttttaaa atagactttg gtaattatag ctcactccaa ggctgataca
1501 gccccaaaga atactcagta gcagaagtta gcttgcagag gcaggagcag cattcttgct
1561 gggacatgat ttggcctgta gggccctctt gtgaaacaca cacagtgcca tttccctgtt
1621 tcttgccttg tagggtaagc tcatctttta gggtgtgcct gctctaacct caggcggttc
1681 cattactgtg tgaatggaag ggaaagggca agttttctgt ctaggttgct tctttaacca
1741 tgactcggta gcagcagctt ttccccactg cagtgttaca gttcactata gaaatcagcc
1801 ttgggaaacc tccattttcc aaatgaatct taaaaatatc ttactttcat gatgtggtgc
1861 ctggttctaa actgatccgg gataagtgtg aaagagattt tacacctcag gggagttatt
1921 cccatctcct tcacatcggt aattaagttc ccataatgtg gtagacagct cttgctcaac
1981 tctcagatac aaaacaccaa tggaacactg accttagtgt cagactgtgg aaggaaacga
2041 gagccgtggc gccatctgcg atgtccccat ctcctcacca ttatagacag ggatgagtta
2101 aaatacttgt cattctgcct actctgtgtt gagtgatcat tagtgtacta cacaactgca
2161 aacaaatggg gtgttctaca ctttagggtg atagtctccc gaaagctgta ataggacctt
2221 gctgaaaaac agtgtgcttg catgagctca caccatatgg aatgcatacg ctcccacaat
2281 gcaggaccac tgtcttgtac ggcagggagg ggtaggtagg tctgtttaaa ccatgccaat
2341 atttagcatc tgtgcctctc cctctagacc gcttcttcat gatccttgaa aataatattt
2401 acttaaagct attaacaaag caaaacgttc acaacaaagt gttagaagat tgtgttttgc
2461 tgagtgatat tcataacagt aaatacattt attttggtct aagtacattc ttggcaatgg
2521 tgaccataat actaaataat atgcatagtt tataaaggtc agtaatttct taggaataaa
2581 taaatatatt ctttactatt attgttaaaa tgttaagaat tctggattac acagtcacct
2641 catttatttt cctacataaa taaataaata aataaataag ccaagttaga ccctgagtgt
2701 tttgtcacgg tggcagctta attaacattt atcctagcaa atacttgctt gaatgtttgg
2761 cttatatttg tggagaagaa agtaagaacc tagatttgca attgaagaga tcattcaagt
2821 ttctcctata agccaaactc agcattaaac ttcagtgagt gtgcaatgct gggaccttct
2881 tctccagttt agagaatact gtgacaggga gttattttaa atttccactg cacagacttc
2941 agatcctggg caagctctgg catgtcaggg tggagggtat agggatgagg tatgcactga
```

Figure 3 (continued)

```
3001 aagaaggagg gggaggggaa ggggaggaag gggaggagga ggaggggaag ggggaggagg
3061 acggggaggg ggaggggag gaggaagagg aggaggagga ggggaagggg gaggaggacg
3121 gggaggaggg aggaggaggg ccttggaaag tcagtggctg gaattcatct ctgaagcaca
3181 gaacctcagt tttaccagag acatctctta aatcccttag gatgcacaca gtattttcc
3241 taagcactac tttcctacaa gtcacaggat cagagtagtc tatgaaatta attgccctgg
3301 ttcctgtaag tgcagggcat gaagaaaaaa aagtacagtc aatcagaatt taccttaggc
3361 taaactcacc agaaaagcct tctctctggg atgataccct tgcagctttg tggggaattg
3421 ggggagttt gctggtggga ggggatggga ggttatttta tggagttaga ttagtagata
3481 gatttcgtat gtctgcatgt acgtatgttc acattcttaa cagcaaattt agaggtcatc
3541 cactcctttg atggaataac tttgaaatat acaatgatat gtaaactcta ggtattgagc
3601 ccacggtgca ggctggcctg acgtctctgt gcctgcagca cccagagagc ctcagtgtct
3661 tgggaaggac ttcacttggc tctgcccta taacacagac ctctgggcct gcattcttcc
3721 atctgataga tctgaaatat ctgagggtct gttggctgca ataaggtgta gtttcccatt
3781 ccttacagga gtcttgtata agtacagtgg taccaagcca ccacctgctg agcttcagga
3841 gagagcgttg agtgtgtctg aatgctccag cagctggcat gccttgcctg tggctctccc
3901 gccatttctc tcttaggcca gccattcctt attgccaccc agaacttctg caggatgatg
3961 gcgtggccct gtatacaatg catttgtag gtctgctctt aatcttcctc tggactttg
4021 ctcctccaga gttacaaatc aacatcatgg gaaagtcact gggtaccagg ttctcaaccc
4081 aaccatgctt agaatcttca gtgtaacaag tttcccagga acggcaagca gggcaagttt
4141 ggggtgttgt tgcaaaagct tccaaatgaa tgtcatactc taaataccac aattgccttt
4201 atcttcctat tcaatatgca aagcagtatt tttatatgtc acattcaccc atgtttacct
4261 acttatgtgt aaggtcttt agtttttaaa aatattcaga ttttacttct gcctatgagt
4321 ggcacaaaga acctcagagt atagtacagt aaacatctga tcggaactct gctcctctag
4381 gtggggcctt tgatagtgtt cattgaagaa tggatggtct aggaagggac cccacctcag
4441 tttgatggca cattggtacc cacagagtct tgagcaattg agtggaccac acaactattt
4501 gtggggaagg gaaattagtg agtttccaaa acacttacag atagggactg actgttagca
4561 gcaacatttc ccctttcct tgctttcttc catagcgtaa gctttacaaa gtagtaccta
4621 gaaaacaaac ttaggccatt cccagaatgc gtacagggaa cagtagcttg ctctttctat
4681 gaggaaagga aagcaaacac acaatttcta ccctgaaaca cttgtctgtc tccttggagt
4741 cctgcttgct tttgttgtct cagcctagtg catccctcc acacagctag gaatggtggt
4801 aaagtctgga tagtaagaaa ggtcacactt gtgttctgaa ctgataaaga tgagctctac
4861 ctgcaaactg ctgtgagcca gaaaatcatg gaatagtagc tttaggacat gtttggaaaa
4921 tggatgtttt tccttggtgt tggtaattg aatcataata taatgtaaga tagaaatagt
4981 taccagagct tgtgtatact tatagatatt aagctctcgg gcagctgagt gagaacaaaa
5041 gtacctgaaa tacaagtatt ttagcttaca aaaatgtata tagtgagaaa gtgatgctaa
5101 gtcctgcttc tcagactggg cgaggccctg ttgagacctg gtaaggccag tctctttatc
5161 ctaaaataaa attgctgttg acttgagaag acatgttgtc ttgcttggag aggtcctgcc
5221 atgtatcagc tccgatcttt aaaaccatgc caagatttct gtctaaatgg tagctggatg
5281 attcagtgtg ggtgttgccc tgttgcaagg agcaggtctt acatgttcta caactggagt
5341 tgcttttctc aagcgataat gttgcttcat ttccattctg attttcttta tactcagcat
5401 tttaagtaaa caagacatta gctaattgat ttaataggga aagtgcccca gatgggtcac
5461 tgcaagtata gcttcagcgg ttggtaggag aaatgtacat taggttgcta tttctttat
5521 gaaattcttt gcacattcct gaaattaaga gtgggttata cttcagccaa atgtcagaga
5581 cagaagtcac atcagtaacc tgtctgtttt aatctaattt cccccacacg aacaggtaaa
5641 atgaatagg caatattaca cagaacttat ttagttagac tttcaagacc gtctgtgatt
5701 gtagaagttc agttattaaa atatgttcct tggtaggaaa tatttctgtt tttcctaaaa
5761 attgtgtttg agttcactgt gtgcttattt agaactgttg ctgtttggct tcatagaggg
5821 aaatgcattt tgcctttctg aatgtaatga ttgatttta ttaaacgtaa tggttggctg
5881 tagctatata gacagacaaa caaacagact ccgtgatttc aggtcaaata ctgaagccca
5941 taagcttttg cttccatttt ataggtctta gtcatctaca ctcctattct cagccttcag
6001 tatgcttata gaagggacac aagggaagag cagacagaga ttgacggcgg gggcggggg
6061 agtaaaacag aatatagcat ttgtgttata tacagagtct agatttaatc cccctgcctc
6121 cacacacatt aacacacatc acatgaaaac aagagagact agaagggaaa gacagaatca
6181 tgagggtgaa tacgaggatc atgtacattg tatgtgtacg tgtgtatgaa aatgtcacaa
6241 cgaaggcagt tatttctgca ggaactaaaa caagtctttg atatgccctg aaggaccaca
6301 aggctattga cgattgagct tcctggatcc agccttttaa gccctgaccc aggagatcta
6361 gaagaaggca taagaatctg tatttaaga agtaccatta cttaatatga cactgtgagc
6421 tgtgggctat aaatgcttaa gaagagctga tcaattaact gtttaccaaa gcaaagtcct
6481 ttcttgttta aaaattccct tacacaaagg acaaggcaaa agggggaaa gagacattaa
```

Figure 3 (continued)

```
 6541 ttgtatattc tggctttagc actagtcatg tgcttttaaa ccaaactcac cctacaatct
 6601 cttgtggatc tgacaggatg aataatactt gctggggag ctagaagaac ttctcagatt
 6661 gagtgcaatc atggggcatc tcacccaca cctctgcccc tgctactgag gggggcattt
 6721 gtaggaaaac atggtatttg aagacatata aagatgtgtg ttctccttac tcatttgtta
 6781 tgcccctgcc agtcatacac cccgcagggc tccctgcagg gcattaggca catggagaag
 6841 gggatgaatg ggaggttgct tagtccacat ttgggaaact ggggtatgga agtcttcagg
 6901 gatgacacag agccgtgcca gtgtgggatg ggttgaaaat ctgagattat ggacagaagt
 6961 tatgggaaca gaagaggaac ttttgaaca ggaagggcta aggagttaac aaaggatgat
 7021 tttcacatgg gggtgcttat cctgacagct cacagccagg ctgagttcac agatgaggag
 7081 actggtgtga ggttagcaag ggccagaggc agagccttgt tgagctttgg ctgcctctaa
 7141 accccttgtt tgactctgag cactgaaatg accaggcata atgtgagtgt attgttagct
 7201 gtgctctagt ttcgtaagaa gcagggccga gggaaggggc ataactcc cctttaaaat
 7261 tcaatgaagg gtgaagtaag agtatgtgca gatgattcgg caaacaaagc gtgggaataa
 7321 gtgcaataaa attgccaggc agaaaagaa tgaggtgcta atttatgtta tagaatggtt
 7381 catctttaaa aaatacttcc tttgatgaaa gaagccagtc acaccaagtg tggaatatct
 7441 agaatacaca atttaggaag aagattagtg gttgctagaa cctgggatgg ggtgatggg
 7501 gggcagaatg actacagatg gaatggaatt ccttgggaa ggatgaaaat attctggaat
 7561 tgttaatggt gatggtcaca tagctctctg aatatagcac acttaacaca aaccaacac
 7621 ccaactgtga gatcatggac ttgtagtaga tgtacttcat gacttctaag ttatatcttt
 7681 ttaaacttat gtgttggatt caaacaggct agaaagcaaa ctaagtattt accatctatg
 7741 tgtaccctca cttctgaact agaaacgagg atggcgtgag cgcccccaga ctggttctga
 7801 tgagttggtg cacatcctga tgttagctgc tgctctgaag gcctggttgg atgggaagag
 7861 atgaggagtg tgtacaggtt gaaggacagg gattattgaa tggtttgtgc acatctggag
 7921 ggtcccctca tctcctccct tgcagaacag aagcacacaa gtctagcaca gcctgtgtag
 7981 ggcttcaaac ctagaattca gtctgtctca tcctggttgt ttttacggtc aataatgaac
 8041 tcctgggaaa taaattttga atgaaactag acattaatat aaaccaaata accacccttt
 8101 aaagaggagg catttctgga agagtgtgtg tagcttgaat ggttcagtat gaagaatgtt
 8161 tatcatggtc atgtaaattc aaatctgagt tttaaaaatg gatctattta tgtgaacaca
 8221 gagccaagga gacgaactta catttagtg atgcaaacat ttgccatcaa atataggggg
 8281 aacaaaacac gataataata ttctctacat gaatcaccaa gttttcctt gaaatgtaga
 8341 gttacttaaa tattcctaac ccttcacaaa gtaaaccaa atccctcctt tctcccaaaa
 8401 ctctttcctg gtacggagaa ggccactatg attttatctt acaagtgtcc ttgtctctgt
 8461 catgcagcat ggggacgagc agctgcagcc acgcttttct gtggctttat catcctgtgc
 8521 atctgcttca ttctctcgtt cttcgccctg tgtggacccc agatgcttgt tttcctgaga
 8581 gtcattggag gcctcctcgc actggctggt aagaccgagt ggcatcagct ttgcatctgt
 8641 gctttcagtg ggcatgggta gagtgttcta ttccatctct atggaagacc tgatttgtcc
 8701 ttggaagtgg gtcaccaagt gcaaaagtat tagaggagat atgtgtttta ggaatctggt
 8761 ccctttgcct ccatgcctta gatggtcttc tgttctctca attcaagcga caagagttgt
 8821 cttatgtgtt tctctctaag tatctccatc cattcaaacc gactccacag actagtgatg
 8881 tacctgccct ggaagtacag taacgttcct gacctcctat cagctccatg ctggctgaag
 8941 ggacctgaat atccccaaat gattttactt gttgaaggag ttttgtgatc tggtgataag
 9001 gtagggtagg gaggagctag acttagaatc tgcagcatag atcctattcc gggtaggtga
 9061 aatctgtagc atagagcctg gccagggag gtggctcagt cataggtgat gtgaagacag
 9121 atgcaggtag gtagacaaag ctcagagtac acttttatta atagaatgca agattctggg
 9181 atttaggagt caggactatt tgaagtttct ggcaaatacc tgtcaaagtg acatggtctc
 9241 agttatcagt tagattttga aatgaaacgg agtcattaga gagatctctc aaacggtcct
 9301 cttccagagg acccaggttc aattcctagc acccacatgt tggatcacaa cttttgtta
 9361 ccctacttcc agaggatcca agtgttatgg tttctacaaa gctacaagca tgtggtacac
 9421 aggtagttgt gcaggcaaaa acacctataa aagtaaaatg cataaaatta ctaaagaaaa
 9481 agtagcaaaa cttggttttc tgaggccaga gatggtgttg ataataaa atcaggcctc
 9541 atcttagttt tcaacatacc aaccaaggac cacaggggaa acagggcaga actccagcca
 9601 tgaactcgga gagacaatct gtatagccag tgttggtact aggccagatg ccctgtgact
 9661 atgtgggtcc catagaaatc aagcttaagc caggagactg atggcaggtc catgttagga
 9721 gaggaaggaa tggaggtaga aaaggagcag gagggaagaa aggaagagag agagagagag
 9781 agagagagag agagagagag agagagagag agagagagaa gaggaggaaa aggacaggaa
 9841 ggagaggagg gagaaaagga ggaagggac taggaaaaca ctttagtgtt tatctgtaga
 9901 actctagaaa taagttaaga tggtgaaaca atagtgaggg caagcaatga tttagccaag
 9961 ctagatactc gtgtcacaga gaataatttt ccatgagttt cctgcgagga tccagccatc
10021 tgtttcatgc agcagacagt catttagttt ggctcatggt aggcaagatt cctctagccc
```

Figure 3 (continued)

```
10081 cttgttagag gaattatcat taaagggaga aactgtgact ggcgagattg ttctgtatgc
10141 cgtgggtgac ggtgacgaac accatgacca agtgcagctt gaggaggaaa gggtgcaagt
10201 ccaagtccat cagaaagcga aggcacagca gcagttcaga ggaaccagag gcaggaaatt
10261 aagcagaagt ggaggagcac tgcctactgg tttgctcagc gctcagcttg gtttcttatg
10321 aaacccaaga cctcatgccc ttgggtggca ttgttcacag tgggctgggc ctttctactc
10381 caatcattaa tatagaaaat gccccacaac atgctcatgg gccagtctga tgagggtgtg
10441 tctttagtca agacccccct gctcctagaa gactgtagct tgtgtcaagg tgccaaacac
10501 taatcagcac accctgcatt ccctcacgca tttgttcatt tgagcggcat actgtgaact
10561 tcttttctc ttctctttag ccatattcca gatcatctcc ctggtaatct accccgtgaa
10621 gtacacacag accttcaggc ttcacgataa ccctgctgtt aattacatct ataactgggc
10681 ctatggcttc ggatgggcgg ccaccatcat cttgattggt tgttccttct tcttctgctg
10741 cctccccaac tacgaggatg accttttggg ggccgccaag cccaggtact tctatccccc
10801 agcctaatgt gggaggaaga gcctgagaaa agcctgctgc aagatggatc tgaggaggaa
10861 actgttctcc aaggcacaag gaacctacgt tgggcaatg ttcatatgat cagaaatgtt
10921 agaataaatg ctaaagaaaa ttcttcataa ttagtgttaa gtttcatgta tgtcgtgtgg
10981 agttaaaaag acttgaattc tgtttgctaa gtatatgcta attttccttt atgtcaattc
11041 tataccattt aagcttcatt tgttaaagaa tatgcctgtg aaacttgata aggtagaaat
11101 gcagcagcct ctcatttaat aatctgatgg ggcttctgtt tttccacata gaatgggttg
11161 tttctgctaa gggctacaga ggaggaaagt cactggcaaa acttccatga ccaaatatcc
11221 tgaaattagt ttgttttttt ttaaaagacc ttattttgag ttttcagtta cataaagaag
11281 cagaagcaga ttggtttcct aagtgagcat catttgtgag aatttttagt cagtgttttg
11341 aacaattatt gttttctaa gcttcatgtt gactttctct gatgcgtaga aaagtgttct
11401 aacgtggctg aggttaagcc gctgtcatta ctgaaatgct aagaattttc ctcttttccc
11461 gtagtgtaga ggggtagggt gtgggcagaa gccgtgttag cacatctgta gtattgtgtg
11521 tgtatgctta gaaccagcgt agaccggatg ggaggatgga ctaggcctaa tccctcccaa
11581 ctggtggatg tgaagaggtc aggtaggaag gcacaggagg gtcaccactg tcacagcagt
11641 gccatgcaga catcctagga gaagacatgg cagtgtttct tctcagtgct tcttcccta
11701 actgagctct gctcacagac agctagaata gattttaact gaaacagaaa cctaaatgta
11761 attaaaaacc tggtcttcct tggtaagcag acttaaaata tctgtatagt acatgcaagt
11821 ggaaaatttg ggaatgcgtg tctctgaata cataccggaa gggctactat tacctttttc
11881 ttaccattta tacttaccta atggaaacga gcttgtttta actatcagaa cactattttg
11941 taaggtgctg caaagacagt tgaagttttc attaccaatt tccccaataa accaggtgtt
12001 caa
```

Figure 3 (continued)

F Pltp:

```
   1 aaccgcggcg aggaggggggg tcggaggccc agacttataa aggctgctgg acccgcgcta
  61 cccgccagac cccgccgccc ggatccccccg cgctgcctgt cgcccacgt gaccacacta
 121 ctaagtgagt tggggcgcgt ccccatcgca tccccagacc ctcgtgagtt gtgtggctca
 181 ctaaatccag gtggggagga gagcggatga aggagggctc cgggatgggg caccagacag
 241 aatgcgttat agcggagtct taggagctag gggagcggag ggactcaggg gatagcgctc
 301 agtcgggcca tccccgcgcg cggcctggga gacctcaagc tactcagcag gaatgcgctt
 361 gtggtcgtcg ccataccaac gcacaagtca gcacacgccc tcctctgaag gaaaagagaa
 421 agtgttggtg ggggatgggg ggctgttcat cctcctgaga tccaaacttg tcacgaggca
 481 gttgcacggg ggaaccgagc cccaaatcct ttggaagcag ggcgcaagtc ttatcgtgct
 541 tcggaacctc ggttttgcat caggcaaaga caagatgatt ggttccgagt gccccaaaca
 601 ctttacgggc agtaacggtc cgggccagca ctccgttcta gttgcatgac caaagagtgg
 661 ttttgagcct ctcagatgac acctgcgact cgaccccacc ctgccccag gcttggtcgc
 721 catggtcctg ctctgggccc tcttcctagc gctcctggca ggtgcccacg ccgagctccc
 781 gggctgcaag atccgcgtca cctccgcggc tctggatctg gtaaggcgc gcggcgggag
 841 ccgtggaccg ggtggggtgc tctggccccg ggcgcgggac ctgagtgtct ccatgctatc
 901 tcagtgaagc aggaaggcct gcgctttctg gaacaagagc tggagaccat caccatccca
 961 gacgtgtacg gcgcaaaggg ccactttac tacaatatct cggagtaagt aaggctcggg
1021 gggccggggt ctcaaaggtg gtgggatgac ctgggacacc gccccagact gggcgggtct
1081 gggcgtggcc aattaaatga ggtgggatcc ataataacga gtaaggctac taggtaaaaa
1141 gactggaggt aggcgggtcc aagaaagggg aatacgaacc agcagaattg tagcttggac
1201 caaagaacac cgcgatgata cactggaaga atttacctgt gggtgagagt ggagtctatc
1261 cagagggtgg cgccaaaaag agggaagccc aggataggag agatagaggt gaggcgatgt
1321 ggggtgagtt aaagtgatgg aggcaaagtc aaaggaccag gtggaaagct cagtctggcg
1381 cacgcctgcc aaaaacaaaa caacaacaaa acagaaacca aaaagacgaa aacagatcta
1441 gcaatcacaa tgtggacaga acacggaggt gtaagcaaga ccatagtttt tacttattta
1501 tttttaagat tttatttaat tttaatgtat gtgcattggt gttttgtctg catgtacgtc
1561 tttgtgagag tgtcgggtcc ccttggaact atagttacag acagttgtga gatactttgt
1621 gggtgctggg aattaaagag gagtcttttt gaagaggagc cagtgctctg aaccgctgag
1681 ctgtctctcc agcccctatt tatttattct taaagattta tttgtttta tttatatgag
1741 tacactgtag ctgtcttcag acacacacca aaaggggaca ttggatctta ttacagaagg
1801 ttgtgagcca ccatgtggtt gctgggaatt gaactcagga gcttggaag gctttggaag agcagtcagt
1861 gctcttaacc actgagctat ctctccagcc ctatttattt atgcttgagg catgatctta
1921 ttacgtagcc ctggctggcc agaattcatt ttgtaaccag gctggccttt aacccagaga
1981 ctgatcggct tttgcctcct gagtgctagg attaaagttg tgtgtgtgtg tgtgtgtgtg
2041 tgtgtgtgtg tgtgtgtgtg tatgtatatc tatatatgtg tgtgtatgcg tgcgcgtatg
2101 tgtatgtata tgtatgaaac catacccagc ttttaaattt tttaaaacaa attttgtgtg
2161 tgtgtaaaat ataatataaa tatatatgta attcctgcaa aaggatcact tgggctcaca
2221 aattcaaggt tagtctgaat gacactgaat gacaaaagga cactctcagt cttttatctt
2281 gttttgtttt gaggcggttt cctctgagta gcgctggctg tcttagaact cacacagaaa
2341 tcaggaggct acctctgccc cctgagtgct gggattaaag gtgtgtgtgg gccaccatgc
2401 ccagtaattc cctatctttt aaatattaaa tgcgttaaaa aataaatgag gaaggcagta
2461 ttcaactcct gggttcagag aacaaatctc ttgagttacc caatacatgt cgggctcttg
2521 aggggcaagg gaaaattcca gaccacccac ctagattgcc cagcttgcag ttagaggagg
2581 gatgggtccc tgcggctggg tgagttggtc ccctttggcc ccacgctga ccctgacccc
2641 tgctctctgc agcgtgaggg tcacacagct gcacctgata tcctcggaac tccacttcca
2701 gccagaccaa gatctgctgc tgaacatctc caacgcatcc ttggggctgc acttccggag
2761 gcagctactc tactggttct tgtgaggacg ctgagctctc aggggtgggg ctggtggctg
2821 ggctggagaa gtcctttaac ctcccaggct tcaatttctc cattcaagag gagggtttgg
2881 aaggttgtgt gacaaagatc aagaagagat ttcaagaggg cttatgagtc tccacccta
2941 gctgaggtct aggcagtgaa tgtctgtgag ggagggtgag tcattttct aaagtggtgt
3001 agacactggt actttgccca ttctccactt cataacttcg aacccatgct tatacaaatg
3061 aactccttgg atcattcaaa acaaaaaaca aaactaaaag tcaaggtgcg gcatattggg
3121 aagaaaggtt caggcacaga agagaatgag aacaacggga gtatatatga tcacaaacat
3181 tttgtacaca cttgaaaaaa taaggtatca tgttgtatgg ggtaaagaga ggggtagaaa
3241 cgtcagttat ctcccactgg ggtgaccatg agcctgcctt tcacagatat gatggggct
3301 acatcaatgc ctcggcggag ggtgtgtcca tccgaacagg tctacagctc tcccaggatt
```

Figure 3 (continued)

```
3361 ccagtggtcg gattaaagtg tccaatgtct cctgcgaggc ctctgtgtct aaaatgaata
3421 tggccttcgg gggaaccttc aggtgagtgt cagccccagg acacacgtcc tgagccccac
3481 agttcaattt tctgggcag aaaaggaaag tgctaaggtt gggagtccca ctgaatccaa
3541 ccaaatccta cttcctccac atctggactc tgtgaacctg gcaagtcac tgacgctcag
3601 agaatgaaat ctattttagc agatacttgt gagcactgtg ttgttagata tagaatattt
3661 agacagtccc tggcatatga taaatatcta agtgttagga ttagtatgtc tgcagctgaa
3721 gctggctcag tggtagagag cctgtctagt atgcatgagg tcctgggttc gttcctcagt
3781 acctgagttt agaaaataaa atggggctgg agagatggct cagcagttaa aagcactgac
3841 ttctcttctg aaggtcctga tttcaaatcc cagcaaccac atggtggctc acaaccatcc
3901 gtaatgagat ctgatgccct cttctgtgtc tgaagacagc tgcagtgtac atacatatag
3961 taaataaatc agaaaagaaa agaaaagaaa aggaaaggaa agaaaagaaa aaagtgctgg
4021 gcgtggtagc acacaccttt aatcccagca ctcgggaggc agaggcaggc tgagtttgag
4081 gccagcctgg tctacagaat gagttccagg acagccagag ctttacagag aaaccctgtc
4141 tcgaaaaaca aaaacaaaaa caaaacagaa aagaaaagaa aagaaaagaa aagaaaagaa
4201 aagaaaagaa aagaaaagaa aaggaaagaa aaaaaacttg tagcaggttt ggagggccac
4261 acgtttaaaa ccccagcact caggaggcag acaggtgggt ctctgagtca gaggccagcc
4321 tggactaggt cataaattct aggtcagcca gggctataga gtgagaaact gtcaaaccaa
4381 acccaacaca tcctgagact cacaggctca gtgtgcactg ttgggtctgc attgcattct
4441 caattataat aacacaaaac cccatggtgg ctcctggatc cctggctctg ttgtttgag
4501 gtaaaaacct ggtagacttg tcatccagtg tttacacatt gtcagatttt gtttgtttcc
4561 caagtgtagc atgttccagg ccctgaggat ttagaaagta ttcagagctc agctagaagg
4621 attcaaacag ttgtcgtgag gaactagaag tgggaccaag gtagctttca gggtggtaag
4681 atttagatgg agggtgatct gagaagcctg cctggaaggg gaggcatctg agcccagtca
4741 ggaggccaca gagggcagga acactgggga gggcatcacg agtatataga atatgggggg
4801 cgggatctct gggaggcttg agaatgtgag gcgggtgaca ggagagggtc aggggtctgt
4861 gaggcttgag ggtcaggggc tggggctcgg ctcctggaga gttctattga ggagctacct
4921 ggaaccaagg agaccctgtt gcacctgttt cttttgggca ctgtcatttc tcctgggcct
4981 ggctcatggg cagggcaggg ttaacccagg ctctcctctc tttgcaggag gatgtataac
5041 tttttctcca cgttcatcac ttctgggatg cggttcctcc tcaaccagca ggtgtgggcg
5101 gtggcaggcc tggggagcag aggaggggtg gcctggttct gagactccct gactctggcc
5161 tggtcctcca gatctgccct gtgctctacc atgctgggac ggtgttgctc aactccctcc
5221 tggacacagt gcccggtgag tcaggtgggg gactggagct ggggccgggg atagaaggaa
5281 gctgtgtgct gctatcatac agcgtctcag agagtcccct tcccggtcca gccatggaac
5341 tgtcctgggt tcagaggtgt cattgacttg ctgtgtagcc ttaggtaagt aaagtcttct
5401 cttggggttc tggtgtcctc cttggactgg tgacccctcc cccaggagtt gtcgaggtgt
5461 taaatacatg cttgctgacc acagggcctt gtttgtcttc atcagcttgc atttcatgca
5521 tttcaattaa catgaatccc tttctatgcc accatgtgtg tctactgttg gtcagtgatc
5581 ttgacctatc gggcccgttg ggtaaagggg gttaaaaagg aaggcagggg aaatgactcc
5641 ttagtcatct taaacacgta aacgcgtttt taactgtgtg tgcatgcatg cacgtgcgtg
5701 tgtgcgtatc tgcatcctgg tgtatgtgtg gaggtcagag gacaacactg tggagtcgat
5761 tgtctccttc ctatgagttc tggggattga acttgggcag cacagttttg gaggcaagct
5821 cctttacctg acgaagccat ttcgccagcc cctcctttc agtcttgctt agtgatttga
5881 tgaaaaccttt acagtagtct tagtagtaga tggagctaac catggcctcc tgattgagcc
5941 cctacagcac accaggctct agctgcttcc catggaaagc caatttgatc ttcgtaagac
6001 ctctgtgagg ggcgtgtcac tacttatgaa tgaaaggcac agagaggtta agcactgggc
6061 ccaatgccac ccagcttgga ctgacccgag ccccttccg cagtgcgcag ttctgtggat
6121 gatctcgtgg gcatcgatta ctcccttctg aaggatcctg tggtctccaa cggcaacctg
6181 gatatggaat tccgggtgag ctgcctgtgt tagtgcctgt gacctctgac tgctgatggg
6241 tttccctcgt ctttgggct gagcacggct ctgaaggtc actctgacct gcggtgactc
6301 ctgcgtccac tgcaggtta ggttcagcct cctagatcgg aggtagagtc ctacctttct
6361 atttctttaa agatttttt tcaagattaa ttaatttatt ttgtgtatgt gagtgcactg
6421 tagctgtctt cagatgcacc agaagagggc actggacccc attacagatg ttgtgagtc
6481 accatgtagg tgctgggaat tgaactcagg acctctgaaa gagcagccag tgctcttaac
6541 ctctgagcca cttctctagc cccagctcta cttttcctaac tgcattctgc atctctgtag
6601 ctccccagaa gtccttacgc cagggacttg cttacgcctt gcctgtctcc tgcctgcccc
6661 agcccctgcc cctgcccctg tgagtcagct gctaatagtc ttctttcggt ttctgagggg
```

Figure 3 (continued)

```
 6721 gatggaatcc aagccctcct tggtcaccac aatctcagga tgttcaagtt cattattgaa
 6781 aatggtgtcc catgtgtggg acatataatc ttcaaacatc cattgggaga tgtgtgtgtg
 6841 tgtgtgtgtg tgtgtgtgtg tgtagtacac atgtggaggt tagaggacag cttgcaagag
 6901 ttgattctcc cctcccatct aggatcctgg ggatcaaact aggatcctca ggattggccg
 6961 caagctccct tacctgctga gccatcttgt aggcctgaca atgctgattg tttgtttgag
 7021 gcaaggtttc tttatgtagc cctggctgtt ctggaactaa ctctgtagac taggctgact
 7081 ttaaagtcac agaagtcctc ttgcctctgc cccaaaatgg tggaattgaa ggcacaaatg
 7141 cttctttttc tcttttttctt ttttctttttt tttaatttat tttggttttt gagacagggt
 7201 ttctctgtgt agccctggct gtcctggaac tcactctgta gaccaggccg gcctcaaact
 7261 cagaaatctg cctgccttta cctcccaagt gctgggatta aaggcgtgtg ccaccaccgc
 7321 ccggctctct ttttctttta aaggtttatt ttcttttctg tgtgtgggtg gctttgcgtg
 7381 catgtattga atgtgtgagg agagtgtcag atacccccgca cttggagaat agacagctgt
 7441 gagctgtcat atggttgctg ggaactgaac ccacatcctc tggaggaacc gctagtgctc
 7501 ttaaccactg agccatctct tcagcccgta actgctattt ttaattatgg ttgaatttgt
 7561 gggtatgtta atttcaattt ttttaatttt ttttttttcat tttgagttca gaaataagta
 7621 ttttagctgg gctgggtggt agtggtgagc gcctttattc ccagcactca ctgagtgagg
 7681 ccagcctgct gtacacacca gaagaatcaa ggctactcag agaaatcctg tctcaaaaaa
 7741 gtattttatt ttagggaatt taagagaaag agtaaggcat tcccggctaa taggatggga
 7801 ccctggaagt acagtactgt ctagctgcta gtctgaggcc ttttttacagg actggtggcc
 7861 gagaccaggg tgaggagaga ggaaggagct ggtcggtcag ggtggctcac ccatgaggtg
 7921 tccaggagcc attttgtttt cagtctcctc aagtatagct tcaaggcagg agtgacagat
 7981 aaccaggaag caggaatcga gcagctcctg gtgttcctgc cccagctag gacttactca
 8041 ctgctggggc agtgtgtgtg tgtgtgtgtg tgtgtgtgtg tgtatgtgtg tgtgtgtgtg
 8101 tgtgtgtttc tgttccacct ggcctgtttc taccttctca tcccttccta ccccaagggg
 8161 taagtgcctt tagggaagga atttgggagc catcagtctg gctccttgga actgagtaag
 8221 ttgtcaggtg tggcagttgg agtacccctc cagtgggccc catttagatg ggacctggag
 8281 agtgatcagt agctctgttt gtttagcatc ggggtgtagt gagggtcctt gactgatggt
 8341 tggttagtga tgtgataggg aagggaagac gagaaaggga ccagggaccc ttgagtggag
 8401 gaaacaattc cctcccagtg ggaacaagca gcgtttatag aacttagcag tccaagccct
 8461 aggcagagaa ccagaataag gctgaaagta gggcacgttc atcaagatgg tcagtggtgg
 8521 cacacgcctt ttatcccagc atttgagagg cagaggctgg tggatctctg tgagttcgag
 8581 gccagcctgg tttacatagt acgtttcaga acagccaggg ctgcacagag agaccctgct
 8641 tcaagagaca aaaacaaaac aaaacaaaaa accaacaagc tgggcatggt ggcgcacgcc
 8701 tttaatccca gcacttggga ggcagaggca ggcagatttc tgagttcaag gccagcctgg
 8761 tctacaaagt gagttccagg acagccagga ctacacagag aaaccctgtc tcaaaaaaac
 8821 aaacaaacaa acaaacaaac aacaaacccc aaaaaaatct gaatcaaagc ccattagcat
 8881 ccttaacagg ctcagacaag catctatcca caattagctt agtggacgtt ctcttctctg
 8941 gccttcgagt gatgaaccca ctctgccttc cagcgttttt gacatctggg acatcaggtg
 9001 aggtcgctcc cagctggatt actcccctt cagtccctgg ccaggaaatc aggaattact
 9061 ggggtgtctt tgaattggat tgaggccttt tcttttgctc aacatgtgct tagaagtagg
 9121 gggggccatc ctgagcccat aattttcagg gcttgttttt tttttttttt ttagacgtag
 9181 tctcactctg tagtgctaga tggctggagc tccatgtag accaggctgg cctcaaattc
 9241 atagagattt atgtgcaaaa agcacaccca ccaggcctgg cagcttcagg ttcttatttc
 9301 acaaatttga agaatgaaat gttggaccac agcggggact tttattagta ttttattata
 9361 gggagatgaa tagaaggcag ggtgcctact gagtaggagt gggtcccagg aaatagggca
 9421 cctgctgtcc ctgctgtatt catttaagg atgtgaagac ttgcacaagg tcagcagttg
 9481 ctatgtgacc acctctgctg tggtcggcag cagaatgttc taaagagtct gcagctcaaa
 9541 tatcctaact tctaatcctg atcccacccc tggcaggctg catgtcctta ggcaaagggt
 9601 ttctccctgc cccacccccc accccacaca cacctgggct ccttacctga tatgtaggta
 9661 caaaggacag cttgagagaa catgccttcc agggctgtgg tgtggacaca ctttctgtta
 9721 gaaacactcc tggtggtaca tgctggtatg ttcaacaca caaaagactg aggcaggagg
 9781 attgccctga agttgaggcc agccagggct acatctcaaa atcatacaaa tagagatggg
 9841 cagtgagtac ctggaactgg gtagccatga tggatatgta agtgctgctg tgattcaaac
 9901 ccctcattta cccggttaca cactttacct tcttctttct tcttcttct cttcttcttc
 9961 ttcttcttct tcttcttctt cttcttcttc ttcttcttcc tcctcctcct cctcctcctc
10021 ctcttcctcc tcctcctctt cttcttcttc ctcttcctct tcctcctcct cttcttcttc
```

Figure 3 (continued)

```
10081 ttcctcttcc tcctcctcct cctcctcctc ctcctcctcc tcttcttctt cttcttcttc
10141 ttcttcttct tcttcttctt cttcttcttc ttcttcttct tctagattta tctatttatt
10201 atatgtaagt acactgtagc tgtcttcaga cacgttttct tctccactcc cactctctcg
10261 ctgtcttcag acaccccaga agagggcatc agatctcatt accaatggct gtgagccatc
10321 atgtggtttc tgggatttga gctcaggacc ttcagaagag cagtcagtgc tcttaacttc
10381 agtcctcttt gtttctttct ggacttaatc atgtttatca atgtgttgcc cactggatgt
10441 aggtgtacca atgggtatgc agtgccaggg aggacagaag gtggagtcat atcccctgga
10501 acgggcagac tgttgagcca ctcgctatgt gggtactggg aattgtgccc agtactctgg
10561 gagagcagca catctggagc ttaacatctg gaccaggtct ccagctccat gccttgcttc
10621 tcgtgctccc tgccctgctc ctctgccctc caagcctctt tgcaatgctt tttgagagat
10681 gggtttgtga gcccctccag agcagccata gagtccattt ccggtggctc ctggctgtgc
10741 ctggcgcgga tccaatctgc cttgaccctg atcttgcgtt cccaatccca gggagcattc
10801 ttccctctga aggaggacaa ctggagcctc cccaacaggg cggtggagcc tcagctggag
10861 gacgacgaga ggatggtgta cgtggccttt tccgagttct tctttgactc tgccatggag
10921 agctacttcc aggctggagc gctgcagctg acacttgttg gggacaaggt atagcagggc
10981 ctgtctgagg gtgggttaag aacggcccac gatagagtcc aatttccctg tctcatttct
11041 acttccccgt tcaggtgccg agtgacctgg acatgcttct gagggccacc tactttggga
11101 gcattgttct cctggtgagt gttggccaga ggctggggtg tggccagagg ctgggttgtg
11161 gccagagttg gaagttaccc cacatacaca acagtgaggt ggcaggtgga gggtatgtag
11221 gagttctttg gtggtggcag gctgtggagg agacggacgc cttttgcctg cggccaagtc
11281 ccccagcctt gccaggtcta tctcccactc tgtgaagcag ggttggcact tcttgccccc
11341 tcgccttcac agagcagctg tgaggttggg agagacccag agtctctgca atgattaggc
11401 tgctcatttg cttacatcat cattattatt attattatta ttattattat tattattatt
11461 attttacaca ggaggagaaa ggaaattaaa attttttaac aggaggttag agatatattt
11521 cagttagtag aatagcatag catgcctaaa gccctgagtt ccatctctag tctgaaaatt
11581 ttgtaaaaaa aaaaaatata tatatatact ccatgggct ggaaagatgc agtgatcttg
11641 ctgctctcaa agatggtttg gtttctagca cctatgtgat gattaacaac tgtctgcaat
11701 tttagttcca gaggacccag cgccctcttc tggcctctga gggcactgca tgtatgtaat
11761 atacagctct acattcgagc aaaactaccc atatacatgg aaataacaaa tatatatatc
11821 tattccatgt gccattagtg aacataatct tagttcaatt ttgtacatga cagaaatccc
11881 ggtcatgcta gccttcccta catacaacct tgtaagcctg tcatgagttt ccaatgaggt
11941 aacacatgta attagcagag cactgctaca gagcgcgtgt cccctgaaac agctggtgtt
12001 gttactgccg tcggtgtctt tgtcatgcga ctgctgagta gttagaagca cagattgtgt
12061 cgtcaaggct gcctgcattc gtctgtcagc tctgcagctg aacaacctca cgaccttgca
12121 caaccttagc ctgtctgcct cagtttccca ggctgaatca gtgagctcca gtttcagagc
12181 aatgctctgt ctcaagaaat aatgttggtt atgtaaaagt gacaaaggaa gccacctaga
12241 attgaccttt agcagggtat atgtacatac gaatagatac atacacacac acagagtggg
12301 gataatagta cctgaaatac ttggttgttt gagacttaaa tgagcgaata catatgctgt
12361 ggtcagaatc atgcttaagg gaatgtttgt ttttgagacc ggatctcatt atcccaggct
12421 aaaatacata catataaatc tgaaagttgc ctgatcctcc tgtctgtact cccaaagact
12481 gggattacag gttttgctac cacacccagc tcagcatcat gtttagcaat aagtaagctt
12541 atgcatttaa tagtattaca tggcccatag agcggccggg agatgagggg gccagggctg
12601 ggatgtttaa gcaaaaaggc catacctagg gagtcccaac tggggtctga gtcagagtgg
12661 gatgcgtgct ataacttcag catttgaagg ctgagccaca ggagcaccac cgctgtccag
12721 ggtttcagga ccagctaggc aacaaagcaa gagcccatct caagagaagg aaggaaagat
12781 gccatttgac taattcttgg ggtcagggtg taggtcagaa gcggggtgag gtggcacccc
12841 atcatctgaa cttgcaaccc cttgcctccg aaagggctga ggctttgtcc cgtgacacca
12901 ccccagtgct cccaccgtga tctgccttcc taactctgcc tcctccagag tccgacagtg
12961 attaactccc cactgaagct gaagctagag gccacgagcc ctccacgttg taccatcaag
13021 ccgtcaggca ccaccatctc catcaccgcc agcgtcacca tcaccttggc cccgcccatg
13081 ttgcccgaag tggagctgtc caagatgatc atggtatgga ccccaggacc agggtacctg
13141 gggttcggtg agaagtgggc tgtggatctt tcctgtttaa acatccccca tgccctttcc
13201 ttcaggaagg ccgtctcagt gctaagttga cactccgggg caaggcgctg cgagtgaagc
13261 tggaccttcg aaggtattcc cagccttagc atctctagga tagtggtacc tgctcaacag
13321 aactgcaggg ctaaagctgg gctagaactc ctgtaaggct atccagagtt atatagtgag
13381 actatgctga gagagagaga gagagagaga gagagagaga gagagagaga gagagagagc
```

Figure 3 (continued)

```
13441 gcgagagaga gcgcgagtaa acatgacaca tacctttaat cccggggatg gtgaccagag
13501 ataggtggat ccttgcaatc ttagaggaga gctagcctgc cctaggtggt gaatttccag
13561 gctgatgaaa caccagtctc aaacaaaagg agggaagggc tatgaacaaa taccctgaat
13621 gctgtcctct aacctttaca tgcatgccaa ggacacacgt acctgcacct acacatccaa
13681 aatctatctg accatgtagc caaagacgat cctgcttgca tctccagtgt gctgggatta
13741 caggcacata ctaccatgtc ctgtctatat aatgctcagg gacggaaccc agagcctagt
13801 gcctggcgac tggcgacact ataccaactg aactacaact cccagctctc aaagcacttt
13861 ttatctcttt ttttccccccc caagacaggg tttctcgtgc agccttggct gtcctggaac
13921 tcactctgta gaccaggctg gccttgaact cagaaatctg cctgcctctg tctcccaagt
13981 gctgggatta aaggcggtca ccaccaccgc ccggcttttt ttgtttgttt gtttttcaag
14041 gcagagtttc tctgtatagc cctggatgtc tggaactcac tctgtagacc aggctggcct
14101 tgaactcaga aatctgcctg cctctgcctc ccaagtgctg ggattaaagg catgggccac
14161 cactgcccat atctctattt ttcttttaag acaatgtctc actatgttgc actaggtaga
14221 ctggcagtgg atgtatagac caggctggct tcaaactcaa actcagagaa gatctaagat
14281 ctgcctctag agtgctggga ttacaggcgt gtgtcaccac tcctggctaa cagtggtttg
14341 tttcttaaac caactcccct gcattctctt gccttctaga agcaggcaaa gcaggtattc
14401 ttagagacaa gcaaattgct tcagtaaggg caaacgacac gcctgcagtc acatagcaga
14461 gaggatggag acattggttt gagtatcaac ctcagctcag ctcagcagga atctggaagt
14521 cattgcatct ttccaaggct catttcctcc tgtgctaaat acaggtgaat accttgtact
14581 tccgagggct gcgtagttaa tggcatcgcc tcaggatgtg ccagtggcta catttgtata
14641 attataattc aacagctgtt gggctgcaga agtcacagtt cattaactag tggctacaga
14701 gtggacagtg tagatacaga agttgtactg tgctgcttcc aggttgaagt gagacaaagg
14761 tagggtctag cccacacagc catgtaactt caagctactt acttgatcaa cttcagtttc
14821 gtcatccgta acaatttcta atagtcccag attctcaggg ctgtgagtga gggctgagtc
14881 actaggtggt ttacagtgtt gcagctcggc caggtaattc tagcaccagg gaggctgaga
14941 taggacattt gaggtgaatt tgaagccagc caagactaac ctatgtagca agacactgtt
15001 tcaagcaaac accataactc caaaaaacaa aacaaccccc ccaaacaaaa caaaacaccc
15061 caaggactga agagttgatt tgaaggaatt tgagaatgag tgtatgagtc ctaaaactca
15121 gagtagaggc aatggcttgt gaccccaaca gtggggaaag atagaagatc cctgggcta
15181 actccccagt cagcttagcc aaacgctgga gctttgggcc aataagagat tctggctcaa
15241 aacatggtgg atggtgtgac catccccatc cttcacatgc acatgtccaa atccactcct
15301 acacacgtgg accttcatgc agacagtctc tctctctccc cactcccaa gtggcacata
15361 tatttatgtg gccctgggaa tggaacccgg gctctgtacc tgctcttcat ctccagtcca
15421 gcatttcagc ttttcccctt ttccttgctt attgttcttc tgttttactt tgttttgtt
15481 gtttttcgag acagggtttc tctatgtagc cctggctgtc ctggaactca ctctagacca
15541 ggctggtcac aaactcagaa atccacctgc ctgtcttctg agtgctggga ttaaaggcat
15601 gcgccaccac tgcctgtttt tgttttgaat gagacagggg cttaatatgt agaccaggct
15661 agcctggaac tcacagagac ccctgcgtc tggagattaa tggcaggatg ttgagattaa
15721 aggtctgtgc caccttggca gctctcaaat ttgtatgtgt gggtatgtgt gtgtgcatgt
15781 aggtgcaaaa gtaatgccct ctcctggagt tccaggacgt cgtcaattgt gtgtcatggg
15841 tgctggttcc cccgagaagt atgagctctt agacactgaa ccatccatca actttctcct
15901 gtcctcttat ttgataagtg tgtggtatgt gtgtggaatg tgtgtatgca tggtgtgtat
15961 gtggtgtggt gtgcgatgtg tgtgatgtat gcatgtggtg tgtatgtgtg tgtgtggtgt
16021 ggtgtgtaat atgtatatgt acgggagcct ggagagatca gaatgcttca gatacctga
16081 agctggagtt ataagccatg tgagctgcca gatgtgggca ctgggaaccg aattcagatc
16141 cgctagaaga gcagcaagcc tcctcccccc ccccccttt ttgtttgtt tttcaagaca
16201 ggatttctct gtgtagtcct gactgtcttg gaacttactc tgtagaccag gctggcctcg
16261 aactcagaaa tccgcctgcc tctgcctccc aagtgcgtgt tccaccactg cccagctagc
16321 agcaagccct ctaagccatc tcttcagtat tgtgcccctc ctcaaaccca ttttgagaca
16381 aaaaaaaaaa aaaatctcac tggggctgtt tgcaaactca agaaagcca cctgcctctg
16441 cctcctgagt gctgggatta aagaaatggg ccaacacagc tggcaggctt tccttttgt
16501 aattaactcg tgtgtgtgag cttatgaaca tatgcattta tgtgtgaggg cactcacgtg
16561 tcacacagtg cattgatggt caaaggtcaa cctgtccagt ctcccctcta ccatgtgtgc
16621 cctagggatc aaactcaagc agtcgggccc tttacccacc acactgagcc attttgcaga
16681 gccattttaa ttcttttgaa taagtttggt atctgacaga gagtaaagat tgttggaatt
16741 tccttagata aaaccatact tatttaccta gccgcagagc gtggcacata ggcattcctg
```

Figure 3 (continued)

```
16801 acaaatgaaa aacagcaggc gccgggcagt ggtggcgcac gcctttaatt ccagcactct
16861 gaggcaggcg gatttcagag ctccaggcca acctggtcta cagagtgagt tccaggacag
16921 ccagggctac acagagaagc cctgtctcaa aaaaaaaaaa aaagacaaaa gaaaaaaaaa
16981 aagaaaagca gtaggcttaa agaaaggggg ctccagagac caaaggcact cagggatgca
17041 cacctgggaa atggcagcta cctgaaggat gattggatag aactgggaag gctgtcactt
17101 gctgccatct tttaggtagg gcccaaggaa agggtgttcc caggtttcac ggtgtatttc
17161 tctcccacag gtttcaaatc tactcaaatc agtctgcgct ggagtctctg gcggtgagtt
17221 ggggatggca aagggtgggt ccaggcctcg ggcaagttg gccgctcact caaacctgta
17281 tgcactgtct gtcgccccc cctgcctttt ttttccccct cagctgatcc cactgcaggc
17341 cccactgaag acactgctgc aaatcggagt gatgcctttg ctgaacggta gggactgagg
17401 gtgggaggat ggagtgggga cacggactaa caaaggggg acggcggtgg atggtggaca
17461 tgacgacaca gatggactga tggacaccca ggctgagctt gcctctctca tccacagagc
17521 gtacctggcg tggggtgcag atcccccttc ctgagggtat caacttcgtg cgtgaggtgg
17581 tgaccaacca cgcggtaagt acattgtgga aaggaggccg tagaccaggg cattcctgtc
17641 cctacaacac cccagtgctt gtctgttttc ccgaaacccc tttacactag ttgctccttc
17701 acatatatat tatttaagta gtaaagattt aacttagaag cagggccatg ctccagagaa
17761 catacgccac gccgcaaagc agctggggcc cctgagggga tttgctcaag agtcttgtgt
17821 ttgtttggag gctgtttcca acaactgaa ccagccaggc tccctgtccc ctcccgcagg
17881 gcttcgtcac tgttggggct gacctccact ttgccaaagg gcttcgagaa gtgattgaca
17941 agaaccgtcc tgcagacgtt gcggcctccc atgtccccc accctctgct gcagctgcct
18001 gagcccatca ccccacctgg gtggctggca ttcaggaacc taactgaagt cttctctgca
18061 cccctgcca accccttccc atctacagtg ttagtggtcc cggtgccaca gagaagagcc
18121 cagttggaag ctatacccga tttaattcca gaattagtca accatcaatt agaatccatc
18181 cacccccctc c
```

G <u>Srxn1:</u>

```
   1 caaggaagag gtatggggct acgcgcgggt ggagcgctcc ggagggcggg tgcggggccc
  61 gggcgcccg agggacaggg accggtggc gcccaggcg gcagcatcca ctcgggctgc
 121 atcgccacg tgcacaacgt accaatcgcc gtgctcatcc ggccgctgcc gtccgtgctg
 181 gacccggcca aagtgcagag cctggtggac acgatcctgg tgagcccgcg gagccttccg
 241 gcccgcgcga gggataaaga gagggcgcgc gggtcggggt ccttgatctg caggagctca
 301 gcttcgcctg tgtgaccttg acggactggc tgagcctccc atggggcccg ggttcctcac
 361 ttggatttgg ccataaaact aatgatccgt cgcaggtact caaagtgctg aggtcacccc
 421 ggagctgatc tttgcctctg ggagcaactc tgttaaagta gttgctgttc tttctgtaca
 481 gaggagaaac tgaggcacag gaagcttgga ttttttttt tttttttttt tagcaacttg
 541 acctatgtca agtgcttaca agatggtacc gtgagacttt acacccaggc aacctgcata
 601 tcctggtgtc tcttctggcc ttgacagtct tggcaatggt ttgggtgtgt catgtctatt
 661 gggaggatct tgtccagtca ggaagtaggc aaggataagg tcagtctatc atggaaggag
 721 ggtcccctca gtaactaggg gttggagttt gtgtcgagtt aggccaacat ggcttcccat
 781 cccttcttcc agcttcttga gattcataga ccctatgacc cctaagtcca cagatgtttt
 841 cgtcctaaaa tttgcacccc tgtcttcctg tgtgaacttc acaagagcag ggactttgcc
 901 atcttggcag ttgccttcaa gctgtgactg atttagccca gtatgctctg tcagcaccaa
 961 tgagcctttg ggcaaacttt ctccacccca ggaagtgctt ccatccctct attgtggtca
1021 ttgttttagc ttttatgtgc tcatgatgct aggaattgcg ctcccctgcg tgcgtgcgca
1081 cgttcagcag gagctccacc attgcgctgc ctccctaaca ttttatccct tcgttgcttc
1141 taattccgta atcattctgt cttgatgtca gcgcctcccc tgcccaccct attgggttg
1201 gccatctgtg acctcacagg cacctgggtg ccccttagca tagctgggat cccggtgggt
1261 tttaatgacc aatttagaca cctcttctat gctgtcacgg gctctggaga caaggaccca
1321 tcttcctagg ccacctgaat atgttgccac aaacaggact gcttgaaata agatacaagt
1381 ccaaagctat gttgtcgtgt ggttttgag acaggatgtg tctctatata acctaggctg
1441 ccatgaaatt catcatcctt ctgtttcagt ctcccgagtg ctggtattac aggtggtttc
1501 caccaggccc agctcaaagt ctatttatt gagctaaaat aagaaccag caggaatgtt
1561 ctcttgaggc ccgaagggaa aatgcacttt cccaagtctt tctttttctt ttgtgtgaca
1621 aaacatcctg acccatgcaa ctttagggtg aaagtttgtt tgtttgtttg tttgtttgtt
```

Figure 3 (continued)

```
1681 tgttttttga gacagggttt ctctgtatag ccctggctgt cctggaactc actctgtaga
1741 ctaggctggc ctcgaactca gaaatccgcc tgcctctgcg tccggagtgc tgggattaaa
1801 ggcttgcgcc accacgcccg gctagggtga aagtcttatt tgactgacag tccatcatgc
1861 cagaggattc ctgatggtag gagcttgagg ccattggtcg tgtatctcca gtcagaatga
1921 tgaaaaacca cttggacacc gctcactttc ttctctttat acagttcggg attctagcct
1981 aaggagtgat gctacccaca gtgggcagat cttcccagct caactcactt aaccaagata
2041 atcccccata ggcatgccca gagaagccaa cctccaaagc cattctggat ttcatcaagt
2101 taacaattga accccttagc tgagggcctc tctcatcttc agagcagcag cagcagcccg
2161 tggagtcctt cccgcctcag gtcattgtga cctctcttgt cacagccttc tgctttcagg
2221 gaacctggtg attacattca atctccttgg caacgcagga caatctcaat tggggaacc
2281 ttaaaaccca cttctatcag caggcttcca ccatgtaagg tgggtttcac aagtcctaac
2341 gattaggaag tgggcatcct gaaggaccat tcttgagccc ccaccctacc ccccactgcc
2401 atgccttcaa cacaaggcct gcttggtcca gctgcctagg ccctctcccc ccatgcatct
2461 cctccctgac ttccaccacc ctgctggatg aacatgggag gccatctgca caacacagct
2521 catcactgct ctgcacagga gtcacagttc aggcatttgg gcttttttct ttttttaaag
2581 atttatttat ttattatatg taagtacact gtagctgtct tcagacacac cagaagaggg
2641 cgtcagatat tgttacggat ggttgtgagc caccatgtgg ttgctgggac ttgaacactg
2701 gacctttgga agagcagtcg ggtactctta cctactgagc catctcacca gccccgaat
2761 ttgggctttt aatctaagct agtccgaatc tgtagcttcc caagtggctc tgtgcccctc
2821 gtcacttcag agagacaggt gggcctcctc ctggcttgtc acctgtgaga ctgtcttcac
2881 agcattgtca tttcttcctt caatctgctc ctgggactga aaccttgtca gggtgagact
2941 ctccttacct cctggctgtg ctgtggtccc ccaagtgtgg gcaagtggac gcaggatgta
3001 tcagtcacat ggttagtaga tcagtgctcc ccaagtgttc tttgggggaa gcccctcact
3061 gccatttgca gcatctgcca tttctctgtc agaaatactc ttggggctga ttttcaagct
3121 gccaggataa cacccaccag cttgcagaac caaccccctaa ggggctaaga ggctgctgct
3181 cctgccagca cgagccctct ggcattttgc cagttctcaa gcatagtgcc atgttctcac
3241 tctgtgaccc ttctctctag gcggaccctg acagtgtgcc cccatcgac gtcctctgga
3301 tcaaagggc ccagggtggc gactactact attcctttgg gggctgccac cgctatgcag
3361 cctaccagca gctgcagaga gagaccattc ctgccaagct cgtgaggtcc acccttcag
3421 acctgaggat gtacctggga gcatccacac cagacttgca atagcaacct cctgatagcc
3481 ccctgcccct ctccacatca gcaccactac ccggcgctca gaagacacat gcagccccca
3541 gtgggcagaa gctgtagatg ggatatgttc tctttattct taagggaggt ctgcctcttg
3601 gtgcctctgc actagctccc aggggctagc tcccaggaat gaggggttc agttcttctg
3661 tctatggaaa gatatcatgg ccttgaccct gaaggagtac caggaaggaa gaaggagat
3721 ggacttggag acaaggactc tcattttaat ctttatgata gcactatatg aactatgtac
3781 taggaagtaa aggaaaaccc aggtcaccat ggcttcagtg agagaagctg gttatccatc
3841 cccatagcct gaactctgga accggcagct aacacagcac tgactaacac agtattgtgt
3901 caacagctca gtgaaggcag ggcttcctct cgggagtcct ttggccttgt cctccttgct
3961 ccttacttcg tagtcgctgt tgctgtgttt ctaggaaccg tgtctgtgct caaggaagaa
4021 acccactgga ccaacttctg tcagaaagga aaaccttgtt caaagtttca ggaccctgtt
4081 ctttgcttat ttgcacatgg tcaccttggt ctgagctagc caccattgtc acccacagct
4141 gcaaagaaag cagaccttag gaaacactgt cacggctgag tgtgactgcc ttgttcatcc
4201 cctggactgg tactgtgttg cctgcagtac cattgggatc ccatagcaag agagggagag
4261 ggagatgtta gttagccttt gctacgaacc aagctgtccc caagctcaac agctaaacag
4321 gtattcattt acccatgatt ctatgggtta gctaagctcc tttgagcagc tcctctgatg
4381 tggcctggtc ctgctcatga gcccatagtc aattgtcacc tcagctgggg ctggttgggc
4441 tggggtcacc ttcaccattg tggcaagtgt tggctgcatt ggcttggtta ctcttgttgc
4501 ctctctcaaa ggtcagttca ggagaattct caagatggcc tcagggttcc aagagagagt
4561 agtagtgaga gggcctggag cggagactca gctgttaaga gcacctacat ggtgattcac
4621 aacactgtca tccctgttcc agatgacctg atgccctctt ctaggctctg tgggcacaga
4681 caaacacatt cgagcaaagc acccaattgc tttctttttg cttttttgaga cacgggtttt
4741 ttctgtgtaa ccctggctgt cctggaactc actgtgcagt accaggctgg ccttgacctc
4801 acggagattt gcctctcctg catcccgagt gctggtatta aagaaggtgt gcactactat
4861 cacccaggta cattttttta aggtgacaag gttcttcag cccctgtgcc aagaatgtgt
4921 ttctgttggt cagttcgttc cttagattca agggttgcaa atggaccgag ctctcagcgg
4981 gaggaaccac aaagaacatt gggctatcgt tcatcacaga tgaatcttgg tgggcaagag
```

Figure 3 (continued)

```
5041 acagaattcc tcactcccac acataagtac tccctttca taagtttgtc acagaagcac
5101 acaaggggcc ttggcatgtc agcctttaag taacggttct caaaacctag aagtcatggc
5161 atggtgtctt cgagagctgg gtaccccagc cctaaggatg tctcagaggc acaatgaggt
5221 ggataatgag gtgggcattc agagggcttt ctgcaaacct agagtccagg aggcaatggg
5281 tgcagcagtg aggtagctat gccacacaga gaccatagtc acttgtcatt ttcaagcctc
5341 tgttttccca gctccatggt gaggacacca gctttcccac ccaccgagtg tcccagaaaa
5401 tgaaattgga aggaataaga tgcatcgtgg tgctggattg attcttggga ccaaaagag
5461 actagggaga gaaagcacat tagcaggtca accaggactc ataccttcca gtttgggtaa
5521 tcttatctct ggggtgggct ggatgaagaa tgtatgggaa ctctagtctc tgcaacttt
5581 ctgtaaatcc aaagtcattc taaaataaaa gtgtatttaa ttaa
```

H <u>Cgref1:</u>
```
   1 gaggcgctgc gggacaggtc tgcccaagga ggggcggtgg ccctcccgtg gctgtcgctc
  61 gctccggact ctgcccggc ctgggcggcg gctgcagccg ggagggcgac gtggaatggc
 121 cacgtggagc cgcccggggg agggccggct gcgggcagcc gggcgagagc ggcgcggtgc
 181 ctatagagtt cacgaagccg gagccccagt cgcgcacagc gccgccgcag caggtgggtc
 241 agactccggc atgggccagg gcttagtggg cggcggggc accgggtacc ttgggggtaa
 301 gggtggagac cttctactgg cggttaggat gcagagagca cagtcctcct catcccctga
 361 ggcttggact gggctgtgga ggtggccctg gcctcctagg accgaccact agggtcatcc
 421 ctgagatgca gatagaggaa aggtggaaag cttccgaggc cctgggttt gatgataggt
 481 ccaagagtcc tcctggccgg cagcggtgtt ctagtagcta gccaggttc cacctcattc
 541 agtagatgta gatgattgaa ggacactgtc cgtcgtcatc cagctgtagg tggctggtct
 601 caggctagct cagatgtgtg cccctttgac tgtatagctg cggtcattta gcctccccc
 661 tccctcgacc gggacactaa gggctaaatc aagggagatg actcgattca ataacttttc
 721 cacttactta gaaatggaat ggatgccctt catggtacca gctcctgtcc tgaaaagatt
 781 caggaggggc gttatggcta ttcgtcaggg atgctgggaa agaaatgtct ctgaaatgag
 841 aagccgtttg acataagcct ccaaagaccc ctgcaacatc gtgaagcatc tgctggccct
 901 agattaacct agattatctc actgtaccat ccctaagacc ctaggaaacc tcgttatctt
 961 aaaaatgaag accctagggc caagggaggt taagacacct gccaagacca cataacagtg
1021 cagagtcaga ggctgaccaa tggtccaacc tcaaggccaa agtctcctcc tgtgagctag
1081 ggcaaaggct taaagaaatt gaaggcagaa ggtcattgtg aagagtgtg tgtgtgtgtg
1141 gtgtgtgtgt gtgtgtgtgt gtctgactcg aataacttcg ctgagctata tgacaactgt
1201 taacgagcag gtacagaagt tttcaggtat ttattacggt agttatgttt atgcatgtta
1261 taattatgga aaatggctag gaccattttt attttattag cagttgttca atggccatgc
1321 tatttctgtt acaaaagctc ttacaagtgc ttaacttgat gtgagtatgg gtaagtcata
1381 ttacacacat cccgtggaag tttggcttaa acaatggcaa gaagcatcga gaaaactaaa
1441 ttagactcca agtgcccatg cagtgccttt aatttttgag gtaattaatt aaataaataa
1501 aattcagact gcaactgaat gctaaggtta tcaggaaggt ccatcctgaa ggtgaaacgg
1561 gtttggaaaa aaacaaacaa acaaacaaaa aaacaaaaaa caacaaaaac aaaaaaacaa
1621 aaaacaaacc ctgagactat taagtaagaa aacctagtga gctgccattg aagcagtgc
1681 tggagcactg gagggtgaga cagagatgac accatacctg aacgcatggg tgaggacatg
1741 ggtgtgtgac ggtgagaaaa acaaagagcc accaaatgtc ttggagttgc tgggcgtggt
1801 ggtgcatccc tgtaattcta gtacttgggt catgagttca gggttatcct cagctacatg
1861 ataagttgga ggccagcctg ggatacatga gacctgtga gatttttaat taattaatta
1921 attaatccaa taattagttg agacagggtc tctctagtcc tcagtgttct ggaacttgtt
1981 ttgtaggcta ggctggcctg gaactcaaga gatccacctg tttctgccat ccaagtattg
2041 ggaataaagg catgtgttta ctgttttat tttgagtgtg tgtgtgtgtg tgtgtgtg
2101 tgtgtgtgt tgtgtggcct gcatgtatgt ctgtgtatca cttgtataca gtgccctcaa
2161 aaggacatag gaggacagaa gagggcctcc ggtcctctgg aactggagtt acagatggag
2221 gttagctaac atatgggtac tgggaactga aacaatgaat agattttgag ccccattgtt
2281 tttttaaaaa aagattttga aggaaccagc aaaatgggtt gaggtacttg caaacaagtc
2341 tggggaccca agttcaaacc tgatatccca caaggtggca ggagagagcc aattcccaag
2401 agttgtcctc tgacctccac aggtgcaccc tggcacacac tggcctacac ttaagcacac
2461 ataaactcaa caataaagta aacaattaaa aactgtttct gaagcaatgg agttctatca
2521 aagggatgct tatatgatgt gtgtataaag acagtacctc aggctacgac aacacacaca
2581 caaacacaca cacacagaag gaattcacta tccgctgctt ctgggttctg tccactatac
2641 acactaaata gttacctatg taaaggactc acaggacaga ggacagtgac tgattcacat
```

Figure 3 (continued)

```
2701 agggagggtt cagaatcatc attgatttct agatcccaga gcagaagtag ttgatagttt
2761 caagacagct acagcaggac aacagacagc aaggcctggg tggctaagta ggttcactct
2821 tacaaagcca gctcttgcat ggctggcatt tggagtatta agatcactta acaggccact
2881 caaaacctag tggtttggat gcaaagatag aggagagcct gagttcccac cgcaccccag
2941 gtcttcagaa gggctccaga tatgatggat gttctcccac tagtgcttgc agatggtctc
3001 aagttgccca gccccaggct cgctgcagct gcacgtgcag agcaggatga aggcagcgcc
3061 agccttgtct cgctcctcct cggcagacta gatgatcata ttgatgcttt agtaccagct
3121 gggcgatggg agtcctctat aggttaaaaa gcagtatcat gcagaatcgt gctcctggga
3181 ttgcagcagg gcaggagacc atacagggag acaccgtttc gtcaagacaa ccagagctag
3241 gtgtggaggt gcatgagttg aatgcctgtt cttgggagcc tgagacaaga ggatttcagt
3301 gagtcggagc tacgtgagtt caaagctagc ctgtgctaca cagcaagacc ttgtttcata
3361 aaaccaccaa aacaaaacaa cttagtagct tcagatgata accttagctt ttctcatgga
3421 tgctgtacac taggcagggc agtggagacc agctttcttc tattctactg ttggttagga
3481 cagctggaag gctcacagtt ggaggatatt ctcacacttg tctgccttgg gggctaggga
3541 ggggtttttt ttttttttgt ttcatttttgt ttttgttttt attttgatt tggttttggt
3601 tttggttttt gagacacaga gagactgaga tactacctgg acctggcagt tttctcagct
3661 atcctagtca cctggaagcc agccactaag tccaaacatg taagaggagg tgacttagac
3721 tccagggtta gtgggaagga aagtaagaac aaacagtaga catgggccag caagatggat
3781 ggcaaaggcc tttggccggt gtttgatccc ctagacctaa ctggtggaag gaaagaactg
3841 atttctgaaa gtggtcctct gacctccact gaggcacaca tgcccacaga cagatggaca
3901 catgcatgca cgtgcataca cacatttata cacacaccac caacaacaac aacaatgcca
3961 acaacaaaat aagcaactgt tttggggacc cctgcagtca gcctaatgag ggaatggatt
4021 agtgggtgag gggacttcct gctgtttcaa aactgccacc cgtttgtcat cagagctctt
4081 ctaaaaagca gcctcagagg ctagtctaga ttacaagtgt tgacagctag ctctgaggga
4141 tttaaattac gtgagtctca ggaacagaca ggaggaaagg actgacttga acgactcagg
4201 tgggaaggcc aggagggaag atgtgtgtga agccaccaca gagcaaccaa gacaacttct
4261 ggaaggcaag cacctcatct catttagcta caactgtggc cccagggaag tgctctgtca
4321 acctgcattg cagatggaga cctgagacag ggaaagcaca cagccagtga gaggcagggc
4381 cttcagttag ggtcctcaca ctccacctt gagttctcct ccttttccta gcagttctgt
4441 atttctgtgt tcctttcttc ctctcagtca ggatcttaca gcattgccta ggttggcctt
4501 gaactcacaa cctcaaaccc caccccatcc ccgccctct gaagagctgg gattataggt
4561 atgtgcctct gcacttggct tctgtttatc tgtctcttat ttaaatatgt gtctcttttc
4621 ctgattatat aattttgtaa tccttaagga gaaaaagtag tttgatctca taccttcagc
4681 tgattgataa ctaagaactt aaacagtaaa gagatgcact ggagagatgg cgcaacaatt
4741 catgggacct gttgttgctc ttgcagagga cctaaaatca gtttttcagcg tccacatcag
4801 tggttttcaa gctgtgggtg tgatcctttg ggggtcaaat gacccttca cagggtcat
4861 atatcagata tcctgcatat cagatatttg tattacagtt cataacagta gcaaaatgag
4921 ttatgaagta gcatcaaaag caattttatg gttgagggtt gataagttat tctctccaga
4981 tgaaaatgag ccaattcaag tcaaattaaa gtacataagg gcaggtttat tggagggtgg
5041 ctctcaggca gattcactgg tcccaaaaaa aaccgggct agggaagttg ccctggggaa
5101 ggagacagag gggaaggaca gagaggaaaa aaagcaggct tgtgcatgaa gggagagaga
5161 aaatgcaaag ggaggaagag aggtaggaga gagagagaaa agtgggtggg ggatagagag
5221 ctcggaaaac atcagcatta tatggggagg agcttctggg ggaggggagg cccagcccct
5281 aggctggaaa gttcacagga gagggcaggg tataccagcc atgcctgtag taggtaggga
5341 ctgagggatg ctgggagaac atggagctca ggtctgtgta aaatatgcac ctcagcaatt
5401 tgtcctgggt ctgaatcaaa acaggggcag tacaacatga gaaactgtat taaagggcca
5461 gcattaggaa agtttgagaa ccacttatcc acatggtggc tcacaactat ctgaaattcc
5521 agttctgagg gatctgatat cctcttctga tttctttggg cacccagtac acatacacac
5581 atgcagacga aacactcaca catactacat acatacatac atacatacat acatacaata
5641 catacaatac aatacataca atcttttaaa gtattttatt tatttattca ttcatttatt
5701 catttattta tttacttgtt tgtttgttta ttttattttg ggttttggag acaggttctc
5761 tctgtgtagc cctgactgtc ttaaaacttt tctgtaaacc aagtcggcct tgaactcaca
5821 aagatccacc tgcttctgcc tccagagtgc tgggattaaa ggtgtgcact accaccaccc
5881 agcaaaagaa tattttaaaa ataagtagcc tggcagtgca ctttcagtgg tagaacattt
5941 gacttgcaag catgaaggct tggatttggc cccagcaat gaaaaacaaa gaaatgaata
6001 gccagacatg atagcacaag tctgaaattc cagcacttgg gaagcagagg cagagggata
6061 tggggcaac ctgggctact taataaaaaa tgtgtatttg cattctataa attgtacagc
6121 tgccttccac ccatgctggc cctcttggtc tgtgtcattg gatttcccat gtgtgttagt
```

Figure 3 (continued)

```
6181 cattttctgc tactgtaaca aacatccaag acaatcgact tataacaaga aaagatttac
6241 ttttaactct tggttttgga ggttttagct cataatcagt tggtctggct gcttttgtac
6301 cctgcctcat gatgtttgac tgggtggatg tatgtacatt gagttgggtg tacatgtgtg
6361 tttggtgtgt gtgtgtgttt agggtgtgtg tgtgtatgtg tgtgtgtgta ggccagaggc
6421 agatgttgag tgtatttctc aacactcact cttcagtttt gagacagggt ttctcactga
6481 tcctggagct cactaatggc ttagctggct ggccagtgag ccccagggac ccacctgtct
6541 ctagctcccc tccccagccc cttcccctgc ccccctctta caagtccgct ggggatggga
6601 tctcaagtct tcatgtacag caagcatgaa gcactttact gactgggccg ctgccccaac
6661 ccaggatcaa cctcttaata ggttccaccc tgtcccatag tgccaagctg ggtattgtat
6721 cttcatgttt aatacacggg ctgttagaag acaacgcaga gccaatgaca ctccatgcta
6781 ccctcttcct ggtctagccc agggtccaca catgctgaca ttctccttct gacctctctg
6841 gcagcaggcc ctctcaacca taatgtgccc cttcttttca tcttagaggc tggacctcat
6901 tcttatcctg gagactatgc acacaaacag ttctcaaggt tgccatctag tccctaacc
6961 cctgctacct gccacacagg tctcgagggc agctctcttt tctacacttc ctctctaacc
7021 ctccagaaag gaacaaggca ccaatctgta gagcctggag ttctgtttag ctccttggag
7081 tttctgttga catttctacc ttccacttcc agctgcggca tccaggtggc ctccaaactc
7141 ttaactgctg cccctattct ttgaatttcc ttgattgttc agatccccag aagtcaggca
7201 tagtgctgtg ggggagtaga aatgggtggg tccttcaagt tcactggaca gacattatct
7261 gaaccgatga ggttcagtga gagatcctgt ctcaaaagat caaggtggct tggcagctac
7321 aggtacttac agtgcaaacc tgggtcctcg agttttatct ctggaactga taaaaacaaa
7381 gactgcacag agttgtcctc tgacctacat atgcacacat caccacaata ttttttttca
7441 atcattgaaa gtttcttatg atcaaggaca gtgatcaaag aaagatagcc catgtcacct
7501 tctgaccctc acaagtccat atatcacatg cgcacacaca ttacagtaca gagaggggga
7561 gggagatgga cacacacaca cacagtggaa aaaacaagca caggcctgta tctgtgatag
7621 cttcatcttt ttctagactt tcactctgat gcttcttgct caaggcagct caaaaggtga
7681 acattttgct tatcttcctg tgagccagga gcttaccggc tctacctcca aactctcaca
7741 gaactgacat ccaccctgga catggatctg aaccttccta gggtcacaga catctcagag
7801 aatcccctga agctacaga atattcttta gaaaaatcaa gtgatggctg agttttaggt
7861 tcagtagagg agagagcctg acccttctgct tggaccacca aacatctgat tatatttctg
7921 cacagagatg gtttttgggg ggggggggtg gctcagattt ggtgggcttc tatctccttg
7981 gaaactcaca tatgtacata cccctgggac aaacctaaaa gctttatgct ttgtgttata
8041 aattgaatca ctttgcattt gactacttcc atatttccat ttccaaatat gtataacata
8101 gagacagcca ggttggtttt gaactcacag tcttcctgcc tcagactcct gagtgctggg
8161 atcatggggc atgtgccagc acaccaagcc tcagtaggtt tttcataaat acagactaac
8221 agtccatctc cctcttagtc tctttgtata cgtttttcatc ttcagtgagt cccaacatcc
8281 taatctatcc ttttactaac tgtaaataaa gtggtctgcc ctagagcaga tacacttaca
8341 tagcacttaa gtgggccaga gggacataag gaggagccct catacccaga actgtctcct
8401 acagagcact ttatagactg gagcagaata tatatgtgtt cttacatgta ggacttatct
8461 tttttttttt ccatttttta ttaggtattt cgctcattta catttgcaat gctataccaa
8521 aagtccccca tagccaccca cccccctctcc cctacccacc cactcccctt ttatggcccct
8581 ggcgttcccc tgtactgggg catataaagt ttgcgtgtcc aatgggcctc tctttcgagt
8641 gatggccgac taggccatct tttgatgcat atgcagctag agtcaagagc tccggggtac
8701 tggttagttc ataatgttgt tccacctata gggttgcaga tcccttagc ttctttggta
8761 ctttctctag ctccttcatt ggggggccatg tgatccatcc aatagccgac tgtgagcatc
8821 cacttctatg tttgctaggc ccaggcatac tctgacaaga gacagctata tcagggtcct
8881 ttcagcataa tcttgctagt gtatgcaatg gtgtcagcat ttggaagctg attatgggat
8941 ggatccccgg atatgctagt gtctacatgg tccatccttt tatctcagct ccaaactttg
9001 tctctgtaac tccttccatg ggtgttttgt tccacttct aaggagggc atagtgttca
9061 cacttcagtc ttcatttttc ttgagtttca tgtgtttagg aaattgtatc ttatatcttg
9121 ggtatcttag gttttgggct aatatccact tatcagtgag tacatattgt gtgagttcct
9181 ttgtgaatgt gttacctcac tcaggatgat gccctccagg tccatccatt tggctaggaa
9241 tttcataaat tcattctttt taatagctga gtagtactcc attgtgtaga tgtaccacat
9301 tttctgtatc cattcctctg ttgagggca tctgggttcc ttccagcttc tggctattat
9361 aaataaggct gctatgaaca tagtggagca tgtgtccttc ttaccagttg gggcatcttc
9421 tggatatatg cccaaggact tatcttgtgt tccatggaag gtgcccatg ggtattcata
9481 gtcctccctg agcaggcatc tttcctccta tgctgaatgg ttccacatgc aaggagggaa
9541 gtcatttctg tctgagccaa ctgaccccg aacactggca gacccctga ctctccactt
9601 ctgttcctag ctccagtttc cagcaggatg ttccagtggc tgatgcaagc gttgatgctg
9661 ccactattgc tgctcccttt aggtcgagct gctcccaagg atggagttgc aaggtaagag
```

Figure 3 (continued)

```
 9721 gattaggaag gcagggctgg ggcaaggaga gttctggaaa gatgttagga ctctagggga
 9781 gccagaagcc tgaagaaata gtctccatca tctccaggta cagcacccca agtagggcct
 9841 tggtgcatgc ttgtagaact ctttgcagcc aagagttcag ctctagccca gtgtgaagca
 9901 tcagaaggaa gccagaaaca cagacagaga ctatcaactt agaataagac ctgacactgg
 9961 gaatgccaag aaaatgggtc gttagcttaa tatctctgac ttactaggac tgctttcttt
10021 tttttaatt atttattatt ataaatgcgt acactgtagc tgtcttcaga tacaccagaa
10081 gagggtgtca gatctcatta cagatggttg tgagccacca tgtggttgct gggatttgaa
10141 ctcaggacct tcggaagagc agtcagtgct cttaaccgct gagccatctc tccagcccta
10201 gaactgcttt cttacagtca gtatgtgcat tgggatcatg ggaaagtgga gcgctggcaa
10261 cagtgaccaa actgtctggg acaactcctg tcacttctgg atcccagggt gatgtgggca
10321 aacagtagcc acatgcagaa gtaggaatac ttgagattct gggcagacat aaagtctggg
10381 ctggcatcca taccctctgt ttcaaaaggg aagaggcatg atgtgccaag gagcaaaatg
10441 ggtctgtaga atcctgggca ctgctaccag cctcaggagg accataagaa accattccgt
10501 cttggcacac actggaccat catcttgggc ctctatcgtg tgtctgctat ggcagcctca
10561 acctcactag gcattttctt ttttaatttt tttaagactt atttatttat tttatgtata
10621 tgtgtacagg cacagatctt tagagacacc agaagagggc atcagatctc actacagatg
10681 gttgtgagcc acaattacag gttgctagga gttgaactct cagaagagaa gcaagtgctc
10741 ttaaccactg aaacagcttg ccagtccctt ctttgtgttt tctaaagtta actaaggcac
10801 ctgagctgca aaacaacagt tttagggatt aaagttctgt ttctagtgac actctagctt
10861 tttccctaca gccttttctg ggaatttgga gggacatctc cctttgagtc ttgagtctgg
10921 ggagaaatct accaagtggc tgctaagcta ggcatgggc tgctgtttct ctcctgttct
10981 aggttggacc ctgaggtaca acagcagctc acacccaacc ctttccagcc aggccctgag
11041 cagctccggt gagtaagttg ggggctttca gcaggcatta actggacaag tgacaggtca
11101 cagacaggac tctccctgct gacttcccac tttttcaata gacatctgca gaattatctc
11161 aagggactag agaagatgga agaggatcct gagcacatgg accgggagca aggtgaaggc
11221 ctggtgctgg gaggatacag gaagggacct ggggctgtgt ggctgccctg tggcttcttg
11281 ctttctctaa cccagattct cttctgtagt cctgctttcg ctctttgctc ttcatgacta
11341 tgaccagaat ggacagctgg acggcctgga gctactgtcc atgctgacag cagctctggc
11401 ccctggagct gcacacttc ccatcaaccc ggtaagcgct cctggaaatc gtgagagact
11461 agcaacttgg agctttggtc cttttcatca tgacttttgg tagactcctg gtaaaaggga
11521 agctcagatc ctatgtggca gggatgaggc tgttggagag cggctgggtt cctgaaaaca
11581 cctctggtaa ctgtttccac aggtgatcct agtagtagac tcggtgctcg agactcagga
11641 cctggatgga gacgggctca tgactcctgc agagctcatc aacttcccag aagtccccaa
11701 acacacagag tcccttcccc cagctctcca ggagccacaa cctgctggaa gtcagccact
11761 tttagccaac agtccactgc agtcagaaac ccagcagtcc ctggggacta aagaaattag
11821 gagccaggta gaggccaaga gggcgtcctt ggagcctgaa caggaggctg gacatcagac
11881 agagggaaaa gtagatatccc taagccctga agaggaggct aggggacagg cagagtctga
11941 aggagatgtt ccaggtccca gagaaggtgc tgaggaacag gtggagatca aggacaatga
12001 aggagaagcc aaagaactgc tggtggaaac actggagagc ctaaacactc caaatgaggc
12061 tgaggctcat agcatccaat tggagaacga tgagatatga gcccgacggc ataggctcaa
12121 gcccctcaga atctcagtgc agagcagaag catggtgttg aatatggtgg ggttagagcc
12181 acctctgaca tggggacggt ggtgcaagct agtaacccca gaagcattga gagctccggg
12241 ctagcctagg ccacatagca agtttgaagc caggctgggc tactgcgtaa gaccctgtct
12301 tgatgagggg gaaaaaagca ctcccatgtc tcctttctgg cttcagtgga aagtaggact
12361 ttctgtgcag ctcagggaga ccataagctg agaagcagct ttcaggccac aaacaaccaa
12421 taaagaacag aacaaatctg tctccacag
```

Figure 3 (continued)

I Ltb4r1:

```
   1 ggcactaaga cagattcaag gattgtatat ccaacaacta gacaagacat taccttctga
  61 tcagcatcag ggaaaccctg taagtatcct aggaatgata tggtgtgtgt gtgtgtgtgt
 121 atttgaatat gtttatgtgt atgtgtgtga gtatgtcagt atggtgtgtg tgtttatgta
 181 tgcgtcagtg tgttgtgtgt gagagagtca gtatggtgtc tgtgtgtgtg tgtgtgtgtg
 241 tgtgtgtgtg tgtggtgtgt gtgtatgtgt gtgtgagtgt gtttatgtgt gtgtgtgaat
 301 gtatgtcagt atgttgtgtg tgtttatgaa tgtgagtgtc agtgtgttat gggtgagtat
 361 gtatgtgagt gtgtgtgtgt gtgtgagtgt gtgtgtgtgt gtgtgagtat ggtgtgtgtg
 421 tttgagtgtg tatgtgaatg tcagtgtgtt gtgggtgagt gtgtgtgtgt gtcagtatgg
 481 tgtgtgtgtc aattataact tgaagagatg tgagacaga atccccaaag aaagcccgac
 541 ctctgtaaag ggatggttct tgtccattaa ctcttccctg ccctgctctt cctggtgccc
 601 catggtcagc tctagagagt gtgggtaggt gactggagaa agtggacagt ggcctcttgg
 661 gagatagagg agttagcctt tcaaggcgtg cacagtgctg aggaaagtct cccagcctgg
 721 tgctgggttc caggctctct taaggaaacg agtgtgaagg gttttggaaa tactgctgtt
 781 gctgtacatt ttgcaactgg gtctgaagca aagaaggggc cccacagcct ggttaggaaa
 841 ttagtctttc tattcaacca ggcgccttta agacaatgag gttggcaggg cgtggtggtg
 901 cacgccttta atcccagcac ttgggaggca gaggcaggca aatttctgag ttcgaggcca
 961 gcctggtcta cagagtgagt tccaggacag ccaggactac acagagaaac cctgtctcaa
1021 aaaaccaaaa aaaaaaaaaa aaaaaaaaaa aaaaaaaaaa agagcaatga ggttgacagt
1081 gatggggtga catattttga aggtgcctct gaaacttctg attttggaga ccagagtact
1141 ccatgctagt ttgatgtggc tgggggtcaa gaatcctttg gctttcccct catggtgtgt
1201 tccactttca ctctctaggt ccttttgatg gctgcaaaca ctacatctcc tgcagcacct
1261 tcttctcctg gtggcatgtc cctgtctctg ttgcccattg ttctactgtc tgtggccctg
1321 gctgtggggc ttcctggcaa tagctttgta gtgtggagca tcctgaaaag gatgcagaaa
1381 cgcacggtca ccgccctgct ggtgctgaac ttggccctgg ccgacttggc tgtgttgctc
1441 actgctccct ttttcctcca ctttctggct cgaggcacct ggagttttag agagatgggt
1501 tgccgcctgt gccactatgt ctgtggaata agcatgtatg ccagtgtcct gcttataacc
1561 atcatgagtc tggaccgatc actggcagtg gcccgccct ttatgtccca aaaggttcgt
1621 actaaggcct ttgcccgatg ggtgctggca ggcatctggg tggtgtcttt tctgctggcc
1681 ataccggtcc ttgtgtaccg tacagtaaaa tggaacaaca ggactctgat ctgcgctccg
1741 aactatccca acaaagagca taaagtcttc catctgctct tcgaagccat cacgggcttc
1801 ctgctgccct tcctagcggt ggtggccagc tactctgaca tcgggcgcag gctgcaggct
1861 cggcgcttcc gccgtagtcg ccgcaccggc cgcctggtgg tgctcattat cctggccttc
1921 gccgccttct ggctgcctta ccacctggtg aacctggtgg aagccggccg cacagtggcc
1981 ggctgggaca agaacagccc tgcggggcag cgtctgaggc tggcccgcta tgtgctcatc
2041 gcgctggcct tcctgagcag cagcgtgaac ccggtgctgt acgcgtgcgc gggcggcggc
2101 ctgctgcgtt cggcgggcgt gggcttcgtg gtcaagctac tggagggcac tggctcggag
2161 gtgtccagca cccgccgcgg gggcactctg gtccagaccc gaaggacac acctgcctgt
2221 cctgagcctg gccccaccga cagcttcatg acttcctcca ccattcctga gtcttcgaag
2281 tgaactgcag taggctgggt tatgacacaa ctcataactc tggcctgacc cacttctgta
2341 cctggaggag aacatgttgg ggactgggct taagcggaag agagggaggg gtggggcaag
2401 tcagggcaga gagacaggat gctctggcct ggcttctgca ggcagcttca cgattaaaac
2461 taaagtctga aatc
```

Figure 3 (continued)

J Cbr3:

```
   1 agtcgcagcg ccgggtccca gaatctagtc ctacgccacg gttttgacca cgcgtgaccc
  61 gctgcccagc cggcccggcc atcaggtggt ccgtgtgtcc ctctgacatg tcgtcctgca
 121 gccgcgtggc cctggtaact ggggctaaca aaggcatcgg ctttgcgatc acgcgtgacc
 181 tgtgtcggaa attctccggg gacgtggtgc tcacggcgcg ggacgaggcg cggggccgcg
 241 cggcggtgca gcagctgcag gcggagggcc tgagcccacg cttccaccag ctggacatcg
 301 acgacccgca gagcatccgt gcgctgcgcg actttctgcg caaggagtac ggggactta
 361 acgtgctggt caacaacgcg ggcatcgcct ttagaagtag gtgtggggct ccaggaggag
 421 gtgtcccggg gttttccgag ggtgctgggc agtgagcctc tgggatccgg aggctgcgcc
 481 atcccgcctg ggtgcacccg gctcgcgctc tgcgtggcga gttccccgt gcggtgactc
 541 gggtgcgggc ccgcccaggc accccactcc atgcccgacc cggccggcgg cctgtgcggg
 601 cctgtgctcc gccggaggcc ctccttggaa ctttcagctg cgcctgtttg gaagaaaacc
 661 ggtctcttgg gaggggacca cgccttgtca agctcatcag ctttctgtcc cacgcacgaa
 721 ggcttttctc agagaagggt cttccaaaaa aatagggttg gagctttcgc ttcgcgtgaa
 781 acaagggcga attcatagat gccagtagat atctgctgag gacaggaaat gggtcgcccg
 841 gacacaatta gcgccctggc acgatagtgg gtttcctacc cgctttaatg gagcgttttg
 901 agaggctctg gcaaaaagga agcgagctct gcttccctcc tcctcgggga actaggtttg
 961 ttattaaact tgcaagtgcg gtttggaaat catcttcctt taggggaaaa aaaacccaaa
1021 aaaacaaaac aagatcgctt actctaacaa atgtccaatt agcaaaatta tccagttgcc
1081 atgtgctgga actgaaacaa acattccagc ttcactgaaa atgctgagag agccggagac
1141 taacgaggga gggagactat tgtgcagccg aaaactctcc agttggccct ggacacccat
1201 aggcgccttg cgtgagagcc aagacaccct tgtacccgca cttccaaact ctggcatgtg
1261 ggctttgggg aaggggaggg gcgagctcac cacctcagcc actctcagcg ttgtcggatg
1321 gaaggtttgg tgaattatgg ccctggaggt tcatacttaa atgtgggcca tgtgtatgca
1381 aatctgagca gcagctgccc caccacacaa gctgaggtct tacaccagcc tcaccagagc
1441 atcttttccc aacctccagg aacctattc aagcttgaga caggaagatc aaaactgagt
1501 gttcttgaga cgcgacatga gcgtggctga tgagaaactt gaggtgtgga ccagaaagtt
1561 ctttccttat gctcttaaga cctttagaat gatcaagttc tagtttaaag gtgtgtgtgt
1621 gtgtacttta cagatgtgtg tatcaccaca ctcagcaaga ctgtcctaaa gttagtacac
1681 tttcccttta gctgttatgt gatgagatcc aacttggcca cacgagtttc agaggaaaat
1741 gtaattcttt tttctttcct tttcttttct tttctttctt tctttctttc tttttttttt
1801 tttttttttt ttttgtgtgc ttttcaaagt ggatgaccca acacccttcg acattcaagc
1861 tgaggtgaca ctgaagacga acttttttgc cactagaaat gtctgcactg agttactgcc
1921 tataatgaaa ccacatggta agtccaaagt aggactactg tccctcggga agtggccctc
1981 ggtccctcaa ataggcaac caacagggac cactcagggc tgccatttgc ttgtgagatg
2041 gagggtaaaa actgccttat tttatcaagg tgtctggctc tgtacttgag ccttttggct
2101 gtggttgtca gaaccctgtg gtactgatca gttcttgggg tctgtgtcat gagctcaacc
2161 tccatcacag actgcagcat ggccccaaag gtctgtgaca gtcttagaga gttgccctcc
2221 tgccccgac attgcaagga tgggcccacc cctgacttat ctgccattat aacagtcctt
2281 ctgttccttt cttatgtcaa acaaacaaac gaacaaacaa acaaaaagct tatgagaagg
2341 tgtttttcta aatgttgtca gctgagagaa tccgaaagaa gtagttttttt gtggggaaca
2401 ccttacctcc agcccatgag ggttcaatat ttattattaa ttatcattag tttccttcta
2461 atgtttattg ggtgcccacc attatacca gcactggtag taaaaactgg gcccatcata
2521 tacaagagga ccctttcatc cacagagcct ggagctgagc tgggagatag agattttcta
2581 acaaagactc taaggtgtga gatgccaac ttgatagaga gaggcacttc tctggggatt
2641 tcccttttct gagattgact gtggttctga ggggaagcgc tgttgttttg ttgttgttgt
2701 ttttttaagg ctttaattta ttttatgtat gagtactcta cctgtatgtg catctgttca
2761 ccagcagagg gcatcagatc tcattacaga tggttgtgag ccaccatgtg gttgctgggg
2821 actgagctca ggacctctgg aagagcagtc agtgctctta acctctgagc catctctcca
2881 gcccccggct attgttttta aaaacataa tgttcagggc cagagagaga gagttcggag
2941 attaagagca cttgttgctc ttgcagaaga catgggctca gttcccatgg tttcctgcac
3001 ctatatagct cacagccatt ggtaactcca gttccagagg atccaacacc ctattctaac
3061 ctctttgggc acagggcaat gtgcacatac atacatacat acatacaggc aaaacactca
3121 tacagacaca tagaataaat agaaattaaa aaatttaatt ttcttaatat tttgaaagag
3181 aattagctca ggatttagga gaattgggtt cccgcccccc cccctatttt ttttttttta
```

Figure 3 (continued)

```
3241 aaccaggatc taactctaca gtgtttctg gccttgaatt tgccttgtag accaggctgg
3301 ccttgaacct ctgacgcctc ccctgcctt tgcttcctgg atgctgggat cccaggcatg
3361 catccctatc ccagcttatc tgtaagaaaa tgtcagtctg aaaactgtag tgagagctga
3421 acttggaccc ctgcccgcca cctgctcact cctccctcat ttcttagtgg gatggattcc
3481 caggaagtct cagcccccc cctcccccc ccccccccc ccccccccc ccccccccg
3541 cacacacctg cgatccctga actcagaagc ccagcttggc cttcactgcc gattgcctga
3601 tcgaataaac ttcattctgt tgaaataaga attacagcat caagtgagag ccaagccatt
3661 ttgaaagtta aaggaaagct ctcagaggta gggggagggg caagaaccag gtgaaccatc
3721 tttaatcaag cctgcagctt cctgccctga gggatctctg actgataggg catctgccta
3781 ggacaggtga cttggctaca cactgttcgc tgaaagacac cgtgcttact atcacggact
3841 tatactttct gtttagcttt tagcaccta ctttccagga tcctaggtct tgcttactca
3901 ctcaagacaa aaaatagctt caacaacaat taagtcacta gagggagcta cttgcctgtt
3961 ctttctttaa aaaacaaaaa caagtggaag ttgtttctgt atgcatggag acacacatag
4021 acacacatgc acaagcatgc atgtgcacac acacacacat gcacactcat gtgtgccaga
4081 caatgctgcc gctggtagat ggtgtggtgt cgtccctctt agagctggct ggaccatctg
4141 gttaatagga tgatctttga tcaccctcca gaacctccca cacatgtgtc cccgcatcaa
4201 agaggacaca agataacttc cccctataat gtggattaga actccctcca aggcacctcg
4261 cagctcctac agttagtgtt tattgtcttc cctgccctct ccctcactcc ctctcttcat
4321 tctctataca ctttgcagac ctaaaacttc atagtccaag ctggccttga actcacagcc
4381 tcccaattgc tggaatcata ttatgaaccc tactgcctct tcagtagctg tgaactttg
4441 ccaatgtgaa tattaactca tattcatgaa ttggttcatt gtcatgttgc tggtatctta
4501 gactaatgaa gttggaacca gagtggagaa tgggtctccc tccagggtgg cttggatgaa
4561 gttatcacta gagatacact tctaggagag gctcagggat ggaggtggct gcccacagcc
4621 ctagccaact gcacatctag ggaattgaga gccttcatcc tgaagtctcc ttcaaggcac
4681 tgttccttgg gattcaggtg ataagaaggg ggattatttg tgttgaaaga ggaggttttt
4741 ggttttgtct ttgttttttt gttttttttt tttttaataa aacggcctga tgattctgtc
4801 acctgccatg gtgacttggc tctagagata gtcacaatag gtacgccggg tctggtctgg
4861 ggtatactcc aggcttttct gccatgacaa ctgctttaaa aaatgaacac agacacgatg
4921 acaactaaag ggtatatctg ctcaagctag gtggaagtta gagttctgaa caaaggaaaa
4981 cctgggtagc tgataccaga agaactgagg atctcaattt gcatagcaca tcccatcctg
5041 actgagcaag ttcttaggag gctgatcctg gcctgcaagt gggatgagtt tgcccctgtg
5101 gtattttaa ctttgaggct tgggtggccc ttgggccctg ggtatctgtt ttgtggcttt
5161 gttgtgaaaa catgaaacag atgtgatccc aaggattcct ccctgatgca gtactttagt
5221 ttccttttgg gtggtcccca gctgccacag atctgcagac ccatgaggca accatcttta
5281 aaagcaaggc ttctcaacct ttctccacca gtgaccttt cactctgggg gaaatttaa
5341 tgcaacagca agtatatgaa attggtaaac caacattttc tgataatgaa ccatcaagac
5401 atttcattta aaatgattct tttaaagctg gggatgtagc tcagttgtta tggtacttgc
5461 ctggcacacc gaggaggtcc tcggtttata tattcctagt aatatataaa ttggatatga
5521 tagcaaatgc ctgcactcct aaggtggagg caggaggatc agaaatccaa ggttaccctc
5581 agctgcctgt agagagtttg aagcacaacc tgagatacat gagactctgt caaaaaaaa
5641 aaaagcacat agaattttac cagttaagat taaggcaaat ttgcatacta atgagatgca
5701 gttcttcttt atttacatag aagtttagat cctggttgag taattggtgc tgcaggatgc
5761 agcaaatctt caacactttc caaattcaa tcaacatttt tattttacaa ccattggtac
5821 caagaccacc tcttcacata aatacatatt acagaatgtt gatagtatgt tagggccatt
5881 tcaaaagtac ttggaaattc tgtcctaagc tcaagccaaa attcatctca ctaatcttaa
5941 gacagcacct ccagcaatag tctttagaat gaaacattct aacataatac agtccaaga
6001 tacactaacc tgatatttgt gtgctgtaga atgaaacatt ctaacataat tcagtccaaa
6061 gttacgccaa cctgatgccc acagactgtg gaatgatggg aggaaaatgt caaaacattg
6121 gttctagcaa ttgatctgtt gttttccgt aagagcagga aacttggcct gtgcaggaac
6181 aagccacggc aggtcaccac atacgagttc cagacttgag tagaagtgtt ttacacggtg
6241 cttcgtggca tttagtagca aaatggcatc taaaatgcac gtgcgtgctc agaaaccaag
6301 gatgcagtaa agtcccgtga cacaaaactg ttgaacactg ccagaaaaac ctcagattta
6361 gagtgcattt gatttttaaat tcattttag acacggcaca ttttttaaac ttttttactat
6421 tacatatatg caaacatata tgtgtataca tgtaaacata atagtaaaaa ggttgcaaa
```

Figure 3 (continued)

```
6481 tatatatcat atatatagtt atagaaggga agcctggtca gtggtagaga tgtgtttgtc
6541 cccttggaat acacacaaac agacacatac acacatacac acacacacag attgtatgtc
6601 ttctagactc gctatttgtt catgcattta tttatttgaa ggggtgtgtg tgtttatatg
6661 catcatgtgt ggatgtcaga ggacaaacca caggactcag ttctcccact ttggagcctc
6721 agaatggaac tctggggctg gagagatggc tcagtggtta agatcactga ctgctcttcc
6781 agaggtcttg agttcagttc ccagcaaccg catgatggct cacaaccatc tgtagcagga
6841 tgctctctct ggtatgtctg agaacagcaa caatgtactg ttgctacata aaagaataaa
6901 taaatctttt ttaaaaatta aaaaaaaaaa aaaagtggaa ctcaggtcat ccggctcaga
6961 ggcaagagcc tttagtgtgg agctgtctcc gcggcttttc cttctgtttt attagcagtt
7021 aaacccacac tgcatggaga ctgcggtgca cacctccgta ccttctgaaa tacccttttgt
7081 gatgggcttt cctggcgttg tctgttgcag gtagagtggt gaacatcagc agtctgcagg
7141 ggttaaaagc ccttgagaac tgcagggaag atcttcagga aaagttccga tgtgacacac
7201 ttaccgaggt ggacctggtc gacctcatga aaaagtttgt ggaggataca aaaaatgaag
7261 tccatgagag ggaaggttgg ccagactcgg cttacggggt gtcgaagctg ggggtgacag
7321 tccttacgag gatcctggcc cggcagctgg atgaaaagag gaaagcggac aggattctgc
7381 tcaatgcctg ctgcccggga tgggtgaaga ccgacatggc gagggaccag ggctcccgga
7441 ccgtggaaga gggggccgaa acccccgttt acttggctct cctgcctcca gatgccactg
7501 aacctcacgg ccagctagtc cgtgacaaag ttgtgcaaac ttggtgaacg tctgctctgg
7561 ggcttgtttg ataaacgtta gcgggagaga tgaatgcagc ctggtgtggt ctgattcttt
7621 cccacatcaa ggggaaggt ccgttcctat ctgcggctct gcaaactcag tctgaacaat
7681 tcgctgtgtc cacactctca gctcatcgtg ttttcaacca gttaatgtgc ctgctttgat
7741 tttcaaatta aaagatttg ttttattt
```

Figure 3 (continued)

K <u>Btg2:</u>
```
   1 agtggtatga aaggcgcagc ccggggaaag tccgggcaga gcccgagagg tggccagacc
  61 gtcatcatcg ttctaataca gctacttcct cagccaccgg tatgagccac gggaagagaa
 121 ccgacatgct cccggagatc gccgccgccg tgggtttcct ctccagtctc ctgaggactc
 181 ggggctgcgt gagcgagcag agactcaagg ttttcagtag ggcgctccag gacgcactga
 241 ccggtgagca cacgtcgggg tcttggaacc actcgggcgc ggccacttct tgcctggggt
 301 gtctttatca ctgttctgtg acggggaccc ctacgcgaac aactccgggt ctcagatgtc
 361 tttctctaat taatctctga ggccactgat ggtcctctgt cccttcggtt aagtccccgt
 421 ctcccagccc tccagtcccc gcctcgctcc cgaggctccg accctcttcc ttgagtacat
 481 tctgagaccc tgacaacacc atgagaaaag tcagtgtgtg tgtgtattca gagtccgagc
 541 tcacccttat ctccgaatct tggagaacaa cagaccctca ggggatgtga agccaggcca
 601 agctgtgcga ctttatgcg caattgaact ttctagacaa ctcttgagtc ctagccactg
 661 ttgctgtata gtcctgagcc tgtcatcata caggcccatt ctgccgcgtg tttacccgct
 721 gcaagttgta atctgggccc cctttgtatt ttttctttt tggtccctct tcaccatctg
 781 ccacctattg tagtacagaa aagagcctgg tagcctagcc aactgcgagg gcggggaggg
 841 ggtgtgtgtg ttatggaggc agggtgtgag ggacggaggt ggaggagtga taagccaccc
 901 tttagcctct gtccgcagct gttataactg gttggttgcc ttgggctgcg atagccatct
 961 ctcaacatgt tggcacagat ctgaggacca acagctgttt catcaaaaca aaaccatttt
1021 ttatccccctt acctttgcta aagatctcaa aactcttctg atgcggaagg gatgagaggc
1081 cttgtgactt gttgggcaac caacaacatt ggccgcttac ctaccggctt tgaaatttca
1141 gtgccttggt cgtcagaggc cctgccggtt cttgctagcc cttcctgcct taaacaggat
1201 tgtgccaaaa atatccatga ccaccataga gcatctacct gaaagctctg gggctgcttt
1261 ccagtgtaca aaaacttgga aaggacccag gaatctttct aagtggcagg gggagtttaa
1321 ggagaggctc ttaaatactg tcgctgagaa gaggaagtct cctccccagc cctctcccct
1381 catcctcccc ttgtggtaaa catcagagaa tgctttctaa cggcgcatct tcctcttgtt
1441 tttttccaca gatcattaca aacaccactg gtttccagaa aaaccatcca aaggttctgg
1501 ctatcgctgt atccgtatca accacaagat ggaccccatc atcagcaagg tggccagcca
1561 gattggactc agccagcccc agctgcaccg gctgctgccc agtgagctga ccctgtgggt
1621 tgatccctat gaagtgtctt accgcatcgg ggaggatggc tccatctgtg tcctgtatga
1681 ggaggccccg gtggctgcct cctatgggct cctcacctgc aagaaccaga tgatgctggg
1741 caggagcagc ccctcgaaga actatgtgat ggccgtctcc agctagatag gagccacccg
1801 accctggcac tctactgttc tcatgctgcc ctgacaacag gccaccgtat acctcaacct
1861 ggggaactgt attttttaaaa tgaagagcta tttatacatg ttttttttt tttttttaa
1921 gaaaagagga aaaaaccaa aagatttttt taaaaaaaa aagaaaaaga aaaacaattc
1981 tttaaaggga gctgcttgga agtggcctcc ccaggtgcct tggagagaa ctgttcttga
2041 ttgcatctgt gagccagtgt ttgcctaggg aatggggttg gggattggcc tagccaaggt
2101 aaaagggggat tcttggctga tcccccagg aggtggtgga agggagcaag gttagcaact
2161 gtgaatgaga ggggtcaggg tctgctctgg gttaccgtcc cagctgggat gcctgtatgc
2221 ctggtccctc tcttactcag gggcattcaa gcctgatctt aaataatact acattgccta
2281 atcttctctt ttgttttcg gctgagatca ggggcagact gaaaggcctc tcctgtccct
2341 tctgttctaa gcagtctctt gaagccgtgt ctcgtttctg agtctaccct tggggggctg
2401 aagagcttgc ttcccagccc ggaatctgtc taaacatttt tggagggtg ggatgtaagg
2461 caggcgcgca aagactttgg ggctaagatg gagaggacct gcacaaaacc tttgctttgc
2521 tctgtgctgc tttgtatggg tggatagtga ataatttagg gatgatttgc aatgaatttt
2581 tgggacccaa agagtatcca atggggggtag gtctttttgga cccagtcctt ccttttggga
2641 accacacgac agtctgaatg ctgctaccac tattccttg agaggtggct caaagctcca
2701 gggaactcca agtcctttct tactgccttc tcttcaagag caaccttccc cattttttct
2761 ttccccttc ctgcggttgg gtcctggagg gccctatttc ctaggacaag cgttctcagt
2821 cactgtgcaa tagtcccagg atgctctgag accggacctc ccagcccctc ctgatgccct
2881 ggtaggtttt agggacccat tcttcccatt cttctagggg ttctgactgg ctggtgggcc
2941 ttgcggagat cttcctgggc cacagggagg gcacctgtgc actgcaggac tacctggtat
3001 tcttgtaggg ctgccatgaa gagtcaaacc ttgggcacag ctttagctcc ttggtgctca
3061 gagcacctgt ggggggaggtt acctctctct ctctcttagt aaaatccaaa tttatttgta
3121 gatgtgtgca atatttactg ttctgggttg gagaaaattg ggaaacactg ggaagaaatg
3181 gctttccttc aggttcagtg acactgatga gggcttctta gaaggcctca agtctctcaa
3241 actgaaggac agagctagag ctagcccgtc accccttggt gaggattccc ttccccgttt
3301 ctctccaccg ccatggcatc ctgtgtccta gatttctcag ctcctcagtt tctgctcaaa
```

Figure 3 (continued)

```
3361 ggtgctattt accaaactct ctgcctgccc gggcagacag gccccagctt cgcacagcct
3421 tcccaggtgg cttcgtctct cttgctttaa ccttaactct gggcccacag acctgagagc
3481 tgtggcctac aacaaagctg tgaattgttc cagatggttc ttgtgttttg tccgcacaca
3541 ggtgcctgcc gtttagaagc tgcctcctgg tctcatgctt aaatcttcaa ttctttactg
3601 tccttgttca ctttagaaat gacaaaccct agagctggac tgttgagcag gcctgtctct
3661 cttattaagt aaaaataaga aatagtggta agtttgtaag ctattctgac agaaaagaca
3721 aaggttacta attgtataat agcgctttta tatggaagac tgtacagctt tatggacaaa
3781 tgtaaacttt ctttttttgtt tttaataaaa atgtagcaga tcgtgtaatg tgtagagaag
3841 gtggaattcc atagcgctga ctggccctct tagatacaaa ccccttcgtg tttcgtggac
3901 ttcatcagtt gtcctgagct ccgtctgcag catgcagacg ttataaaaga taccctaggt
3961 ttgtgacgag gttgcttcca ttgcatcccc tctccttggg aggcggctcc atacttctgt
4021 ccttgtgaat attgtcacag gtctcttaaa aaacaaacaa acaaaaaagc ccaaaaacca
4081 atatgttatc tgcacactct gcagccagtt ccatagtttt gctcttggcc attcagcaca
4141 ttgaagagct ggccagctgt gtccacatct gcgcaagcaa gccaccacgg ctggaaacta
4201 tataaagaaa agaaaccatc cagaaagttc caaagacaca agacttgggt ttggcacaca
4261 ctaagcacac cagtgcactc gatgcgactg c
```

Figure 4

A Gpx2:
```
   1 agtcatcccg ggaatgctca aaggcccttt gtgaagtcct ttcggtcttc tccggctcct
  61 cctttcttcc caccggtcta aaggacttaa ggaggctcac agagcagggc agggctcact
 121 gctcttcagc atggcttaca ttgccaagtc gttctacgat ctcagtgccg ttggcctgga
 181 tggggagaag atagacttca atacgttcag aggcagggct gtgctgattg agaatgtggc
 241 gtcactctga ggaacaacta cccgggacta caaccagctc aatgagctgc aatgtcgctt
 301 tcccaggcgc ctggtagttc tcggcttccc ttgcaaccag ttcggacatc aggtgaggag
 361 ttccttgggt tctatccaag gagttgatgg acagagcttg agtggaagaa agggttgagt
 421 gtgtcttggg atatctggac ttgaagggca tgctgcatca attgaggtct aggtgaatgt
 481 aaaacatcac agggaagaag tagatatggt ctaagagtaa gcattgaggg tgtgccttt
 541 agtactgtct ttccaaaatg agggttgctt ccaggtctct ccactgtgtc tttgagtact
 601 tcattagtta cttgttgaac aaatgagtgg agaaaatagg ttaagaatca ctacgttggc
 661 atggagggac attcctgtac tcctaggatt gatgtgagtt tggcactaac ctgggcttac
 721 cagcaaggtc tcaaaaaaat cactgtgcat acagctcagt gggtagatta cttgcccagc
 781 ctatgtgaaa ccatgggttt gatcctaagt gttgcataag ccagctgtga tagcttacct
 841 ctaatcccag cacttggaag atggagacag gaaggtcaga aattcaaggt gatccctga
 901 ctatagcaaa tatgaacctg aagaactcgt cttagacaaa caattgggat tgagatgtcg
 961 gtgacttggg agtccttact tagttccggt tgccttggtt caatgcttta atggctctga
1021 gaccattgag agaggtggct tagttttctg tttgagtttc cacatgtgtt ggtttaatag
1081 aagttgactt agctcataag tttactgtga ggctcatggc ataagacaca tgaaaagtaa
1141 ggagagagat gtggaaatag tgtgcgagta ttatttaaag gcttgtttct aatcagcaag
1201 ctggaaaagg aatatgggag aagggaaagg tccgaagcgt gcactcacct cctctggaca
1261 tcacgtgcgc cttctgtctc tgaataacag gtcagattct tacagagctt cagcatgcac
1321 gcctcaagct atctttagg gattctgttt ctctttatga tttaactgta ctagcaagcc
1381 aggtgtccct aagtggactc tctaattaga gtcgtcatag ttcaaattgc agtggcagga
1441 aggtacacag gaaggatgtc tgggacatac acaggaagga tggctgagat aaaccagaga
1501 cccagccatc actatgctca caggtccttc cccctgaagc ctctgttcag actttgccgg
1561 ggagagacag gaagggctaa accccattgg aggtgtttct caacccagga gatgcctctg
1621 gccttacacc tcacttgtgg ctggctggct ggctggctgg ctgctgaaag gagtcataac
1681 tcaatatcta cagagccaga gcacaatcag ggcagaggaa agggaaaatg gtaggttgtg
1741 tgcaagcatg cacatttgtg gacatcacat cattgtgggt cctggactaa ttaaaccta
1801 actgacaact tttaccaaca gcaggtagaa gtgcctcctt tccttctctt ccctgatctc
1861 aaggttcctt aaagcaccaa acaccattat gttaattgcc cagggtagat tagggcctga
1921 agcaactgtt aaaaagtgct gaatctctaa ctacatttgt ttgtttgttt gcttgtttat
1981 tggaatgtgt gtgagggtgt gcacacacca cagtgcatgg atagaggtta gagcacaatt
2041 tgtgagagtg gactctcctt aaatcatgtg gtattccctg gcctccaaag ttttgggtgt
2101 agcctccttt ccaccaaggc cataactggt gagatggttc aatgggcaaa agcacttgcc
2161 gcaaacctga tgacctaaat tcagttctca gaactcaggt ggtagaagga gagaagtcaa
2221 tttcataggt tgttctctga cgtgcaaagg tggcactcag tataaaataa atgtaaaaag
2281 tacaaaaacc cacaacacaa tggcagagag agagagagag agagagagag agagagagag
2341 agagagagaa aggcagagca aatggagaag aaacacatat gtgcaacaca catgtgcaca
2401 cacaggaagg agagatcatg gaggagtgtt ggggaagaaa agatttgcac tggtgcaccc
2461 tgggtttctt ctcccttct tcatgctctt tgtcttctca tccaggagaa ctgtcagaac
2521 gaggagatcc tgaacagcct caagtatgtc cgacctgggg gtgggtacca gcccacctt
2581 agtcttaccc aaaagtgtga cgtcaatggg cagaacgagc atcctgtctt tgcctacctg
2641 aaagacaagc tgccctaccc ttatgatgac ccgttctccc tcatgaccga tcccaagctc
2701 atcatatgga gtcccgtgcg ccgctcagac gtgtcctgga actttgagaa gttcctcata
2761 gggccagaag gggagccctt ccgtcgctac agccgcagct tccagaccat caacatcgag
2821 cctgacatca aacggctcct caaagttgcc atctagatga gagctgctca gcccaggaat
2881 ctcccactgt ttcccctgag cagtcttcct cagggctcag tgtaccctcg ggagaccctg
2941 ggagaccaag gcattccctg aatatcgtcc ccttgccttc cctaccggcc atttccttta
3001 gctccctcaa ggctctgggg gagtttgctt ggggctctaa gtctggggta ggttctgggc
3061 cttcacagaa tgatggcatc ttcctaaacc cttctgggag atgtctgaga agttgtgaag
3121 ggtccagagc cagtctgctt tagagtccaa taaagtgtag gtgtggcaat
```

Figure 4 (continued)

B <u>Ltb4r2:</u>
```
   1 gatgtctgtc tgctaccgtc cgcctgggaa tgagacacta ctgagctgga agggctcgcg
  61 ggccaccggc actgcctttc tactgctggc ggcgttgctg ggactgccag gcaatggctt
 121 cgtagtatgg agcttagcgg gctggcggcc cacggcgggc cggccactgg cggccacact
 181 tgtgctgcac ctggccctgg ccgacggcgc ggtgctgctg ctcacgccgc tctttgtggc
 241 tttcctcagc caagaggctt ggcccttggg ccaggtgggc tgcaaggcgg tgtactacgt
 301 gtgcgcgctc agcatgtacg ccagcgtgct gctcaccggc ctgctcagcc tgcagcgctg
 361 cctggctgtc actcggccct tcctggctcc ccgactcgcg agcccgcgcc tggccgccg
 421 cttgctgctg ggggtctggc tggccgccct ggtgctcgcc gtcccggccg cggtctaccg
 481 ccacctctgg ggcgggcgcg tgtgtcagct gtgccaccca tcgccagtgc acgcagctgc
 541 tcatctgagc ctggagaccc tgactgcctt cgtcttgcct tttgggaccg tgctcggctg
 601 ctatggcgtg acgctggcgc ggttgcgagg agcgcgctgg ggctcggggc gacaaggcac
 661 acgggtgggt cgtctggtga gcgccatcgt gctggccttt ggcttgctct gggctcccta
 721 ccacgcggtc aatctcctac aggcggtggc cgcgctcgct ccgccggaag gaccctggc
 781 caggctcggc ggggcgggcc aggcggcgcg cgctggaact acagccttgg ctttcttcag
 841 ttccagcgtc aacccagtgc tctatgtctt cactgcgggg gatttgctgc cgcgggccgg
 901 gcctcggttc cttactcgac tcttcgaggg ctctggggag cccgagggg cagccgctc
 961 tagggagggt accatggaac tccgaactac tcctaagctg aaagtaatgg ggcagggcag
1021 gggcaatgga gaccctggag gcggagatgg gggcaagacg agaaagaca gtcaagaatg
1081 gta
```

C <u>Ddit4l:</u>
```
   1 agcggccggg tgcagcctgt gctggtgggc gcggtggccc gcagccttcg gcttgctgca
  61 ggactgtgca ggggaccact gtccaagctt cggactactg aggggcgcct gcctcggttt
 121 acccttcagc gtctggtgaa atccggcagg tgagcgaccc gaggaggcgg gatagggcag
 181 ggtcgcttcc cagttgtgct gactttccag ctacttccag cctgttggct ttagttggcg
 241 cctccgctcc tagggctttg tcaacttgag ttgctaaggc tggtccctcc ctttggaagg
 301 gcagtgcccg ggctagttcg ccctggcgat gccgggactc tgaggagcct gtgcacttct
 361 tgcgtgcttt tgcaaacttc tcactttttc ctcccagcgc ctagggaaag atccgttctg
 421 ctccgcgagg gaaacagagc cgttgaccat ggttcaacg ggcagtttga gcagtaagaa
 481 cccggccagc atttcagagt tgttggacgg tggctatcac cctgggagtc tgctaagtgg
 541 tgagtctctg ggctgtccac ctctttccta tccgaaggtt gcggggcccc tctctagtgt
 601 aagcgtccct gcctgagtgc gcgagacttc atctcctcct agagacacag aggactatga
 661 aaccatctg agatctcttt ctaaacttcc tttgcattgt ctgcccacca aaaacaaacg
 721 taaggggaat aatgcgttgt tccagtctgc taagaggctc ttggggatga agttccctat
 781 ctcatggttg gaacattaag tgtacaggct gggtgtgttt aaagacatgc gcttacttgt
 841 gtagctagca ccaccacgtc cgtccccct cccccccccc cccaaattc tccctttct
 901 gtttgccacc taatccttct ctttcccgtc tccagaagac catccttcgg cattttgtta
 961 ccacgttagt tttgctttta gaatgttaaa taataagtgt atatgctctt ctcagttcgg
1021 tttgctttcc caccgtgtga tgttgtagag ttatacactt acctcatcag tgagttcctt
1081 ttcgttgcta agtaagattc tattatgaaa tgcacccact gtgcattaat gtcagaagaa
1141 aacttgaaca gccctggttc tacaggaatc atcatttgca acttgaaacg tcaatttcta
1201 atctgacaga ctattcaact atggaagagt ggtgtgagca tatattaagt ggcttaagct
1261 ctttagattt tcttcatcta taagataata ttataattct aaatttgtct gtcttcaatg
1321 tggataaaaa tacagatatg atttggaatc tatttgttgg aatttaaaaa ataaaacaaa
1381 aaacaaaaaa caagcagtgc cctctaagtg agctaatgac atagaaaacc aggagaggag
1441 aggaaggctc gtggccgcag tgtggcatgg cacccggcca agtagtagga ttaatttgga
1501 aggtaggtga ccaaatgcag agctatcttt ttcctctga gtaaacctaa ctttgttttc
1561 ctgggactgt tttgttttgc tcagctaaga aaaactgacc cagcccggtt ataaataaac
1621 tcaggaacct caaaagtcct ctctcctctg cgagcaaact tgaatcaaac aggtcaaagc
1681 caacactgga cctccaggcc atcctagtaa ggacttctaa cgaaaactaa ggctggtaga
1741 tcattagcat tgggacaggc tcactttaca gcgtttgaaa ccattctgca cgccaacggt
1801 cccttgtta agcaatagtg atgattttta ttccagatgt tctgcatgga cttgtgaaaa
1861 aaaactaaaa taaacttgga aaaccctaca gagagagcaa ggggggaaagg agatcactag
1921 taatcttgga tgaccttgga cagatttttg ccacataatc ctcaagacta cggggagaga
1981 agaaattgta aaagagggtt gttttaacct attcattatg tttatcagag tctttagggc
2041 atagatgagc tttcagtcct gaaaggttag aaggcctgtt ctattaccta catggttaac
```

Figure 4 (continued)

```
2101 agcaaaattg agatgagaga aagcagtatt aaaagcaggt agatatgaag ctagaagtgg
2161 ccagtcttac tatgccagta agacctcgta caccttgctt ctctgttcac taaaactttc
2221 atttctttca gatttcgact actgggatta tgttgtccct gagcccaacc tcaacgaggt
2281 ggtatttgaa gagacaacat gccagaattt ggttaaaatg ttggagaact gtctgtccag
2341 atcaaagcaa accaaacttg gttgctctaa ggtcttggtc cctgagaaac tgacccagag
2401 aattgctcaa gatgtcctgc ggctctcgtc cacggagccc tgcggccttc ggggttgtgt
2461 tatgcacgtg aacttggaga ttgaaaatgt atgtaaaaag ctggatagga tcgtgtgtga
2521 tgctagcgtg gtgccgacct tgagctcac gcttgtgttt aagcaggaga gctgccgtg
2581 gaccagcctc aaggacttct tctttagcag aggtcgcttc tcctcaggcc ttaagcgaac
2641 tctgattctc agctcaggat ttcgacttgt gaagaaaaaa ctgtactccc tgattggaac
2701 gacagtcatt gaagagtgct aaggaggaaa aacaattaaa ggcccctaat gagtggataa
2761 taaacctctg aagctatcca gccagtcatt tgtagtttgc ctgcttgccc tcaccaggaa
2821 atcccagatt taggccctt tccttctgtg tgtctcaccc atagcaaccc actttaaagg
2881 ctgatttttt ttttttttgt ccagcttta agacataatt caagagagca aattgcccac
2941 atatgtgtcc atatgggata gaatggaata aggaggaaaa agaagcaatc tcctttaatt
3001 ttatatttgg tctcatattt agcaggtagt cttagcaaca gagcaagatc cactttgcct
3061 aatttgactt tcatgtgccc agggcttgct gttattgtac ccgcctctct ctctctctct
3121 ctctctctct ctgtgtgtgt gtgtgtgt gtgtatat atatatct gtctgtctct
3181 ctctgtctct ctgtctctct ctctcctc ccctccctcc ctctctgaga gccatcttt
3241 caatgacagg acctgacaag atgatgtgca gccccatcaa aacatataga gatctgcact
3301 accagcttcc tccctgaatt tgaagagctt ttacacaaga gggtacagtt aaattgatcc
3361 gctggattaa aacatcacct tacatagagc gaataaacat cacagtgaca agagcatggc
3421 ttccctgcct ggtggtctcc ccacacccgt gcccaggaga cacgagaagt gtgcctctta
3481 ctgcaatgat tacatgatgg ctttcagtgc ctttgtagta ttgtgtcaac ttggttttcc
3541 tagttaccaa ctgttgaatg ttatcatttt ttacattgtc tttgagtaga taaaaaaaaa
3601 aaaagaaatg actgtctttt tgcatagagt tgatttgact gagcaaatat tgattaccca
3661 tctctaaaga tggagaaggg taatttcaga tcccgtccct ttcggatcca ctaggtcaca
3721 ttgctgcttt gtgccaccaa gatgcttcct ctccagtgaa gtgtctcacc acatggcagt
3781 tagctcatct ctggtctttt ctaggaactg gatcaccttt ccttaacatc acacttcttt
3841 ttagttacca atgtgcttat attggcagag cctgacttga ctctgagatg ttgttgctac
3901 cacagactag atatgaaagt cctatgataa cttaagacaa tcactgcaca tacccagctc
3961 catccactat atcacagccc attcctagga aacagcaaat gcctctttg cttagctttt
4021 gcttcatttc aagtaactag atgtttctca ggttttatgg ccatgagaca atttaccttc
4081 cacgtaactc tgttctattc agcaaggtct tttcttcctt gggtcatgga aagtaacatt
4141 ttcgggtcac ctgcctaggc cttcagtatg agtttgtata cctcaggcac cagcttggct
4201 gggacaaatg tcttcatcct gaccttacac aaacaagcct gatagttact ggtcttatgg
4261 gtgacctagg acatcactgt tccaatgagc acgtcttcta acttggggag gtaccacgga
4321 gctagtcttc acaagactgg gccagtaggc aaaaccctgt tgatctgtag gcttacagat
4381 gcccaggttc tgaaggtcgc tgtgtttctg tagctgtttt gagtcttgct ggggaagatg
4441 gtgaggcttc tcaggcatgg acatagatct tttacccgtt agcagttctc tggttctcct
4501 gcccatttga ctctcaaaat agtaatggct gaaggaggct cttgcaataa caatcctgtt
4561 aaagtcaatt ttttacaata aatgttata tattttt
```

Figure 4 (continued)

D Fosl1:

```
   1 ctgtctgtag aggcggcttg ccacccgagc agagggtcgt gaagttccga gcggaccggt
  61 ccacagaggt tcatctggag aggtgggtcc cctgcgaggt gaaaggcgcc gctgagacac
 121 gcccccaccc cccgtggtgc aagtggttca gcccaagaac tttt cattca taaaaaagac
 181 cagactccga gaggcgcgag tgagtcagaa ccgcagccgc caacgcggac cctaccgaac
 241 atccagccca gggcatgtac cgagactacg gggaaccggg accgagctcc ggggctggca
 301 gcccgtacgg tcgccccgcg cagccccgc aagctcaggc acagaccgcc cagcagcagg
 361 tgagactggc cgaatcgtcg gggggggggg gacctgagtt tggacagcat cagggatgct
 421 gggattagtc tagtttgctc cgggatttgg actgggcc cgagcagcat ctgactctgg
 481 tggtcgcgac cgaggatcct gcacgttctg tgtggtcggg gaacctatgt acccggtggc
 541 caaggggacg agcgcagcgg gaagcgcgaa tatctgcgaa ttccccttct cgctcgcccg
 601 tatctcccta gctgactgtc tttctgcccc tccgtctccg ttacgtcttt acatttcctc
 661 ctatctgccc ctaatacgct gtccctctaa atacctgccc catccctgcc tggacaggat
 721 cagaggtgtt ctccatctcc agttaataac tgggacctgg ggtctgggca catagagacg
 781 gggtccatca gaactcagcc gggacagaga attcttagca gcctgtccga ggctgtccgt
 841 gtgttgctct ggttgtccgt gtcctttat ccggtcaagt cctcatctct ttgtgcgcag
 901 tatagagccc atgggcccca ggcagtggtt ccgaggggtt cctggagacc acgaagtgtt
 961 gggatgtgcg cggggtcacc tgcccggcca cactcgcgct ccacattctc ggcacccgac
1021 gtctctcact gctggatagg ggcacttgag aggttgcagg tgtccatttc ctgtcgaggg
1081 gccgcgagca cgtgtcgcca ggggagggaa ggagctgcgt ccgtttcgcc gagtcacagc
1141 gggccgagtc actgaggctg agtcaccctg ggtgccct cctcctggc cccaaacggc
1201 ccctaaggac cgacgacctg ggagcgagag atgcccctgg cagtgcttct agcccagaac
1261 gggggtcact gagatgctgg gtcccccagt attgggctgg ggacatagct gtccagactt
1321 gcctaagcat gtgaggtgct tcctggactg gaggggcccc acatcttag ctcacagagc
1381 ttgaacccag ttttctctcc cagaacgctg agccccacc cccaccgaca ctcaatccca
1441 acacatgcct cagatttctg caagaaaagg aaggaaagga tgccagaccc cttataggag
1501 gcttttactc tcttcacttt atttcatgga cttaaaaaac cccatcaatt ttgaactttc
1561 aagttttttaa gtcgacagct aggcatgcat ttaatcccag cattcaggag gcagaggcag
1621 gcagatctct gggagtttga agccaatttg gtctacaaag tgacttccag gtcagctaga
1681 gctacataat agagatcctg tctcaaaact taaaaataa aaacaaaaa caaagccga
1741 ttaaaactct gatttctgag ctatgagagc tggcttctca acagcaatgg aacgttgaat
1801 gatgttaata acagggaaac tgagactaaa taacatgccc cagtctcaaa gccatcaat
1861 ggccaagctc caagctgatg ctggactccc aagctctggt gctacatgtc tatagtcttg
1921 gtgcctggga ggtagaggca gaggaatcgt gagtttaggt ctagcctgag ctatgtgaga
1981 tcctgcccac cccaccccg gcccccaaac aacaaattct catcctgatt ctcagaattg
2041 ccttgggagc tagaagctga aagtatgccc atctgtgagg actgggtctc aaatcttagt
2101 ttctacttac tagctgtggg tctatggcca actgctctcc tgtctgaaaa caggattatg
2161 gcagctgtgt gagtcactat ttgttaaata gttggaacag tgttacgcag tccatacttg
2221 atttaaaaca aaaaaccaaa ctatctctgg tggggaaaca gacagacgaa gagagacatt
2281 ttgtgacctg cccaaaatca cacagctcct gaacaagtaa gtttctggtt gccaaatgtt
2341 gctccttgtg gtctcccaaa actggtatct acactgaggt gaagggagac agaagtccag
2401 cctctgtccc cgggaagccc ctcagtccac acagaccta tcatttccct tcttatctct
2461 cagaagttcc accttgtgcc aagcatcgac agcagcagcc aggaactgca ctggatggtg
2521 cagcctcatt tcctgggacc cactggctat ccccgacctc tggcctatcc ccagtacagt
2581 cccctcagc cccggccagg agtcatacga gccctagggc cacctccggg ggtgcgtcgc
2641 aggccctgcg agcaggtaag aaacagcgat gtttcactt ccatagcccg taggggtcct
2701 actagacagg gacaggatct tgctacgagg gaatttctat tcagcattga agttcctgag
2761 aggccaagaa ggaggtaaaa ggtcaccttt gagtcaagga aggcttcctg gagaaggcta
2821 cacgttaacc taaccacgg ataggatttg cgtatggaag ctgaaaagaa tcttctggga
2881 ggagggttgg aggcacagaa ttgaggtgaa ggggacagag tgttaagtga gcatgtctcc
2941 actgtctgac gtgcacaggg tggaaggaag cctgatgctg gctttgtacc tcggggtgac
3001 tcttcttttc aacagtcacg gaatctcagc ctatttcttt taattatcac aaaagtgag
3061 tggcagtgg tggctcacac cttaaatttc agcactgggg aggcagaggc aggtggatct
3121 ctgggttcaa ggccagcctg gtttacagag tgagttccag gacagccaag gctacagaga
3181 aaccctgtct caagaaaggg aaaaaaaag tgaatgggaa atgtatttca atttttccat
3241 cttccatcag aggaagtgaa gcatagaggg gtactcactt gtccagattc atacaaatgt
3301 gagtaatgag acaggactgg tcctggcctg aggtctactc aactcccaaa gtcagagctt
```

Figure 4 (continued)

```
3361 aatgagccac tgtctcaatg ggagctcaca gaaggctgca gagggagtga gctgagaact
3421 tttgcctccc tgaatgcctt tctaaaataa agaagggtgt gttttggttg gtttgtagag
3481 gtggggtctt gagagcctcc tgccttccca agtgctagga gtataggtgt atgctagata
3541 cccgacaggg atgacggatc ttttaggcca tagcactttc tttcctctcc ctgaagtact
3601 gagactgagt ctagtgcagg gaggcctcca tactaaaaag ctgggtgtac ccgtaatccc
3661 agaactcgga aaatcaagac aggaggagcc attcaagtca cgctcagaaa catggagagt
3721 ttaaggtcag cctgggatat ataaaccccta tctccgataa ccaaacaaca atcaaagcaa
3781 acctgactta agtgttaagt aggaaagaat atgctgtaag tcatcagcct ggctggggga
3841 ctgaccgcct ctgagggact gaagaacctg cttcaagccc ggagccctgc actcaacccc
3901 tagtggatgc acacacagat ccttgccatg atggctcgaa gagggatggc aagaccctgg
3961 gagatatgtg agattggcca gagaagagcc agcaacaggc ttcccagcaa gggaacagct
4021 tacctctgtg atcagctggg gcgtgagcaa gaggcaagcc cagggtgaat ccttccttta
4081 gccctgtcct gaggagacac cttttgacca cgggtactag tgggttggag ctgtgagctg
4141 tgggtaggtg gcttccctc ggtgtgctct ggaacttgaa caaatcactc atccttcctg
4201 agcttcctca catgtgagtg tgcagagatc tggatgggtg actcagcagc ggctctggct
4261 gctccttaga ggatccgggt tccaatctca gcacccacgt ggcaactcac tgtccacaac
4321 gtcccccaaa ggttctgatg ccctcttctg gcctccacca gcactgaatg cacaaggtgc
4381 tcatacaaac acacaggcaa aatactcaga ggtaaatttg ttctttttt tctttgaga
4441 cagggtttct ctgtatagcc ctggctgtcc tagaactcac tctacagacc aggctggcct
4501 caaactcaca gaggcatctg cctgcctccc aagtgttggg accaaagatg tatgccatca
4561 ctataagcct ttttttttt tgtaaatttt atttatgaat gagtgcttcc atgtatacct
4621 tcatgccagg agagggcatc agatcctatt ataggtggtt gtgagccacc gtgtgtggct
4681 gggatttgaa ctcaggacct ctgaaagagg agctcttaac tgctaaaaca tctctctagc
4741 cccagtctac atattttaaa tctttttta agattgattt atttattata cataagtaca
4801 ttgtagctgt cttcagacac tccagaagag ggcgtcagat cttgttatgg atgattgtga
4861 gccaccatgt ggttgctggg atttgaactc aggacctttg gaagagtagt caatgctctt
4921 acccgctgag ccatctcacc agccccttt ttaatcttta aaaaaaaaag gggggggcc
4981 tggagagatg gctcagccgt taagagcact gaatgctttt ccagaggtcc tgagttcaat
5041 tcccaacaac cacatggtag ctcacaacca tctgtaatgg gatccaatgc cctcttctgg
5101 tgtatctgaa gacagcaagg gtctactcac atatgttaaa taaataaata aaaatttaaa
5161 agccaggtgg tgttggttca gacagcagat ctctgtttaa ggccagcctg gtctgatcta
5221 caaaccaagt tccaggacag ccagggctac acagagaaac cctctaaaaa accaatctat
5281 gtaggggtg ctggtgaaat ggctccgtgg gtaaaggtac ttgctgcgaa attaatgacc
5341 tgagttcaat ccttgaaatc cacacagtag aaggagagaa ccaacctcca agggtgctat
5401 gacacacaca cacacacaca cacacacaca cacacacaca cacacacaca cacgactata
5461 tatatgaata tatgactcta gccaggcata gtgtggcaca tgcctttaat cacagtactt
5521 gggaggcaga ggcaggtgaa gtttgaggcc agcctacaga gtgaattcca tgacagctag
5581 aactatgaag atgaaccctg tctttaaaaa caacagcaac ataaagaatc tatgtaggga
5641 agctggaagg gatgctgata cagtctgcaa tcctattact ctagaggtgg aagccaaaga
5701 atcaggggtt tcaggccggt cttgcctata cactgagcta aaggccagcc tgggacacat
5761 gagactttgt ctcttttaaa aagacaaaac aaggggggttg gttagatggc tcagtgggta
5821 agagcaccca actgctcttc tgcaggtccg aagttcaaat cccagcaacc acatggtggc
5881 tcacaaccat ctgtaacgaa atctgagtcc ctcttctgga gtgtctgaaa caactacag
5941 tgtacttaca tataataaaa ataaataaat cttaaaaaaa aaaaaaaag acaaaacaag
6001 ccagatgagg tctgtgagtt ccaggccagc ctggtctata aatcaagttc aaggccaggc
6061 agggctactc agagattctg tctaaaatac aaagaaacaa aactacaaaa agcagaaaaa
6121 ggaatctacg aaagggctgg tgaagggtg taactcagtg gtagagcatt gccgagcta
6181 gcatgtacca agccatgggt ttgatcccta gcactaagca aaagaaaagt cctacaaagg
6241 gctttgttgg catagtagat tgattcccag tagcttttgg cactcaagag cacttctac
6301 aattcacagc tcctggggga agaaatccca tcttccacag atgaggaggc tgagagtcct
6361 gtgaaagag ataatcatgt ctcatacact caggagagaa ggctacttct gcctgagaaa
6421 tgaaaaggct tcctggggtc ccaacatctt agtccagtcc taagatgcgg aagggaggaa
6481 gatcaaagtt tacagagagg gaaagcattt caggaaagaa accagcagta aagctaggtg
6541 tgtgtgagct ggaaatgtca ccaatgagat gacaagcgtc cggtacagag aagcaactgt
6601 ggagtgttgg gtggtggcac ctagactaca gactgaagga aagctggatg accagctcag
6661 ggcagctggt ggctcagagt cagcctcatt gtctccttc ttctatccca acctagatca
```

Figure 4 (continued)

```
6721 gcccagagga ggaagagcgc cgcaggtgtga gacgcgagcg gaacaagcta gcagctgcta
6781 agtgcagaaa ccgaagaaag gagctgacag acttcctgca ggcggtgagc atcatcccca
6841 ggcccggacc cacagagccc caagaggggt ctcggctccc aagaacacaa aagacccaaa
6901 attactcctc aggactctgt catcctccct gcctgtgggg aagtcctgga aaaaggataa
6961 gggaaagtgg cttaaatatt gtttgtcggg cttcgaggca gagtcgaaga tggtaggcag
7021 caattctcct aagatgcccc cgtctgatgg gagtcatggc cattttctcc cagaggctca
7081 cgggagggag ttgcagtcca gacttgttgg ggatgacagg cacagtccct actccagcct
7141 gaggcttggg gatctttagc cttcattttc ctatctttct gctaatcctg taaaggagac
7201 cgacaaattg gaggatgaga aatcggggct gcagcgagag attgaagagc tgcagaagca
7261 gaaggaacgc cttgagctgg tgctggaagc ccatcgcccc atctgcaaaa tcccagaagg
7321 agacaagaag gacccaggtg gttctggcag caccagcggt gctagcagcc caccagcccc
7381 cggccgccca gtgccttgca tctcccttc tccaggaccc gtacttgaac cggaagcact
7441 gcatacccc acgctcatga ccacaccctc tctgactcct tttactccga gtctggtttt
7501 cacctatcct agcacaccag aaccttgctc ctccgctcac cgaaagagta gcagcagcag
7561 tggcgacccc tcctccgacc ccctgggctc tcctacactc ctggctttgt gaggcaccca
7621 gccacatccc ttgctggtgc tactccaagc catccccttt ctcccattga tccagcaggc
7681 ctggaccata ccttgcccc aaaccagcag atcttttatc tcttccgact agaacaaaca
7741 cattatgctt tgatgtagag ccagcttgga ggggatcccc aaagctgctc actgttttc
7801 tagagctggc ctatcataat ttgcacaaaa ttagaggaaa atatgttccc tctgccagag
7861 aacgcctggc agcccagact ttgtagatcc caggggtcc tttgacaccc ttaccccttg
7921 cagaccactt tcccacacca cgtcactttc ttcatgttat ccagcctact ctacacctag
7981 acagaaggtg ccctttgact agcctagaac actaactcac acagcatcaa cagccagcag
8041 caccggacat cctgcaggct cctcctgaat ggcacaacgc aggaggcgcc aggggcttct
8101 gtgaggagcg gagctgcact ccctagctct gagaagcgct tagcttcagg gtatccgagc
8161 ctccaccgca agggcagctg ctatttattt tcctaaagag actattttta tacaaaccttt
8221 ccaaaatgga ataaaaggct t
```

E Egr1:

```
   1 cgagagatcc cagcgcgcag aacttgggga gccgccgccg cgattcgccg ccgccgccag
  61 cttccgccgc cgcaagatcg gccctgccc cagcctccgc ggcagccctg cgtccaccac
 121 gggccgcggc taccgccagc ctgggggccc acctacactc ccgcagtgt gcccctgcac
 181 cccgcatgta acccggccaa ccccggcga gtgtgccctc agtagcttcg gccccgggct
 241 gcgcccacca cccaacatca gttctccagc tcgctggtcc gggatggcag cggccaaggc
 301 cgagatgcaa ttgatgtctc cgctgcagat ctctgacccg ttcggctcct ttcctcactc
 361 acccaccatg gacaactacc ccaaactgga ggagatgatg ctgctgagca cggggctcc
 421 ccagttcctc ggtgctgccg aaccccaga gggcagcggc ggtaatagca gcagcagcac
 481 cagcagcggg ggcggtggtg ggggcggcag caacagcggc agcagcgcct caatcctca
 541 aggggagccg agcgaacaac cctatgagca cctgaccaca ggtaagcgt ggtctgcgcc
 601 gaggctgaat ccccttcgt gacgacccaa acgtccagtc ctttcctgca ggacctgtt
 661 tctatccctt agggatggga ctggggtttc cctctatttc acacagctcc agggtcttgt
 721 gttagaggga tgtctaggga cacccctac cctccatcct tgcgggtgcc cggaaggcag
 781 gacgtttgtt ttggatggag aactcaagct gcgtgggtgg ctggaggggg tggggggag
 841 ggtttgtttt gatgagcggg gttgccccct ccccgcgcg cgcggtgtcg cgcgccttgt
 901 ttgcagattg ttccccaagg caggcgtgaa atctgtgacc agggatgtcc cgccgccag
 961 ggtcggggc gcgcattagc tgtagccact agggtgctgg cgggattccc tcgcccgcgc
1021 agcctcgctg cggagcgctc tcggagctgc agtagagggg ggattctctg tttgcgtcag
1081 ctgttgaaat gggctctgcc actggagcag gtccaggaac attgcaatct gctgctatca
1141 attattaacc acatcgggag tcagtggtag ccgggcgacc tcttgccagg ccgcttcggg
1201 tctcatcgtc cagtgattcc tctccagtaa ccaggcctct ctgttccctt tcctgccaga
1261 gtccttttct gacatcgctc tgaataatga aaggcgatg gtggagacga gttatcccag
1321 ccaaacgact cggttgcctc ccatcaccta ctggccgc ttctccctgg agcccgcacc
1381 caacagtggc aacactttgt ggcctgaacc ccttttcagc ctagtcagtg cctcgtgag
1441 catgaccaat cctccgacct cttcatcctc ggcgccttct ccagctgctt catcgtcttc
1501 ctctgcctcc cagagccgc ccctgagctg tgccgtgccg tccaacgaca gcagtcccat
1561 ctactcggct gcgcccacct ttcctactcc aacactgac attttttcctg agccccaaag
1621 ccaggccttt cctggctcgg caggcacagc cttgcagtac ccgcctcctg cctaccctgc
```

Figure 4 (continued)

```
1681 caccaaaggt ggtttccagg ttcccatgat ccctgactat ctgtttccac aacaacaggg
1741 agacctgagc ctgggcaccc cagaccagaa gcccttccag ggtctggaga accgtaccca
1801 gcagccttcg ctcactccac tatccactat taaagccttc gccactcagt cgggctccca
1861 ggacttaaag gctcttaata ccacctacca atcccagctc atcaaaccca gccgcatgcg
1921 caagtacccc aaccggccca gcaagacacc cccccatgaa cgcccatatg cttgccctgt
1981 cgagtcctgc gatcgccgct tttctcgctc ggatgagctt acccgccata tccgcatcca
2041 cacaggccag aagcccttcc agtgtcgaat ctgcatgcgt aacttcagtc gtagtgacca
2101 ccttaccacc cacatccgca cccacacagg cgagaagcct tttgcctgtg acatttgtgg
2161 gaggaagttt gccaggagtg atgaacgcaa gaggcatacc aaaatccatt taagacagaa
2221 ggacaagaaa gcagacaaaa gtgtggtggc ctccccggct gcctcttcac tctcttctta
2281 cccatcccca gtggctacct cctacccatc ccctgccacc acctcattcc catcccctgt
2341 gcccacttcc tactcctctc ctggctcctc cacctaccca tctcctgcgc acagtggctt
2401 cccgtcgccg tcagtggcca ccacctttgc ctccgttcca cctgctttcc ccacccaggt
2461 cagcagcttc ccgtctgcgg gcgtcagcag ctccttcagc acctcaactg gtctttcaga
2521 catgacagcg accttttctc ccaggacaat tgaaatttgc taaagggaat aaaagaaagc
2581 aaagggagag gcaggaaaga cataaaagca caggagggaa gagatggccg caagaggggc
2641 cacctcttag gtcagatgga agatctcaga gccaagtcct tctactcacg agtagaagga
2701 ccgttggcca acagcccttt cacttaccat ccctgcctcc cccgtcctgt tccctttgac
2761 ttcagctgcc tgaaacagcc atgtccaagt tcttcacctc tatccaaagg acttgatttg
2821 catggtattg gataaatcat ttcagtatcc tctccatcac atgcctggcc cttgctccct
2881 tcagcgctag accatcaagt tggcataaag aaaaaaaaat gggtttgggc cctcagaacc
2941 ctgccctgca tctttgtaca gcatctgtgc catggatttt gttttccttg gggtattctt
3001 gatgtgaaga taatttgcat actctattgt attatttgga gttaaatcct cactttgggg
3061 gagggggag caaagccaag caaaccaatg atgatcctct attttgtgat gactctgctg
3121 tgacattagg tttgaagcat tttttttttc aagcagcagt cctaggtatt aactggagca
3181 tgtgtcagag tgttgttccg ttaattttgt aaatactgct cgactgtaac tctcacatgt
3241 gacaaagtat ggtttgtttg gttgggtttt gttttgaga attttttttgc ccgtcccttt
3301 ggtttcaaaa gtttcacgtc ttggtgcctt tgtgtgaca cgccttgccg atggcttgac
3361 atgcgcagat gtgagggaca cgctcacctt agccttaagg gggtaggagt gatgttttgg
3421 gggaggcttt gagagcaaaa acgaggaaga gggctgagct gagctttcgg tctccagaat
3481 gtaagaagaa aaaatttaaa caaaaatctg aactctcaaa agtctatttt tctaaactga
3541 aaatgtaaat ttatacatct attcaggagt tggagtgttg tggttaccta ctgagtaggc
3601 tgcagttttt gtatgttatg aacatgaagt tcattatttt gtggttttat tttactttgt
3661 acttgtgttt gcttaaacaa agtaacctgt ttggcttata aacacattga atgcgctcta
3721 ttgcccatgg gatatgtggt gtgtatcctt
```

Figure 10
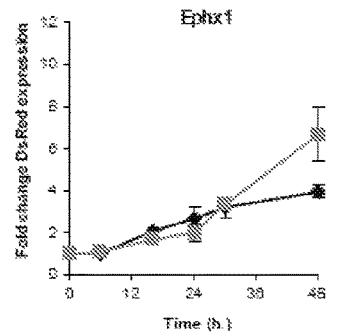
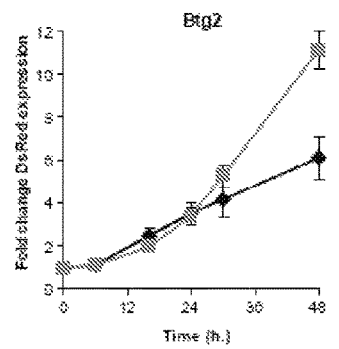
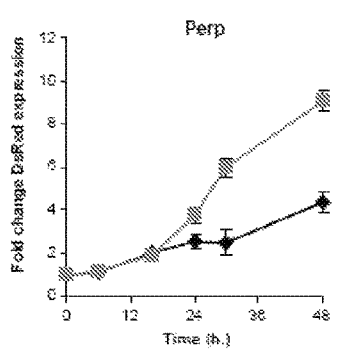
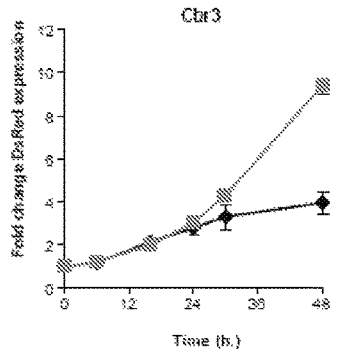
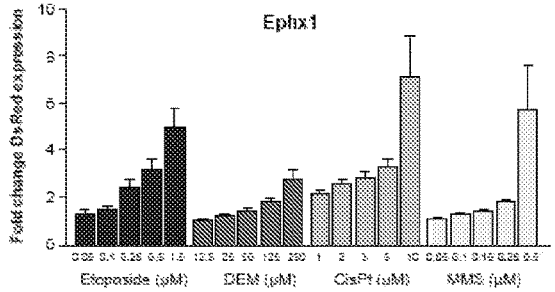
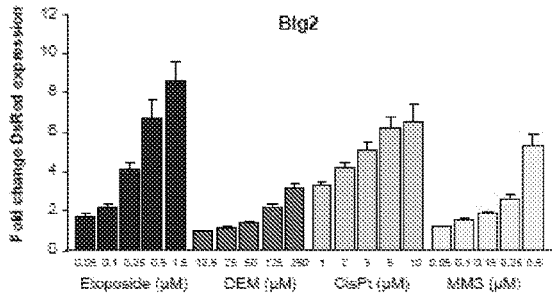
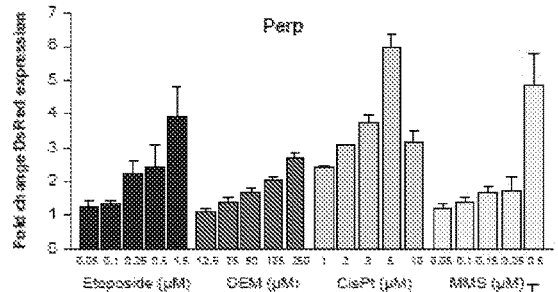
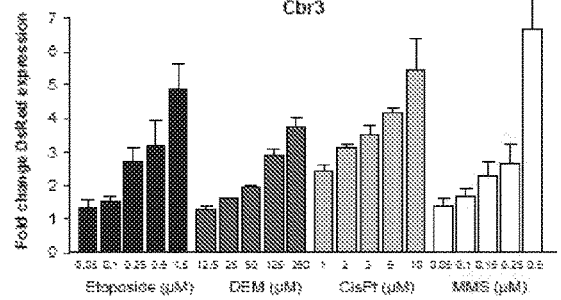
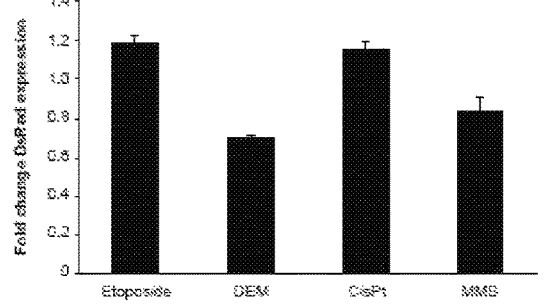

Figure 15
A
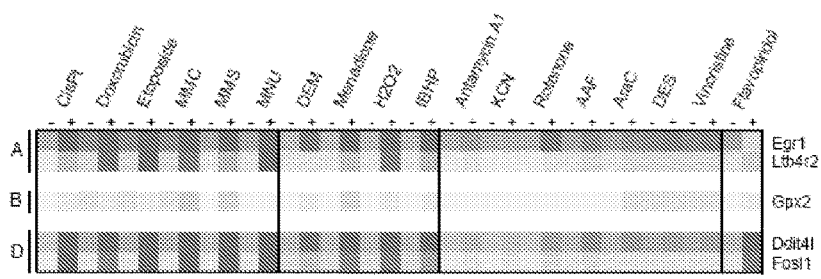
B
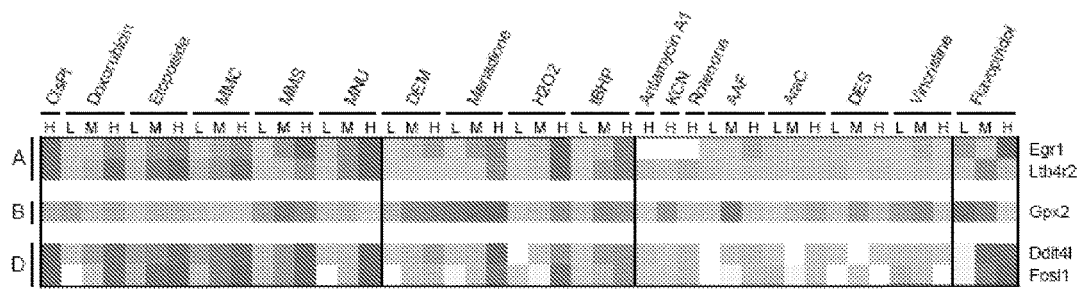

Figure 16
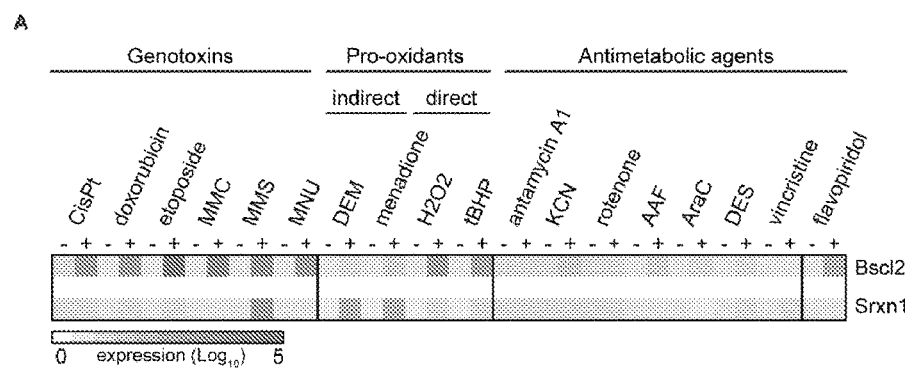
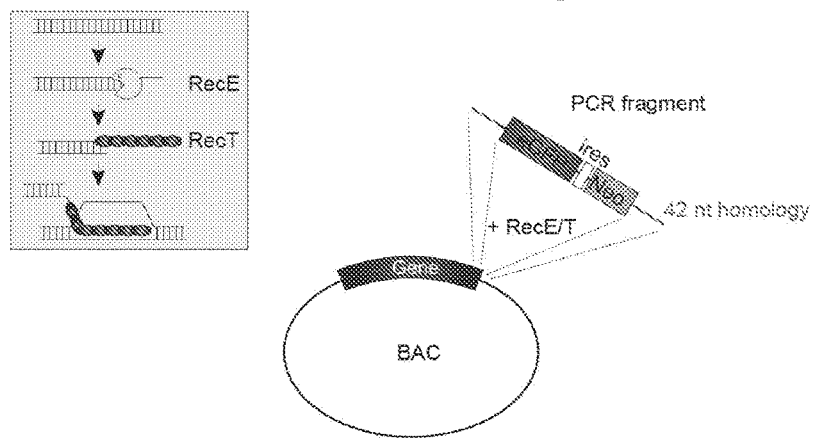
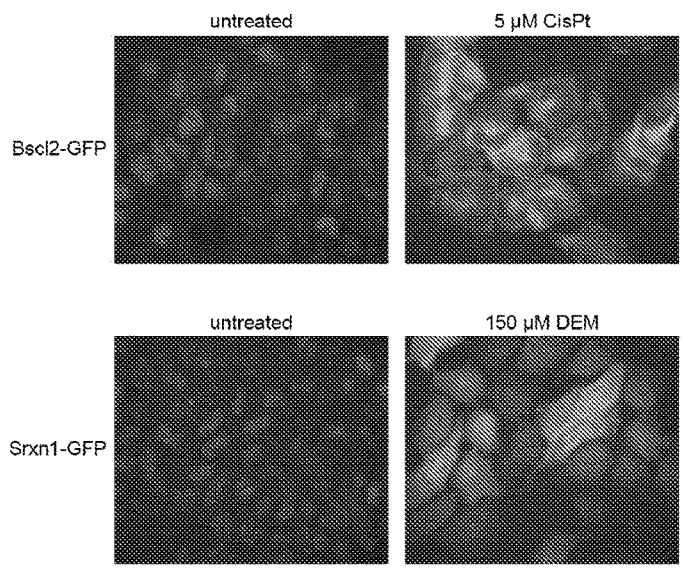

Figure 16 (continued)
D
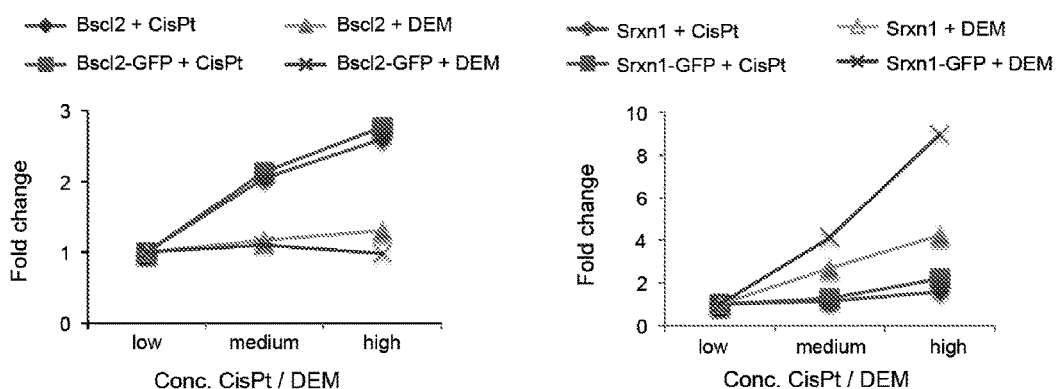
E
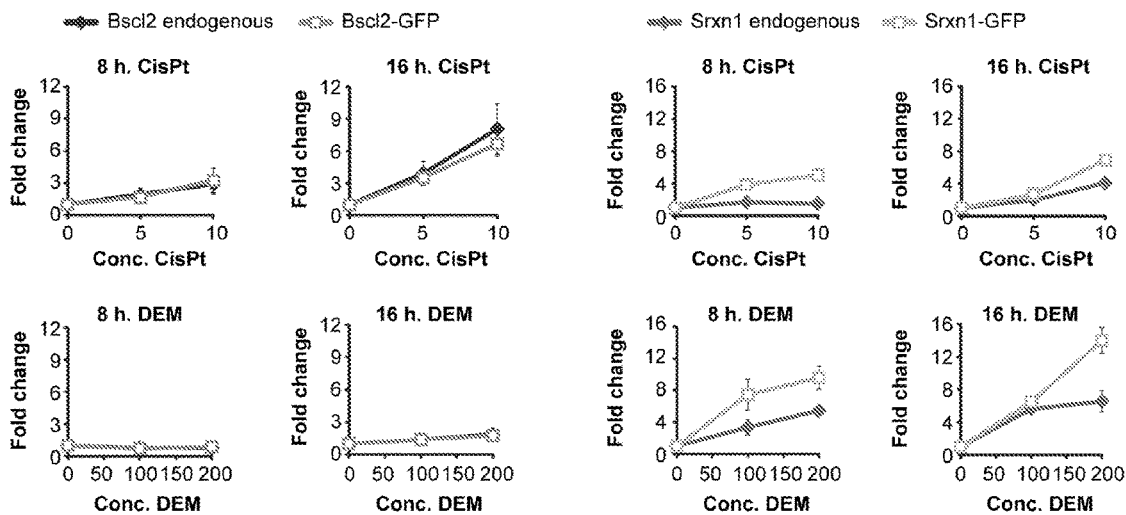

Figure 17 (continued)
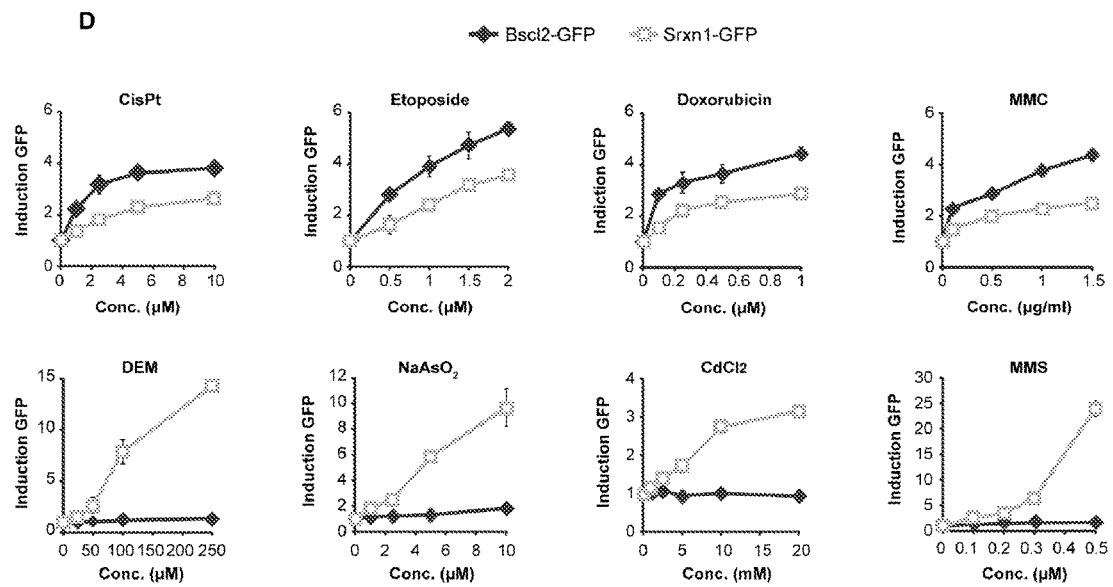
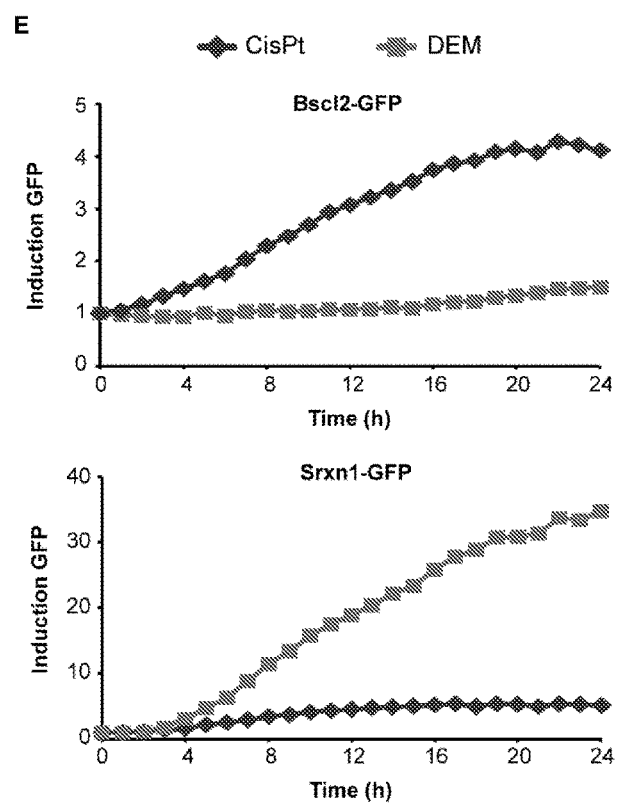

Figure 19
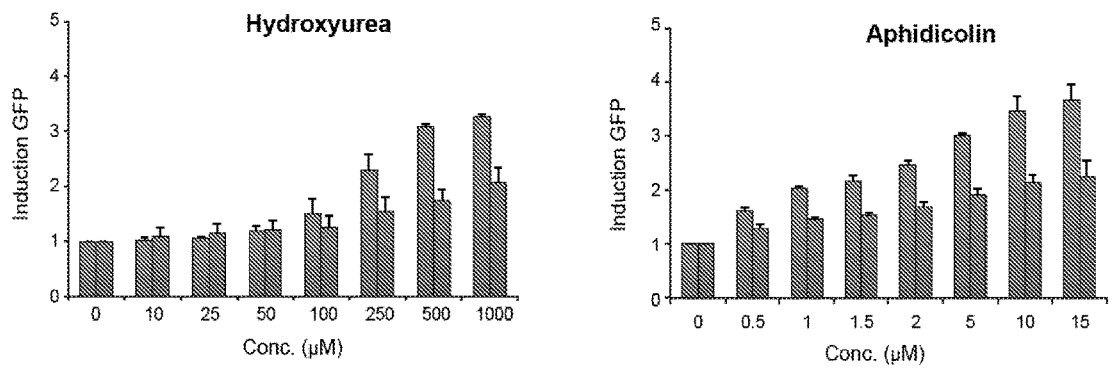
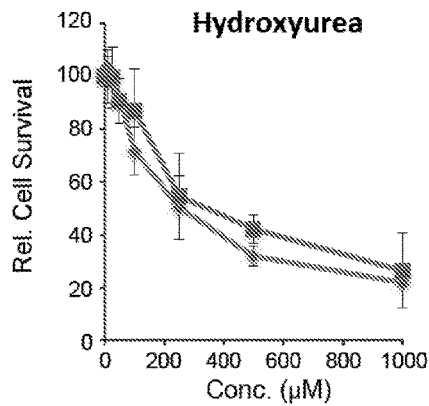
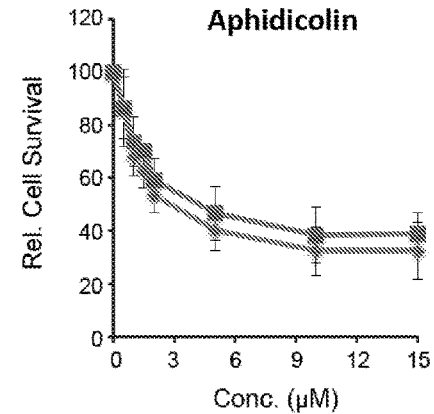

Figure 29
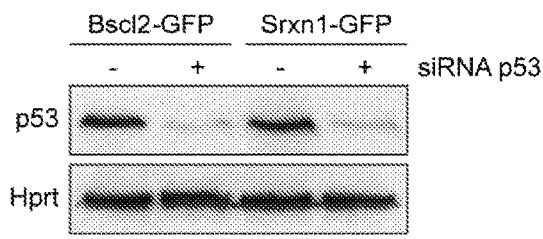
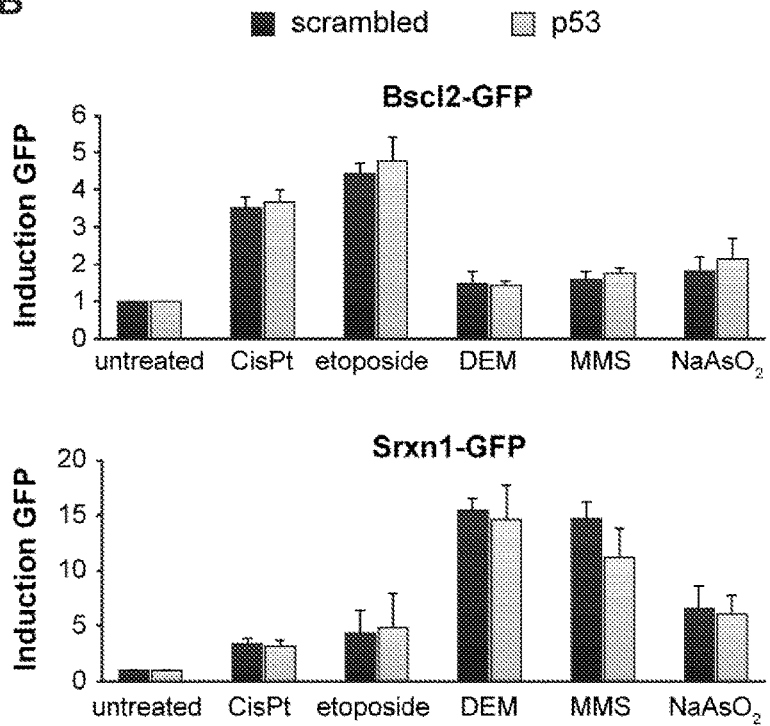
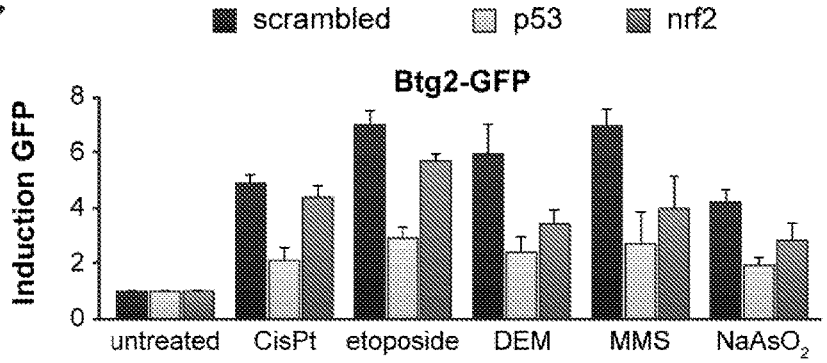

SEQUENCE LISTING

<160> NUMBER OF SEQ ID NOS: 90

<210> SEQ ID NO 1
<211> LENGTH: 1462
<212> TYPE: DNA
<213> ORGANISM: Mus musculus

<400> SEQUENCE: 1

```
gtaagcaggc agggattata acaaggatcc ttcctggggt tttcacaaga aagaaggagc      60
aaaggttata aaatactgaa gtctgcgtgt gtgcgcatgc acgcgctcta gagagagagt     120
gtgcagggta ctcttgtgga gtcagaaaaa ctcttgagtt ctcccccacc accttgatgg     180
ttgaaactca ctgggcctgc agtcaaacac ctgtacctgt tcagccattt ggttatgaca     240
cccagggaat agttagacct tcctacccag aacgatttgt cacctaaaac tagaacagcc     300
gggcatggtg gcgcacgcct ttaatcccag cattcaggga ggcagaggca ggcggatctc     360
tgagtttgag gccagcctgg tctacaaagt gagttccagg acagccaggg ctatacagag     420
aaaccctgtc tcgaaaaacc aaaaagaata aaaacaaaaa caaaacaact aggacattta     480
aatgtagccc aggatccaaa acatatatgt acgttcactc agaccaaaaa gcttctaggc     540
ggtggcctgg atcccctaac cctttgccgg gatctcactc taggaggcat tcttgagaca     600
tggtttccag tcagacgaca ttctgaaccc ttgtgatgtt ttcagttacc ttgaggagaa     660
aataaaaaag ccccaattca acaagaaaac aaatttatta cttatttaga tcccacagag     720
accaaggaac agggtgctcc aagatggcct gtttaacaca tttgtgttat tacatacacc     780
tcaaagggaa cctctactca ggcgagattc ttatgcaaaa ctcactctgg gcttcttggg     840
tcccagtcct agtgactggt tgttttaagt caggatttca ttgtgtattg tgtgtcgtcg     900
tggctggctt ggaactcaga gatccatctg cctctgtgtg tgtccaacac ctccggagtg     960
ttggtcacca cactgaactt aagaacccat gactgcttta ggtgtctccc catccccact    1020
ccccgtgatt ggtctccaaa gcatgtctag ttccagattc tatgggacag agaacctgac    1080
tctgactttg agagggcagg ggcagccatt ttaagaccag aggatcgcat aagggatcgt    1140
tccctattgg gaacgctggg gaccgccatt ttaagagcac cctcggcgcg tgcctccatg    1200
cgggtacgaa caggcagccg ccatcttggg cattggctgc cgcgccgagt cgccctgtcc    1260
```

| | |
|---|---|
| cgccccacgg cctctcgggc cacctccccc cggggctgct gtccctgggc ctgcggaaac | 1320 |
| ccaccctgct cgcccttgtg tggttctcgc cgcttacgtt gcgcgctcgt gtgaatgctc | 1380 |
| cgcggcttct gagcgctcgt tttaacaacc ccccactggg ggcgctcggg caccttatac | 1440 |
| tttgcgatct ccaatcctta ca | 1462 |

<210> SEQ ID NO 2
<211> LENGTH: 1479
<212> TYPE: DNA
<213> ORGANISM: Mus musculus
<400> SEQUENCE: 2

| | |
|---|---|
| acacaccaga agagggcatc agatcccatt acagatggtt gtgagccacc atgtggttgc | 60 |
| tgggatttga actcaggacc ttccgaagag cagtcggtgc tcttaacctc tgagccatct | 120 |
| caccagcccc tttctttctt tttcaagaca gggtttctct gtgtgaccct ggctgtcctg | 180 |
| gaactttctc tgtagaccag gctggcatca tagtcaaaga tctgcctgcc tctggctcct | 240 |
| actcaaggaa tgctgggaat aaaggtgtag ccaccattgc ccagcacatt agaatgtttc | 300 |
| catctacact tgttaagaa caatacgttt actgctttgc tgaatggctg gaggcagcgc | 360 |
| tcctgtggga acagtttaga gggcgctatg aaacaagcct ggactataca ctgcagagga | 420 |
| ggacggcagg tgtgcaaacg gtgtgctggg gaggggaagg agctgcagta cctggaaatc | 480 |
| ccaggttccc agagaggatt gaggacacac tatccaggag ttccacggag gaggaatga | 540 |
| gttgaatgtg ttcactggag agaaaccggc tctccgttag aacggagagg gtttgggcca | 600 |
| tgatgagcag cgaaggaggc tggagatcag aggtgagagt gaaaatagg atccctacgc | 660 |
| ttcacatgtg tgtaggatga taaacctgga ccccgcggca ggcactgcta ggccctcaca | 720 |
| gtggtgtgcc tggtcatctt gtctgtgtgg ctgctgaagc ctgagaaggt tctaggcgag | 780 |
| tcttaggagg gccgcggggg taaagacagg gcactgggca ggctggctaa tggagagcag | 840 |
| gttagcccca agggtgccag gaactgtggt tgtcctactc ctgcttgctg gctaggcagc | 900 |
| gctctctccc tcctccctgt gctggcctct gcttggtgtc catgcctcct gggcttcaga | 960 |
| tcagccagcc tcacagggtg cacttaacga caaacttcag gtttgtgtgt tcattccaca | 1020 |
| cttcactatt ttatttgtgg ttctgggaat gaactccagc gccttgccca cgcgagacac | 1080 |
| tctaccctca agctttatcc ccagatgttt gctcactgac tggttcgctt ataaaatggt | 1140 |
| tacaacgaac tgctaggaag gtgagaggaa ggctgtagca ccaggccagc ttgggctctt | 1200 |
| gtgtgtagag tccacagact gcagagttta aactgccaat accctgttca gaacagcaga | 1260 |
| ctttgccaga ataggtgaaa caccttagct agatgctcag ctagccttgg ccaaccagcc | 1320 |
| aactcggggg tggggccaag gcctgggcgg ggctagtggg ggcggggcta acaggcagct | 1380 |
| ggtgtcacca gctcagcagc aggcaaagag gctcaagagg agtttgagag tggaggaact | 1440 |
| gcacaccagc cgccgcggga gtaggaaccc gagagcgac | 1479 |

<210> SEQ ID NO 3
<211> LENGTH: 1618
<212> TYPE: DNA
<213> ORGANISM: Mus musculus
<400> SEQUENCE: 3

| | |
|---|---|
| gaggagccct ggtttcagag ccccgctatc attaacaggg cctgggggtg catactggtc | 60 |
| atcccagcac tccagaggca gaggccgagg gatcaaaggc tcaaggacat ctttgactac | 120 |
| ataatgggtt tgagggtaca ggaacttctt cctccccaaa agggatagaa cttactggca | 180 |

| | |
|---|---|
| gcatgtgagc cggaatggaa atgattctaa atcatgggga tgccaatgga tacaagaaaa | 240 |
| ggaagaatgt agcatttttc ctttaaaaaa aaattttttt ttatgtgtat gtgtgtactt | 300 |
| gcatgagttt atgtgcacca tgtgcaggaa agtgcctaca aagcccagaa gagggcatca | 360 |
| gattcattgg aaatggaatt acagatggtt atggctgtca tatgggtgct gggagcagaa | 420 |
| cccaggtcct tgttagggc aggaagcact ctagccactg gccacctct ctagcctcaa | 480 |
| aatccggata tatatatata attttattt attttaaatt gtatctaatt gtgtgtctgc | 540 |
| ttgtaggtgc agatgccaca gagcccagtg gtatcagacc tcctggagct agagttacag | 600 |
| actgatgtga gtcgcctggg tgggtaccgg aaccaaatct aggtcctctg caaatgcaat | 660 |
| aagcactcta accgctgagc catctctccc atcacaaacg catcatttta aatagacgtt | 720 |
| tagtatgttt ttctctcccc aacccaacct gacatttgat tcccccagct ttagacacac | 780 |
| tgaggcaact aacctggcca gctcagttgg aaaagaggca gttctgaaaa agagagtgga | 840 |
| ccggtggagg ctcaacacca ttagcaggcc ctgcacctgc tgctttaagc ctcctgtcct | 900 |
| tagggagtcc ccactacaaa cccaaatatt cccagtatgc aggtatgtaa atggtggta | 960 |
| agcaagtctt cgttgtccct cacagaggtg gaacacagta cagactgggt tggctactga | 1020 |
| ggaggaagga aggaagccaa gagaatccct cagcttggca tggaagaggt agcggggaca | 1080 |
| aggaattgta gtgtcctcag agagtctgtt ggtgcagcct gtggagagc taaacaggat | 1140 |
| tcaggtcagg ctgtgagttg gaaaaggaca ggtctcagtg aactgagcct ggaacagagg | 1200 |
| tggaggcgac cctgaaggta gagtcatggt agggttaggg aacagagatc cagaggctca | 1260 |
| ggtaaaaaga tgaacagaaa ggagcctgag gtgacccgag gagcgggagg ctcccgcgtg | 1320 |
| ctgagtgagc cgcaggagca ggctggtggc gcgcgggcgc gtgtccctg tggtgcaggg | 1380 |
| tggccacact ggcggggcgc cccgcgtgg gccgctagcc caagatggcg atggaggggc | 1440 |
| gggcgagctg gccgcggccc cggccccgc gccggccccc gctcgggccc cggcccggga | 1500 |
| ggccgcgccc ccgcccgcgg cgccgcgcct cccggagcca ctgacgcccg gcgcgccctc | 1560 |
| ccccggcggc ggcccaggcg cccggacgcg gcggcagcgg cccgagcccg gccctatg | 1618 |

<210> SEQ ID NO 4
<211> LENGTH: 2904
<212> TYPE: DNA
<213> ORGANISM: Mus musculus

<400> SEQUENCE: 4

| | |
|---|---|
| tcagcaggcc tgggtctgtt cagtcctggg tggggactag ctttctggcc ttcaggaaca | 60 |
| tgtcttgaca tgttcagccc tggaattgaa gaggtggggc tgcttcagtg cagggtggtg | 120 |
| gagacctgat gatacccaac taccagctgt ggggtgagga ggagcatgaa tggagacaga | 180 |
| gaccccagat aattaaggac gtcccacttt gccagcagaa taaaaggtgg tatgtatctt | 240 |
| gtgacatgta tcaggtgaag gatgcttttg tgcatctgtg tgtgtgtgcc tggggtgtgt | 300 |
| atgtgtcagg tactgtatgt agtcattttg tcactttgtc attttggggt ctggagggct | 360 |
| cctccaacca tgtttctgag tatacattca cgtgcaatgg tgtgcctgac tatacattca | 420 |
| agtgcaaggc caagaatgtt tgttagaaag actgagtagt cccagactta ataaatattt | 480 |
| gttgagtact tttgtggtgc tctgggaagc cagaagttgt ttaaaataaa tctctccaac | 540 |
| accagtaggg taaggcaca ggaggtcaca gcactcagca gttcagtata agcctttatt | 600 |
| caagctgttt tctcccaaag taaacagaca gacaatgtca cttctatctg agaagcctgg | 660 |

```
aggccaaggg gatttgggca gttttgacat cctgtgctgg cccctgacag cccagccctg    720
ggatggacga cttggatgca gggactggac cgttcaggag ctggggcatt gtgggagtgg    780
ccattatgtc tgtcctggtt tgggggtctg aagggggtcc ttcaactgtg tttctgaaca    840
ggatgaggct tttgaggggg gttgggaagg tggccaagcc cttcccagac ttccaccccc    900
catcacagaa gaggaggcct gtctaggtca gctaaatccg aggaggaaga ctgggcatgt    960
ctgggcagcg atctctagac atcggagagc agatgtcaga actcacagct tctccaaagc   1020
aggattttga tcttttaact aaagatatcc gttcaaacta agactccagt ctctgcttta   1080
tttaaaattt ttgtttgtgt ttgttttgag agagagagga atttgttttt gttttagagg   1140
caggatgtca tgtaaccttg atgaattatt ggtcctcctg tttctgtctc ctgagtgccg   1200
ggattacaga tgtatgccgc tatcatctag atgatgcctt actagggatc caactcctgg   1260
cttcatacat gttaggcaag cgctatatta acggagctac atcccttttt ggatgcatgg   1320
tgatctcaga tagctcaggc tagccttgag ctccaaatcc ccctgcctc ccaagtaccg    1380
tgatttcagg catgtacctc tatgcttagc tgagatggtg gtcttgctat gtagcccatg   1440
tgaccaggct ggatcgtgta acaagactga agaaaacccc cttctgctgg gtgtgatggc   1500
tcagacctgt agtcttaact ctaagcaagg aagttaaggc aggaagattg ccttgaatat   1560
gagggccacc ctgggctaca tagcgaggcc tcgtctcaaa agaccccaaa cagaaggaaa   1620
taaaactgac tagagacatg gaggaaggtg ggaacggaga atgtcttact gctatgtctg   1680
tcaggaacat ccgtagatgt ttctagaatt gtcctttatc aatgtcattt tagtggactg   1740
tctggatctt gggaggggga gtattagaca tttccctcat tttggaccca gagaaagaaa   1800
tctgcaagca gagtactctg ggcagcttgc cagaggtcag caggtagcca ttagtgtggt   1860
cccagtcagg tcttgatgct ctcacttgca ggatgtatta tggtgtgaga atgttcaca    1920
tgctggcttc tgaagagggg agaggggagg taaggagcct ggcggctgtt tttcttggta   1980
gtccgtggtc tgagaactgg actcaatctc cccgatttct gaggcggttg acagcatcct   2040
ttccttctgt ggaactgctt tcctcgtctg tgagacaggg aggaaatgat cgcgttctgg   2100
acccgatgtc cgaggggctt ctgggaggag ggggaaaaaa atctccagac atagtgggac   2160
ttcttgggat tttaaactat ttttttattat ttatgggctt gttttgtttt tgagagggtc   2220
tcaatggata gcccaggctg gtcttgaacc tgtaacgccc ctcgtgcctc aatctcccaa   2280
gtataggatt ccaggctttt gctatcatac tcaaatgatc aatttattta tatttgaaac   2340
agtgtcacat atttcaagtt ggtctccatc ggaataggta gctgtcaaaa cgaccttgaa   2400
tgcctatttc cccctcctca cccccactg ggcgctgtta ttacagacgt gaccccgcat    2460
gcccagttta tggggccctg gagctccaac ccagggcttc acttccagca agttaggcaa   2520
acactgtacc aacagaccca cctcccgaaa cccaggattt tatttactaa tatcagtgat   2580
ctggaaaaga gttagtcctt cccacagttg gtcaggaca gacccataaa cactcactca    2640
gctctaactg tactgttgtt catagatgta tgtggctctg ctggtgcgct gcgtgacaag   2700
agaatagccc aggtgtgggg gaggggaggg cgcgccctct taacgcgcgc cggttctagc   2760
tgtctggcgc gggcttagat tcccagaggg gaggcgggc cagcgagtcc ccgggatcgg    2820
tgaaggagtg ggttggtcct gcctctgagg gggcggggcc tgggccgacg ctataaggag   2880
gcagctcgac gccaactgca gcag                                          2904

<210> SEQ ID NO 5
<211> LENGTH: 1650
```

```
<212> TYPE: DNA
<213> ORGANISM: Mus musculus

<400> SEQUENCE: 5
attgcctggt gttatggttt atgccggtca cgtggtgtct tggctttagg catcaattag      60
tttagctttt gttattttta ccttgagaaa taaactatat cttattcccc tttgagccga     120
cagaaccaat taattactat agtctctttc agagattctg aacagtcaaa attacctttg     180
accagattga tattaaggag tccctctcca caaaactgtg gaaattgtat cacaagaatg     240
aggacataat ataaacatat atatatatgc gtgtgtgtgt gtgtattcca aaattattca     300
ttaagacacc agtggaaact catttgattg gtaaaaatac dactttttcca cacaggacat    360
agctagctaa atatttttca ttacgtttga aagcctttag gtcctaacgt ttagggcata     420
cgcaccgcac ttgtcctgtg ggcaatgaac cttgctcaac gtgtatgtgc ctctgcggtt     480
ttcaggactg aaatgcttac tggtttctgc taagtgaagg ctgggtagtg atattctttg     540
gactctgaga cagatcttct cagtgttctt agtctatgcg tcctagtaac tacttctgtt     600
gcgagcgtct tgtgtaagaa ggaaatacca ctgagtgctt tccatatctt taaactgaca     660
tgaggtgtca gaagatttcg gggcacgggg taaaaagtga atgctctggt tgatctctcc     720
ctggccacca ttgacctggc actgggaatt tgtttctctc agcgccactc ctggctgatg     780
ccccacccetc cctgctacaa gtgaagattc ttagggacag aagctagctc aggatttggg     840
gaggatttca gttgcttgtg catgctgaca cgtgcttata tttgaaaaaa caaaaactgt     900
gtaaagtaga tagaaagggt agatgtgtgg ggaacacact aactgggca aagggaactg      960
aagttatcaa caccaaagct acccggatta agagacagcc tccgcaacct agagtgagcc    1020
actgggacct gctggtcacc cagcctgaac caccagagca cagaacattt gcgtgtctat    1080
ggcagcaaga gccaaggtcc aaaggtagat ccgggcagga agtgtaggat ctgcctgtgg    1140
aagccaggga cagacgctcc caggtttgaa cccacaagtc cttacatttt agggcccatc    1200
atttatttca caggctattg ggatgtcctg ggcacggtgc ttggagctca agtgtagcct    1260
tagccatgct ccttacactg tgttaattta gggcagagca caggctggcg ctggagtgtc    1320
cacaggtgtg tgcgctgggc tggcggcaat ctggtgggac tgcaggcggc tggaggcaca    1380
ggcacgccca ccctggcgac gagcccgggg cgagcctgag ctctgccgcc cgggtgaccc    1440
agcaggtcgg ggcggtgcgc tctgagtcac cggaatcaag gtgtggctgg agcgccgctc    1500
ccccgccgcc agcccggggg ccgcgtcttc gggggagccg cctcttcctt tagtcgcggt    1560
gtcagcgctc gcaggaccac tcttggccgc tgctcctgcc cggcgttcct ccgctccgcg    1620
cccgccgcca ccgacgacat gctgcgctgc                                     1650

<210> SEQ ID NO 6
<211> LENGTH: 1799
<212> TYPE: DNA
<213> ORGANISM: Mus musculus

<400> SEQUENCE: 6
ataatatgta atgtattata cataatacat ataatatttt atatgtatat gtatcactag      60
ggatatggca gagaatctac acagcactta aaccatctat gtttacaata accttacact     120
aaacctgggg gatgtagctc acttggtaga gtgcctaaca tgcacaggtc ctgtatgcag     180
tatccccagc accagacaga ccaggagtga tgctgtacat ctgtaatccc agcattctgg     240
cgatggaggc aggagaagcc aaagttcaag accacccttta gttgcataga gaattcagag     300
```

| | |
|---|---|
| ccagcctggg ctacatgaga acctttctca accctccctc ccctccaaaa caaaaacaaa | 360 |
| accccactcc ctccccaaac ctttaatata tactatttta gatacgattt agaaggagaa | 420 |
| aatcgcctga gctatttata caataagtgt cctgaggctg acatcctagg atgtaagcgc | 480 |
| tggtccctca gagagaaggc ttcttgagct accaatccta cctcacactg ttttggaaca | 540 |
| atccttgaat tctgcattta cagtcacaga attgtctcaa cctcaacctc cagtttcctg | 600 |
| ccagagagcc agcctcacag actataagaa ggtaaaacca gatctagagt gattagccat | 660 |
| tctggttcgc ttgggactga gtggattccc gtgggtagtt ctgaatccag aaggtcctg | 720 |
| gacaaaacaa gactattggg tcagctgagc tggctgagtg ctgagtgtta agtatatgct | 780 |
| cagcaaacat ctttatcagt tcccccttc catttcgccc gcatggctac aaaaagaaag | 840 |
| caagcatcta ctgtctgttt tccactgtga tgctcggaac tgtgcggggc ggtgcacggg | 900 |
| gtgaggggga ctgtgcaaag cagccacctc caagtcctca ctaaagaatt cagagttcct | 960 |
| caggaaggcc aaacctccct ctgggatgat cgcttttcca ataggggaag gtccctgggg | 1020 |
| ccctaaaagc caatcaagta ggttgggtc tcataacaaa gccagcggga gacggttgtg | 1080 |
| agagaaaaga aaggggaatg accgtagggc attggctttc gctggcctag cgtggaagcc | 1140 |
| gagtgggagt tcccataagg aggcactcgg tgctgggtga ggaaactgag gctccgcagc | 1200 |
| caagtgaagg agtttgttta ggagcgtgca ggaattgctg tgtgattgga attccacagc | 1260 |
| agtggtttgg caagccgctt tcttcacttt tctcgctctt ttaggagcga gtcccccact | 1320 |
| tgtccagaca gcagctaggc ttgtcacagg ctccgtactg ccctatccac cctcccaact | 1380 |
| gccagcgtcc cgccccgtcc cctcccagcc cccaaggagg agggaagaac cgcggcgagg | 1440 |
| agggggtcg gaggcccaga cttataaagg ctgctggacc cgcgctaccc gccagacccc | 1500 |
| gccgccggga tccccgcgc tgcctgtcgc ccacgtgac cacactacta agtgagttgg | 1560 |
| ggcgcgtccc catcgcatcc ccagaccctc gtgagttgtg tggctcacta aatccaggtg | 1620 |
| gggaggagag cggatgaagg agggctccgg gatgggcac cagacagaat gcgttatagc | 1680 |
| ggagtcttag gagctagggg agcggaggga ctcaggggat agcgctcagt cgggccatcc | 1740 |
| ccgcgcgcgg cctgggagac ctcaagctac tcagcaggaa tgcgcttgtg gtcgtcgcc | 1799 |

<210> SEQ ID NO 7
<211> LENGTH: 1464
<212> TYPE: DNA
<213> ORGANISM: Mus musculus

<400> SEQUENCE: 7

| | |
|---|---|
| gggaaccaga gaaaccctct agaaggatta ggtaatctaa aatttcatta gtagatgcta | 60 |
| aggggtcata ggtggtcagt ggtctgcatt cctatgtcag aagcggtcaa ccatgtgatg | 120 |
| agatagggct gcccaggaca gatggcctat tctgagataa ggaattttcc cattttgtg | 180 |
| gttatttcag tctgttcttt gggaggtggt tttatgatct tgttctgaat tttatggtat | 240 |
| gttcctagag ctggtgtctt atgccttggt ttctgggact tatggtctat tcctgaagtt | 300 |
| ggttccttat agccttaaa aaaaaaaaa aagcaagccg ggggggggg gggggcgtg | 360 |
| gtggcgcaag cctttaatcc cagcagagga ggcagaggca ggtggatttc tgagttcgag | 420 |
| gccagcctgg tctacaaagt gagttccagg acagccaggg cttcagagaa accctgtctt | 480 |
| gaaaaacaaa aaccaaaaca aacaaaaaag gctggttctt caaatggagc caaatggggt | 540 |
| ttatactgtc ctttcaacat cagcttcctcg aatggaaatat tacagagacg atgatgtaca | 600 |
| ggatccaggt tgacttggaa gtggctcagc ctctctaggg acactcattg ttggaaacca | 660 |

```
cgcaccaggc taggaggaag cacaagtcac aggagcgggc ttgtacagct gttcatgctg    720
gatacttgct gtgtagtcag gtgacctgtc tttcagcggt tttttattgt tttgtttccc    780
tggagtggac ctactttggg gaggcccttc agtaaccata cctatttcta tttcctggat    840
atgtttagat gatttgcgac acgcggaact tcagagcaga accataaaga atcagcacaa    900
ctcaagccac tgtggggagt tcctgacgct gagcctagat gagagacagc gctgggatcc    960
aaagcgatct atggagcggt gttgcccgga tttgggcctc ggctcactca ctcattagct   1020
ccataccttg tgagtgtgtg tgtgtgtggg gggggcggt cataactttt ctgtgcctca    1080
gtttccttca ctgtaaaatg gaattggcat cgtgctcagc tagcagggtc gctctgaaat   1140
gtgagtaggt catcacactt ggctttactt cgtggaggcc actgttccca gcttctactg   1200
agagccgact catcctctct gggcagatct gaccgcccgc gtcctcgcct cggagggcct   1260
gagtcaccac gctgtgcgtc acccgcgcct ctgctccgcg acctgcaaat tcaccctgag   1320
tcagcggccg ggcgcgtcca ttgagcgcat cgcgagggg cggcagagcg ccacggcggg    1380
cagtgggcag ctaggtcaga gtgagacacg cagggaggga ggggcggcga gtcaagcggc   1440
tcggggacag gtaggatcac agcg                                          1464

<210> SEQ ID NO 8
<211> LENGTH: 1501
<212> TYPE: DNA
<213> ORGANISM: Mus musculus

<400> SEQUENCE: 8
cactgagcca agccagccgt gcccaaaagt gcctcgtccc ccacaaacga aggccagtct     60
gaggggcttg tggctgtgat ggctgctgac tgaaggtccc gaggcatgaa agttttattt    120
gaagggtttt ttgtttgttt gttttttgtt ttgttttgtt ttgtttgttt tttttgagac    180
agggtttctc tgtatagccc tggctgtcct ggaactccct ctgtagacca ggctggcctc    240
gaactcagaa atccacctgc ctctgcctcc caagtgctgg gattaaaggc gtacgccacc    300
acgcccagct tatttgaagg ttttatttat ttattattta tatgagtaca ccgtagctgt    360
cttctgacac accagaagag ggcatcagat cccattacag gtggttgtga gccaccacat    420
ggttgctggg aattgaactc aggacctctg gaagagcagt cagtgctctt aaccattgac    480
ccatctctct agcccccatg aagttattta aaaacaaaaa atctaagtcc atgggccagt    540
gggcaaggag gtagcctaga gctcaggcag agggacttac tactgggata aaagtaggtg    600
tgtgacactc cgtcttgatc ataaagccgt ggtcctagag ctgcagcatt tgcactggaa    660
aacttgttcc tgtggctgtg gtctcgtcta gcacacagcc ccatcacctc tccctgcaca    720
cacgcctctc cccgtacatg aagcctcctc ttcttactgc ttatgctccc cgggacctga    780
tcccttccct ggaatctcag ctccatcaac ttgagaggac tttgttccca tgtcgtgata    840
cctataacct gctcgatact gtcacattct tagataatcg gccaggtatg gccacactg     900 ctctttccag ttgaaggcca caatcacaca tactaacagt aagtcattct ttttagtcac    960
taacgagttt ctcagataaa gccagtgaca cccacacagc ataatcaaag gcacttttta   1020
atgagcacca gcctcacatc tgtctagttt taattatttc tgtctctctc ataccacacc   1080
cctgcctcat caatacatgt ctatgtgtct aatacacaca tgcacatcag actcaccatt   1140
ctgtgactct gtatacacag aaccgactca ctactctgtt tcttgaatac atgcctcata   1200
tagatgtttc accagccgcc cacactcaca aatccttccc agcctgtcat acgcacatac   1260
```

| | |
|---|---|
| atactcagcc acaccagctc gtcacactca aaatcacaaa ccagtctgcc tccatctgag | 1320 |
| tcacagtgac acacactgag gactccatcc atcttctctc agatccacat ggaacaaggc | 1380 |
| caggtggagg cgctgcggga caggtctgcc caaggagggg cggtggccct cccgtggctg | 1440 |
| tcgctcgctc cggactctgc ccgggcctgg gcggcggctg cagccgggag ggcgacgtgg | 1500 |
| a | 1501 |

<210> SEQ ID NO 9
<211> LENGTH: 1501
<212> TYPE: DNA
<213> ORGANISM: Mus musculus

<400> SEQUENCE: 9

| | |
|---|---|
| ccttcctctg ctgtctactc tccaccttac acacccatg tggtcagaga gatccttcct | 60 |
| caactctgcc ctctgttttt gctgtggttt cagctcccct tttcatcata tcctctgctt | 120 |
| gacagttact gggccaatgc tgatctggct tttctcaact gacagcaggt gagggcactg | 180 |
| ggggacaaaa gggacatcag tgatcaccat tatgctgctt tgcctaagaa gtgacagagt | 240 |
| gaaagacaaa cagaaaggcc cgtgcagact ggagggctgt gttcttggtg ctacgggaca | 300 |
| cttcaaagag agccagcatc cttctttttg tcgagggag tagaaggctg tggtggcttt | 360 |
| acaaattctt agatgctctt gtggtagggc tggaggagg tagggctgct ggccctgagc | 420 |
| catcctgtct cttcttcatt ctcagtatcc cctagcttag cccacattct ccctgtcaga | 480 |
| gttgaaacca gacggtacaa ggctgtaggg atacaggaaa gaagtgtgga ttcttgccta | 540 |
| gatcccagaa ggaaagtcca ccagggctgc taaatggcct gggtaaggta aggggaagac | 600 |
| atccgtattt tgtgtcatga aggagatcaa ttagactttg atgtctctca taagaatgg | 660 |
| agaattggtt aacctggaac gggcagtgct ggatgtggct tgtctcttat agccacacca | 720 |
| cagttgtggt ctgacctgcc tgaagtcaag attaggttgt ggttctcttc tttcatttt | 780 |
| tcacattctc attgatattc tttctctttg taaccctcct cctcctctct ctctctctct | 840 |
| ctctctctct ctctctctct ctctctctct cctctctccc atatagccta gggtggcctt | 900 |
| gaccccaata tgctgttttt aataccatga taccctaact cacaacaata cacagaacat | 960 |
| aggcggtcaa cctaatctaa aagcgcatta atcaaaaaac tacagcatgt gcaggttgtt | 1020 |
| aatgtgaagt acaaagataa tatttttaaa atcagcagtc tcaatcttag ccttctccct | 1080 |
| tgcttccttc tcctacaatt caatccgtaa ctttgctcac tcctcctgtc tagacctgca | 1140 |
| cttttagacc acaccccaag ccaagtcact cctggcaccc ctcttcctta cttcactgcc | 1200 |
| cctttctggc tactactcac ttagccccac ccaaagagtc ttcctctctt ttggactgcg | 1260 |
| ttggaacaca gactgtccca ccccaacagt gaagggagg gtgggggttt tcagcctcac | 1320 |
| cctcaggaag atgctccccc gccccgcctc ctttgctctg ctctgtggta cttcctctct | 1380 |
| ggctgactta gctgacagac ctagaagtgg gaccaggacc ctggcactaa gacagattca | 1440 |
| aggattgtat atccaacaac tagacaagac attaccttct gatcagcatc agggaaaccc | 1500 |
| t | 1501 |

<210> SEQ ID NO 10
<211> LENGTH: 1504
<212> TYPE: DNA
<213> ORGANISM: Mus musculus

<400> SEQUENCE: 10

| | |
|---|---|
| cattgctgcc ttgatcacat aaccaaagaa aaagcgattt aagagcgggt ttatcctggc | 60 |

```
tcacagttcg agagtccaac actgtggggt cctaaccaca tgagcataag acagatggtc      120
aaactgtgtg tggggttgg gaggaagggg gcggggttcc cgtgtatgca gaggtcagag       180
gttgacaaat gtcttctgct attcatctct tcctgattct ttgaggcagg gtctctcact      240
tgaaccagac cttgcagact tggctaatca gctcgcctcc ggaaatcctg cttctggggt      300
cacacagcag ccacactgcc ccacgttgtg tggagcgggg atttgaactc tagtcctcat      360
aaccttcacc cacggagcca gctccacagc cttggcccag ctcactttct ccgtttcatt      420
cagtccagca tcccagtccc tggaacggta ctgagcttag ggtgggcctc ctaccccagt      480
cagcctaact gagaaactcc ctcagagaca ggctgagaga gaggtctgtc tcctagatcc      540
tctcaagtta acatcacagg caggctaggc ccccacagag ctcaccttcc tcacctcatt      600
tgaaacagaa ggtggagtcc gtaataagag gctaaggcag tttggccgga tcagctcggg      660
aaacgctgaa tcactgtgag tgaggactta attgtccttc agcatcacaa tccctagcca      720
agtaggatca gcacagagtc gattccaccc aagaagggag gaggtctgat tgcgtgccca      780
catttagaca cgcctggaat tttgttagta ggttcagcat ctccttggga gatgactcgc      840
atagactgag accaatgcag atgtatttgc atacccagta cacttggaat aaaccaaaga      900
ccggcactga ggactcccgt actactcaaa acagttcgat aaacatgagc cttctctctc      960
caccgtgggg gcgcactcga gacctccagc cgagagggct cgcccacacc tgttcagtct     1020
actcccaggc actgttccct gaagtccctg agcaaaccgc ggggtgtgtt aagtaatctc     1080
agagcgagtt ccgcagaagc aaacatttgc attctgcaga gaacgacggg ttctcgccca     1140
agaaaattac ggagcatttg ttttcctcct tttgaagttt ccccaaaata gttgtttcaa     1200
tccgactgcc acgagtcctg ctgacccctt cctttgggag cagcgcttgt ccctgaccac     1260
tgcttagctc ggaaccagga tctctacact ggccggcggg cggcgggca ggcgagcggc      1320 aggaggcgga cccttcggga acagacggct cctcctcaga ggggagggac aggcttctca     1380
aggccttgct ctctagcagt cgcagcgccg ggtcccagaa tctagtccta cgccacggtt     1440
ttgaccacgc gtgacccgct gcccagccgg cccggccatc aggtggtccg tgtgtccctc     1500
tgac                                                                  1504

<210> SEQ ID NO 11
<211> LENGTH: 1491
<212> TYPE: DNA
<213> ORGANISM: Mus musculus

<400> SEQUENCE: 11
gatgaaatgt cttgctggtc aggcaaatga gtccaggcaa cctggcaagg gggggagggg       60
ttgtctcaga tggtttgagc aaggcaagag caagcagatg gacactttag aaaaagactc      120
tttccgggaa ggtgctttgg gcatgggagg ggaaggaacc cactgagatt atttagggat      180
gaagaagcca acagtcttgg gaccaggtct gaggaagcaa aaagagggtc tgggtgctat      240
agggacagtg atcagtagct ttgtctgaaa gggggaacag ggagggaggt agctttagag      300
ggagcactag acatttagag ggagggatag agcatgtggg aaaagggaca gaagtattga      360
tgggaagtcc actgaagaaa aacaagcagc aaaacagaca gtggagagaa agggaagag      420 ggaaatgggg tagggtggat acagaggatc caggtaggga agctggtggc tcagaccagg      480
gatacaggga gagaagcctg gcttagaact cagggaaaac aggatttac acaagccatg       540 gcgctaaatt caggccccat cctgtgcagg gctcagagat gtgggtgaca agttgcccca     600
```

```
ctcagtagtc tgcctagctt cctggcacca gtccctgagc ccctgcgtgt agacaagcca    660
gacctgaagc ctttcctctg gggagctagt gtttacaaaa gcctcagtgc acaaaaagga    720
aggaaaacaa tcagggaaga gggaggggca gggaactgat ggaaaacttt gtacaattca    780
caccagatta cttaaacaca cacacacaca cacacacaca cacacacaca cacacacaca    840
cacacacaca cacagacact gccatttaaa ggaaagtgag tgctggaaaa ataaccctac    900
ggacagaaaa tactctcctc gacactcctc ccaccaaaca gtgagagctg attactttta    960
ggcaattaca gaagaggaag agcagaattt gttgggggag gtggaattat tatggaagca   1020
aaaagaatac aatccccatt gctgaaaaca cgaggaaccc gttttgatca gctgggggga   1080
tgagtggcag agatgttcag gtagggggt gaacggctct gtcagtgtct gtcaggagac    1140 atggagaaa taacatcggc gagggcatcc tggaggaggc agcaggcaac ctgggttttg     1200
gcgctgtgca gagacgacgt ccgggcatgc ccggtgtagc gcgcttcctc tgcccaggtc   1260
caaggccctc tcccgcctgc ctcccacagc acgggagtcc ggtgcttgtt cccaataatg   1320
acgtcagtga gcgatgacct cagcgcctgg gaggcgcggg cgagctggcg ggcggggcgg   1380
agaggggcgg gcgcaggcgg aggggagagg cgagacaccg gaggggcacg cccccatccg   1440
ccagcgtcgg ccaatgggcg ccaccgacgg ctccccgcct ccccgagtgg t            1491
```

<210> SEQ ID NO 12
<211> LENGTH: 37
<212> TYPE: DNA
<213> ORGANISM: Artificial Sequence
<220> FEATURE:
<223> OTHER INFORMATION: Bscl2 forward primer

<400> SEQUENCE: 12
cgcgcgagac tcgtaagcag gcagggatta taacaag                              37

<210> SEQ ID NO 13
<211> LENGTH: 41
<212> TYPE: DNA
<213> ORGANISM: Artificial Sequence
<220> FEATURE:
<223> OTHER INFORMATION: Bscl2 reverse primer

<400> SEQUENCE: 13
ctgggggtcg actgtaagga ttggagatcg caaagtataa g                         41

<210> SEQ ID NO 14
<211> LENGTH: 28
<212> TYPE: DNA
<213> ORGANISM: Artificial Sequence
<220> FEATURE:
<223> OTHER INFORMATION: Ephx1 forward primer

<400> SEQUENCE: 14
cggaattcac acaccagaag agggcatc                                        28

<210> SEQ ID NO 15
<211> LENGTH: 28
<212> TYPE: DNA
<213> ORGANISM: Artificial Sequence
<220> FEATURE:
<223> OTHER INFORMATION: Ephx1 reverse primer

<400> SEQUENCE: 15
ggggtaccgt cgctctcggg ttcctact                                        28

```
<210> SEQ ID NO 16
<211> LENGTH: 28
<212> TYPE: DNA
<213> ORGANISM: Artificial Sequence
<220> FEATURE:
<223> OTHER INFORMATION: Nope forward primer

<400> SEQUENCE: 16
cggaattcga ggagccctgg tttcagag                                        28

<210> SEQ ID NO 17
<211> LENGTH: 28
<212> TYPE: DNA
<213> ORGANISM: Artificial Sequence
<220> FEATURE:
<223> OTHER INFORMATION: Nope reverse primer 1

<400> SEQUENCE: 17
acgcgtcgac catcgccatc ttgggcta                                        28

<210> SEQ ID NO 18
<211> LENGTH: 28
<212> TYPE: DNA
<213> ORGANISM: Artificial Sequence
<220> FEATURE:
<223> OTHER INFORMATION: Cdkn1a forward primer 1

<400> SEQUENCE: 18
cggaattctt tctggccttc aggaacat                                        28

<210> SEQ ID NO 19
<211> LENGTH: 28
<212> TYPE: DNA
<213> ORGANISM: Artificial Sequence
<220> FEATURE:
<223> OTHER INFORMATION: Cdkn1a reverse primer

<400> SEQUENCE: 19
ggggtacctc gagctgcctc cttatagc                                        28

<210> SEQ ID NO 20
<211> LENGTH: 28
<212> TYPE: DNA
<213> ORGANISM: Artificial Sequence
<220> FEATURE:
<223> OTHER INFORMATION: Perp forward primer

<400> SEQUENCE: 20
cggaattctt tgagccgaca gaaccaat                                        28

<210> SEQ ID NO 21
<211> LENGTH: 30
<212> TYPE: DNA
<213> ORGANISM: Artificial Sequence
<220> FEATURE:
<223> OTHER INFORMATION: Perp reverse primer

<400> SEQUENCE: 21
acgcgtcgac gcggagcgga ggaacgccgg                                      30

<210> SEQ ID NO 22
<211> LENGTH: 29
<212> TYPE: DNA
<213> ORGANISM: Artificial Sequence
<220> FEATURE:
<223> OTHER INFORMATION: Pltp forward primer
```

<400> SEQUENCE: 22
ccgctcgaga gcctgggcta catgagaac                                29

<210> SEQ ID NO 23
<211> LENGTH: 30
<212> TYPE: DNA
<213> ORGANISM: Artificial Sequence
<220> FEATURE:
<223> OTHER INFORMATION: Pltp reverse primer

<400> SEQUENCE: 23
cccaagctta agcgccattc ctgctgagta                               30

<210> SEQ ID NO 24
<211> LENGTH: 28
<212> TYPE: DNA
<213> ORGANISM: Artificial Sequence
<220> FEATURE:
<223> OTHER INFORMATION: Srxn1 forward primer

<400> SEQUENCE: 24
cggaattcgg gaaccagaga aaccctct                                 28

<210> SEQ ID NO 25
<211> LENGTH: 29
<212> TYPE: DNA
<213> ORGANISM: Artificial Sequence
<220> FEATURE:
<223> OTHER INFORMATION: Srxn1 reverse primer

<400> SEQUENCE: 25
cggggtaccc gctgtgatcc tacctgtcc                                29

<210> SEQ ID NO 26
<211> LENGTH: 29
<212> TYPE: DNA
<213> ORGANISM: Artificial Sequence
<220> FEATURE:
<223> OTHER INFORMATION: Cgref1 forward primer

<400> SEQUENCE: 26
ccctgagatt ctcactgagc caagccagc                                29

<210> SEQ ID NO 27
<211> LENGTH: 27
<212> TYPE: DNA
<213> ORGANISM: Artificial Sequence
<220> FEATURE:
<223> OTHER INFORMATION: Cgref1 reverse primer

<400> SEQUENCE: 27
ccctggtcga ctccacgtcg ccctccc                                  27

<210> SEQ ID NO 28
<211> LENGTH: 30
<212> TYPE: DNA
<213> ORGANISM: Artificial Sequence
<220> FEATURE:
<223> OTHER INFORMATION: Ltb4r1 forward primer

<400> SEQUENCE: 28
gactagatct ccttcctctg ctgtctactc                               30

<210> SEQ ID NO 29
<211> LENGTH: 30

```
<212> TYPE: DNA
<213> ORGANISM: Artificial Sequence
<220> FEATURE:
<223> OTHER INFORMATION: Ltb4r1 reverse primer

<400> SEQUENCE: 29
gctagtcgac agggtttccc tgatgctgat                                      30

<210> SEQ ID NO 30
<211> LENGTH: 31
<212> TYPE: DNA
<213> ORGANISM: Artificial Sequence
<220> FEATURE:
<223> OTHER INFORMATION: Cbr3 forward primer

<400> SEQUENCE: 30
cggaattcca ttgctgcctt gatcacataa c                                    31

<210> SEQ ID NO 31
<211> LENGTH: 30
<212> TYPE: DNA
<213> ORGANISM: Artificial Sequence
<220> FEATURE:
<223> OTHER INFORMATION: Cbr3 reverse primer

<400> SEQUENCE: 31
acgcgtcgac gacacacgga ccacctgatg                                      30

<210> SEQ ID NO 32
<211> LENGTH: 27
<212> TYPE: DNA
<213> ORGANISM: Artificial Sequence
<220> FEATURE:
<223> OTHER INFORMATION: Btg2 forward primer

<400> SEQUENCE: 32
cgggagatct gatgaaatgt cttgctg                                         27

<210> SEQ ID NO 33
<211> LENGTH: 24
<212> TYPE: DNA
<213> ORGANISM: Artificial Sequence
<220> FEATURE:
<223> OTHER INFORMATION: Btg2 reverse primer

<400> SEQUENCE: 33
gataagtcga caccactcgg ggag                                            24

<210> SEQ ID NO 34
<211> LENGTH: 1506
<212> TYPE: DNA
<213> ORGANISM: Mus musculus

<400> SEQUENCE: 34
gcctagggat tctgtcatgc cctcagaaga attaagttct tgccaccatt tatggcatcg     60
aaagactcca ttcccacttg gataatggaa acttgttctt agggagctgt cagacaatga    120
gctccacacc cttaaacaag ctatgcagca gaagtgaagg cactcccggg aagtagtttc    180
tttgtctccc aacaaatcag atccggaagg ctgggtgcca ctcttgctga ctctcttcta    240
ggagacagct ctcactggat aggaaaacat ttgccttatt aaaatagcca ggataaaccc    300
aatggttagt tttactgatg ggggaaatca agggtttctg aaaagttcct gattcagtta    360
gctcatgctt ggaccgtgga gtggcattat ggtcttttca gctgctgagc tcccaagagt    420
```

```
gggctccgat gacagccctc agcaggccag agatcgccca tcatacatgg ctggctttga    480
ggatgtctta gtggcctacc tggaaccgca gctgcttgc cttcctgcat gtcacctcct     540
gtgaggagag ggtcacacat tcacacaagc ctcctccaaa aagtctcaga gactgaacct    600
gtctgagagg gagataggta cagttgtcta cccagaattt taccatccat tctgagggtc    660
ctgatcacta agtcagcaag gactccatcc tcatgactgg cttgggaatg agagcggag     720
gtggatgtcc taatgtagga catgctacag tacagggaca agaccccag tgttctccag     780
gacaaggaac atcattcact aaaaggcttc ctaagacaaa cacatcttcg tccctctgcc    840
tggtgcaaac tgaggcactg gaaaacaaca cactctcctc ccaagggtcc ctttgattcc    900
acttgagaat tcagacccaa gcatatcttg tctcccacaa ctcagagact gatgctctaa    960
taaatgtgtt gagacagatg tctgtgccag gcaaaatcaa cttgctgggg caagcagaag   1020
tcaatcttgc atcctccctc ccttcttcc tccccacttg acctttatgg ctctggtttc    1080
cagcaaggag tgaattattc acatctgctc acagatatca aattggccct ttccaggttg   1140
ccagtggggt ggggcagaag gtggctttgt tcagtggcag taagtgggag gagctacagc   1200
cttgttcaaa cagttcacag gtgggtacct gttttttgct aagtcatccc gggaatgctc   1260
aaaggccctt tgtgaagtcc tttcggtctt ctccggctcc tcctttcttc ccaccggtct   1320
aaaggactta aggaggctca cagagcaggg cagggctcac tgctcttcag catggcttac   1380
attgccaagt cgttctacga tctcagtgcc gttggcctgg atggggagaa gatagacttc   1440
aatacgttca gaggcagggc tgtgctgatt gagaatgtgg cgtcactctg aggaacaact   1500
acccgg                                                              1506

<210> SEQ ID NO 35
<211> LENGTH: 1499
<212> TYPE: DNA
<213> ORGANISM: Mus musculus

<400> SEQUENCE: 35
ggataattgc acagaaactg agatttactg ttagtaaacc ccttaactga gcacagtccc     60
tgttctcctg actgggagcc tccaaggctc tcctagttcc ctagcttctt gagtcctgag   120
tatcccgagc ttatccccgt cccgcgggaa ataaacacag gacacaccag gttcttccac   180
ggttaacttt tacttcttaa acatagtgag gtagacaaag aaggctcaga aagtgtgtgg   240
cttaaatact tttggtgacg tgtctaaact aggactggta gcaacaccca tgatcctcat   300
gcaccctggg gataggttaa agccccagg ggttgggcaa aagccccgga gacggactgg    360
tggctttggc tggctgtgtt ctcgcagctg cgcacaaaga ggtttagcac catctagtgg   420
cggcacatat attgcagccc tttacacctg agaaacacaa agtgcctgga cagctttgtg   480
acctagccag cttcatttct catgccagct ggagcccag ccagggccac ttcaggcacc    540
aatcaagggc aaattatagg ggtataacac ctctagggca atcctccctc aatgggcatg   600
ccctagtttt attctgcctt aggtattctg tatacctcag ggtcctgatg gctagtcatg   660
gggagcaatg cattggattg ttctcctctt cctggtgtgt gtgacacaca cacacacaca   720
cacacacaca cacacacaca cacacacaca gagagagaga gagagagaga gagagaggtg   780
gaggtcagag tcagtgttag aatctattga gctagaattc caaatagtta tgagctgcct   840
aacacggtgc tggaaaacaa acccaggtcc tctggctgag cagcaaatgt tcttagccac   900
tgagccattt cttcagcctt cttcctgatc ttttttttt tttcttcctg atcttaatat    960
gttccgtccc tccccagtgt tatgatctcc accctaaac caggttgtaa gctcttatta   1020
```

```
cccaaatgca tagccttagg cctgagcatc atgtattaca ctgaaatgtc accggcaact    1080
gagtaatagc tgtagggtgg aggggctctg acaggccccc aaagaaactg aagcagaaga    1140
ggacactccg caggaacgga aggttgaaac aagcaaaagg agagcagctg ggagagcgcc    1200
ttgtttgggt tacttctctg ttgcctgcaa gccatggagg ctagatagaa cataaacatt    1260
gcaggaggtg ggctgaaagg actggggcca gaggtgggga gatgtgggag cagtcgttag    1320
caggtacaac tgctcttctc cgcaggctga gccttctctg cacctcagcc ttatcctgct    1380
tcctggggag gctggcctcc acatgcctgg gcctgtcagt gatgggaagg agtaggatga    1440
aggagggccc agggtgagca ccatcttgtc cctctccatt cttgactcat cctctccgc     1499
```

<210> SEQ ID NO 36
<211> LENGTH: 1500
<212> TYPE: DNA
<213> ORGANISM: Mus musculus

<400> SEQUENCE: 36

```
aaaatggacc ttcaagctgg ctttagtttc tgttgctctg cctgcaagtg tcctcccact      60
gatctgttta tcacactctc tttaccactt ttgttgttgt ttttccttct gagagttttt     120
ttagcctgga cagcggatcc tacttctcaa ggccctaacc tgcaggtcct tccttgcacg     180
tggggaccca aagtgtgcgg gagtggtgct ggaacctggc cttgaatgag gttcaccctc     240
accccaagta tctcggtctc ttccttttct gatccacctc aaccatctca gcaacctcag     300
caacctcgct gggaacgccc acccattgca aaccctgtgc cactggcgca gggcagcagg     360
aagggtggct tagtaaagtt agaagaaaac gtttggcatc gtgcttttag tggtgtccca     420
gaccctctgt tccctcttgc tcaagactcc ccggaaagag tcgcagagct tatcctagca     480
ggacaactct ttattctcat gccccacaag cttttttaaag accactaaag cttaaacttc     540
ttcccaaaca agcccaccgg gaacttttgc ttctgggaat ggcaattgct cctaactatc     600
ctgcggctgg agcaggcaac tgagatcctg ttagtggttt tgtttagttt cttggcactg     660
gccctcttca attcaagttc tgtgcctttc gaagccaggt cttagaacag gccaggctc     720 gccctggccg cggagaaaaa cggtttagtc acagatgtag tatccccaaa gatgccccat     780
tgattcctga gtcagctga agctagagag cccttaccac atcccgacca cctgcgggga     840
gactgggtgc ggactggagc tgatgggtta gagtcagaac atgggcataa aggatgctca     900
cagagcacag tgtcaactaa gccaaatact tattcagaat gacacagcaa agttttgggt     960
catgcctaac aggacctgga gcttctagct gcttgaaaag ttccatagcc aaaacctgag    1020
cagtctgagc ctggaagcag gcaagctgtg ggcaggggct cacgccaaag aatctaggtt    1080
agtggccgaa gggagatgct ctttaggagg gtgaccagtg ccaactcag ggtgaccagt     1140 ggccaactca ggaagcagca ggtgtccgcc caaggcgagg ctgatcacca actcccaggg    1200
gcttgcctgg gccctgcct gggaaggaac tgaaaggtga cctgaccctg caggggcggg    1260
ccggggcacg ggcccgagcg agtggcgcag gtgggcgtgc cggccaggag gagaggcggg    1320
acctataaag cgctctccat tcgggaggcg gagcggccgg gtgcagcctg tgctggtggg    1380
cgcggtggcc cgcagccttc ggcttgctgc aggactgtga aggggaccac tgtccaagct    1440
tcggactact gagggggcgcc tgcctcggtt tacccttcag cgtctggtga aatccggcag    1500
```

<210> SEQ ID NO 37
<211> LENGTH: 1500
<212> TYPE: DNA

<213> ORGANISM: Mus musculus

<400> SEQUENCE: 37

| | |
|---|---|
| cctgaggaca agtttcttca gtctccattg agatggaaga atcagagaa agagttttgg | 60 |
| gacccatgct ctcccagtct gccattcttc gtgtacgtac aatgtaaagg cttgaagctc | 120 |
| atggcctgac ttggtcacca gactcagcca cttactcagt ggccttgagc aactcatttc | 180 |
| aatacctgtc agcctcagtt tttcccatct gagaagtggg ggttatgatg gcatttacct | 240 |
| cctcagcaca cctggtcagg acctcacccg tatcaaggcc tttcacatac ttccaaagtg | 300 |
| ggctggtgac acacatagta ctggaggagt gcctccagtc agaccttcag tcaagaagcc | 360 |
| ttactgactg tgtctcagga cacctatgtc cttctgtagg cgctctctgc ctgtagaggc | 420 |
| ctggattaaa gcttgtgata gctccagaga cggtctcaaa catgtagcgc cttctatctg | 480 |
| tgggtacact aaatgccact tcacgtagta ttcaaatata acaacatttc ataaccctgg | 540 |
| tttgtcaata acctttcagt ctatcaaaaa ccttgacaac agttgaaact gggtgtggag | 600 |
| gggcacattt gtaatgtctg ccctccactt gagaagtgaa agcaggttat tctaagctac | 660 |
| ataaggagtt caaggccaac ctgcacaaca agagaccta tctacaaaag ccaggtgtga | 720 |
| tggtggcaca gtccaacact tgagaggtga cggaaggatc aggagttcaa gggcagcctc | 780 |
| aactagatac ctgagaccct gtctcaacca acctccctcc acaaaccaca agcaaagcaa | 840 |
| actcaactaa agaaacttct caccccactt gagaggagcg tcttaagtc aggactgcag | 900 |
| acttgggtga cagttggaat gattctctcc aggtaaataa tgatgatgat aataataacc | 960 |
| catatttata attcacttcc cagctttcag acactctccc cgttcttctt tctaagtctt | 1020 |
| ggcgcgaggc caggcggcca caggattttg tttcgccctg tgttgggaac cttggctagt | 1080 |
| ctgaacgggg cggggcgcag ttgcaagccc caacttcggc aaggtgcgtc aggggggaatc | 1140 |
| ctcggtgcac ctgggcgcgg caaggaaatt gcaccatgta tgggcagctg cgtcagaggg | 1200 |
| gggcgtggcc gccgcggatg ctaggggacg ccaagtcggt cgcttctgt ctgtagaggc | 1260 |
| ggcttgccac ccgagcagag ggtcgtgaag ttccgagcgg accggtccac agaggttcat | 1320 |
| ctggagaggt gggtcccctg cgaggtgaaa ggcgccgctg agacacgccc caccccccg | 1380 |
| tggtgcaagt ggttcagccc aagaactttt cattcataaa aaagaccaga ctccgagagg | 1440 |
| cgcgagtgag tcagaaccgc agccgccaac gcggacccta ccgaacatcc agcccagggc | 1500 |

<210> SEQ ID NO 38
<211> LENGTH: 1500
<212> TYPE: DNA
<213> ORGANISM: Mus musculus

<400> SEQUENCE: 38

| | |
|---|---|
| tggggctccc gaaatacaac cagagaccta cagagggcag caccgagccg taaacgggtc | 60 |
| ctccgcactg caagcttggg gtcgccagac tgcccaaagc caagtccccc tctttaggac | 120 |
| agggcagggt tcgtgcccga ccagtccctg gcctggataa aagtcaggaa gtgtctaacc | 180 |
| atcacaagaa ccaacagatc ctggcgggga cttaggactg acctagaaca atcagggttc | 240 |
| cgcaatccag gtccccaaag gtgggatcct caaccgcagg acgagggaa tagcctttcg | 300 |
| attctgggtg gtgcattgga agcccaggc tctaaaaccc ccaacctact gactggtggc | 360 |
| cgagtatgca cccgactgct agctaggcag tgtcccaaga accagtagcc aaatgtcttg | 420 |
| gcctcagttt tcccggtgac acctggaaag tgacctgcc attagtagag gctcaggtca | 480 |
| gggccccgcc tctcctgggc ggcctctgcc ctagcccgcc ctgccgctcc tcctctccgc | 540 |

```
aggctcgctc ccacggtccc cgaggtgggc gggtgagccc aggatgacgg ctgtagaacc      600
ccggcctgac tcgccctcgc ccccgcgccg ggcctgggct tccctagccc agctcgcacc      660 cggggggccgt cggagccgcc gcgcgcccag ctctacgcgc ctggcgccct ccccacgcgg     720
gcgtccccga ctcccgcgcg cgctcaggct cccagttggg aaccaaggag ggggaggatg      780 ggggggggggg gtgtgcgccg acccggaaac gccatataag gagcaggaag gatccccgc      840 cggaacagac cttatttggg cagcgcctta tatggagtgg cccaatatgg ccctgccgct      900
tccggctctg ggaggagggg cgagcggggg ttggggcggg ggcaagctgg gaactccagg     960
cgcctggccc gggaggccac tgctgctgtt ccaatactag gctttccagg agcctgagcg     1020
ctcgcgatgc cggagcgggt cgcagggtgg aggtgcccac cactcttgga tgggagggct    1080
tcacgtcact ccgggtcctc ccggccggtc cttccatatt agggcttcct gcttcccata    1140
tatggccatg tacgtcacgg cggaggcggg cccgtgctgt tccagaccct tgaaatagag   1200
gccgattcgg ggagtcgcga gagatcccag cgcgcagaac ttggggagcc gccgccgcga   1260
ttcgccgccg ccgccagctt ccgccgccgc aagatcggcc cctgccccag cctccgcggc   1320
agccctgcgt ccaccacggg ccgcggctac cgccagcctg ggggcccacc tacactcccc   1380
gcagtgtgcc cctgcacccc gcatgtaacc cggccaaccc ccggcgagtg tgccctcagt   1440
agcttcggcc ccgggctgcg cccaccaccc aacatcagtt ctccagctcg ctggtccggg   1500
```

```
<210> SEQ ID NO 39
<211> LENGTH: 29
<212> TYPE: DNA
<213> ORGANISM: Artificial Sequence
<220> FEATURE:
<223> OTHER INFORMATION: Gpx2 forward primer

<400> SEQUENCE: 39
ccgctcgagg cctagggatt ctgtcatgc                                       29

<210> SEQ ID NO 40
<211> LENGTH: 30
<212> TYPE: DNA
<213> ORGANISM: Artificial Sequence
<220> FEATURE:
<223> OTHER INFORMATION: Gpx2 reverse primer

<400> SEQUENCE: 40
cccaagcttc cgggtagttg ttcctcagag                                      30

<210> SEQ ID NO 41
<211> LENGTH: 36
<212> TYPE: DNA
<213> ORGANISM: Artificial Sequence
<220> FEATURE:
<223> OTHER INFORMATION: Ltb4r2 forward primer

<400> SEQUENCE: 41
gcgggaggag atctggataa ttgcacagaa actgag                               36

<210> SEQ ID NO 42
<211> LENGTH: 30
<212> TYPE: DNA
<213> ORGANISM: Artificial Sequence
<220> FEATURE:
<223> OTHER INFORMATION: Ltb4r2 reverse primer

<400> SEQUENCE: 42
```
ggtcgtcgac gcggagagga tgagtcaaga                                30

<210> SEQ ID NO 43
<211> LENGTH: 29
<212> TYPE: DNA
<213> ORGANISM: Artificial Sequence
<220> FEATURE:
<223> OTHER INFORMATION: Ddit4l forward primer

<400> SEQUENCE: 43
gccagatcta aaatggacct tcaagctgg                                 29

<210> SEQ ID NO 44
<211> LENGTH: 29
<212> TYPE: DNA
<213> ORGANISM: Artificial Sequence
<220> FEATURE:
<223> OTHER INFORMATION: Ddit4l reverse primer

<400> SEQUENCE: 44
gctgtcgacc tgccggattt caccagacg                                 29

<210> SEQ ID NO 45
<211> LENGTH: 30
<212> TYPE: DNA
<213> ORGANISM: Artificial Sequence
<220> FEATURE:
<223> OTHER INFORMATION: Fosl1 forward primer

<400> SEQUENCE: 45
gccagatctc ctgaggacaa gtttcttcag                                30

<210> SEQ ID NO 46
<211> LENGTH: 29
<212> TYPE: DNA
<213> ORGANISM: Artificial Sequence
<220> FEATURE:
<223> OTHER INFORMATION: Fosl1 reverse primer

<400> SEQUENCE: 46
gctgtcgacg ccctgggctg gatgttcgg                                 29

<210> SEQ ID NO 47
<211> LENGTH: 29
<212> TYPE: DNA
<213> ORGANISM: Artificial Sequence
<220> FEATURE:
<223> OTHER INFORMATION: Egr1 forward primer

<400> SEQUENCE: 47
gccagatctt ggggctcccg aaatacaac                                 29

<210> SEQ ID NO 48
<211> LENGTH: 29
<212> TYPE: DNA
<213> ORGANISM: Artificial Sequence
<220> FEATURE:
<223> OTHER INFORMATION: Egr1 reverse primer

<400> SEQUENCE: 48
gctgtcgacc ccggaccagc gagctggag                                 29

<210> SEQ ID NO 49
<211> LENGTH: 9165
<212> TYPE: DNA
<213> ORGANISM: Mus musculus

<400> SEQUENCE: 49

```
gctgggctgc tgctccccca cccccacccc caccctgaca cagcacttag cacctgaatc    60
ttggtttctt tcagtgaccc accgttcttc agagctagga aaatgtaaca ctctacaggt   120
gatcagcttc tagatcacca ctttctacca cgtgagtgac cgcgagctggg agacccagag   180
gtaacccatc aggaagatag ctaaagaaat gatacatcaa agaagagaag ctggggcaag   240
agagacatgc agagaccaga tcaaaggatc agacaaagac gaggtaaggc accttgccac   300
gagagttagt gtgaatgttg tgaacacagg tgggcttctc ggagtgggga gtagggtggc   360
aagagttggc actggggaaa tagggaatcg attggaaatt tttcatgtaa tttgagtgga   420
ttactactat tcaaaaagat gtgcattggc cttgcctcct ggaggacgtt atccagacga   480
tgccaccatc agaaatctag tctcatggtt ttttgtaggg attttgaggt tggctgcatc   540
acgtgggtca cagaaggtca atcacgcagc ataaaaactg gagactgaaa ggggttgaaa   600
tgccgccacg cttgactagc ggacggcacc atctgcgcac acaacacaca agattcagat   660
tctggcaggg tgcaaggctc tctgagctcc agttggactc ctacaggccc aaggaactct   720
actgaattta caaaaaacaa acaaacaaaa caaacaaaa caaaatcagc atttatttca   780
cacctccatt caatcacact gaaaagacag gtggtaaagg tatgggcaga gggttgtggt   840
tgaggcctgg aaaggaggac caaggagtcc cagactgcgt tggagattat aatgggtcct   900
ttggtcactt aactaaagtg taatgggcag agacactggg gagcaaagca ttttacaggc   960
tctgccctct atgcaaggct cagccccgt aggcgattga cagttgggcg gggcttcctc  1020
ggcagccgga actgccttct gtatattgcc tgggcagcga gaggccggtg agtctgcctc  1080
gccgcggtgg cgatctggtg tacaccgcat taccccaggg gtgggcgccg cagcgtcggc  1140
cacagggtgc tgtgcggggg tagggtcac ttcctccgtg agcgagcaca ggtccaggca  1200
gaggaaagaa actcttggga ggcaattttg actgctctaa ggctgctggc tttgagccag  1260
actggccggc tgtgcaacct taggcaagtc actcacctcc ttgcaaacct ctggcatttt  1320
ggatccatgt catctgggtt tcgagagaga tttaaaggcc tcgttctctg tacgttatac  1380
ttctgtgaat gtatcaagga ggtttgtccc aggctcccga aactggagga agaggctgga  1440
agcacactca gtggagggag gtgaaggagt aattggaaga gaagcgcatg tgaagcaatg  1500
actttgcttt gccctgctac ctctagtttt caaagccagt tgaataagct tttttgtctc  1560
cagctaccct ggaaaagaaa ctgtcttttc ccttctcttt ctccaggaac cttcagctgc  1620
cctatcccat ggccaagggt atcgtccctg tggaagacca gccaggaact caaagcctga  1680
ggctggggcc agacccctg ctgtccccat catggtcaat gacccaccag tccccgcctt  1740
actgtgggcc caggaagtgg gccacgtctt ggcaggccgt gcccgcaggc tgatgctgca  1800
gtttggggtg ctcttctgca ccatccttct tttgctttgg gtgtctgtgt tcctctatgg  1860
ctccttctac tactcctaca tgccgacggt cagccacctc agcccgtgc acttccacta  1920
caggtgagaa ggctgctcca ttcaagtaga tggatcttaa cttgaaaatt acttcaggga  1980
cttgtggagt ctctcctctg ttgaatccca gtattgaccg agggtgaaat cttattctag  2040
tgtgctatca ggacttctgc cctcctgagc caaggcttga gcaggtctgg gctggtaggg  2100
ctttagggtt ctaggtctgc ctctgctgga aattgtggtt aagaactgag aaaaagagcc  2160
tggtcacgtg tgtaatacca gtctggggag gctgagttgg gagaattagc atgagttcca  2220
ggccagcctg gaagacaggt tgagaacttg tctcaagggg gtctaaaaaa aaaaaaaga  2280
```

```
ctaggaaaag aaagtcactt ttagccgggc agtggtggtg catgcctgta atcccagcac    2340
ttgggaggca gaggcaggtg gatttctgag ttcgaggcca gcctggtcta cagagtgagt    2400
tccaggacag ccaggactgc acagagaaac cctgtctcga aaaaaaaaa aaatcacttt    2460 tagaccaagt agggctcagc gtctgttctg ttgaggttgc atgaaaccttt tgagccaatt    2520 caactgccat ggcatctaag aattacactg gctttattaa cacgtgagct attaggaaat    2580
acctcctttg ccttttagtg tactgccact caccccaat ggtacattca gtaacccaag    2640
gcagtcctac tgctaaccta gccttcgagt tcatatccat tttactcaca ctgccaaagt    2700
ctctgtatgt ctcccagcaa tggctatgag acaaattaac atatacagaa aacgctttta    2760
tgatcattgg tttaaaacct tttttcccc tgtcccaaat ccctaatctt gtgttgtcat    2820
ttctaaggta gacccatgta aacacttagg gaacatgaat ccttttttaa taattatttt    2880
tgtttcatgt gcattggtgt tttgcctgcc cgtgtggttg tgtgaaggtg tcagatcccc    2940
tgcaactgga gttacaggcg gtcgtgagct gccacgtggt tgctgggaat tgaactcagg    3000
tcctctgcaa gagtaaccag tgctcttgac caatgggcca tctctccagc cccaagggag    3060
cacgagtctt acatacatgg ggtatatgta tgtatactga ggtaggagct gtgtaccata    3120
tactatgtgc agttttgcgt ataatttatc tttaaaagac atatccatag gtcctttagg    3180
atgaatttct ttttccaacc tagtccagaa ctgctgaatc agactcttta ggagagggac    3240
cctaaaatcc acatgccctg agatcttcaa gggagcctat agaaacctg agtgtccttc    3300 ggctcctccc tatgggttct gttctcatga ggaagagaat gaaagtctta ttaggatctc    3360
ctgactctag tgtccacttc tgttctccat ttcctgtaat ggggaaaagg gatgagtgag    3420
gggaggggcc ctagagacta ggtgtgtgag caggtaggct gggcaggctg gcacctcaca    3480
aagcattgtt catcccttct catttaggac agactgtgat tcctccaccg cctctctctg    3540
ctctttccct gttgccaatg tctcactggc taagagtgga cgtgatcggg tgagtatgag    3600
aactagacag aggctttgat tgcttgagga agatggggag agcagggatt gagcaaccga    3660
gattgaagag aaaggctctg acgcaaacgg gtggaaaaga aaatctggaa gttggtccca    3720
gtcactgtga tacatatctg taatgccagc actaggagga aaaagacaca gggagattat    3780
tccaaatctg atatcagctt gggcttcata gccagaccct atctctctag aggctctgat    3840
aaaaaataga attacaagct taaaatgtcc cttgatatca aaaataaaa caaaaaggga    3900 ctttgagaat taatgtcatt ttttattaaa tgaggttttt ctagttgtca gtcttaactt    3960
gaacattttt ttaaagtggt atttaagaag aaactgactt tatagtagaa tatcagctct    4020
ggcacagtgg cacacatcta taatcacaat acttaacata gaaggatgct gcccaggctg    4080
gcctcgcacg ctgagatcca cttgcctttg cctcctaagt gtggccatca ccacgcaagg    4140
gaggatatct tgagtttagg agttaagagc atcctgaata agttagttca aggcctctca    4200
ttaaaaaaaa aacaaaggag cttgggaggt agaggcagaa aggctagcct ggactattta    4260
aaaaataaaa agtagtttac cttaaagtta tggtcactat gtctccgcct cctatgtgct    4320
ggagttaaag gtacgccatg taccaatcca gactggaagt gagtaacctc agacgtgctc    4380
ggcttcctaa gcgttgggat tgttaggaag tgggcaccac cgtgccaggc ttggatttct    4440 ttttctttt ttttttctt acacaccaga agagggcttg ggatcccatt acagatggtt    4500
gtgagtcacc atgtgattgc tgggaattga actcaggacc tctggaagag tagtcagtgc    4560
tcttaactgc tgagccatct ctccagaccc tcttaatagg tttattaagt taaaatttat    4620
atgagataca gtttacctct taaggtatac agtcgtcgtc atatcattcg atgcatgtat    4680
```

```
ttgggacaga gtttcactat gtagccttgg ctggcctgga actggccatt tcaaccaggt    4740
tggccttgaa tccacagctc tcctcctccc tttggcctct tgtgtgctgg gattaaaacc    4800
atgcactgcc gccccaggca gttctattgt ttttaataag ttcagtgttg cacgcatact    4860
gatataaata gacaaactta atcttttttt taaattaata agcactctgc ctttaaaaat    4920
gaagaaagac caggataaca agatgatctg ccactgcagt gattgtgcaa gagctgacta    4980
gggaggcaga gcagcacttg cttaattagc aagtgagggc agactaggcc caggggaca     5040 gctccggcgg cacacaggcc tgaatcacag atgccccagt tggcaatgtg actgttcact    5100
tttgaaaaag aaatgcaaca gggcacttct cgtaaacata gtagtccaag acagacctaa    5160
gagctcacag ggtgaatgtg gtggtgcaag cctaaaatgt cagcgccaga ggctgaggca    5220
agtgaagttc tatgaatttg aggctttgta gtcagtgctt ggctagccag agatatgtag    5280
caagacccac ttaaaacaca gggttctcta cctgacaacc caaccctag gccccaaata     5340 aaatcaaacc agcaaacaaa atagaagtct ggaaagccag ggtgtccagt gaccagcagg    5400
gggcagcatc aaatcatgat taaacaatga aagaccaaa gggattttgt tgagttctta     5460
agcagagaca gtacatttta aaaaaaaaaa aaatagatta agacatacca ggcacggtgg    5520
cacatacctt taatcacagc actggggagg cagaggcaag cagctctctg aatttgaggc    5580
caacctgatc tacagagtga gttccaggcc agtctcaaaa caccacaatt ttttttttt     5640 tttaacaaga tgtgtgttac cttgggcagg tactgatgta tggacagcca tatcgagtca    5700
ccttagagct tgaactgccc gaatcccctg tgaatcaaga cttgggcatg ttcttagtca    5760
ctgtttcatg ttataccaga ggtggccgaa tcatctccac ttcttcacgc tcagtaagtg    5820
tttatggaca atactggaat gtttgaacaa tgatgggaga atcagaatat cgggctagtg    5880
tttcaaaaga agacctcctt ggctctgaga tcaggcctaa accagataag tgaagaagct    5940
gtttaataag cttaacattt gccaaacact ggtatcctat ggtgtgccca aattcagggt    6000
aaataataca ggtatccttt tttaaattat tcatttattg tatgtatgta agtacactgt    6060
cgctgtcttc agacacacaa gaagagtgca tcagatccca ttacagatgg ttgtgagcca    6120
ccatgtggtt gaactcagga cctctggaag agcagtcagt gctcttaacc actgagccat    6180
ctccccagcc caatacagct gttcttaaaa caagcagaca ccagaaacat accagctttg    6240
agataactga cttaattgct agagttttag agtaacttct tcctaacaag actaggaaga    6300
aatgctgggt tcttactagc atgtgttgaa cactcattca acactgagcc ccattggtaa    6360
actgtcaaca gagtcaccac atttgaggaa agctttaggt gggatgctgg gacacagatc    6420
ccagcccaga aggcagacca cgtgcaagca gactgcttac ctcagggagg taattttga     6480 gaggggcttt ctctgtgttg gaattaggaa atggggtcag gaagtaggga gtgttactag    6540
aacaggtgga aaggttgggt aggtggtgac tggaagttag agagagaaag tgaaggagca    6600
gggagcctgg aatgagcgag cgagcgtgtt gcttagcatg ggcagatgga cccagcgcct    6660
gtccccaatc tgtcctctcg gccgtcaggt gatgctgcat taccgctcgc agctgctcca    6720
ggtgctcgac acgctgctgt tctccagcct cctgctgttt ggcttcgctg aacagaagca    6780
gctcctggaa gtagaactct actctgacta tagggagaat tcggtaagtg gctgacagag    6840
ttaggagaca actcttcaac gagcccaaga ttgtacctga aagcccatg gacagtcaac      6900 tgcaagagcc acagactgga agtagacctc atactgactc tgctctcacc ttgcacccte    6960 gcagtatgtg ccaacaactg gagcaattat tgagatccac agcaagcgca tccagatgta    7020
```

```
tggagcctac ctccggatcc atgcccactt cactgggctc aggtaaaaaa gccacggaag    7080
gaaacatcga cagcttttcct ataccctgcc ctaaaatgaa gagagttcca ggcagaggtg   7140
accagtaaca atcacatcat attttacaaa ggccagaggt ggttctccct ggcttcactg    7200
tgcttgtcac cttcaagag agcttcttaa aaatgccatg tgaaggggc ttggagagat      7260
ggctcagggt ttaagagcac ccacaaggtt agttccagga gatctcattt attcttctgg    7320
ggacaccagg catccatgtg atatgtgtac gtacatccag gcaaatactc agacatatac    7380
agatgtgaat atcctgtagg agatgacaga ccccttcgtt ccagcactgg atgggcctga    7440
ggcaagaaat cttgaactac aaagcaagac tctcaacata aataatgaaa agggaaaacg    7500
aaaagtatcc gatgagccgg gtgtagtccc gtgtctagcc cctggttctc agacaacaaa   7560
gtgagatccg tatacacaca caaccactct ggcccaataa aatctccgtg caatccactg    7620
ccttgttgga ctggctcaga aagtattgga gtgactagag gagttacagt cgaagccatt    7680
gaaatgctgt ggccttgtga ttctgagatg gcctggaatc cttggccttt attagaacct    7740
ggtgcagggt ggtctggaac ctgggcaggg gagtgggtgc cacagtggca gaaggcagct    7800
ccagccatcc tcactcaggc tgtcctacaa atcttcttgg agtgatagtg tcgagtgcta    7860
tccagtaacc gctgttccct tcctgaccct gtttctcacc tcaggtacct gctgtacaac    7920
ttccccatga cctgcgcctt cgtgggtgtg ccagcaact tcacgttcct cagcgtcatc     7980
gtgctcttca gctatatgca gtgggtgtgg ggtgctgtct ggccccgcca ccgcttctct    8040
ctgcaggtct caaggggcaa aggccccgtt tttcttccct tggtggtcag gggcatgtta    8100
gggctagggt atgattgctg cggaggggag tcaggcctca ctgctcagtg gttactgctc    8160
cacaggttaa tatccgacaa agggataact cacaccacgg gccccgcgt cggatctcgc     8220
gccatcagcc aggtaacctg gttggttgac agtatccttg aagggtaggc tggctgggtt    8280
agagggttgg cctgcctcca ctatgaagta tgcagtactc tggaactaag gattcgagga    8340
agaggtagag ttggcactgc aagccaagga taaccactga ccctagctgt cctctgtttg    8400
tggaacctga aggtcaggaa tctacccagc agtcggatgt gacggaggat ggtgagagcc    8460
ctgaagatcc ctcaggaaca ggtatgttca gttcctcttc ctcgctcctc atccccagca    8520
ctcacctgca gtgcctggct ctcaccttct gtctcacctc tgtttcccct tggctgaaga    8580
gggccagctg tctgaggaag agaaaccaga gaagcggccc ctgaatggag aggaggagca    8640
agagccagag gctagtgatg gtgagggcac tgtgtgatgg ggagggcact gtgtgatggg    8700
gagggcactg tgtgatgggg agggcactgt gtgatgggga gggtactgtg tgatggggag    8760
ggcactgtgt gatgggagg gcactgtgtg atgggaggg cactgtgtga tggggagggc      8820
actgtgtgat ggggagggca ctgtgtgatg ggtgatggt ggtggggatg tgtgatggag      8880
tgatggtggt ggggatgcta tcccacccct cctagcctgt ctcactcaca ttttgtttgg    8940
cccttttctg gctctgcttc aggctcctgg gaagatgcag ctttgctgac agaggccaac    9000
ccacctacct ctgcctcagc atctgccctt gcccctgaga ctctgggtag cctcaggcaa    9060
cgcccgacct gctccagttc ctgaacaaag ggtgaattcc tcacattcca gcgctttccc    9120
atcatacacc ttttcccttg ctcccttaat aaactatttt gtggc                    9165
```

<210> SEQ ID NO 50
<211> LENGTH: 27940
<212> TYPE: DNA
<213> ORGANISM: Mus musculus

<400> SEQUENCE: 50

```
ggagtttgag agtggaggaa ctgcacacca gccgccgcgg gagtaggaac ccgagagcga      60
ccctgacagt aagctccggg gacagcagcg gcactccagc gtgagagttg cgagggcttc     120
gcgtatctcc cgcagctaaa tgcgcttccc cttatcctaa gaccgatcca ggcgtgcaat     180
aggccatgct tcttagtcct gcatctgatg ctccatcctc ttccagggc gtcaacccct      240
tgcttgcgct tcggaagcaa ggggtgggtg ctgcgcctga cagcgatgct ggctcctcag     300
cccctggtt tccccgcccg cccgcccccc catgcatgtt tgtcccttgg gttccaggct      360
tgctacttgc ccaggcacct gagccaatcc aggtagctga gggcgccgtc caagtgactc     420
ttaattttaa cttctccagt ctgcacctcc cgtcatttaa acttccggcg ccagaagtc      480
tggatagcct ttctggcatc tggttggcgg gatcaggagg gaggtggagg gatccggtat     540
gtatgcatgc gcgttgacag tagggctgtg cctttgctgg cattctgtgc tgctggcagg    600
attgtagaga tggacatctg cgacatttgc ttctctgcct ccgatttcgg cctgatcttt    660
tttttaaagt cgcagagccc cagaggctca cattgttttt actgtgacag tgacttcctc   720
cctcaagtgg aggctttcac tggctgtgcg tggtctgact tcacacaaga cttgaagctg   780
agggggctgg ggggaagggt ggaacaaaaa cgtgggcgtg ttcagcaaag actttccatt   840
ccctaatacc cacaccaggc gggccacgtg agggcttcct gtgtccctaa agaagtatgt   900
tcagtgcaac cgtgctcaac gacacggact gactgttcag acactgcccc ccacccaccc   960
accctgggga tagcagggaa tgtgttctca tgggctctgg gagcttttga atgcagacaa  1020
caaacaaaat tcaaggtcct gggtcagatc cccaacacca cataataaat aaacatatct  1080
ttgtaaaata taaattatat ttgtgagctg taggaaatag gaggtcataa agagggagca  1140
ggactgttga ctagagagga agaggccaca ctttcacact ccagagggtc aggagggtca  1200
ggagtgcgcc tcactactca gtatccagct gcacaaggct gaggagaaca tgcaaaggcc  1260
ctgaggcaga ggtgcgcctg ctgtgggtgg cttttatgtc ctcagttgcc ctctggaaga  1320
gagaccagag tcagtgagga ggctccaagc tttcagctgc ccctccgacc aagaaaacaa  1380
gatttcccta gaccctcggg tgctcctgga gtcagctggg tgaccttcag caccatccct  1440
aatcccatg ttatctggtg tgactgcacc agcctttggc tgtgccttac acacctgctg   1500
cccagatgaa ctgagaggga aatgcatggg gaacagaggg agggatttt agtgaaaggg   1560
tgagagcctc caccagaccc ctggggtcca gtttctgccc agagcccaac tagagcacag  1620
tggtacccac aaaaagccct gtaaggatga gtagtgtctc tcctccatgc ccagcagctc  1680
cagcatgccc aggcatagcc ctactgatct ggtgcctcca cccttttgt ttttgtttc    1740
ccctgggatc ctggccctgg atcaagtatt tgaagggcag aggcccaagt tccacttcct  1800
ggttcttgtt ttaagacctc agagtatggg aacacagcct ggctgagggg atgagggaca  1860
acagagaata agattggagg caggagagcc actagtcagt gccactggcc ttttggggtt  1920
acctgcaggg ggtcttcagg ccaagctagt atcatggtgg agtcaccagg gagctgtgtt  1980
gataagactg ggaaaggatg tccaagaggg agcccagcct cagccaggaa ccttctcctg  2040
catggtggtg cccagggaat ggggggggg gggaggcgtc tggctctcca tcctcagaca  2100
taatcaattt cacaaactgg ttcaaaggag caaagtgccc tgctaccagg cttattgat   2160
ttactgagga aaaccacagt tcatgctttc tccccagaga gcaactgttt tccctctcag  2220
agtgtctagc gtgctccttc caccattaca ggctggggt gacatctgac tcctggccca   2280
gtgcctgcct tcccttgact gctacttggc catcctcact ttcctgtgga gccaagccac  2340
```

```
ggtgcagagc cacacctatg cgctcttcca aggctgaggg gttcacttta gggggacagt    2400
gttgtttcag ctgtgttact aaaatgtctt tacagaaaac tcctcttgac caactgacaa    2460
acaagcctta tttgtgctta agaaggtgga gtctttgctg cctctagcag tgcagaggct    2520
gaggcgcagt gatgcagtgt gggtgtctct ttggctcttc tgctcagatt ctcttcactg    2580
aacttcctct ctgaactcta agtgctcttt aaacacaggg caatgccctt tagttcttag    2640
ggttgtgatt ttacatgtgg tgataaattc aagagccagg ccttcctcag ctgcaaggac    2700
agagctctgc actatggctg tgtggcccgt ggctttccct gttaacatcc agtcaggtgc    2760
agctaggatc ttaacctcgg gtgcagaaag ggatttcagg gttagtcagt atgaagtaga    2820
attggagatt attaagaaaa gattttagta tagacgttaa aagagcaaca tgaacacgta    2880
tctattcgtc tcagataggc agcaatgaca agtgattcca cagaagaaca acttgatgaa    2940
cccttgaatg gactgtgctt acaggaacat aagtgaggga gtctttacag cattgtgggt    3000
gacttggggc agtttcatca ctgataagtc ccaatttatc accaagagct ctaccctccc    3060
ttcaggtaac tgtagttacc ctacctcctg catactctac cagccccacc ctagcccagc    3120
ctgggcccac ttatactgat agcaaactag tggtgggcag ctgaggtggt ttgaaagaaa    3180
atgaactccc cataggttca tagggagtgg tcctattagg aggtgtggac ttgttggaga    3240
agcggccttg ttggagacag tgtgtcactg gggcgggcct tgaggtgtca gatgctcagg    3300
ctgtacttgt ggttctgtct cttcctgctg tctacagacc cagatgtaga actctcagct    3360
tcctctccag caccatgtct gcctgcatgc cgccatgctt cccaccatga tgacaatgga    3420
ctaaacttct ctactataag tcagccccaa ttaaatcttt ccttctaaga cttgctgagt    3480
tgtggtctct cttcacagca atagaaatcc tcactaaggc agtgggaaag ggtaagtgac    3540
tgatggccct cagttctgct ccatctaggg tgtgttagga tctccattgc cctaggccta    3600
gttatcactc ccttgcctta atgttatctc tgctccttga tggtgatagg atggagaaag    3660
ttgccacagt gccacactgg tgcccacctc agggtgagtg ccattccgag agggtcccac    3720
tgaggtaggt gctttggtgg cttttgaagt ctccctgttc aaaggattga gaagattgaa    3780
aatgttttag cattcacgtt tttatctaca ctttatttag caactaggat tatgctgagg    3840
tttgtggggt tcattgtaca cgtgtttgct gataagagag aagtatgggg tttttttttt    3900
ttaagcaggt caaaggaact cttactacac gtcgcaagga gttggaggca tgtgctttga    3960
ctgctaagca cggttaagtc ttatttgtgg gcttctctca aaggattatg gtcccttgcc    4020
agccatttga aagttccttg aagagactta aacagatcct ggggttgagg gctcctctat    4080
ctccctgtct ttctgtaagt actaccacaa tgttacaaca gtccagggcc tctctgaact    4140
tcctctagac agtggatgcc tgacacatga gtgttcctgc catggacaca tctggctggc    4200
tttaatctgc ctgcagtttt cttcatgacc tgggaaggct gtgggatgcc atggtcaggg    4260
ttaggaggtc ccagagcctc catgtggcat cacagggaca cagtgaaact tctataaact    4320
gaggacatgg ccactccaag gcatggttaa ctggaaagtt tttattgtgt atatgagaga    4380
gtgccgctag aggtatcctg atgggtttgg aacagagaga gagaaagtca taaactgagc    4440
atggccagca gactgcatgg gccacgagag aaggcttgat tctaaaatcc atctctagag    4500
agatgagagc agaggtactt ggcactggga aaagacagat tagcctgtct ccctgtcaca    4560
tacaaatgaa aggccatttc cccaaatgct ggtgactaga caaacgccgg cattgctcta    4620
gaacttggga agctggcttc cctctactaa aggagccatt tccttaacac tggcagaagg    4680
gacaaacggc taactctggt gcctgatagc acgacaaagc ccatgctggc ctccaggtcc    4740
```

```
ctcagtatta caagggccta gctctttcta cctcctccag accccaagc ttctccagct      4800
catggccttc ctccccagct gtccatttct tccaaccctg ctaattctgc tgtgtacact      4860
ctgggtcttc ccttgatctt catccctcca tcccccaacc cccacccac gctgttctct      4920
tgcttctctc atggccaggt ccagtctact ggccttgttc aatctactgc tccctgtctc      4980
tgctctggac tcttccaagg cctctggctg ttctctccct catatctaca atgaaaacct      5040
tcctcttcac catgtcatgg aacaatcaca tcaccagctc acacactcac aggtaaattt      5100
acccatgttt taccttggtt ccatggcttt ctataaactg taagaggatg ctgtctggag      5160
aaacttagag accctccctt gtctaaattg taagcaaatc cgctctcctt ggagagtttg      5220
tttcttaaat cttttttagaa tataaggcag tcagactgca ggtttctgga cctaagtccc      5280
cggggaatgt cagggcagtt tagggagct ggtcttccct gcttactcag ggaattatgc       5340
cttccttctt gcttgcctct ggcagaccta ctgcccaacc agcttgtctc tcagaggaaa      5400
cagaaccacc cagaaaatgg aaaggaactc atctcccgct gcaaggtggc tctgttctct      5460
ccccattgtg caccctactg tgggaggcct cccagcccct gttaggatcc tgacttctga      5520
gaacctgtgt tcaaagagat gatactgggg cagagcatct taaagtcaga gaagatgatg      5580
gctccggcat ctgaacctct gcagctacct ggggagtttc cttttctttt caccgtggat      5640
tgaccccagg gcctcataaa tgctaggcac ggtgctctgc tattgagcta cacccagttc      5700
cctccacagg cttttgaact ccttacttgt agccctgga gacctgacgc tctcttgaga       5760
cctaggcatt gctacaggca aattcaacac tctcccagcc tccaatgaaa acccagaga      5820
gcagtgctgg aaggctagcc aggcctcacg gggcagccag gaagttcttc ctgtacccac      5880
acagcaagga gggtggattg gactactcaa aagccttgca ggttctgttg caggctatcg      5940
aggacacttt caggctatga aggttccagg ccacaggtta taatctctga ggatccgctg      6000
ggtatggtgt ggacaatgca cggcacagag tggcttgtgg agggaggata gtgcatgctg      6060
gacagtctac tcctgctact ccagcctggg catccatcaa cccagctcaa cagcaggcat      6120
gggctagcct tcctccttaa aggaggtgag atgcacttct agacatttaa agccagtgga      6180
aaacttgaca gatcctatt ggatcatcag agctggagat gggaaagggc acagggacct       6240
aacagtgcag ctcccctgcc cttctctcct tataggactt aaaaacctgt gtcacagcat      6300
tgagggggat agtgaatcca tgctggctga cagcatagtg ggaaaggatg tgcccacatg      6360
agggaggctc taaaagccat cccaagttca tgcatgcaca cacacacaca cacacttaat      6420
ggagcatgtt tgtttgagag cccatgaagt agagtcaaga ggccattgtc aatgagatct      6480
cagacacatc tgcactagaa tctgcctgag accgtgtaaa acaatcattt ctaactaatt      6540
aacgagctag ctttcacaga ctccttaagt ttaaagctta taaacacagg cttaagtcaa      6600
tacatttaag tggctttttcc acaccggaag tatcctccct ctctaaaggc atccagggcc      6660
tgccctccca cccgtactat cccgccctc cctagttaac tcctctgtgg gggtgaccag       6720
actaaggcct ggagaagcag tccctgtcct taggaggggt caggggcagc actgaaggcc      6780
tggcctccag ctgggctggc cctggcctct ggtgtgcttc agcagtgcac cctccagatg      6840
gtgaagtctc tgctgacacc acactgggct ctcctcacct tgccctgctt atcctctttc      6900
ctatattgcc ttgaaatgca cccaaaacct tctcttgctg gttgactcta gccttctctc      6960
cttagctcac atccaaggct gtgccaccta ggcaccggca cagagggcac accacagctg      7020
agccaccaca gcacagggac agtggcactg agggagaaca gactggccct tagccatctg      7080
```

```
tgtggtccaa ggaagcctct gcttagccat cactgaccag cctgaaacct ggagtggtga    7140
gcaggctgca ctgtcagaag gaaggcctgg gggttgtcag caaagacatt tgcacccctt    7200
cctttttgtgg caggctgact ggaacacaag agggggccaaa tgcctcccct tcccctgctta    7260
gagtttcctc acttccctag gaaggggagat ggagttgctg ggccagtcag atccagggtc    7320
aaaaggaggt cacacctctc tctctccctc tgacacctga aggcagcagg tacttcccct    7380
cagctcccac agtcaccaag gcaaagtgta gatgccagga tctctggtca ccaccaggcg    7440
atctcacata gcctctctga gggagcgtgc cttatgtcca gtcagatcca gggcctgctg    7500
ccaacagtgg caaggctctc tgcacttact cttggccgtt gttctggaaa agccctgagt    7560
ttccaggcct gtgatctgcc ctacagagac cacatctgct gagtcactat agctggtat     7620
tagagggcaa tctcagggag catgcctctc tctctctctc tctctctctc tctctctctc    7680
tctctctctc tctctctggg taaagagaac aggtttctct ccaagggcag ttggctgacc    7740
ccaactatga ggcttgcagt gactgcctct gaccccacac ttatctctag tcttgctcca    7800
cacttaacaa taatcctcaa tccattagct ccgcagacta gactgagaaa taagctgtat    7860
gctattactt aagaaaaatt taaaatcttc ttcaatcaaa acttctagtg tctacgttat    7920
gatccagaga acttatctca ttcagtcagt gttgaattat tattcagtaa gtgccagggt    7980
ctgagaatac agagggaacc aagggtgctt gcctatagtg agaggggcac aggccctggt    8040
gtaacagcta agcccaggca gaactgaagg ccatgggaat aaacagccac ctcagagctc    8100
tggaacaaga gaggttgctg ggcataggaa ctgaacaaag atggttaggg tctgtggctc    8160
aagcgagtac agggggagat gggtcatcag acttggaacc atggtaaatt ccttgaggtg    8220
tgtgtgtgtg tgtgtgtgtg ttggagatgt ggactgggaa tggaatcccc atcctctgaa    8280
agactagcga agctcttctg agtcatcttc ccagcctggg gttacaatgt tgtaacatat    8340
gtatccagct gttttgttttg gttttttggt ttttttggt gttttgtttt gttttgtttt    8400
gttttgtttt gttttgtttt gtttgacagt tattatattt atatgaagtg ttggttttag    8460
tttggttttg ttgttgtcgt ttttaagatt ttatttattt atcttatgta tgtgggtaca    8520
ctgtaactga acagatggtt gtgagctttc atgtagttgt tgggtttaag attttatta     8580
ttaattttat gtatgtgggt acactgtagc tgaacagatg gttgtgagct ttcatgtggt    8640
tgttgggaat tgattttag gaccttctgct cgctctggtc aacccactc actcagtccc    8700
tgctcgctct ggcccaaaga tttatttatg attatacata agtacactgt agctgtcttc    8760
agatgcacca gaagggggatg tcagatctca ttacggtgtg ttgtgagcca ccttatagtt    8820
gctgggattt gaactcagga ccttcggaag agcagtctta actgctgagc catctcatca    8880
gccctggtt ttggttttc aacacatctt ctttactaag caaccaatcc tttccttggg     8940
gagaatacct taactctaag aaaaaatgg tttcctttg ctttttgtaac actaggcatc     9000
aaacatctca catgagctag gagccatgcc aacagcccg ccctccaata gaatggcttc     9060
ctcttcaact gcaattctct gggcacaggt ctttctcatt ggaaaattgg gttacaaagc    9120
aaatgaaag actactggaa gaatgaaacc tttggtacaa gataaattga ccttcagttt     9180
ccagtgctag catgtcaaaa aggaacttgg gacttgttat ttttgtttcc agagtctttc    9240
ctgatatcct ctaactttgg tgttttgaag aggttagaat gttctctgct gcaaaagaaa    9300
tagaccacac agaagacttt gttgcaactg ttcactacag ggtagagcct cagcagacag    9360
cagtgagacc cctgacaatg agaacaggac ttctctgagc taatagcaca gacatgcacc    9420
ccctaggaca tggtttacag aacgtggatg gtcacgggcc tatctggact gagcttggct    9480
```

```
taacccgtct ggatcacagc ttcggtgagg gcacatgggc aggacagtgg gcatcccagg   9540
acataggtgt ctccactctc tcaccttcag cctggttctg tgcacatatg ctgctgtaga   9600
cggcttggat atgagagtcc cacatagtga attaggggaa aggaaaggac acccacgttg   9660
gtggagcacc tgctcagggc cattcattcg tcatcggtag cctgataggt tgatgatccc   9720
cacactctag ataacaaagg ctcaaggggt tttataactt atccagagtc tcgaagctgc   9780
tgtgatagaa ctgcaaatgg atccagcaaa ggaagaaaac atactagaac cccccttact   9840
gtgcctccaa gatctcctgc ccctaaagcc agatgcatcc aagcttctaa ttgtggcacc   9900
atggctcaga agctctggag gacaacagca ggcagcatcc tcactgtccc tccaaatgtg   9960
ctaccatgct actcagatca cagacactgc atggtacatc catgactgct aatggcacta  10020
gcatgtcaca tcctccagga gactcatggt tgggtcttcc ctctgaacca actctttcag  10080
gaactgggct atctggagtt gacctctcct aaaaggtcta tgaaaagtg agagtccagg  10140
tgaactttc atgaccacct gaactgaaga tggcatctcc ctgtgagact ttcactgagg  10200
tgaactgtgt cagcattctt atctttacta gattcataca gacctttatt ctttatccaa  10260
tgacctccaa tatctttgta gttatgcttt ggaagaaatg ctgtggaact tatagatgtg  10320
tcgatgggat aagaaagggt gctagaacca ccttttctgt agactctgaa tgaagccaga  10380
cccaagtcta tcctgctctg aattgtgggc atctcaatgc ttagtctagg ggaagggtta  10440
tgtgggcaaa gatataccca tagacagcag gcaccagctc tgactggtca gactccaggc  10500
tctatgtttt ccaggtggca ctacctactc atgttcagag aaaggcattg catattatcc  10560
ttccaggagg agggaggaaa gactcacagt ctaggaggtt ccttgggggc cacagtacct  10620
gggctcgtca gtgagtgttc tgaggtccca gggctggtat gaaagtttca gactgtaaac  10680
acatactgag aaagcaggct agagaggggg catgcagcac atgtgagcaa atgtacataa  10740
caacagatat attcttcagc catgaattgt aattctcaaa agcacggagc tatgcatttc  10800
ctgtttccag ttcttacctt aagtaagtgt tgggataggt tggttggttg gtgggctgct  10860
tggttggctg gttgacaggc tggttggttg gttggttgat tggttcgttg gttggttggc  10920
tagttggttg gttggttgac tggctggctg gctagttggt tggctggttg attttttaaag  10980
gtccatgaag agtggatttg cctttactgt tgattggcaa atgcagcaaa cccaacctgc  11040
agcaggacaa tgccagtggc tatttgaggc taatcagaaa taacatttct gtgcacctttt  11100
cttacctgct cttaagtaat gactgttggt caggtggggt gaactgaggc attgcagcca  11160
atcctgcttt gtagtctgag acccagtgac tccaaggccc atcaacttac acttgagcaa  11220
agtacaccac cattttacat agtggataat acttatattc tcctacctgg attattctaa  11280
gaaacaaagc ctttacatta ctctttagct ttgtcacttt tgtgcccccac tgtatgcttg  11340
agttttttgg agaacaatac tttccaagac accacataga tgcagtggta actgcatctg  11400
agtgacatag ggtacctga cttcaggctc accattgtga tcactagggt gccctatat  11460
aattaatgga tacatagtat atccatcata gatacattga acaaaagaat catttacaac  11520
ctgggcagga tggagccggg aagtgggaga tgccactatt tgtgatcaca cctttgggga  11580
tttgttgtct acttggagtc ttttggggag gaagagacta tgaagaggaa aataagaact  11640
ttgcagagtt ggttctttcc attcatcatg tcgctccctg agagcaaaca tagcctgtca  11700
ggcttagcag caagtacttt tactccctga gccttcttgc agaccaacac acagttttaa  11760
actaggaatt acttctaaaa tgtctgttta cactttcagg ccacggtcac ccatgggtaa  11820
```

```
acaaaacctc ctaagggttg ggctctgggg caagctggcc aagaggcatc ctagtgccct    11880
tttgcctgga tcctggtgtt ttggttttt tccgatggag ctccagcact gaaccctcag    11940
cactgatcct ccgggtactg gtgactgtca ctgtcactgt ggttcagttt gctgtctgaa    12000
gtccaggtga taactgctct gtgcacacag tggatcagct gagtcatcgg ggctatgaaa    12060
ttatataaag tcagggctgg tagggactcc acgcagccac cctcaccggc atgctgtgac    12120
cagggaggaa tcacggagcc cccacttagc cctggtgaac agcggagcat gctggaataa    12180
ttctgcccag aaaaagacaa gcaggcacct ctgttcccag ggaaaacagg ggcactttgg    12240
gcctccctgc tgcagtcagg caggggctga ctgtcaagtt ccctgggcag actggccagc    12300
tttcccactt ggctcttctt gtagctctcg tggtaacatc atacaaaatt ggtcttctct    12360
cagtggccct cgggcgacag gtgacagtat tccatcttct ccaagaagag gactttatag    12420
taggaacaga gagtctctag aaatgaaaaa caacaacaac aacaacaaca aagtccctgt    12480
ttaaattcag gactcatcct cagtcgtttc taacttgttt tgattcaagt tggtctcacc    12540
acctgacgga tcagggatct gaagacaagg actgaaggag agacaaaaag gcttggtctg    12600
ggggcctggg aatggaatgg tgggatgtac accatacgtt tacagataga cagacagaca    12660
gacagacaga cagacagaca cacacacaca cacacacaca cacacataca cacacaccaa    12720
tatcctctca ctaggatggg caagactttc tctctggcac ccagactctt gggaaacatt    12780
ctcacagaga ctcagagaca ttgagccaca cagatgttac agcccagaga gggagatggg    12840
aaggaagtag aagattgtat tcacaggaca tggcctttat ggagggctgt actgggatct    12900
caatgtccca gtgactttgc ctgatggtgc ctaggttacc tctcttgaga tctgtggcag    12960
tattcgatgt gggtgataag gtctctggtc agagaggggc tggccatggg ggaggttata    13020
tctgtgtggc accagttcct gatgatggat gggtatggag gaagacacag aggtggctct    13080
gggactgaca gtaggtcggg gaagatcagt atggtccctg ccagacagaa gcagtttcca    13140
cttgagattt gttccacatc agggtgtaag tactcccacc ccattatcca catctctgtg    13200
gaagccccac agctggcttt ctgtgtggct tggtatcact ggaaatggca tgtagtggac    13260
cagttcttag cttaaatggg cagctttccg caggaacaaa cctgggggcct ctacaaacat    13320 tgatgggcct gaccatctga ttttagcagg tggagtgtgc acatatgttt ttctaacagg    13380
ttttatcctg ccttgagatt ccacgatctg ctctgtcaac ccagactagt cctgactata    13440
tagagtgacc agtgaaacct ctcttccctt gctccaaggg tagttcatgt tcctgccaag    13500
ctgggcgctg tcctaggagg atggaagctg aggagcctgg ccacaatgct gggctgggat    13560
ctctctggta ttggcttgca gagacctggt tcttcttcct tcctcctgag agaaaagaca    13620
aaagattcag acccatgggt gttaacatac agcttggatt ttctgaaaca taatagcaca    13680
tgcctacaga aactggagac acagttacag aggggccagg ataggttgag gactagagaa    13740
gcaacatgtt cagggtgtaa ggtttctctt tgttgagatg acaatatcct aacatcatct    13800
gtgccagcgg ttgcctgtgt ccatgagtac actccaaaca attgcattgt acacttgaaa    13860
cgggcacacg gtagggtgtg tatatcctct ttcaaaaaaa ctatttaaaa tacccagaga    13920
tggcagccat agttgagggt cagctcctga acattgtccc attctcagct ggactcaggg    13980
tcccaggacc tctgacctcc cactttccct gtgcccatg aaccctcctt ccaggaccac    14040
acatagaatg taccccctct tttcacacat cagggtatag agagtgcctc ctgagaagcc    14100
tcaggaacag aaagcccctc agaagcccca aaccccaaa tgcagccccc acctgcact    14160 gttgaagccg ccatctacag ttcccagggg ttgggcaatt ctcactacct agtaaagtta    14220
```

```
tgattgggct cgtctctctt aacattatgc agatgtttat attggatacc attagcattg   14280
ttggcctaaa taagaaaatt attggccaga catgatgcct agaaaacctg aggcaggaag   14340
atggctgtgg ttcatggcca acctggatgc cattgccaac ctccatctca aacatcatta   14400 aaactttaa aagaaggacc agtgtttctc cgagtattac tattgatttg gaacagtgg    14460 agcaaggcaa acagaataca ctgagaaggg ctggagagat ggctccgcca tttcagatga   14520
gattcacaac taaaagcata agagaataca caggccatta aagtatgccc tcattagaaa   14580
agatggaaac aaagggagtt gtttaaaggc aaaaacaagg agtatggaac ttagccatga   14640
tatagacctt gcctataata cttgagacca gggattattt cccagtgacc agaatattaa   14700
taatattaaa cacagataaa tttaaaacaa agatgcagta aattagtact ttgaaacagt   14760
aactttggcc actgtcatta ataaggaaag tggatttgga gtgaggcaga agacactggc   14820
caaacagttg ttcttgcaga agtgctattg tgtgggctgt ggcagccact gggcaaacat   14880
agggcatggc aaaggcttct ccagtggctg tcagtcatgt agaacaatcc attgctcaga   14940
aacggtcctt gtgggtctga cacaagaaac tccattttca ttctggctgt attgactttt   15000
ttcacaaggc aaacatgaat aggtccggga gtggatcata cagtagttat tttctggttg   15060
gtgtgacaaa atacacccaa ggagctactt aatggatgga actttgcttt gatctgttct   15120
tgactagtca atcctggcag ggcaggcgtg gcctctgagg agctgctggt gactggtcac   15180
attgtatcca cagtcagaga gagctgaaca ctgaagctca gatctcttgg ttctttatt   15240 cagcatgggg ctctagtgct tggagaggca ccaaccaaat tcaaagtggc tcttcccacc   15300
gcagatcagc tcctctggag gcactgtcac agttataccct gcaaccttgt ctcctgaggg   15360
gctctaagtt ccatcagggt gacagctgag atgaaccctc acatttggga atgagctggg   15420
gaagagcctt tctgataact tgcatcccta gcaagccagg caccaggcca ggttgtccct   15480
cttgctgatg tgtcctctca tctcccagga gtcatgtggc tggaactcat cctggcttct   15540
gtgctgggct ttgtcatcta ctggtttgtc tcccgggaca aggaggagac cttaccactt   15600
gaagatgggt ggtggggccc agggtcaaag ccatcagcca aagaagatga gagcatccgg   15660
cccttcaagg tggaaacatc agatgaggag atcaaggtga cacccccctt cccaggcagg   15720
gcagaaccaa agggacggtc ctgctgtgtt cccctgggac cagagtgggg acatgactga   15780
ggaaggagct ttgaaaatgg aacatcctga ggtttccctg gccactcttc tccctgaggt   15840
catgtgcatt ttgctcctaa aaggacttct ctccttccta tccccatttc tctagctact   15900
tctcctcccc ctcaccaggc ccaggaagct gctggtagaa ccattgtgtg caccatagac   15960
tgaagaaagc tcccatcccc ccacctccct gtctgcccac ttgatgctgg tacagtttaa   16020
gagacagagt gagcaggtgt cccgggctga catggaagtc acagctacag aagggagtgg   16080
cgctcagggc atgtagtagc atggagacca cacggtcagc cttagacaag cccttactgt   16140
gtattgacca ctcctgggcc catcatgtcc ctataacaag tctgcccatt gtcacctgtt   16200
gtggcatctc tcaaaggttg gccctgatgc tgagaatagt acagcagagg gtcccaggtg   16260
ctggagggca cagactgagg attgtaagtc tcagggccct ggccttttcca cacagagctg   16320 gagtcagaaa ggatgggctg gtgggtaggg gatgggagaa ggaagtctcc tgaggagcc    16380 agtcagtcac aagggatcag accttacatg gccatccttc ctttcacccc tgtgatcctt   16440
gggcagctac tgtgtcaggt gctctgtgga gtgctgggaa gtcagagacc cttccctcac   16500
acagcccagc gtttagcatc cacacatggt aaggtaatga aaacatcaag agatacagtg   16560
```

```
acccacacgt cagtggagat taatgtcact ggggcactaa caaaaggtca ccgaagttcc    16620
caggaggaag ggattgagag cagggtctgg actgaagcca agggcgagca gctgaggttc    16680
atgtgcgggg catgctgggc tctagctgct gagggtgaag ctgagctctg aggatcagct    16740
ctggatggag tctaaggttt ccaaacctgt tcggggagg ccaggggaca tgaaaatctc     16800
tgtgaataat gacactgagc ccctccaaga ggcaccaggc acgtccctca gctggaatgc    16860
tgaactttga tctgcatcca gtgtgtttgg agcctgtgcc ctgggcaggc catttgtctg    16920
tgttaggatc gtttgatgct gtacagcaag ggcgggcacg ccatggctca agggcaagta    16980
tagcctgcct gttgttcatt aactgcccct taatagctta tttgtctgta aagggtgtg     17040 gggggaaaat aaatacatta attaatgctc ctgcaggggt cacccgtgtc cacggcctct    17100
ctgctcctgc aggggtcacc cgtgtccaca gtctctctgc tcctgcaggg gtcatctata    17160
gccgctcctt tgttgctggg agaaagtgga acccttgcat cttctgtaca atcttgctat    17220
ttacaaagtt tgccaattct acaactatag gtggtttggt gatttaagtg agtgttgatc    17280
acacacctaa gaaatgagaa gatgactggg gtcgagctaa gcgggaggac acatcatgtg    17340
tggcatgtgc aaagccttcc attctctccc tgaatgtccc ccaccctacc ccagcacaag    17400
agagatagat gaaaggggaa acctgaagcc tgcaggagag accaccttgg cccctctagg    17460
atccagtgac atgcatgggt gccctgtgtg gcttctccat ggtgaccatc tatagcttgg    17520
agggtttcct ctgagttgtg cacacaagcc ctctcctgtc tctgccaccc accctgactt    17580
cttcactgca ggacttgcac cagaggatag ataggttccg ggcatcccca cctttggagg    17640
gcagtcgctt ccactatggc ttcaactcca gctacctgaa gaaagtggtg tccttctgga    17700
ggaatgagtt tgactggagg aagcaggtgg agatcctcaa ccaatacccca cactttaaga   17760 ccaagattga aggtgagatt ccagaacacc aggcaggatg ggggaagcag ggatgggtgt    17820
gaactcagga gcagccttcc tgcatatgtc aaccgtactg tgcacctcag ggtcaagtgg    17880
tagatcactg agatgtcatg gttccaccatc ttgccaggat gtaccaatga tgctgagtca   17940
gtaagctgtt agtctgtagc gctaaactaa agagcagagc agtggttgtg caacctgaga    18000
cctgcaaact ccagtcagca gtgtagagag gcccttgagc agcgtctata caggaagcct    18060
ggaggctgga catgacctgc ctaggctcag ccccgataga attgcaggtt agacagttct    18120 ataggggttct tagtggtcca tcctatgata aactgtcctg tccaccatgg ccctcaacct    18180
cacagcccag cccctcacct gctgtcactc agactaacca tgaagacagg aagttaacac    18240
tttaattcca gggagggtga ccccaggatc attttatcta aactcatatt ttccttagta    18300
gaacgcaaat ttttaactac ccacagactc agaatgaagc agagtatgtt taatgctgtt    18360 aatttttta accctcttat ttttcttgtg gtaaaataca tgtaacataa cattctccaa     18420
ccagtggctc agtggcaata ggtgtgacgt tctgtggcat taagaagggt cactgttggg    18480
caggctctag ctctaattta ataagaatta acaatgataa cagtaacctt aaatttctct    18540
attctaagaa ttgcaagggt accctgtca gtgtgtctcc aacctagacg caagtctgct     18600
gaccttacat gagctaccgg ggagagcccg tgagcatgag agcatggatg tggattcgtt    18660
tctaacttta taatcagatg atgtggcact aaaatttgaa ttaaaaataa cttcacttca    18720
acaaataacc acttaaatta acttgaatat ggcagtaagt ttagcaacag aggagaaccc    18780
tgggagatat gtagtgagaa aatttaggtt ccaaaatagc acaaacatag acttttagtt    18840
ttgttaaaag ggagttatgt actggaagtg tttcttgaaa atgtggacta tattaaaaga    18900
aacctaagat cacaggtcag gcagggtcct gggaaagacc ctgaaaagtg aagtcagatt    18960
```

```
aaagcccaga acccagaatc acacagccct ggatgtgtat tatcagtgtc acacgctgtt    19020
gaaaagggac acagtgaagc tgtgtggttg tctgttgtcc tagcccttgg aaggcagagg    19080
caggaggatc acaactgaga gtcgaactag gacctgatta taggttttcaa aaagaaaata   19140 taaatttttc agtgtgacac catgagcaaa ccttaaggat attgtattgt cctgggtgtc    19200
gagtgtcact cacaaagagc agactcatga tgccacctat gtgtctgaaa cagagaaaca    19260
tggagaaaga gactcagtgg gctggggaca tgctaaccat gtgcaggatg gtgtggtggg    19320
gagatgctgc ctgtgtatgg gatgctgtcg tggggagatg ctgactgtgt gcaggatcct    19380
gtggtgggga gatgctgact gtgtgcagga tgctgtcgtg gggagatgct gactgtgtgc    19440
aggatgctgt ggtggggaga tgctgactgt gtgcaggatg ctgtggtggg gagatgctga    19500
ctgtgtgcag gatgctgtgg tggggagatg ctgcctgtgt gcaggatgct gtagtgggga    19560
gatgctgact gtgtgcagga tgctgtagtg gggagatgct gactatgtgc agggtgctgt    19620
ggtggggaga tgctgactgt gtgcaggatg ctgtggtggg gagatgctga ctgtgtgcag    19680
gatgctgtgg tgatggcaga tgactgagct ctagggattg atctgctttt acagccatag    19740
tgacagacaa tgcaggtgag ggctgtggct catatggacc atttgcctcg agtgtgcagg    19800
gccttggatc cagctccagc accacaaact gaatggagga aattttttaat gaataatttt   19860 gagaaggtaa aaggtttagt ttggggatgg agcgaaggct tggcagttaa gagcactttg    19920
taggcttgta gagaaccagg cttcctagca ccaatgtgat ggcccacacc agttccagga    19980
caccagatgc cctcttttga cctctgcaag cgccatgcat tcctgtgaca tacagacata    20040
catgcaacag aacactcata tgcatacaat aaaataaatc ttaaaaagtt tggttttata    20100
attagaaaat ggtaacaaat gcttcagtcc aaacctgtgg aaaacttaca cattttgtat    20160
ctgtttatag tagaaaaatt aaatatatat accacaaaaa caaaattaaa gtactcggtt    20220
atactttaat cctcctggag gattactttg tacagttttg tcatttatac ttgagaactt    20280
caaacctctg cctacagaat tgcataaagt cttggccctc ggtgctgtag cccatggttt    20340
actatggtgt gaagtcaatg tgcgctctgc agaaaccaca cttgggcttt tcctgggctt    20400
ctgacactca ctttaggcac aactctcact cagccccagt accacagagg aaacaagcta    20460
ctctgtaggg aactggggag ctaagctttc ttgtttgaca aattaggtat gtgaaatgca    20520
cttgtgtgcg tgtgcatgtg cgtgtgtgag tgtgtgtgtg tgtgtgagtg tgtgtgtgtg    20580
tgtgtgtgtg ttgctgagca ctgaacatgg ggcctcctgt gtactaggca agtgatctgc    20640
caatctattg aatcattgaa taagtgggta tttaaagcat tttaacttct aacttttca    20700 cgtcaggcag gttcatcaga atgaaagctg cacgtgactg ctgcgtttat gcacacggtc    20760
aatacagtca gcaattccag catggcttcc cctcgatgag aagctgctgg ctgctggtgg    20820
ttgctgaggg aggggaaatc cttttttctct ggggaggcag ctgattctag gttggccagg    20880
gccatgcaga cagcactacc tggacttagt gggttagaaa acagacaac aagaacacgg     20940 gaggggagtc ctgaggagta gggtgctacc aagatacata tatgtgtatt ctgtgtatgt    21000
atatattagt gtattataga tactgtgtac tatatatatt atgcacatgt aaaaattatg    21060
cacatgaaga ataagttaaa ctactgcatt tttacaagaa tacagcccca tgtaagtaaa    21120
tatacagtgc ctagagctgt ctgtaaagct gagctatacc acggccatgg caaggacatt    21180
taatttgatg gctatgagct cttttcctatg tcagctgagc acgtggatga tagttgctcc   21240
acaggactgt cctgcagtgg gacctccttc cctcagcctg aatgctctgt ccctcaccct    21300
```

```
gaccgtctct gtccccaggg ctggacatcc acttcatcca cgtgaaacct ccccagctgc    21360
cctcaggccg cactccaaag cccttgctga tggtgcacgg ctggcctggc tccttctatg    21420
agttctacaa gattatccca ctgctgacag accccaagac ccacggcctg agtgatgagc    21480
acgtgtttga agtcatctgt ccctcaattc ctggctatgg cttctcagag gcatccagca    21540
agaaaggtac agggtcctga agggacatcc agactgtcat cacagtgcct gctagggaca    21600
gcaccactct aagtcctatt atgctgtgtg gctcacaggc ccattggtgg cttcaatgtt    21660
ctaaggaaga cataaccagg ctcattgcac tgtgatctgg gtcttcttta gggcaccaaa    21720
gttccgtctg tctggtcccc tttgagctac tgtctcctta gtctggagaa agagaggtct    21780
gttgaatttc atgactcccc gttcagtgct cattgcactg gtacgttgtc atgtgatttt    21840
ggagttcagt gaagcaggct ctggaggcaa ggatgctaac accccacttc aagtccctat    21900
ttgagacgca agcatgttta tctgcaagtg ttcttcagga cacacagtcc tgggtcaggc    21960
tggccctgac tctgcaatgg ggagagggaa aaacagcaag cagctcagag tatttaaaat    22020
gttgcatccc tgggctagag agatggctca gcaattaaga gcactgactg gccaggcagt    22080
ggtggcgcat gcctttaatc ccagcacttt gcaggcagag gcaggcagat ttctgagttc    22140
aaggccagcc tggtctacag agtgagttcc agcaggacag ccagggctac acagagaaac    22200
tttgtctcca aaaaaaaaaa aaaaaaaaaa gcactgactg ctcttccaga agtcatgagt    22260
tcaatcccca acaactacac tgtggctcac agccatctat gatgggatct gatccctct     22320 tctagtgtgt ctgaaaacag tgactctggt gtgtttgaag acagtgatgg tgtacttaga    22380
tacataaaat gaataaataa atctttaaaa aagaagaaaa aaaccttgca tcccaaagac    22440
agctgagaag acaaacttat ttccagcaga cgctgctatt gtttagccca acagtggagt    22500
ctcatccacg gggagaaact cctccgccag tctccccctc tccccgttgc ttgctttctc    22560
agggaggtgc cttactcacc tctgcaggcg aatgtacact tatggtttgg tgaggttttg    22620
ctattttatc tgctgctgct gctgtactca ataaactcat tcgaagccca aagtacagca    22680
accatagacc tttcggccaa ccgtttagaa cagtctctct gctcccttct cactcaggtt    22740
taaattcggt ggccactgcg aggatcttct acaagctgat gtcacggctg gcttccaga    22800 agttctacat tcaaggcggc gactgggggt ctctcatctg caccaacata gcccagatgg    22860
tgcccaagtg agtttgcatg gcgcagcctc accaggctct gtgggtgggt ggaatccaca    22920
caggacgcgg gactgttcac cccaagccct cttcagcagt ctctgagact tgggacttcc    22980
ttggccaggt ctcccaggcc cagaggcttg cggacctgag acagaggaaa cagatcttcc    23040
cccattgggt ggaaaaggcc gtgttgaccc ttgggatagc tgtggcagct gtctaagcag    23100
aggaaagaga ctctaataaa tcatgtggga caaggtctag agcagccctg caagaacac     23160 tctagaacac tttcttcttc cccagccaca ggttcaaccc agtggatgcc ccagagggaa    23220
ggggctaaag ggggccggct tgtgttcttc tgtcctgctg cctctcctct cctctccctct   23280 cctctcctct cctctcctct cctctcctct cctctcctct cctctcctct cctctccctc    23340
cttctccctc tcctctcctg tccttcccag cagctgagct cacctgtgcc tgttcctctg    23400
cctacagcca cgtgaaaggt ttgcacttga atatgtcttt catttcaaga aacatttatt    23460
ccctgacccc tctcctgggc caacgttttg ggagatttct tggctacaca gagaaggatc    23520
tggagctctt gtacccattc aaggaaaagg ttttctacaa catcatgagg gagagtggct    23580
acttacacat ccaggccacc aagccggaca ctgtgggtaa gcacaccggg gcagtggagc    23640
ccagagggaa tctcactgcc cctgagcgca cagcttacag caagaaaccc ctgacaagga    23700
```

```
agcagaaatc tctgttttct ctactgagaa ctgaaccaag gcatcacact gtgtgacaag   23760
tgatctgtca tttaccacag ctagagttcc acatatgaga gacagaggct atgggaaccc   23820
cacaagtttt aggctagcct agtctacaca gcgagtttca agccatcctg ggctacatag   23880
caagacactt tactagagag gggtggttgt aagaaaaaa gaaagaaac taaaaattgt     23940 agtttataaa gaaaattata aatgctcaaa caatagtttg ttcaaaggta tggagaatac   24000
aaatcatttt gtagtttata caaggctcat taccacccag agtaaccaag cctgatgata   24060
cacggaggcc tggtgcctca gcaaggtctg taacccagct gctctggagg ctgcagcaag   24120
aggatcaaga aagtcaaggc ctgcccatgt gccttagacc ctatttcaga atagacaaac   24180
gtgttgggag gcagctgagt ggaagaatcc ttacttcaaa cctgttaagt ccctaggtcc   24240 aaccccagt ccagaaggaa aaatagcact gaaaaaatg tgtttcttct tgataggcca    24300
gaatcatttg aactctcctg gttttctatc tttgacagag ctgtgaagaa gctaaaaggc   24360
agagctaggt gggaccaccc tagtacagtg gttctcagcc ttcctaatgc ttcaatcctt   24420
tcaaacagtt cctcatgttg tgactcccaa ccgtaaagtt atttctcttg ttatttcata   24480
gctataattt tgttactgct atgaatcgtc atgtaaatat ctgatatgca ggatatcaga   24540
tatgcaaccc ctgtgaaagg gtcatgggac cctaaaggga tcacaaccca cagtttgaca   24600
attgatgccc tagaagatgc aaggactgtc aggtgtcctc tggatgtccc ctgagtccac   24660
tcagaggaca cctgggagtc agtttgccca ctgtggagcc tcccacaacg cccatggtag   24720
ctccacgccc acagcaagga cacctcctga tcacaatagc actttataaa gtcaggctgt   24780 cttcccgtt gcgatgcaga tgttcgtgct atgactggga atgtaaaaaa tccaaaatac    24840
agcagaaaga agtcagtctc tggctctcct tccagccaca ctccccagaa gagctcacca   24900
gcattgtccc ttatgcatgt tgtaaacgca ggtccacatg tcccagactc agtcaatggc   24960
ctctttggtc agtcccccctt gctcccctaa ctaggggtcc tagagcactg ttgcctctac   25020
ttatcctcag ggactgaagt cacacagcga ggactccgtg ttcttgctcc tttggctcac   25080 cgtgacccctt gtgagtgtct gtactgctat ctctgccatg atgtttaaag ctggtcatgg   25140
tacctagggc ctcaggaatg ctatgcatat actgcccccct gctggttcaa tgactggaat   25200
tgtattttaa ctagtgggta tattaagatt tatttgtaat taactatcaa ttttatacca   25260
agatacagcc catatcttct gtgaatctca tgagattgta gagaatattg atctcctctt   25320
gctatatgag gctactcagg ccagggtgca cagctagacc tgccaccct ctgtggcacc     25380 cacataccte tctcctggag tcacatactc tctgggggcca ggcttgaacc cctcccttgc   25440
tcctcccatc caggctgtgc tctgaatgac tctcctgtgg gcctggctgc ctacatctta   25500
gagaagttct ccacctggac caagtcagaa taccgtgaac tggaggatgg aggcctggag   25560
aggtgaggcc ccaccttttc tgtcagaact catccccagg ctctgcctct ctcggcctga   25620
cattctaccc ctgtctccag acaccccata gggaagccag caagcttctt ctctgtttgg   25680
cttgtgcacc tcctactcta tgccctcatt aggaatgggg aggtagacac aagaaagggc   25740
ctgtgacttg tgaagcacca tagttggggg tcagacaaaa tatgcgtgcc aggaagtccc   25800
cacagcagca aataccccttg tggaagaata gctgaagcct gtcacttggg ccctatacat   25860
ccatgagctc tgtggagagc gatgggaggg gacagagctg tgagattgca tgggtgtgag   25920
ggtaactgct gtgtcctctg acacagtgct ctgtcacagg agcttggcct gatgccaagc   25980 tccttttttgg cactgtcaca ctgaggggca gagactgcaa gacatcccag tggggtgtcc   26040
```

| | | | | |
|---|---|---|---|---|
| actcggagcc | tgggtccaca | aaggtagcgc | ttggataaaa | tatggtactg | aagagagagt | 26100 |
| tccatgtggt | ctgcttgatc | cttggtagat | atcacagaac | atgtgagtag | cagcatctaa | 26160 |
| ggatgctagg | aagtcttatt | gactacagag | aagagacagg | aaaggacaga | gggacagaca | 26220 |
| gactaagagg | acagagccct | ataagtgcct | cactcctaca | gacccaagca | atatacacag | 26280 |
| ttacagggtg | caggactgag | agagaatagg | agtggaagtt | gggttgggga | aggcagctgg | 26340 |
| tagaaagggg | taacatgaga | ccagatagtg | cagttaccac | agggaagagg | cgctaacatg | 26400 |
| gccaagaagg | cagatggagg | taacttacct | gcagatcaca | attcctgtgg | ggcagaaaaa | 26460 |
| ccttgaaact | ctagccccag | acacagtgga | cactggtgtc | ttctagacta | agatgttctc | 26520 |
| atggcaagga | agcttgggct | gtggtagact | catggccatc | agaacacatg | caatgttgaa | 26580 |
| acttttggag | gagtcagcag | ccgggattga | ttgggtcacc | agggttaaga | ggccacgtgg | 26640 |
| agctacagct | agtcacagtt | aagactcaga | agactgtagg | cctgaaacac | tgatgtcagc | 26700 |
| gagtgtcatg | gaggggatga | gagccctctg | cagtgggcaa | tctaaagcta | aacacagagg | 26760 |
| ctcttctaca | gcacagacag | ctaccaggga | aggctggagt | tgttccctgt | ggaaggccac | 26820 |
| accctgagt | ggcaggttta | agtcattagt | cctgccctgg | gctcccagca | tgtgagaggt | 26880 |
| aggcattgtc | tgttgtggtg | accctgaaga | gggcagccct | ttattcttga | cagccatagc | 26940 |
| tttcactgag | cctgggcatc | ctgtgtgttt | tcccaggaag | ttctccctgg | aagatctgct | 27000 |
| gactaacatc | atgatctact | ggacgacagg | aaccattgtc | tcctcccagc | gcttctacaa | 27060 |
| ggaaaacttg | gccagggtg | tcatggtcca | tagacatgag | gggtaagcct | ggctgagcag | 27120 |
| gaggcagggc | tggggctagg | ggatggttac | catctgtcct | ttaactcaga | gaaggcttga | 27180 |
| tggacaggtg | agaaagatac | cagacatcct | gagtatccac | ttcttcataa | ttgtcaggta | 27240 |
| ctttgggatt | cacaggccta | tgtagagacc | ctcaggtgag | agcaaagaga | tggtccagta | 27300 |
| aggtgggcat | cagaggttgc | ccatttcctg | cttgggtgac | cctccctggc | agacaaggtc | 27360 |
| cctaatgaat | gaaaatggcg | gtctataatg | agagggtagt | ggaagccctt | gccattatgg | 27420 |
| ctccatctga | cctagccaag | tcctccccag | gccctgggag | tcctctctgg | gaacaggaga | 27480 |
| acacagcccc | tcacctcatc | tctcttcccc | acaggatgaa | ggtctttgtg | cccactggct | 27540 |
| attcagcctt | cccttctgag | atcctgcatg | ccccagaaaa | gtgggtgaag | gtcaagtacc | 27600 |
| ccaaactcat | ctcctattcc | tacatggaac | gtgggggcca | cttttgctgcc | ttcgaagagc | 27660 |
| ccaagcttct | ggcccaggac | atccgcaagt | tcgtgtccct | ggctgagctg | cagtgatgac | 27720 |
| gctacacacc | aaccatggct | ttagcagcag | ccctggttcc | ttcccagtca | tacttatgga | 27780 |
| agatgtgccc | ttcagagga | ataagtttgt | tccctgacca | cactggggga | cccagacttc | 27840 |
| aaccccacag | agtcctctct | taccaccccc | atatgcttcg | ccccactgca | tagctgtgtt | 27900 |
| aagctacatg | gctttaatga | taaatgggtt | tatttctaag | | | 27940 |

<210> SEQ ID NO 51
<211> LENGTH: 36408
<212> TYPE: DNA
<213> ORGANISM: Mus musculus

<400> SEQUENCE: 51

| | | | | |
|---|---|---|---|---|
| tatggcgcgg | gcggacacgg | gccgcgggct | cctggtgctg | accttctgcc | tgctgtccgc | 60 |
| gcgcggtaag | ggcccgggtg | gcccgcagtcg | cgagtgggcg | tccccggcgc | ccgcgatgct | 120 |
| tgcgcgccgg | gggctgtggg | gacttgcccc | caggggtgt | gtgtccttgc | tgtgcacagc | 180 |
| ctggcaccgt | gcgtgtcccc | ctgcgcgtgg | cccttgtgca | tgtgaggttt | gcatgtgtgt | 240 |

```
gtcctgcggg ggtggggtg tcctgcgggg gaacgtgtcc acagcgcgtg cctaaggcgc    300
cgggtagcat cgccagcgcg cgggtggctg caagcgggac atgattctgc cctgcccgca    360
agcgtctcgc ggtcgcgagt gtgcctgaga gagcgggcgg ggaggagtg tacacttaca     420 cctccatttg tgtcgggtgc gtgtgtaact ggatgggact gagctaatat ttggccttgg    480
cttttgggga gtgtccttgc tcttgatggg ggcggcggtg agaaaaacca cactcaactt    540
tgcccaatgg gtgtggcccc tggggccagc tagggaggtt gggggaatgt ggaggtgttg    600
tggacccaaa cccagggttc ggagtgggc tggggaagg gcaggaaacc agttgctttg      660
ccgaacgcgt ccaacactcg ctctctggat gggacgcgtg tcactcctgc ccaccccca    720 agggcggacc agggaagcgt ggacgagatc agcaaggccc cctccagtgc ccaggtccta    780
gtgttgggta gggtcaaggg taaggatcac aactgtccac accaaagaaa ggactggggg    840 cgggggaga cgaagtgtcc aagtgtgtat gccaaagctg tttttaccac ccccggccct     900
ctcactctca gtgggtgtg cgtttggggg acagcccaaa ggaggttagg tggtagggcc     960 tggagggga tgggctgccc gctttgttcg attacttctt gccttccctg ccgaggggg     1020 agttaaggat gtgtccgggg cgagtcgggg agggacttgg cagtggggt ggggaggggg    1080 attttctcc agctgctgcg gctttccaga gagactgggc caggccacgt gggagggaga    1140
caggagggga ggcggggggt ggtggaaagg agcctccgct gggccaaccc caggcccatc    1200
tccaggaaaa cagcgggtgg gagagtgctg gaaacagctc ggaccccttgc tctccccgca   1260 agacacgccc ctttcccctcc gagacccctga accggctgg gagcccatag aagctcggtg    1320 cgtgggctg ggccgcagaa gcgggagggc ccggagttgt caggtgaacg cggcgccagg    1380
gaaatgtcag agaggtgtct tgtctgtctt tgcggagccc aaaggattaa ggaatagttg    1440
cacttcccct cctcctcttc ctcctcctcc tcctcccctcc tgttcttccc aaagctccag   1500
gaacgcggga tcctgctgg caaccgcacc cgcgctttat taaatacttc tgaggcttca    1560
ggccgggaca ccgggtagag tgttgggaga ctggactctt cttcccagtg aactgactga    1620
ggagcgggca ttgggattct ccctgtctgc tacctgactg gctactgcaa ctactattct    1680
taccctggtt taacctcctt tgagtgtgta aacctctgca gtctgcagac accctacag     1740 agtggaggtc ttcccttctt ttcacagtat ttgctgagca ctctttatag gttaacatgt    1800
gcctgatgcc cagaacgtgg tgaataaggc cctagaccca gactgtccgt catagggtca    1860
ggacaaggag ccaggactag caaggtactg cagaagagag gctcctcctg gggagacctg    1920
gaaaggttct gaagaaaacg atggagagag gaaaagccag ccctgcagag ggaggagtct    1980
tccagatcaa gcaggggtg ccaacgctgg gaggcgattt aattcacatc attgcatcaa    2040
gctaaatctg gctggagttt agaatatggc ggtgggagtt gggcaggtgg gggaggggtg    2100
ggcctcatat ccagagagga ggcgaaggag gaagtcccag ctcacaaagt gcagtgccag    2160
tctcactgaa gttctggcc tgagaccctc ctgccccact gagggaagcg cccctgtcct     2220
ggggaagagg tggccatcca agagagagtg gtggcagcca gtggaatagt agcttgggtg   2280
gctggattct aaagatactg agcaagtgga atcagtaggg tgtgagcata gactgacgac    2340
tttttgtttg ttatttttatt atatgtgttc gtctatgcac catgtatgtg tgcccagtgc    2400
ctgtggaagc cagctgatag tgtcagatcc actggaactg cagttacatg gttgggagcc    2460
accatgtggg tgctggaaac tggacccagg tggtcatgac gcgtagccag tgcttttgac    2520
cactgaggca tccctccagg ccctgtagtg gggttttaa ggagtgagga aagtcaaacg      2580
```

```
taacagtctt cccagcaaag ccaacatgag cagaatgaag ggcagtacca gggataggta    2640
caatggcagt ggttggctag tcccccgaca ttgcccttgg gtcaaagatt gggtctgtga    2700
gctcatagga gtgagacctc catctgaggt caatggtagg aaactgagct cttcactat    2760 aagaaaaagt ggggctcccc cttcccctta gaatttggag ctctgagaac acagggaact    2820
cttcctcacc cgtgaagccc ctctctacca tcccttctc agccttgata ctcaggggcc     2880
catcttagag atttgccacc agagccaaca ctagaacctt tttaaaaat gctatatgtt      2940 aatatatgta tgtatgtgta tatatatata tatatataga gagagagaga gagagagaga    3000
gagagaaaga gagagagaga gattgagagc atgtacattg attggtgttt tgcctacatg    3060
tatatcaggg tgaaggtgtc agatttctct ggaactggag ttataagcag ctgcaaacgg    3120
ctatgtgggt gggtttcgaa aattgaactc tggtcctcta aaagagccat ctcttcaact    3180 cttgacccctt ctttttaatag tgactctttt tggggggggg gaggggttga aaacaaggtt   3240
tctctgtgta gtcctggctg tcctggaact cactctgtag accagactgt cctgaactc    3300 aaagacccat ctgcttctgc ctcctgagtg ctgaaagtgt gccaccatca ctcggtttta    3360
atagtgactc tgctgtaatt tacctgtgag cttgtgagta ttttcgtgac ctcattaacc    3420 ctatattat agataaattt ttttcctaaa gataccttct tcaagctaaa gaatctcatc    3480
atataatgtc agcactcaaa gaaacatagg aagctaggct tcatgatgcc tatctgtaac    3540
cccagtactt gaaagactga ggcaggagga ttgctatgag ttcagtgcca gtctaaacta    3600
tataataacc taactaactc acttcaaaaa aagagaacga aatttgctat gagtccattt    3660
tacagatgag aaacctgagc aactgcctag agtatgcaa ataggaactg atctggagct     3720
agaccggtcg cctgactctt ctttgtaagg cagaccagcc actcttccca ggaatttggt    3780
gcacacatac caagttcctt gtctctgtac ttctgccttc cataagagaa gttagcagct    3840
ttaggtcgga gtcttctctc tggttggccc aaggctatgg aatcctttt cacctacctc     3900 ctacttgctc caaaggctct gaggtacagc aaccagatgc agaacagatg tcactgccag    3960
gcgtgtctgg ggcgcccagg agcccggggg gggggtggg ggggagaga atctgtggag      4020 aagatcccag cttgatcagg gaaagaaagt gagggttgag taaggggaac cagaaaggaa    4080
gccctgaagc ccagcatgct cccttctggg ccaggccagc tgtagctcct cctgtatcct    4140
ggcaagagct ccagcctgtg gatatggagg gacactgggg acattgggat caaggaggct    4200
aagggccaat gagctttccc ctggagtaca aatcggtatt ctccaacaca cggtaagaaa    4260
cgtattactt tgtggtaacc ttgttacgta gttttaagga cagagcgcta ggctatctga    4320
gacccaggtg ggctctgaag aaagataact gtaagcatgt gaactgtaga gcagagccca    4380
caggctcccc acccttagga tgtgcagact aaggttcaca atgaccttac tcttctgctt    4440
ccatgtgctt tttgtttgcc tgttccaaac aggtccaatg tagcccaggc tagccttgaa    4500
ctcactatat aaccttgacc tttgattctt ctgcctctac cctctaagtg ttgggctcac    4560
aggattcccc gccacacagt ttatgcagtg ctggaaccaa tcccagggtt tcacatattc    4620
taaataagca tactaccaac tgagactatc ctgagttccc aatttcagtg ttattacagc    4680
attttattcg gtgtctagta gaagctacat agtatgccat gaaatttctt cctgtattat    4740
tcagatcatt cttagccctg aagagactta ctatattttt acagataaca aagaggaggc    4800
ttggaaaggc ataagggatt ctatgatatt atttgagagg gtctgcatgt ctacacggcc    4860
atttgaggaa tttgtgttgg atatctattc tacacaacat ggtgttttag atgccaaagc    4920
ctaaaggcca actaggataa aatcctaaga gattattaag gacagaccaa aaacaggacc    4980
```

```
agggttatag ctcacttggt agagtgcttt gcccagcatg caagtggccc tatggcctag    5040
ccagtcatcc tagtacttgg gacttagaag caagagaatc agaagttcaa ggtcattctc    5100
agctgcacat agagttcagg accagcctgg gttacatggg actttgtctc aaaaaaacag    5160
tctagactgg tcactgcagc aatccagcat ccagttcccc caaggcagga agaggaggga    5220
caagtatcta agtcagactg gttcaaagcc tttctaagaa gtagcaaggg agcccacaag    5280
gcactctcaa gagactttca gtgacttgtt agggataggt aggtgggcaa ggatattagg    5340
gggcccagat ggaagcaagc catgttgtat gtggctttgc gtcaccctag aggacactga    5400
gcctccttct caggattgta gatagaggga cggttgaggc cctccttgtg tccttggcag    5460
ccatctggac tctccttcca gctgttggag ggagggacgt agtgtgtggt aaggaaggtg    5520
gccaagattc tagaagaaat tgacttgtgc ctcttgagaa gaaagagtgg cctatggtgt    5580
caggaaggat cgcccttcct gagaacaagc cataaatctg tgcagagggt gagggaatct    5640
ctgccatttg tggcaagtcc ttggccttgc tcccctcccc cacctacaca tcctgtcctt    5700
cctgaacatt cctttgaaaa tggaaccgaa ctcaggttcc tgataacttc accaaatagc    5760
tccaatgaga ccctggaact ctctagcaaa ttgcctttat gactaggttt tcataggtgt    5820
cataaaatct aatttatcct cttaagtgag caaaagggct tctcatagcc catgatggca    5880
caatctgtaa aagaagtaga ggcaggttga tcaagaacaa acagcctgag ctgaatagtg    5940
aggccgtgtc tcaaaaaaac agaaagaaaa aacaaaacaa aacaaaacaa aacaaagaaa    6000
gaaaacacct gtttgaaaac taagattggg gggcaagccc agtggcagaa gcctttaatc    6060
tcagtactca gggcagaagt aggtagactc tctgtgagtt caaggctaga ctttcagatt    6120
gagttctagg atagactggg ctatgtgaaa agaccttgtc tcgaaaagaa agaaaagaa     6180 aagaaaagaa aagaaaagaa aggaaaagaa aagaaaagaa aagaaaagaa aagaaaagaa    6240
aaaagaaaag attgagaaat ggctgggaga cccccaaaac agaacttctg catctctgat    6300
ggactctcac gaaaaaaaga aagaggagga gaaggaggaa gaagaagaag agaattgagg    6360
gaagcctctg tcctgtaggg aaaagactgg tgatcagcag gtctcctggt acctgctgcg    6420
tgcttccttc atatcagtct aaggaagaat ggaaataaat gcttgtgcaa agtggaagtc    6480
agccatgcag tgggttgggg gagcaagagg ccttggacaa gaaaggtcta ctctctttca    6540
gatatgacta ctatggactt ggcagtggag agatcatacc atgttaaagt aaacattgct    6600
atttaaacat tgcagagtac aaggaagttt aaaaataaag gtagaggtta gggagacagc    6660
tcagtgatta agagcatgtg ttgttcttgc agaggacccc agtttggttc ccagcatgga    6720
agttcagatc cttcagagga tctgaagcct tcttttgacc tccacaggca tcatgcatgc    6780
atatggtgca catacatata ttcaggcaaa acacataaca ataaatgttt gtggttttgt    6840
tttgttttgt tttttttttt attaaatagc atttcaggct atctgttaat ggaagaattt    6900
agtttggttt tctgtgtgtg tgtgtgtgtg tgtgtgtgtg tgtgtgtgtg caagcacgcg    6960
cacacacaca cacacacaca cactccattt gcatgtattc ctgcatgaca gatgagggca    7020
tcaatcctgt tatagagagt tgtgaaccac catgtgggtg ctgggaattg aactcagccc    7080
ctggtttgat tttcttgaaa caaggtttca tgtagtccag gctggacttg aatccctata    7140
ttgtggagga tgacctagaa ctttgtgagt gtgatgctgg gaattgaact tagggcctca    7200
agcatgccag gcaagcgctc ttaatcactg agcacttgaa cttctggccc tcctgcctcc    7260
acctccttag tgctgctatt ttcttttttcg ggtgtgtact gctaagcact aattatccag    7320
```

```
agctagagga tcaaccctag ggcctgctag cctgagctac atccctagcc cccgaagaag    7380
ttcgatggaa atatttgagt ttgaatctcc ttgtttaagg ttggagaaac tgagacagaa    7440
gggtgtgtgg gatgagctaa tccaagatgg tgcaagaaag gactggacct agagtcctgg    7500
cgacggggac caatgatggt agagaggcac aaagttcggt tcacctctag gtgagaggaa    7560
aaattcttag gagacttcca gatggcgttt gaaaatcttc cctggaggaa ggcggagaag    7620
tctcctgaag agcggctggt gtctgggcaa agtttcctgg aaaacctctt tttcaggagc    7680
aactgcaccc cctttcctca tcccccagtt gcgggttcag cccctgaaag tcagattccc    7740
ccacaccacc gctctctcct gtcgctagct tcctcatcgg tagaatggac cttgaacttc    7800
tgagaagttg ccactgaaat gagtctgcta gggctcatgg cgcagacctg cttctctcag    7860
aggcggatcc ctgttctttc tgcatcttcg tccctgtggc tttcccagat tccgccttgt    7920
tgggctcctc tgaggtggcg aagttagaca tctgctgatc catgaatatt caggaaggga    7980
actggagctc ctggggcccc gctgccagcc accagcccct ctggcggctg tcctgcccgc    8040
cagagcccag gctgctgaca tacccagcag ctgctcgggc cccaactgtt cacattgttt    8100
gttctgcacg gcaggggatt tttcaagccc cggacatgct ttaggggtg gggaggctgc    8160 cagaggactc gaagattcgt gttctgtggg gcttttctcc cctgaaatcc aagcctccag    8220
ttctgcctct ggaccggagc atttgaagct gctgggctgg gagcccaggc ttgccttcca    8280
caactctgaa tttgaatcat ggaatctggg gctttagaag agaaaggact gaatgctaag    8340
ggcagcaaag agcgtttgtg tagctcctta ccgtatgccc agggtcttac agaatgaggc    8400
tttgggcata gttgtgtagt gagctttcgc ctgacctgca caaaaactgt ggttctgttc    8460
ccagtaccga accaaaaaaa aggtggagtt tctctacttc ttgagtgatg ttcttcaggg    8520
tctggcctga acccctgaca ggctcagtag catcttcatt ttaaatatgt ggaaaccgag    8580
taccagagag gacacctggc tgtcacagct ggcaggcgaa atggcaagac tgggaccttg    8640
gtgtgtgtgt gtgtgtgtgt gtgtgtgtgt gtgtgtgtgt gtgtgtgtgt gtgtgtgccc    8700
atgagaatgt ataggtgttt atgaggaggt cagagatcat cgttctttt ttaaggtgag    8760 ggcatggatg agatggagtt tcctgaggct accagcaaca cgaaacacct ggtgtcctgt    8820
atacacctgg ttcactacag ctgaggagga gggagacttt gaggaggagg aagtggcctg    8880
gagctgtctc agcagctaaa acattggagc aaagtgatgg ctttattcac tcagagtctg    8940
tctgctggcc ataacggctg cgcaaatgct gtcttaccct gacatcactt gtacagacag    9000
aaaccaccac aaaagcaact tcacagtaat aatataagtt agattgcaat aattataata    9060
aactacattt taataataaa tatattaaaa taagtagagg aaaattattt tagatttatt    9120
tcttttattt gatgcgtatg agtgttttgc tgtggatatg tgtgtgcagc tgcctgggcc    9180
tcagatccct cagaactgga gctacacatg accgtgaact cctatgcgga tgctaggaac    9240
tgaaccctag tactccgcaa gagtagcaaa tacccttcct tagtggctga gccacttatc    9300
cagtccccat cttaatttca gaaacagggt ctcttactga actcagagat tgactttcag    9360
attggcaaaa ctggctccag ggactctcct gtctccacct tcccagctct gtgattgcag    9420
ctgttagtgt gagaatccaa agtcggatcg gcacagccgt gtggaaaaca ctttccacct    9480
gggccatgtc tccagcccct ggaaccttga ctgggagggg actgccttct tccctagccc    9540
tgtgtatctc tcagggcagc catgagccag aactgtccag cagagctctg ctgaaggagt    9600
ggaagggtgg tgatctggtc aggcccttc tgacccttta tccttacat ttcttcccag    9660 attccctccc ctcagccagc taggacttta ttattactat tattattatt attattatta    9720
```

```
ttattattaa ttttatgtgt atatgtattt tgcctgcatg tatgcctctg tgtaccatgt    9780
gtgtgcctgc tgcctgcaga ggccatcaga gaggatcaga gttccctgga actggagttg    9840
tggatggttg tgagctgatg gggtgctgag cctgagtccc agtcctctga acaaacagct    9900 agtactttt tttttttttt tttttttgag acagggtttc tctgtgtagc cctggctgtc     9960
ctggagctca ctttgtagac caggctggcc ttgaactcag aaatctgcct gcctctgcct    10020
cctgagtgct gggattaaag gcacgtactc ccggcacagc tagtactctt aaccccctgaa  10080 ccatctctcc agttcctggg ctgtcttatt ctgctttgaa tgctgtagga aggaaacatg    10140
ggcacacaga ggggtcgagt gtgttgacca gtgtagcaga cagaggaaca tgtgtatagg    10200
ggaccatagt tggaacactg tgggttgttc gtggcatggt actgtatttg ctctggaaca   10260
gagatctttg tatcagtgga taaactgaga ctcagaagaa gagcccagtc caaggccgta   10320
catcttcccg actgccaacc tttcctgctt tgtccctcca gccttgctgg agaccttggc   10380
ttgggtgact gagttcttat gggacaggga gggagcagga caactgtgac aaagcactcc   10440
aatgggaagc tattgccccg tgacaatgag caggccccgt tgaagcattg attatgataa   10500
gaaatatttt ccctttgtga ttattgccct gagatgggat agtgtatgct ctattctaat   10560
cctccttctc ttcccttcat ggcaggggca gtgttagggt ctatgggcag catacgtgta   10620
cacacacaca cacacacaca cacactcatg ccttacacac atagtacatt tctcagagtt   10680
ttccagctac aacatttttc aagcttgagg tatgagcaac agtggtgggg atgagacatt   10740
ggattcctgg aggactaaaa ccactaagcc accacacagt gccaggcaat gctacaccac   10800
gtacacatca cccagcgacc attcataaca gccctaaaag gacagaactg ctctgtattt   10860
ttaaaaccaa gaaacaactc acaatttata tagaatttac cacgtatata ggttaaaaaa   10920
aaaatttttt ttgagacaga cttttcatgta gtccagactg gcttccaatt tctacatagc   10980
tgaagaatga ggaagaccct gaactattga tcatcctgcc tccttctctg tagtgttggg   11040
attacaggtg tgcactaccc cactcagtta cccactcggt gctaggggcc aaactcaggc   11100
cttaaggcat gctatgcaaa tgctctacca tctgagccat agccccccccc accaccacca   11160 tccactctac cctgtggttt tgaatctact aataaggtta tgttgccttg ccactgtct    11220 aattctagaa cctttccata aaaaagaaac gtcatactcc ttagtggtca ttccccattc   11280
ctctctgctc aagactcctg gtaaccatta ctctactttc tgacttatgg acattccaca   11340
gaaatggggt cccaaagtgt gtggtggctg gtggctggtg gctttcactt ggcatgaagt   11400
ttccagggtt tttctatgca ctagcatgcg gaatgtttca tccccttctgc tgactgagta   11460 aaatattagt tacttatcag gcgaagagca acatttggg tcaagtctac cttctggctg    11520
ttgtaataaa gctgctgtga gttgggtctt tcgtgggcaa agaagttaaa ccatggggag   11580
atgggccttg agaagtaagg ggctgttggc aaagaaaatg gatgcagatg gtcacagggt   11640
ctttccttaa gtgattgaca ctgggtggtg catcagggac caggaggcca cacaccacag   11700
ccctggtgtc tcttccttct cacaggggag ctgccattgc cccaggagac aactgtcaag   11760
ctgagctgtg atgagggacc cctgcaagtg atcctgggcc ctgagcaggc tgtggtgctg   11820
gactgcactt tggggctac agctgctggg cctccgacca gggtgacatg gagcaaggat    11880
ggagacactg tactagagca tgagaacctg cacctgctac ccaatggctc cctgtggctg   11940
tcctcacccc tagagcaaga agacagcgat gatgaggaag ctcttaggat ctggaaggtc   12000
actgagggca gctattcctg tctggcccac agcccgctag gagtggtggc cagccaggtt   12060
```

```
gctgtggtca agcttgccag taagtgcttg catctctggg gtgagggtgg agatttggag    12120
accaaagggg acagaaggga tagggagaag gatctaaagt tagttacctg catcagaacc    12180
gggagcccag cccaggttcc ctgcctcctg tcctgtccca ctcactgggt cccctcttgc    12240
tgttagctac tcttgctgct cggtgttcca tcagccaggt cttcactcca tcaacctcct    12300
ttctcaccct ttgagttcta gtgtatagga ctggcttgtc tgccaggaag aggtcaggag    12360
cccaaaggtt tctcttcctg tttcctaccc acacaccaca gtgtacaagg atataaccat    12420
gacctatcct ggcactggct ccttagggct ctctagaggt accaggaaat actgtgatgg    12480
taatgttgga catgggtaca acatgctttg gattacacac tgccagtacc atctgaccag    12540
caatcctttc ttagcccttg gctaccactg tgctctccct cactgtgggt ttgctcagct    12600
gtgtgtccat gactctgcgt tctgtgccac tgtgctgaca gcaatctctc ttctcttctc    12660
ttctcttctc ttctcttctc ttctcttctc ttctcttctc ttctcttctc tttctctctc    12720
tctctctctc tctctctctc tctctctcca ccatgttcat ccccagcact cgaagacttc    12780
tctctgcacc ccgagtccca gattgtggag gagaacggga cagcacgctt tgaatgccac    12840
accaagggcc ttccagcccc catcattact tgggaaaagg accaggtgac cgtgcctgag    12900
gagtcccggt gagtgaccct cagggagtct gccccagtgt gcaggacata gggttctggg    12960
acatgcttag aactgggatt cttacagcca aggtgctcca tttgcctaaa ctcacccaag    13020
agccaaccac tagcccgact cctggcccag tgagaaggtt tcctctctgg aagagaagct    13080
acccaccagg ctgaggtgca tagaactagg ggacagtcta gagctcttcc aagcactgct    13140
ggtccacact tgctttatca agggctctaa gagccagaca gcagctatga tctattcaag    13200
accacatcag gggccacggg cagaagactg gcttctgctc tgctctttcc aaggttcctc    13260
tggagtttct ccatggactc ctacttctct tcctatctct gctctaccct gtcaggcaca    13320
ggcatctctg accagcaggc tacagggtct atttggtcc attcacttct ctttttataa    13380
agatagtatt ggtggaacaa tcctggggaa ggttctaggt tgaatgccaa gcagaggaca    13440
accaggattt ggcccctgct gtggcctcct gatgcacaca cagcagacca gaacccagag    13500
gctcactgcc tctgggggctt ctgggttggc ttcacatctt ggtcctcacc ccatggatcc    13560
ttacacatct ttgggaaatg cgcctccaaa ggtctctccc aggcattctg caaccctctg    13620
ctgcatggaa atgcgatccc caccccgaca cacacttaga aacattggct tgcacatcac    13680
tcccaagtac atccaactcc gtcttgactg ttgggctgcc tcatcattgc tgactttga     13740
cccagtggtg ggagtagaag gtgtagaaaa gtcacagaac acctttgatc aggtaaagtc    13800
aacagatagc atccttgttg acagagtgca gtttggtctc cactcatcct tggcacatcc    13860
agttcagctc ttgtctccct atatctgtga aatgaaatgt gaagggcatt cggctaaatt    13920
gtaattttcc aaatgtgacc tctgtagcat gtttgtttgt tgtttgtttt gtcttagata    13980
aggtcttatt gtagctcagg ctagcctcaa actctcagca ttagtcaggg atgatcttga    14040
actcatgatc ttcctctctg cttggtactg aaatatcagt ttatgtggta ttggggatgg    14100
aacccagagc ttcaggcatg ctaagcaagt attcttagca actgagctac atccccagcc    14160
cgaagacata tttttaaaat acatataaac aaaaaaggag gaaaaaatta tctcattgcc    14220
caaccactgt tatttagaca ggatggtcaa ttgtttcctg acacagggtc ttgctaggta    14280
gcccaggctg gccttctgcc tcagcttccg cagtcctgga attacaggcc tgtgccaaca    14340
tctctggccc cttttattat tgtggttttg ttttctctc attgttaggt ttctgcattg     14400
ttttgaacag ggtctccctg tgaacaccag gcttgtctag acctcagtgt gtagacgagg    14460
```

```
ctgtcctcct caaaacagtg ggaatcagac ttcccttccc cgcatctaat tcaggccaca   14520
gacctcaccc attaggtggg gctgccagct tccaggcccc agaagtgctt gccaccaagt   14580
cctctgaaaa ttgatcctgg cctataaata gaccaggctc acatgtccca gcacattgtg   14640
tcagggaata aagaaatgtc taaagcagca actagattat ggccaaggta tgtattttg    14700 catgtgccca gatatacaga tattctaatg acaaactcag ctcagtggtc acaagagatc   14760
gcattcctta gagttggctg tgagcatttg cagctcaaat acactctgtc aggggaaagg   14820
cacatacttt tgtaacagat gacaaaggct aaacactaag gcagttccct ggtatttatg   14880
atttacccat ctatctgtct gtccgtccga tcatccacca tccatctgtc tgtctgtctg   14940
tgtctgtcta tcaatttcaa ggcagggtct gatgtggcct aggctgactt tgaattccta   15000
actctccatc cattcgtcca cccaccatcc accatccacc atccatccat ccatccatct   15060
gtctatctgt ctatctattt aaaggcagaa aggtagggtc ccatgtggcc taggctggct   15120
ttcagcgcct agttctcttg cttctacctc ctaagtgcta caattgcagg caagtgctac   15180
cacaccatga ggtgttgagc ttaggaccca gcacgtccag agttttgtgt atgctagaca   15240
atccactctc ccacctgaac tccaccctag cctcacttac attcatctct agtaatagga   15300
gatacctttt ttttccatgg gagccagcca tgaatgaaac taaaaaaaga atttatatta   15360
aaatgccaaa atgcagccgg gcgtggtggc acacaccttt aatcccagca cttgggaggc   15420
agaggcaggc ggatttctga gttcagggcc agcctggtct acagagtgag ttctaggaca   15480
gcgagggcta cacagagaaa ccctgtctca aaaaaccaaa aaaaaaaaaa gaaaaaaaga   15540 aaaaaaagc caaaatgcac attatagaat gaaagggaa gcccctcctg actgaacgca    15600
ggccttacca ttttgagtat tccaccatcc tcatcctcac tccagaccag cctaactcaa   15660
aaacaaaaag gttttcattt tgtaaaattc aacaaataag agtgctcaac aatcccctc    15720 acaagggaa ccccaagcac tacaaaagct ttgccaacca tgtgcctcaa cctgtcattt    15780
atctgtttcc ccaaaccaga attgcttcct ttttgtttgt tttaaatatt tttgtgccca   15840
tacatgtttt ttttttcatt tattttatgt atatgagtac actgcaagct gtcttcagac   15900
acaccagaag agggccatta cagatggttg tgagccacca cgtggttgct gggacttgaa   15960
ctcaggacct ctggaagagc agtcagtgct cttaactgct gagccatctc accagcccca   16020
gaattgtttc ttaagcacta ttttgtaact tctcccctac tagccaatac atttcagtca   16080
tctttcagaa gccagagttt ctaaaaccac attgtaacaa aaccagaaca ggtttagaca   16140
gccctgggga ggcagggcag caccttgcct ctggctgcag ctacagctct gtgcccgagg   16200
aaaggagcag gcagatccat tcctgcacac aaagtgaagg aaatgctatt gctcaaggaa   16260
caggtttgct cttagcactt ggtgctccct tttcctggca ccaagattcg aaagtggagg   16320
taatccccta ggggaactgg ctggatggag gatggagggg aaggaaaagc cacagattgc   16380
agcatgtgaa gtagagtcgg ccgtgagggg tggtctttct catctgattt ctcatggcag   16440
tagattgggt actggcccag atgtctccct acatgtttct cctgcttccc cgcccccatc   16500
tctctactgt agcacatctg tgagtgcatc tggagctgag gtgagaggtt gggtgtggga   16560
caaaggctca cctgggcaga tgagggaagg actggtccca ccatattccc aagaatgtct   16620
cccaataccc ttcttcagtc ccttggccat ctcaccgctc ccatacttag gtttccttag   16680
cccctgcttt tccaggaaca aagagccttc cccagcaccc aatgccctgt cgccctatgg   16740
ttccacccag tctgtacact taagattctc actacctgga gctgaccccc gtagaaggcc   16800
```

```
tcatcacctc ctgactggtt gaacatactc agtgcccacc atccccaac ctccctgccc      16860 caagtttctc aagcaaggtc tcctggcttt ctcaaccttc tctcctgcag gtctggtaag      16920
aaggccccgt cttcctggtc ttctaaattg ctttgtggat tgctgggtag aaactattgg      16980
aaaccacacc catccctccc acagccacac ctagctatga gcaggggcct gaacttggcc      17040
tctaggacca gaagacctgg cctcaagatg tcttgtagca tagtgtcaca tcatctacaa      17100
tggcctccaa cgcactgtgt ggcacaggat gaccttcagc ttctgattct cctgcctcca      17160
cctccctaac gctgtcatta caggcgtgga gcgttactga ttcacacagt gctgaagatg      17220
gaagtggggt ctggtgcaag ctagacaagc cttctactca tggaaccata tccccagccc      17280
ctggttttgg gctgtaactg ctccagcatg aagaccctgg gtgaatgcac taccctgagc      17340
ttcaattttg ttaccataaa atggaggttg tgattctcct gcctcttggg attcctttga      17400
gggtcagagg agatgaggga ataagggaat ttttgttagg aagagggaaa ggaaatgcag      17460
gtaagaggtt aataaaggtg gagcaagcag agagatgacg gcttggcagt tgtaaatgcg      17520
agctactcct ctggagttag ctcccagcac cacatcaggc cgctcgccac tgccagtaac      17580
tgcagctcca tctgcaacgc cagccctttc ctcaacttgg caggcacctg cgctaaggca      17640
cacacacaca aacgctgttt ctgttgttgg tttttaatct tccaggggtg aaaaaaaaag      17700
gtttaaaaca tccaaaatct ttttttgttt gtttgcttgt ttgggttttt ttcgagacag      17760
ggtttctctg tgtagtcttg gctgtcctgg aactcactct gtagaccagg ctggcctcga      17820
actcagaaat ctgcctgcct ctgcctccca agtgctggga tcaaaggcgt gcaccaccac      17880
gcctggctaa aacattcaaa ttcttaaaat ggtatatgtg tgtaataaaa agttaggctt      17940
cgggctggtg agatggctca atgggtaaga gcactgactg ctcttctgaa ggtccagagt      18000
tcaaatccta gcaaccacat ggtaggtcac aaccacctgt aatgagatct gatgccctct      18060
tctggtgtgt ctgaagtcgg ctacattgta cttacatata ataaataaat aaatctttaa      18120
aaaaaaaaaa agttaggctt ctcacacctc cagcttccag gctaccaggc cccctcctca      18180
gaaacaactt cctttttctgg ggacattcag tacatataca atctagtaag aatttggctc      18240
tgagtgtgtt atcctgcggc accaaagcac acagtgcgga gggcgcctgg acctgccgcg      18300
ttccattgca ggaggtgccc acacctgtga ggccaggata cacccaacag tttccagcct      18360
ctgcacaggg ctgcagtaaa cactgacatg caggtgctgt gtgtgtctga ctgactgtga      18420
tagagtccca gaagtcccag ggctagatga acagctcctt gctgttggat catgctacca      18480
gcttgtccag aaaagagcat gtcctgggtg atgcctgctg gacagatgtg ccttctgtga      18540
tttccttacc cacccgcctg agctgttagt aaaccatttg gtctttgcca gtctgttagg      18600
tgagggttgg catttctgtc cctcagggcc acccctctct atcgccttcc cacacctcac      18660
aggctccctc tgctccttcc caaggctcat cactcttccc aatggcgtcc tccagatcct      18720
agatgtccag gacagtgatg caggctccta ccgctgcgtg gccaccaatt cagcccgcca      18780
acgattcagc caggaggcct cgctcactgt ggccctcaga ggtaagggga tttctgggga      18840
cagctatact gggaatgaaa gtgactagac ccgggtcttt ggaaagctga ttgagtagta      18900
attctacatg ggatagacct agggtttggg actccaactg gcaggggtg ggggtggggg      18960 tggggttcgt tccttatggg gtgtctgtgt ttcctacggt tgcacaagaa ctggtgaaca      19020
ggcaaggtat ccaaatgccc tgcagcctct ggtcccttct gcccttccag gtgccttaaa      19080
ggctttgggc tagaggttca cccaatctcc ttatgtatgc caaactggct cctcacctgt      19140
actctggtcc ttttctgcct ttcttttccc catttttttt aaacatttat tttgtgtgtt      19200
```

```
catacacaag tcccatagca ctcatgaaca gagaaggatt tgtggaagtc ggttgtcttc      19260
ttccacttag tgggttcctg ggatccgtca gacttggcag caagcatctg tagctagaag      19320
tctcttttct gcctctcttt gaaaagcccc tgccaggatt aggtagtaac aagggcactg      19380
gtttgggggg tcacgaagac ctgttttgaa tcctgactct cctcaccatc tgtgtgaccc      19440
tgagatggga atggaaagtg cttggcattc agcagctgct ccacagatct cactgcaagc      19500
ctcccccaag gttgctcact tgtgtcatcc ctcctcttca ctggttccat cctctagtcc      19560
ctaggctgag gctccaggcc atccttgcgc gctctccagc actaggtcta tgcttccccc      19620
tgctggacaa atcaggtgtt caatgttgtg ccacaaggag agagagttgg acacagaaac      19680
acatcgtgaa gcttctttgc taaaaacaac agcccacctt ttttttttggg ggggggtgtt      19740 tttttgagac agggtttctc tgtatagccc tggctgtcct ggaactcact tgtagacca       19800 ggctggcctc gaactcagaa atccgcctgc ttctacctcc tgagtgctgg gattaaagtt      19860
gtgcgccacc aggcccggct taacagccca ccttttgctt gtagaactct gaggtacttt      19920
ggaaaggcat ctgcctgact cacacaacaa cttatagaca gtcttagaac tagagctggg      19980
tgctgagtct aaggcagatg ccatgggagc tggatttggg cggggaaata tgggggaggt      20040
atggtctacc cagtaacttg tggggtttca cttgtgtcgg agagcattct tctggctcca      20100
agagaaagaa ctccaaggcc tacgccagct ctgcttgaca gttgctttcc ccttctgaca      20160
gaaagaacca tgacgcccca ggcccctgc tttgggcatt cagaagcagt aattggcaag       20220
ctaaccctgt cctatcttca ctacaggtc tttggaggct accaggggc aggatgtggt         20280 cattgtggca gccccagaga acaccacggt agtgtctgga cagagtgtag tgatggagtg      20340
cgtggcctct gctgaccca cccctttgt gtcctgggtc cgacagggtg agtgctgagg         20400
aaagaggagg aggagactgg ggaagtgggc aagatggtac agtatttcac aggctccaag      20460
tcaggagctt ctgcctaaag atagaaggag agaattgact ccttagagtt gtccttgac       20520 ttccatagca catgcaagca agctcacatg tacacacatt catgcagtaa taaagtctaa      20580
agaaggttgt attaaagccc agtggtggtg gcacacatcc ttaatcccag cactgggag       20640 gcagaggcag gcggggctct gagtttgagg ccagcctggt ctacagagca agttcaggt       20700 aaccagggct actcagagga aaccctactt tggaaaattc tggggtggg aggagagaga       20760 gacacagaga gacagagaga gcgagggaca gagagacaga gacaggcaga cacacacaca      20820
cacacacaca cacacacaca cacacacaga gagagagaga gagagagaga gagagagaga      20880
gagagagaga gagagattgt attaaatatc tgctccgccc accagagacc atttagccat      20940
cgtttaccca cctcccttct gcttttccac ctagggatca gagtaagaag gaactgggat      21000
tcaaaccagc ggctgtgatg cagctttgca gggatgtagt gggaacctcg tagttggaga      21060
gggtgtagag ggacagttcc agcgtccccc tccagcctgc tccttctctg tcaccagatg      21120
gaaagcctat ctccacggat gtcatcgttc tgggccggac caatctactc atcgccagcg      21180
cgcagcctcg gcactctgga gtctatgtct gccgagccaa caagccccgc acgcgtgatt      21240
tcgccactgc ggctgctgag ctccgagtgc ttggtaagga agggctggtg ctgggggacg      21300
ttaaggatgg gtgtgtgtta gagggagaag gggcggtcct agaagactaa atgtgagggg      21360
gaccacatgg gaggagtctg aatttttctga ttggtggtga ttgttggagg actggattcc     21420
gtagctgggg ggggggggg agggaatggg gcgatttgag acgggggtg ggggggcgga        21480 tttaaagcct ggtttgggtc atgaggagtg agagtgcagg cgagcaggag tggggtgagg      21540
```

```
ttatggaagg agatagtgga atggtctagg ggggtgtgtg aagcccagaa tctgtacgtg    21600
gtagcactca gaaaactgtg gcaggagcgt gagttcgata ccagccctag ctacagagtt    21660
gagaccagct acagagtgaa aagtctatct caaaaacaaa attattaaac aatgacaatg    21720
tcttaggcta ttaagtccct atgagtgtgt gcaggccatg gtgagtgtat tgcggtcaca    21780
gactgagttg agacaaggtt tcttgttcac ttcatactcc aggctagctg gcccggggaa    21840
ttctggggaa tctcctgtct ctgtctccta ggaatgctgg gattaatcag ttggggtgat    21900
gctgaggcgg gcagatcaga aattcaaggc caacctgggc tataaagag ctttctcaat     21960 acaacagaaa actgggggac caggcttgct gaaagctgga gtaactgctg gtataagaa     22020 gccacgggga ggagaaagtg aagttacagc ctagagctca aaagctggaa atctgctggg    22080
cttgggagaa aggaggacta gcccaggagg ggtcgagtct agtggaccag agctgggccc    22140
gtatgactag gggagaggac ctcagggtga ggcttgggcg cggtgttggg acacttggag    22200
aggggtaggc cctcttgtca gagtctccct tctgccccct agctgcccca gccatctcgc     22260
aggcgcccga ggcgctctcg cggacgcggg ccagcaccgc gcgcttcgtg tgccgggcgt    22320
ccggggagcc acggcccgcg ctgcactggc tgcacgacgg gatcccgttg cgacccaatg    22380
ggcgcgtcaa ggtgcagggc ggtggcggca gcttggtcat cactcagatc ggccttcagg    22440
acgctggcta ctaccagtgc gtagcagaaa acagcgcggg aactgcctgt gccgctgcgc    22500
ccctggcggt agtggtgcgc gaggggctgc ccagcgcccc gactcgggtc acagccacgc    22560
cgctgagcag ctcctctgtg ctggtggcct gggagcggcc tgagttgcac agcgagcaaa    22620
tcattggctt ctctcttcac taccaaaagg caagggtat gtctactctt gaccgcggga     22680
atcccagtta gggcaagtat gggatggata attaaagatg agaggaaggg atggggagca    22740
atactgctgg gaagtgatct agtattagag aatggagtgt acacgcactc cttgacggag    22800
agaatgcttc tctttccagg gttaaaggag ccatcttcca cccccagcta actaactgca    22860
ggacgggctc cttcaattag cacggggagc ttcctggcct attatggaat caatgcaata    22920
agtagactag atggcagagg catttctatc cttcacccta gattgtctgt aacaatttag    22980
ctatacatag accagtagga tccccagaca gtctccagct agtcagacat ggagtgggct    23040
gtgacagtcc ctttgtcccc cccgtgctac cacctcagga gtggacaatg tggagtacca    23100
gtttgcagta aacaatgaca ccacagagct gcaggttcgg gacctggaac ccaacacgga    23160
ttatgagttc tacgtggtgg cctactccca gctgggggcc agccgaacct ccagcccagc    23220
cctggtgcat acactggacg atggtaggac ctctgaacct gcagtgacct gggacccaga    23280
gacactccca ctcagggaca gtgtggccca aggccctctt ccctgccttg tgatgtctgt    23340
tgtgccctat aaagcagtgg gcagaggttc ttcttcccag tgtaaaatgg ggaaactggg    23400
gctcagaaaa tgaaaatgac ttgccaagct cagcagggca gctgggactt gagcccagct    23460
ctgagccccc ataccatgca gcccttcttc ctaacataca tttactaccc agccattgga    23520
tatgaaagct tctggcccac actgtccact agccttggga tagaaaggat gtctccgcat    23580
cctccagcgt agggctcccc tgagaggctc cctccctccc tccctcagat cctgggcctg    23640
ggcctacttc tgacttgctg tgtgacctgg gcaagtctct gatcactcct gactgtgtct    23700
tatcttccct gttggtggag cggagctcac gccaatgttc ttctgtctca gtcccagcg    23760 cagcacccca gcttaccttg tccagcccca acccctcgga catcagggtg catggctgc    23820 ccctgccctc cagcctgagc aatggacagg tgctgaagta caagatagag tacgtttgg    23880 ggaaggaagg tgagtggggc cggggaggta cagagatgtc agtgggaatg gggtcctcc    23940
```

```
cctagatgag ggacgttgtc agtggaagtg gagcctaatt ggggcatggg atgagaaagc    24000
tctggaaaag agcattggga gactagatag cccaatgtgt aaagtatgtg tgcaagccca    24060
aaggcctgag ttcaatctca gacttcatgt taaaaaaaaa aaagcctggc acagtggtag    24120
gtgcctgctt gtaatcccag cagggggag gtggagacac ggggacacct tgagctcact    24180
gggctaaacc agtgagttcc aggccagcga gagtccctgt gcagaagaga aggtggacaa    24240
taccagagaa atgacaacag aggttgtcat ctgacctcca catgtatgtg tacacacacc    24300
tgcacatagg tgaacactca cactcatgga cacacacgga cacagggttt cggggcagtt    24360
gaggaaaagg gaaagcaaag agggtcagta gcctgcgcac agataaggag ggtgatcagt    24420
gggaccttgg actgttccct ttctgtgaag ggagcaattt acccagtgga tccttggaac    24480
ccttctaggt ttttgtgttt gtttattttt taagatgtat ttatttattt tatgtatatg    24540
agttctctat ctgcacgccc acctgcatgc cagaagaggg aatcagatcc cagtacagat    24600
ggttgtgagc cacagtgtgg ttgctgggaa ttgaactcag gacctctgga agagcagtca    24660
gtgctcctaa caattgagcc atctctccag ccccagaaac cttctggttt acacaccaga    24720
gaagatgtgg gaggctgcag gagtgcacat gagacatggg ctgctcctac tggggagatg    24780
atgctggtct gggggaggtg atgtggttgg gaaaggaatg gagagtgagg aaaagaaaag    24840
tggtgagggt cagggtaaag ctaaagagag aggcaggagg ctgatgggag acagcagtca    24900
gggctcctga caccagggac tgcttagtgt ccttagccag ccatcaagcc tgtgtaagag    24960
gtgtgtactg gctgttgctg ttggttcaca gggaggaaaa gttcatgcct tggtttctcc    25020
atatggaacg gaggccaatg ggcttcagca gcgataggta gaagcccagg gtcaacctgg    25080
aggcatgaaa cctgcctccg tgctgagggg tcagtgccca gaggaccctg ggacctgaa     25140 atggaaaagt caatgtgata aatttaaaga ttgatggtcc cccaatgaag gacacccagc    25200
agcctatcct ttttgtccca gaagatcagg ttttctccac cgaggtgcct ggaaatgaga    25260
cacaacttac gttaaactca cttcagccaa acaaagtgta ccgagtccgg atttcagctg    25320
gcactggcgc tggctatgga gtccttctc agtggatgca gcacaggaca cctggtgtgc    25380
acaaccagag ccatggtatg gacctacacg ggcagactgg acagcgggga caggtgctct    25440
gtggccttag atattgcccc tgttattgcc tgttattgcc accccccccc ccccacaaac    25500
acacacttga tgcacccgga aggcctgggt gtaggagtga agggctgggc tcaaatatct    25560
ccttgttcac tctgtgactt tgacaagcca ctcgcatctc cagagcttcg gtactaccaa    25620
ggatgatagc aggactagtc attgtaatta tacacagagt ggtcggcata gaacaggagc    25680
tccttgggtt gagaccacgg ctcacttgac agagtgcttg cctagcatgt acaaagcact    25740
aaattcaatc cccaggacca cataaaccca gcatacctct gatcctggca gttcaaggtc    25800
tgcctcacct acctagtgag ttggggacca gcctaggagg tatgaaactc tgtatcaaag    25860
aaaggaagga acccattaaa agctagctgg cttttgccaag aggcccaaac agtagagtgg    25920
ttaaatggct acaaagtctc caggcaggtg ctagtggagg ctcatgcctt taatcccagc    25980
actcgagagg tggaggcagg cagatttctg aatttgaaga cagcctggtc tacaccaagg    26040
ttacacagag aaaccctgtc tcaaaaaacc agaaagaaa aaagactaca aagtcagcta    26100
ccatattcag acattagaca agctatagct taaaaaaaa aaaaaaaaa aaagctggat    26160 tatggaatta taagaatggg ccgggcgcgg tggcgcacgc atgcctttga tcccagtact    26220
cgggaggcag aggcaggcgg atttctgagt tcgagcctgg tctacaaagt gagttccagg    26280
```

```
acagccaggg ctacacagag aaaccctgtc tcgaaaaaag aaaagaaaa agaaaaaaaa    26340 atgaatgaag taaaaatata caaaggctgc caaggtcgcc cagctaataa aggggcttgc    26400
tccattttct ggggatctga cttccaatgt ctccccagaa tttatatgat gagtgagtct    26460
acagcttgcg gcctctgacc gccaccagca cgcacataaa ttaaataaat actttaaatt    26520 tttaaaata catatacaaa atgtttgaaa tggggtctga cacacagcca accctctact    26580
cttgggctcc gagtgttgct cgtcgtgttg atggtcccaa atctccctca tgatctcagc    26640 agcccttga ccatactaac tctttcaaga gacctgcaga agccctctg cccctgaccg    26700 cgggcctgcg cagacacgcc ccctgctgtc tcttgtgcgt gcccggcaga cgcgcctgcg    26760
cagctaacat gcagagctca aacccaccgg gaagtggcag agtggagcag ttagggaaag    26820
cccaggcaca gctctatgct gtgctccgcc cctgccctgc accggctcac ctccctgacc    26880
acttcactcc tcattctctt cccttgtcc ccatcatctt cctctgcccc ccagttccct    26940
ttgcccctgc agaattgaag gtgagggcaa agatggagtc cctggtggtg tcatggcagc    27000
cgccccctca ccccacccag atctctggat acaaactcta ctggagagag gtgggaacag    27060
aggaggaggc agatggtgac cgcccccag ggggtcgtgg agatcaagct tgggacgtcg    27120
ggcccgtgcg gctgaagaag aaagtgaagc agtatgaact gacccagtta ggtgagtagg    27180
cttgggcttg ggagggtcat gggcaagcta agcacacgga gagtgacact catggccttt    27240
ccccagtccc tggcaggctg tacgaggtga agctcgtagc tttcaacaaa cacgaggacg    27300
gctacgctgc tgtgtggaag ggcaagacgg agaaggcgcc cacgccaggt gaggggagg    27360 caggcggggg tcttggagcc ttcttttcct ttttctttat cagccagcaa gccgtgtgca    27420
tgccacagcc acccggccca ccctcctggg cagaaatcct cctgctctag acatgcccct    27480
cattctcaag ctaagcagag cgaacggag agattggaaa gagaaactcc gtgtccgatg    27540
cgtgattcct ggctcaagct ttaaccttta aacagctttt tagatcgcat ccacgtatac    27600
cacatggtcc gtcagattat cccataattc ttttttttaa agacttactt acttatttta    27660
tgtatatgag tacactgtag ctgtcttcag acacaccaga agagggcacc agatcccatt    27720
acagatggtt gtggcttctg ggaattgaac tccagacctc tagaaaagca gtcagtgctc    27780
tcaaccactg agccatctct ccagccccac cccataattc ttaagcaggg gcaagcacaa    27840
cacagtggtt tgtcaccctg acgatccagc ctgacagtca aagaaacct gggttctaat    27900 tccagcgagt tcagtttttt cattgagcaa atattttacc taagtatcta ccacatgaca    27960
gctctgttct ggaaacttag taatgaacaa catgaataag gtatctgctc tcttggagct    28020 tatttatgc ttatctaata aacatttgtc atcaccaaat agtatacact gtcccacagt    28080
cttctacctg ctttgtaagc agcctcctaa ggacactcat gaggggacag tgagatggtt    28140
cagcagggaa ggtgattgct acaagccaca tgacctgagc ttggtttctg cacccccccc    28200
caaattgtcc tctgctcccc cacatgcaca cagcagcaca ctccctccct tccctccaca    28260
caataaatgt gtgactgaga agatgcagga gttaagaatt ttaaatatgt tttaaagatg    28320
tatttatgta tttatatgtg tgagtacact gtcactgttg ctatcttcag acacagcaga    28380
agaggtcact agatcccatt atagatggtt gtgagccacc atgtggttgc tgggaattga    28440
actcagggac tctggaagag cagtcagtgc ttaaccgctg agccctctct tcagccccca    28500
gaattttaaa tatttaaag aagtaaatat aagaaaaga agaaaatgt caagatgtag    28560 gtattgtcat cagatcctta taagaataga aaatgatggc acagagaggt taaacaactt    28620
ctctaaagcc acatacatag ctaggaagtg gcagcaatgg agcctggctc cagagtcagg    28680
```

```
gcatgctttc tctgtcacat tctcatcagc catgggatat gtcacagtca ctctatgtgt    28740
gacctaagca aaaaaaaatc acttccattc ttgggagcct cagctgcagt aggaataatg    28800
tcacccaact cacaggatca caagagaggc ccggtgccag ctgtggtatc acacagctgt    28860
aacccctgtg ctaaaggacc agaggcacaa ggatggagaa ttacaggcca gcctaggcta    28920
ctacataatg agattctgcc tcaaaaataa gaggggaaa ggccaaatga aacctactga    28980
gaccatgtac gtccacctac tctctgcaca cttgggtttc ccctctaga cctgcctatc    29040 cagagggggc caccgctgcc tcctgcccat gtccacgcag agtcaaacag ctccacttcc    29100
atttggcttc ggtggaagaa gccagacttt accactgtca agattgtcaa ctacactgta    29160
cgcttcggcc cctgggggct caggaatgct tccctggtca cctactatac caggtatcag    29220
tgagggggga gtgtagctgg ggtggtagac tagcgggttc agctgtggtg aggccacacc    29280
caggatctac acagatgtct tttccgtgac tgctgacctg ggggtaata atgagggatg    29340 ggattccccc atccctcagt ggcagaatgt gtggtcagcc tttggtgaga gtggatgcaa    29400
gactagaggc ttccatccgt tggctggcac cctgccggcc catcattcgg aagatagctt    29460
aaggagctgc tgttctgatt gggaagacac cctgtgaaag ccaacagaga gagaaactaa    29520
gctgaggata gacacttcag gagcgattgg tcccccaggt gcagaataac ttagattaat    29580
tcgggaaagc gtcccagagg agagaagggc ttgctttgga gatgagacat ggaataacat    29640
atgtccggcc tttctgtggt ttgcctggct gtgtgtggga ggggaggttg tgggcccaac    29700
aagcagctcc ctccagggtg gggcctggct ggaggcaggg gcttctgtct ggggttctgc    29760
ctggcttgag gcctgtctga gggcactagt cctatccctt ctcctggaag ctctggagaa    29820
gacattctca ttggcggcct gaaaccattt accaagtacg agtttgcggt acagtcccac    29880
ggagtggata tggatgggcc cttggctcc gtcgtagaac gctccaccct gcctgaccgt    29940
gagtatccac tgcccgctcc ccacctgtgc caccatttgc tgggtctgag gaaggaagaa    30000
gaagaggagg ctgtgccctc atccccttag ttagggctgt gtctctgact ctccacccct    30060
tcccctgtgc tgcagggcct tcaacacctc cttctgacct gcgcctgagc ccctgacac    30120 catccaccgt tcggttacac tggtgtcccc ccacggagcc caatggtgag attgtggagt    30180
atctaattct ctacagcaac aaccacaccc agcccgaaca ccagtggaca ctgctcacca    30240
cagagggtaa ggacgcccac ccctgcctcc ttgcccttttt gttccaaggg tctctgggat    30300
tggaggctga agctactgtc tgggtgcaaa gttggtttgc ccatggtgct ttggcctcct    30360
gccaccctgt ctcctcccac ttcccaccac aggaaacatc ttcagtgcag aggtccatgg    30420
cctagagagt gacactcggt atttcttcaa gatgggagcc cgcacagagg tggggcctgg    30480
gcccttttcc cgcttgcagg atgtgattac tctgcaaaag acattctcag gtaccaggca    30540
ggagggagaa ggcccttggg acaactggag gccccaagac ccctggattg ctcccaagg    30600 ccctgccttc tggaaattac attttctttta cctttggaacc ctaaggtgtg ggggatggag    30660
aagcagtgac agcttgatag agggactgtc atagctttga ggggtctttt attattttat    30720
tctctctgtg tgtgttttggc acagtgcata tgcgaaggtc agaggacatc agagagttgg    30780
ttttgtgggg atcttgcttt gcctggaggg ttgggtgagc tcctgagttc tgtgaagaag    30840
tggtcaatag gctggataga cactcacaag ggctcaatta agatacaaaa tgagatccca    30900
gggctcctta ttgtaaatta ttgaagatgt gaagatgagc cagtggggca ttagccacac    30960
ataggactga ggagcatgaa gccctgagtc caaatgcaca cacacacaca cacacacaca    31020
```

```
cacacacaca cacaccgtaa aacttggctg tggctgctgt aatccttgct gaggatgcag  31080
agacaggata tttctggggc tgagagggac tggggaagtc acgtgatgta gacctctgat  31140
ctccacacta catatacatg cccttagatg aacatataca gacatgacac acacatgtgt  31200
gcacctagag cccaccttgg ttatacatat ataccacatg agagcccttg ttgccaggag  31260
gaaaacaact tcactgaaga gctgattcta tagagtccag ttttgtgagg agtggcaggt  31320
tctgtacagc agggaagacc gtggtggact cagtatgagg cccagtaaga tcccgtggct  31380
ctctctattc caatcagaag ggagtgagct tccaaaccag gtgtgaacca ggtgtggtac  31440
tgcacacctt tgatctccgt cctggtttat gagcactgct tccttctgac ctggagtcac  31500
actgttctcc cccgcagact ccttggatgt gcacgccgtc acgggcatca tcgtgggtgt  31560
ctgcctgggc cttctctgcc tcctggcctg catgtgtgct ggcctacgac gaagctccca  31620
caggtgaacc ggggaaccac tgagaccact gagttaccag gaagggctgc agagtggaca  31680
aaggagcgtg tccttccctg ctgccccgga agcccagta tagataggc tatggagctg  31740 gagtgaagtt cagtgctaca tgtgccccca tgtgaggccc tgggcgtcat cctcagtagc  31800
acaaaacaag tggataattt atttattagg attctgagat gaaggattga ggtgttgttc  31860
tcatgagaat gtagaataaa cttagggaag ccccaggact ccccacctca gtaacagcgg  31920
gctgagctac ctgtgggctt ccctcatggc ttaaatggaa atggcccatc tcgccataca  31980
aggaagcgtg ccatctgagg ggtcaggccg agtggacttg tattccttcc tttctgtttg  32040
attgcaccac accaggaaac caaatccact cttgtccgac cataactttt gttctgttga  32100
tcacagggaa gccctgcccg gattgtcctc ctcaggcacc ccaggaaacc cagcgctcta  32160
cacaagagct cgacttgggc cccccagtgt ccctgctgcc catgagttgg agtccctcgt  32220
gcatcctcgt ccccaggatt ggtccccacc accctcagat gtggaagaca aggctgaagt  32280
acacagcctt atgggtggca gtgtttcaga ttgccggggc cactccaaga gaaaggtgag  32340
actggagtct cttcaggtca gggactcaca cgaacccatt cccaaatcaa acaccagggg  32400
gcaccagagc acaacttctg acggtgagat gcgctcgcgc gcacacacac acacacacac  32460
acacacacac acacacacac acacacaggc actgaaccat acagagaaag cctgtccata  32520
ccacctggga ggatcccaga gctgtgtttt cgagagcacc catacttctc ttcacttacc  32580
taatatggag aaaagaggct ggtcactttt gctgtggcca agtagggctg gccccagaat  32640
aaggtgaaac cccataggcc aggtgttctg ggggcacacc ctgaccaagt ggacagtcag  32700
tcttcccatc tcttcacttt cctctgcaat tagaaagagt ccagcaagct tgggagcttt  32760
ggattttgca catcaactgt tgttaggctt atgggtccgc ccttcccatt ctccctacct  32820
cagttctcac ctctgtcccg gggtggggct ttagtgtgga gtttagtgtt atctggagat  32880 aacagggtc cacaggtctg gaccctgcat gcccatactg tcttcttcct tctctgcaga  32940
tctcctgggc tcaggcaggg ggaccaaact gggcaggctc ctgggcaggc tgtgagctgc  33000
cccagggtag tggtccaagg ccggctctga cccgtgctct gctgcctcca gcgggaaccg  33060
ggcagacact gctgctgcaa gccctggtat atgacgccat aaaggttggt tggtgctgtt  33120
tgagagggag ggagaggcag gatgggagg caggagggaa agtccccccct ccatgcactt  33180 ccagggacag aagtgtattt gaaagacctt gtagcttcca aaggggagtg ggtgacagga  33240
agccagtgtg gagcttcttt acctggtcct aagtgactta cagtagactt acagagtatc  33300
tgaaggtggc cttagcccct tagatacggc cagcgcctcc ttgtcttcgt ggaggttctg  33360
ggtctagtac tttctggtag cctgagtgag ggcaaacgtg tgacattctg cgtttctcat  33420
```

```
ctctgccaga gcctgagcgt cgtctcttct taggtggaac agtgcttgta tcatctaatg   33480
gggagtcagc ctctccccc gcccccaat atgttggtca ttttctgaag accattctca   33540
gtggtgctca cctagccttt tgttctccac tctgccagag caacgggaga aagaagccgt   33600
ccccagcctg caggaatcag gtggaagctg aggtcattgt ccactccgac ttcggtgcat   33660
ccaaaggatg tcctgacctc cacctccaag acctggagcc agaggaacca ctgactgcag   33720
agactctgcc ttccacgtct ggagctgtgg atctgtctca aggagcagac tggctgggca   33780
gggagctggg agggtgccaa ccaacaacca gtgggccaga gaggctcacc tgcttgccag   33840
aagcagccag tgcctcctgc tcctgctcag acctccagcc cagcactgct atagaggagg   33900
cccctgggaa aagctgccag cccaaagccc tgtgtcctct aacagtcagc ccaagccttc   33960
ccagggcccc tgtctcctct gctcaggtcc cctgagcaga aggcagatat ggctcaggaa   34020
catgccatgc atggctacac atgtgtgtac tagagatatc cataagtcct tggagcctct   34080 tagggtccctt tggctggggt tggggagaac tttactctcc ctcatattct gcatcacata   34140
caggagggac ttgagacaca gctctgtgta atggacacgt gtgaagtcgt gtgtgtgtgt   34200
gtgtgtgtgt gtgctggttg agctaggaaa cctctcccta tgtagcactc actgtggcct   34260
agttgaccct ccgtggcagg atggtgtaac agtgatcagt gccagctctt tgagctttta   34320
gccttgtcac ctagccttt attacactct gagagtgtct ccagtgctgt gtctacaaag   34380
acagcgccag cccctcttct gtcagctgtg ctgagcagag tgccagtcaa ctccacgggc   34440
ctatgacacc gcagcctacc acagcatggc tgtcatcccc ctggcctcct aaggtccaga   34500
tgtctgggtg aacccagctc agctcccctc tcctttgagc atctctgtac ctaattttgt   34560
aatctgggaa gtgcctggtt tgggaaatct tctttcgcac cctgtccctc tctgcccctt   34620
ccttcatttg ttctggtgat ctgtctcatg tcatcttgct cgattatcct ggggcccttc   34680
tctttcccat gatgccctg atttcctcac tgctgttttc atttctgtct gccatgcttg   34740
tctttatgtc gtgtgttct cgtccctgag ttcaacctat gcacccttc ctaacaacat   34800 gactacctca tgtctgcttc agaccatagt gtgaccctg gtccccaca gctccctgc   34860 caaccgcctt cctgggcaga tgacccactc caagtagatc tggaaaagac cttgtggctt   34920
gtctggctgc cctcccttg tgttgagat gagaaggttt tctatggaag agatgagtcc   34980
aggctgcaca ggggaacccc caagaagggg tagggagtga aaccaagagg ctgaaaaaaa   35040
atggctgcca cccatctgca cagagagatg ggtgtgtgct tttgacgtgc agtcctggct   35100
gaaactgaag gggtgaggag aggggagcta ctggggctgc catggctcag ttccctgacc   35160
ctggagccct gaacctggct tcagagtagc aaagagtttc ctccaagatg ctgtaaggga   35220
agtctttgca taggaaaagg gcggctggct cattttattt tatctttctt tacactgaat   35280
cccaaaatca tcttaccaca aagggccaag cctgactggt atttcctgag tcacaagagc   35340
catgccatct ctctggtttc tcacctcagt catgtcccag aattgtcaga tccagtggca   35400
tctgtgctct tgctgcacat cttctctattt caactggctg gcacatcaag tgttaactct   35460
ggcttctggg ccaagttaga ataaccagt ctattttccc tttatttat tttatttat   35520 tttattttat gtctttcagt ggagttgtag cttctgaaag cgtctgtgtt tattagcctt   35580
gtgtgtcact catgtttgac cccacccaca tttccttctc ctccctctt cagccagcct   35640 atgataacac taaagattat taatgctggc ttcgtatctc attaaagaca ggattgtcac   35700
ttgaactact tctatagcat tcaaagtggc cacggccaac accaccgtat gtttcttcat   35760
```

| | |
|---|---:|
| tgctctgaag gtcaagagcc tcattttgtt ttcctggtta gatttttttc ctccttgcct | 35820 |
| tgaatgaaat aaccgtttta acagtaggct cttagcatca caccacatag tcattcctca | 35880 |
| tgttcttgtt taacaagcac tgaggttctg gtttaaatta aatagctgca aatgagacaa | 35940 |
| tttataaccc attaggctgg gtggaaaatt gtttctcaaa agcaaataag taataaatct | 36000 |
| ggtatctgcc tataactcac agttgataag aaagtagcca gaactcacta gcattatata | 36060 |
| tgatttgggt tctgagtaac tggggagtgt tagctttgtg actttgtagc agcaggtctt | 36120 |
| attaggaaag tctgttggcc ttttacaggg cattagtccc tttgtcgttt gccatggatg | 36180 |
| ccttaagttc tttggagtct catttaagaa tttcttttct cgaagcatga caagtgtatg | 36240 |
| caatacttac atgctcactc gtttacctgt gcttagtttg tgctgggtta tttaattgca | 36300 |
| ctttccagca tcatgcttcc tccttacaaa tatgatattc tttattgtta cactaaggtg | 36360 |
| ttgatcatgt atctgtccct gtaaagaatt aataaactat tttccaga | 36408 |

<210> SEQ ID NO 52
<211> LENGTH: 6948
<212> TYPE: DNA
<213> ORGANISM: Mus musculus

<400> SEQUENCE: 52

| | |
|---|---:|
| cagccgagag gtgtgagccg ccgcggtgtc agagtctagg ggaattggag tcaggcgcag | 60 |
| atccacagcg atatccagac attcagaggt gagagcttcg tggcagggaa caatagttct | 120 |
| tccccgtagc aatgcgctga gcccagtggg tgtccccaga agtgtgtgtg tgtgtgtgtg | 180 |
| tgtgtgtgtg tggtgatgag tggatcacct gtgtgtgtat atgtgtattt gtgcgtgccc | 240 |
| gccagagtca caggtgtgtc cgcggcaggt ggatgacggg tgtgggtctg agcgtccgtg | 300 |
| gtggctgaag gcttcgtttg ttggagtgtg acgagggtca ggctatgtcg cggactcggc | 360 |
| atacagagtc tgaactccag gaccacggat ggcagccact cttccagtcc ttggagaccg | 420 |
| ggtccgagcg atgctggcg gggatcggct accgggagct cgcttctggt tgccaatgtt | 480 |
| tctagggatt ccaggtgcgg ctcgcccaaa gcgtgagaat gaagctcacg gtgccccgag | 540 |
| atgggtcctg ggtggcggtt gtgacaagct tcggcgagtc tatctagagc ttagcgcaga | 600 |
| gcggttctcc gatcccatgg gtgccgccgg atccccggtc cttgtgaacc aagtgccctg | 660 |
| tttcgcggta gccaccaccc cactgggctc tgaggtcagc gcgagctgtg tcctccgccc | 720 |
| tcgggatcgt gcctgggcac gtcctagagg acaggcgagg aggtgactca ttgtgacaag | 780 |
| gagaccccgg gcactggatt gagaccgaaa tcgcgccaca actggggatg ggtcagtggc | 840 |
| agcccagaag ccccttcccc tgcccgggta cagcctcgtt cctgccccgt ccctccccc | 900 |
| gcgcggcaca gtgacctatt tggcgggcac agtatgttcc cagggaaccc gggacacggg | 960 |
| gaggtccagg acgcggtgtc cggtcccgc tcggcggcgc gccctcgggg acagggagtc | 1020 |
| tgggcgggtc ctgtccaccc tgccagcccg gaagcgcaa agggtcccac ccaccgcgcc | 1080 |
| caccacgacc cggaccagtg accgtggggc gcgagaggag cccgcactgt agagcggccg | 1140 |
| gtatcctcgc ggagtgaggc ttacgggtgc cgtacatcag acgccccggg gctggggccc | 1200 |
| tcgacccagt ccacacccag tgtaggaagg tgaccaggct gagtgcgccc actagggcac | 1260 |
| atccattcca ctcggaacct ccggggacaa gggctacact tgcaccctgg tcgtgcggga | 1320 |
| aatactttgg gcttgggttt ggcatttggg ggcgcgctgg cagcttcctc tgtcccctac | 1380 |
| gtcgcgtttc agagaggaca ctcaggcggt ttttgttgt cctcgccctc atctatttt | 1440 |
| attttccagg gatctgactc atcgcgtgct ttgggcgtgg agatcaaggt ggaggggcc | 1500 |

```
agagctaaga gcactttctt tgctctcgag tgtccgtgcg tgcgtgtgtg cgtgcgtgcg   1560
tatgtgtgtg tgtgtgtgtg tctgtgtacg tgcgtgtgtg tgtgtgtgtg tatgcgtgcg   1620
cgcgcgcgcg ctcagtctgg tttcccaaca taggcgggaa tttaggaagc ctgggctcat   1680
cgtgacgtgt tttgtggccc ggggtccccc tcctttcctc tcctctctcc accccagggt   1740
gacgcgcagc tccggtgccc aagcagtttt ggcgggcggg cagcgccggg caggaaactg   1800
actcaccact ccttgctcgg cctacgcgcc gcctaccgag cgccatttcc tgagtgcaca   1860
gcgcccccta ccggcatcag tgaggactgc aaggccggct aggcgcgggt ggcaccacgg   1920
gcttctgcca cccccaccgc ggcttaaagg gaattaaaat atgcctgatg ccagataca    1980
agtgattta gcagggtgtg ctagcggact attagggagg cgtggcccctt gagagacaag   2040
gtggagatcg tgcccctctt gggttcctgg tcttatcttc agctatgaaa aactggggac   2100
tatccagcct tagccgagtc cattggtgtc ttcccttcct tcctctggcc cctgtgagct   2160
accgtctggg gaagggcacc aaacttgttt ttcggctcag tttgtctggg gaaatgagcc   2220
aatctatatt tctatatcta tatagatctc tctctctgtc tctgtgtgtg tgtgaaagag   2280
agacagagac agagagacaa gcttacaaaa tggcccccagc taccagtact atatagacag   2340
gctggcccag tggcctggaa ctcataagga tcacgtgcct ctggtggagt gctgggatta   2400
aagactctcc ccataacatg gagctcagtc tatatttaat aaaaagcttt ttccagctga   2460
ttttaatgga gtcctctggt catgcccctc aaggtgagaa gacgagagaa tgatcaatac   2520
tagaccaaaa gggtctgaat tcaaaccccg cttgtgagcc ctgtgccttt ggacacacat   2580
tctgaacctg gattagctct gccgtaaaag aatgtgatat tgccatctat taacgatagc   2640
ttttggtggc ttacaactgc aatcccagca cactagaggc agaggcagga ggatgactga   2700
gttgtactaa aggatgtgaa taggccccaa gctctacctg taggcagagg ccatctgagg   2760
tcctttaggc ctctgaggtc tgcacccttga gaatccttttt gcgggcagtg ggaatccttg   2820
ttagacctgt gtttcggttg gttggtgttt agccaggctc tcactatgca caccaggatg   2880
gccttcaact cacagacatt ttgcctctgc ctcccgagtg ctgtgttttg ggaattggct   2940
gttttactta tttatggaag ccacaatgct ggccacgttc cctatgtagt agccaaggta   3000
gaccctgaac ttcttttccct acctctgcct ccagcgatta caggtgtgtg ccgccacacc   3060
cagttttata gagagctcct tgcttagcac aaggcccagg ctttaccatc ggggccccag   3120
acgcttcatc tcttctggct tcctaccttg aatcatagtc tgggtacccc cttctctctt   3180
ccagctgtgg gcaaactcac cctgaggtct taaggagctg ggcgtgtgta tgtgtgtggt   3240
agtgtatgtg gtaagagccc aggggtctt gcctcaggaa gccactgggg ctcaccttgc   3300
aagctcaaag gccctcctta gaagctgcat cccctagtct tggagtcagg atgggccact   3360
caggtatccc tctttcctgg agaggagcca ggtaaaccaa caccctttaac ttttttttt   3420
ttttcagtgc ctgtaaaacg ggttccttgg gcacaggcta taggcacgtc tggggctggg   3480
aggtgtctag actccagatt acctgatctg cctggcagga tgtggctcag cctgggagag   3540
agccttaacc ccgctccacc ccttcagact ctcctctccc ccaggctact gcctcccccc   3600
aggctgctgc ctccccccag gctactgcct cccccaggc tgctgcctcc tcccaggcta   3660
ctgcctcctc ccaggctgct gcctcctccc aggctactgc ctgccagcgt cctttggaaa   3720
ggcctccagc ctggagcacc tgtcagtgac agtgggaggg aggagggc agggaggagg    3780
ctctgtcaga attaggggca gagaggcacg ctcatggctt ctgtttctca ggattgccta   3840
```

```
tgttaactta gttcattctc aaatagggag cccagagatg ttagggtact tattcggggt    3900
cacccagcaa agccttgatt ctgatctggg cagtctagct ccggcattct cgcgcctctc    3960
tcccagccac catgccagcc tcgcgagtat gctgccacaa ccacactggc taagaaacag    4020
aggctggaga catggagtca cttttttaaaa ctggtgccaa gtagcagcac taatgctata    4080
cagtttatgt gtagtatccc aaagtccagg gcactttttt tttttttttt tttttttttt    4140
tttttttttt ttgagacagg atgtctctgt atagccctgg ctgtcctgga actcactttg    4200
tagaccaggc tggcctcgaa ctcagaaatc cgcctgcctc tgcctcccga gtgctgggat    4260
taaaggcgtg tgccaccacg cccggctgtc cagggtactt ttgattggcc tgatggagtt    4320
aatcaccaag acagcagggt agggagacca ctggacctag caattcacac gtatttggga    4380
tgttcacacc catgaagaac acgttagcac attgattttg ctaatagaa ttcctggggt    4440 aaacaggacg gtgactccta cttctgtgga catcacccgt gaccttgggg tgcagggctg    4500
gctgaactca acaccacct tagtctcatg gtgtggtgga aaagcacctg caaggaccag    4560
agggagcctg aagactgtga tggggtagtt tccatagtga cccgggtcct tcttgtgttt    4620
cagccacagg caccatgtcc aatcctggtg atgtccgacc tgttccgcac aggagcaaag    4680
tgtgccgttg tctcttcggt cccgtggaca gtgagcagtt gcgccgtgat tgcgatgcgc    4740
tcatggcggg ctgtctccag gaggcccgag aacggtggaa ctttgacttc gtcacggaga    4800
cgccgctgga gggcaacttc gtctgggagc gcgttcggag cctagggctg cccaaggtct    4860
acctgagccc tgggtcccgc agccgtgacg acctgggagg ggacaagagg cccagtactt    4920
cctctgccct gctgcagggg ccagctccgg aggaccacgt ggccttgtcg ctgtcttgca    4980
ctctggtgtc tgagcggcct gaagattccc cgggtgggcc cggaacatct cagggccgaa    5040 aacgaggca gaccagcctg acaggtaagg acaggagcag agaaggagaa agatcctgca    5100
agaggcctgg agaggagagg ccaccatttg aggatggcct ttacagagaa cattccagcc    5160
cttccccacc accaagccat tccataggcg tgggacctcg tggggctcag aggaacagtt    5220
gatgttcata tgatccaggc attttttctct gcagtgaccg aaatgcccag gatagtgtgg    5280
tgattggcag tagagctcta agaagggagc cgggctgaag agatggctca gcagatgagg    5340
gcacttactc ttgctgaggg cctgattccc agcaccggaa atgacaactt cctataacta    5400
actctgggcg ttgggggatc taccctctct agagccctgt ccctctgacc aggaggtgtt    5460
gtgccctgtg gctgtggctt ttccccacga tgagccacat gtcccttaga ctctggggaa    5520
tgatgtcctt ccccttggca tctggcctga catctgttct ctctccacag atttctatca    5580
ctccaagcgc agattggtct tctgcaagag aaaaccctga agtgcccacg ggagccccgc    5640
cctcttctgc tgtgggtcag gaggcctctt cccatcttc ggccttagcc ctcactctgt    5700
gtgtcttaat tattatttgt gttttaattt aaacgtctcc tgtatatacg ctgcctgccc    5760
tctcccagtc tccaaactta aagttattta aaaaagaac aaaacaaaac aaaaaaaacc    5820
aaaacaaaac aaacctaaat tagtaggacg gtagggccct tagtgtgggg gatttctatt    5880
atgtagatta ttattattta agcccctccc aacccaagct ctgtgttttcc tataccggag    5940 gaacagtcct actgatatca acccatctgc atccgtttca cccaaccccc ctcccccat     6000 tccctgcctg gttccttgcc acttcttacc tgggggtgat cctcagacct gaatagcact    6060
ttggaaaaat gagtaggact ttggggtctc cttgtcacct ctaaggccag ctaggatgac    6120
agtgaagcag tcacagccta gaacagggat ggcagttagg actcaaccgt aatatcccga    6180
ctcttgacat tgctcagacc tgtgaagaca ggaatggtcc ccactctgga tcccctttgc    6240
```

-continued

```
cactcctggg gagcccacct ctcctgtggg tctctgccag ctgcccctct attttggagg    6300
gttaatctgg tgatctgctg ctcttttccc ccacccata cttccccttc tgcaggtcgg     6360
caggaggcat atctaggcac ttgccccaca gctcagtgga ctggaaggga atgtatatgc    6420
agggtacact aagtgggatt ccctggtctt accttaggca gctccagtgg caaccccctg    6480
cattgtgggt ctagggtggg tccttggtgg tgagacaggc ctcccagagc attctatggt    6540
gtgtggtggt gggggtgggc ttatctggga tggggacccc agttgggggtt ctcagtgact   6600 tctcccattt cttagtagca gttgtacaag gagccaggcc aagatggtgt cttgggggct    6660
aagggagctc acaggacact gagcaatggc tgatcctttc tcagtgttga ataccgtggg    6720
tgtcaaagca cttagtgggt ctgactccag ccccaaacat ccctgtttct gtaacatcct    6780
ggtctggact gtctacccct agcccgcacc ccaagaacat gtattgtggc tccctccctg    6840
tctccactca gattgtaagc gtctcacgag aagggacagc accctgcatt gtcccgagtc    6900
ctcacacccg accccaaagc tggtgctcaa taaatacttc tcgatgat               6948
```

<210> SEQ ID NO 53
<211> LENGTH: 12003
<212> TYPE: DNA
<213> ORGANISM: Mus musculus

<400> SEQUENCE: 53

```
gggggccgcg tcttcggggg agccgcctct tcctttagtc gcggtgtcag cgctcgcagg      60
accactcttg gccgctgctc ctgcccggcg ttcctccgct ccgcgcccgc cgccaccgac     120
gacatgctgc gctgcggcct ggcctgcgag cgctgcaggt ggatcctgcc cctgctgctg    180
ctcagcgcca tcgccttcga catcatcgcg ctggccggcc gcggctggct gcagtctagc    240
aaccacatcc agacatcgtc gctttggtgg aggtgtttcg acgagggcgg cggcagcggc    300
tcctacgacg atggctgcca gagcctcatg gagtacggtg agtggccgcc gcctccggga    360
agcccttggg ggcctgagct gtggtagcag ctggagctga tctttaaaag gtcaggggta    420
gtgggtgttt caaagtccgc ttagagttca aacttcagaa gcagcagttt tgggtgaccc    480
gaatcaggct caaccctgaa agactccaac tcatttaaaa gtaaagtttc tcagttacca    540
gtgcaaactg atgccagtca ttgcaaagta cgtataaaaa taataatat gccagggtga     600 attcatttca tttcatctaa cttaaacttt ttttttttaa tcttatgaga agtcctttc     660 aggccaagta ggagcagtta tgatttagat agatatttca gtatcttagc tgtggagctg    720
tttcatgttc attcttgttc tggggagtgg ccttcgttga aaagtgaatg ttaaggaagt    780
ttatctgagt ctgatttaaa atcggagaag taaacacttc actgaagttg agttgccact    840
tttaacacat cgcagggaaa ctctgtacac atcgcagggg aactctgttt gcctctgcca    900
gggaaaggcc ccaagtactt gatttacaag ttagtagtag tctttgaaaa aacaaaacca    960
agaaaagcct tttctccctc aagcaagtgt ccctcctgtt taggatggag acagtagtga   1020
ccagcagtgt gtagggagca gtgtgcaggc tttacgggtc agtttgcccc ctttaaagga    1080
agcaagttac tttttttgtt ttcattcatt ttctagatta accataactt gattcttttc   1140
ctaaagcacc caggacttct gccagacgct gtttggtttg ggtctggcc cttatcagct     1200 ttttctccct ggaagaactt cctcagacag ggaggcaggc aataaaagga gaagactaca    1260
gatattcctg cttgttttaa aaggcctttg ctctacctaa aaacaggcat aaatgcttgg    1320
cttacaggac tttctattgc ttcgaatctt ttagttctta caggcattgt gctgccttgg    1380
```

```
aataacctag ctgtttctta aaatgaattc aaactcaagt ctttcagggg ctataagagg   1440
tatgcttgta ggttttaaa atagactttg gtaattatag ctcactccaa ggctgataca    1500
gccccaaaga atactcagta gcagaagtta gcttgcagag gcaggagcag cattcttgct   1560
gggacatgat ttggcctgta gggccctctt gtgaaacaca cacagtgcca tttccctgtt   1620
tcttgccttg tagggtaagc tcatctttta gggtgtgcct gctctaacct caggcggttc   1680
cattactgtg tgaatggaag ggaaagggca agttttctgt ctaggttgct tctttaacca   1740
tgactcggta gcagcagctt ttccccactg cagtgttaca gttcactata gaaatcagcc   1800
ttgggaaacc tccattttcc aaatgaatct taaaaatatc ttactttcat gatgtggtgc   1860
ctggttctaa actgatccgg gataagtgtg aaagagattt tacacctcag gggagttatt   1920
cccatctcct tcacatcggt aattaagttc ccataatgtg gtagacagct cttgctcaac   1980
tctcagatac aaaacaccaa tggaacactg accttagtgt cagactgtgg aaggaaacga   2040
gagccgtggc gccatctgcg atgtccccat ctcctcacca ttatagacag ggatgagtta   2100
aaatacttgt cattctgcct actctgtgtt gagtgatcat tagtgtacta cacaactgca   2160
aacaaatggg gtgttctaca ctttaggggtg atagtctccc gaaagctgta ataggacctt   2220
gctgaaaaac agtgtgcttg catgagctca caccatatgg aatgcatacg ctcccacaat   2280
gcaggaccac tgtcttgtac ggcaggggag ggtaggtagg tctgtttaaa ccatgccaat   2340
atttagcatc tgtgcctctc cctctagacc gcttcttcat gatccttgaa aataatattt   2400
acttaaagct attaacaaag caaaacgttc acaacaaagt gttagaagat tgtgttttgc   2460
tgagtgatat tcataacagt aaatacattt attttggtct aagtacattc ttggcaatgg   2520
tgaccataat actaaataat atgcatagtt tataaaggtc agtaatttct taggaataaa   2580
taaatatatt ctttactatt attgttaaaa tgttaagaat tctggattac acagtcacct   2640 catttattt cctacataaa taaataaata aataataag ccaagttaga ccctgagtgt    2700
tttgtcacgg tggcagctta attaacattt atcctagcaa atacttgctt gaatgtttgg   2760
cttatatttg tggagaagaa agtaagaacc tagatttgca attgaagaga tcattcaagt   2820
ttctcctata agccaaactc agcattaaac ttcagtgagt gtgcaatgct gggaccttct   2880
tctccagttt agagaatact gtgacaggga gttattttaa atttccactg cacagacttc   2940
agatcctggg caagctctgg catgtcaggg tggagggtat agggatgagg tatgcactga   3000
aagaaggagg gggaggggaa ggggaggaag gggaggagga ggaggggaag ggggaggagg   3060
acggggaggg ggaggggggag gaggaagagg aggaggagga ggggaagggg gaggaggacg   3120
gggaggaggg aggaggaggg ccttggaaag tcagtggctg gaattcatct ctgaagcaca   3180
gaacctcagt tttaccagag acatctctta aatcccttag gatgcacaca gtattttcc    3240 taagcactac tttcctacaa gtcacaggat cagagtagtc tatgaaatta attgccctgg   3300
ttcctgtaag tgcagggcat gaagaaaaaa agtacagtc aatcagaatt taccttaggc    3360
taaactcacc agaaaagcct tctctctggg atgatacctt gcagctttg tggggaattg    3420 gggggagttt gctggtggga ggggatggga ggttatttta tggagttaga ttagtagata   3480
gatttcgtat gtctgcatgt acgtatgttc acattcttaa cagcaaattt agaggtcatc   3540
cactcctttg atggaataac tttgaaatat acaatgatat gtaaactcta ggtattgagc   3600
ccacggtgca ggctggcctg acgtctctgt gcctgcagca cccagagagc tcagtgtct    3660 tgggaaggac ttcacttggc tctgcccta taacacagac ctctgggcct gcattcttcc   3720
atctgataga tctgaaatat ctgagggtct gttggctgca ataaggtgta gtttcccatt   3780
```

```
ccttacagga gtcttgtata agtacagtgg taccaagcca ccacctgctg agcttcagga    3840
gagagcgttg agtgtgtctg aatgctccag cagctggcat gccttgcctg tggctctccc    3900
gccatttctc tcttaggcca gccattcctt attgccaccc agaacttctg caggatgatg    3960
gcgtggccct gtatacaatg cattttgtag gtctgctctt aatcttcctc tggacttttg    4020
ctcctccaga gttacaaatc aacatcatgg gaaagtcact gggtaccagg ttctcaaccc    4080
aaccatgctt agaatcttca gtgtaacaag tttcccagga acggcaagca gggcaagttt    4140
ggggtgttgt tgcaaaagct tccaaatgaa tgtcatactc taaataccac aattgccttt    4200
atcttcctat tcaatatgca aagcagtatt tttatatgtc acattcaccc atgtttacct    4260
acttatgtgt aaggtctttt agtttttaaa aatattcaga ttttacttct gcctatgagt    4320
ggcacaaaga acctcagagt atagtacagt aaacatctga tcggaactct gctcctctag    4380
gtggggcctt tgatagtgtt cattgaagaa tggatggtct aggaagggac cccacctcag    4440
tttgatggca cattggtacc cacagagtct tgagcaattg agtggaccac acaactattt    4500
gtggggaagg gaaattagtg agtttccaaa acacttacag atagggactg actgttagca    4560
gcaacatttc cccttttcct tgctttcttc catagcgtaa gctttacaaa gtagtaccta    4620
gaaaacaaac ttaggccatt cccagaatgc gtacagggaa cagtagcttg ctctttctat    4680
gaggaaagga aagcaaacac acaatttcta ccctgaaaca cttgtctgtc tccttggagt    4740
cctgcttgct tttgttgtct cagcctagtg catcccctcc acacagctag gaatggtggt    4800
aaagtctgga tagtaagaaa ggtcacactt gtgttctgaa ctgataaaga tgagctctac    4860
ctgcaaactg ctgtgagcca gaaaatcatg gaatagtagc tttaggacat gtttggaaaa    4920
tggatgtttt tccttggtgt tggtaatttg aatcataata taatgtaaga tagaaatagt    4980
taccagagct tgtgtatact tatagatatt aagctctcgg gcagctgagt gagaacaaaa    5040
gtacctgaaa tacaagtatt ttagcttaca aaaatgtata tagtgagaaa gtgatgctaa    5100
gtcctgcttc tcagactggg cgaggccctg ttgagacctg gtaaggccag tctctttatc    5160
ctaaaataaa attgctgttg acttgagaag acatgttgtc ttgcttggag aggtcctgcc    5220
atgtatcagc tccgatcttt aaaaccatgc caagatttct gtctaaatgg tagctggatg    5280
attcagtgtg ggtgttgccc tgttgcaagg agcaggtctt acatgttcta caactggagt    5340
tgcttttctc aagcgataat gttgcttcat ttccattctg atttttcttta tactcagcat    5400 tttaagtaaa caagacatta gctaattgat ttaatagga aagtgcccca gatgggtcac    5460
tgcaagtata gcttcagcgg ttggtaggag aaatgtacat taggttgcta tttcttttat    5520
gaaattcttt gcacattcct gaaattaaga gtgggttata cttcagccaa atgtcagaga    5580 cagagtcac atcagtaacc tgtctgtttt aatctaattt cccccacacg aacaggtaaa    5640
atgaataggg caatattaca cagaacttat ttagttagac tttcaagacc gtctgtgatt    5700
gtagaagttc agttattaaa atatgttcct tggtaggaaa tatttctgtt tttcctaaaa    5760
attgtgtttg agttcactgt gtgcttattt agaactgttg ctgtttggct tcatagaggg    5820
aaatgcattt tgcctttctg aatgtaatga ttgattttta ttaaacgtaa tggttggctg    5880
tagctatata gacagacaaa caaacagact ccgtgatttc aggtcaaata ctgaagccca    5940
taagcttttg cttccatttt ataggtctta gtcatctaca ctcctattct cagccttcag    6000
tatgcttata gaagggacac aagggaagag cagacagaga ttgacggcgg gggcgggggg    6060
agtaaaacag aatatagcat ttgtgttata tacagagtct agatttaatc ccctgcctc    6120
```

```
cacacacatt aacacacatc acatgaaaac aagagagact agaaggggaa gacagaatca   6180
tgagggtgaa tacgaggatc atgtacattg tatgtgtacg tgtgtatgaa aatgtcacaa   6240
cgaaggcagt tatttctgca ggaactaaaa caagtctttg atatgccctg aaggaccaca   6300
aggctattga cgattgagct tcctggatcc agccttttaa gccctgaccc aggagatcta   6360
gaagaaggca taagaatctg tattttaaga agtaccatta cttaatatga cactgtgagc   6420
tgtgggctat aaatgcttaa gaagagctga tcaattaact gtttaccaaa gcaaagtcct   6480
ttcttgttta aaaattccct tacacaaagg acaaggcaaa agggggaaa gagacattaa    6540 ttgtatattc tggctttagc actagtcatg tgcttttaaa ccaaactcac cctacaatct   6600
cttgtggatc tgacaggatg aataatactt gctgggggag ctagaagaac ttctcagatt   6660
gagtgcaatc atgggcatc tcaccccaca cctctgcccc tgctactgag ggggcatttt   6720
gtaggaaaac atggtatttg aagacatata aagatgtgtg ttctccttac tcatttgtta   6780 tgccctgcc agtcatacac cccgcagggc tccctgcagg gcattaggca catggagaag   6840
gggatgaatg ggaggttgct tagtccacat ttgggaaact ggggtatgga agtcttcagg   6900
gatgacacag agccgtgcca gtgtgggatg ggttgaaaat ctgagattat ggacagaagt   6960
tatgggaaca gaagaggaac tttttgaaca ggaagggcta aggagttaac aaaggatgat   7020
tttcacatgg gggtgcttat cctgacagct cacagccagg ctgagttcac agatgaggag   7080
actggtgtga ggttagcaag ggccagaggc agagccttgt tgagctttgg ctgcctctaa   7140 acccccttgtt tgactctgag cactgaaatg accaggcata atgtgagtgt attgttagct   7200
gtgctctagt ttcgtaagaa gcagggccga gggaaggggc ataactcc cctttaaaat    7260 tcaatgaagg gtgaagtaag agtatgtgca gatgattcgg caaacaaagc gtgggaataa   7320
gtgcaataaa attgccaggc agaaaaagaa tgaggtgcta atttatgtta tagaatggtt   7380
catctttaaa aaatacttcc tttgatgaaa gaagccagtc acaccaagtg tggaatatct   7440
agaatacaca atttaggaag aagattagtg gttgctagaa cctgggatgg gggtgatggg   7500
gggcagaatg actacagatg gaatggaatt ccttgggga ggatgaaaat attctggaat    7560
tgttaatggt gatggtcaca tagctctctg aatatagcac acttaacaca aaccaacac    7620 ccaactgtga gatcatggac ttgtagtaga tgtacttcat gacttctaag ttatatcttt   7680
ttaaacttat gtgttggatt caaacaggct agaaagcaaa ctaagtattt accatctatg   7740
tgtaccctca cttctgaact agaaacgagg atggcgtgag cgcccccaga ctggttctga   7800
tgagttggtg cacatcctga tgttagctgc tgctctgaag gctggttgg atgggaagag    7860 atgaggagtg tgtacaggtt gaaggacagg gattattgaa tggtttgtgc acatctggag   7920
ggtcccctca tctcctccct tgcagaacag aagcacacaa gtctagcaca gcctgtgtag   7980
ggcttcaaac ctagaattca gtctgtctca tcctggttgt ttttacggtc aataatgaac   8040
tcctgggaaa taaattttga atgaaactag acattaatat aaaccaaata accaccttt    8100 aaagaggagg catttctgga agagtgtgtg tagcttgaat ggttcagtat gaagaatgtt   8160
tatcatggtc atgtaaattc aaatctgagt tttaaaaatg gatctattta tgtgaacaca   8220
gagccaagga gacgaactta cattttagtg atgcaaacat ttgccatcaa atatagggg    8280 aacaaaacac gataataata ttctctacat gaatcaccaa gttttccctt gaaatgtaga   8340
gttacttaaa tattcctaac ccttcacaaa gtaaaaccaa atccctcctt tctcccaaaa   8400 ctcttttcctg gtacggagaa ggccactatg atttatctt acaagtgtcc ttgtctctgt    8460
catgcagcat ggggacgagc agctgcagcc acgcttttct gtggctttat catcctgtgc   8520
```

```
atctgcttca ttctctcgtt cttcgccctg tgtggacccc agatgcttgt tttcctgaga   8580
gtcattggag gcctcctcgc actggctggt aagaccgagt ggcatcagct ttgcatctgt   8640
gctttcagtg ggcatgggta gagtgttcta ttccatctct atggaagacc tgatttgtcc   8700
ttggaagtgg gtcaccaagt gcaaaagtat tagaggagat atgtgtttta ggaatctggt   8760
ccctttgcct ccatgcctta gatggtcttc tgttctctca attcaagcga caagagttgt   8820
cttatgtgtt tctctctaag tatctccatc cattcaaacc gactccacag actagtgatg   8880
tacctgccct ggaagtacag taacgttcct gacctcctat cagctccatg ctggctgaag   8940
ggacctgaat atccccaaat gattttactt gttgaaggag ttttgtgatc tggtgataag   9000
gtagggtagg gaggagctag acttagaatc tgcagcatag atcctattcc gggtaggtga   9060
aatctgtagc atagagcctg ggccagggag gtggctcagt cataggtgat gtgaagacag   9120
atgcaggtag gtagacaaag ctcagagtac acttttatta atagaatgca agattctggg   9180
atttaggagt caggactatt tgaagtttct ggcaaatacc tgtcaaagtg acatggtctc   9240
agttatcagt tagattttga aatgaaacgg agtcattaga gagatctctc aaacggtcct   9300
cttccagagg acccaggttc aattcctagc acccacatgt tggatcacaa ctttttgtta   9360
ccctacttcc agaggatcca agtgttatgg tttctacaaa gctacaagca tgtggtacac   9420
aggtagttgt gcaggcaaaa acacctataa aagtaaaatg cataaaatta ctaaagaaaa   9480
agtagcaaaa cttggttttc tgaggccaga gatggtgttg atagaataaa atcaggcctc   9540
atcttagttt tcaacatacc aaccaaggac cacaggggaa acagggcaga actccagcca   9600
tgaactcgga gagacaatct gtatagccag tgttggtact aggccagatg ccctgtgact   9660
atgtgggtcc catagaaatc aagcttaagc caggagactg atggcaggtc catgttagga   9720
gaggaaggaa tggaggtaga aaaggagcag gagggaagaa aggaagagag agagagagag   9780
agagagagag agagagagag agagagagag agagagagaa gaggaggaaa aggacaggaa   9840
ggagaggagg gagaaaagga ggaagggac  taggaaaaca ctttagtgtt tatctgtaga   9900
actctagaaa taagttaaga tggtgaaaca atagtgaggg caagcaatga tttagccaag   9960
ctagatactc gtgtcacaga gaataatttt ccatgagttt cctgcgagga tccagccatc  10020
tgtttcatgc agcagacagt catttagttt ggctcatggt aggcaagatt cctctagccc  10080
cttgttagag gaattatcat taaagggaga aactgtgact ggcgagattg ttctgtatgc  10140
cgtgggtgac ggtgacgaac accatgacca agtgcagctt gaggaggaaa gggtgcaagt  10200
ccaagtccat cagaaagcga aggcacagca gcagttcaga ggaaccagag gcaggaaatt  10260
aagcagaagt ggaggagcac tgcctactgg tttgctcagc gctcagcttg gtttcttatg  10320
aaacccaaga cctcatgccc ttgggtggca ttgttcacag tgggctgggc ctttctactc  10380
caatcattaa tatagaaaat gccccacaac atgctcatgg gccagtctga tgagggtgtg  10440
tctttagtca agaccccct gctcctagaa gactgtagct tgtgtcaagg tgccaaacac  10500
taatcagcac accctgcatt ccctcacgca tttgttcatt tgagcggcat actgtgaact  10560 tcttttctc ttctctttag ccatattcca gatcatctcc ctggtaatct accccgtgaa  10620
gtacacacag accttcaggc ttcacgataa ccctgctgtt aattacatct ataactgggc  10680
ctatggcttc ggatgggcgg ccaccatcat cttgattggt tgttccttct tcttctgctg  10740
cctccccaac tacgaggatg accttttggg ggccgccaag cccaggtact tctatccccc  10800
agcctaatgt gggaggaaga gcctgagaaa agcctgctgc aagatggatc tgaggaggaa  10860
```

```
actgttctcc aaggcacaag gaacctacgt ttgggcaatg ttcatatgat cagaaatgtt    10920
agaataaatg ctaaagaaaa ttcttcataa ttagtgttaa gtttcatgta tgtcgtgtgg    10980
agttaaaaag acttgaattc tgtttgctaa gtatatgcta attttttcctt atgtcaattc   11040
tataccattt aagcttcatt tgttaaagaa tatgcctgtg aaacttgata aggtagaaat    11100
gcagcagcct ctcatttaat aatctgatgg ggcttctgtt tttccacata gaatgggttg    11160
tttctgctaa gggctacaga ggaggaaagt cactggcaaa acttccatga ccaaatatcc    11220
tgaaattagt ttgttttttt ttaaaagacc ttattttgag ttttcagtta cataaagaag    11280
cagaagcaga ttggttttcct aagtgagcat cattgtgag aatttttagt cagtgttttg    11340
aacaattatt gttttctaa gcttcatgtt gactttctct gatgcgtaga aaagtgttct    11400
aacgtggctg aggttaagcc gctgtcatta ctgaaatgct aagaattttc ctctttttccc   11460
gtagtgtaga ggggtagggt gtgggcagaa gccgtgttag cacatctgta gtattgtgtg    11520
tgtatgctta gaaccagcgt agaccggatg ggaggatgga ctaggcctaa tccctcccaa    11580
ctggtggatg tgaagaggtc aggtaggaag gcacaggagg gtcaccactg tcacagcagt    11640
gccatgcaga catcctagga gaagacatgg cagtgtttct tctcagtgct tcttcccta    11700
actgagctct gctcacagac agctagaata gattttaact gaaacagaaa cctaaatgta    11760
attaaaaacc tggtcttcct tggtaagcag acttaaaata tctgtatagt acatgcaagt   11820
ggaaatttg gaatgcgtg tctctgaata cataccggaa gggctactat tacctttttc     11880
ttaccattta tacttaccta atggaaacga gcttgtttta actatcagaa cactattttg    11940
taaggtgctg caaagacagt tgaagttttc attaccaatt tccccaataa accaggtgtt    12000
caa                                                                 12003

<210> SEQ ID NO 54
<211> LENGTH: 18191
<212> TYPE: DNA
<213> ORGANISM: Mus musculus

<400> SEQUENCE: 54
aaccgcggcg aggaggggggg tcggaggccc agacttataa aggctgctgg acccgcgcta      60
cccgccagac cccgccgccc ggatccccg cgctgcctgt cgccccacgt gaccacacta     120
ctaagtgagt tggggcgcgt ccccatcgca tccccagacc ctcgtgagtt gtgtggctca    180
ctaaatccag gtggggagga gagcggatga aggagggctc cgggatgggg caccagacag    240
aatgcgttat agcggagtct taggagctag gggagcggag ggactcaggg gatagcgctc    300
agtcgggcca tccccgcgcg cggcctggga gacctcaagc tactcagcag gaatgcgctt    360
gtggtcgtcg ccataccaac gcacaagtca gcacacgccc tcctctgaag gaaaagagaa    420
agtgttggtg ggggatgggg ggctgttcat cctcctgaga tccaaacttg tcacgaggca    480
gttgcacggg ggaaccgagc cccaaatcct ttggaagcag ggcgcaagtc ttatcgtgct    540
tcggaacctc ggttttgcat caggcaaaga caagatgatt ggttccgagt gccccaaaca    600
ctttacgggc agtaacggtc cgggccagca ctccgttcta gttgcatgac caaagagtgg    660
ttttgagcct ctcagatgac acctgcgact cgaccccacc ctgccccag gcttggtcgc     720
catggtcctg ctctgggccc tcttcctagc gctcctggca ggtgcccacg ccgagctccc    780
gggctgcaag atccgcgtca cctccgcggc tctggatctg ggtaaggcgc gcggcgggag    840
ccgtggaccg ggtggggtgc tctggccccg ggcgcgggac ctgagtgtct ccatgctatc    900
tcagtgaagc aggaaggcct gcgctttctg gaacaagagc tggagaccat caccatccca    960
```

```
gacgtgtacg gcgcaaaggg ccacttttac tacaatatct cggagtaagt aaggctcggg    1020
gggccggggt ctcaaaggtg gtgggatgac ctgggacacc gccccagact gggcgggtct    1080
gggcgtggcc aattaaatga ggtgggatcc ataataacga gtaaggctac taggtaaaaa    1140
gactggaggt aggcgggtcc aagaaagggg aatacgaacc agcagaattg tagcttggac    1200
caaagaacac cgcgatgata cactggaaga atttacctgt gggtgagagt ggagtctatc    1260
cagagggtgg cgccaaaaag agggaagccc aggataggag agatagaggt gaggcgatgt    1320
ggggtgagtt aaagtgatgg aggcaaagtc aaaggaccag gtggaaagct cagtctggcg    1380
cacgcctgcc aaaacaaaa caacaacaaa acagaaacca aaaagacgaa aacagatcta    1440
gcaatcacaa tgtggacaga acacggaggt gtaagcaaga ccatagtttt tacttattta    1500
tttttaagat tttatttaat tttaatgtat gtgcattggt gttttgtctg catgtacgtc    1560
tttgtgagag tgtcgggtcc ccttggaact atagttacag acagttgtga gatactttgt    1620
gggtgctggg aattaaagag gagtcttttt gaagaggagc cagtgctctg aaccgctgag    1680
ctgtctctcc agcccctatt tatttattct taaagattta tttgttttta tttatatgag    1740
tacactgtag ctgtcttcag acacacacca aaagggggaca ttggatctta ttacagaagg    1800
ttgtgagcca ccatgtggtt gctgggaatt gaactcagga gctttggaag agcagtcagt    1860
gctcttaacc actgagctat ctctccagcc ctatttattt atgcttgagg catgatctta    1920
ttacgtagcc ctggctggcc agaattcatt ttgtaaccag gctggccttt aacccagaga    1980
ctgatcggct tttgcctcct gagtgctagg attaaagttg tgtgtgtgtg tgtgtgtgtg    2040
tgtgtgtgtg tgtgtgtgtg tatgtatatc tatatatgtg tgtgtatgcg tgcgcgtatg    2100
tgtatgtata tgtatgaaac catcccagc ttttaaattt tttaaaacaa attttgtgtg    2160
tgtgtaaaat ataatataaa tatatatgta attcctgcaa aaggatcact tgggctcaca    2220
aattcaaggt tagtctgaat gacactgaat gacaaaagga cactctcagt cttttatctt    2280
gttttgtttt gaggcggttt cctctgagta gcgctggctg tcttagaact cacacagaaa    2340
tcaggaggct acctctgccc cctgagtgct gggattaaag gtgtgtgtgg gccaccatgc    2400
ccagtaattc cctatctttt aaatattaaa tgcgttaaaa aataaatgag gaaggcagta    2460
ttcaactcct gggttcagag aacaaatctc ttgagttacc caatacatgt cgggctcttg    2520
aggggcaagg gaaaattcca gaccaccac ctagattgcc cagcttgcag ttagaggagg    2580
gatgggtccc tgcggctggg tgagttggtc ccctttggcc cccacgctga ccctgacccc    2640
tgctctctgc agcgtgaggg tcacacagct gcacctgata tcctcggaac tccacttcca    2700
gccagaccaa gatctgctgc tgaacatctc caacgcatcc ttggggctgc acttccggag    2760
gcagctactc tactggttct tgtgaggacg ctgagctctc aggggtgggg ctggtggctg    2820
ggctggagaa gtcctttaac ctcccaggct tcaatttctc cattcaagag gagggtttgg    2880
aaggttgtgt gacaaagatc aagaagagat ttcaagaggg cttatgagtc tccacccta    2940 gctgaggtct aggcagtgaa tgtctgtgag ggagggtgag tcatttttct aaagtggtgt    3000
agacactggt actttgccca ttctccactt cataacttcg aacccatgct tatacaaatg    3060
aactccttgg atcattcaaa acaaaaaaca aaactaaaag tcaaggtgcg gcatattggg    3120
aagaaaggtt caggcacaga agagaatgag aacaacggga gtatatatga tcacaaacat    3180
tttgtacaca cttgaaaaaa taaggtatca tgttgtatgg ggtaaagaga ggggtagaaa    3240
cgtcagttat ctcccactgg ggtgaccatg agcctgcctt tcacagatat gatgggggct    3300
```

```
acatcaatgc ctcggcggag ggtgtgtcca tccgaacagg tctacagctc tcccaggatt    3360
ccagtggtcg gattaaagtg tccaatgtct cctgcgaggc ctctgtgtct aaaatgaata    3420
tggccttcgg gggaaccttc aggtgagtgt cagccccagg acacacgtcc tgagccccac    3480
agttcaattt tctggggcag aaaaggaaag tgctaaggtt gggagtccca ctgaatccaa    3540
ccaaatccta cttcctccac atctggactc tgtgaacctg ggcaagtcac tgacgctcag    3600
agaatgaaat ctattttagc agatacttgt gagcactgtg ttgttagata tagaatattt    3660
agacagtccc tggcatatga taaatatcta agtgttagga ttagtatgtc tgcagctgaa    3720
gctggctcag tggtagagag cctgtctagt atgcatgagg tcctgggttc gttcctcagt    3780
acctgagttt agaaaataaa atggggctgg agagatggct cagcagttaa aagcactgac    3840
ttctcttctg aaggtcctga tttcaaatcc cagcaaccac atggtggctc acaaccatcc    3900
gtaatgagat ctgatgccct cttctgtgtc tgaagacagc tgcagtgtac atacatatag    3960
taaataaatc agaaagaaaa agaaagaaa aggaaaggaa agaaaagaaa aaagtgctgg    4020
gcgtggtagc acacaccttt aatcccagca ctcgggaggc agaggcaggc tgagtttgag    4080
gccagcctgg tctacagaat gagttccagg acagccagag ctttacagag aaaccctgtc    4140
tcgaaaaaca aaaacaaaaa caaaacagaa aagaaaagaa aagaaaagaa aagaaaagaa    4200
aagaaaagaa aagaaaagaa aaggaaagaa aaaaaacttg tagcaggttt ggagggccac    4260
acgtttaaaa ccccagcact caggaggcag acaggtgggt ctctgagtca gaggccagcc    4320
tggactaggt cataaattct aggtcagcca gggctataga gtgagaaact gtcaaaccaa    4380
acccaacaca tcctgagact cacaggctca gtgtgcactg ttgggtctgc attgcattct    4440
caattataat aacacaaaac cccatggtgg ctcctggatc cctggctctg ttgtttgag    4500 gtaaaaacct ggtagacttg tcatccagtg tttacacatt gtcagatttt gtttgtttcc    4560
caagtgtagc atgttccagg ccctgaggat ttagaaagta ttcagagctc agctagaagg    4620
attcaaacag ttgtcgtgag gaactagaag tgggaccaag gtagctttca gggtggtaag    4680
atttagatgg agggtgatct gagaagcctg cctggaaggg gaggcatctg agcccagtca    4740
ggaggccaca gagggcagga acactgggga gggcatcacg agtatataga atatggggg    4800 cgggatctct gggaggcttg agaatgtgag gcgggtgaca ggagagggtc aggggtctgt    4860
gaggcttgag ggtcaggggc tggggctcgg ctcctggaga gttctattga ggagctacct    4920
ggaaccaagg agaccctgtt gcacctgttt cttttgggca ctgtcatttc tcctgggcct    4980
ggctcatggg cagggcaggg ttaacccagg ctctcctctc tttgcaggag gatgtataac    5040 ttttctcca cgttcatcac ttctgggatg cggttcctcc tcaaccagca ggtgtgggcg    5100
gtggcaggcc tggggagcag aggaggggtg gcctggttct gagactccct gactctggcc    5160
tggtcctcca gatctgccct gtgctctacc atgctgggac ggtgttgctc aactccctcc    5220
tggacacagt gcccggtgag tcagggtggg gactggagct ggggccgggg atagaaggaa    5280
gctgtgtgct gctatcatac agcgtctcag agagtcccct tcccggtcca gccatggaac    5340
tgtcctgggt tcagaggtgt cattgacttg ctgtgtagcc ttaggtaagt aaagtcttct    5400
cttggggttc tggtgtcctc cttggactgg tgacccctcc cccaggagtt gtcgaggtgt    5460
taaatacatg cttgctgacc acagggcctt gtttgtcttc atcagcttgc atttcatgca    5520
tttcaattaa catgaatccc tttctatgcc accatgtgtg tctactgttg gtcagtgatc    5580
ttgacctatc gggcccgttg ggtaaagggg gttaaaaagg aaggcagggg aaatgactcc    5640
ttagtcatct taaacacgta aaacgcgttt taactgtgtg tgcatgcatg cacgtgcgtg    5700
```

```
tgtgcgtatc tgcatcctgg tgtatgtgtg gaggtcagag gacaacactg tggagtcgat    5760
tgtctccttc ctatgagttc tggggattga acttgggcag cacagttttg gaggcaagct    5820
cctttacctg acgaagccat ttcgccagcc cctccttttc agtcttgctt agtgatttga    5880
tgaaaacctt acagtagtct tagtagtaga tggagctaac catggcctcc tgattgagcc    5940
cctacagcac accaggctct agctgcttcc catggaaagc caatttgatc ttcgtaagac    6000
ctctgtgagg ggcgtgtcac tacttatgaa tgaaaggcac agagaggtta agcactgggc    6060
ccaatgccac ccagcttgga ctgacccgag ccccttcccg cagtgcgcag ttctgtggat    6120
gatctcgtgg gcatcgatta ctcccttctg aaggatcctg tggtctccaa cggcaacctg    6180
gatatggaat tccgggtgag ctgcctgtgt tagtgcctgt gacctctgac tgctgatggg    6240
tttccctcgt ctttggggct gagcacggcc ctgaaaggtc actctgacct gcggtgactc    6300
ctgcgtccac tgcagggtta ggttcagcct cctagatcgg aggtagagtc ctacctttct    6360 atttcttta agatttttt tcaagattaa ttaatttatt ttgtgtatgt gagtgcactg    6420
tagctgtctt cagatgcacc agaagagggc actggacccc attacagatg gttgtgagtc    6480
accatgtagg tgctgggaat tgaactcagg acctctgaaa gagcagccag tgctcttaac    6540
ctctgagcca cttctctagc cccagctcta ctttcctaac tgcattctgc atctctgtag    6600
ctccccagaa gtccttacgc cagggacttg cttacgcctt gcctgtctcc tgcctgcccc    6660
agcccctgcc cctgcccctg tgagtcagct gctaatagtc ttctttcggt ttctgagggg    6720
gatggaatcc aagccctcct tggtcaccac aatctcagga tgttcaagtt cattattgaa    6780
aatggtgtcc catgtgtggg acatataatc ttcaaacatc cattgggaga tgtgtgtgtg    6840
tgtgtgtgtg tgtgtgtgtg tgtagtacac atgtggaggt tagaggacag cttgcaagag    6900
ttgattctcc cctcccatct aggatcctgg ggatcaaact aggatcctca ggattggccg    6960
caagctccct tacctgctga gccatcttgt aggcctgaca atgctgattg tttgtttgag    7020
gcaaggtttc tttatgtagc cctggctgtt ctggaactaa ctctgtagac taggctgact    7080
ttaaagtcac agaagtcctc ttgcctctgc cccaaaatgg tggaattgaa ggcacaaatg    7140 cttcttttc tcttttctt ttttctttt tttaatttat tttggttttt gagacagggt    7200
ttctctgtgt agccctggct gtcctggaac tcactctgta gaccaggccg gcctcaaact    7260
cagaaatctg cctgccttta cctcccaagt gctgggatta aaggcgtgtg ccaccaccgc    7320
ccggctctct ttttctttta aaggtttatt ttcttttctg tgtgtgggtg gctttgcgtg    7380
catgtattga atgtgtgagg agagtgtcag atacccgca cttggagaat agacagctgt    7440
gagctgtcat atggttgctg ggaactgaac ccacatcctc tggaggaacc gctagtgctc    7500
ttaaccactg agccatctct tcagcccgta actgctattt ttaattatgg ttgaatttgt    7560
gggtatgtta atttcaattt ttttaatttt tttttttcat tttgagttca gaaataagta    7620
ttttagctgg gctgggtggt agtggtgagc gcctttattc ccagcactca ctgagtgagg    7680
ccagcctgct gtacacacca gaagaatcaa ggctactcag agaaatcctg tctcaaaaaa    7740 gtatttatt ttagggaatt taagagaaag agtaaggcat tcccggctaa taggatggga    7800
ccctggaagt acagtactgt ctagctgcta gtctgaggcc ttttacagg actggtggcc    7860 gagaccaggg tgaggagaga ggaaggagct ggtcggtcag ggtggctcac ccatgaggtg    7920
tccaggagcc attttgtttt cagtctcctc aagtatagct tcaaggcagg agtgacagat    7980
aaccaggaag caggaatcga gcagctcctg gtgttcctgc ccccagctag gacttactca    8040
```

```
ctgctggggc agtgtgtgtg tgtgtgtgtg tgtgtgtgtg tgtatgtgtg tgtgtgtgtg      8100
tgtgtgtttc tgttccacct ggcctgtttc taccttctca tcccttccta ccccaagggg      8160
taagtgcctt tagggaagga atttgggagc catcagtctg gctccttgga actgagtaag      8220
ttgtcaggtg tggcagttgg agtacccctc cagtgggccc catttagatg ggacctggag      8280
agtgatcagt agctctgttt gtttagcatc ggggtgtagt gagggtcctt gactgatggt      8340
tggttagtga tgtgatagggg aagggaagac gagaaaggga ccaggaccc ttgagtggag       8400
gaaacaattc cctcccagtg ggaacaagca gcgtttatag aacttagcag tccaagccct      8460
aggcagagaa ccagaataag gctgaaagta gggcacgttc atcaagatgg tcagtggtgg      8520
cacacgcctt ttatcccagc atttgagagg cagaggctgg tggatctctg tgagttcgag      8580
gccagcctgg tttacatagt acgtttcaga acagccaggg ctgcacagag agaccctgct      8640
tcaagagaca aaacaaaac aaaacaaaaa accaacaagc tgggcatggt ggcgcacgcc        8700
tttaatccca gcacttggga ggcagaggca ggcagatttc tgagttcaag gccagcctgg      8760
tctacaaagt gagttccagg acagccagga ctacacagag aaaccctgtc tcaaaaaaac      8820
aaacaaacaa acaaacaaac aacaaacccc aaaaaaatct gaatcaaagc ccattagcat      8880
ccttaacagg ctcagacaag catctatcca caattagctt agtggacgtt ctcttctctg      8940
gccttcgagt gatgaaccca ctctgccttc cagcgttttt gacatctggg acatcaggtg      9000
aggtcgctcc cagctggatt actcccccttt cagtccctgg ccaggaaatc aggaattact     9060
ggggtgtctt tgaattggat tgaggccttt tcttttgctc aacatgtgct tagaagtagg      9120
gggggccatc ctgagcccat aattttcagg gcttgttttt tttttttttt ttagacgtag     9180
tctcactctg tagtgctaga tggctggagc tcctatgtag accaggctgg cctcaaattc      9240
atagagattt atgtgcaaaa agcacaccca ccaggcctgg cagcttcagg ttcttatttc      9300
acaaatttga agaatgaaat gttggaccac agcgggggact tttattagta ttttattata    9360
gggagatgaa tagaaggcag ggtgcctact gagtaggagt gggtcccagg aaatagggca      9420
cctgctgtcc ctgctgtatt cattttaagg atgtgaagac ttgcacaagg tcagcagttg      9480
ctatgtgacc acctctgctg tggtcggcag cagaatgttc taaagagtct gcagctcaaa      9540
tatcctaact tctaatcctg atcccacccc tggcaggctg catgtcctta ggcaaagggt      9600
ttctccctgc ccccaccccc accccacaca cacctgggct ccttacctga tatgtaggta     9660
caaaggacag cttgagagaa catgccttcc agggctgtgg tgtggacaca ctttctgtta      9720
gaaacactcc tggtggtaca tgctggtatg ttccaacaca caaagactg aggcaggagg        9780
attgccctga agttgaggcc agccagggct acatctcaaa atcatacaaa tagagatggg      9840
cagtgagtac ctggaactgg gtagccatga tggatatgta agtgctgctg tgattcaaac      9900
ccctcattta cccggttaca cactttacct tcttctttct tcttcttct cttcttcttc      9960
ttcttcttct tcttcttctt cttcttcttc ttcttcttcc tcctcctcct cctcctcctc     10020
ctcttcctcc tcctcctctt cttcttcttc ctcttcctct tcctcctcct cttcttcttc    10080
ttcctcttcc tcctcctcct cctcctcctc ctcctcctcc tcttcttctt cttcttcttc     10140
ttcttcttct tcttcttctt cttcttcttc ttcttcttct tctagattta tctatttatt     10200
atatgtaagt acactgtagc tgtcttcaga cacgttttct tctccactcc cactctctcg     10260
ctgtcttcag acaccccaga agagggcatc agatctcatt accaatggct gtgagccatc     10320
atgtggtttc tgggatttga gctcaggacc ttcagaagag cagtcagtgc tcttaacttc     10380
agtcctcttt gtttctttct ggacttaatc atgtttatca atgtgttgcc cactggatgt     10440
```

```
aggtgtacca atgggtatgc agtgccaggg aggacagaag gtggagtcat atcccctgga   10500
acgggcagac tgttgagcca ctcgctatgt gggtactggg aattgtgccc agtactctgg   10560
gagagcagca catctggagc ttaacatctg gaccaggtct ccagctccat gccttgcttc   10620
tcgtgctccc tgccctgctc ctctgccctc caagcctctt tgcaatgctt tttgagagat   10680
gggtttgtga gcccctccag agcagccata gagtccattt ccggtggctc ctggctgtgc   10740
ctggcgcgga tccaatctgc cttgaccctg atcttgcgtt cccaatccca gggagcattc   10800
ttccctctga aggaggacaa ctggagcctc cccaacaggg cggtggagcc tcagctggag   10860
gacgacgaga ggatggtgta cgtggccttt tccgagttct tctttgactc tgccatggag   10920
agctacttcc aggctggagc gctgcagctg acacttgttg gggacaaggt atagcagggc   10980
ctgtctgagg gtgggttaag aacggcccac gatagagtcc aatttccctg tctcatttct   11040
acttccccgt tcaggtgccg agtgacctgg acatgcttct gagggccacc tactttggga   11100
gcattgttct cctggtgagt gttggccaga ggctggggtg tggccagagg ctgggttgtg   11160
gccagagttg gaagttaccc cacatacaca acagtgaggt ggcaggtgga gggtatgtag   11220
gagttctttg gtggtggcag gctgtggagg agacggacgc cttttgcctg cggccaagtc   11280
ccccagcctt gccaggtcta tctcccactc tgtgaagcag ggttggcact tcttgccccc   11340
tcgccttcac agagcagctg tgaggttggg agagacccag agtctctgca atgattaggc   11400
tgctcatttg cttacatcat cattattatt attattatta ttattattat tattattatt   11460
attttacaca ggaggagaaa ggaaattaaa attttttaac aggaggttag agatatattt   11520
cagttagtag aatagcatag catgcctaaa gccctgagtt ccatctctag tctgaaaatt   11580
ttgtaaaaaa aaaaaatata tatatatact ccatggggct ggaaagatgc agtgatcttg   11640
ctgctctcaa agatggtttg gtttctagca cctatgtgat gattaacaac tgtctgcaat   11700
tttagttcca gaggacccag cgccctcttc tggcctctga gggcactgca tgtatgtaat   11760
atacagctct acattcgagc aaaactaccc atatacatgg aaataacaaa tatatatatc   11820
tattccatgt gccattagtg aacataatct tagttcaatt ttgtacatga cagaaatccc   11880
ggtcatgcta gccttcccta catacaacct tgtaagcctg tcatgagttt ccaatgaggt   11940
aacacatgta attagcagag cactgctaca gagcgcgtgt cccctgaaac agctggtgtt   12000
gttactgccg tcggtgtctt tgtcatgcga ctgctgagta gttagaagca cagattgtgt   12060
cgtcaaggct gcctgcattc gtctgtcagc tctgcagctg aacaacctca cgaccttgca   12120
caaccttagc ctgtctgcct cagtttccca ggctgaatca gtgagctcca gtttcagagc   12180
aatgctctgt ctcaagaaat aatgttggtt atgtaaaagt gacaaaggaa gccacctaga   12240
attgaccttt agcagggtat atgtacatac gaatagatac atacacacac acagagtggg   12300
gataatagta cctgaaatac ttggttgttt gagacttaaa tgagcgaata catatgctgt   12360
ggtcagaatc atgcttaagg gaatgttttgt ttttgagacc ggatctcatt atcccaggct   12420
aaaatacata catataaatc tgaaagttgc ctgatcctcc tgtctgtact cccaaagact   12480
gggattacag gttttgctac cacacccagc tcagcatcat gtttagcaat aagtaagctt   12540
atgcatttaa tagtattaca tggcccatag agcggccggg agatgagggg gccagggctg   12600
ggatgtttaa gcaaaaggc catacctagg gagtcccaac tggggtctga gtcagagtgg   12660
gatgcgtgct ataacttcag catttgaagg ctgagccaca ggagcaccac cgctgtccag   12720
ggtttcagga ccagctaggc aacaaagcaa gagcccatct caagagaagg aaggaaagat   12780
```

```
gccatttgac taattcttgg ggtcaggtg taggtcagaa gcggggtgag gtggcacccc    12840
atcatctgaa cttgcaaccc cttgcctccg aaagggctga ggctttgtcc cgtgacacca    12900
ccccagtgct cccaccgtga tctgccttcc taactctgcc tcctccagag tccgacagtg    12960
attaactccc cactgaagct gaagctagag gccacgagcc ctccacgttg taccatcaag    13020
ccgtcaggca ccaccatctc catcaccgcc agcgtcacca tcaccttggc cccgcccatg    13080
ttgcccgaag tggagctgtc caagatgatc atggtatgga ccccaggacc agggtacctg    13140
gggttcggtg agaagtgggc tgtggatctt tcctgtttaa acatcccca tgcccttcc     13200 ttcaggaagg ccgtctcagt gctaagttga cactccgggg caaggcgctg cgagtgaagc    13260
tggaccttcg aaggtattcc cagccttagc atctctagga tagtggtacc tgctcaacag    13320
aactgcaggg ctaaagctgg gctagaactc ctgtaaggct atccagagtt atatagtgag    13380
actatgctga gagagagaga gagagagaga gagagagaga gagagagaga gagagagagc    13440
gcgagagaga gcgcgagtaa acatgacaca tacctttaat cccggggatg gtgaccagag    13500
ataggtggat ccttgcaatc ttagaggaga gctagcctgc cctaggtggt gaatttccag    13560
gctgatgaaa caccagtctc aaacaaaagg agggaagggc tatgaacaaa taccctgaat    13620
gctgtcctct aaccttttaca tgcatgccaa ggacacacgt acctgcacct acacatccaa    13680
aatctatctg accatgtagc caaagacgat cctgcttgca tctccagtgt gctgggatta    13740
caggcacata ctaccatgtc ctgtctatat aatgctcagg gacggaaccc agagcctagt    13800
gcctggcgac tggcgacact ataccaactg aactacaact cccagctctc aaagcacttt    13860
ttatctcttt ttttcccccc caagacaggg tttctcgtgc agccttggct gtcctggaac    13920
tcactctgta gaccaggctg gccttgaact cagaaatctg cctgcctctg tctcccaagt    13980
gctgggatta aaggcggtca ccaccaccgc ccggcttttt ttgtttgttt gtttttcaag    14040
gcagagtttc tctgtatagc cctggatgtc tggaactcac tctgtagacc aggctggcct    14100
tgaactcaga atctgcctg cctctgcctc ccaagtgctg ggattaaagg catgggccac    14160
cactgcccat atctctattt ttcttttaag acaatgtctc actatgttgc actaggtaga    14220
ctggcagtgg atgtatagac caggctggct tcaaactcaa actcagagaa gatctaagat    14280
ctgcctctag agtgctggga ttacaggcgt gtgtcaccac tcctggctaa cagtggtttg    14340
tttcttaaac caactccctt gcattctctt gccttctaga agcaggcaaa gcaggtattc    14400
ttagagacaa gcaaattgct tcagtaaggg caaacgacac gcctgcagtc acatagcaga    14460
gaggatggag acattggttt gagtatcaac ctcagctcag ctcagcagga atctggaagt    14520
cattgcatct ttccaaggct catttcctcc tgtgctaaat acaggtgaat accttgtact    14580
tccgagggct gcgtagttaa tggcatcgcc tcaggatgtg ccagtggcta catttgtata    14640
attataattc aacagctgtt gggctgcaga agtcacagtt cattaactag tggctacaga    14700
gtggacagtg tagatacaga agttgtactg tgctgcttcc aggttgaagt gagacaaagg    14760
tagggtctag cccacacagc catgtaactt caagctactt acttgatcaa cttcagtttc    14820
gtcatccgta acaatttcta atagtcccag attctcaggg ctgtgagtga gggctgagtc    14880
actaggtggt ttacagtgtt gcagctcggc caggtaattc tagcaccagg gaggctgaga    14940
taggacattt gaggtgaatt tgaagccagc caagactaac ctatgtagca agacactgtt    15000
tcaagcaaac accataactc caaaaaacaa aacaacccc ccaaacaaaa caaaacaccc     15060
caaggactga agagttgatt tgaaggaatt tgagaatgag tgtatgagtc ctaaaactca    15120
gagtagaggc aatggcttgt gaccccaaca gtggggaaag atagaagatc cctggggcta    15180
```

-continued

```
actccccagt cagcttagcc aaacgctgga gctttgggcc aataagagat tctggctcaa    15240
aacatggtgg atggtgtgac catccccatc cttcacatgc acatgtccaa atccactcct    15300
acacacgtgg accttcatgc agacagtctc tctctctccc cactccccaa gtggcacata    15360
tatttatgtg gccctgggaa tggaacccgg gctctgtacc tgctcttcat ctccagtcca    15420
gcatttcagc ttttcccctt ttccttgctt attgttcttc tgttttactt tgttttttgtt    15480 gttttttcgag acagggtttc tctatgtagc cctggctgtc ctggaactca ctctagacca    15540
ggctggtcac aaactcagaa atccacctgc ctgtcttctg agtgctggga ttaaaggcat    15600
gcgccaccac tgcctgtttt tgttttgaat gagacagggt cttaatatgt agaccaggct    15660
agcctggaac tcacagagac cccctgcgtc tggagattaa tggcaggatg ttgagattaa    15720
aggtctgtgc caccttggca gctctcaaat ttgtatgtgt gggtatgtgt gtgtgcatgt    15780
aggtgcaaaa gtaatgccct ctcctggagt tccaggacgt cgtcaattgt gtgtcatggg    15840
tgctggttcc cccgagaagt atgagctctt agacactgaa ccatccatca actttctcct    15900
gtcctcttat ttgataagtg tgtggtatgt gtgtggaatg tgtgtatgca tggtgtgtat    15960
gtggtgtggt gtgcgatgtg tgtgatgtat gcatgtggtg tgtatgtgtg tgtgtggtgt    16020
ggtgtgtaat atgtatatgt acgggagcct ggagagatca gaatgcttca gataccctga    16080
agctggagtt ataagccatg tgagctgcca gatgtgggca ctgggaaccg aattcagatc    16140
cgctagaaga gcagcaagcc tcctcccccc cccccccttt ttgttttgtt tttcaagaca    16200
ggatttctct gtgtagtcct gactgtcttg gaacttactc tgtagaccag gctggcctcg    16260
aactcagaaa tccgcctgcc tctgcctccc aagtgcgtgt tccaccactg cccagctagc    16320
agcaagccct ctaagccatc tcttcagtat tgtgcccctc ctcaaaccca ttttgagaca    16380
aaaaaaaaaa aaaatctcac tggggctgtt tgcaaactca agaaagcca cctgcctctg    16440 cctcctgagt gctgggatta agaaatgggg ccaacacagc tggcaggctt tccttttttgt    16500 aattaactcg tgtgtgtgag cttatgaaca tatgcattta tgtgtgaggg cactcacgtg    16560
tcacacagtg cattgatggt caaaggtcaa cctgtccagt ctcccctcta ccatgtgtgc    16620
cctagggatc aaactcaagc agtcgggccc tttacccacc acactgagcc attttgcaga    16680
gccattttaa ttcttttgaa taagtttggt atctgacaga gagtaaagat tgttggaatt    16740
tccttagata aaaccatact tatttaccta gccgcagagc gtggcacata ggcattcctg    16800
acaaatgaaa aacagcaggc gccgggcagt ggtggcgcac gcctttaatt ccagcactct    16860
gaggcaggcg gatttcagag ctccaggcca acctggtcta cagagtgagt tccaggacag    16920
ccagggctac acagagaagc cctgtctcaa aaaaaaaaaa aaagacaaaa gaaaaaaaaa    16980 aagaaagca gtaggcttaa agaaaggggg ctccagagac caaaggcact cagggatgca    17040
cacctgggaa atggcagcta cctgaaggat gattggatag aactgggaag gctgtcactt    17100
gctgccatct tttaggtagg gcccaaggaa agggtgttcc caggtttcac ggtgtatttc    17160
tctcccacag gtttcaaatc tactcaaatc agtctgcgct ggagtctctg gcggtgagtt    17220
ggggatggca aagggtgggt ccaggcctcg gggcaagttg gccgctcact caaacctgta    17280
tgcactgtct gtcgcccccc cctgcctttt ttttccccct cagctgatcc cactgcaggc    17340
cccactgaag acactgctgc aaatcggagt gatgcctttg ctgaacggta gggactgagg    17400
gtgggaggat ggagtgggga cacggactaa caaagggggg acggcggtgg atggtggaca    17460
tgacgacaca gatggactga tggacaccca ggctgagctt gcctctctca tccacagagc    17520
```

-continued

```
gtacctggcg tggggtgcag atcccccttc ctgagggtat caacttcgtg cgtgaggtgg    17580
tgaccaacca cgcggtaagt acattgtgga aaggaggccg tagaccaggg cattcctgtc    17640
cctacaacac cccagtgctt gtctgttttc ccgaaacccc tttacactag ttgctccttc    17700
acatatatat tatttaagta gtaaagattt aacttagaag cagggccatg ctccagagaa    17760
catacgccac gccgcaaagc agctggggcc cctgagggga tttgctcaag agtcttgtgt    17820
ttgtttggag gctgtttcca aacaactgaa ccagccaggc tccctgtccc ctcccgcagg    17880
gcttcgtcac tgttggggct gacctccact ttgccaaagg gcttcgagaa gtgattgaca    17940
agaaccgtcc tgcagacgtt gcggcctccc atgtcccccc accctctgct gcagctgcct    18000
gagcccatca ccccacctgg gtggctggca ttcaggaacc taactgaagt cttctctgca    18060 cccctgcca accccttccc atctacagtg ttagtggtcc cggtgccaca gagaagagcc     18120
cagttggaag ctatacccga tttaattcca gaattagtca accatcaatt agaatccatc    18180 caccccctc c                                                          18191
```

<210> SEQ ID NO 55
<211> LENGTH: 5624
<212> TYPE: DNA
<213> ORGANISM: Mus musculus

<400> SEQUENCE: 55

```
caaggaagag gtatggggct acgcgcgggt ggagcgctcc ggagggcggg tgcggggccc      60
ggggcgcccg agggacaggg acccggtggc gcccagggcg gcagcatcca ctcgggctgc     120
atcgccacgt gcacaacgt accaatcgcc gtgctcatcc ggccgctgcc gtccgtgctg     180
gacccggcca aagtgcagag cctggtggac acgatcctgg tgagcccgcg gagccttccg     240
gcccgcgcga gggataaaga gagggcgcgc gggtcgggt ccttgatctg caggagctca     300
gcttcgcctg tgtgaccttg acggactggc tgagcctccc atggggcccg ggttcctcac     360
ttggatttgg ccataaaact aatgatccgt cgcaggtact caaagtgctg aggtcacccc     420
ggagctgatc tttgcctctg ggagcaactc tgttaaagta gttgctgttc tttctgtaca     480
gaggagaaac tgaggcacag gaagcttgga tttttttttt tttttttttt tagcaacttg     540
acctatgtca agtgcttaca agatggtacc gtgagacttt acacccaggc aacctgcata     600
tcctggtgtc tcttctggcc ttgacagtct tggcaatggt ttgggtgtgt catgtctatt     660
gggaggatct tgtccagtca ggaagtaggc aaggataagg tcagtctatc atggaaggag     720
ggtcccctca gtaactaggg gttggagttt gtgtcgagtt aggccaacat ggcttcccat     780
cccttcttcc agcttcttga gattcataga ccctatgacc cctaagtcca cagatgtttt     840
cgtcctaaaa tttgcacccc tgtcttcctg tgtgaacttc acaagagcag ggactttgcc     900
atcttggcag ttgccttcaa gctgtgactg atttagccca gtatgctctg tcagcaccaa     960
tgagcctttg ggcaaacttt ctccacccca ggaagtgctt ccatccctct attgtggtca    1020
ttgttttagc ttttatgtgc tcatgatgct aggaattgcg ctcccctgcg tgcgtgcgca    1080
cgttcagcag gagctccacc attgcgctgc ctccctaaca ttttatccct tcgttgcttc    1140
taattccgta atcattctgt cttgatgtca gcgcctcccc tgcccaccct attgggtttg    1200
gccatctgtg acctcacagg cacctgggtg ccccttagca tagctgggat cccggtgggt    1260
tttaatgacc aatttagaca cctcttctat gctgtcacgg gctctggaga caaggaccca    1320
tcttcctagg ccacctgaat atgttgccac aaacaggact gcttgaaata agatacaagt    1380
ccaaagctat gttgtcgtgt ggttttgag acaggatgtg tctctatata acctaggctg     1440
```

```
ccatgaaatt catcatcctt ctgtttcagt ctcccgagtg ctggtattac aggtggtttc    1500
caccaggccc agctcaaagt ctattttatt gagctaaaat aagaaaccag caggaatgtt    1560
ctcttgaggc ccgaagggaa aatgcacttt cccaagtctt tcttttttctt ttgtgtgaca   1620 aaacatcctg acccatgcaa ctttaggggt aaagtttgtt tgtttgtttg tttgtttgtt    1680
tgttttttga gacagggttt ctctgtatag ccctggctgt cctggaactc actctgtaga    1740
ctaggctggc ctcgaactca gaaatccgcc tgcctctgcg tccggagtgc tgggattaaa    1800
ggcttgcgcc accacgcccg gctagggtga aagtcttatt tgactgacag tccatcatgc    1860
cagaggattc ctgatggtag gagcttgagg ccattggtcg tgtatctcca gtcagaatga    1920
tgaaaaacca cttggacacc gctcactttc ttctctttat acagttcggg attctagcct    1980
aaggagtgat gctacccaca gtgggcagat cttcccagct caactcactt aaccaagata    2040
atcccccata ggcatgccca gagaagccaa cctccaaagc cattctggat tcatcaagt     2100 taacaattga accccttagc tgagggcctc tctcatcttc agagcagcag cagcagcccg    2160
tggagtcctt cccgcctcag gtcattgtga cctctcttgt cacagccttc tgctttcagg    2220
gaacctggtg attacattca atctccttgg caacgcagga caatctcaat ttggggaacc    2280
ttaaacccca cttctatcag caggcttcca ccatgtaagg tgggtttcac aagtcctaac    2340
gattaggaag tgggcatcct gaaggaccat tcttgagccc ccaccctacc ccccactgcc    2400
atgccttcaa cacaaggcct gcttggtcca gctgcctagg ccctctcccc ccatgcatct    2460
cctccctgac ttccaccacc ctgctggatg aacatgggag gccatctgca caacacagct    2520
catcactgct ctgcacagga gtcacagttc aggcatttgg gcttttttct ttttttaaag    2580
atttatttat ttattatatg taagtacact gtagctgtct tcagacacac cagaagaggg    2640
cgtcagatat tgttacggat ggttgtgagc caccatgtgg ttgctgggac ttgaacactg    2700
gacctttgga agagcagtcg ggtactctta cctactgagc catctcacca gcccccgaat    2760
ttgggctttt aatctaagct agtccgaatc tgtagcttcc caagtggctc tgtgcccctc    2820
gtcacttcag agacaggt gggcctcctc ctggcttgtc acctgtgaga ctgtcttcac      2880
agcattgtca tttcttcctt caatctgctc ctgggactga aaccttgtca gggtgagact    2940
ctccttacct cctggctgtg ctgtggtccc ccaagtgtgg gcaagtggac gcaggatgta    3000
tcagtcacat ggttagtaga tcagtgctcc ccaagtgttc tttgggggaa gcccctcact    3060
gccatttgca gcatctgcca tttctctgtc agaaatactc ttggggctga ttttcaagct    3120
gccaggataa cacccaccag cttgcagaac caaccctaa ggggctaaga ggctgctgct     3180
cctgccagca cgagccctct ggcattttgc cagttctcaa gcatagtgcc atgttctcac    3240
tctgtgaccc ttctctctag gcggaccctg acagtgtgcc cccatcgac gtcctctgga     3300 tcaaaggggc ccagggtggc gactactact attcctttgg gggctgccac cgctatgcag    3360
cctaccagca gctgcagaga gagaccattc ctgccaagct cgtgaggtcc accctttcag    3420
acctgaggat gtacctggga gcatccacac cagacttgca atagcaacct cctgatagcc    3480
ccctgcccct ctccacatca gcaccactac ccggcgctca gaagacacat gcagccccca    3540
gtgggcagaa gctgtagatg ggatatgttc tctttattct taagggaggt ctgcctcttg    3600
gtgcctctgc actagctccc aggggctagc tcccaggaat gaggggttc agttcttctg     3660 tctatggaaa gatatcatgg ccttgaccct gaaggagtac caggaaggaa gaaaggagat    3720
ggacttggag acaaggactc tcattttaat ctttatgata gcactatatg aactatgtac    3780
```

```
taggaagtaa aggaaaaccc aggtcaccat ggcttcagtg agagaagctg gttatccatc   3840
cccatagcct gaactctgga accggcagct aacacagcac tgactaacac agtattgtgt   3900
caacagctca gtgaaggcag ggcttcctct cgggagtcct ttggccttgt cctccttgct   3960
ccttacttcg tagtcgctgt tgctgtgttt ctaggaaccg tgtctgtgct caaggaagaa   4020
acccactgga ccaacttctg tcagaaagga aaaccttgtt caaagtttca ggaccctgtt   4080
ctttgcttat ttgcacatgg tcaccttggt ctgagctagc caccattgtc acccacagct   4140
gcaaagaaag cagaccttag gaaacactgt cacggctgag tgtgactgcc ttgttcatcc   4200
cctggactgg tactgtgttg cctgcagtac cattgggatc ccatagcaag agagggagag   4260
ggagatgtta gttagccttt gctacgaacc aagctgtccc caagctcaac agctaaacag   4320
gtattcattt acccatgatt ctatgggtta gctaagctcc tttgagcagc tcctctgatg   4380
tggcctggtc ctgctcatga gcccatagtc aattgtcacc tcagctgggg ctggttgggc   4440
tggggtcacc ttcaccattg tggcaagtgt tggctgcatt ggcttggtta ctcttgttgc   4500
ctctctcaaa ggtcagttca ggagaattct caagatggcc tcagggttcc aagagagagt   4560
agtagtgaga gggcctggag cggagactca gctgttaaga gcacctacat ggtgattcac   4620
aacactgtca tccctgttcc agatgacctg atgccctctt ctaggctctg tgggcacaga   4680
caaacacatt cgagcaaagc acccaattgc ttttcttttg cttttgaga cacgggtttt   4740 ttctgtgtaa ccctggctgt cctggaactc actgtgcagt accaggctgg ccttgacctc   4800
acggagattt gcctctcctg catcccgagt gctggtatta agaaggtgt gcactactat   4860 cacccaggta catttttta aggtgacaag gtttcttcag cccctgtgcc aagaatgtgt   4920
ttctgttggt cagttcgttc cttagattca agggttgcaa atggaccgag ctctcagcgg   4980
gaggaaccac aaagaacatt gggctatcgt tcatcacaga tgaatcttgg tgggcaagag   5040
acagaattcc tcactcccac acataagtac tccctttttca taagtttgtc acagaagcac   5100
acaaggggcc ttggcatgtc agcctttaag taacggttct caaaacctag aagtcatggc   5160
atggtgtctt cgagagctgg gtacccccagc cctaaggatg tctcagaggc acaatgaggt   5220
ggataatgag gtgggcattc agaggggctt ctgcaaacct agagtccagg aggcaatggg   5280
tgcagcagtg aggtagctat gccacacaga gaccatagtc acttgtcatt ttcaagcctc   5340
tgttttccca gctccatggt gaggacacca gctttcccac ccaccgagtg tcccagaaaa   5400
tgaaattgga aggaataaga tgcatcgtgg tgctggattg attcttggga ccaaaaagag   5460
actagggaga gaaagcacat tagcaggtca accaggactc ataccttcca gtttgggtaa   5520
tcttatctct ggggtgggct ggatgaagaa tgtatgggaa ctctagtctc tgcaacttt   5580 ctgtaaatcc aaagtcattc taaaataaaa gtgtatttaa ttaa   5624
```

<210> SEQ ID NO 56
<211> LENGTH: 12449
<212> TYPE: DNA
<213> ORGANISM: Mus musculus

<400> SEQUENCE: 56

```
gaggcgctgc gggacaggtc tgcccaagga ggggcggtgg ccctcccgtg gctgtcgctc    60
gctccggact ctgcccgggc ctgggcggcg gctgcagccg ggagggcgac gtggaatggc   120
cacgtggagc cgcccggggg agggccggct gcgggcagcc gggcgagagc ggcgcggtgc   180
ctatagagtt cacgaagccg gagccccagt cgcgcacagc gccgccgcag caggtgggtc   240
agactccggc atgggccagg gcttagtggg cggcgggggc accgggtacc ttggggtaa   300
```

```
gggtggagac cttctactgg cggttaggat gcagagagca cagtcctcct catccctga     360
ggcttggact gggctgtgga ggtggccctg gcctcctagg accgaccact agggtcatcc    420
ctgagatgca gatagaggaa aggtggaaag cttccgaggc ccctgggttt gatgataggt    480
ccaagagtcc tcctggccgg cagcggtgtt ctagtagcta gccagggttc cacctcattc    540
agtagatgta gatgattgaa ggacactgtc cgtcgtcatc cagctgtagg tggctggtct    600
caggctagct cagatgtgtg ccccttgac tgtatagctg cggtcattta agcctccccc     660
tccctcgacc gggacactaa gggctaaatc aagggagatg actcgattca ataacttttc    720
cacttactta gaaatggaat ggatgccctt catggtacca gctcctgtcc tgaaaagatt    780
caggaggggc gttatggcta ttcgtcaggg atgctgggaa agaaatgtct ctgaaatgag    840
aagccgtttg acataagcct ccaaagaccc ctgcaacatc gtgaagcatc tgctggccct    900
agattaacct agattatctc actgtaccat ccctaagacc ctaggaaacc tcgttatctt    960
aaaaatgaag accctagggc caggggaggt aagacacct gccaagacca cataacagtg     1020
cagagtcaga ggctgaccaa tggtccaacc tcaaggccaa agtctcctcc tgtgagctag    1080
ggcaaaggct taaagaaatt gaaggcagaa ggtcattgtg gaagagtgtg tgtgtgtgtg    1140
gtgtgtgtgt gtgtgtgtgt gtctgactcg ataacttcg ctgagctata tgacaactgt     1200
taacgagcag gtacagaagt tttcaggtat ttattacggt agttatgttt atgcatgtta    1260
taattatgga aaatggctag gaccattttt attttattag cagttgttca atggccatgc    1320
tatttctgtt acaaaagctc ttacaagtgc ttaacttgat gtgagtatgg gtaagtcata    1380
ttacacacat cccgtggaag tttggcttaa acaatggcaa gaagcatcga gaaaactaaa    1440
ttagactcca agtgcccatg cagtgccttt aattttgag gtaattaatt aaataaataa     1500
aattcagact gcaactgaat gctaaggtta tcaggaaggt ccatcctgaa ggtgaaacgg    1560
gtttggaaaa aaacaaacaa acaaacaaaa aacaaaaaa caacaaaaac aaaaaaacaa     1620
aaaacaaacc ctgagactat taagtaagaa aacctagtga gctgccattg gaagcagtgc    1680
tggagcactg gagggtgaga cagagatgac accatacctg aacgcatggg tgaggacatg    1740
ggtgtgtgac ggtgagaaaa acaaagagcc accaaatgtc ttggagttgc tgggcgtggt    1800
ggtgcatccc tgtaattcta gtacttgggt catgagttca gggttatcct cagctacatg    1860
ataagttgga ggccagcctg ggatacatga daccctgtga gattttttaat taattaatta    1920
attaatccaa taattagttg agacagggtc tctctagtcc tcagtgttct ggaacttgtt    1980
ttgtaggcta ggctggcctg gaactcaaga gatccacctg tttctgccat ccaagtattg    2040
ggaataaagg catgtgttta ctgttttat tttgagtgtg tgtgtgtgtg tgtgtgtgtg     2100
tgtgtgtgtg tgtgtggcct gcatgtatgt ctgtgtatca cttgtataca gtgccctcaa    2160
aaggacatag gaggacagaa gagggcctcc ggtcctctgg aactggagtt acagatggag    2220
gttagctaac atatgggtac tgggaactga acaatgaat agattttgag ccccattgtt     2280
tttttaaaaa aagattttga aggaaccagc aaaatgggtt gaggtacttg caaacaagtc    2340
tggggaccca agttcaaacc tgatatccca caaggtggca ggagagagcc aattcccaag    2400
agttgtcctc tgacctccac aggtgcaccc tggcacacac tggcctacac ttaagcacac    2460
ataaactcaa caataaagta aacaattaaa aactgtttct gaagcaatgg agttctatca    2520
aagggatgct tatatgatgt gtgtataaag acagtacctc aggctacgac aacacacaca    2580
caaacacaca cacacagaag gaattcacta tccgctgctt ctgggttctg tccactatac    2640
```

```
acactaaata gttacctatg taaaggactc acaggacaga ggacagtgac tgattcacat    2700
agggagggtt cagaatcatc attgatttct agatcccaga gcagaagtag ttgatagttt    2760
caagacagct acagcaggac aacagacagc aaggcctggg tggctaagta ggttcactct    2820
tacaaagcca gctcttgcat ggctggcatt tggagtatta agatcactta acaggccact    2880
caaaacctag tggtttggat gcaaagatag aggagagcct gagttccac cgcaccccag      2940 gtcttcagaa gggctccaga tatgatggat gttctcccac tagtgcttgc agatggtctc    3000
aagttgccca gccccaggct cgctgcagct gcacgtgcag agcaggatga aggcagcgcc    3060
agccttgtct cgctcctcct cggcagacta gatgatcata ttgatgcttt agtaccagct    3120
gggcgatggg agtcctctat aggttaaaaa gcagtatcat gcagaatcgt gctcctggga    3180
ttgcagcagg gcaggagacc atacagggag acaccgtttc gtcaagacaa ccagagctag    3240
gtgtggaggt gcatgagttg aatgcctgtt cttgggagcc tgagacaaga ggatttcagt    3300
gagtcggagc tacgtgagtt caaagctagc ctgtgctaca cagcaagacc ttgtttcata    3360
aaaccaccaa aacaaaacaa cttagtagct tcagatgata accttagctt ttctcatgga    3420
tgctgtacac taggcagggc agtggagacc agctttcttc tattctactg ttggttagga    3480
cagctggaag gctcacagtt ggaggatatt ctcacacttg tctgccttgg gggctaggga    3540
ggggtttttt tttttttgt ttcattttgt ttttgttttt attttgatt tggttttggt       3600 tttggttttt gagacacaga gagactgaga tactacctgg acctggcagt tttctcagct    3660
atcctagtca cctggaagcc agccactaag tccaaacatg taagaggagg tgacttagac    3720
tccagggtta gtgggaagga aagtaagaac aaacagtaga catgggccag caagatggat    3780
ggcaaaggcc tttggccggt gtttgatccc ctagacctaa ctggtggaag gaaagaactg    3840
atttctgaaa gtggtcctct gacctccact gaggcacaca tgcccacaga cagatggaca    3900
catgcatgca cgtgcataca cacatttata cacacaccac caacaacaac aacaatgcca    3960
acaacaaaat aagcaactgt tttggggacc cctgcagtca gcctaatgag ggaatggatt    4020
agtgggtgag gggacttcct gctgtttcaa aactgccacc cgtttgtcat cagagctctt    4080
ctaaaaagca gcctcagagg ctagtctaga ttacaagtgt tgacagctag ctctgaggga    4140
tttaaattac gtgagtctca ggaacagaca ggaggaaagg actgacttga acgactcagg    4200
tgggaaggcc aggagggaag atgtgtgtga agccaccaca gagcaaccaa gacaacttct    4260
ggaaggcaag cacctcatct catttagcta caactgtggc cccagggaag tgctctgtca    4320
acctgcattg cagatggaga cctgagacag ggaaagcaca cagccagtga gaggcagggc    4380
cttcagttag ggtcctcaca ctccacccttt gagttctcct cctttttccta gcagttctgt    4440 atttctgtgt tccttcttc ctctcagtca ggatcttaca gcattgccta ggttggcctt    4500
gaactcacaa cctcaaaccc caccccatcc ccgcccctct gaagagctgg gattataggt    4560
atgtgcctct gcacttggct tctgtttatc tgtctcttat ttaaatatgt gtctcttttc    4620
ctgattatat aattttgtaa tccttaagga gaaaagtag tttgatctca taccttcagc    4680
tgattgataa ctaagaactt aaacagtaaa gagatgcact ggagagatgg cgcaacaatt    4740
catgggacct gttgttgctc ttgcagagga cctaaaatca gttttcagcg tccacatcag    4800
tggttttcaa gctgtgggtg tgatcctttg ggggtcaaat gacccttca cagggagtcat     4860 atatcagata tcctgcatat cagatatttg tattacagtt cataacagta gcaaaatgag    4920
ttatgaagta gcatcaaaag caattttatg gttgagggtt gataagttat tctctccaga    4980
tgaaaatgag ccaattcaag tcaaattaaa gtacataagg gcaggtttat tggagggtgg    5040
```

```
ctctcaggca gattcactgg tcccaaaaaa aaccggggct agggaagttg ccctggggaa    5100
ggagacagag gggaaggaca gagaggaaaa aaagcaggct tgtgcatgaa gggagagaga    5160
aaatgcaaag ggaggaagag aggtaggaga gagagagaaa agtgggtggg ggatagagag    5220
ctcggaaaac atcagcatta tatggggagg agcttctggg ggaggggagg cccagcccct    5280
aggctggaaa gttcacagga gagggcaggg tataccagcc atgcctgtag taggtaggga    5340
ctgagggatg ctgggagaac atggagctca ggtctgtgta aaatatgcac ctcagcaatt    5400
tgtcctgggt ctgaatcaaa acaggggcag tacaacatga gaaactgtat taaagggcca    5460
gcattaggaa agtttgagaa ccacttatcc acatggtggc tcacaactat ctgaaattcc    5520
agttctgagg gatctgatat cctcttctga tttctttggg cacccagtac acatacacac    5580
atgcagacga aacactcaca catactacat acatacatac atacatacat acatacaata    5640
catacaatac aatacataca atcttttaaa gtatttatt tatttattca ttcatttatt    5700
catttattta tttacttgtt tgtttgttta tttatttg ggttttggag acaggttctc    5760
tctgtgtagc cctgactgtc ttaaaacttt tctgtaaacc aagtcggcct tgaactcaca    5820
aagatccacc tgcttctgcc tccagagtgc tgggattaaa ggtgtgcact accaccaccc    5880
agcaaaagaa tattttaaaa ataagtagcc tggcagtgca ctttcagtgg tagaacattt    5940
gacttgcaag catgaaggct tggatttggc ccccagcaat gaaaaacaaa gaaatgaata    6000
gccagacatg atagcacaag tctgaaattc cagcacttgg gaagcagagg cagagggata    6060
tgggggcaac ctgggctact taataaaaaa tgtgtatttg cattctataa attgtacagc    6120
tgccttccac ccatgctggc cctcttggtc tgtgtcattg gatttcccat gtgtgttagt    6180
cattttctgc tactgtaaca aacatccaag acaatcgact tataacaaga aaagatttac    6240
ttttaactct tggttttgga ggttttagct cataatcagt tggtctggct gcttttgtac    6300
cctgcctcat gatgtttgac tgggtggatg tatgtacatt gagttgggtg tacatgtgtg    6360
tttggtgtgt gtgtgtgttt agggtgtgtg tgtgtatgtg tgtgtgtgta ggccagaggc    6420
agatgttgag tgtatttctc aacactcact cttcagtttt gagacagggt ttctcactga    6480
tcctggagct cactaatggc ttagctggct ggccagtgag ccccagggac ccacctgtct    6540
ctagctcccc tccccagccc cttccctgc ccccctctta caagtccgct ggggatggga    6600
tctcaagtct tcatgtacag caagcatgaa gcacttact gactgggccg ctgccccaac    6660
ccaggatcaa cctcttaata ggttccaccc tgtcccatag tgccaagctg ggtattgtat    6720
cttcatgttt aatacacggg ctgttagaag acaacgcaga gccaatgaca ctccatgcta    6780 ccctcttttct ggtctagccc agggtccaca catgctgaca ttctccttct gacctctctg    6840
gcagcaggcc ctctcaacca taatgtgccc cttcttttca tcttagaggc tggacctcat    6900
tcttatcctg gagactatgc acacaaacag ttctcaaggt tgccatctag tcccctaacc    6960
cctgctacct gccacacagg tctcgagggc agctctcttt tctacacttc ctctctaacc    7020
ctccagaaag gaacaaggca ccaatctgta gagcctggag ttctgtttag ctccttggag    7080
tttctgttga catttctacc ttccacttcc agctgcggca tccaggtggc ctccaaactc    7140
ttaactgctg cccctattct ttgaatttcc ttgattgttc agatccccag aagtcaggca    7200
tagtgctgtg ggggagtaga aatgggtggg tccttcaagt tcactggaca gacattatct    7260
gaaccgatga ggttcagtga gagatcctgt ctcaaaagat caaggtggct tggcagctac    7320
aggtacttac agtgcaaacc tgggtcctcg agttttatct ctggaactga taaaaacaaa    7380
```

```
gactgcacag agttgtcctc tgacctacat atgcacacat caccacaata ttttttttca    7440
atcattgaaa gtttcttatg atcaaggaca gtgatcaaag aaagatagcc catgtcacct    7500
tctgaccctc acaagtccat atatcacatg cgcacacaca ttacagtaca gagagggga    7560
gggagatgga cacacacaca cacagtggaa aaaacaagca caggcctgta tctgtgatag    7620
cttcatcttt ttctagactt tcactctgat gcttcttgct caaggcagct caaaaggtga    7680
acattttgct tatcttcctg tgagccagga gcttaccggc tctacctcca aactctcaca    7740
gaactgacat ccaccctgga catggatctg aaccttccta gggtcacaga catctcagag    7800
aatcccctga aagctacaga atattcttta gaaaaatcaa gtgatggctg agttttaggt    7860
tcagtagagg agagagcctg accctttgct tggaccacca aacatctgat tatatttctg    7920
cacagagatg gttttttggg ggggggggtg gctcagattt ggtgggcttc tatctccttg    7980
gaaactcaca tatgtacata cccctgggac aaacctaaaa gctttatgct ttgtgttata    8040
aattgaatca ctttgcattt gactactccc atatttccat ttccaaatat gtataacata    8100
gagacagcca ggttggtttt gaactcacag tcttcctgcc tcagactcct gagtgctggg    8160
atcatggggc atgtgccagc acaccaagcc tcagtaggtt tttcataaat acagactaac    8220
agtccatctc cctcttagtc tctttgtata cgttttcatc ttcagtgagt cccaacatcc    8280
taatctatcc ttttactaac tgtaaataaa gtggtctgcc ctagagcaga tacacttaca    8340
tagcacttaa gtgggccaga gggacataag gaggagccct cataccccaga actgtctcct    8400
acagagcact ttatagactg gagcagaata tatatgtgtt cttacatgta ggacttatct    8460
tttttttttt ccattttta ttaggtattt cgctcattta catttgcaat gctataccaa    8520
aagtcccca tagccaccca ccccctctcc cctacccacc cactccccttt tatggccct    8580
ggcgttcccc tgtactgggg catataaagt ttgcgtgtcc aatgggcctc tctttcgagt    8640
gatggccgac taggccatct tttgatgcat atgcagctag agtcaagagc tccggggtac    8700
tggttagttc ataatgttgt tccacctata ggggtttgcaga tccctttagc ttcttttggta   8760
cttctctag ctccttcatt gggggccatg tgatccatcc aatagccgac tgtgagcatc    8820
cacttctatg tttgctaggc ccaggcatac tctgacaaga gacagctata tcagggtcct    8880
ttcagcataa tcttgctagt gtatgcaatg gtgtcagcat ttggaagctg attatgggat    8940
ggatccccgg atatgctagt gtctacatgg tccatccttt tatctcagct ccaaactttg    9000
tctctgtaac tccttccatg ggtgttttgt tcccacttct aaggagggc atagtgttca    9060
cacttcagtc ttcattttc ttgagtttca tgtgtttagg aaattgtatc ttatatcttg    9120
ggtatcttag gttttgggct aatatccact tatcagtgag tacatattgt gtgagttcct    9180
ttgtgaatgt gttacctcac tcaggatgat gccctccagg tccatccatt tggctaggaa    9240
tttcataaat tcattctttt taatagctga gtagtactcc attgtgtaga tgtaccacat    9300
tttctgtatc cattcctctg ttgagggca tctgggttcc ttccagcttc tggctattat    9360
aaataaggct gctatgaaca tagtggagca tgtgtccttc ttaccagttg gggcatcttc    9420
tggatatatg cccaaggact tatcttgtgt tccatggaag gtggcccatg ggtattcata    9480
gtcctccctg agcaggcatc tttcctccta tgctgaatgg ttccacatgc aaggagggaa    9540
gtcatttctg tctgagccaa ctgacccccg aacactggca gaccccctga ctctccactt    9600
ctgttcctag ctccagttc cagcaggatg ttcagtggc tgatgcaagc gttgatgctg    9660
ccactattgc tgctccctttt aggtcgagct gctcccaagg atggagttgc aaggtaagag    9720
gattaggaag gcagggctgg ggcaaggaga gttctggaaa gatgttagga ctctagggga    9780
```

```
gccagaagcc tgaagaaata gtctccatca tctccaggta cagcaccca agtagggcct      9840
tggtgcatgc ttgtagaact ctttgcagcc aagagttcag ctctagccca gtgtgaagca      9900
tcagaaggaa gccagaaaca cagacagaga ctatcaactt agaataagac ctgacactgg      9960
gaatgccaag aaaatgggtc gttagcttaa tatctctgac ttactaggac tgctttcttt     10020
ttttttaatt atttattatt ataaatgcgt acactgtagc tgtcttcaga tacaccagaa     10080
gagggtgtca gatctcatta cagatggttg tgagccacca tgtggttgct gggatttgaa     10140
ctcaggacct tcggaagagc agtcagtgct cttaaccgct gagccatctc tccagcccta     10200
gaactgcttt cttacagtca gtatgtgcat tgggatcatg ggaaagtgga gcgctggcaa     10260
cagtgaccaa actgtctggg acaactcctg tcacttctgg atcccagggt gatgtgggca     10320
aacagtagcc acatgcagaa gtaggaatac ttgagattct gggcagacat aaagtctggg     10380
ctggcatcca taccctctgt ttcaaaaggg aagaggcatg atgtgccaag gagcaaaatg     10440
ggtctgtaga atcctgggca ctgctaccag cctcaggagg accataagaa accattccgt     10500
cttggcacac actggaccat catcttgggc ctctatcgtg tgtctgctat ggcagcctca     10560
acctcactag gcattttctt ttttaatttt tttaagactt atttatttat tttatgtata     10620
tgtgtacagg cacagatctt tagagacacc agaagagggc atcagatctc actacagatg     10680
gttgtgagcc acaattacag gttgctagga gttgaactct cagaagagaa gcaagtgctc     10740
ttaaccactg aaacagcttg ccagtccctt ctttgtgttt tctaaagtta actaaggcac     10800
ctgagctgca aaacaacagt tttagggatt aaagttctgt ttctagtgac actctagctt     10860
tttccctaca gccttttctg ggaatttgga gggacatctc cctttgagtc ttgagtctgg     10920
ggagaaatct accaagtggc tgctaagcta ggctatgggc tgctgtttct ctcctgttct     10980
aggttggacc ctgaggtaca acagcagctc acacccaacc ctttccagcc aggccctgag     11040
cagctccggt gagtaagttg ggggcttca gcaggcatta actggacaag tgacaggtca     11100
cagacaggac tctccctgct gacttcccac tttttcaata gacatctgca gaattatctc     11160
aagggactag agaagatgga agaggatcct gagcacatgg accggagca aggtgaaggc     11220
ctggtgctgg gaggatacag gaagggacct ggggctgtgt ggctgccctg tggcttcttg     11280
cttttctctaa cccagattct cttctgtagt cctgctttcg ctctttgctc ttcatgacta     11340
tgaccagaat ggacagctgg acggcctgga gctactgtcc atgctgacag cagctctggc     11400
ccctggagct gcacactttc ccatcaaccc ggtaagcgct cctggaaatc gtgagagact     11460
agcaacttgg agctttggtc cttttcatca tgacttttgg tagactcctg gtaaaaggga     11520
agctcagatc ctatgtggca gggatgaggc tgttggagag cggctgggtt cctgaaaaca     11580
cctctggtaa ctgtttccac aggtgatcct agtagtagac tcgtgctcg agactcagga     11640
cctggatgga gacgggctca tgactcctgc agagctcatc aacttccag aagtccccaa     11700
acacacagag tccttccccc cagctctcca ggagccacaa cctgctggaa gtcagccact     11760
tttagccaac agtccactgc agtcagaaac ccagcagtcc ctggggacta agaaaattag     11820
gagccaggta gaggccaaga gggcgtcctt ggagcctgaa caggaggctg acatcagac     11880
agagggaaaa gtagataccc taagccctga agaggaggct aggggacagg cagagtctga     11940
aggagatgtt ccaggtccca gagaaggtgc tgaggaacag gtggagatca aggacaatga     12000
aggagaagcc aaagaactgc tggtggaaac actggagagc ctaaacactc caaatgaggc     12060
tgaggctcat agcatccaat tggagaacga tgagatatga gcccgacggc ataggctcaa     12120
```

-continued

| | |
|---|---|
| gcccctcaga atctcagtgc agagcagaag catggtgttg aatatggtgg ggttagagcc | 12180 |
| acctctgaca tggggacggt ggtgcaagct agtaacccca gaagcattga gagctccggg | 12240 |
| ctagcctagg ccacatagca agtttgaagc caggctgggc tactgcgtaa gaccctgtct | 12300 |
| tgatgagggg gaaaaaagca ctcccatgtc tcctttctgg cttcagtgga aagtaggact | 12360 |
| ttctgtgcag ctcagggaga ccataagctg agaagcagct ttcaggccac aaacaaccaa | 12420 |
| taaagaacag aacaaatctg tctccacag | 12449 |

<210> SEQ ID NO 57
<211> LENGTH: 2474
<212> TYPE: DNA
<213> ORGANISM: Mus musculus

<400> SEQUENCE: 57

| | |
|---|---|
| ggcactaaga cagattcaag gattgtatat ccaacaacta gacaagacat taccttctga | 60 |
| tcagcatcag ggaaaccctg taagtatcct aggaatgata tggtgtgtgt gtgtgtgtgt | 120 |
| atttgaatat gtttatgtgt atgtgtgtga gtatgtcagt atggtgtgtg tgtttatgta | 180 |
| tgcgtcagtg tgttgtgtgt gagagagtca gtatggtgtc tgtgtgtgtg tgtgtgtgtg | 240 |
| tgtgtgtgtg tgtggtgtgt gtgtatgtgt gtgtgagtgt gtttatgtgt gtgtgtgaat | 300 |
| gtatgtcagt atgttgtgtg tgtttatgaa tgtgagtgtc agtgtgttat gggtgagtat | 360 |
| gtatgtgagt gtgtgtgtgt gtgtgagtgt gtgtgtgtgt gtgtgagtat ggtgtgtgtg | 420 |
| tttgagtgtg tatgtgaatg tcagtgtgtt gtgggtgagt gtgtgtgtgt gtcagtatgg | 480 |
| tgtgtgtgtc aattataact tgaagagatg gtgagacaga atcccaaag aaagcccgac | 540 |
| ctctgtaaag ggatggttct tgtccattaa ctcttccctg ccctgctctt cctggtgccc | 600 |
| catggtcagc tctagagagt gtgggtaggt gactggagaa agtggacagt ggcctcttgg | 660 |
| gagatagagg agttagccctt tcaaggcgtg cacagtgctg aggaaagtct cccagcctgg | 720 |
| tgctgggttc caggctctct taaggaaacg agtgtgaagg gttttggaaa tactgctgtt | 780 |
| gctgtacatt ttgcaactgg gtctgaagca agaaggggc cccacagcct ggttaggaaa | 840 |
| ttagtctttc tattcaacca ggcgcccttta agacaatgag gttggcaggg cgtggtggtg | 900 |
| cacgccttta atcccagcac ttgggaggca gaggcaggca aatttctgag ttcgaggcca | 960 |
| gcctggtcta cagagtgagt tccaggacag ccaggactac acagagaaac cctgtctcaa | 1020 |
| aaaaccaaaa aaaaaaaaaa aaaaaaaaaa aaaaaaaaa agagcaatga ggttgacagt | 1080 |
| gatgggtga catattttga aggtgcctct gaaacttctg attttggaga ccagagtact | 1140 |
| ccatgctagt ttgatgtggc tggggtcaa gaatcctttg gctttcccct catgggtgtg | 1200 |
| tccactttca ctctctaggt ccttttgatg gctgcaaaca ctacatctcc tgcagcacct | 1260 |
| tcttctcctg gtggcatgtc cctgtctctg ttgcccattg ttctactgtc tgtggccctg | 1320 |
| gctgtggggc ttcctggcaa tagctttgta gtgtggagca tcctgaaaag gatgcagaaa | 1380 |
| cgcacggtca ccgccctgct ggtgctgaac ttggccctgg ccgacttggc tgtgttgctc | 1440 |
| actgctccct ttttcctcca ctttctggct cgaggcacct ggagttttag agagatgggt | 1500 |
| tgccgcctgt gccactatgt ctgtggaata agcatgtatg ccagtgtcct gcttataacc | 1560 |
| atcatgagtc tggaccgatc actggcagtg gcccgcccct ttatgtccca aaaggttcgt | 1620 |
| actaaggcct ttgcccgatg ggtgctggca ggcatctggg tggtgtcttt tctgctggcc | 1680 |
| ataccggtcc ttgtgtaccg tacagtaaaa tggaacaaca ggactctgat ctgcgctccg | 1740 |
| aactatccca acaaagagca taaagtcttc catctgctct tcgaagccat cacgggcttc | 1800 |

| | |
|---|---|
| ctgctgccct tcctagcggt ggtggccagc tactctgaca tcgggcgcag gctgcaggct | 1860 |
| cggcgcttcc gccgtagtcg ccgcaccggc cgcctggtgg tgctcattat cctggccttc | 1920 |
| gccgccttct ggctgcctta ccacctggtg aacctggtgg aagccggccg cacagtggcc | 1980 |
| ggctgggaca agaacagccc tgcggggcag cgtctgaggc tggcccgcta tgtgctcatc | 2040 |
| gcgctggcct tcctgagcag cagcgtgaac ccggtgctgt acgcgtgcgc gggcggcggc | 2100 |
| ctgctgcgtt cggcgggcgt gggcttcgtg gtcaagctac tggagggcac tggctcggag | 2160 |
| gtgtccagca cccgccgcgg gggcactctg gtccagaccc cgaaggacac acctgcctgt | 2220 |
| cctgagcctg gccccaccga cagcttcatg acttcctcca ccattcctga gtcttcgaag | 2280 |
| tgaactgcag taggctgggt tatgacacaa ctcataactc tggcctgacc cacttctgta | 2340 |
| cctggaggag aacatgttgg ggactgggct taagcggaag agaggggagggg gtggggcaag | 2400 |
| tcagggcaga gagacaggat gctctggcct ggcttctgca ggcagcttca cgattaaaac | 2460 |
| taaagtctga aatc | 2474 |

<210> SEQ ID NO 58
<211> LENGTH: 7769
<212> TYPE: DNA
<213> ORGANISM: Mus musculus

<400> SEQUENCE: 58

| | |
|---|---|
| agtcgcagcg ccgggtccca gaatctagtc ctacgccacg gttttgacca cgcgtgaccc | 60 |
| gctgcccagc cggcccggcc atcaggtggt ccgtgtgtcc ctctgacatg tcgtcctgca | 120 |
| gccgcgtggc cctggtaact ggggctaaca aaggcatcgg ctttgcgatc acgcgtgacc | 180 |
| tgtgtcggaa attctccggg gacgtggtgc tcacggcgcg ggacgaggcg cggggccgcg | 240 |
| cggcggtgca gcagctgcag gcggagggcc tgagcccacg cttccaccag ctggacatcg | 300 |
| acgacccgca gagcatccgt gcgctgcgcg actttctgcg caaggagtac ggggggactta | 360 |
| acgtgctggt caacaacgcg ggcatcgcct ttagaagtag gtgtgggggct ccaggaggag | 420 |
| gtgtcccggg gttttccgag ggtgctgggc agtgagcctc tgggatccgg aggctgcgcc | 480 |
| atcccgcctg ggtgcacccg gctcgcgctc tgcgtggcga gttcccccgt gcggtgactc | 540 |
| gggtgcgggc ccgcccaggc accccactcc atgcccgacc cggccggcgg cctgtgcggg | 600 |
| cctgtgctcc gccggaggcc ctccttggaa ctttcagctg cgcctgtttg gaagaaaacc | 660 |
| ggtctcttgg gagggaccca cgccttgtca agctcatcag cttttctgtcc cacgcacgaa | 720 |
| ggcttttctc agagaagggt cttccaaaaa aatagggttg gagctttcgc ttcgcgtgaa | 780 |
| acaagggcga attcatagat gccagtagat atctgctgag acaggaaat gggtcgcccg | 840 |
| gacacaatta gcgccctggc acgatagtgg gtttcctacc cgctttaatg gagcgttttg | 900 |
| agaggctctg gcaaaaagga agcgagctct gcttccctcc tcctcgggga actaggtttg | 960 |
| ttattaaact tgcaagtgcg gtttggaaat catcttcctt tagggaaaaa aaacccaaa | 1020 |
| aaaacaaaac aagatcgctt actctaacaa atgtccaatt agcaaaatta tccagttgcc | 1080 |
| atgtgctgga actgaaacaa acattccagc ttcactgaaa atgctgagag agccggagac | 1140 |
| taacgaggga gggagactat tgtgcagccg aaaactctcc agttggccct ggacacccat | 1200 |
| aggcgccttg cgtgagagcc aagacaccct tgtacccgca cttccaaact ctggcatgtg | 1260 |
| ggctttgggg aaggggaggg gcgagctcac cacctcagcc actctcagcg ttgtcggatg | 1320 |
| gaaggtttgg tgaattatgg ccctggaggt tcatacttaa atgtgggcca tgtgtatgca | 1380 |

```
aatctgagca gcagctgccc caccacacaa gctgaggtct acaccagcc tcaccagagc   1440 atcttttccc aacctccagg aaccctattc aagcttgaga caggaagatc aaaactgagt   1500
gttcttgaga cgcgacatga gcgtggctga tgagaaactt gaggtgtgga ccagaaagtt   1560
ctttccttat gctcttaaga cctttagaat gatcaagttc tagtttaaag gtgtgtgtgt   1620
gtgtacttta cagatgtgtg tatcaccaca ctcagcaaga ctgtcctaaa gttagtacac   1680 tttccctttta gctgttatgt gatgagatcc aacttggcca cacgagtttc agaggaaaat   1740
gtaattcttt tttcttttct tttcttttct tttctttctt tctttctttc tttttttttt   1800
tttttttttt ttttgtgtgc ttttcaaagt ggatgaccca acacccttcg acattcaagc   1860
tgaggtgaca ctgaagacga acttttttgc cactagaaat gtctgcactg agttactgcc   1920
tataatgaaa ccacatggta agtccaaagt aggactactg tccctcggga agtggccctc   1980
ggtccctcaa atagggcaac caacagggac cactcagggc tgccatttgc ttgtgagatg   2040
gagggtaaaa actgccttat tttatcaagg tgtctggctc tgtacttgag cctttttggct   2100 gtggttgtca gaaccctgtg gtactgatca gttcttgggg tctgtgtcat gagctcaacc   2160
tccatcacag actgcagcat ggccccaaag gtctgtgaca gtcttagaga gttgccctcc   2220
tgcccccgac attgcaagga tgggcccacc cctgacttat ctgccattat aacagtcctt   2280
ctgttccttt cttatgtcaa acaaacaaac gaacaaacaa acaaaaagct tatgagaagg   2340 tgttttcta aatgttgtca gctgagagaa tccgaaagaa gtagtttttt gtggggaaca   2400
ccttacctcc agcccatgag ggttcaatat ttattattaa ttatcattag tttccttcta   2460
atgtttattg ggtgcccacc attataccca gcactggtag taaaaactgg gcccatcata   2520
tacaagagga ccctttcatc cacagagcct ggagctgagc tgggagatag agattttcta   2580
acaaagactc taaggtgtga gatggccaac ttgatagaga gaggcacttc tctgggggatt   2640 tccctttttct gagattgact gtggttctga ggggaagcgc tgttgttttg ttgttgttgt   2700
ttttttaagg ctttaattta ttttatgtat gagtactcta cctgtatgtg catctgttca   2760
ccagcagagg gcatcagatc tcattacaga tggttgtgag ccaccatgtg gttgctgggg   2820
actgagctca ggacctctgg aagagcagtc agtgctctta acctctgagc catctctcca   2880
gcccccggct attgttttta aaaacataa tgttcagggc cagagagaga gagttcggag   2940
attaagagca cttgttgctc ttgcagaaga catgggctca gttcccatgg tttcctgcac   3000
ctatatagct cacagccatt ggtaactcca gttccagagg atccaacacc ctattctaac   3060
ctctttgggc acagggcaat gtgcacatac atacatacat acatacaggc aaaaacactca   3120 tacagacaca tagaataaat agaaattaaa aaatttaatt ttcttaatat tttgaaagag   3180
aattagctca ggatttagga gaattgggtt cccgcccccc ccccctattt ttttttttta   3240
aaccaggatc taactctaca gtgttttctg gccttgaatt tgccttgtag accaggctgg   3300
ccttgaacct ctgacgcctc cccctgcctt tgcttcctgg atgctgggat cccaggcatg   3360
catccctatc ccagcttatc tgtaagaaaa tgtcagtctg aaaactgtag tgagagctga   3420
acttggaccc ctgcccgcca cctgctcact cctccctcat ttcttagtgg gatggattcc   3480
caggaagtct cagccccccc ccctccccccc ccccccccc ccccccccc cccccccccg   3540 cacacacctg cgatccctga actcagaagc ccagcttggc cttcactgcc gattgcctga   3600
tcgaataaac ttcattctgt tgaaataaga attacagcat caagtgagag ccaagccatt   3660
ttgaaagtta aaggaaagct ctcagaggta ggggagggg caagaaccag gtgaaccatc   3720
tttaatcaag cctgcagctt cctgcccctga gggatctctg actgataggg catctgccta   3780
```

```
ggacaggtga cttggctaca cactgttcgc tgaaagacac cgtgcttact atcacggact   3840
tatactttct gtttagcttt tagcacctta ctttccagga tcctaggtct tgcttactca   3900
ctcaagacaa aaatagctt caacaacaat taagtcacta gagggagcta cttgcctgtt   3960 cttcttaa aaacaaaaa caagtggaag ttgtttctgt atgcatggag acacacatag   4020
acacacatgc acaagcatgc atgtgcacac acacacacat gcacactcat gtgtgccaga   4080
caatgctgcc gctggtagat ggtgtggtgt cgtccctctt agagctggct ggaccatctg   4140
gttaatagga tgatctttga tcaccctcca gaacctccca cacatgtgtc cccgcatcaa   4200
agaggacaca agataacttc cccctataat gtggattaga actccctcca aggcacctcg   4260
cagctcctac agttagtgtt tattgtcttc cctgccctct ccctcactcc ctctcttcat   4320
tctctataca ctttgcagac ctaaaacttc atagtccaag ctggccttga actcacagcc   4380
tcccaattgc tggaatcata ttatgaaccc tactgcctct tcagtagctg tgaacttttg   4440
ccaatgtgaa tattaactca tattcatgaa ttggttcatt gtcatgttgc tggtatctta   4500
gactaatgaa gttggaacca gagtggagaa tgggtctccc tccagggtgg cttggatgaa   4560
gttatcacta gagatacact tctaggagag gctcagggat ggaggtggct gcccacagcc   4620
ctagccaact gcacatctag ggaattgaga gccttcatcc tgaagtctcc ttcaaggcac   4680
tgttccttgg gattcaggtg ataagaaggg ggattatttg tgttgaaaga ggaggttttt   4740
ggttttgtct ttgttttttt gttttttttt tttttaataa aacggcctga tgattctgtc   4800
acctgccatg gtgacttggc tctagagata gtcacaatag gtacgccggg tctggtctgg   4860
ggtatactcc aggcttttct gccatgacaa ctgctttaaa aaatgaacac agacacgatg   4920
acaactaaag ggtatatctg ctcaagctag gtggaagtta gagttctgaa caaaggaaaa   4980
cctgggtagc tgataccaga agaactgagg atctcaattt gcatagcaca tcccatcctg   5040
actgagcaag ttcttaggag gctgatcctg gcctgcaagt gggatgagtt tgcccctgtg   5100
gtatttttaa ctttgaggct tgggtggccc ttgggccctg ggtatctgtt ttgtggcttt   5160
gttgtgaaaa catgaaacag atgtgatccc aaggattcct ccctgatgca gtactttagt   5220
ttccttttgg gtggtcccca gctgccacag atctgcagac ccatgaggca accatcttta   5280
aaagcaaggc ttctcaacct ttctccacca gtgacctttt cactctgggg gaaattttaa   5340
tgcaacagca agtatatgaa attggtaaac caacattttc tgataatgaa ccatcaagac   5400
atttcattta aaatgattct tttaaagctg gggatgtagc tcagttgtta tggtacttgc   5460
ctggcacacc gaggaggtcc tcggtttata tattcctagt aatatataaa ttggatatga   5520
tagcaaatgc ctgcactcct aaggtggagg caggaggatc agaaatccaa ggttaccctc   5580
agctgcctgt agagagtttg aagcacaacc tgagatacat gagactctgt caaaaaaaaa   5640
aaaagcacat agaattttac cagttaagat taaggcaaat ttgcatacta atgagatgca   5700
gttcttcttt atttacatag aagtttagat cctggttgag taattggtgc tgcaggatgc   5760
agcaaatctt caacactttc caaaattcaa tcaacatttt tattttacaa ccattggtac   5820
caagaccacc tcttcacata aatacatatt acagaatgtt gatagtatgt tagggccatt   5880
tcaaaagtac ttgaaattc tgtcctaagc tcaagccaaa attcatctca ctaatcttaa   5940
gacagcacct ccagcaatag tctttagaat gaaacattct aacataatac agtccaaga   6000 tacactaacc tgtatttgt gtgctgtaga atgaaacatt ctaacataat tcagtccaaa   6060
gttacgccaa cctgatgccc acagactgtg gaatgatggg aggaaaatgt caaaacattg   6120
```

```
gttctagcaa ttgatctgtt gttttttccgt aagagcagga aacttggcct gtgcaggaac    6180
aagccacggc aggtcaccac atacgagttc cagacttgag tagaagtgtt ttacacggtg    6240
cttcgtggca tttagtagca aaatggcatc taaaatgcac gtgcgtgctc agaaaccaag    6300
gatgcagtaa agtcccgtga cacaaaactg ttgaacactg ccagaaaaac ctcagattta    6360
gagtgcattt gattttaaat tcattttag acacggcaca ttttttaaac tttttactat     6420
tacatatatg caaacatata tgtgtataca tgtaaacata atagtaaaaa ggtttgcaaa    6480
tatatatcat atatatagtt atagaaggga agcctggtca gtggtagaga tgtgtttgtc    6540
cccttggaat acacacaaac agacacatac acacatacac acacacacag attgtatgtc    6600
ttctagactc gctatttgtt catgcattta tttatttgaa ggggtgtgtg tgtttatatg    6660
catcatgtgt ggatgtcaga ggacaaacca caggactcag ttctcccact ttggagcctc    6720
agaatggaac tctggggctg gagagatggc tcagtggtta agatcactga ctgctcttcc    6780
agaggtcttg agttcagttc ccagcaaccg catgatggct cacaaccatc tgtagcagga    6840
tgctctctct ggtatgtctg agaacagcaa caatgtactg ttgctacata aagaataaa    6900
taaatctttt ttaaaaatta aaaaaaaaa aaagtggaa ctcaggtcat ccggctcaga     6960
ggcaagagcc tttagtgtgg agctgtctcc gcggcttttc cttctgtttt attagcagtt    7020
aaacccacac tgcatggaga ctgcggtgca cacctccgta ccttctgaaa tacccctttgt   7080
gatgggcttt cctggcgttg tctgttgcag gtagagtggt gaacatcagc agtctgcagg    7140
ggttaaaagc ccttgagaac tgcagggaag atcttcagga aaagttccga tgtgacacac    7200
ttaccgaggt ggacctggtc gacctcatga aaaagtttgt ggaggataca aaaaatgaag    7260
tccatgagag ggaaggttgg ccagactcgg cttacggggt gtcgaagctg ggggtgacag    7320
tccttacgag gatcctggcc cggcagctgg atgaaaagag gaaagcggac aggattctgc    7380
tcaatgcctg ctgcccggga tgggtgaaga ccgacatggc gagggaccag ggctcccgga    7440
ccgtggaaga ggggggccgaa accccgtttt acttggctct cctgcctcca gatgccactg    7500
aacctcacgg ccagctagtc cgtgacaaag ttgtgcaaac ttggtgaacg tctgctctgg    7560
ggcttgtttg ataaacgtta gcgggagaga tgaatgcagc ctggtgtggt ctgattcttt    7620
cccacatcaa gggggaaggt ccgttcctat ctgcggctct gcaaactcag tctgaacaat    7680
tcgctgtgtc cacactctca gctcatcgtg ttttcaacca gttaatgtgc ctgctttgat    7740
tttcaaatta aaaagatttg tttttatttt                                    7769

<210> SEQ ID NO 59
<211> LENGTH: 4291
<212> TYPE: DNA
<213> ORGANISM: Mus musculus

<400> SEQUENCE: 59
agtggtatga aaggcgcagc ccggggaaag tccgggcaga gcccgagagg tggccagacc      60
gtcatcatcg ttctaataca gctacttcct cagccaccgg tatgagccac gggaagagaa     120
ccgacatgct cccggagatc gccgccgccg tgggtttcct ctccagtctc ctgaggactc     180
ggggctgcgt gagcgagcag agactcaagg ttttcagtag ggcgctccag gacgcactga     240
ccggtgagca cacgtcgggg tcttggaacc actcgggcgc ggccacttct tgcctggggt     300
gtctttatca ctgttctgtg acggggaccc ctacgcgaac aactccgggt ctcagatgtc     360
tttctctaat taatctctga ggccactgat ggtcctctgt cccttcggtt aagtcccgt     420
ctcccagccc tccagtcccc gcctcgctcc cgaggctccg accctcttcc ttgagtacat    480
```

```
tctgagaccc tgacaacacc atgagaaaag tcagtgtgtg tgtgtattca gagtccgagc    540
tcacccttat ctccgaatct tggagaacaa cagaccctca ggggatgtga agccaggcca    600
agctgtgcga cttttatgcg caattgaact ttctagacaa ctcttgagtc ctagccactg    660
ttgctgtata gtcctgagcc tgtcatcata caggcccatt ctgccgcgtg tttacccgct    720
gcaagttgta atctgggccc cctttgtatt ttttcttttt tggtccctct tcaccatctg    780
ccacctattg tagtacagaa aagagcctgg tagcctagcc aactgcgagg gcggggaggg    840
ggtgtgtgtg ttatggaggc agggtgtgag ggacggaggt ggaggagtga taagccaccc    900
tttagcctct gtccgcagct gttataactg gttggttgcc ttgggctgcg atagccatct    960
ctcaacatgt tggcacagat ctgaggacca acagctgttt catcaaaaca aaccattttt   1020
ttatcccctt acctttgcta aagatctcaa aactcttctg atgcggaagg gatgagaggc   1080
cttgtgactt gttgggcaac caacaacatt ggccgcttac ctaccggctt gaaatttca    1140 gtgccttggt cgtcagaggc cctgccggtt cttgctagcc cttcctgcct taaacaggat   1200
tgtgccaaaa atatccatga ccaccataga gcatctacct gaaagctctg ggctgctttt   1260
ccagtgtaca aaaacttgga aaggacccag gaatctttct aagtggcagg gggagtttaa   1320
ggagaggctc ttaaatactg tcgctgagaa gaggaagtct cctccccagc cctctcccct   1380
catcctcccc ttgtggtaaa catcagaaa tgctttctaa cggcgcatct tcctcttgtt    1440
tttttccaca gatcattaca aacaccactg gtttccagaa aaaccatcca aaggttctgg   1500
ctatcgctgt atccgtatca accacaagat ggacccccatc atcagcaagg tggccagcca   1560
gattggactc agccagcccc agctgcaccg gctgctgccc agtgagctga ccctgtgggt   1620
tgatccctat gaagtgtctt accgcatcgg ggaggatggc tccatctgtg tcctgtatga   1680
ggaggccccg gtggctgcct cctatgggct cctcacctgc aagaaccaga tgatgctggg   1740
caggagcagc ccctcgaaga actatgtgat ggccgtctcc agctagatag gagccacccg   1800
accctggcac tctactgttc tcatgctgcc ctgacaacag gccaccgtat acctcaacct   1860
ggggaactgt atttttaaaa tgaagagcta tttatacatg tttttttttt ttttttttaa   1920
gaaaagagga aaaaaccaa aagatttttt ttaaaaaaaa aagaaaaaga aaacaattc    1980 tttaaaggga gctgcttgga agtggcctcc ccaggtgcct ttggagagaa ctgttcttga   2040
ttgcatctgt gagccagtgt ttgcctaggg gaatgggttg gggattggcc tagccaaggt   2100
aaaaggggat tcttggctga tcccccccagg aggtggtgga agggagcaag gttagcaact   2160
gtgaatgaga ggggtcaggg tctgctctgg gttaccgtcc cagctgggat gcctgtatgc   2220
ctggtccctc tcttactcag gggcattcaa gcctgatctt aaataatact acattgccta   2280
atcttctctt ttgttttttcg gctgagatca ggggcagact gaaaggcctc tcctgtccct   2340
tctgttctaa gcagtctctt gaagccgtgt ctcgtttctg agtctaccct tgggggcctg   2400
aagagcttgc tcccagccc ggaatctgtc taaacatttt ttggagggtg ggatgtaagg    2460
caggcgcgca aagactttgg ggctaagatg gagaggacct gcacaaaacc tttgctttgc   2520
tctgtgctgc tttgtatggg tggatagtga ataatttagg gatgatttgc aatggaattt   2580
tgggacccaa agagtatcca atgggggtag gtctttggga cccagtcctt ccttttggga   2640
accacacgac agtctgaatg ctgctaccac tattcctttg agaggtggct caaagctcca   2700
gggaactcca agtcctttct tactgccttc tcttcaagag caaccttccc cattttttct   2760 ttccccttc ctgcggttgg gtcctggagg gccctatttc ctaggacaag cgttctcagt   2820
```

| | |
|---|---|
| cactgtgcaa tagtcccagg atgctctgag accggacctc ccagcccctc ctgatgccct | 2880 |
| ggtaggtttt agggacccat tcttcccatt cttctagggg ttctgactgg ctggtgggcc | 2940 |
| ttgcggagat cttcctgggc cacagggagg gcacctgtgc actgcaggac tacctggtat | 3000 |
| tcttgtaggg ctgccatgaa gagtcaaacc ttgggcacag ctttagctcc ttggtgctca | 3060 |
| gagcacctgt gggggaggtt acctctctct ctctcttagt aaaatccaaa tttatttgta | 3120 |
| gatgtgtgca atatttactg ttctgggttg gagaaaattg ggaaacactg ggaagaaatg | 3180 |
| gctttccttc aggttcagtg acactgatga gggcttctta gaaggcctca agtctctcaa | 3240 |
| actgaaggac agagctagag ctagcccgtc accccttggt gaggattccc ttccccgttt | 3300 |
| ctctccaccg ccatggcatc ctgtgtccta gatttctcag ctcctcagtt tctgctcaaa | 3360 |
| ggtgctattt accaaactct ctgcctgccc gggcagacag gccccagctt cgcacagcct | 3420 |
| tcccaggtgg cttcgtctct cttgctttaa ccttaactct gggcccacag acctgagagc | 3480 |
| tgtggcctac aacaaagctg tgaattgttc cagatggttc ttgtgttttg tccgcacaca | 3540 |
| ggtgcctgcc gtttagaagc tgcctcctgg tctcatgctt aaatcttcaa ttctttactg | 3600 |
| tccttgttca ctttagaaat gacaaaccct agagctggac tgttgagcag gcctgtctct | 3660 |
| cttattaagt aaaaataaga aatagtggta agtttgtaag ctattctgac agaaaagaca | 3720 |
| aaggttacta attgtataat agcgctttta tatggaagac tgtacagctt tatggacaaa | 3780 |
| tgtaaacttt cttttttgtt tttaataaaa atgtagcaga tcgtgtaatg tgtagagaag | 3840 |
| gtggaattcc atagcgctga ctggccctct tagatacaaa ccccttcgtg tttcgtggac | 3900 |
| ttcatcagtt gtcctgagct ccgtctgcag catgcagacg ttataaaaga taccctaggt | 3960 |
| ttgtgacgag gttgcttcca ttgcatcccc tctccttggg aggcggctcc atacttctgt | 4020 |
| ccttgtgaat attgtcacag gtctcttaaa aaacaaacaa acaaaaaagc ccaaaaacca | 4080 |
| atatgttatc tgcacactct gcagccagtt ccatagtttt gctcttggcc attcagcaca | 4140 |
| ttgaagagct ggccagctgt gtccacatct gcgcaagcaa gccaccacgg ctggaaacta | 4200 |
| tataagaaa agaaaccatc cagaaagttc caaagacaca agacttgggt ttggcacaca | 4260 |
| ctaagcacac cagtgcactc gatgcgactg c | 4291 |

<210> SEQ ID NO 60
<211> LENGTH: 3170
<212> TYPE: DNA
<213> ORGANISM: Mus musculus

<400> SEQUENCE: 60

| | |
|---|---|
| agtcatcccg ggaatgctca aaggcccttt gtgaagtcct ttcggtcttc tccggctcct | 60 |
| cctttcttcc caccggtcta aaggacttaa ggaggctcac agagcagggc agggctcact | 120 |
| gctcttcagc atggcttaca ttgccaagtc gttctacgat ctcagtgccg ttggcctgga | 180 |
| tggggagaag atagacttca atacgttcag aggcagggct gtgctgattg agaatgtggc | 240 |
| gtcactctga ggaacaacta cccgggacta caaccagctc aatgagctgc aatgtcgctt | 300 |
| tcccaggcgc ctggtagttc tcggcttccc ttgcaaccag ttcggacatc aggtgaggag | 360 |
| ttccttgggt tctatccaag gagttgatgg acagagcttg agtggaagaa agggttgagt | 420 |
| gtgtcttggg atatctggac ttgaagggca tgctgcatca attgaggtct aggtgaatgt | 480 |
| aaaacatcac agggaagaag tagatatggt ctaagagtaa gcattgaggg tgtgcctttt | 540 |
| agtactgtct ttccaaaatg aggggttgctt ccaggtctct ccactgtgtc tttgagtact | 600 |
| tcattagtta cttgttgaac aaatgagtgg agaaaatagg ttaagaatca ctacgttggc | 660 |

```
atggagggac attcctgtac tcctaggatt gatgtgagtt tggcactaac ctgggcttac    720
cagcaaggtc tcaaaaaaat cactgtgcat acagctcagt gggtagatta cttgcccagc    780
ctatgtgaaa ccatgggttt gatcctaagt gttgcataag ccagctgtga tagcttacct    840
ctaatcccag cacttggaag atggagacag gaaggtcaga aattcaaggt gatccctga    900
ctatagcaaa tatgaacctg aagaactcgt cttagacaaa caattgggat tgagatgtcg    960
gtgacttggg agtccttact tagttccggt tgccttggtt caatgcttta atggctctga   1020
gaccattgag agaggtggct tagttttctg tttgagtttc cacatgtgtt ggtttaatag   1080
aagttgactt agctcataag tttactgtga ggctcatggc ataagacaca tgaaaagtaa   1140
ggagagagat gtggaaatag tgtgcgagta ttatttaaag gcttgtttct aatcagcaag   1200
ctggaaaagg aatatgggag aagggaaagg tccgaagcgt gcactcacct cctctggaca   1260
tcacgtgcgc cttctgtctc tgaataacag gtcagattct tacagagctt cagcatgcac   1320
gcctcaagct atcttttagg gattctgttt ctctttatga tttaactgta ctagcaagcc   1380
aggtgtccct aagtggactc tctaattaga gtcgtcatag ttcaaattgc agtggcagga   1440
aggtacacag gaaggatgtc tgggacatac acaggaagga tggctgagat aaaccagaga   1500
cccagccatc actatgctca caggtccttc ccctgaagc ctctgttcag actttgccgg   1560
ggagagacag gaagggctaa accccattgg aggtgtttct caacccagga gatgcctctg   1620
gccttacacc tcacttgtgg ctggctggct ggctggctgg ctgctgaaag gagtcataac   1680
tcaatatcta cagagccaga gcacaatcag ggcagaggaa agggaaaatg gtaggttgtg   1740
tgcaagcatg cacatttgtg gacatcacat cattgtgggt cctggactaa ttaaaccta   1800
actgacaact tttaccaaca gcaggtagaa gtgcctcctt tccttctctt ccctgatctc   1860
aaggttcctt aaagcaccaa acaccattat gttaattgcc cagggtagat tagggcctga   1920
agcaactgtt aaaaagtgct gaatctctaa ctacatttgt ttgtttgttt gcttgtttat   1980
tggaatgtgt gtgagggtgt gcacacacca cagtgcatgg atagaggtta gagcacaatt   2040
tgtgagagtg gactctcctt aaatcatgtg gtattccctg gcctccaaag ttttgggtgt   2100
agcctccttt ccaccaaggc cataactggt gagatggttc aatgggcaaa agcacttgcc   2160
gcaaacctga tgacctaaat tcagttctca gaactcaggt ggtagaagga gagaagtcaa   2220
tttcataggt tgttctctga cgtgcaaagg tggcactcag tataaaataa atgtaaaaag   2280
tacaaaaacc cacaacacaa tggcagagag agagagagag agagagagag agagagagag   2340
agagagagaa aggcagagca aatggagaag aaacacatat gtgcaacaca cacatgcaca   2400
cacaggaagg agagatcatg gaggagtgtt ggggaagaaa agatttgcac tggtgcaccc   2460
tgggtttctt ctcccttctt tcatgctctt tgtcttctca tccaggagaa ctgtcagaac   2520
gaggagatcc tgaacagcct caagtatgtc cgacctgggg gtgggtacca gcccaccttt   2580
agtcttaccc aaaagtgtga cgtcaatggg cagaacgagc atcctgtctt tgcctacctg   2640
aaagacaagc tgccctaccc ttatgatgac ccgttctccc tcatgaccga tcccaagctc   2700
atcatatgga gtcccgtgcg ccgctcagac gtgtcctgga actttgagaa gttcctcata   2760
gggccagaag gggagccctt ccgtcgctac agccgcagct tccagaccat caacatcgag   2820
cctgacatca aacggctcct caaagttgcc atctagatga gagctgctca gcccaggaat   2880
ctcccactgt ttcccctgag cagtcttcct cagggctcag tgtaccctcg ggagaccctg   2940
ggagaccaag gcattccctg aatatcgtcc ccttgccttc cctaccggcc atttccttta   3000
```

```
gctccctcaa ggctcttggg gagtttgctt ggggctctaa gtctggggta ggttctgggc   3060
cttcacagaa tgatggcatc ttcctaaacc cttctgggag atgtctgaga agttgtgaag   3120
ggtccagagc cagtctgctt tagagtccaa taaagtgtag gtgtggcaat              3170
```

<210> SEQ ID NO 61
<211> LENGTH: 1083
<212> TYPE: DNA
<213> ORGANISM: Mus musculus

<400> SEQUENCE: 61

```
gatgtctgtc tgctaccgtc cgcctgggaa tgagacacta ctgagctgga agggctcgcg    60
ggccaccggc actgcctttc tactgctggc ggcgttgctg ggactgccag gcaatggctt   120
cgtagtatgg agcttagcgg gctgcggcc cacggcgggc cggccactgg cggccacact    180
tgtgctgcac ctggccctgg ccgacggcgc ggtgctgctg ctcacgccgc tctttgtggc   240
tttcctcagc caagaggctt ggcccttggg ccaggtgggc tgcaaggcgg tgtactacgt   300
gtgcgcgctc agcatgtacg ccagcgtgct gctcaccggc ctgctcagcc tgcagcgctg   360
cctggctgtc actcggccct tcctggctcc ccgactgcgc agcccggccc tggcccgccg   420
cttgctgctg ggggtctggc tggccgccct ggtgctcgcc gtcccggccg cggtctaccg   480
ccacctctgg ggcgggcgcg tgtgtcagct gtgccaccca tcgccagtgc acgcagctgc   540
tcatctgagc ctggagaccc tgactgcctt cgtcttgcct tttgggaccg tgctcggctg   600
ctatggcgtg acgctggcgc ggttgcgagg agcgcgctgg ggctcggggc gacaaggcac   660
acgggtgggt cgtctggtga cgccatcgt gctggccttt ggcttgctct gggctcccta    720
ccacgcggtc aatctcctac aggcggtggc cgcgctcgct ccgccggaag gaccctggc    780 caggctcggc ggggcgggcc aggcggcgcg cgctggaact acagccttgg ctttcttcag   840
ttccagcgtc aacccagtgc tctatgtctt cactgcgggg gatttgctgc cgcgggccgg   900
gcctcggttc cttactcgac tcttcgaggg ctctggggag gcccgagggg gcagccgctc   960
tagggagggt accatggaac tccgaactac tcctaagctg aaagtaatgg ggcagggcag  1020
gggcaatgga gaccctggag gcggagatgg gggcaagacg gagaaagaca gtcaagaatg  1080
gta                                                                1083
```

<210> SEQ ID NO 62
<211> LENGTH: 4597
<212> TYPE: DNA
<213> ORGANISM: Mus musculus

<400> SEQUENCE: 62

```
agcggccggg tgcagcctgt gctggtgggc gcggtggccc gcagccttcg gcttgctgca    60
ggactgtgca ggggaccact gtccaagctt cggactactg aggggcgcct gcctcggttt   120
acccttcagc gtctggtgaa atccggcagg tgagcgaccc gaggaggcgg gatagggcag   180
ggtcgcttcc cagttgtgct gactttccag ctacttccag cctgttggct ttagttggcg   240
cctccgctcc tagggctttg tcaacttgag ttgctaaggc tggtccctcc ctttggaagg   300
gcagtgcccg ggctagttcg ccctggcgat gccgggactc tgaggagcct gtgcacttct   360
tgcgtgcttt tgcaaacttc tcacttttc ctcccagcgc ctagggaaag atccgttctg    420
ctccgcgagg gaaacagagc cgttgaccat ggttgcaacg ggcagtttga gcagtaagaa   480 cccgccagc atttcagagt tgttggacgg tggctatcac cctgggagtc tgctaagtgg    540
tgagtctctg ggctgtccac ctcttttccta tccgaaggtt gcggggcccc tctctagtgt   600
```

```
aagcgtccct gcctgagtgc gcgagacttc atctcctcct agagacacag aggactatga    660
aacccatctg agatctcttt ctaaacttcc tttgcattgt ctgcccacca aaacaaacg     720 taagggaat aatgcgttgt tccagtctgc taagaggctc ttggggatga agttccctat    780
ctcatggttg gaacattaag tgtacaggct gggtgtgttt aaagacatgc gcttacttgt    840
gtagctagca ccaccacgtc cgtccccct ccccccccc cccaaattc tcccttttct      900 gtttgccacc taatccttct ctttcccgtc tccagaagac catccttcgg cattttgtta   960
ccacgttagt tttgctttta gaatgttaaa taataagtgt atatgctctt ctcagttcgg  1020
tttgctttcc caccgtgtga tgttgtagag ttatacactt acctcatcag tgagttcctt  1080
ttcgttgcta agtaagattc tattatgaaa tgcacccact gtgcattaat gtcagaagaa  1140
aacttgaaca gccctggttc tacaggaatc atcatttgca acttgaaacg tcaatttcta  1200
atctgacaga ctattcaact atggaagagt ggtgtgagca tatattaagt ggcttaagct  1260
ctttagattt tcttcatcta taagataata ttataattct aaatttgtct gtcttcaatg  1320
tggataaaaa tacagatatg atttggaatc tatttgttgg aatttaaaaa ataaaacaaa  1380
aaacaaaaaa caagcagtgc cctctaagtg agctaatgac atagaaaacc aggagaggag  1440
aggaaggctc gtggccgcag tgtggcatgg cacccggcca agtagtagga ttaatttgga  1500
aggtaggtga ccaaatgcag agctatcttt tttcctctga gtaaacctaa ctttgttttc  1560
ctgggactgt tttgttttgc tcagctaaga aaaactgacc cagcccggtt ataaataaac  1620
tcaggaacct caaaagtcct ctctcctctg cgagcaaact tgaatcaaac aggtcaaagc  1680
caacactgga cctccaggcc atcctagtaa ggacttctaa cgaaaactaa ggctggtaga  1740
tcattagcat tgggacaggc tcactttaca gcgtttgaaa ccattctgca cgccaacggt  1800 cccttttgtta agcaatagtg atgatttta ttccagatgt tctgcatgga cttgtgaaaa  1860
aaaactaaaa taaacttgga aaaccctaca gagagagcaa ggggggaaagg agatcactag  1920 taatcttgga tgaccttgga cagatttttg ccacataatc ctcaagacta cggggagaga  1980
agaaattgta aaagagggtt gttttaacct attcattatg tttatcagag tctttagggc  2040
atagatgagc tttcagtcct gaaaggttag aaggcctgtt ctattaccta catggttaac  2100
agcaaaattg agatgagaga aagcagtatt aaaagcaggt agatatgaag ctagaagtgg  2160
ccagtcttac tatgccagta agacctcgta caccttgctt ctctgttcac taaaactttc  2220
atttctttca gatttcgact actgggatta tgttgtccct gagcccaacc tcaacgaggt  2280
ggtatttgaa gagacaacat gccagaattt ggttaaaatg ttggagaact gtctgtccag  2340
atcaaagcaa accaaacttg gttgctctaa ggtcttggtc cctgagaaac tgacccagag  2400
aattgctcaa gatgtcctgc ggctctcgtc acggagccc tgcggccttc ggggttgtgt   2460
tatgcacgtg aacttggaga ttgaaaatgt atgtaaaaag ctggatagga tcgtgtgtga  2520
tgctagcgtg gtgccgacct tgagctcac gcttgtgttt aagcaggaga gctgcccgtg   2580
gaccagcctc aaggacttct tctttagcag aggtcgcttc tcctcaggcc ttaagcgaac  2640
tctgattctc agctcaggat ttcgacttgt gaagaaaaaa ctgtactccc tgattggaac  2700
gacagtcatt gaagagtgct aaggaggaaa acaattaaa ggcccctaat gagtggataa   2760
taaacctctg aagctatcca gccagtcatt gtagtttgc ctgcttgccc tcaccaggaa   2820
atcccagatt taggcccttt tccttctgtg tgtctcaccc atagcaaccc actttaaagg  2880
ctgatttttt ttttttttgt ccagctttta agacataatt caagagagca aattgcccac  2940
```

| | |
|---|---|
| atatgtgtcc atatgggata gaatggaata aggaggaaaa agaagcaatc tcctttaatt | 3000 |
| ttatatttgg tctcatattt agcaggtagt cttagcaaca gagcaagatc cactttgcct | 3060 |
| aatttgactt tcatgtgccc agggcttgct gttattgtac ccgcctctct ctctctctct | 3120 |
| ctctctctct ctgtgtgtgt gtgtgtgtgt gtgtgtatat atatatatct gtctgtctct | 3180 |
| ctctgtctct ctgtctctct ctctctcctc ccctccctcc ctctctgaga gccatctttt | 3240 |
| caatgacagg acctgacaag atgatgtgca gccccatcaa acatataga gatctgcact | 3300 |
| accagcttcc tccctgaatt tgaagagctt ttacacaaga gggtacagtt aaattgatcc | 3360 |
| gctggattaa acatcacct tacatagagc gaataaacat cacagtgaca agagcatggc | 3420 |
| ttccctgcct ggtggtctcc ccacacccgt gcccaggaga cacgagaagt gtgcctctta | 3480 |
| ctgcaatgat tacatgatgg cttcagtgc ctttgtagta ttgtgtcaac ttggttttcc | 3540 |
| tagttaccaa ctgttgaatg ttatcatttt ttacattgtc tttgagtaga taaaaaaaaa | 3600 |
| aaaagaaatg actgtctttt tgcatagagt tgatttgact gagcaaatat tgattaccca | 3660 |
| tctctaaaga tggagaaggg taatttcaga tcccgtccct ttcggatcca ctaggtcaca | 3720 |
| ttgctgcttt gtgccaccaa gatgcttcct ctccagtgaa gtgtctcacc acatggcagt | 3780 |
| tagctcatct ctggtcttt ctaggaactg gatcacctt ccttaacatc acacttcttt | 3840 |
| ttagttacca atgtgcttat attggcagag cctgacttga ctctgagatg ttgttgctac | 3900 |
| cacagactag atatgaaagt cctatgataa cttaagacaa tcactgcaca tacccagctc | 3960 |
| catccactat atcacagccc attcctagga acagcaaat gcctcttttg cttagctttt | 4020 |
| gcttcatttc aagtaactag atgtttctca ggttttatgg ccatgagaca atttaccttc | 4080 |
| cacgtaactc tgttctattc agcaaggtct tttcttcctt gggtcatgga agtaacatt | 4140 |
| ttcgggtcac ctgcctaggc cttcagtatg agtttgtata cctcaggcac cagcttggct | 4200 |
| gggacaaatg tcttcatcct gaccttacac aaacaagcct gatagttact ggtcttatgg | 4260 |
| gtgacctagg acatcactgt tccaatgagc acgtcttcta acttggggag gtaccacgga | 4320 |
| gctagtcttc acaagactgg gccagtaggc aaaaccctgt tgatctgtag gcttacagat | 4380 |
| gcccaggttc tgaaggtcgc tgtgtttctg tagctgtttt gagtcttgct ggggaagatg | 4440 |
| gtgaggcttc tcaggcatgg acatagatct tttacccgtt agcagttctc tggttctcct | 4500 |
| gcccatttga ctctcaaaat agtaatggct gaaggaggct cttgcaataa caatcctgtt | 4560 |
| aaagtcaatt ttttacaata aaatgttata tattttt | 4597 |

<210> SEQ ID NO 63
<211> LENGTH: 8241
<212> TYPE: DNA
<213> ORGANISM: Mus musculus

<400> SEQUENCE: 63

| | |
|---|---|
| ctgtctgtag aggcggcttg ccacccgagc agagggtcgt gaagttccga gcggaccggt | 60 |
| ccacagaggt tcatctggag aggtgggtcc cctgcgaggt gaaaggcgcc gctgagacac | 120 |
| gcccccaccc cccgtggtgc aagtggttca gcccaagaac ttttcattca taaaaaagac | 180 |
| cagactccga gaggcgcgag tgagtcagaa ccgcagccgc caacgcggac cctaccgaac | 240 |
| atccagccca gggcatgtac cgagactacg ggaaccggg accgagctcc ggggctggca | 300 |
| gcccgtacgg tcgccccgcg cagccccgc aagctcaggc acagaccgcc cagcagcagg | 360 |
| tgagactggc cgaatcgtcg gggggggggg gacctgagtt tggacagcat caggatgct | 420 |
| gggattagtc tagtttgctc cgggatttgg actggggccc cgagcagcat ctgactctgg | 480 |

```
tggtcgcgac cgaggatcct gcacgttctg tgtggtcggg gaacctatgt acccggtggc    540
caaggggacg agcgcagcgg gaagcgcgaa tatctgcgaa ttccccttct cgctcgcccg    600
tatctcccta gctgactgtc tttctgcccc tccgtctccg ttacggtctt acatttcctc    660
ctatctgccc ctaatacgct gtccctctaa atacctgccc catccctgcc tggacaggat    720
cagaggtgtt ctccatctcc agttaataac tgggacctgg ggtctgggca catagagacg    780
gggtccatca gaactcagcc gggacagaga attcttagca gcctgtccga ggctgtccgt    840
gtgttgctct ggttgtccgt gtccctttat ccggtcaagt cctcatctct ttgtgcgcag    900
tatagagccc atgggcccca ggcagtggtt ccgaggggtt cctggagacc acgaagtgtt    960
gggatgtgcg cggggtcacc tgcccggcca cactcgcgct ccacattctc ggcacccgac   1020
gtctctcact gctggatagg ggcacttgag aggttgcagg tgtccatttc ctgtcgaggg   1080
gccgcgagca cgtgtcgcca ggggagggaa ggagctgcgt ccgtttcgcc gagtcacagc   1140
gggccgagtc actgaggctg agtcaccctg ggtgcccctc ccttcctggc ccaaacggc    1200 ccctaaggac cgacgacctg ggagcgagag atgcccctgg cagtgcttct agcccagaac   1260
gggggtcact gagatgctgg gtcccccagt attgggctgg ggacatagct gtccagactt   1320
gcctaagcat gtgaggtgct tcctggactg gagggccccc acatccttag ctcacagagc   1380
ttgaacccag ttttctctcc cagaacgctg agccccacc cccaccgaca ctcaatccca   1440
acacatgcct cagatttctg caagaaaagg aaggaaagga tgccagaccc cttataggag   1500
gcttttactc tcttcacttt atttcatgga cttaaaaaac cccatcaatt ttgaactttc   1560
aagtttttaa gtcgacagct aggcatgcat ttaatcccag cattcaggag gcagaggcag   1620
gcagatctct gggagtttga agccaatttg gtctacaaag tgacttccag gtcagctaga   1680
gctacataat agagatcctg tctcaaaact taaaaaataa aaacaaaaa caaaagccga   1740 ttaaaactct gatttctgag ctatgagagc tggcttctca acagcaatgg aacgttgaat   1800
gatgttaata acagggaaac tgagactaaa taacatgccc cagtctcaaa gcccatcaat   1860
ggccaagctc caagctgatg ctggactccc aagctctggt gctacatgtc tatagtcttg   1920
gtgcctggga ggtagaggca gaggaatcgt gagtttaggt ctagcctgag ctatgtgaga   1980
tcctgcccac cccacccccg gcccccaaac aacaaattct catcctgatt ctcagaattg   2040
ccttgggagc tagaagctga aagtatgccc atctgtgagg actgggtctc aaatcttagt   2100
ttctacttac tagctgtggg tctatgggca actgctctcc tgtctgaaaa caggattatg   2160
gcagctgtgt gagtcactat tgttaaata gttggaacag tgttacgcag tccatacttg   2220
atttaaaaca aaaaaccaaa ctatctctgg tggggaaaca gacagacgaa gagagacatt   2280
ttgtgacctg cccaaaatca cacagctcct gaacaagtaa gtttctggtt gccaaatgtt   2340
gctccttgtg gtctcccaaa actggtatct acactgaggt gaagggagac agaagtccag   2400
cctctgtccc cgggaagccc ctcagtccac acagaccta tcatttccct tcttatctct   2460
cagaagttcc accttgtgcc aagcatcgac agcagcagcc aggaactgca ctggatggtg   2520
cagcctcatt tcctgggacc cactggctat ccccgacctc tggcctatcc ccagtacagt   2580
ccccctcagc cccggccagg agtcatacga gccctagggc cacctccggg ggtgcgtcgc   2640
aggccctgcg agcaggtaag aaacagcgat gttt cacttt ccatagcccg tagggtcct    2700 actagacagg gacaggatct tgctacgagg gaatttctat tcagcattga agttcctgag   2760
aggccaagaa ggaggtaaaa ggtcaccttt gagtcaagga aggcttcctg gagaaggcta   2820
```

-continued

```
cacgttaacc taaaccacgg ataggatttg cgtatggaag ctgaaaagaa tcttctggga    2880
ggagggttgg aggcacagaa ttgaggtgaa ggggacagag tgttaagtga gcatgtctcc    2940
actgtctgac gtgcacaggg tggaaggaag cctgatgctg gctttgtacc tcggggtgac    3000
tcttcttttc aacagtcacg gaatctcagc ctatttcttt taattatcac aaaaagtgag    3060
tgggcagtgg tggctcacac cttaaatttc agcactgggg aggcagaggc aggtggatct    3120
ctgggttcaa ggcagcctg gtttacagag tgagttccag gacagccaag gctacagaga     3180
aaccctgtct caagaaaggg aaaaaaaaag tgaatgggaa atgtatttca atttttccat    3240
cttccatcag aggaagtgaa gcatagaggg gtactcactt gtccagattc atacaaatgt    3300
gagtaatgag acaggactgg tcctggcctg aggtctactc aactcccaaa gtcagagctt    3360
aatgagccac tgtctcaatg ggagctcaca gaaggctgca gagggagtga gctgagaact    3420
tttgcctccc tgaatgcctt tctaaaataa agaagggtgt gttttggttg gtttgtagag    3480
gtggggtctt gagagcctcc tgccttccca agtgctagga gtaggtgt atgctagata      3540
cccgacaggg atgacggatc ttttaggcca tagcactttc tttcctctcc ctgaagtact    3600
gagactgagt ctagtgcagg gaggcctcca tactaaaaag ctgggtgtac ccgtaatccc    3660
agaactcgga aaatcaagac aggaggagcc attcaagtcc cgctcagaaa catggagagt    3720
ttaaggtcag cctgggatat ataaacccta tctccgataa ccaaacaaca atcaaagcaa    3780
acctgactta agtgttaagt aggaaagaat atgctgtaag tcatcagcct ggctggggga   3840
ctgaccgcct tgagggact gaagaacctg cttcaagccc ggagccctgc actcaacccc     3900
tagtggatgc acacacagat ccttgccatg atggctcgaa gagggatggc aagaccctgg    3960
gagatatgtg agattggcca gagaagagcc agcaacaggc ttcccagcaa gggaacagct    4020
tacctctgtg atcagctggg gcgtgagcaa gaggcaagcc cagggtgaat ccttcccttta   4080
gccctgtcct gaggagacac cttttgacca cgggtactag tgggttggag ctgtgagctg    4140
tgggtaggtg gcttcccctc ggtgtgctct ggaacttgaa caaatcactc atccttcctg    4200
agcttcctca catgtgagtg tgcagagatc tggatgggtg actcagcagc ggctctggct    4260
gctccttaga ggatccgggt tccaatctca gcacccacgt ggcaactcac tgtccacaac    4320
gtcccccaaa ggttctgatg ccctcttctg gcctccacca gcactgaatg cacaaggtgc    4380
tcatacaaac acacaggcaa aatactcaga ggtaaatttg ttcttttttt tcttttgaga    4440
cagggtttct ctgtatagcc ctggctgtcc tagaactcac tctacagacc aggctggcct    4500
caaactcaca gaggcatctg cctgcctccc aagtgttggg accaaagatg tatgccatca    4560
ctataagcct tttttttttt tgtaaatttt atttatgaat gagtgcttcc atgtatacct    4620
tcatgccagg agagggcatc agatcctatt ataggtggtt gtgagccacc gtgtgtggct    4680
gggatttgaa ctcaggacct ctgaaagagg agctcttaac tgctaaaaca tctctctagc    4740
cccagtctac atattttaaa tcttttttta agattgattt atttattata cataagtaca    4800
ttgtagctgt cttcagacac tccagaagag ggcgtcagat cttgttatgg atgattgtga    4860
gccaccatgt ggttgctggg atttgaactc aggacctttg aagagtagt caatgctctt     4920
acccgctgag ccatctcacc agccccttttt ttaatcttta aaaaaaaaag gggggggcc    4980
tggagagatg gctcagccgt taagagcact gaatgctttt ccagaggtcc tgagttcaat    5040
tcccaacaac cacatggtag ctcacaacca tctgtaatgg gatccaatgc cctcttctgg    5100
tgtatctgaa gacagcaagg gtctactcac atatgttaaa taaataaata aaaatttaaa   5160
agccaggtgg tgttggttca gacagcagat ctctgtttaa ggccagcctg gtctgatcta    5220
```

```
caaaccaagt tccaggacag ccagggctac acagagaaac cctctaaaaa accaatctat    5280
gtaggggtg ctggtgaaat ggctccgtgg gtaaaggtac ttgctgcgaa attaatgacc     5340
tgagttcaat ccttgaaatc cacacagtag aaggagagaa ccaacctcca agggtgctat    5400
gacacacaca cacacacaca cacacacaca cacacacaca cacacacaca cacgactata    5460
tatatgaata tatgactcta gccaggcata gtgtggcaca tgcctttaat cacagtactt    5520
gggaggcaga ggcaggtgaa gtttgaggcc agcctacaga gtgaattcca tgacagctag    5580
aactatgaag atgaaccctg tctttaaaaa caacagcaac ataaagaatc tatgtaggga    5640
agctggaagg gatgctgata cagtctgcaa tcctattact ctagaggtgg aagccaaaga    5700
atcaggggtt tcaggccggt cttgcctata cactgagcta aaggccagcc tgggacacat    5760
gagactttgt ctcttttaaa aagacaaaac aaggggttg gttagatggc tcagtgggta    5820
agagcaccca actgctcttc tgcaggtccg aagttcaaat cccagcaacc acatggtggc    5880
tcacaaccat ctgtaacgaa atctgagtcc ctcttctgga gtgtctgaaa caactacag    5940
tgtacttaca tataataaaa ataaataaat cttaaaaaaa aaaaaaaag acaaaacaag    6000
ccagatgagg tctgtgagtt ccaggccagc ctggtctata aatcaagttc aaggccaggc    6060
agggctactc agagattctg tctaaaatac aaagaaacaa aactacaaaa agcagaaaaa    6120
ggaatctacg aaagggctgg tgaaggggtg taactcagtg gtagagcatt tgccgagcta    6180
gcatgtacca agccatgggt ttgatcccta gcactaagca aagaaaagt cctacaaagg    6240
gctttgttgg catagtagat tgattcccag tagcttttgg cactcaagag cacctttctac   6300
aattcacagc tcctggggga agaaatccca tcttccacag atgaggaggc tgagagtcct    6360
gtgaaaagag ataatcatgt ctcatacact caggagagaa ggctacttct gcctgagaaa    6420
tgaaaaggct tcctggggtc ccaacatctt agtccagtcc taagatgcgg aagggaggaa    6480
gatcaaagtt tacagagagg gaaagcattt caggaaagaa accagcagta agctaggtg    6540
tgtgtgagct ggaaatgtca ccaatgagat gacaagcgtc cggtacagag aagcaactgt    6600
ggagtgttgg gtggtggcac ctagactaca gactgaagga aagctggatg accagctcag    6660
ggcagctggt ggctcagagt cagcctcatt gtctcccttc ttctatccca acctagatca    6720
gcccagagga ggaagagcgc cgcagggtga gacgcgagcg gaacaagcta gcagctgcta    6780
agtgcagaaa ccgaagaaag gagctgacag acttcctgca ggcggtgagc atcatcccca    6840
ggcccggacc cacagagccc caagaggggt ctcggctccc aagaacacaa agacccaaa    6900
attactcctc aggactctgt catcctccct gcctgtgggg aagtcctgga aaaggataa    6960
gggaaagtgg cttaaatatt gtttgtcggg cttcgaggca gagtcgaaga tggtaggcag    7020
caattctcct aagatgcccc cgtctgatgg gagtcatggc cattttctcc cagaggctca    7080
cgggagggag ttgcagtcca gacttgttgg ggatgacagg cacagtccct actccagcct    7140
gaggcttggg gatctttagc cttcattttc ctatctttct gctaatcctg taaaggagac    7200
cgacaaattg gaggatgaga atcggggct gcagcgagag attgaagagc tgcagaagca    7260
gaaggaacgc cttgagctgg tgctggaagc ccatcgcccc atctgcaaaa tcccagaagg    7320
agacaagaag gacccaggtg gttctggcag caccagcggt gctagcagcc caccagcccc    7380
cggccgccca gtgccttgca tctccctttc tccaggaccc gtacttgaac cggaagcact    7440
gcataccccc acgctcatga ccacaccctc tctgactcct tttactccga gtctggtttt    7500
cacctatcct agcacaccag aaccttgctc ctccgctcac cgaaagagta gcagcagcag    7560
```

| | |
|---|---|
| tggcgacccc tcctccgacc ccctgggctc tcctacactc ctggctttgt gaggcaccca | 7620 |
| gccacatccc ttgctggtgc tactccaagc catccccttt ctcccattga tccagcaggc | 7680 |
| ctggaccata cccttgcccc aaaccagcag atctttatc tcttccgact agaacaaaca | 7740 |
| cattatgctt tgatgtagag ccagcttgga ggggatcccc aaagctgctc actgttttc | 7800 |
| tagagctggc ctatcataat ttgcacaaaa ttagaggaaa atatgttccc tctgccagag | 7860 |
| aacgcctggc agcccagact ttgtagatcc caggggtcc tttgacaccc ttaccccttg | 7920 |
| cagaccactt tcccacacca cgtcactttc ttcatgttat ccagcctact ctacacctag | 7980 |
| acagaaggtg ccctttgact agcctagaac actaactcac acagcatcaa cagccagcag | 8040 |
| caccggacat cctgcaggct cctcctgaat ggcacaacgc aggaggcgcc aggggcttct | 8100 |
| gtgaggagcg gagctgcact ccctagctct gagaagcgct tagcttcagg gtatccgagc | 8160 |
| ctccaccgca aggcagctg ctatttattt tcctaaagag actattttta tacaaacctt | 8220 |
| ccaaaatgga ataaaaggct t | 8241 |

<210> SEQ ID NO 64
<211> LENGTH: 3750
<212> TYPE: DNA
<213> ORGANISM: Mus musculus

<400> SEQUENCE: 64

| | |
|---|---|
| cgagagatcc cagcgcgcag aacttgggga gccgccgccg cgattcgccg ccgccgccag | 60 |
| cttccgccgc cgcaagatcg gcccctgccc cagcctccgc ggcagccctg cgtccaccac | 120 |
| gggccgcggc taccgccagc ctgggggccc acctacactc cccgcagtgt gccctgcac | 180 |
| cccgcatgta acccggccaa ccccggcga gtgtgccctc agtagcttcg gccccgggct | 240 |
| gcgcccacca cccaacatca gttctccagc tcgctggtcc gggatggcag cggccaaggc | 300 |
| cgagatgcaa ttgatgtctc cgctgcagat ctctgacccg ttcggctcct ttcctcactc | 360 |
| acccaccatg gacaactacc ccaaactgga ggagatgatg ctgctgagca acggggctcc | 420 |
| ccagttcctc ggtgctgccg aaccccaga gggcagcggc ggtaatagca gcagcagcac | 480 |
| cagcagcggg ggcggtggtg gggcggcag caacagcggc agcagcgcct caatcctca | 540 |
| aggggagccg agcgaacaac cctatgagca cctgaccaca ggtaagcggt ggtctgcgcc | 600 |
| gaggctgaat ccccttcgt gacgacccaa acgtccagtc ctttcctgca cggacctgtt | 660 |
| tctatcccctt agggatggga ctggggtttc cctctatttc acacagctcc agggtcttgt | 720 |
| gttagaggga tgtctaggga caccccctac cctccatcct tgcgggtgcc cggaaggcag | 780 |
| gacgtttgtt ttggatggag aactcaagct gcgtgggtgg ctggagggg tgggggggag | 840 |
| ggtttgtttt gatgagcggg gttgcccct ccccgcgcg cgcggtgtcg cgcgccttgt | 900 |
| ttgcagattg ttccccaagg cagggctgaa atctgtgacc agggatgtcc cgccgcccag | 960 |
| ggtcggggc gcgcattagc tgtagccact agggtgctgg cggattccc tcgcccgcgc | 1020 |
| agcctcgctg cggagcgctc tcggagctgc agtagagggg ggattctctg tttgcgtcag | 1080 |
| ctgttgaaat gggctctgcc actggagcag gtccaggaac attgcaatct gctgctatca | 1140 |
| attattaacc acatcgggag tcagtggtag ccgggcgacc tcttgccagg ccgcttcggg | 1200 |
| tctcatcgtc cagtgattcc tctccagtaa ccaggcctct ctgttccctt tcctgccaga | 1260 |
| gtccttttct gacatcgctc tgaataatga gaaggcgatg gtggagacga gttatcccag | 1320 |
| ccaaacgact cggttgcctc catcacccta tactggccgc ttctcccctgg agcccgcacc | 1380 |
| caacagtggc aacactttgt ggcctgaacc ccttttcagc ctagtcagtg gcctcgtgag | 1440 |

-continued

```
catgaccaat cctccgacct cttcatcctc ggcgccttct ccagctgctt catcgtcttc    1500
ctctgcctcc cagagcccgc ccctgagctg tgccgtgccg tccaacgaca gcagtcccat    1560
ctactcggct gcgcccacct ttcctactcc caacactgac attttcctg agccccaaag     1620 ccaggccttt cctggctcgg caggcacagc cttgcagtac ccgcctcctg cctaccctgc    1680
caccaaaggt ggtttccagg ttcccatgat ccctgactat ctgtttccac aacaacaggg    1740
agacctgagc ctgggcaccc cagaccagaa gcccttccag ggtctggaga accgtaccca    1800
gcagccttcg ctcactccac tatccactat taaagccttc gccactcagt cgggctccca    1860
ggacttaaag gctcttaata ccacctacca atcccagctc atcaaaccca gccgcatgcg    1920
caagtacccc aaccggccca gcaagacacc cccccatgaa cgcccatatg cttgccctgt    1980
cgagtcctgc gatcgccgct ttctcgctc ggatgagctt acccgccata tccgcatcca     2040
cacaggccag aagcccttcc agtgtcgaat ctgcatgcgt aacttcagtc gtagtgacca    2100
ccttaccacc cacatccgca cccacacagg cgagaagcct tttgcctgtg acatttgtgg    2160
gaggaagttt gccaggagtg atgaacgcaa gaggcatacc aaaatccatt taagacagaa    2220
ggacaagaaa gcagacaaaa gtgtggtggc ctccccggct gcctcttcac tctcttctta    2280
cccatcccca gtggctacct cctacccatc ccctgccacc acctcattcc catccctgt     2340 gcccacttcc tactcctctc ctggctcctc cacctaccca tctcctgcgc acagtggctt    2400
cccgtcgccg tcagtggcca ccacctttgc ctccgttcca cctgctttcc ccacccaggt    2460
cagcagcttc ccgtctgcgg gcgtcagcag ctccttcagc acctcaactg gtctttcaga    2520
catgacagcg acctttctc ccaggacaat tgaaatttgc taaagggaat aaaagaaagc     2580
aaagggagag gcaggaaaga cataaaagca caggagggaa gagatggccg caagaggggc    2640
cacctcttag gtcagatgga agatctcaga gccaagtcct tctactcacg agtagaagga    2700
ccgttggcca acagccctt cacttaccat cctgcctcc ccgtcctgt tccctttgac       2760 ttcagctgcc tgaaacagcc atgtccaagt tcttcacctc tatccaaagg acttgatttg    2820
catggtattg ataaatcat ttcagtatcc tctccatcac atgcctggcc cttgctccct     2880
tcagcgctag accatcaagt tggcataaag aaaaaaaaat gggtttgggc cctcagaacc    2940 ctgcccctgca tctttgtaca gcatctgtgc catggatttt gttttccttg gggtattctt   3000
gatgtgaaga taatttgcat actctattgt attatttgga gttaaatcct cacttttgggg  3060 gaggggggag caaagccaag caaaccaatg atgatcctct attttgtgat gactctgctg    3120
tgacattagg tttgaagcat ttttttttc aagcagcagt cctaggtatt aactggagca     3180
tgtgtcagag tgttgttccg ttaattttgt aaatactgct cgactgtaac tctcacatgt    3240
gacaaagtat ggtttgtttg gttgggtttt gttttgaga atttttttgc ccgtccttt      3300 ggtttcaaaa gtttcacgtc ttggtgcctt ttgtgtgaca cgccttgccg atggcttgac    3360
atgcgcagat gtgagggaca cgctcacctt agccttaagg gggtaggagt gatgttttgg    3420
gggaggcttt gagagcaaaa acgaggaaga gggctgagct gagctttcgg tctccagaat    3480
gtaagaagaa aaaatttaaa caaaaatctg aactctcaaa agtctatttt tctaaactga    3540
aaatgtaaat ttatacatct attcaggagt tggagtgttg tggttaccta ctgagtaggc    3600
tgcagttttt gtatgttatg aacatgaagt tcattatttt gtggttttat tttactttgt    3660
acttgtgttt gcttaaacaa agtaacctgt ttggcttata aacacattga atgcgctcta    3720
ttgcccatgg gatatgtggt gtgtatcctt                                      3750
```

<210> SEQ ID NO 65
<211> LENGTH: 28
<212> TYPE: DNA
<213> ORGANISM: Artificial Sequence
<220> FEATURE:
<223> OTHER INFORMATION: Ephx1 forward primer

<400> SEQUENCE: 65
cggaattcac acaccagaag agggcatc                                          28

<210> SEQ ID NO 66
<211> LENGTH: 31
<212> TYPE: DNA
<213> ORGANISM: Artificial Sequence
<220> FEATURE:
<223> OTHER INFORMATION: Cbr3 forward primer

<400> SEQUENCE: 66
cggaattcca ttgctgcctt gatcacataa c                                      31

<210> SEQ ID NO 67
<211> LENGTH: 27
<212> TYPE: DNA
<213> ORGANISM: Artificial Sequence
<220> FEATURE:
<223> OTHER INFORMATION: Btg2 forward primer

<400> SEQUENCE: 67
cgggagatct gatgaaatgt cttgctg                                           27

<210> SEQ ID NO 68
<211> LENGTH: 28
<212> TYPE: DNA
<213> ORGANISM: Artificial Sequence
<220> FEATURE:
<223> OTHER INFORMATION: Perp forward primer

<400> SEQUENCE: 68
cggaattctt tgagccgaca gaaccaat                                          28

<210> SEQ ID NO 69
<211> LENGTH: 28
<212> TYPE: DNA
<213> ORGANISM: Artificial Sequence
<220> FEATURE:
<223> OTHER INFORMATION: Ephx1 reverse primer

<400> SEQUENCE: 69
ggggtaccgt cgctctcggg ttcctact                                          28

<210> SEQ ID NO 70
<211> LENGTH: 30
<212> TYPE: DNA
<213> ORGANISM: Artificial Sequence
<220> FEATURE:
<223> OTHER INFORMATION: Cbr3 reverse primer

<400> SEQUENCE: 70
acgcgtcgac gacacacgga ccacctgatg                                        30

<210> SEQ ID NO 71
<211> LENGTH: 24
<212> TYPE: DNA
<213> ORGANISM: Artificial Sequence
<220> FEATURE:
<223> OTHER INFORMATION: Btg2 reverse primer

```
<400> SEQUENCE: 71
gataagtcga caccactcgg ggag                                          24

<210> SEQ ID NO 72
<211> LENGTH: 30
<212> TYPE: DNA
<213> ORGANISM: Artificial Sequence
<220> FEATURE:
<223> OTHER INFORMATION: Perp reverse primer

<400> SEQUENCE: 72
acgcgtcgac gcggagcgga ggaacgccgg                                    30

<210> SEQ ID NO 73
<211> LENGTH: 24
<212> TYPE: DNA
<213> ORGANISM: Artificial Sequence
<220> FEATURE:
<223> OTHER INFORMATION: YWHAD-1 forward primer

<400> SEQUENCE: 73
ctggtgatga caagaaagga attg                                          24

<210> SEQ ID NO 74
<211> LENGTH: 18
<212> TYPE: DNA
<213> ORGANISM: Artificial Sequence
<220> FEATURE:
<223> OTHER INFORMATION: YWHAD-2 forward primer

<400> SEQUENCE: 74
gccgacacac cccatcag                                                 18

<210> SEQ ID NO 75
<211> LENGTH: 22
<212> TYPE: DNA
<213> ORGANISM: Artificial Sequence
<220> FEATURE:
<223> OTHER INFORMATION: DsRed-1 forward primer

<400> SEQUENCE: 75
agtacggctc caaggtgtac gt                                            22

<210> SEQ ID NO 76
<211> LENGTH: 19
<212> TYPE: DNA
<213> ORGANISM: Artificial Sequence
<220> FEATURE:
<223> OTHER INFORMATION: DsRed-2 forward primer

<400> SEQUENCE: 76
gtgaagctgc ccggctact                                                19

<210> SEQ ID NO 77
<211> LENGTH: 21
<212> TYPE: DNA
<213> ORGANISM: Artificial Sequence
<220> FEATURE:
<223> OTHER INFORMATION: Ephx1-1 forward primer

<400> SEQUENCE: 77
caaagccatc agccaaagaa g                                             21

<210> SEQ ID NO 78
```

<210> SEQ ID NO 79
<211> LENGTH: 20
<212> TYPE: DNA
<213> ORGANISM: Artificial Sequence
<220> FEATURE:
<223> OTHER INFORMATION: Ephx1-2 forward primer

<400> SEQUENCE: 78
tgtgggctgt gctctgaatg             20

<210> SEQ ID NO 79
<211> LENGTH: 22
<212> TYPE: DNA
<213> ORGANISM: Artificial Sequence
<220> FEATURE:
<223> OTHER INFORMATION: Hprt forward primer

<400> SEQUENCE: 79
ttgctcgaga tgtcatgaag ga             22

<210> SEQ ID NO 80
<211> LENGTH: 19
<212> TYPE: DNA
<213> ORGANISM: Artificial Sequence
<220> FEATURE:
<223> OTHER INFORMATION: YWHAD-1 reverse primer

<400> SEQUENCE: 80
ggtgtgtcgg ctgcatctc             19

<210> SEQ ID NO 81
<211> LENGTH: 20
<212> TYPE: DNA
<213> ORGANISM: Artificial Sequence
<220> FEATURE:
<223> OTHER INFORMATION: YWHAD-2 reverse primer

<400> SEQUENCE: 81
gcaatggctt catcgaaagc             20

<210> SEQ ID NO 82
<211> LENGTH: 18
<212> TYPE: DNA
<213> ORGANISM: Artificial Sequence
<220> FEATURE:
<223> OTHER INFORMATION: DsRed-1 reverse primer

<400> SEQUENCE: 82
catcacgcgc tcccactt             18

<210> SEQ ID NO 83
<211> LENGTH: 23
<212> TYPE: DNA
<213> ORGANISM: Artificial Sequence
<220> FEATURE:
<223> OTHER INFORMATION: DsRed-2 reverse primer

<400> SEQUENCE: 83
gtactgctcc accacggtgt agt             23

<210> SEQ ID NO 84
<211> LENGTH: 26
<212> TYPE: DNA
<213> ORGANISM: Artificial Sequence
<220> FEATURE:
<223> OTHER INFORMATION: Ephx1-1 reverse primer

<400> SEQUENCE: 84

```
aacctatcta tcctctggtg caagtc                                         26

<210> SEQ ID NO 85
<211> LENGTH: 20
<212> TYPE: DNA
<213> ORGANISM: Artificial Sequence
<220> FEATURE:
<223> OTHER INFORMATION: Ephx1-2 reverse primer

<400> SEQUENCE: 85
aggcctccat cctccagttc                                                20

<210> SEQ ID NO 86
<211> LENGTH: 24
<212> TYPE: DNA
<213> ORGANISM: Artificial Sequence
<220> FEATURE:
<223> OTHER INFORMATION: Hprt reverse primer

<400> SEQUENCE: 86
agcaggtcag caaagaactt atag                                           24

<210> SEQ ID NO 87
<211> LENGTH: 21
<212> TYPE: DNA
<213> ORGANISM: Artificial Sequence
<220> FEATURE:
<223> OTHER INFORMATION: Nope reverse primer 2

<400> SEQUENCE: 87
agggccgggc tcgggccgct g                                              21

<210> SEQ ID NO 88
<211> LENGTH: 28
<212> TYPE: DNA
<213> ORGANISM: Artificial Sequence
<220> FEATURE:
<223> OTHER INFORMATION: Cdkn1a forward primer 2

<400> SEQUENCE: 88
cggaattcag ggtaaaggca caggaggt                                       28

<210> SEQ ID NO 89
<211> LENGTH: 21
<212> TYPE: DNA
<213> ORGANISM: Artificial Sequence
<220> FEATURE:
<223> OTHER INFORMATION: Nope reverse primer 2

<400> SEQUENCE: 89
agggccgggc tcgggccgct g                                              21

<210> SEQ ID NO 90
<211> LENGTH: 28
<212> TYPE: DNA
<213> ORGANISM: Artificial Sequence
<220> FEATURE:
<223> OTHER INFORMATION: Cdkn1a forward primer 2

<400> SEQUENCE: 90
cggaattcag ggtaaaggca caggaggt                                       28
```

POLYNUCLEOTIDES COMPRISING A REPORTER SEQUENCE OPERATIVELY LINKED TO A REGULATORY ELEMENT

This invention relates to methods for detecting agents that are genotoxic or are oxidative stress-inducing, and to molecules and cell lines that may be employed in such methods.

The listing or discussion of an apparently prior-published document in this specification should not necessarily be taken as an acknowledgement that the document is part of the state of the art or is common general knowledge.

DNA damage may be induced by a range of agents including ultraviolet light, X-rays, free radicals, methylating agents and other mutagenic compounds. DNA damage can also be caused indirectly either by agents that affect enzymes and proteins which interact with DNA (including polymerases and topoisomerases) or by promutagens (agents that can be metabolised to become mutagenic). Any of these agents may directly or indirectly cause damage to the DNA that comprises the genetic code of an organism and cause mutations in genes. Such agents may be collectively known as genotoxic agents.

Exposure to a range of agents may also directly or indirectly lead to the production of reactive oxygen species that can react with various cellular biomolecules and affect their functionality. These agents are collectively known as oxidative stress-inducing agents.

Industry yearly develops millions of new chemical compounds for a wide range of applications. These compounds may react with various cellular structures and organelles, including DNA, proteins and lipids and affect multiple cellular processes. Reactivity towards cellular DNA of exposed organisms may cause mutations, affect genome stability and may ultimately lead to the development of genetic diseases and cancer. Compound exposure may also result in the formation of reactive oxygen species which have also been implicated in cellular dysfunctioning, the generation of mutations and aging. One regulator in the cellular response to a wide variety of cellular stressors is the p53 tumor suppressor gene [1]. The p53-induced stress responses include activation of DNA repair systems, cell cycle checkpoints, activation of gene transcription and protein expression, and induction of apoptosis or cellular senescence. Activation of these pathways provides protection against the mutagenic and possibly oncogenic consequences of exposure to DNA damaging and oxidative stress-inducing compounds and enhances organism survival.

A worldwide legislation demands rigorous testing of new chemicals for potential genotoxic or other deleterious properties of newly developed chemical compounds. For the chemical and pharmaceutical industries it is important that these tests are cheap, fast and predictive for human health risk. In addition, these tests should preferably be applicable as high-throughput assays and should provide insights into the mode of toxicity of the compounds.

Various in vitro assays for genotoxicity testing are currently in use.

The oldest and widely used test is the Ames test, which is a *Salmonella* based test for bacterial mutagenicity. However, the Ames test has a relatively low sensitivity and fails to establish genotoxicity of compounds that interact with cellular structures that are specific for eukaryotic cells. Further, due to the low mutation frequencies that are induced by compounds, the Ames test is not suitable as a high-throughput test system.

Other tests for bacterial mutagenicity include those that depend on the bacterial SOS response that is activated upon exposure to genotoxic compounds. The SOS/umu-assay is a *Salmonella* bacterial test that is based on beta-galactosidase expression under control of the umuC stress response [2]. In the Vitotox assay, a bioluminescent marker is placed under control of the SOS response [3], and the assay was recently developed to increase testing throughput [4].

To establish genotoxicity in a eukaryotic test system, various yeast-based assays have been developed. The DELL assay is based on reversion mutations in modified *Saccharomyces cerevisiae* strains containing a deletion in the his3 gene [5, 6]. Reversion depends on intrachromosomal recombination and is therefore restricted to specific classes of carcinogens. The Greenscreen (GS) assay uses the enhanced green fluorescent protein (eGFP) coupled to the RAD54 DNA damage repair gene [7]. Validation of the yeast Greenscreen assay showed high specificity and sensitivity in the identification of a large collection of known genotoxic compounds [8].

Development of sensitive mammalian cell based genotoxicity tests, which are more relevant for risk assessment in higher organisms, has proven challenging [9]. The comet assay depends on higher mobility of cells with DNA breaks, in agarose gels and is a widely used test for chromosomal damage. The assay is often used in combination with a chromosomal aberration test or an in vitro micronucleus test. However, these assays have reduced sensitivity, will only score positive when using compounds that induce DNA strand breaks and are not suitable for high throughput screening. Recently there has been efforts to improve the throughput of the comet assay [10].

H2AX is a specific variant of the H2A histone protein family and is rapidly phosphorylated by various kinases, including ATM and ATR, involved in the DNA damage response. It was proposed that phosphorylation of H2AX ($\gamma$H2AX) could be used as a sensitive marker for detection of DNA damage [11]. Recent evaluation of the $\gamma$H2AX assay shows that phosphorylation of H2AX can be used to assess genotoxicity [12].

The Greenscreen HC assay uses the human lymphoblastoid TK6 cells and is a validated mammalian in vitro test for genotoxicity [9, 16]. The assay depends on an eGFP reporter linked to the GADD45a (Growth Arrest and DNA Damage) gene. GADD45a is regulated by the p53 tumor suppressor and plays an important role in cell cycle control, DNA repair mechanisms and signal transduction and thereby is required for genome maintenance [17]. The GreenScreen HC GADD45a assay provides a reliable and sensitive genotoxicity test that allows discrimination between genotoxic and non-genotoxic carcinogens [18]. The fluorescent eGFP reporter can be detected using flow cytometry thereby allowing screening in a high throughput setup. However, the GreenScreen HC assay is solely representative for the global p53 response and provides little mechanistic information on the reactivity of genotoxic compounds.

Given the demand for genotoxicity assays, there remains a demand for fast and highly sensitive, animal free test systems to establish the genotoxicity of both known and novel chemical compounds.

Surprisingly and unexpectedly, the inventors have now identified 16 genes in mice that can serve as biomarkers for exposure to genotoxic stress, namely Bscl2 (Bernardinelli-Seip congenital lipodystrophy 2 homolog (human)), Cbr3 (carbonyl reductase 3), Ephx1 (epoxide hydrolase 1, microsomal), Nope (immunoglobulin superfamily, DCC subclass, member 4), Cdkn1a (cyclin-dependent kinase inhibitor 1A (P21)), Perp (TP53 apoptosis effector), Pltp (phospholipid transfer protein), Srxn1 (sulfiredoxin 1 homolog (*S. cerevisiae*)), Cgref1 (cell growth regulator with EF hand domain 1), Ltb4r1 (leukotriene B4 receptor 1), Btg2 (B-cell translocation gene 2, anti-proliferative), Gpx2 (glutathione peroxidise 2), Ltb4r2 (leukotriene B4 receptor 2), Ddit4l (DNA-damage inducible transcript 4-like), Fosl1 (Fos-like antigen 1), and Egr1 (Early growth response 1). The inventors have developed highly sensitive mouse embryonic stem cell systems that allow establishing genotoxicity at non-cytotoxic concentrations.

Accordingly, a first aspect of the invention provides a polynucleotide comprising a reporter polynucleotide operatively linked to a regulatory element of a gene selected from a group consisting of the genes Bscl2, Cbr3, Ephx1, Nope, Cdkn1a, Perp, Pltp, Srxn1, Cgref1, Ltb4r1, Btg2, Gpx2, Ltb4r2, Ddit4l, Fosl1, and Egr1, which regulatory element stimulates expression of the reporter sequence in response to a genotoxic or oxidative stress-inducing agent.

By 'reporter sequence' we include the meaning of a polynucleotide whose expression is detectable by means of a suitable assay. For example, the polynucleotide may be one whose expression can be detected directly, for instance by using RT-PCR according to standard procedures in the art and as described in Example 1. In one embodiment, the reporter sequence is not the naturally occurring polynucleotide of the gene whose regulatory element the reporter sequence is operatively linked to. Alternatively, expression of the polynucleotide can be detected indirectly. For example, the polynucleotide may encode a reporter protein, and expression of the encoded reporter protein assessed. By 'reporter protein', we include the meaning of a protein that can be detected by means of an appropriate assay. It will be appreciated that the reporter protein may be one that is directly detected (e.g. a light emitting reporter protein) or one that is indirectly detected (e.g. an enzyme that produces a detectable signal).

In an embodiment, the reporter sequence is one that encodes any of DsRed fluorescent protein, horse radish peroxidise (HRP), Green Fluorescent Protein (GFP) (or an analogue or derivative thereof), luciferase, chloramphenicol acetyl transferase (CAT) or β-galactosidase. However, it may encode any protein whose cellular quantity can be accurately and rapidly assessed.

The reporter sequence may be fatal to the cells, or alternatively may allow cells to survive under otherwise fatal conditions. Cell survival can then be measured, for example using colorimetric assays for mitochondrial activity, such as reduction of WST-1 (Boehringer). WST-1 is a formosan dye that undergoes a change in absorbance on receiving electrons via succinate dehydrogenase.

Several techniques are available in the art to detect and measure expression of a reporter sequence which would be suitable for use in the present invention. Many of these are available in kits both for determining expression in vitro and in vivo.

For example, levels of mRNA transcribed from a reporter sequence can be assayed using RT-PCR (see Example 1). The specific mRNA is reverse transcribed into DNA which is then amplified such that the final DNA concentration is proportional to the initial concentration of target mRNA.

Levels of expression can also be determined by measuring the concentration of a reporter protein encoded by the reporter sequence. Assaying protein levels in a biological sample can occur using any suitable method. For example, protein concentration can be detected by a range of antibody based methods including immunoassays, such as ELISAs and radioimmunoassays. In one such assay, a protein-specific monoclonal antibody can be used both as an immunoadsorbent and as an enzyme-labelled probe to detect and quantify a specific protein. The amount of the protein present in the sample can be calculated by reference to the amount present in a standard preparation using a linear regression computer algorithm. In another ELISA assay, two distinct specific monoclonal antibodies can be used to detect the specific protein. In this assay, one of the antibodies is used as the immunoadsorbent (primary antibody) and the other as the enzyme-labelled probe (secondary antibody).

Suitable enzyme labels include those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes such as iodine ($^{125}I$, $^{121}I$) carbon ($^{14}C$), sulfur ($^{35}S$), tritium ($^{3}H$), indium ($^{112}In$), and technetium ($^{99m}Tc$), and fluorescent labels such as fluorescein and rhodamine, and biotin.

The concentration of a specific protein expressed by a reporter sequence may also be detected in vivo by imaging, for example when testing an agent in an animal model. For example, the reporter sequence may encode a bio-illuminescent reporter protein, or a fluorescent reporter protein.

Conveniently, the reporter protein is a light emitting protein (e.g. fluorescent) and its concentration is measured by assessing the light emitted, for example by using a fluorometer, or flow cytometry (eg. fluorescence assisted cell sorting (FACS) analysis), or fluorescence microscopy (eg confocal immunofluorescence microscopy) and (automated) live cell imaging.

In a preferred embodiment, the reporter sequence is one that encodes the light emitting reporter protein Discosoma sp red fluorescent protein (DsRed), and light emitting derivatives thereof. DsRed is from the reef coral Discosoma sp. and is readily detectable by virtue of its red light emission. An advantage of using a red fluorescent marker compared to the commonly used GFP is that it allows analysis of compounds that show green autofluorescence.

Derivatives of DsRed include polypeptide analogues, mutants or fragments of DsRed which are able to emit light.

One such derivative is DsRed-Express. DsRed-Express is a rapidly maturing variant of DsRed which contains nine amino acid substitutions that enhance solubility, reduce green emission, and accelerate maturation [43]. Recent development of a particular non-cytotoxic DsRed variant, DsRed-express2 [34], has been shown to allow stable and high expression of red fluorescent proteins in mammalian cells, and so in a particularly preferred embodiment, the reporter sequence is one that encodes DsRed-Express 2. The DsRed-Express2 sequence may be obtained from the pDsRed-express2.1 plasmid (e.g. obtained from Clontech), which is shown in FIG. 5A.

In a further preferred embodiment, the reporter sequence is one that encodes GFP.

Where the reporter sequence encodes an enzyme, determining the expression of a reporter sequence may comprise measuring the activity of the enzyme. Enzyme assays typically measure either the consumption of substrate or production of product over time. It is appreciated that a large range of methods exist for determining the concentrations of substrates and products such that many enzymes can be assayed in several different ways as is well known in the art (e.g. Bergmeyer (1974)).

The reporter sequences can be operatively linked to the specified regulatory element using standard molecular biology techniques.

By 'operatively linked' we include the meaning that the reporter sequence and regulatory element are linked such that the regulatory element is able to regulate the expression of the reporter sequence with which it is associated.

By a 'regulatory element of a gene' we include the meaning of a polynucleotide sequence that regulates the expression of a gene with which it is associated. Thus, when the regulatory element is operatively linked to a reporter sequence, the regulatory element is one that regulates expression of that reporter sequence. In the context of the invention, the regulatory element is also one that stimulates expression of the reporter sequence in response to a genotoxic or oxidative stress-inducing agent. By 'stimulates expression', it is understood that the regulatory element may act to switch on expression of the reporter sequence (i.e. from an undetectable level) in the presence of a genotoxic or oxidative stress-inducing agent, or it may act to increase existing expression of the reporter sequence in the presence of a genotoxic or oxidative stress-inducing agent.

Whether or not a particular regulatory element stimulates expression of a reporter sequence in response to a genotoxic or oxidative stress-inducing agent can be assayed using routine methods, including, for example, those described above and detailed in the Examples. For example, a polynucleotide comprising a candidate regulatory element operatively linked to a reporter sequence may be transfected into a cell, and expression of the reporter sequence assessed in the presence and absence of a genotoxic or oxidative stress-inducing agent.

It is appreciated that the regulatory element generally contains one or more regulatory sequence motifs that are able to bind to particular transcription factors. In this way, expression is regulated by one or more transcription factors binding to the regulatory element in the presence of a genotoxic or oxidative stress-inducing agent.

By the genes Bscl2, Cbr3, Ephx1, Nope, Cdkn1a, Perp, Pltp, Srxn1, Cgref1, Ltb4r1, and Btg2, we include mouse genes Bscl2 (NC_000085; SEQ ID No: 58), Cbr3 (NC_000082; SEQ ID No: 49), Ephx1 (NC_000067; SEQ ID No: 50), Nope (NC_000075; SEQ ID No: 51), Cdkn1a (NC_000083; SEQ ID No: 52), Perp (NC_000076; SEQ ID No: 53), Pltp (NC_000068; SEQ ID No: 54), Srxn1 (NC_000068; SEQ ID No: 55), Cgref1 (NC_000071; SEQ ID No: 56), Ltb4r1 (NC_000080; SEQ ID No: 57), and Btg2 (NC_000067; SEQ ID No: 59), whose polynucleotide sequences (downstream of the promoter) are listed in FIG. 3, and whose expression has been shown to be upregulated in response to genotoxic or oxidative stress.

By the genes Gpx2, Ltb4r2, Ddit4l, Fosl1, and Egr1 we include mouse genes Gpx2 (NC_000078; SEQ ID No: 60), Ltb4r2 (NC_000080; SEQ ID No: 61), Ddit4l (NC_000069; SEQ ID No: 62), Fosl1 (NC_000085; SEQ ID No: 63) and Egr1 (NC_000084; SEQ ID No: 64), whose polynucleotide sequences (downstream of the promoter) are listed in FIG. 4, and whose expression has been shown to be upregulated in response to genotoxic or oxidative stress.

It is appreciated that various types of transcription factors, and therefore regulatory sequences, are highly conserved in mammals. Thus, the inventors believe that if a regulatory element of one of the mouse genes Bscl2, Cbr3, Ephx1, Nope, Cdkn1a, Perp, Pltp, Srxn1, Cgref1, Ltb4r1, Btg2, Gpx2, Ltb4r2, Ddit4l, Fosl1, and Egr1, is conserved with a regulatory element of an orthologue of the respective gene, and the required transcription factors are available (some transcription factors are tissue and cell type specific), the regulatory elements will function in the same way. Accordingly, by the genes Bscl2, Cbr3, Ephx1, Nope, Cdkn1a, Perp, Pltp, Srxn1, Cgref1, Ltb4r1, Btg2, Gpx2, Ltb4r2, Ddit4l, Fosl1, and Egr1, we also include orthologues of the mouse genes Bscl2, Cbr3, Ephx1, Nope, Cdkn1a, Perp, Pltp, Srxn1, Cgref1, Ltb4r1, Btg2, Gpx2, Ltb4r2, Ddit4l, Fosl1, and Egr1, that are present in other species (eg human, rat, monkey, dog and horse). Orthologues of mouse genes Bscl2, Cbr3, Ephx1, Nope, Cdkn1a, Perp, Pltp, Srxn1, Cgref1, Ltb4r1, Btg2, Gpx2, Ltb4r2, Ddit4l, Fosl1, and Egr1, can be readily identified by a person of skill in the art, for example using sequence comparison programmes. Preferably, the orthologue has a polynucleotide sequence with at least 60%, or 65%, or 70%, or 75%, or 80%, or 85% or 90% sequence identity with the coding polynucleotide sequence (eg cDNA sequence) of the corresponding mouse gene, whose sequence (downstream of the promoter) is provided in FIGS. 3 and 4, and more preferably 95% and 99% sequence identity.

Typically, the regulatory element of a gene comprises the promoter of the gene since the promoter immediately upstream of the transcription initiation site is expected to contain most of the regulatory sequence motifs that bind to transcription factors. Thus, the regulatory element may comprise the promoter sequence of a gene selected from a group consisting of the genes Bscl2, Cbr3, Ephx1, Nope, Cdkn1a, Perp, Pltp, Srxn1, Cgref1, Ltb4r1, Btg2, Gpx2, Ltb4r2, Ddit4l, Fosl1, and Egr1.

The regulatory element is conveniently a polynucleotide fragment upstream of the transcription start site of the gene. For example, the regulatory element may comprise at least a 400, 500, 600, 700, 800, 900, 1000, 1100, 1200, 1300, 1400, 1500, 1600, 1700, 1800, 1900 or 2000 base pair polynucleotide sequence immediately upstream of the transcription start site of the gene. Transcription start sites of the genes Bscl2, Cbr3, Ephx1, Nope, Cdkn1a, Perp, Pltp, Srxn1, Cgref1, Ltb4r1, and Btg2 are indicated in FIG. 1. Transcription start sites of the genes Gpx2, Ltb4r2, Ddit4l, Fosl1, and Egr1 are indicated in FIG. 2.

In a preferred embodiment, the regulatory element comprises at least a 1400 or 1500 base pair polynucleotide sequence immediately upstream of the transcription start site of the gene.

In a preferred embodiment, the regulatory element of a gene selected from a group consisting of the genes Bscl2, Cbr3, Ephx1, Nope, Cdkn1a, Perp, Pltp, Srxn1, Cgref1, Ltb4r1, and Btg2, comprises the respective polynucleotide sequences listed in FIG. 1 (SEQ ID Nos: 1-11).

In a preferred embodiment, the regulatory element of a gene selected from a group consisting of the genes Gpx2, Ltb4r2, Ddit4l, Fosl1, and Egr1 comprises the respective polynucleotide sequences listed in FIG. 2 (SEQ ID Nos: 34-38).

It is appreciated that genes typically have multiple regulatory sequences which may or may not be adjacent to one another. For example, regulatory sequences of genes can reside up to megabase distances away from the transcription initiation site. While regulatory sequences for the common basic transcription factors often reside close to the transcription initiation site of a gene (eg. within a few hundred base pairs), regulatory sequences responsible for responding to particular stimuli (eg. regulating expression in response to genotoxic stimuli) may either reside within a few hundred base pairs of the transcription initiation site, or further away from it. Thus, it is understood that not all regulatory sequences of a gene may be located in the promoter directly upstream of its transcription initiation site.

Accordingly, in one embodiment, the regulatory element corresponds to two or more regulatory sequences which act together to increase expression of a reporter sequence in the presence of a genotoxic or oxidative stress-inducing agent. In other words, the regulatory element may comprise one or more portions of the gene, which portions have been joined together.

In an embodiment, the regulatory element of the gene comprises sequences downstream of the promoter sequence. For example, the regulatory element may comprise polynucleotide sequences that bind transcription factors which promote gene expression following DNA damage, or may comprise a 3' untranslated region (UTR).

In an embodiment, the regulatory element comprises at least one exon of the respective gene, or at least one intron of the respective gene, or at least one exon and one intron of the respective gene.

In an embodiment, the regulatory element comprises an enhancer sequence of the respective gene, which acts to enhance gene expression in response to a genotoxic or oxidative stress-inducing agent.

In an embodiment, the regulatory element comprises a regulatory sequence motif that is known to bind a transcription factor which serves to increase gene expression in response to a genotoxic or oxidative stress-inducing agent. Thus, the regulatory element may comprise a p53 binding motif.

In a preferred embodiment, the regulatory element of a gene comprises the whole gene, such that the gene sequence encoding the endogenous protein is operatively linked to a reporter sequence. The polynucleotide sequences (downstream of the promoter) of each of the genes: Bscl2, Cbr3, Ephx1, Nope, Cdkn1a, Perp, Pltp, Srxn1, Cgref1, Ltb4r1, and Btg2, are provided in FIG. 3 and the polynucleotide sequences of each of the genes: Gpx2, Ltb4r2, Ddit4l, Fosl1, and Egr1 (downstream of the promoter) are provided in FIG. 4. Without wishing to be bound by any theory, the inventors believe that in this way, all regulatory sequences of the gene are captured in the regulatory element such that expression of the reporter sequence will better mimic expression of the endogenous gene. Methods for linking a whole gene to a reporter sequence are known in the art, and include, for example, BAC TransgeneOmics technology (Poser et al, 2008 *Nature Methods*, 5: 409-415) described in the Examples.

It is appreciated that the regulatory element may be a functional derivative, or a variant (eg in which one or more nucleotides have been substituted or deleted), or a portion of one of the sequences mentioned above.

For example, the regulatory element may be a variant of any of the sequences listed in FIGS. 1A-K or FIG. 2A-E, having at least, for example, 60%, 65%, 70%, 80%, 85%, 90%, 95%, 96%, 97%, 98% or 99% sequence identity with said sequences, provided that the variant is one that stimulates expression of a reporter sequence operatively linked to it in response to a genotoxic or oxidative stress-inducing agent.

Percent sequence identity between two polynucleotides may be determined by any suitable method known in the art, for example by using appropriate computer programs such as WU-BLAST-2 (Altschul et al., Methods in Enzymology 266:460-480 (1996)) and Blast search, MacVector and Vector NTI (eg AlignX program in Vector NTI version 11) (Invitrogen).

In another example, the regulatory element may be a portion of any of the sequences listed in FIGS. 1A-K or FIGS. 2A-E or variants of said sequences, which portions have at least, for example, 20%, 30%, 40%, 50%, 60%, 70%, 80%, 90%, 95%, 96%, 97%, 98% or 99% of the bases of said sequences, provided that the portion is one that stimulates expression of a reporter sequence operatively linked to it in response to a genotoxic or oxidative stress-inducing agent. Conveniently, the portion is at least 50 bp or 100 bp or 200 bp or 300 bp or 400 bp or 500 bp or 600 bp or 700 bp or 800 bp or 900 bp or 1000 bp or 1100 bp or 1200 bp or 1300 bp or 1400 bp or 1500 bp in length.

Now that the importance of the sixteen genes identified by the inventors in genotoxic and oxidative stress has been realised, it is appreciated that any regulatory element of the genes can be readily identified by assessing whether or not expression of a reporter sequence operatively linked to a putative regulatory element is activated in the presence of a genotoxic or oxidative stress-inducing agent. The regulatory element may also be identified by conducting mutagenesis on a promoter of a gene selected from a group consisting of the genes Bscl2, Cbr3, Ephx1, Nope, Cdkn1a, Perp, Pltp, Srxn1, Cgref1, Ltb4r1, Btg2, Gpx2, Ltb4r2, Ddit4l, Fosl1, and Egr1, when in natural association with the respective gene, and assessing whether or not expression of the gene occurs.

Typically, the regulatory elements activate expression of a reporter sequence in response to a genotoxic agent selected from any of an agent causing base damage, an agent causing bulky DNA adducts, an agent causing single-stranded DNA breaks, an agent causing double-stranded DNA breaks, an agent causing intra-strand crosslinks, or an agent causing inter-strand crosslinks. Thus, the genotoxic agent may be an intercalator, a topoisomerase II poison or a methylating agent or an alkylating agent. It will be appreciated that there are no genotoxic agents that selectively induce only one type of DNA damage. Hence, as well as causing base damage, the genotoxic agent may also cause bulky DNA adducts.

Preferably, the regulatory element stimulates expression of a reporter sequence in response to any of cisplatin, mitomycin C, doxorubicin, etoposide, methylmethane sulphonate, and N-methylnitrosurea, or to any of the genotoxic or oxidative stress-inducing compounds mentioned in the Examples, such as a genotoxin or pro-oxidant as suggested by the European Centre for Validation of Alternative Methods (ECVAM) (see Tables 2 and 3).

The regulatory element may stimulate expression of a reporter polynucleotide in response to oxidative stress-inducing agent such as a pro-oxidant and including any of hydrogen peroxide, t-butyl hydroperoxide, menadione and diethyl maleate.

It will be understood that some agents may induce both genotoxicity and oxidative stress to varying degrees.

Exposure to high concentrations of genotoxic or oxidative stress-inducing compounds rapidly induces apoptosis to protect cells against the mutagenic effects of DNA damage. Thus, it is preferred if the regulatory element stimulates expression of the reporter sequence in response to a non-cytotoxic concentration of a genotoxic or oxidative stress-inducing agent. Preferably, the regulatory element stimulates expression of the reporter sequence in response to a concentration of genotoxic or oxidative stress-inducing agent that induces apoptosis in less than 35% of a population of cells, such as less than 30%, 20% or 10% of a population of cells. Methods for assessing apoptosis are well known in the art and include annexin V and caspase 3 staining assays as described in Example 1.

The polynucleotide may be RNA (eg mRNA) or DNA, although typically it is DNA.

It will be appreciated that the polynucleotide of the first aspect of the invention may be incorporated into a vector and used as an expression cassette. Accordingly, a second aspect of the invention provides a vector comprising a polynucleotide according to the first aspect of the invention.

Suitable vectors are ones which propagate in and/or allow expression of the reporter sequence in prokaryotic (e.g. bacterial) or eukaryotic (e.g. mammalian) cells. For example, the vector may be a plasmid, a cosmid, a phage or a bacterial artificial chromosome (BAC). The polynucleotide sequence of the vector will depend upon the nature of the intended host cell, the manner of the introduction of the polynucleotide of the first aspect of the invention into the host cell, and whether episomal maintenance or integration is desired. Conveniently, the vector comprises at least one selectable marker such as antibiotic resistance (e.g. kanamycin or neomycin).

Vectors are useful to replicate the polynucleotide of the first aspect of the invention, and are also useful to transfect cells with the polynucleotide, and may also promote expression of the reporter sequence.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T-antigen-producing cells, such as COS-1 cells. Another example is pcDNA3.1 (neo) (Invitrogen) for use in COS-1 or COS-7 cells. An example of an inducible mammalian expression vector is pMSG, also available from Pharmacia (Piscataway, N.J., USA). This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

In a preferred embodiment, the vector which comprises the polynucleotide of the first aspect of the invention is pDsRed-expression2.1 plasmid (Clontech; Strack et al, "A noncytotoxic DsRed variant for whole-cell labelling" Nat Methods, 2008, 5(11): 955-7 (FIG. 5)).

Any suitable method known in the art may be used to construct vectors containing the polynucleotide of the first aspect of the invention. One such method involves ligation via homopolymer tails. Homopolymer polydA (or polydC) tails are added to exposed 3' OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase. For example, using appropriate primers in PCR reactions, the regulatory element of the polynucleotide of the first aspect of the invention may be produced so as to be flanked by desired restriction enzyme sites. The regulatory element may then be cloned into a vector that contains a reporter sequence downstream of where the regulatory element is inserted.

A further method uses synthetic molecules called linkers and adaptors. DNA fragments with blunt ends are generated by bacteriophage T4 DNA polymerase or E. coli DNA polymerase I which remove protruding 3' termini and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end.

Synthetic linkers containing a variety of restriction endonuclease sites are commercially available from a number of sources including International Biotechnologies Inc, New Haven, Conn., USA.

Generating a BAC comprising the polynucleotide of the first aspect of the invention may be done using BAC TransgeneOmics technology as described in Poser et al, 2008 Nature Methods, 5: 409-415.

A third aspect of the invention provides a cell comprising a polynucleotide according to the first aspect of the invention, or a vector according to the second aspect of the invention. Such cells may be used to replicate the polynucleotide of the first aspect of the invention, or may be used in a genotoxic or oxidative stress-inducing screening assay, as discussed in more detail below.

The cell can be either prokaryotic or eukaryotic.

It is appreciated that construction and amplification of the polynucleotide of the first aspect of the invention is conveniently performed in bacterial cells, whereas the use of the polynucleotide for genotoxic or oxidative stress-inducing screening is typically limited to mammalian cells.

Bacterial cells are preferred prokaryotic host cells and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells or cell lines, preferably vertebrate cells or cell lines such as those from a mouse, rat, monkey or human. The cells may be stem cells (e.g. embryonic stem cells) or they may be immortalised cells (e.g. hTert immortalised primary human fibroblasts), or they may be primary cells such as hepatocytes (e.g. obtained through differentiation of stem cells). Yeast host cells include YPH499, YPH500 and YPH501 which are generally available from Stratagene Cloning Systems, La Jolla, Calif. 92037, USA. Preferred insect cells are Sf9 cells which can be transfected with baculovirus expression vectors.

Cells used for expressing the reporter sequence are ideally stably transfected. However, it is appreciated that non-stable transfectants (eg when using viral expression vectors) may also be used.

Preferably, the cell used for expressing the reporter sequence is one that has a non-compromised DNA damage response. For example, the cell may have a functional DNA repair response and so be capable of one or more of, and preferably all of, inter-strand crosslink repair, base excision repair, homologous recombination, and non-homologous end joining. The cell may have operational cell cycle checkpoints, such as G1-S, intra S, G2 and mitosis checkpoints. The cell may have a functional apoptotic pathway. Methods of determining whether a cell has a non-compromised DNA damage response are routine in the art, and include, for example, sequence analysis of genes, and functional assays of proteins (eg following genotoxic insult), known to be involved in the DNA damage response.

In a particular embodiment, the cell has a functional p53 protein which is required for the functionality of some cell cycle checkpoints and for the induction of apoptosis. Thus, the cell may be an embryonic stem cell or a hTert immortalised primary human fibroblast.

The inventors have found that mouse embryonic stem cells are particularly useful cell lines in the method of the invention. Thus, in a particularly preferred embodiment, the cell is a mouse stem cell, most preferably an embryonic stem cell.

It is appreciated that a non-genotoxic or a non-oxidative stress-inducing agent may be converted into a genotoxic or into an oxidative stress-inducing agent, respectively, within a cell. Thus, in order to identify such agents in a genotoxic or oxidative stress-inducing screening assay, the cell is conveniently a cell that expresses metabolising enzymes, such as an hepatocyte (eg Hep G2 or an hepatocyte derived from an embryonic stem cell), or a STO (mouse embryonic fibroblast) cell, or a lung epithelial cell (eg one grown in 3D cell culture).

Transformation of appropriate cells with a vector is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (2001) *Molecular Cloning, A Laboratory Manual*, 3$^{rd}$ Ed. Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation may also be used as described in Example 1.

It is appreciated that in addition to the transformed host cells themselves, the present invention also contemplates a culture of those cells, preferably a monoclonal (clonally homogeneous) culture, or a culture derived from a monoclonal culture, in a nutrient medium.

It will be understood that the polynucleotide of the first aspect of the invention or vector of the second aspect of the invention may be incorporated into a cell of an organism in vivo, or into the cell of a tissue ex vivo. Thus, the invention also includes an organism or tissue that comprises the polynucleotide of the first aspect of the invention or vector of the second aspect of the invention. For example, it will be appreciated that the invention includes a non-human transgenic mammal that comprises a cell of the third aspect of the invention. Preferably, the mammal is a laboratory animal, such as any of a rodent (eg mouse or rat), a primate, a dog or a cat.

In this way, the polynucleotide of the first aspect of the invention can be used to screen for genotoxic or oxidative stress-inducing agents in vivo or ex vivo. For example, the polynucleotide may be incorporated into a laboratory animal such as a primate, mouse or rat that can be used to screen for genotoxic or oxidative stress-inducing agents.

It will be appreciated that the organism or tissue may comprise more than one of the polynucleotides, vectors or cells of the invention, each one containing a regulatory element of a different gene.

The invention provides an organism or tissue that comprises (i) a cell that comprises a polynucleotide comprising a reporter sequence operatively linked to a regulatory element of the Bscl2 gene, and (ii) one or more cells that comprise a reporter sequence operatively linked to a regulatory element of a gene, which regulatory element stimulates expression of the reporter sequence in response to a genotoxic agent or to an oxidative stress-inducing agent. Thus, the organism or tissue may comprise (i) a cell that comprises a polynucleotide comprising a reporter sequence operatively linked to a regulatory element of the Bscl2 gene, and (ii) one or more cells that comprise a polynucleotide comprising a reporter sequence operatively linked to a regulatory element of a gene selected from a respective one or more of (e.g. 2, 3, 4, 5, 6, 7, 8, 9, 10, 11, 12, 13, 14 or 15 of) Srxn1, Cbr3, Ephx1, Nope, Cdkn1a, Perp, Pltp, Cgref1, Ltb4r1, Btg2, Gpx2, Ltb4r2, Ddit4l, Fosl1 and Egr1. It is appreciated that the cells comprising the various reporter sequences operatively linked to regulatory elements may be the same or different. In other words, the organism or tissue may comprise a cell that comprises a polynucleotide comprising a reporter sequence operatively linked to a regulatory element of the Bscl2 gene, and, either in the same or respectively different cells, one or more polynucleotides that comprise a reporter sequence operatively linked to a regulatory element of a gene, which regulatory element stimulates expression of the reporter sequence in response to a genotoxic agent or to an oxidative stress-inducing agent. Thus, it is also appreciated that the invention provides a cell that comprises more than one polynucleotide or vector of the invention, each one containing a regulatory element of a different gene (eg Bscl2 and Srxn1 genes).

Where the organ or tissue or cell contains a regulatory element from more than one gene, it is appreciated that the different regulatory elements may be responsive to different genotoxic or oxidative stress-inducing agents. For example, the regulatory element of one gene may be responsive specifically to genotoxic agents and the regulatory element of another gene responsive specifically to oxidative stress-inducing agents. Thus, by exposing more than one polynucleotide comprising a regulatory element according to the invention, to an agent, the mode of toxicity of that agent can be assessed. As described in Examples 4 and 5, the inventors have found that Bscl2 reporters are selectively activated following exposure to genotoxic stress, Srxn1 reporters are selectively activated following exposure to oxidative stress, and Btg2 reporters are activated by both genotoxic and oxidative stress. Thus, by exposing different reporters to an agent, it is possible to categorise that agent as a primarily a genotoxic or primarily an oxidative-stress inducing compound, or both a genotoxic and oxidative-stress inducing compound.

In a preferred embodiment, the organ or tissue comprises a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene. It is understood that the cells may be same.

In a further preferred embodiment, the organ or tissue comprises a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene, and a cell that comprises a polynucleotide comprising a reporter sequence operatively linked to a regulatory element of the Btg2 gene. It is understood that the cells may be the same.

In one embodiment, regulatory elements that respond in a specific way (e.g. to genotoxic agent or oxidative stress-inducing agents or classes thereof) are operatively linked to different reporter sequences. For instance, a regulatory element that is responsive to genotoxic agents may be linked to a first reporter sequence and a regulatory element that is responsive to oxidative stress-inducing agents may be linked to a second reporter sequence. In this way, the property of the agent can readily be determined by the readout from the different reporter sequences.

The polynucleotide of the first aspect of the invention or vector of the second aspect of the invention may be stably integrated into the genome of a cell in vivo or ex vivo, using standard methods in the art. For example, the polynucleotide may be integrated by regular transgene methods such as cre-lox. Alternatively, the polynucleotide may be somatically incorporated. For example, somatic incorporation of reporter constructs in rodents (e.g. mice or rats) can be achieved through tail vein injection.

The invention does not provide a process for cloning a human being, nor does it provide a process for modifying the germ line identity of human beings, nor does it provide a use of a human embryo for industrial or commercial purposes, nor does it provide a process for modifying the genetic identity of animals which are likely to cause them suffering without any substantial medical benefit to man or animal, and also animals resulting from such a process.

As described in Example 1, the inventors have found the polynucleotides of the first aspect of the invention to be particularly useful in genotoxic or oxidative stress-inducing screening assays. Accordingly, a fourth aspect of the invention provides a method of detecting a genotoxic or an oxidative stress-inducing agent comprising subjecting a cell according to the third aspect of the invention to a test agent; and assessing the expression of the reporter sequence.

It is appreciated that cells containing different regulatory elements, may be subjected to a test agent, and so the invention similarly provides a method of detecting a genotoxic or oxidative stress-inducing agent comprising (a) subjecting one or more cells that comprise a reporter sequence operatively linked to a regulatory element of a gene, which regulatory element stimulates expression of the reporter sequence in response to a genotoxic agent or to an oxidative stress-inducing agent, to a test agent, and (b) assessing the expression of the one or more reporter sequences; wherein at least one cell subjected to a test agent in step (a) comprises a polynucleotide comprising a reporter sequence operatively linked to a regulatory element of the Bscl2 gene.

Thus, the method may involve subjecting cells to a test agent, wherein the cells contain regulatory elements of different genes operatively linked to a reporter sequence, provided that at least one cell comprises a polynucleotide comprising a reporter sequence operatively linked to a regulatory element of the Bscl2 gene. By using different regulatory elements, it is believed that more potentially genotoxic and oxidative stress-inducing agents can be detected, and also further insight into the mode of toxicity can be gained. It is appreciated that the different regulatory elements may be operatively linked to the same or different reporter sequences. It is also understood that the polynucleotides that comprise the different regulatory elements operatively linked to a reporter sequence may be present in the same or different cells.

In one embodiment, (i) a cell that comprises a polynucleotide comprising a reporter sequence operatively linked to a regulatory element of the Bscl2 gene, and (ii) one or more cells that comprise a polynucleotide comprising a reporter sequence operatively linked to a regulatory element of a gene selected from a respective one or more of (e.g. 2 or 3 or 4 or 5 or 6 or 7 or 8 or 9 or 10 or 11 or 12 or 13 or 14 or 15 of) Srxn1, Cbr3, Ephx1, Nope, Cdkn1a, Perp, Pltp, Cgref1, Ltb4r1, Btg2, Gpx2, Ltb4r2, Ddit4l, Fosl1 and Egr1, are subjected to a test agent. The cells of (i) and (ii) may be the same or different. Thus, a cell that comprises a Bscl2-reporter (i.e. a reporter sequence operatively linked to a regulatory element of the Bscl2 gene) and one or more cells that respectively comprise any of a Srxn1-reporter, Cbr3-reporter, Ephx1-reporter, Nope-reporter, Cdkn1a-reporter, Perp-reporter, Pltp-reporter, Cgref1-reporter, Ltb4r1-reporter, Btg2-reporter Gpx2-reporter, Lbt4r2-reporter, Ddit4l-reporter, Fosl1-reporter and Egr1-reporter, may be subjected to a test agent. In a particularly preferred embodiment, a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene, are subjected to a test agent, which cells may or may not be the same. In a further preferred embodiment, a cell that comprises a polynucleotide comprising a reporter sequence operatively linked to a regulatory element of the Bscl2 gene, and cell that comprises a polynucleotide comprising a reporter sequence operatively linked to a regulatory element of the Srxn1 gene, and a cell that comprises a polynucleotide comprising a reporter sequence operatively linked to a regulatory element of the Btg2 gene, are subjected to a test agent, which cells may or may not be the same.

It is appreciated that the test agent may be any physical or chemical agent in the environment to which organisms are exposed. Thus, the method may be used to screen compounds, such as candidate medicaments, food additives, plasticisers or cosmetics to assess whether it is safe to expose an organism (e.g. human) to the compounds. Alternatively, the method may be used to assess contamination of samples with genotoxic or oxidative stress-inducing agents. For instance, the presence of genotoxic or oxidative stress-inducing agents in water supplies or in industrial effluents may be assessed.

Preferred reporter sequences include those described above with respect to the first aspect of the invention. Thus, the method may involve assessing the expression of any one or more reporter proteins such as a DsRed fluorescent protein, horse radish peroxidise (HRP), Green Fluorescent Protein (GFP) (or an analogue or derivative thereof), luciferase, chloramphenicol acetyl transferase (CAT) or β-galactosidase, in the presence of a test agent. Preferably, the method involves assessing the expression of a DsRed fluorescent protein (e.g. DsRed-express2) by FACS or assessing the expression of GFP by fluorescence microscopy (eg confocal immunofluorescence microscopy) or (automated) live cell imaging. It is also appreciated that in this aspect of the invention, the reporter sequence may be the naturally occurring polynucleotide of the gene whose regulatory element the reporter sequence is operatively linked to.

When cells containing different regulatory elements are exposed to the test agent, it is appreciated that the different regulatory elements may be operatively linked to the same or different reporter sequences. As discussed above, it may be desirable to operatively link regulatory elements that respond in a specific way (e.g. to genotoxic agent or oxidative stress-inducing agents or classes thereof or to both genotoxic and oxidative stress-inducing agents) to different reporter sequences, such that the mode of toxicity of a particular agent can be readily determined from the reporter readout.

In one embodiment, the method is performed in vitro. By in vitro we include the meaning of cell-based assays. By cell-based assays we include the meaning of cell cultures in two dimensions, such as on plastic or glass culture plates, as well as cell cultures which are cultured in three dimensional matrices. These matrices may be composed of natural matrix components and contain, for example, collagen, fibronectin, laminin, or matrigel, or they may be composed of artificial matrix components.

Conveniently, the method is performed by growing cells transfected with a vector that comprises a reporter sequence operatively linked to a regulatory element of a gene, which regulatory element stimulates expression of the reporter sequence in response to a genotoxic agent or to an oxidative stress-inducing agent (e.g. one or more cells according to the third aspect of the invention), incubating the cells with a genotoxic or oxidative stress-inducing agent, and assessing the expression of the one or more reporter sequences from a sample of the cells.

It may be desirable to compare the expression of the reporter sequence in the one or more reporter cells used in the method of the invention, to expression in control cells that contain the reporter sequence but which lack the regulatory element of a gene which regulatory element stimulates expression of the reporter sequence in response to a genotoxic agent or to an oxidative stress-inducing agent (e.g. regulatory elements of any of the genes Bscl2, Cbr3, Ephx1, Nope, Cdkn1a, Perp, Pltp, Srxn1, Cgref1, Ltb4r1, Btg2, Gpx2, Ltb4r2, Ddit4l, Fosl1, and Egr1).

To enable high-throughput analysis, the cells may be seeded on a multiwell plate, such as a 96-well plate. For example, as described in Example 1, cells containing a fluorescent reporter protein (eg DsRed) may be seeded on a multiwell plate and expression assessed by flow cytometry.

In another embodiment, the method is performed in vivo or ex vivo. For example, one or more polynucleotides that comprise a reporter sequence operatively linked to a regulatory element of a gene, which regulatory element stimulates expression of the reporter sequence in response to a genotoxic agent or to an oxidative stress-inducing agent (e.g. polynucleotides of the first aspect of the invention), each polynucleotide comprising a different regulatory element may have been incorporated into either the same or respectively different cells of a living organism (e.g. a laboratory animal such as a mouse or rat), and the expression of the one or more reporter sequences in the organism assessed in the presence and absence of a test agent. Conveniently, the method is performed in vivo using transgenic animals (e.g. mice) and expression of reporter sequences assessed using whole-body small animal imaging machines. Alternatively, the one or more polynucleotides that comprise a reporter sequence operatively linked to a regulatory element of a gene, which regulatory element stimulates expression of the reporter sequence in response to a genotoxic agent or to an oxidative stress-inducing agent, each polynucleotide comprising a different regulatory element may have been incorporated into a tissue ex vivo, and the expression of the reporter sequences in the tissue assessed in the presence and absence of a test agent. Performing the method ex vivo typically involves using isolated cells from transgenic animals. For example, following hydrodynamic tail injection of the polynucleotide of the first aspect of the invention into a mouse or rat, reporter activity may be assessed in liver slices ex vivo.

As mentioned above and exemplified in Example 6, the polynucleotide of the first aspect of the invention can be used in a genotoxic or oxidative stress-inducing screening assay to detect non-genotoxic agents or non-oxidative stress-inducing agents that may be converted into genotoxic agents or oxidative stress-inducing agents in a cell. To do so, it is appreciated that either the cells containing polynucleotides such as the polynucleotide of the first aspect of the invention (i.e. that comprise a reporter sequence operatively linked to a regulatory element of a gene, which regulatory element stimulates expression of the reporter sequence in response to a genotoxic agent or to an oxidative stress-inducing agent) are metabolically active, or that metabolising cells are added to the cells (either as feeder cells or as a co-culture), or that a metabolising cell extract (eg. liver extract such as rat S9 mix) is added to the cells.

Expression of the reporter sequence may be assessed at several intervals over time. For example, expression may be assessed at 8 h, 12 h, 16 h, 24 h, 30 h and 48 h after incubation with the test agent.

As mentioned above, the inventors have identified 16 genes whose expression is activated in response to genotoxic or oxidative stress-inducing agents, and which therefore may be used as biomarkers for genotoxic or oxidatively induced stress. It follows that an agent may counteract genotoxic or oxidative stress by reducing or preventing the expression of such genes upon exposure to a genotoxic or oxidative stress-inducing agent. In this way, the reporter sequence of the first aspect of the invention may also be used to identify agents that counteract genotoxic or oxidative stress, for example by assessing the expression of the reporter sequence in the presence of a genotoxic or oxidative stress-inducing agent and by determining what effect a test agent has on expression.

Accordingly, a fifth aspect of the invention provides a method of detecting an agent to counteract genotoxic or oxidative stress, the method comprising:

a) subjecting a cell according to the third aspect of the invention to a genotoxic or oxidative stress-inducing agent, and to a test agent; and b) assessing the expression of the reporter sequence.

It may be desirable to use cells in the method that comprise a different regulatory element operatively linked to a reporter sequence, either in the same or different cells. It is appreciated that the different regulatory elements may be operatively linked to the same or different reporter sequences. For example, it may be desirable to operatively link regulatory elements that respond in a specific way (e.g. to genotoxic agent or oxidative stress-inducing agents or classes thereof or to both genotoxic and oxidative stress-inducing agents) to different reporter sequences, such that the counteracting effect of an agent on different types of toxicity can be readily determined by the reporter readout from the reporter sequences.

Thus, the invention similarly provides a method of detecting an agent to counteract genotoxic or oxidative stress, the method comprising a) subjecting one or more cells that comprise a reporter sequence operatively linked to a regulatory element of a gene, which regulatory element stimulates expression of the reporter sequence in response to a genotoxic agent or to an oxidative stress-inducing agent, to a genotoxic or oxidative stress-inducing agent, and to a test agent; and b) assessing the expression of the one or more reporter sequences;

wherein at least one of the cells comprises a polynucleotide comprising a reporter sequence operatively linked to a regulatory element of the Bscl2 gene.

Thus, step (a) may comprise subjecting either the same or respectively different cells that comprise different regulatory element operatively linked to a reporter sequence, to a genotoxic or oxidative stress-inducing agent, and to a test agent. It is appreciated that the different regulatory elements may be operatively linked to the same or different reporter sequences.

In one embodiment, (i) a cell that comprises a polynucleotide comprising a reporter sequence operatively linked to a regulatory element of the Bscl2 gene, and (ii) one or more cells that comprise a polynucleotide comprising a reporter sequence operatively linked to a regulatory element of a gene selected from a respective one or more of (e.g. 2 or 3 or 4 or 5 or 6 or 7 or 8 or 9 or 10 or 11 or 12 or 13 or 14 or 15 of) Srxn1, Cbr3, Ephx1, Nope, Cdkn1a, Perp, Pltp, Cgref1, Ltb4r1, Btg2, Gpx2, Ltb4r2, Ddit4l, Fosl1, and Egr1, are subjected to a genotoxic or oxidative stress-inducing agent, and to a test agent. It is understood that the cells may be the same or different.

In a particularly preferred embodiment, a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene are subjected to a genotoxic or oxidative stress-inducing agent, and to a test agent.

In a further preferred embodiment, a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene, and a cell that comprises a polynucleotide comprising a reporter sequence operatively linked to a regulatory element of the Btg2 gene, are subjected to a genotoxic or oxidative stress-inducing agent, and to a test agent.

By an agent that 'counteracts genotoxic or oxidative stress' we include the meaning of an agent that prevents or reduces DNA damage caused by a genotoxic agent, or the oxidative stress caused by an oxidative stress-inducing agent.

An agent that counteracts genotoxic or oxidative stress is expected to reduce the expression of a reporter sequence relative to the expression of the reporter sequence in the absence of the agent. Conveniently therefore, the method comprises first assessing the expression of the reporter sequence in the presence of a genotoxic or oxidative stress-inducing agent, but in the absence of a test agent, and subsequently comparing the expression with the expression of the reporter sequence in the presence of a genotoxic or oxidative stress-inducing agent, and a test agent.

Accordingly, the invention includes a method of determining whether an agent (e.g. compound) can counteract genotoxic or oxidative stress, the method comprising:

a) subjecting a cell according to the third aspect of the invention to a genotoxic agent or an oxidative stress-inducing agent;

b) determining the effect of the genotoxic agent or oxidative stress-inducing agent on the expression of the reporter sequence;

c) subjecting the cell to a test agent; and d) determining whether the test agent counteracts the effect of the genotoxic agent or oxidative stress-inducing agent on the expression of the reporter sequence.

Similarly, it is appreciated that the invention includes a method of determining whether an agent (e.g. compound) can counteract genotoxic or oxidative stress, the method comprising:

a) subjecting one or more cells that comprise a reporter sequence operatively linked to a regulatory element of a gene, which regulatory element stimulates expression of the reporter sequence in response to a genotoxic agent or to an oxidative stress-inducing agent, to a genotoxic agent or an oxidative stress-inducing agent;

b) determining the effect of the genotoxic agent or oxidative stress-inducing agent on the expression of the one or more reporter sequences;

c) subjecting the one or more cells to a test agent; and d) determining whether the test agent counteracts the effect of the genotoxic agent or oxidative stress-inducing agent on the expression of the one or more reporter sequences; wherein at least one of the cells in step (a) comprises a polynucleotide comprising a reporter sequence operatively linked to a regulatory element of the Bscl2 gene. It is appreciated that the cells in step (a) containing different regulatory elements operatively linked to reporter sequences may be the same or different, and that the different regulatory elements may be operatively linked to the same or different reporter sequences.

By "counteracts the effect of the genotoxic agent or oxidative stress-inducing agent on the expression of the reporter sequence" we include the meaning of determining whether the test agent reduces the expression of the reporter sequence, stimulated by a genotoxic or oxidative stress-inducing agent.

It is appreciated, however, that the expression of the reporter sequence in the presence of a genotoxic or oxidative stress-inducing agent alone may already be known, in which case it is only necessary to assess the expression of the reporter sequence in the presence of both the genotoxic or oxidative stress-inducing agent, and test agent.

Preferences for the cell, the genotoxic or oxidative stress-inducing agent and methods for assessing expression of the reporter sequence for this and subsequent aspects of the invention are as mentioned above.

The test agent may be any compound. Examples include any of a polypeptide, a peptide, a nucleic acid, a small molecule (e.g. less than 5000 daltons), or a natural product.

The method of the fifth aspect of the invention may be performed in vitro, in vivo or ex vivo, in the same way as the method of the fourth aspect of the invention.

A sixth aspect of the invention provides a kit of parts comprising:

(i) a cell according to the third aspect of the invention; and (ii) a means for detecting expression of the reporter sequence.

The invention similarly provides a kit of parts comprising:

(i) one or more cells that comprise a reporter sequence operatively linked to a regulatory element of a gene, which regulatory element stimulates expression of the reporter sequence in response to a genotoxic agent or to an oxidative stress-inducing agent; wherein at least one of the cells comprises a polynucleotide comprising a reporter sequence operatively linked to a regulatory element of the Bscl2 gene; and, optionally, (ii) one or more means for detecting expression of the one or more reporter sequences.

It is appreciated that the cells in part (i) containing different regulatory elements operatively linked to reporter sequences may be the same or different.

Thus, the kit of parts may contain one or more cells that comprise a different regulatory element (e.g. 2, 3, 4 or 5 different regulatory elements) operatively linked to a reporter sequence. The cells may the same or different. It is appreciated that the different regulatory elements may be operatively linked to the same or different reporter sequences.

In one embodiment, the kit of parts comprises (i) a cell that comprises a polynucleotide comprising a reporter sequence operatively linked to a regulatory element of the Bscl2 gene, and (ii) one or more cells that comprise a polynucleotide comprising a reporter sequence operatively linked to a regulatory element of a gene selected from a respective one or more of Srxn1, Cbr3, Ephx1, Nope, Cdkn1a, Perp, Pltp, Cgref1, Ltb4r1, Btg2, Gpx2, Ltb4r2, Ddit4l, Fosl1, and Egr1. It is understood that the cells may be the same or different.

In a particularly preferred embodiment, the kit of parts comprises a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene.

In a further preferred embodiment, the kit of parts comprises a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene, and a cell that comprises a polynucleotide comprising a reporter sequence operatively linked to a regulatory element of the Btg2 gene.

The means for detecting expression of the reporter sequence may be any suitable means that can be used to assess expression of a particular reporter sequence. For example, if expression of the reporter sequence is assessed directly by RT-PCR, the means may comprise a primer or probe. Alternatively, if expression of the reporter sequence is assessed by assessing the expression of a reporter protein encoded by the polynucleotide, the means may be an agent that can be used to measure expression of the reporter protein, such as an antibody or an enzyme substrate.

It may be desirable to compare expression to that of a control cell which lacks the regulatory element and/or reporter sequence present in the cell of the kit of parts (e.g. cell of the third aspect of the invention). Thus, the kit may further comprise a cell which does not contain a reporter sequence operatively linked to a regulatory element of a gene which regulatory element stimulates expression of the reporter sequence in response to a genotoxic agent or to an oxidative stress-inducing agent (e.g. a regulatory element from a gene selected from a group consisting of the genes Bscl2, Cbr3, Ephx1, Nope, Cdkn1a, Perp, Pltp, Srxn1, Cgref1, Ltb4r1, Btg2, Gpx2, Ltb4r2, Ddit4l, Fosl1, and Egr1). For example, the kit may further comprise a cell which does not contain a polynucleotide according to the first aspect of the invention, or a vector according to the second aspect of the invention.

A further aspect of the invention provides a method of determining the effect of a genotoxic agent or an oxidative stress-inducing agent, the method comprising subjecting a cell according to the third aspect of the invention to a genotoxic agent or an oxidative stress-inducing agent; and assessing the expression of the reporter sequence. It is believed that by assessing the effect of various genotoxic agents or oxidative stress-inducing agents, agents may be classified by their effect and insights gained into modes of toxicity.

Similarly, the invention provides a method of determining the effect of a genotoxic agent or an oxidative stress-inducing agent, the method comprising the steps of (a) subjecting one or more cells that comprise a reporter sequence operatively linked to a regulatory element of a gene, which regulatory element stimulates expression of the reporter sequence in response to a genotoxic agent or to an oxidative stress-inducing agent, to a genotoxic agent or an oxidative stress-inducing agent; and (b) assessing the expression of the one or more reporter sequences, wherein at least one of the cells comprises a polynucleotide comprising a reporter sequence operatively linked to a regulatory element of the Bscl2 gene.

Thus, step (a) may comprise subjecting one or more cells that comprise a different regulatory element (e.g. 2, 3, 4 or 5 different regulatory elements) operatively linked to a reporter sequence, to a genotoxic or oxidative stress-inducing agent, and to a test agent. The cells may the same or different. It is appreciated that the different regulatory elements may be operatively linked to the same or different reporter sequences.

In one embodiment, (i) a cell that comprises a polynucleotide comprising a reporter sequence operatively linked to a regulatory element of the Bscl2 gene, and (ii) one or more cells that comprise a polynucleotide comprising a reporter sequence operatively linked to a regulatory element of a gene selected from a respective one or more of Srxn1, Cbr3, Ephx1, Nope, Cdkn1a, Perp, Pltp, Cgref1, Ltb4r1, Btg2, Gpx2, Ltb4r2, Ddit4l, Fosl1, and Egr1, are subjected to a genotoxic or oxidative stress-inducing agent. It is understood that the cells of (i) and (ii) may be the same or different.

In a particularly preferred embodiment, a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene are subjected to a genotoxic or oxidative stress-inducing agent.

In a further preferred embodiment, a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene, and a cell that comprises a polynucleotide comprising a reporter sequence operatively linked to a regulatory element of the Btg2 gene, are subjected to a genotoxic or oxidative stress-inducing agent.

The method may be performed in vitro, in vivo, or ex vivo as described above.

A yet further aspect of the invention provides a method of selecting an agent (e.g. compound) that reduces expression of the reporter sequence in the polynucleotide of the first aspect of the invention, the method comprising:

a) subjecting a cell according to the third aspect of the invention to a test agent;

b) assessing the effect of the test agent on the expression of the reporter sequence; and c) selecting a test agent that reduces expression of the reporter sequence.

Similarly, the invention includes a method of selecting an agent that reduces expression of one or more reporter sequences, the method comprising:

a) subjecting one or more cells that comprise a reporter sequence operatively linked to a regulatory element of a gene, which regulatory element stimulates expression of the reporter sequence in response to a genotoxic agent or to an oxidative stress-inducing agent, to a test agent;

b) assessing the effect of the test agent on the expression of the one or more reporter sequences; and c) selecting a test agent that reduces expression of the one or more reporter sequences;

wherein at least one of the cells subjected to a test agent, comprises a polynucleotide comprising a reporter sequence operatively linked to a regulatory element of the Bscl2 gene.

Thus, step (a) may comprise subjecting cells that comprise a different regulatory element (e.g. 2, 3, 4 or 5 different regulatory elements) operatively linked to a reporter sequence, to a test agent. The cells may the same or different. It is appreciated that the different regulatory elements may be operatively linked to the same or different reporter sequences.

In one embodiment, (i) a cell that comprises a polynucleotide comprising a reporter sequence operatively linked to a regulatory element of the Bscl2 gene, and (ii) one or more cells that comprise a polynucleotide comprising a reporter sequence operatively linked to a regulatory element of a gene selected from a respective one or more of Srxn1, Cbr3, Ephx1, Nope, Cdkn1a, Perp, Pltp, Cgref1, Ltb4r1, Btg2, Gpx2, Ltb4r2, Ddit4l, Fosl1, and Egr1 are subjected to a test agent. It is understood that the cells may be the same.

In a particularly preferred embodiment, a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene are subjected to a test agent.

In a further preferred embodiment, a cell that comprises a polynucleotide comprising a reporter sequence operatively linked to a regulatory element of the Bscl2 gene, and a cell that comprises a polynucleotide comprising a reporter sequence operatively linked to a regulatory element of the Srxn1 gene, and a cell that comprises a polynucleotide comprising a reporter sequence operatively linked to a regulatory element of the Btg2 gene, are subjected to a test agent.

As discussed above in relation to other methods of the invention, the method may be performed in vitro, in vivo or ex vivo.

It is appreciated that in this and other screening methods of the invention, the one or more cells may be subjected to a combination of different test agents and the effect of the combination of test agents on the expression of the reporter sequences assessed. Examples of suitable test agents include those listed above.

Suitable methods for assessing the expression of the reporter sequence are as described above. By 'reduces expression' it is understood that the expression may be switched off (i.e. to an undetectable level), or that existing expression may be decreased.

It is appreciated that the method of this aspect of the invention may be performed with or without first subjecting the one or more cells to a genotoxic or oxidative stress-inducing agent, depending upon the background level of expression of the one or more reporter sequences in the absence of a genotoxic or oxidative stress-inducing agent.

If the background expression is very low for example, it may be desirable to first subject the one or more cells to a genotoxic or oxidative stress-inducing agent so that a baseline level expression of the one or more reporter sequences can be established to which the expression of the one or more reporter sequences in the presence of a genotoxic or oxidative stress-inducing agent can be compared. Of course, this may not be necessary if the baseline expression of the one or more reporter sequences in the presence of a genotoxic or oxidative stress-inducing agent is known. Alternatively, the background expression of the one or more reporter sequences may be used as the baseline expression to which expression in the presence of a genotoxic or oxidative stress-inducing agent is compared to, in which case it is not necessary to first subject the cells to a genotoxic or oxidative stress-inducing agent.

Preferably, the method is performed on isolated cells. Thus, the invention includes a method of selecting an agent or a combination of agents that reduce expression of the reporter sequence in the polynucleotide of the first aspect of the invention, the method comprising:

a) culturing a cell according to the third aspect of the invention (eg a cell line) in a suitable medium;

b) optionally adding a genotoxic or oxidative stress-inducing agent to the medium;

c) adding a test agent or combination of test agents to said medium;

d) assessing the effect of the test agent or combination of test agents on the expression of the reporter sequence; and e) selecting a test agent or combination of test agents that reduces expression of the reporter sequence.

Similarly, the invention includes a method of selecting an agent or a combination of agents that reduce expression of one or more reporter sequences, the method comprising:

a) culturing one or more cells (e.g. cell line) that comprise a reporter sequence operatively linked to a regulatory element of a gene, which regulatory element stimulates expression of the reporter sequence in response to a genotoxic agent or to an oxidative stress-inducing agent, in a suitable medium;

b) optionally adding a genotoxic or oxidative stress-inducing agent to the medium;

c) adding a test agent or combination of test agents to said medium;

d) assessing the effect of the test agent or combination of test agents on the expression of the one or more reporter sequences; and e) selecting a test agent or combination of test agents that reduces expression of the one or more reporter sequences;

wherein at least one of the cells comprises a polynucleotide comprising a reporter sequence operatively linked to a regulatory element of the Bscl2 gene.

Preferences for the cell and the genotoxic or oxidative stress-inducing agent include those listed above.

The invention will now be described in more detail with the aid of the following Figures and Examples.

FIG. 1: Polynucleotide sequences of PCR fragments containing regulatory elements of genes (A) Bscl2, SEQ ID No: 1; (B) Ephx1, SEQ ID No: 2; (C) Nope, SEQ ID No: 3; (D) Cdkn1a, SEQ ID No: 4; (E) Perp, SEQ ID No: 5; (F) Pltp, SEQ ID No: 6; (G) Srxn1, SEQ ID No: 7; (H) Cgref1, SEQ ID No: 8; (I) Ltb4r1, SEQ ID No: 9; (J) Cbr3, SEQ ID No: 10; (K) Btg2, SEQ ID No: 11. Forward and reverse primers are indicated below the sequence of each PCR fragment. Transcription start sites are indicated in a box in each sequence.

(A) Forward, SEQ ID No: 12; Reverse, SEQ ID No: 13; (B) Forward, SEQ ID No: 14; Reverse, SEQ ID No: 15; (C) Forward, SEQ ID No: 16; Reverse, SEQ ID No: 17; Reverse 2, SEQ ID No: 89 (D) Forward (2900 bp), SEQ ID No: 18; Reverse, SEQ ID No: 19; Forward (2364 bp), SEQ ID No: 90 (E) Forward, SEQ ID No: 20; Reverse, SEQ ID No: 21; (F) Forward, SEQ ID No 22; Reverse, SEQ ID No: 23; (G) Forward, SEQ ID No: 24; Reverse, SEQ ID No: 25; (H) Forward, SEQ ID No 26; Reverse, SEQ ID No: 27; (I) Forward, SEQ ID No: 28; Reverse, SEQ ID No: 29; (J) Forward, SEQ ID No: 30; Reverse, SEQ ID No: 31; (K) Forward, SEQ ID No: 32; Reverse, SEQ ID No: 33.

FIG. 2: Polynucleotide sequences of PCR fragments containing regulatory elements of genes (A) Gpx2, SEQ ID No: 34; (B) Ltb4r2, SEQ ID No: 35; (C) Ddit4l, SEQ ID No: 36; (D) Fosl1, SEQ ID No: 37; (E) Egr1, SEQ ID No: 38. Forward and reverse primers are indicated below the sequence of each PCR fragment. Transcription start sites are indicated in a box in each sequence.

(A) Forward, SEQ ID No: 39; Reverse, SEQ ID No: 40; (B) Forward, SEQ ID No: 41; Reverse, SEQ ID No: 42; (C) Forward, SEQ ID No: 43; Reverse, SEQ ID No: 44; (D) Forward, SEQ ID No: 45; Reverse, SEQ ID No: 46; (E) Forward, SEQ ID No 47; Reverse, SEQ ID No: 48.

FIG. 3: Polynucleotide sequences of genes (downstream of promoter).

(A) Bscl2; NC_000085; SEQ ID No: 58; (B) Ephx1; NC_000067; SEQ ID No: 50; (C) Nope; NC_000075; SEQ ID No: 51; (D) Cdkn1a; NC_000083; SEQ ID No: 52; (E) Perp; NC_000076; SEQ ID No: 53; (F) Pltp; NC_000068; SEQ ID No: 54; (G) Srxn1; NC_000068; SEQ ID No: 55; (H) Cgref1; NC_000071; SEQ ID No: 56; (I) Ltb4r1; NC_000080; SEQ ID No: 57; (J) Cbr3; NC_000082; SEQ ID No: 49; (K) Btg2; NC 000067; SEQ ID No: 59.

FIG. 4: Polynucleotide sequences of genes (downstream of promoter).

(A) Gpx2; NC_000078; SEQ ID No: 60; (B) Ltb4r2; NC_000080; SEQ ID No: 61; (C) Ddit4l; NC_000069; SEQ ID No: 62; (D) Fosl1; NC_000085; SEQ ID No: 63; (E) Egr1; NC 000084; SEQ ID No: 64.

FIG. 5: Cloning of promoter region by cloning a ~1500 bp fragment upstream of transcription start site that is believed to contain most of the regulatory promoter sequences. Also shown is a diagram of the pDsRed-Express 2.1 vector.

FIG. 6: Compound class specificity of Ephx1, Btg2, Perp and Cbr3 genes. Changes in gene expression of the endogenous biomarker genes were established by quantitative RT-PCR following a 16 hrs treatment of ES cells with indicated compounds. Depicted values are the average of tree independent experiments and error bars represent the standard deviation.

FIG. 7: Sensitivity of mouse ES cells to different genotoxic agents was established by determining the apoptotic response after exposure. (A) Apoptosis as percentage of subG1 cells using flow cytometry and (B) by using a Caspase3 activity assay. Error bars indicate the standard deviation of three independent experiments. (C) Percentage of apoptotic cells by Annexin-V staining at different times after exposure to increasing concentrations of Cisplatin.

FIG. 8: DsRed reporter cell lines for genotoxicity and oxidative stress assessment. (A) Flow cytometry analysis of DsRed expression in monoclonal mouse ES cell lines containing a DsRed fluorescent reporter driven by a putative biomarker gene promoter. As controls a promoterless and CMV-driven DsRed reporter cell line were used. Cell lines were exposed to 10 µM Cisplatin (Ephx1, Btg2, Perp, CMV, Promotorless) or 250 µM DEM (Cbr3) for 16 hrs. (B) Clonal survival of wild type mouse ES cells and the DsRed reporter cell lines after treatment with Cisplatin and Etoposide. Shown data is the average of three independent experiments. Error bars represent the standard deviation.

FIG. 9: Expression kinetics of the Ephx1-DsRed reporter mimics the expression changes of the endogenous gene. (A) Expression levels of the DsRed reporter and the endogenous Ephx1 gene as determined by quantitative RT-PCR. (B) Ratio between DsRed and Ephx1 expression. Background expression of Ephx1-DsRed is higher than that of the endogenous Ephx1 gene, while the response to CisPt is comparable. Shown data are the average of four experiments.

FIG. 10: Differential response of the DsRed reporter cell lines to genotoxic and oxidative stress-inducing agents. (A) DsRed reporter cell lines were exposed to 0.5 µM Etoposide or 5 µM Cisplatin and total DsRed fluorescence was determined using flow cytometry after different times of exposure. (B) DsRed reporter cell lines were exposed to increasing concentrations of the DNA damage-inducing agents Cisplatin, Etoposide, MMS and the oxidative stress-inducer DEM. The increase in total DsRed fluorescence was determined after 30 hrs. of exposure using flow cytometry. (C) Ratio of fold changes in DsRed expression of Btg2 vs. Cbr3 DsRed reporter cell lines after exposure to different agents. Exposure to the DNA damaging agents (Cisplatin, Etoposide) resulted in a ratio of approximately 1.2. while induction of oxidative stress (DEM, MMS) resulted in a ratio of approximately 0.8. All data shown are the average of four independent experiments. Error bars indicate the standard error of the mean.

FIG. 11: Compound class specificity of the reporter cell lines. (A) At each dose of compounds used the ratio of fold change (=relative reactivity) were calculated for each combination of two reporter cell lines. The relative reactivity of every pair of reporter cell lines was used to determine which combination of cell lines discriminated best between exposure to genotoxic and oxidative stress-inducing compounds. Values were calculated from at least four independent experiments and error bars represent standard error of the mean. (B) Fold change ratio between Btg2-DsRed and Cbr3-DsRed after exposure to the DNA damaging agents doxorubicin and mitomycin C (MMC) and the pro-oxidant $CuSO_4$.

FIG. 12: DsRed reporters are not activated by general cytotoxic stress. (A) DsRed reporter cell lines were exposed to increasing concentrations of Cisplatin (CisPt), Wyeth-14, 643 and Cyclosporin-A (CsA) and cell viability was determined by Alamar blue staining. (B) DsRed reporter cell lines were exposed to increasing concentration of CisPt, CsA, Wyeth-14,643 and DES. Total DsRed fluorescence was determined 24, 30 and 48 hrs. after exposure using flow cytometry. Depicted values are the average of three independent experiments and error bars indicated the standard error of the mean.

FIG. 13: Differential response of the GFP reporter cell lines generated by BAC TransgeneOmics to genotoxic and oxidative stress-inducing agents. GFP reporter cell lines were exposed to increasing concentrations of the DNA damage-inducing agents Cisplatin, Doxorubicin, MMC, and the oxidative stress-inducer DEM and $CuSO_4$. The increase in total GFP fluorescence was determined after 30 hrs of exposure using flow cytometry. All data shown are the average of 3 independent experiments. Error bars indicate the standard deviation.

FIG. 14: DsRed reporter cell lines for genotoxicity and oxidative stress assessment. Flow cytometry analysis of DsRed expression in monoclonal mouse ES cell lines containing a DsRed fluorescent reporter driven by five different putative biomarker gene promoters. Cell lines were exposed to 10 µM Cisplatin for 16 hrs.

FIG. 15: Genes being upregulated upon exposure to different genotoxic agents. We performed genome-wide expression profiling of mouse ES cells that were exposed to a wide variety of genotoxic compounds. (A) Genes that showed the highest change in expression upon exposure (+) compared to untreated controls (−), were grouped in three gene sets based on fold change and p-value. Gene set A contains genes that are induced by DNA damaging agents, gene set B contains genes that show specificity for oxidative stress. Gene set D contains genes that are activated by compounds that induce DNA damage, oxidative stress and the cell cycle inhibitor flavopiridol. (B) Responsive genes show a dose dependent increase in gene expression following exposure to the compounds tested. Data in the heatmaps is the average of three independent treatments and array hybridizations. Cells were exposed to low (L), medium (M) and high (H) concentrations of compounds that induce >10%, 10-30% or 30-50% apoptosis respectively.

FIG. 16: GFP-based mES reporter cells for genotoxicity and oxidative stress. (A) Two putative biomarker genes, selected after genome-wide transcription profiling of mES cells, show a selective response to DNA damaging agents (Bscl2) or pro-oxidants (Srxn1). The red intensity in the heatmap represents for every treatment the expression level under non-treated and treated conditions. (B) Selected genes were fused to a GFP fluorescent reporter using BAC transgenomics. (C) Fluorescence microscopy analysis of Bscl2-GFP and Srxn1-GFP reporter cells following exposure to cisplatin (CisPt) or DEM. (D) Expression of the GFP reporters was compared to expression of the endogenous biomarker genes after exposure to CisPt and DEM by quantitative RT-PCR. (E) Expression of the GFP reporters was compared to expression of the endogenous biomarker genes after 8 or 16 h exposure to CisPt and DEM by quantitative RT-PCR.

FIG. 17: The Bscl2-GFP and Srxn1-GFP mES reporter cells show specificity for genotoxic compounds or pro-oxidants respectively. (A) GFP reporter cells were exposed to CisPt and DEM and the induction in total GFP fluorescence of intact cells was determined by flow cytometry. (B) Toxicity of CisPt and DEM is comparable in the reporter cell lines. Survival of the Bscl2-GFP and Srxn1-GFP reporter cells was determined as the fraction of intact cells after 24 h treatment by flow cytometry. (C) Specific activation of the Bscl2-GFP reporter by the DNA damaging agents mitomycin C (MMC), doxorubicin and etoposide and of Srxn1-GFP after exposure to the oxidative stress-inducing agents sodium arsenite (NaAsO2), methyl methanesulphonate (MMS) and cadmium chloride (CdCl2). (D) GFP reporter cells were exposed to the DNA damaging agents CisPt, etoposide, doxorubicin and mitomycin C (MMC) or to the oxidative stress-inducing agents DEM, sodium arsenite (NaAsO$_2$), cadmium chloride (CdCl$_2$) and methyl methanesulphonate (MMS) for 24 h and the induction in total GFP fluorescence of intact cells was determined by flow cytometry. (E) Kinetics of Bscl2- and Srxn1-GFP reporter induction upon exposure to genotoxins or pro-oxidants. Bscl2-GFP and Srxn1-GFP reporter cells were exposed to 5 µM CisPt or 100 µM DEM and GFP expression was determined by live cell imaging up to 24 h exposure.

FIG. 18: Activation of the Srxn1-GFP reporter for oxidative stress depends on ROS production. (A) Bscl2-GFP and Srxn1-GFP mES reporter cells were treated with different concentration of the pro-oxidant DEM. The cells were simultaneously incubated with increasing concentrations of the ROS-scavenger n-acetyl cysteine (NAC). (B) Srxn1-GFP reporter cells were exposed to the pro-oxidants DEM, NaAsO2, CuSO4 and CdCl2. Increasing concentrations of NAC were added to the cells to reduce ROS levels.

FIG. 19: Activation of the Bscl2-GFP DNA damage reporter is associated with inhibition of DNA replication. (A) Bscl2-GFP and Srxn1-GFP mES reporter cells were treated with increasing concentrations of hydroxyurea and aphidicolin. (B) Cell viability of Bscl2-GFP and Srxn1-GFP reporter cell after exposure to hydroxyurea and aphidicolin.

FIG. 20: Activation of the Bscl2-GFP reporter depends on the ATR DNA damage signaling pathway. The Bscl2-GFP and Srxn1-GFP mES reporter cell lines were treated with the DNA damaging agent CisPt or the DNA replication inhibitor aphidicolin in the presence of specific inhibitors for ATM (ku55933), ATR (schisandrin B) or Chk1/Chk2 signaling (UCN01).

FIG. 21: Activation of the Bscl2-GFP DNA damage reporter is independent of p53 and expression of Srxn1-GFP oxidative stress reporter is controlled by the Nrf2 antioxidant pathway. siRNA knockdown of p53 and Nrf2 in the Bscl2-GFP and Srxn1-GFP reporter cells followed by exposure to the genotoxic compounds CisPt or etoposide and to the pro-oxidants DEM, MMS and NaAsO2.

FIG. 22: Sensitivity and specificity of the GFP reporter assays using ECVAM class 1 compounds. Bscl2-GFP and Srxn1-GFP reporter cells were exposed to increasing concentrations of ECVAM-recommended carcinogens that should be positive in an in vitro genotoxicity assay. Induction of the GFP reporters was determined after 24 h exposure by flow cytometry.

FIG. 23: Sensitivity and specificity of the GFP reporter assays using ECVAM class 2 compounds. Bscl2-GFP and Srxn1-GFP reporter cells were exposed to increasing concentrations of ECVAM-recommended non-carcinogens that should be negative in an in vitro genotoxicity assay. Induction of the GFP reporters was determined after 24 h exposure by flow cytometry.

FIG. 24: Sensitivity and specificity of the GFP reporter assays using ECVAM class 3 compounds. Bscl2-GFP and Srxn1-GFP reporter cells were exposed to increasing concentrations of ECVAM-recommended compounds that are non-carcinogens or non-genotoxic carcinogens and which scored positive in one in vitro/in vivo genotoxicity test. Induction of the GFP reporters was determined after 24 h exposure by flow cytometry.

FIG. 25: Sensitivity and specificity of the GFP reporter assays using additional (geno)toxic compounds. Bscl2-GFP and Srxn1-GFP reporter cells were exposed to increasing concentrations of (geno)toxic compounds with different reactive properties. These compounds were not specifically recommended by ECVAM for validation of in vitro genotoxicity testing. Induction of the GFP reporters was determined after 24 h exposure by flow cytometry.

FIG. 26: Bscl2-GFP reporter induction by progenotoxins that require metabolic activation. (A) Bscl2-GFP reporter cells were treated with increasing concentrations of aflatoxin B1 (AFB1), benzo [a] pyrene (B[a]P), cyclophosphamide and dimethylbenz(a)anthracene (DMBA) either in the presence of S9 rat liver extract plus the required cofactors or in the presence of the cofactors only. After 3 h incubation, S9 mix and genotoxins were removed by washing and culturing of cells was continued for 24 h in regular culture medium.

GFP reporter activity was established after 24 h by flow cytometry. (B) Relative cell survival was determined by the fraction of intact cells following exposure by flow cytometry.

FIG. 27: Activation of the Srxn1-GFP reporter depends on ROS production and is controlled by the Nrf2 pathway. (A) Bscl2-GFP and Srxn1-GFP mES reporter cells were treated with different concentration of the pro-oxidants DEM, $CuSO_4$, $NaAsO_2$, $CdCl_2$ or MMS and simultaneously incubated with increasing concentrations of the ROS-scavenger N-acetyl cysteine (NAC). GFP reporter induction was determined after 24 h incubation by flow cytometry. (B) Western blot analysis of Bscl2-GFP and Srxn1-GFP reporter cells that had been transfected with siRNAs against Nrf2. Nrf2 protein level was determined 4 days after transfection. Hprt protein level was used as loading control. (C) Bscl2-GFP and Srxn1-GFP reporter cells were exposed to 10 μM CisPt, 1.5 μM etoposide, 150 μM DEM, 0.5 mM MMS or 10 μM $NaAsO_2$ after knockdown of Nrf2 by siRNA transfection. GFP reporter activation was determined after 24 h exposure by flow cytometry.

FIG. 28: Activation of the Bscl2-GFP DNA damage reporter is associated with inhibition of DNA replication. (A) Bscl2-GFP and Srxn1-GFP mES reporter cells were treated with increasing concentrations of hydroxyurea and aphidicolin. GFP reporter activation was determined after 24 h exposure by flow cytometry. Survival of Bscl2-GFP and Srxn1-GFP reporter cell after exposure to hydroxyurea and aphidicolin was determined by the fraction of intact cells by flow cytometry. (B) Western blot analysis of cells that were exposed to 10 μM CisPt or 1.5 μM Aph in the presence of ATR (schisandrin B) or ATM (ku55933) inhibitors. Phosphorylation of the ATM target Kap-1, ATR target Chk1 and p53 was investigated. Detection of Hprt was used as control for equal protein loading. (C) Bscl2-GFP and Srxn1-GFP mES reporter activation by the DNA damaging agent CisPt or the DNA replication inhibitor Aph in the presence of specific inhibitors for ATM, ATR or Chk1/Chk2 signaling (UCN-01) was determined after 24 h by flow cytometry.

FIG. 29: Activation of the Bscl2-GFP and Srxn1-GFP reporters is independent of p53. (A) Western blot analysis of p53 expression in the Bscl2-GFP and Srxn1-GFP reporter cells after transfection with siRNAs against p53. (B) Induction of the Bscl2-GFP and Srxn1-GFP reporters upon exposure to 10 μM CisPt, 15 μM etoposide, 150 μM DEM, 0.5 mM MMS or 10 μM $NaAsO_2$ after p53 knockdown by siRNA transfection. (C) Induction of the Btg2-GFP reporter by several (geno)toxic compounds after transfection with siRNAs against p53, Nrf2 or a scrambled siRNA pool as control.

EXAMPLE 1

Novel Highly Sensitive Reporter Cell System for Genotoxicity and Oxidative Stress Risk Assessment Introduction Exposure of organisms to genotoxic or oxidative stress-inducing agents can result in cell death and development of various genetic diseases, including cancer. Existing test systems for genotoxicity display low specificity and often require animal testing. Therefore, there is a strong demand for fast and highly sensitive, animal-free test systems to establish the genotoxicity or oxidative stress-inducing capacity of both known and novel chemical compounds.

We have identified genes that can serve as biomarkers for exposure to genotoxic or oxidative stress. Promoters of selected genes were fused to a DsRed reporter gene and stably integrated in mouse ES cells. Established reporter cell lines displayed significant DsRed expression upon exposure to genotoxic agents already at concentrations that did not induce apoptosis. Exposure of DsRed reporter cell lines to various known non-genotoxic carcinogenic compounds did not induce DsRed expression. By QPCR we confirmed that changes in expression of the DsRed biomarkers after exposure to genotoxic stress are comparable to that of the respective endogenous genes.

Mouse embryonic stem (ES) cells are undifferentiated pluripotent cells that have the unique capability to divide unlimited. ES cells have an intact DNA damage response including the p53 pathway [20, 21] and are highly sensitive to various DNA damaging agents [22]. Therefore, mouse ES cells are highly suitable to use as an in vitro mammalian cell based assay for genotoxicity testing.

In conclusion, we generated highly sensitive mouse ES cell systems that allow establishing genotoxicity or oxidative stress-inducing capacity of compounds at non-cytotoxic concentrations. In addition, the fluorescent DsRed markers provide an easy and sensitive tool to study the DNA damage response in mammalian stem cells.

Materials and Methods

ES Cell Culture and Treatments

C57/Bl6 B4418 wild type ES cells were cultured as described previously [23]. Prior to exposure, cells were cultured on gelatin-coated plates in the absence of MEF feeders. Sub-confluent ES cells were exposed to different concentrations of genotoxic and non-genotoxic agents for 8 or 24 hours. Used concentrations: Cisplatin (CDDP: 10 μM), mitomycin C (MMC: 0.1-0.5-1.5 μM), N-methylnitrosurea (MNU: 0.1-0.5-2 μM), methyl methanesulfonate (MMS: 0.1-0.2-0.5 mM), etoposide (Etop: 0.1-0.5-2 μM), doxorubicin (Dox: 0.01-0.05-0.2 μM), four pro-oxidant agents: hydrogen peroxide ($H_2O_2$: 25-50-200 μM), t-butyl hydroperoxide (t-BHP: 25-50-100 μM), menadione (MEN: 25-50-100 μM), diethyl maleate (DEM: 25-100-250 μM), and three non-genotoxic agents: diethylstilbestrol (DES: 0.5-2.5-10 μM), Wyeth14,643 (1-50-250 μM), and Cyclosporine-A (CsA: 0.5-2.5-10 μM). All compounds were prepared freshly in DMSO, PBS or Medium and added directly to the culture medium.

Generation of DsRed Reporter Cell Lines 1.5 Kb PCR fragments, containing the promoter sequence and transcription start site (TSS) of the putative biomarker genes (Sharov A A, Dudekula D B, Ko. M S. 2006. CisView: a browser and database of cis-regulatory modules predicted in the mouse genome. DNA Res. 2006 Jun. 30; 13(3):123-34.) were inserted into the cloning site of pDsRed-express2.1 plasmid (Clontech). Primer sequences are summarized in Table 1. The DsRed reporter plasmids were stably transfected into wild type mouse ES cells using electroporation and various stable monoclonal cell lines were established. Mouse ES cells containing a promoterless DsRed or a CMV-driven DsRed reporter were generated as control cell lines. Sensitivity of the DsRed reporter cell lines to genotoxic compounds was determined using a clonal survival assay as described previously [22].

Detection of DsRed Expression

DsRed expression in the reporter cell lines was determined using flow cytometry (BD FACSCanto II). Cells were seeded on gelatin-coated 96 wells plates 24 prior to exposure and subsequently exposed to various genotoxic agents. Cells were washed with PBS, trypsinized and resuspended into PBS+2% serum for FACS analysis.

Induction of the DsRed reporters was compared to expression of the endogenous genes using quantitative real time (qRT-PCR). Cells were exposed to various genotoxic agents and total RNA was isolated after 6, 16 and 24 hours using the RNeasy mini kit (Qiagen). cDNA was synthesized using oligo(dT)$_{12-18}$ primers and SuperscriptIII reverse transcriptase (invitrogen) according to the manufacturer's instructions. Expression of DsRed and Ephx1 was determined using FastStart SYBR Green Master (Rox) QPCR mix on a 7900HT Fast Real-Time PCR System (Applied Biosystems). Relative expression was normalized using expression of the YWHAD and HPRT genes. See Table 1 for primer sequences.

Results

Expression of Ephx1, Cbr3, Btg2 and Perp Genes is Increased Upon Exposure to Genotoxic and Oxidative Stree Inducing Agents Changes in expression upon exposure to different genotoxic and oxidative-stress inducing agents were assessed by quantitative RT-PCR (FIG. 6). Ephx1, of which expression in induced upon exposure to DNA damaging agents, is an epoxide hydrolase that is located at the membrane of the endoplasmic reticulum where it is important in the biotransformation of aromatic compounds [27]. The oxidative stress-induced Cbr3 gene encodes an NADPH-dependent

TABLE 1

Sequences of oligonucleotides used in this study

| Gene | Forward primer (5'-3') | Reverse primer (5'-3') |
|---|---|---|
| Amplification biomarker promoter region | | |
| Ephx1 | CGGAATTCACACACCAGAAGAGGGCATC (SEQ ID No: 65) | GGGGTACCGTCGCTCTCGGGTTCCTACT (SEQ ID No: 69) |
| Cbr3 | CGGAATTCCATTGCTGCCTTGATCACATAAC (SEQ ID No: 66) | ACGCGTCGACGACACACGGACCACCTGATG (SEQ ID No: 70) |
| Btg2 | CGGGAGATCTGATGAAATGTCTTGCTG (SEQ ID No: 67) | GATAAGTCGACACCACTCGGGGAG (SEQ ID No: 71) |
| Perp | CGGAATTCTTTGAGCCGACAGAACCAAT (SEQ ID No: 68) | ACGCGTCGACGCGGAGCGGAGGAACGCCGG (SEQ ID No: 72) |
| qRT-PCR | | |
| YWHAD-1 | CTGGTGATGACAAGAAAGGAATTG (SEQ ID No: 73) | GGTGTGTCGGCTGCATCTC (SEQ ID No: 80) |
| YWHAD-2 | GCCGACACACCCCATCAG (SEQ ID No: 74) | GCAATGGCTTCATCGAAAGC (SEQ ID No: 81) |
| DsRed-1 | AGTACGGCTCCAAGGTGTACGT (SEQ ID No: 75) | CATCACGCGCTCCCACTT (SEQ ID No: 82) |
| DsRed-2 | GTGAAGCTGCCCGGCTACT (SEQ ID No: 76) | GTACTGCTCCACCACGGTGTAGT (SEQ ID No: 83) |
| Ephx1-1 | CAAAGCCATCAGCCAAAGAAG (SEQ ID No: 77) | AACCTATCTATCCTCTGGTGCAAGTC (SEQ ID No: 84) |
| Ephx1-2 | TGTGGGCTGTGCTCTGAATG (SEQ ID No: 78) | AGGCCTCCATCCTCCAGTTC (SEQ ID No: 85) |
| Hprt | TTGCTCGAGATGTCATGAAGGA (SEQ ID No: 79) | AGCAGGTCAGCAAAGAACTTATAG (SEQ ID No: 86) |

Apoptosis Assay

DsRed reporter cell lines were seeded on gelatin-coated 6 well plates and treated as described above. After 24 hr., adherent cells were trypsinized and combined with the detached cells in the culture medium. Cell pellets were washed with PBS and resuspended in 0.5 ml Annexin V staining buffer (10 mM HEPES pH 7.4, 150 mM NaCl, 5 mM KCL, 1.8 mM CaCl$_2$ and 1 mM MgCl$_2$) containing freshly added 1 ul/ml FITC-conjugated AnnexinV (Home made). Cells were incubated for 15 min. at room temp in the dark and analyzed by flow cytometry. Alternatively, apoptosis was determined using a Ac-DEVD-AMC-based Caspase3 activity detection assay as described in Kruse et al (Mutat Res, 2007. 617(1-2): p. 58-70).

carbonyl reductase that is involved in the reduction of a large number of biological and pharmacological compounds [28]. The Btg2 and Perp genes respond to a broader spectrum of DNA damage and stress-inducing compounds and expression of both genes has been suggested to depend on the p53 tumor suppressor gene [29, 30]. Btg2 is involved in regulation of the G1 to S phase transition of the cell cycle, while Perp is a membrane protein involved in cell-cell adhesion [31-33].

For each compound a low concentration that induced less than 10% apoptosis, a medium concentration that induced between 10-30% apoptosis and a high concentration that resulted in 30-50% apoptosis, was used. Apoptosis measurements were performed by determining the percentage of sub-G1 cells using flow cytometry and by measuring caspase 3 activity. FIG. 7A-B shows the results for Etoposide, doxorubicin, MNU and MMC (see Table 2 for a complete list of compounds used). In addition, we determined the level of apoptosis in time after exposure to different concentrations of CisPt by Annexin-V staining (FIG. 7C).

linking agent Cisplatin by quantitative RT-PCR. Both genes were transcriptionally activated by Cisplatin (FIG. 9A). The transcriptional activation of the Ephx1-DsRed reporter and the endogenous Ephx1 gene was enhanced with increasing dose of Cisplatin and continued to increase even after 24 h

TABLE 2

Genotoxic compounds used in study

| Compound | Abbreviation | Concentrations | Mode of action |
| --- | --- | --- | --- |
| Cis-Platin | CisPt | 1-10 uM | Intra- and interstrand crosslinks. Lesions on G or A. |
| Doxorubicin | Dox | 0.001-0.2 uM | Intercalating agent. Inhibits progression of topoisomerase-II. |
| Etoposide | Etop | 0.1-2 uM | Topoisomerase-II inhibitor. |
| Mitomycin-C | MMC | 0.1-1.5 ug/ml | DNA crosslinking agent. Interstrand and intrastrand crosslinks and mono aducts at guanine. |
| Methyl Methane Sulphonate | MMS | 0.05-0.5 mM | Alkylating agent, methylates DNA on N7-deoxyguanine and N3-deoxyadenine. |
| Diethyl Malonate | DEM | 25-250 uM | Glutathion depletion, results in increased levels of oxigen radicals. |
| Menadione | MEN | 5-100 uM | Vitamin K. Prooxidant. |
| Hydrogen Peroxide | $H_2O_2$ | 25-200 uM | Produces oxigen radicals resulting in protein and DNA damage |
| Tert-butyl Hydroperoxide | tBHP | 25-100 uM | Prooxidant. Depletion of cellular stores of GSH and oxidation of functionally important SH groups on mitochondrial enzymes |
| Antimycin A1 | Ant-A1 | 0.5-10 uM | Mitochondrial toxin. Respiratory chain inhibitor |
| Potassium Cyanide | KCN | 0.5-5 uM | Mitochondrial toxin. Respiratory chain inihbitor |
| Rotenone | Rot | 1-10 uM | Mitochondrial toxin. Respiratory chain inhibitor |
| 2-Acetylamino Fluorene | 2-AAF | 10-100 uM | CYP450 substrate. AF and AAF adducts at C(8) and N(2) position of guanine. |
| Cytosine arabinoside | AraC | 0.05-5 uM | Incorporated into DNA. Chain terminator. |
| Vincristine | Vin | 1-100 uM | Microtubule disruption. Blocks cells in mitosis |
| Flavopiridol | Flavo | 10-100 uM | Cyclin-dependent kinase (cdk) inhibitor. Downregulation of Bcl-2. Causes cell cycle arrest and apoptosis |
| Cyclosporin A | CsA | 0.5-10 uM | Non-genotoxic carcinogen. Immuno suppressor |
| Wyeth-14,643 | Wyeth | 1-250 uM | Non-genotoxic carcinogen. Peroxisome proliferator |

Generation of Fluorescent Reporter Cell Lines

A 1500 bp DNA fragment upstream of the transcription start site of each of mouse genes Cbr3, Ephx1, Nope, Cdkn1a, Perp, Pltp, Srxn1, Cgref1, Ltb4r1, Bscl2, and Btg2 was fused to a recently described highly stable DsRed fluorescent protein reporter gene [34].

These promoter fragments were cloned upstream of the DsRed-express2 reporter [34] and transfected into mouse ES cells. In addition, control cell lines were generated containing either a promoterless or a CMV promoter driven DsRed reporter gene. Multiple stable clones for each construct were analyzed for DsRed expression upon exposure to genotoxic or oxidative stress-inducing agents using flow cytometry (FIG. 8A and data not shown). For every biomarker gene a DsRed reporter cell line was selected based on low background DsRed expression and a strong increase in DsRed expression after exposure to different genotoxic compounds (FIG. 8A).

Promoterless DsRed cells did not show any DsRed expression irrespective of exposure to genotoxic agents, while the CMV-driven reporter displayed constitutive high DsRed expression when untreated but appeared to be somewhat responsive to genotoxic treatment, in agreement with previous reports [35, 36].

Cytotoxicity of the reporter cell lines for the tested compounds was similar compared to wild type ES cells (FIG. 8B), indicating that both DsRed expression and integration of the reporter gene in the cellular genome did not affect cellular sensitivity.

DsRed Reporter Vs. Endogenous Gene Activation

We tested to what extent the changes in DsRed mRNA expression of our reporter genes upon genotoxic stress resembled the transcriptional activation of the endogenous biomarker genes. mRNA expression levels of the Ephx1-DsRed reporter and the endogenous Ephx1 gene were determined at different times after exposure to the DNA crossof exposure. This suggests that the Ephx1 and DsRed messenger RNAs are stable and accumulate in the cells. Direct comparison of the increase in mRNA for Ephx1 and DsRed shows that the transcription activation by Cisplatin is similar for both genes but that the DsRed expression levels in untreated cells are higher than of Ephx1 (FIG. 9B). High background expression of the DsRed reporter is possibly caused by integration of the gene in a transcriptionally active region in the genome. However, the DsRed expression in untreated cells apparently does not affect transcriptional induction upon exposure to genotoxic agents.

Highly Sensitive and Selective Biomarkers

We next determined the time-dependent increase in DsRed expression in the reporter cell lines after exposure to Cisplatin and the topoisomerase II poison Etoposide. DsRed reporter cell lines were grown in 96-wells microplates, exposed to these two compounds and DsRed fluorescence was monitored using high-throughput flow cytometry at various time points. In all four reporter cell lines, both genotoxic agents induced a strong, up to 12-fold increase in total DsRed fluorescence (FIG. 10A). DsRed expression gradually increased in time, even at 48 hours after treatment, but specifically at higher genotoxicant concentrations, high levels of apoptotic cells negatively influenced the reliability of the assay. These findings indicate that the DsRed protein is rather stable and accumulates in the cells, increasing the sensitivity of the reporter cell systems.

To determine the sensitivity and specificity of the reporter cell lines for detection of either genotoxic or oxidative stress, cells were exposed to increasing concentrations of different classes of genotoxic agents: Cisplatin, Etoposide, the methylating agent methylmethane sulphonate (MMS) and the oxidative stress inducer diethyl malonate (DEM). DsRed expression was determined at 30 hours after treatment using flow cytometry. In all reporter cell lines a clear induction of DsRed expression upon exposure to the different agents could be observed (FIG. 10B). However, the extent of induction was clearly different for some of the reporter cell lines. Btg2, Ephx1 and Perp were relatively more responsive to DNA damaging agents, while Cbr3 responded more strongly to the oxidative stress inducer DEM.

To determine the differential response of the reporter cell lines to these two classes of compounds, we calculated for every combination of two reporter cell lines the ratio of fold changes of reporter expression at each dose of the compounds used. The average ratio between two reporter cell lines was used to determine which combination of reporter cell lines allows best discrimination between genotoxic and oxidative stress-inducing compounds (FIG. 11A). The fold induction ratio of Btg2-DsRed and Cbr3-DsRed proved to be most informative. While the ratios for the DNA damaging agents tested, i.e. Cisplatin and Etoposide were all around 1.2, the ratio for MMS and DEM was 0.8. Although the alkylating agent MMS is genotoxic, various reports show that exposure to MMS results in high levels of oxidative stress due to GSH depletion [37-39]. We verified the use of these cell lines for the detection of genotoxicity and oxidative stress by calculation the fold change ratio between Btg2-DsRed and Cbr3-DsRed following exposure to the genotoxic compounds doxorubicin and mitomycin C and to the oxidative stress inducer copper sulphate (FIG. 11A). Together these results indicate that the generated DsRed reporter cell lines can be used to identify genotoxic activity of compounds and in addition can help to discriminate between direct acting DNA damaging agents and oxidative damage-inducing compounds.

Reporter Activity Specific for Genotoxic Agents

To investigate whether the reporter cell lines were selectively reactive for genotoxic carcinogens or oxidative stress, cells were exposed to a number of non-genotoxic carcinogenic compounds i.e. the immunosuppressant Cyclosporin A (CsA), the peroxisome proliferator Wyeth-14,643 and the synthetic hormone diethylstilbestrol (DES) [40] at concentrations that clearly affected cell viability (FIG. 12A). While exposure of the reporter cell lines to Cisplatin resulted in a clear induction of DsRed expression, exposure to these non-genotoxic carcinogens did not induce any reporter activation, not even at the highest concentrations (FIG. 12B). These results indicate that activation of the DsRed reporter genes is not part of a general cellular stress response. The reporter cell lines therefore may provide a highly sensitive system for assessment of genotoxicity or oxidative stress.

Discussion

Recently, visualization of the activation of cellular stress pathways using fluorescent or chemi-illuminescent reporter cell lines has become an attractive approach to identify potential (cyto)toxic properties of chemical agents [16, 19]. Various assays, like the Vitotox and Greenscreen HC tests, show that the use of luminescent or fluorescent markers for the DNA damage response provides a reliable tool for genotoxicity prediction. However, these systems provide only limited information about the mode of toxicity of the tested compounds. Depending on the reactivity of compounds, various cellular pathways are activated upon exposure. Reporters that would be able to discriminate between the different DNA damage response and cellular stress pathways would not only predict (geno)toxicity of compounds but would also provide insight in the mode of toxicity.

In this study, we have identified biomarker genes which have low background expression and a robust induction upon agent exposure. To monitor biomarker induction, promoter regions of the identified genes were placed upstream of the DsRed Express-2 fluorescent marker gene. This DsRed variant is non-cytotoxic allowing stable and high expression of red fluorescent protein in mammalian cells [34]. Indeed, expression of DsRed Express-2 reporters in mouse ES cells did not affect cellular growth or sensitivity to various genotoxic compounds (FIG. 8B). An advantage of using a red fluorescent marker, compared to the commonly used eGFP, is that it allows analysis of compounds that show green autofluorescence [41]. For four of the identified biomarker genes, a stably integrated fluorescent reporter mES cell line was selected that fulfilled the criteria of displaying low basal background expression and a robust induction upon cytotoxicant exposure.

In the four selected ES cell lines, expression of the DsRed reporters that is driven by the selected biomarker promoters closely followed the induction of the endogenous genes upon exposure to genotoxic stress (FIG. 9). Basal DsRed biomarker expression in untreated cells was higher compared to the endogenous genes possibly because of positional effects of the integration site in the genome on gene expression. However, the higher basal expression of the reporters did not influence their ability to sensitively detect DNA damage-induced expression. This indicates that the strategy cloning of promoter regions upstream of a fluorescent reporter gene and expression in mammalian cells allows development of stable and highly specific in vitro systems for genotoxicity testing.

Other genotoxicity test systems have been described previously that rely in fluorescent or luminescent reporter activation in response to cellular exposure to DNA damaging agents. The bacterial Vitotox screen depends on a luciferase gene that is under control of the bacterial DNA damage SOS signaling system and the yeast Radarscreen is based on a β-galactosidase reporter that is controlled by the promoter of the Rad54 DNA repair gene. Validation of these genotoxicity assays using the ECVAM compound list indicated that both systems show a low number of false positives and false negatives [42]. Both assays showed a strong correlation (80-90%) with the Ames mutagenicity and in vitro clastogenicity tests. The mammalian Greenscreen HC assay that depends on expression of a GFP-tagged GADD45a gene that is activated by the p53-dependent DNA damage response. Also validation of this genotoxicity test system indicated a low percentage of false positives and negatives and a good correlation with mutation induction [18].

These data confirm that monitoring the activation of the DNA damage response can be used as a reliable tool to predict genotoxicity of mutagenicity of compounds. Preliminary data indicate that also the DsRed-based reporter cell lines provide a reliable test system to assess genotoxicity after exposure to a selection of ECVAM recommended list of compounds (data not shown). In contrast to the majority of current genotoxicity assays, the DsRed reporter cell systems provides additional information about the mode of toxicity of compounds.

The sensitivity of the bacterial Vitotox, yeast RadarScreen and the mammalian Greenscreen HC assays is relatively low compared to our mES cell baser reporter system.

The use of stem cells as a basis for a (geno)toxicity test system contributes to the sensitivity of the assay. mES cells are proficient in all the major DNA damage response pathways, including the p53-dependent signalling pathway. The use of ES cells as reporter system allows detection of genotoxicity of compounds at 10 to 100-fold lower concentrations compared to the Vitotox and Greenscreen HC assays (FIG. 10 and [16, 42]). Although for many compounds the concentration used for testing might not be a relevant issue, it becomes important when compounds are poorly soluble in water or show autofluorescence. Indeed, our DsRed reporter cell lines show increased DsRed expression upon exposure to various genotoxic agents already low cytotoxic concentrations (FIG. 10). In addition, due to its high stability the DsRed proteins will accumulate in the cells which will further increase the sensitivity of the cell system.

In conclusion, we generated a mES cell base fluorescent reporter system that can be used for genotoxicity assessment of compounds. We have created four independent cell lines that express reporter genes with different substrate specificity. We showed that these reporter cell lines are able to discriminate between genotoxic compounds and pro-oxidants.

EXAMPLE 2

Performance of Srxn1, Bscl2 and Btg2 as Biomarkers for Genotoxic and Oxidative Stress-Inducing Agents FIG. 13 demonstrates activated expression of GFP in reporter cell lines generated by BAC TransgeneOmics. Each of genes Srxn1, Bscl2 and Btg2 were fused to GFP via BAC recombineering. GFP expression in response to the genotoxic agents Cisplatin, Doxorubicin and MMC, and the oxidative stress-inducing agents DEM and $CuSO_4$ was increased. The results confirm the use of these genes as biomarkers for genotoxic and oxidative stress-inducing agents.

EXAMPLE 3

Performance of Ltb4ra, Cgref1, Cdkn1a, Pltp, and Nope as Biomarkers for Genotoxic and Oxidative Stress-Inducing Agents FIG. 14 demonstrates activated expression of DsRed in mouse ES cells driven by the promoter regions of each of Ltb4ra, Cgref1, Cdkn1a, Pltp, and Nope. Reporter cell lines were generated as described in Example 1. The results confirm the use of these genes as biomarkers for genotoxic and oxidative stress-inducing agents.

EXAMPLE 4

Identification of Five Genes (Gpx2, Ltb4r2, Ddit4L, Fosl1 and Egr1) as Biomarkers for Genotoxic or Oxidative Stress We have identified genes that could serve as potential biomarkers for exposure to genotoxic stress by exposing mouse embryonic stem (ES) cells to various genotoxic compounds and changes in gene expression were determined.

Materials and Methods

ES Cell Culture and Treatments (See Example 1)

Transcription Profiling

Total RNA was isolated using the RNeasy mini kit (Qiagen, Valencia, Calif.) according to the manufacturer's protocol. RNA quality and integrity was assessed with the Agilent 2100 Bioanalyzer system (Agilent technologies, Palo Alto, Calif.). RNA sample labeling and hybridization on Affymetrix arrays (Genechip Mouse Genome 430A arrays) was performed according to the manufacturer's protocols (Affymetrix). The data were analyzed using Rosetta Resolver (Rosetta Biosoftware, Seattle, Wash., USA). Upon importing the Affymetrix Genechip data (CEL files), data pre-processing including background correction and normalization was performed. Triplicate hybridizations were combined and the data points were compared to control treatments to create log ratios and associated p-values for the significance of differential expression. Genes with a false discovery rate (FDR) of 10% were identified as differentially expressed. In order to identify biomarker candidates, we divided our compounds into 2 classes: 1-DNA damage agents (CDDP, Dox, Etop, MMC, MMS, MNU), 2-prooxidant agents (H2O2, t-BUP, Dem, Men), and selected only genes with pvalues<0.01 and fold change>2 for all the treatments belonging to a class of compounds. To select the most significantly expressed genes, we combine the multiple treatments points for each class, we summed the logarithms of the multiple testing corrected p-values (log(pvalues)) and the fold change. A number of biomarker candidates either responsive to DNA damage or to prooxidants were identified with the lowest summed log(pvalues) and the highest summed fold change.

Results

Identification of Putative Biomarkers

Five genes have been identified that can serve as biomarkers for genotoxicity or oxidative stress. To establish the cellular response to genotoxic stress, we exposed mouse embryonic (ES) cells to various genotoxic agents. ES cells are p53 proficient and are capable of indefinite cell division without transformation, in contrast to the majority of established mammalian cell lines.

We first established cytotoxicity of various DNA damaging agents in mouse ES cells by measuring apoptosis (see Example 1 and FIG. 7).

TABLE 4

Genotoxic compounds used in study

| Compound | Abbreviation | Concentrations | Mode of action |
| --- | --- | --- | --- |
| Cis-Platin | CisPt | 1-10 uM | Intra- and interstrand crosslinks. Lesions on G or A. |
| Doxorubicin | Dox | 0.001-0.2 uM | Intercalating agent. Inhibits progression of topoisomerase-II. |
| Etoposide | Etop | 0.1-2 uM | Topoisomerase-II inhibitor. |
| Mitomycin-C | MMC | 0.1-1.5 ug/ml | DNA crosslinking agent. Interstrand and intrastrand crosslinks and mono aducts at guanine. |
| Methyl Methane Sulphonate | MMS | 0.05-0.5 mM | Alkylating agent, methylates DNA on N7-deoxyguanine and N3-deoxyadenine. |
| Diethyl Malonate | DEM | 25-250 uM | Glutathion depletion, results in increased levels of oxygen radicals. |
| Menadione | MEN | 5-100 uM | Vitamin K. Prooxidant. |
| Hydrogen Peroxide | $H_2O_2$ | 25-200 uM | Produces oxigen radicals resulting in protein and DNA damage |
| Tert-butyl Hydroperoxide | tBHP | 25-100 uM | Prooxidant. Depletion of cellular stores of GSH and oxidation of functionally important SH groups on mitochondrial enzymes |

TABLE 4-continued

Genotoxic compounds used in study

| Compound | Abbreviation | Concentrations | Mode of action |
| --- | --- | --- | --- |
| Antimycin A1 | Ant-A1 | 0.5-10 uM | Mitochondrial toxin. Respiratory chain inhibitor |
| Potassium Cyanide | KCN | 0.5-5 uM | Mitochondrial toxin. Respiratory chain inihbitor |
| Rotenone | Rot | 1-10 uM | Mitochondrial toxin. Respiratory chain inhibitor |
| 2-Acetylamino Fluorene | 2-AAF | 10-100 uM | CYP450 substrate. AF and AAF adducts at C(8) and N(2) position of guanine. |
| Cytosine arabinoside | AraC | 0.05-5 uM | Incorporated into DNA. Chain terminator. |
| Vincristine | Vin | 1-100 uM | Microtubule disruption. Blocks cells in mitosis |
| Flavopiridol | Flavo | 10-100 uM | Cyclin-dependent kinase (cdk) inhibitor. Downregulation of Bcl-2. Causes cell cycle arrest and apoptosis |
| Cyclosporin A | CsA | 0.5-10 uM | Non-genotoxic carcinogen. Immuno suppressor |
| Wyeth-14,643 | Wyeth | 1-250 uM | Non-genotoxic carcinogen. Peroxisome proliferator |

These concentrations were used to determine the changes in gene expression using microarray analysis of the complete cellular transcriptome upon exposure to various genotoxic agents. RNA was isolated from cells, 8 h. after exposure to increasing concentrations of various genotoxic agents and subsequently hybridized on Affymetrix arrays. After normalization and background correction, genes that displayed the highest change in expression after treatment were identified, based on both fold change and p-value (FIGS. 15A and 15B). Data analysis showed that Gpx2, Ltb4r2, Ddit4l, Fosl1, and Egr1 are highly upregulated, confirming a specific response to DNA damage. Based on this, we have identified five genes as putative biomarkers for genotoxic stress.

Generation of DsRed Reporter Cell Lines

Regulatory elements of the selected genes are fused to a DsRed reporter gene and stably integrated into mouse ES cells. The fluorescent DsRed markers provide an easy and sensitive tool to study the DNA damage response in mammalian stem cells.

A panel of highly sensitive mouse ES cells that allow assessment of genotoxicity is developed. The assay is based on expression of a DsRed fluorescent marker gene under control of different promoters that are specifically activated upon exposure to DNA damaging agents. Genotoxicity can be tested at non-cytotoxic concentrations and detection of DsRed fluorescence using flow cytometry allows usage of these cell lines as a high throughput assay.

The cell lines are generated, DsRed expression detected, and apoptosis assayed by, for example, methods described in Example 1.

Sensitivity

Sensitivity of the reporter cell lines for detection of genotoxic stress is assessed by exposing the cells to increasing concentrations of the genotoxic agents cisplatin, etoposide, the methylating agent methylmethane sulphonate (MMS) and the indirect oxidative stress inducer diethyl malonate (DEM). At different times after treatment DsRed expression is determined using flow cytometry. Used concentrations of the different compounds is based on the level of apoptosis induction in wild type ES cells (FIG. 7).

Not only exposure to genotoxic agents has been shown to induce cancer but also non-genotoxic compounds have been implicated in carcinogenesis although their mode of action is largely unknown. To investigate whether the reporter cell lines can be used to discriminate between genotoxic and non-genotoxic carcinogens, cells are exposed to cyclosporine A (CsA), Wyeth-14643 and diethylstilbestrol (DES). The concentrations of the non-genotoxic compounds that are used for the exposures are based on their effect on cell proliferation (data not shown). DsRed expression is determined by flow cytometry.

Exposure to high concentrations of genotoxic compounds rapidly induces apoptosis to protect cells against the mutagenic effects of DNA damage. Apoptosis can be easily determined by annexin V or caspase 3 staining assays, for example as described above. To further establish the sensitivity of the reporter cell lines, DsRed expression in the reporter cells is compared to apoptosis induction after exposure to increasing doses of genotoxic agents.

The genes that are identified as putative biomarkers for genotoxicity are selected based on strong transcriptional activation upon exposure to genotoxic agents. The promoter regions of these genes are fused to a fluorescent reporter gene and stable integrated in mouse ES cells. Ideally, the changes in DsRed expression upon genotoxic stress would closely resemble the transcriptional activation of the endogenous biomarker genes. Expression levels of the reporter genes and the endogenous genes are determined at different times after exposure to a genotoxic agent by quantitative RT-PCR.

EXAMPLE 5

GFP Reporter Cell Systems for DNA Replication Inhibition and Oxidative Stress

Summary

Industry yearly develops a large number of new chemical compounds for a wide range of applications that benefit society. Following environmental, occupational, accidental or medical exposure of humans, these compounds may react or interact with various cellular structures and organelles, including DNA, proteins and lipids with possible (geno) toxic consequences. Current approaches for evaluating the safety of chemicals and products are resource- and time-intensive, making it difficult to meet the demands of evaluating the safety of an ever-increasing number of chemicals. Monitoring activation of specific cellular signalling pathways upon exposure to various classes of (geno)toxic carcinogens will on one hand allow assessment of potential (geno)toxic properties of chemicals, and on the other hand can provide more insight into the primary mode of toxicity of compounds.

We have constructed two reporters encoding C terminal green fluorescent GFP-tagged fusion proteins. The Bscl2-GFP reporter is selectively activated after exposure to DNA damaging agents. Induction of the reporter is associated with inhibition of DNA replication and activation of the ATR DNA damage signaling pathway. The Srxn1-GFP reporter is specifically induced upon oxidative stress and is part of the Nrf2 antioxidant response pathway. Employment of these mES reporter cell lines can provide insight into the primary reactive properties of known and unknown chemicals.

Results

FIG. 16 shows GFP fluorescence-based mES reporter cell systems can be used to detect genotoxicity and oxidative stress.

FIG. 17 demonstrates that GFP reporters are specific for genotoxic and oxidative stress.

FIG. 19 shows Bscl2-GFP reporter activation by DNA replication inhibition.

Figure 21:
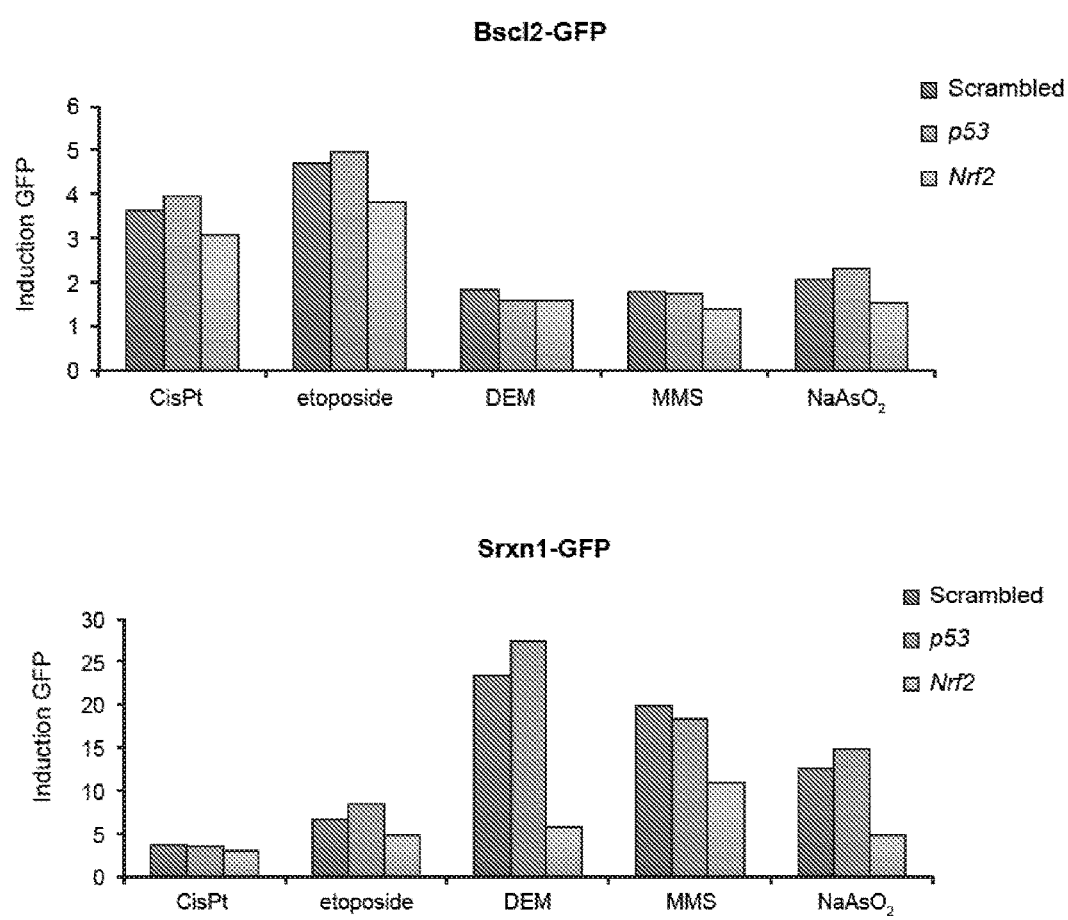
Figure 22:
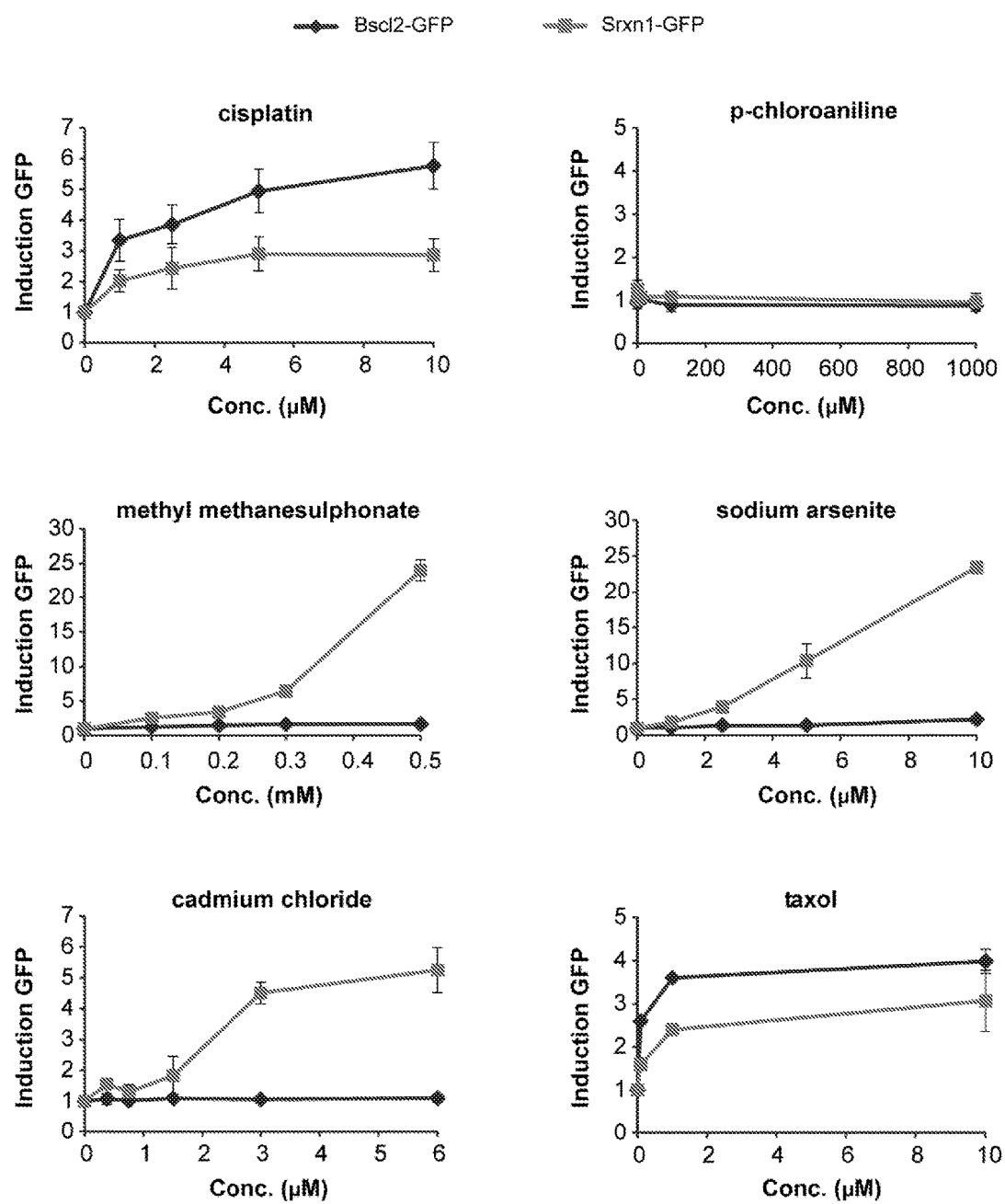
Figure 23:
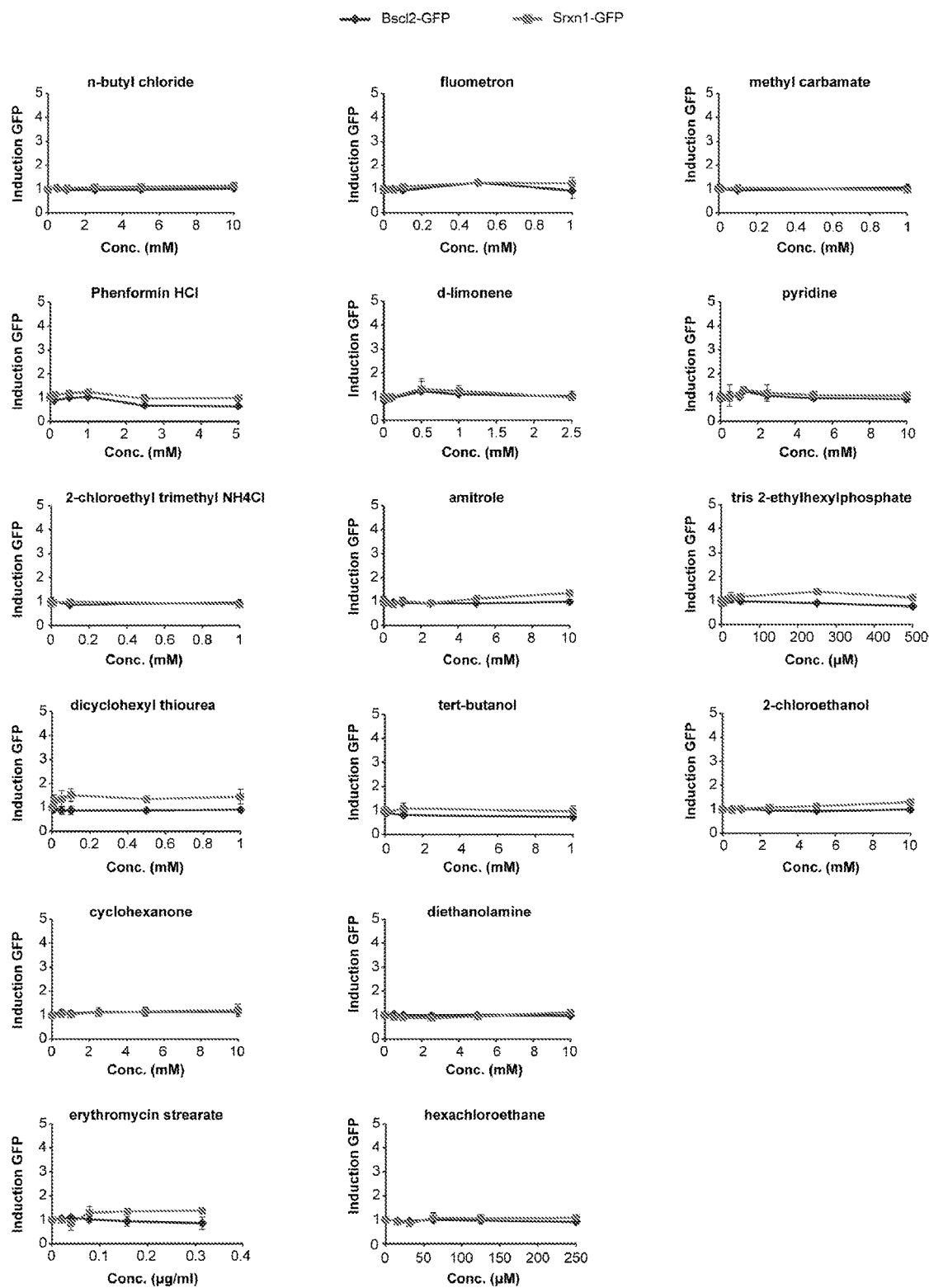
Figure 24:
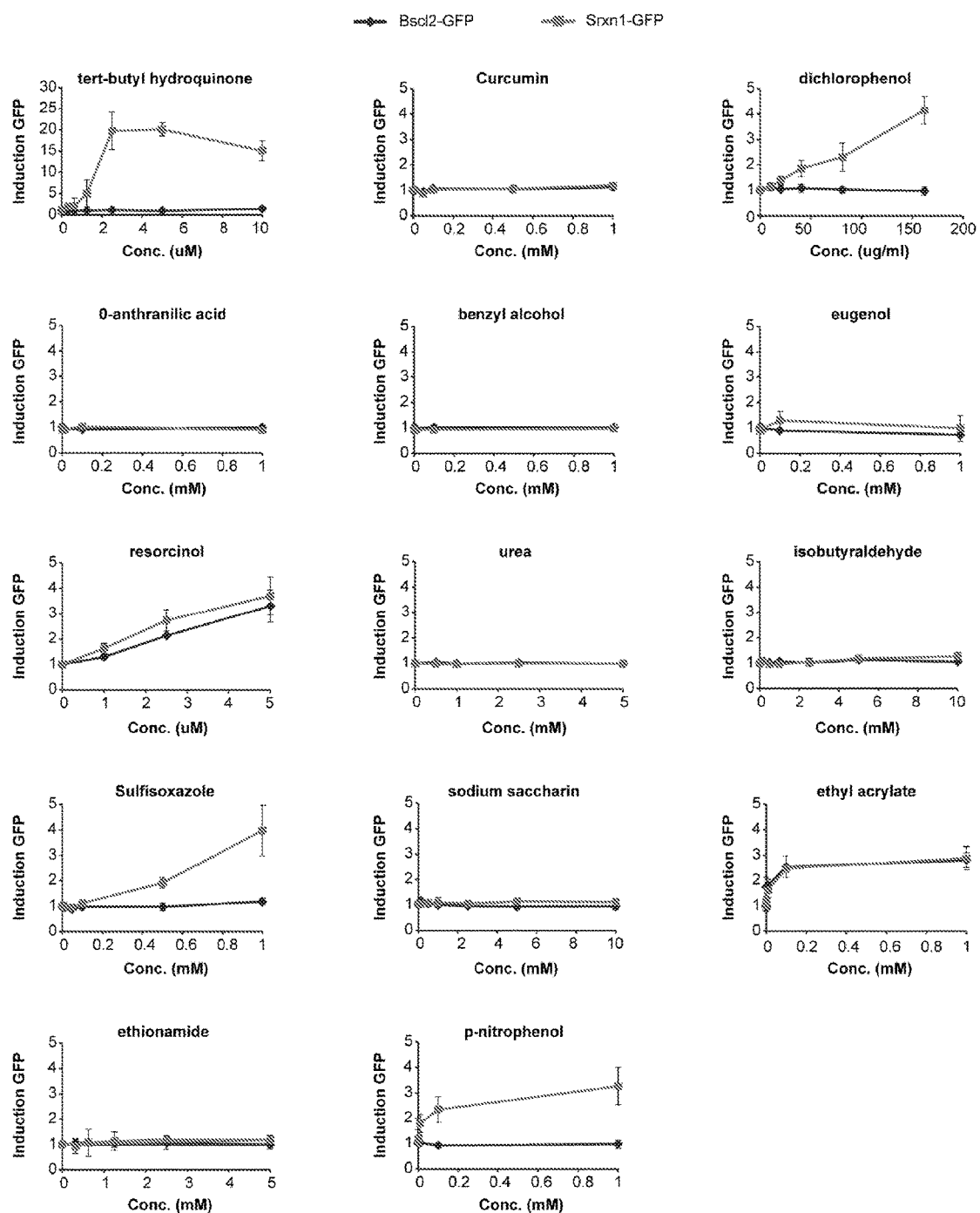
Figure 25:
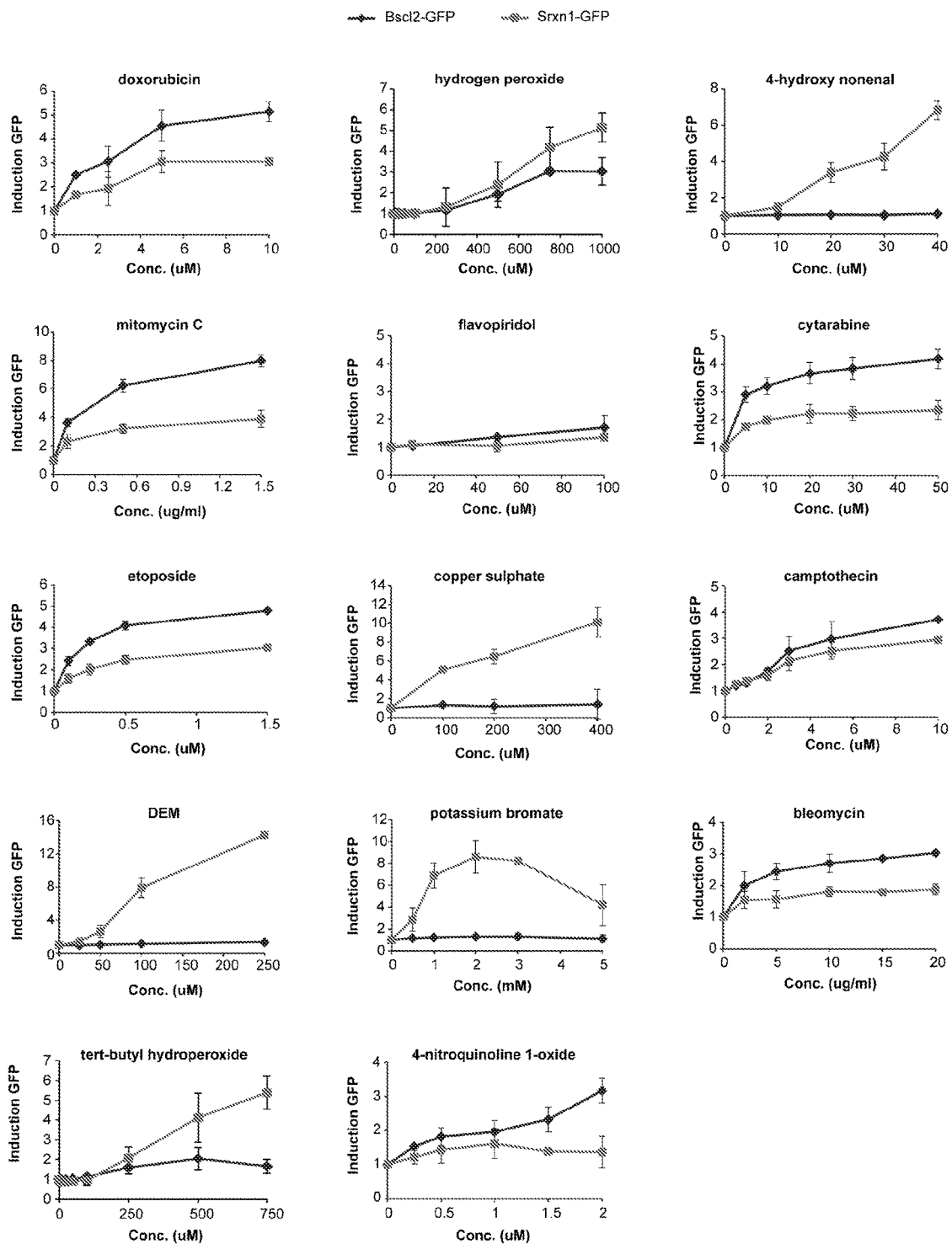

FIG. 21 focuses on the interaction between p53 and Nrf2 signalling pathways and GFP reporter activation.

Conclusions

Mouse embryonic stem cell systems can detect genotoxic or oxidative stress-inducing properties of chemicals.

Bscl2-GFP reporter for DNA damage is activated upon DNA replication inhibition

Bscl2-GFP reporter expression depends on the ATR damage signalling pathway but is p53 independent.

Srxn1-GFP reporter for oxidative stress is activated in response to ROS production and is controlled by the Nrf2 pathway.

EXAMPLE 6

The ToxTracker Assay: GFP Reporter Systems That Provide Mechanistic Insight Into the Genotoxic Properties of Chemicals Summary Here we describe the generation of a novel GFP-based (geno)toxicity assay, ToxTracker, consisting of different mES reporter cell lines that are preferentially responsive to genotoxic compounds or to agents that induce oxidative stress. The Bscl2-GFP genotoxicity reporter is activated upon replication inhibition and depends on the ATR-Chk1 signaling pathway. However, Bscl2-GFP expression is not regulated by the p53 tumor suppressor. The Srxn1-GFP reporter is activated upon increased levels of oxidative stress and is controlled by the Nrf2 anti-oxidant pathway. A third GFP reporter cell line based on the p53-responsive Btg2 gene is activated upon exposure to a broad spectrum of (geno)toxic compounds. The ToxTracker assay provides a powerful tool for (geno)toxic risk assessment of novel chemicals while providing mechanistic information on the genotoxic and/or oxidative properties of a compound.

Materials and Methods

ES Cell Culture and Treatments

C57/B16 B4418 wild type mouse ES (mES) cells were cultured in ES knockout medium (Gibco) containing 10% FCS, 2 mM glutamax, 1 mM sodium pyruvate, 100 µM β-mercaptoethanol and leukemia inhibitory factor (LIF) as previously described (Hendriks et al, 2011). Mouse ES cells were propagated on irradiated primary mouse embryonic fibroblasts as feeders according to established protocols. Cells were seeded 24 h prior to chemical exposure on gelatin-coated plates in BRL-conditioned ES cell medium in the absence of feeder cells. For analysis of compounds that require metabolic activation, cells were exposed for 3 h in the presence of 1% S9 rat liver extract in 3.2 mM KCl, 0.8 mM $MgCl_2$, 0.5 mM glucose-6-phosphate and 0.4 mM NADP. After 3 h cells were washed with PBS and cultured for 24 h in BRL-conditioned medium without the tested compounds. In all other treatments cells were continuously exposed for 24 h before GFP reporter analysis. For the inhibition of ATM, ATR and Chk1/Chk2 signaling in response to replication stress, cells were seeded 24 h prior to exposure in gelatin-coated 96-wells plates. Cells were exposed to 10 µM cisplatin (CisPt) or 1.5 µM aphidicolin (Aph) for 24 h in the presence of Ku55933 ATM inhibitor (0, 2, 5, 10 µM), schisandrin B ATR inhibitor (0, 6, 15, 30 µM) or UCN-01 Chk1/Chk2 inhibitor (0, 100, 200 nM).

Generation of GFP Reporter Cell Lines

The GFP reporters were generated by BAC recombineering as described above (Poser et al, 2008). Bacterial strains with a BAC containing the biomarker gene were selected using mouse BAC finder and ordered from BACPAC. The putative biomarker genes on the BAC were modified with a C-terminal GFP green fluorescent marker (Poser et al, 2008) using the Quick & Easy BAC modification Kit (Gene Bridges). Electrocompetent bacterial BAC strains were first transformed with the pRed/ET plasmid that contains the RecE and RecT recombination enzymes. PCR fragments encoding a GFP-ires-neomycin/kanamycin reporter cassette were generated using primers that each contain 50 nucleotide additional sequence homologous to the 3' sequence of the biomarker gene on the BAC. These homologous sequences on both the 5' and 3' ends of the PCR fragment allow RecE/T-mediated site-specific recombination of the GFP-ires-Neo selection cassette at the 3' end of the biomarker gene on the BAC. BAC strains that contain pRed/ET were grown at 37° C. for 30 minutes in the presence of L-arabinose to induce expression of the recombination enzymes. Subsequently, BAC strains were transformed with the GFP-ires-Neo PCR fragment by electroporation, incubated at 37° C. for 2 h to allow recombination of the PCR fragment with the BAC and plated on kanamycin selection plates. Individual clones were analyzed for proper integration of the GFP cassette by PCR. Modified BACs were isolated using the Nucleobond PC100 DNA isolation kit (Macherey Nagel).

Mouse ES cells were seeded on gelatin-coated culture dishes 24 h prior to transfection. Modified BACs were transfected into the mES cells using Lipofectamine 2000 (Invitrogen) according as described previously (Poser et al, 2008). Monoclonal mES cell lines were selected based on the level of induction of the GFP reporter after exposure to genotoxic compounds or pro-oxidants. GFP expression was determined by flow cytometry.

siRNA Transfection

The GFP reporter cells were transfected with SMARTpools of four individual siRNAs against Nrf2 or p53 (Dharmacon). A scrambled non-targeting siRNA pool was used as negative control. A siRNA against kif11, an essential gene that encodes a kinesin-like protein, was used to determine transfection efficiency. Kif11 knockdown is lethal for mES cells. siRNA transfections were performed in gelatin-coated 96-wells cell culture plates. 1 µM siRNA was mixed with 0.1 µl Dharmafect 1 transfection reagent in 20 µl serum-free medium per transfection. The siRNA mix was transferred to the 96-wells plate and subsequently 11.000 mES reporter cells were seeded in each well. Cells were washed after 16 h with PBS and cultured in fresh BRL-conditioned ES cell medium. After 48 h cells were treated with various genotoxic and oxidative stress inducing compounds. After 24 h incubation, induction of the GFP reporters was determined by flow cytometry.

Detection of GFP Expression

Cells were seeded on gelatin-coated 96 wells plates and 24 hours later subsequently exposed to various genotoxic agents. All tested compounds were dissolved in DMSO or PBS and diluted in fresh BRL-condition ES cell medium just before incubation with the cells. After 24 h exposure, cells were washed with PBS, trypsinized and resuspended into PBS+2% serum, immediately followed by flow cytometry analysis (Guava easyCyte 6HT, Millipore).

GFP reporter expression in mES cells was visualized by confocal immunofluorescence microscopy and live cell imaging. Cells were seeded at low density on fibronectin-coated glass cover slips. For confocal microscopy analysis, the cells were exposed to 5 µM CisPt or 150 µM DEM for 24 h and subsequently fixed with 2% paraformaldehyde in PBS. GFP reporter expression was visualized using a Leica TCS SP2 confocal microscope. For live cell imaging, cells were plated on glass bottom 96 well culture plates (Greiner) and exposed to 5 µM CisPt or 100 µM DEM. GFP reporter activation was determined using a Nikon TiE2000 microscope equipped with a Perfect Focus System and an automated microscope stage at 37° C. with 5% $CO_2$ delivery to the sample plate location. Images were acquired with a 20× (NA 0.75) dry Plan Apochromat objective and the image acquisition was controlled by EZ-C1 software (Nikon). In each well, an image from the same position was acquired every 15 minutes for a period of 24 hours. Automated image analysis of individual images was performed using Image-Pro Plus software (MediaCybernetics) to calculate the induction of overall cellular fluorescence.

Quantitative RT-PCR Analysis of Reporter Expression

Induction of the GFP reporters was compared with the expression of the endogenous gene using quantitative real time PCR (qRT-PCR). Cells were exposed to the genotoxic agent CisPt or the pro-oxidant DEM and total RNA was isolated after 8 or 16 hours using the RNeasy mini kit (Qiagen). cDNA was synthesized using oligo(dT)$_{12-18}$ primers and SuperscriptIII reverse transcriptase (Invitrogen) according to the manufacturer's protocol. Expression of the GFP reporter and the endogenous biomarker gene was determined using specific primers against the 3'-UTR of either gene with the FastStart SYBR Green Master (Roche) QPCR mix on a 7900HT Fast Real-Time PCR System (Applied Biosystems). Relative expression was normalized using expression of the YWHAD and Hprt genes.

Western Blot Analysis

Activation of the ATM and ATR signaling pathways in response to CisPt and Aph was determined by Western blot analysis. Cells were lysed in Laemmli protein sample buffer after 24 h exposure and subjected to SDS-PAGE. Proteins were transferred to PVDF membrane (Millipore) and detected using antibodies against phospho-Kap1 (Bethyl laboratories), phospho-Chk1 (Bethyl laboratories), phospho-p53 (Cell signaling) or Hprt (Santa Cruz) as protein loading control. Proteins were visualized using enhanced chemoluminescence (ECL).

Validation of GFP Reporter Cell Lines

The mES GFP reporter cells were exposed to at least five different concentrations of 50 genotoxic and non-genotoxic compounds. The selection of compounds was largely based on the ECVAM suggested list of chemicals for validation of in vitro genotoxicity test assays (Kirkland et al, 2008). Compound concentrations that were used for the validation were based on cytotoxicity, where the highest concentration induced significant cell death (10-25% viable cells after 24 h treatment). Cell viability was determined by flow cytometry as the fraction of intact cells after 24 h of treatment compared to untreated cells. For compounds that did not affect cell viability, a maximum concentration of 10 mM was used. Induction of GFP fluorescence in the reporter cells was determined after 24 h exposure by flow cytometry.

Testing Criteria

Activation of a reporter cell line was considered positive when exposure to at least two different concentrations of a compound resulted in >1.5 fold induction of GFP expression which is at least 5 times higher than the standard deviation in background fluorescence. To determine if a reporter gene was activated by a compound, only concentrations that resulted in >25% cell survival were taken into account. At higher cell killing levels GFP induction would often not increase anymore with dose. All presented data are the summary of at least three independent experiments. All shown error bars represent standard deviations.

Results

GFP-Based Reporters for Genotoxicity and Oxidative Stress

We have found two putative biomarker genes to be responsive to either DNA damaging chemicals or to oxidative stress (see Examples 2 and 5, and FIG. 16). The Bscl2 gene was shown to be selectively responsive to genotoxic compounds. The Bscl2 gene is defective in patients suffering from Berardinelli-Seip congenital lipodystrophy and encodes the Seipin protein (Magre et al, 2001)(Szymanski et al, 2007). So far, the Bscl2 gene has not been implicated in the cellular DNA damage response. The Srxn1 gene encodes the sulfiredoxin-1 protein that reduces oxidized cysteines in peroxiredoxins (Prxs) in the peroxisomes. Srxn1 plays an important role in the defense against cellular oxidative stress (Chang et al, 2004).

To allow physiological regulation of gene expression we used BAC recombineering (Poser et al, 2008) (FIG. 16B) to generate Bscl2- and Srxn1-based green fluorescent reporters. Following transfection multiple mES cell lines containing either the Bscl2-GFP or Srxn1-GFP reporter were evaluated for their responsiveness to either the DNA damaging agent cisplatin (CisPt) or the indirect pro-oxidant diethyl maleate (DEM) and a single clonal cell line for either construct was selected for further studies. Bscl2-GFP correctly localized to the endoplasmic reticulum, while Srxn1-GFP was located in both the nucleus and cytoplasm as reported previously, indicating that the GFP tag did not affect their localization (FIG. 16C). By quantitative real-time PCR (qRT-PCR), we compared the responsiveness of the GFP reporters with the corresponding endogenous genes. The Bscl2-GFP reporter was selectively induced upon exposure to CisPt but not to DEM (FIGS. 16D and E). Both the basal level and the kinetics of induction of the GFP reporter were comparable to that of the endogenous Bscl2 gene. The Srxn1-GFP reporter was somewhat responsive to CisPt but highly induced after exposure to DEM. The specificity of the Srxn1-GFP reporter was comparable to endogenous Srxn1 although the extent of induction of the GFP reporter appears to be slightly higher compared to the endogenous gene.

Sensitivity and Specificity of the mES GFP Reporter Cell Lines

To investigate the sensitivity and specificity of the mES Bscl2-GFP and Srxn1-GFP reporter cell lines, cells were exposed to increasing concentrations of the genotoxic compounds CisPt, etoposide, doxorubicin and mitomycin C (MMC) or the oxidative stress-inducing agents DEM, sodium arsenite ($NaAsO_2$), cadmium chloride ($CdCl_2$) and methyl methanesulphonate (MMS). Although MMS is a DNA alkylating agent, we and others have previously shown that the primary toxic response of cells after exposure to MMS is strongly correlated with oxidative stress induction, likely due to the direct reaction of MMS with gluthatione and other proteins (Hendriks et al, 2011)(Wilhelm et al, 1997)(Ashino et al, 2003). The Bscl2-GFP reporter was significantly induced after exposure to all tested genotoxic compounds in a concentration-dependent fashion but hardly responded to either of the pro-oxidants or the alkylating agent MMS (FIG. 17D). In contrast, the Srxn1-GFP reporter cells was highly responsive to all oxidative stress-inducing agents including MMS, but was also induced by the genotoxic compounds, albeit to a lesser extent than the Bscl2-GFP reporter. Cytotoxicity of CisPt and DEM was comparable in the Bscl2-GFP and Srxn1-GFP reporter cells, indicating that induction of the GFP reporters is not correlated with general cellular stress (FIG. 17B). In addition, both GFP reporter cell lines were equally sensitive to CisPt and DEM indicating that expression of the GFP reporters is not cytotoxic.

We evaluated the dynamic response of the GFP reporter cell lines by using time-lapse live cell imaging confocal microscopy and quantitative image analysis (FIG. 17E). The Srxn1-GFP reporter was readily induced upon exposure to DEM but was hardly responsive to CisPt along the entire time period. Expression of the Srxn1-GFP reporter was clearly detectable after 8 h exposure to DEM and reached a plateau after 24 h exposure. Reversely, the Bscl2-GFP reporter was preferentially induced upon exposure to CisPt, in agreement with the flow cytometry analysis (FIG. 17D). Bscl2-GFP expression became visible as early as 12 h and steadily increased up to 24 h after start of treatment.

Validation of the GFP Reporters

To further establish the sensitivity and specificity of the Bscl2-GFP and Srxn1-GFP reporters, they were exposed to a wide variety of carcinogenic and non-carcinogenic compounds, as suggested by the European Center for Validation of Alternative Methods (ECVAM) (Kirkland et al, 2008). ECVAM Class 1 compounds consists of in vivo carcinogens that are either positive or negative in the Ames bacterial mutagenicity test or that should score positive in an in vitro genotoxicity assay. ECVAM Class 2 compounds are Ames negative, non-genotoxic carcinogens or non-carcinogens that should be negative in in vitro genotoxicity tests and ECVAM Class 3 compounds are Ames negative but score equivocal or positive in an in vitro genotoxicity assay. In total exposures to 50 different mainly ECVAM-suggested genotoxins, pro-oxidants and non-genotoxins were performed (Table 3 and FIGS. 22-25). All ECVAM class 1 compounds scored positive in one or both GFP reporter cell lines, except p-chloroaniline. Although this compound is an in vivo carcinogen, it was also not identified as genotoxin in other in vitro genotoxicity assays (Birrell et al, 2010) (Westerink et al, 2010). All tested ECVAM class 2 compounds failed to induce the GFP reporters. The ECVAM class 3 compounds that were previously identified as genotoxin in other in vitro genotoxicity assays also induced the GFP reporters. Interestingly, nearly all of the ECVAM class 3 compounds that scored positive, selectively induced expression of the Srxn1-GFP reporter, suggesting that the primary toxic properties of these compounds are associated with the induction of oxidative stress. An additional collection of non-ECVAM suggested compounds were all correctly identified as genotoxic or oxidative stress-inducing chemicals. Together these data show that the Bscl2-GFP and Srxn1-GFP reporter cells, referred to us as the ToxTracker assay, provide a sensitive and selective test to establish potential toxic activities of chemicals. In addition, by integrated evaluation of results from both reporters, the ToxTracker assay can provide insight in the primary toxic properties of compounds.

TABLE 3

Sensitivity and specificity of the Bscl2-GFP and Srxn1-GFP reporters in detection of genotixic and oxidative properties of chemicals.

| Chemical | CAS number | Ames test[1] | In vivo genotoxicity[1] | In vitro genotoxicity[1] | mES DsRed reporters[2] | Bscl2-GFP/Srxn1-GFP GFP Induction | Prim. toxic properties | Information |
|---|---|---|---|---|---|---|---|---|
| ECVAM class 1 | | | | | | | | |
| 1. Ames-positive in vivo genotoxins. | | | | | | | | |
| Cisplatin | 15663-27-1 | Pos. | Pos. | Pos. | Pos. | Pos. | Genotoxin | DNA crosslinking agent. Used in cancer treatment. |
| MMS | 66-27-3 | Pos. | Pos. | Pos. | Pos. | Pos. | Pro-oxidant | Alkylating agent. Strong mutagen. |
| Cadmium Chloride | 10108-64-2 | Pos. | Pos. | Pos. | Pos. | Pos. | Pro-oxidant | Inorganic carcinogen |
| p-chloroaniline | 106-47-8 | Pos. | Pos. | Equivocal | Neg. | Neg. | | Non-carcinogenic. Used in herbicides and pesticides |
| 2. In vivo genotoxins, neg. or equivocol in Ames. | | | | | | | | |
| Sodium arsenite | 7784-46-5 | Neg. | Pos. | Pos. | Pos. | Pos. | Pro-oxidant | Inorganic carcinogen. Oxidant. |
| Taxol | 33069-62-4 | Neg. | Pos. | Pos. | Pos. | Pos. | Genotoxin | Aneugen. Used in cancer treatment. |
| ECVAM class 2 | | | | | | | | |
| 1. Non-carcinogens, neg. in in vivo genotoxicity tests. | | | | | | | | |
| n-butyl chloride | 109-69-3 | Neg. | nd | Neg. | Neg. | Neg. | | |
| Phenformin HCl | 834-28-6 | Neg. | nd | Neg. | Neg. | Neg. | | |
| (2-chloroethyl)trimethyl-ammonium chloride | 999-81-5 | Neg. | nd | Neg. | Neg. | Neg. | | |

TABLE 3-continued

Sensitivity and specificity of the Bscl2-GFP and Srxn1-GFP reporters in detection of genotixic and oxidative properties of chemicals.

| | | | | | | |
|---|---|---|---|---|---|---|
| N,N-dicyclohexyl thiourea | 1212-29-9 | Neg. | nd | Neg. | Neg. | Neg. |
| Cyclohexanone | 108-94-1 | Neg. | nd | Neg. | Neg. | Neg. |
| Erythromycin stearate | 643-22-1 | Neg. | nd | Neg. | Neg. | Neg. |
| Fluometron | 2164-17-2 | Neg. | nd | Neg. | Neg. | Neg. |
| 2. Non-genotoxic carcinogens. | | | | | | |
| D-limonene | 5989-27-5 | Neg. | nd | Neg. | Neg. | Neg. |
| Amitrole | 61-82-5 | Neg. | Neg. | Neg. | Neg. | Neg. |
| Tert-butyl alcohol | 75-65-0 | Neg. | Neg. | Neg. | Neg. | Neg. |
| Diethanolamine | 111-42-2 | Neg. | Neg. | Neg. | Neg. | Neg. |
| Hexachloroethane | 67-72-1 | Neg. | Neg. | Neg. | Neg. | Neg. |
| Methyl carbamate | 598-55-0 | Neg. | Neg. | Neg. | Neg. | Neg. |
| Pyrldlne | 110-86-1 | Neg. | Neg. | Neg. | Neg. | Neg. |
| Tris(2-ethylhexyl)phosphate | 78-42-2 | Neg. | Neg. | Neg. | Neg. | Neg. |

| | | Genotoxicity profile | | | | | |
|---|---|---|---|---|---|---|---|
| Chemical | CAS number | Ames test[1] | In vivo genotoxicity[1] | In vitro genotoxicity[1] | mES DsRed reporters[2] | Bscl2-GFP/ Srxn1-GFP | Information |
| ECVAM class 3 | | | | | | | |
| 1. Non-carcinogens, neg. or equivocal in in vivo genotoxicity tests. | | | | | | | |
| Tert-butylhydroquinone | 1948-33-0 | Neg. | Neg. | Pos. | Pos. | Pos. | Pro-oxidant |
| o-anthranilic acid | 118-92-3 | Neg. | Neg. | Pos. | Pos. | Neg. | |
| 1,3-Dihydroxybenzene (Resorcinol) | 108-46-3 | Neg. | Neg. | Pos. | Pos. | Pos. | Equivocal |
| Sulfisoxazole | 127-69-5 | Neg. | Neg. | Equivocal | Neg. | Pos. | Pro-oxidant |
| 2. Non-carcinogens, no in vivo genotoxicity data. | | | | | | | |
| Ethionamide | 536-33-4 | Neg. | nd | Weak Pos. | Neg. | Neg. | |
| Curcumln | 458-37-7 | Neg. | nd | Pos. | Neg. | Neg. | |
| Benzyl alcohol | 100-51-6 | Neg. | nd | Weak Pos. | Neg. | Neg. | |
| Urea | 57-13-6 | Neg. | nd | Pos. | Neg. | Neg. | |
| 3. non-genotoxic carcinogens, carcinogen by irrelevant mechanism. | | | | | | | |
| Sodium saccharin | 128-44-9 | Neg. | Neg. | Equivocal | Neg. | Neg. | |
| 4. Supplementary list, in vitro genotoxicity unclear. | | | | | | | |
| p-Nitrophenol | 100-02-7 | Neg. | nd | Equivocal | Neg. | Pos. | Pro-oxidant |
| 2,4-dichlorophenol | 120-83-2 | Neg. | Weak Pos. | Pos. | Pos. | Pos. | Pro-oxidant |
| Eugenol | 97-53-0 | Neg. | Equivocal | Pos. | Neg. | Neg. | |
| Ethyl acrylate | 140-88-5 | Neg. | Weak Pos. | Pos. | Neg. | Neg. | |
| Isobutyraldehyde | 78-84-2 | Neg. | Equivocal/Pos. | Pos. | Neg. | Neg. | |
| Propyl gallate | 121-79-9 | Neg. | Equivocal | Pos. | Pos. | Pos. | Equivocal |
| Additional | | | | | | | |
| Doxorubicin | 23214-92-8 | Pos. | Pos. | Pos. | Pos. | Pos. | Genotoxin DNA intercalating chemical. Topoisomerase II inhibitor. |
| Mitomycin C | 50-07-7 | Pos. | Pos. | Pos. | Pos. | Pos. | Genotoxin DNA crosslinking agent. Used in cancer treatment. |
| Etoposide | 33419-42-0 | Neg. | Pos. | Pos. | Pos. | Pos. | Genotoxin Topoisomerase II poison. |
| Diethyl maleate | 141-05-9 | nd | nd | nd | Pos. | Pos. | Pro-oxidant Pro-oxidant. |
| Tert-butyl hydroperoxide | 75-91-2 | Pos. | Neg. | Neg. | Neg. | Pos. | Pro-oxidant Pro-oxidant. |
| Hydrogen peroxide | 7722-84-1 | Pos. | Neg. | Neg. | Neg. | Pos. | Pro-oxidant Pro-oxidant. |
| Flavopiridol | 146426-40-6 | nd | nd | nd | Pos. | Neg. | Cdk2 inhibitor. Cell cycle blocking agent. |
| Copper sulfate | 7758-98-7 | nd | nd | nd | nd | Pos. | Pro-oxidant Used as herbicide, fungicide and pesticide. |

TABLE 3-continued

Sensitivity and specificity of the Bscl2-GFP and Srxn1-GFP reporters in detection of genotixic and oxidative properties of chemicals.

| | | | | | | | | |
|---|---|---|---|---|---|---|---|---|
| Potassium bromate | 7758-01-2 | Pos. | Pos. | Pos. | nd | Pos. | Pro-oxidant | Pro-oxidant. Used as flour additive. |
| 4-Nitroquinelone-1-oxide | 56-57-5 | Pos. | Pos. | Pos. | nd | Pos. | Genotoxin | UV-mimetic agent. |
| 4-Hydroxy-2-nonenal | 75899-68-2 | Neg. | Neg. | Pos. | nd | Pos. | Pro-oxidant | Lipid peroxidation product. |
| Cytarabine | 147-94-4 | Neg. | nd | Pos. | nd | Pos. | Genotoxin | DNA chain terminator. Used in chemotherapy. |
| Camptothecin | 7689-03-4 | Neg. | Neg. | Pos. | nd | Pos. | Genotoxin | Topoisomerase I Inhibitor |
| Bleomycin | 11056-06-7 | Pos. | Pos. | Pos. | nd | Pos. | Genotoxin | Radiomimetetic agent. |

[1]Data extracted from Kirkland et al., Mutat. Res. 653 (2008), 99-108.
[2]Hendriks et al., Mutat Res., 709-710 (2011), 49-59.

GFP Reporter Induction by Compounds that Require Metabolic Activation

Figure 26:
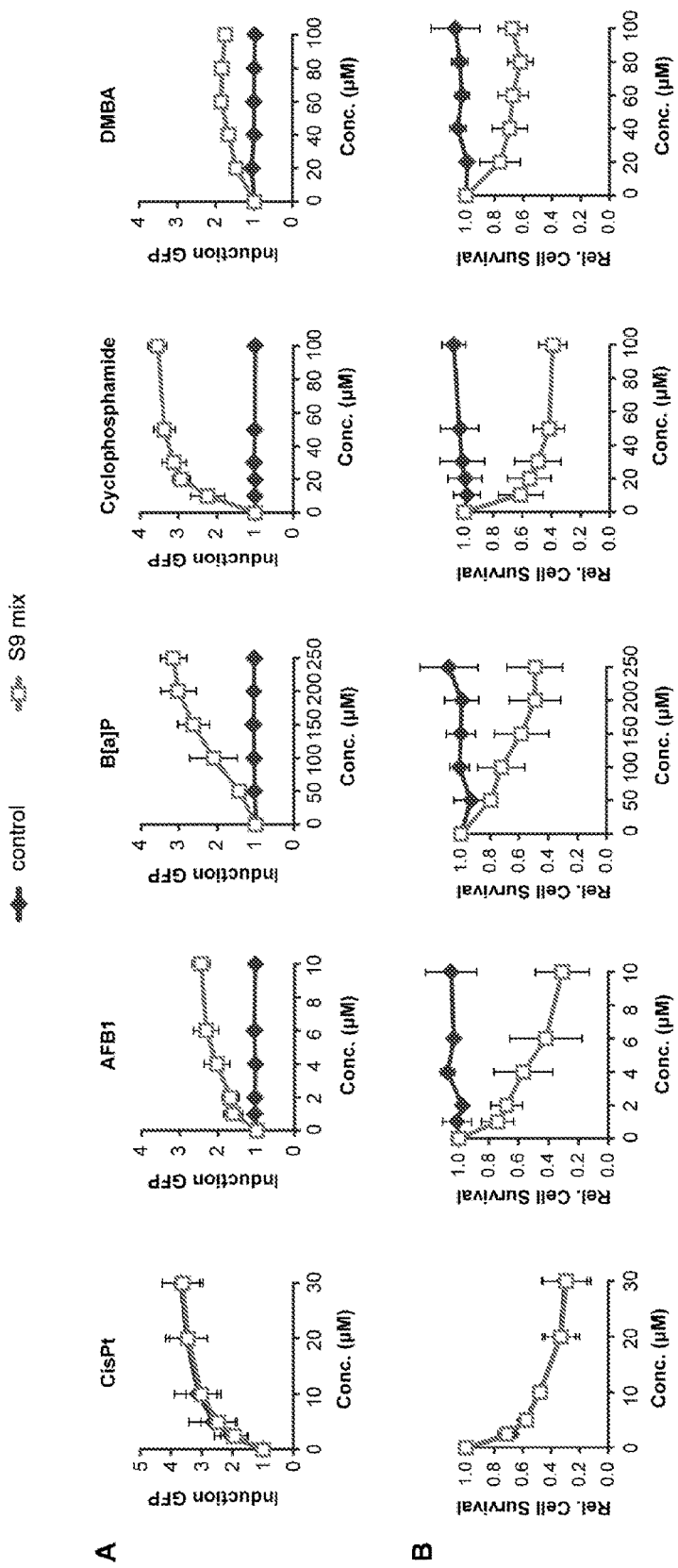

To test the performance of the ToxTracker assay in the detection of genotoxic chemicals that require biotransformation we exposed Bscl2-GFP reporter cells to various pro-genotoxic compounds in the presence of S9 rat liver extract. All four tested carcinogenic compounds (aflatoxin B1 (AFB1), benzo[a]pyrene (B[a]P, cyclophosphamide and dimethylbenz(a)antracene (DMBA)) induced expression of the Bscl2-GFP reporter only when incubated in the presence of rat S9 mix (FIG. 26). In agreement, S9-dependent activation of these pro-genotoxins resulted in reduced survival of the reporter cells.

Srxn1-GFP Reporter is Induced by ROS and Controlled by Nrf2 Signaling

Figure 27:
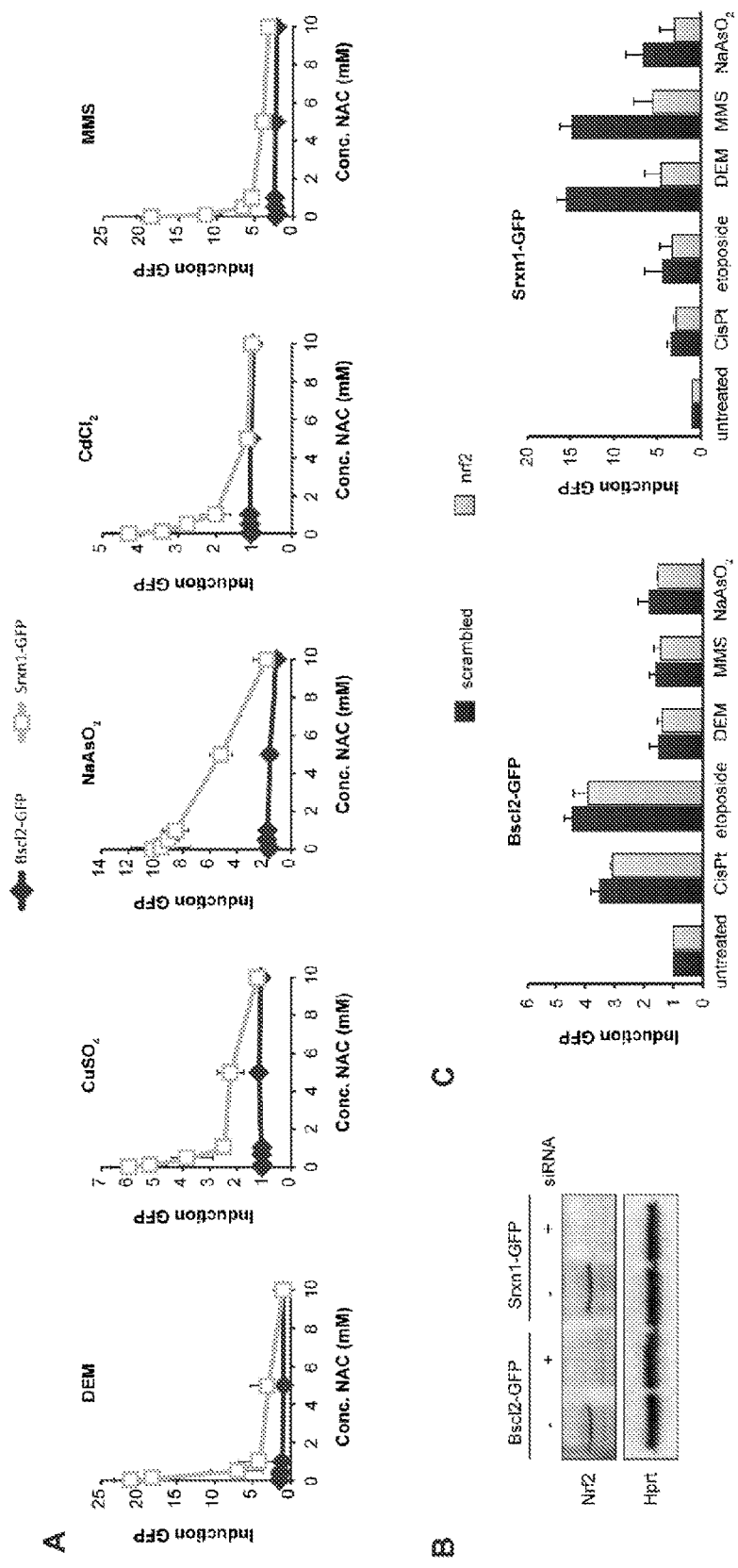

To investigate whether induction of the Srxn1-GFP reporter upon exposure to oxidative stress-inducing compounds was directly related to ROS production, we treated Bscl2-GFP or Srxn1-GFP reporter cells with the pro-oxidants DEM, $CuSO_4$, $NaAsO_2$, $CdCl_2$ and the DNA alkylating agent MMS, in the presence of the ROS scavenger N-acetyl cysteine (NAC). Incubation of cells with NAC did not affect cell viability or reporter activity (data not shown). Exposure of Srxn1-GFP reporter cells to the various pro-oxidants, including MMS, resulted in a strong, concentration-dependent increase in expression of the GFP reporter (FIG. 27A). Addition of the ROS scavenger completely inhibited activation of the reporter, indicating that induction of the Srxn1-GFP reporter directly depends on the production of oxygen radicals. In line with our previous results, the Bscl2-GFP reporter was not induced by pro-oxidant exposure.

Nrf2 is a key regulator of the induced expression of anti-oxidative enzymes in response to oxidative stress (Hayes and McLellan, 1999). Also Srxn1 has previously been identified as a potential Nrf2 target gene (Singh et al, 2009). To investigate whether the Nrf2 pathway controls expression of the Srxn1-GFP reporter, we exposed reporter cells to various genotoxic and oxidative stress-inducing agents following siRNA mediated knock down of Nrf2 (FIG. 27B). Srxn1-GFP was preferentially induced by the pro-oxidants DEM, MMS and $NaAsO_2$ while the Bscl2-GFP reporter was selectively activated by the genotoxic agents CisPt and etoposide. The response of both GFP reporter cell lines to genotoxic agents was not affected by Nrf2 knockdown. In contrast, induction of the Srxn1-GFP reporter by pro-oxidants was strongly decreased after knockdown of Nrf2, indicating that Srxn1-GFP is under control of the Nrf2 anti-oxidant response (FIG. 27C).

Bscl2-GFP Reporter is Activated by DNA Replication Stress

The Bscl2-GFP reporter is activated by a wide variety of genotoxic chemical compounds with different reactive properties (FIGS. 16A and 17E and Table 3). CisPt and MMC are DNA crosslinking agents, etoposide and doxorubicin induce DNA double strand breaks during DNA replication by inhibition of topoisomerase II, while MNU methylates DNA. We assessed which mechanism exposure to these compounds with different chemical reactive properties resulted in induction of the Bscl2 gene. A common property of genotoxic compounds is that they cause DNA damage that can interfere with transcription and DNA replication. To investigate whether activation of the Bscl2-GFP reporter is correlated with DNA replication stress, we exposed the reporter cell lines to different DNA replication inhibitors. Hydroxyurea (HU) inhibits the enzyme ribonucleotide reductase, thereby depleting the pool of free ribonucleotides in the cells, while aphidicolin (Aph) directly inhibits DNA polymerases. Both drugs inhibit DNA replication without inflicting DNA damage. Exposure of Bscl2-GFP cells to HU or Aph resulted in a significant induction of GFP expression, indicating that activation of the Bscl2-GFP reporter by various genotoxic agents is related to DNA replication stress (FIG. 28A). Exposure of Srxn1-GFP cells to HU or Aph resulted in slight reporter activation, in agreement with its limited activation by various genotoxic agents (FIGS. 28A and 17E).

Bscl2-GFP Reporter Activation by ATR-Dependent DNA Damage Signaling

To investigate the involvement of various DNA damage response kinases in activation of the GFP reporters, we treated cells with the DNA crosslinking agent CisPt or the DNA replication inhibitor Aph in the presence of inhibitors of ATM (ku55933), ATR (schisandrin B) (Hickson et al, 2004)(Nishida et al, 2009) or Chk1 and Chk2 (UCN-01) (Yu et al, 2002). ATR inhibition diminished Chk1 and p53 phosphorylation, while inhibition of ATM prevented phosphorylation of Kap1 and p53 in response to CisPt and Aph (FIG. 28B). Bscl2-GFP reporter activation could almost completely be repressed by either the ATR or the Chk1/Chk2 inhibitor, but was unaffected by the ATM inhibitor (FIG. 28C). These data indicate that the Bscl2-GFP reporter is activated by the ATR-Chk1 signaling pathway in response to stalled DNA replication forks. As previously, while the Srxn1-GFP reporter is also slightly activated upon exposure to CisPt or Aph, its activation is not dependent on the ATM or ATR DNA damage signaling pathways.

Bscl2-GFP Reporter Activation is p53-Independent

The p53 tumor suppressor plays a central role in the DNA damage response (Meek, 2009). p53 is activated by various cellular signaling pathways, including the ATM-Chk2 and ATR-Chk1 kinases, (see also FIG. 28B), and controls the activity of DNA repair systems, cell cycle checkpoints and apoptosis. Interestingly, induction of the Nrf2 pathway also appears to trigger p53 activation (Wakabayashi et al, 2010). Meanwhile, p53 also affects expression of Nrf2 target genes (Wakabayashi et al, 2010). To investigate whether the Bscl2-GFP and Srxn1-GFP reporters were under control of p53, we transiently knocked down p53 expression by siRNAs (FIG. 29A), exposed cells to various genotoxic and oxidative stress-inducing compounds and analyzed GFP reporter activation. Activation of neither the Bscl2-GFP nor the Srxn1-GFP reporter by any of the tested compounds was affected by p53 knockdown (FIG. 29B). To confirm that the extent of p53 knockdown was sufficient to prevent activation of p53 target genes, we employed a Btg2-GFP reporter. Btg2 is a known p53 target gene that is transcriptionally activated upon exposure to genotoxic and oxidative stress (Rouault et al, 1996). Exposure of Btg2-GFP reporter cells to genotoxic agents as well as pro-oxidants resulted in increased expression of the reporter (FIG. 29C). Knockdown of p53 resulted in a strongly reduced induction of the Btg2-GFP reporter after exposure to all tested compounds. Interestingly, also knockdown of Nrf2 resulted in decreased Btg2-GFP reporter activation, specifically after exposure to oxidative stress-inducing compounds.

Discussion

Figure 5:
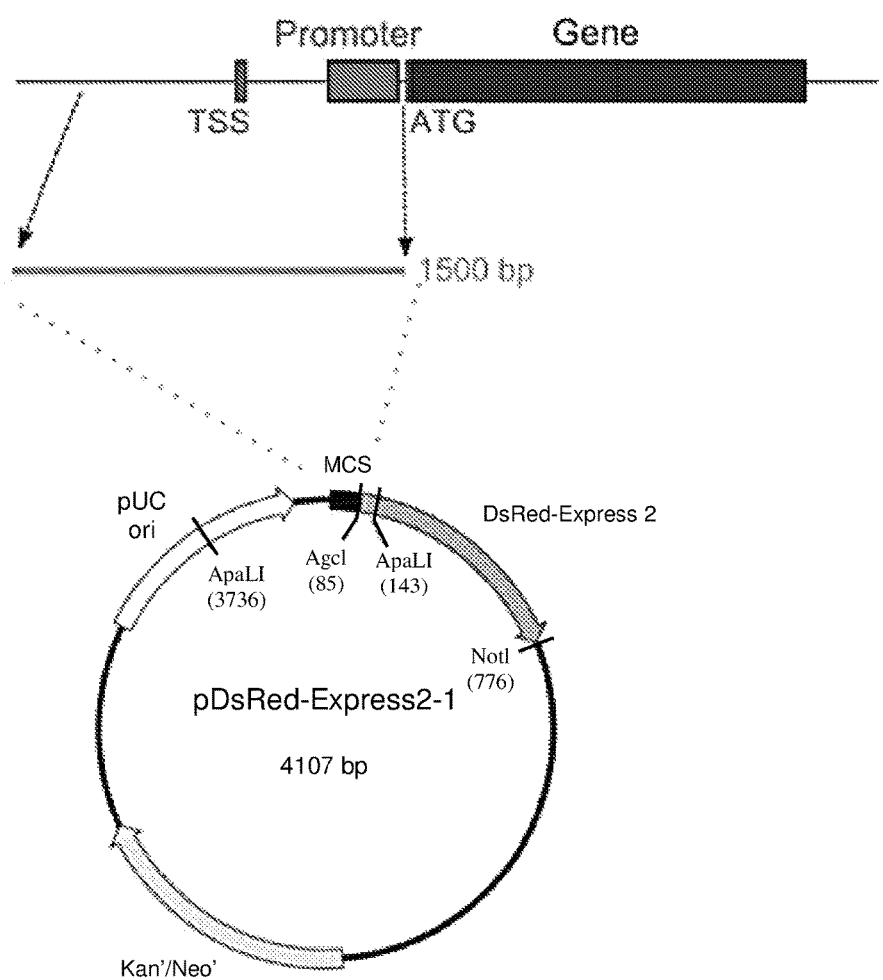
Figure 6:
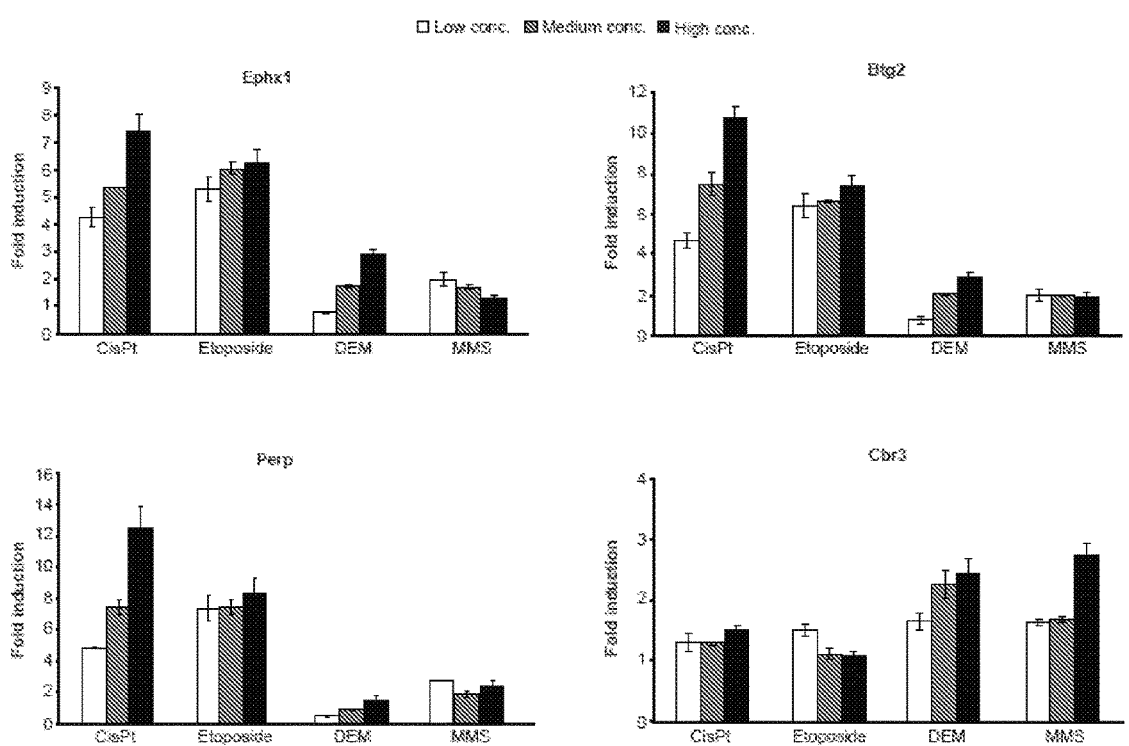
Figure 7:
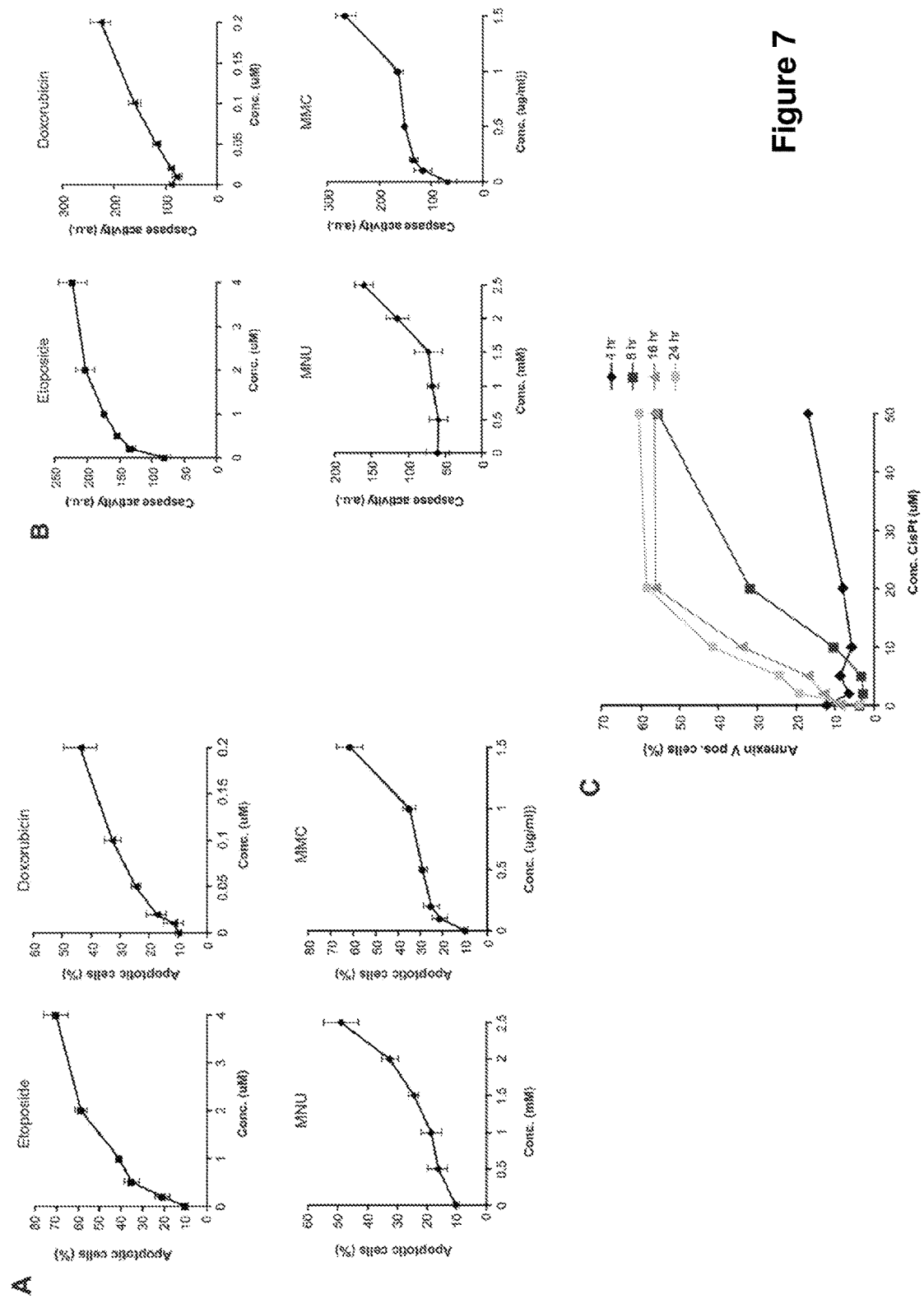
Figure 8:
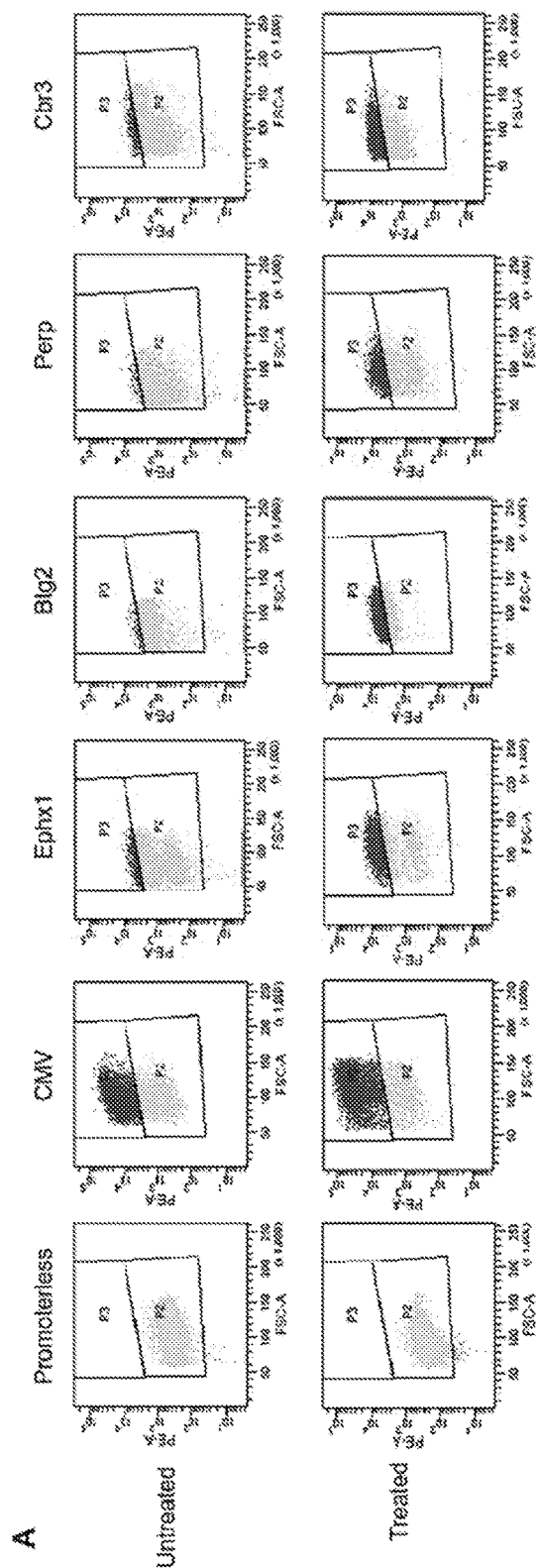
Figure 8:
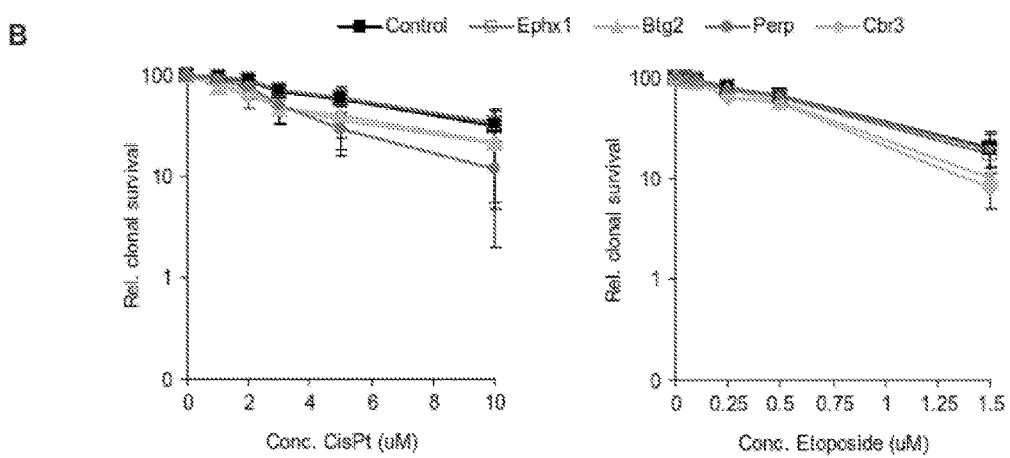
Figure 9:
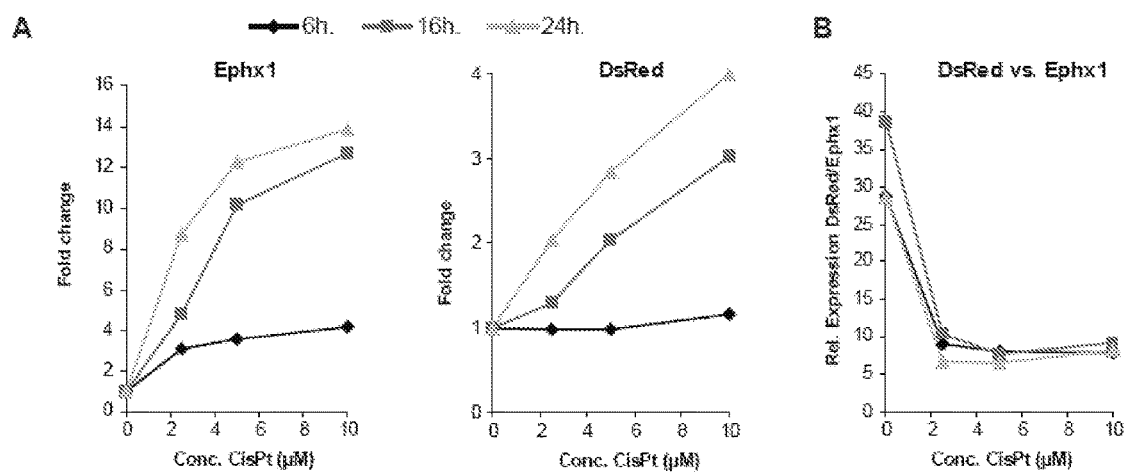
Figure 11:
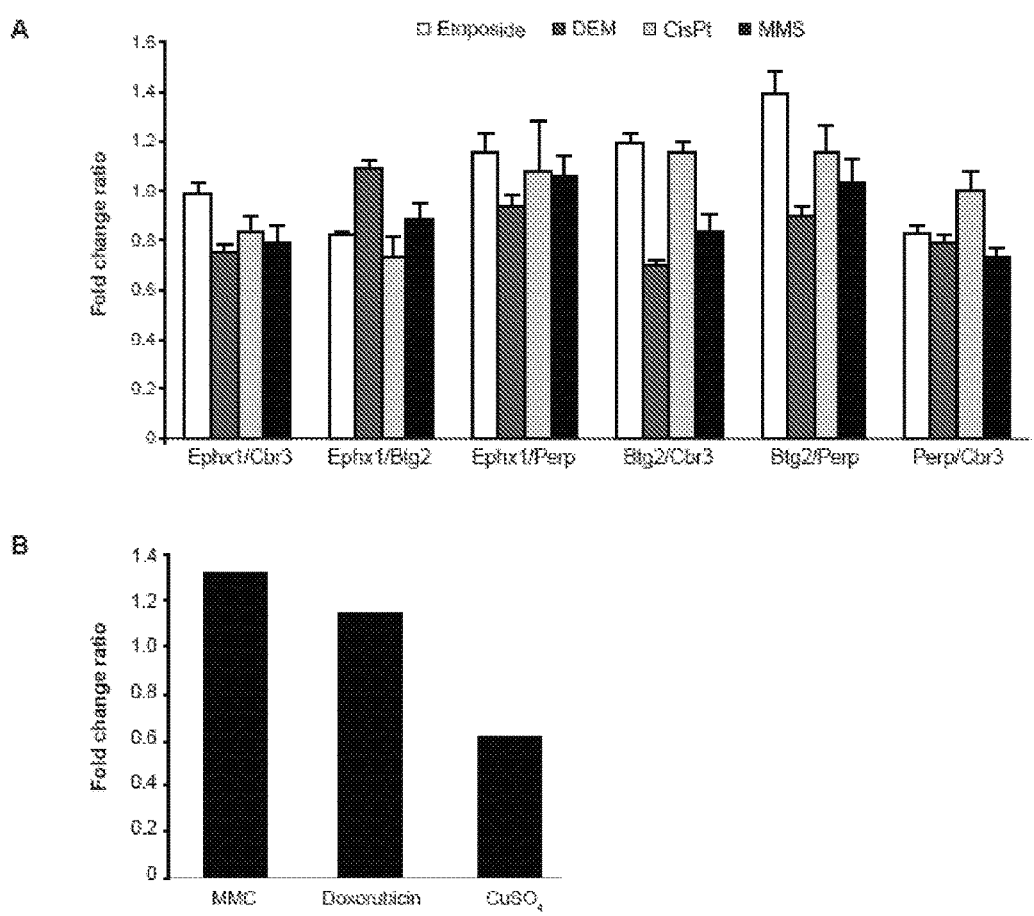
Figure 12:
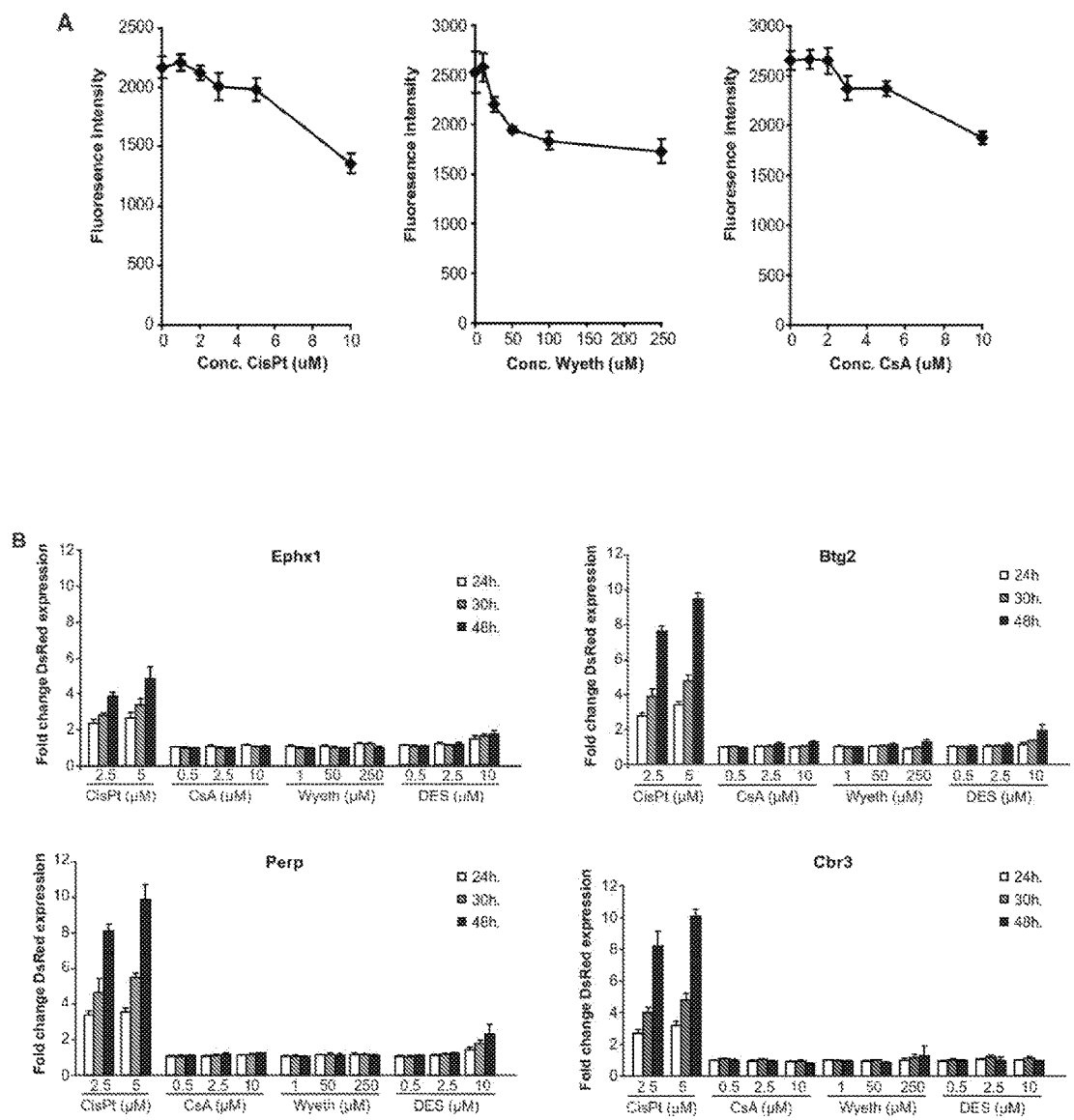
Figure 13:
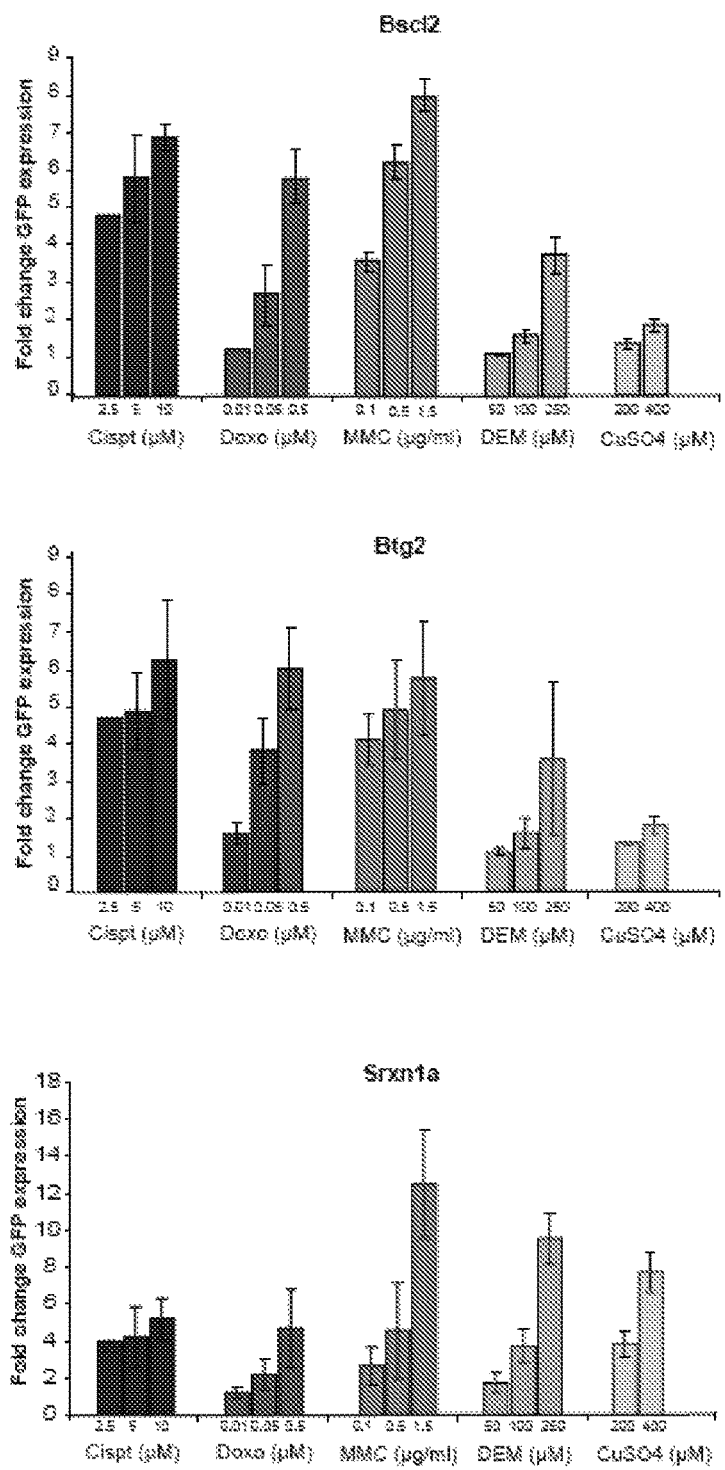
Figure 14:
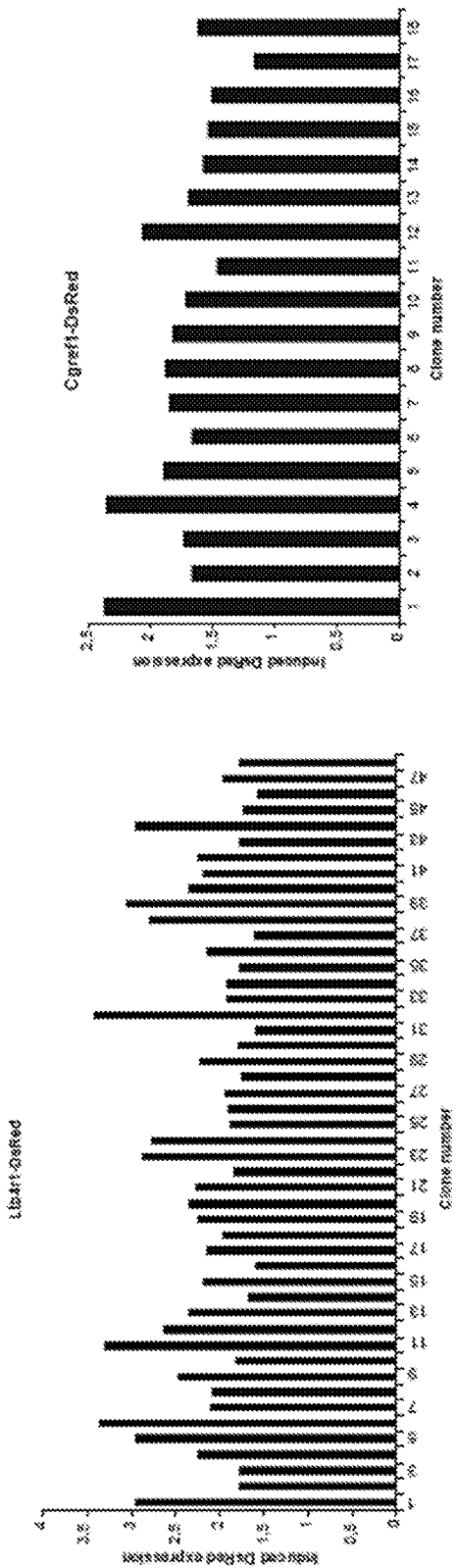
Figure 14:
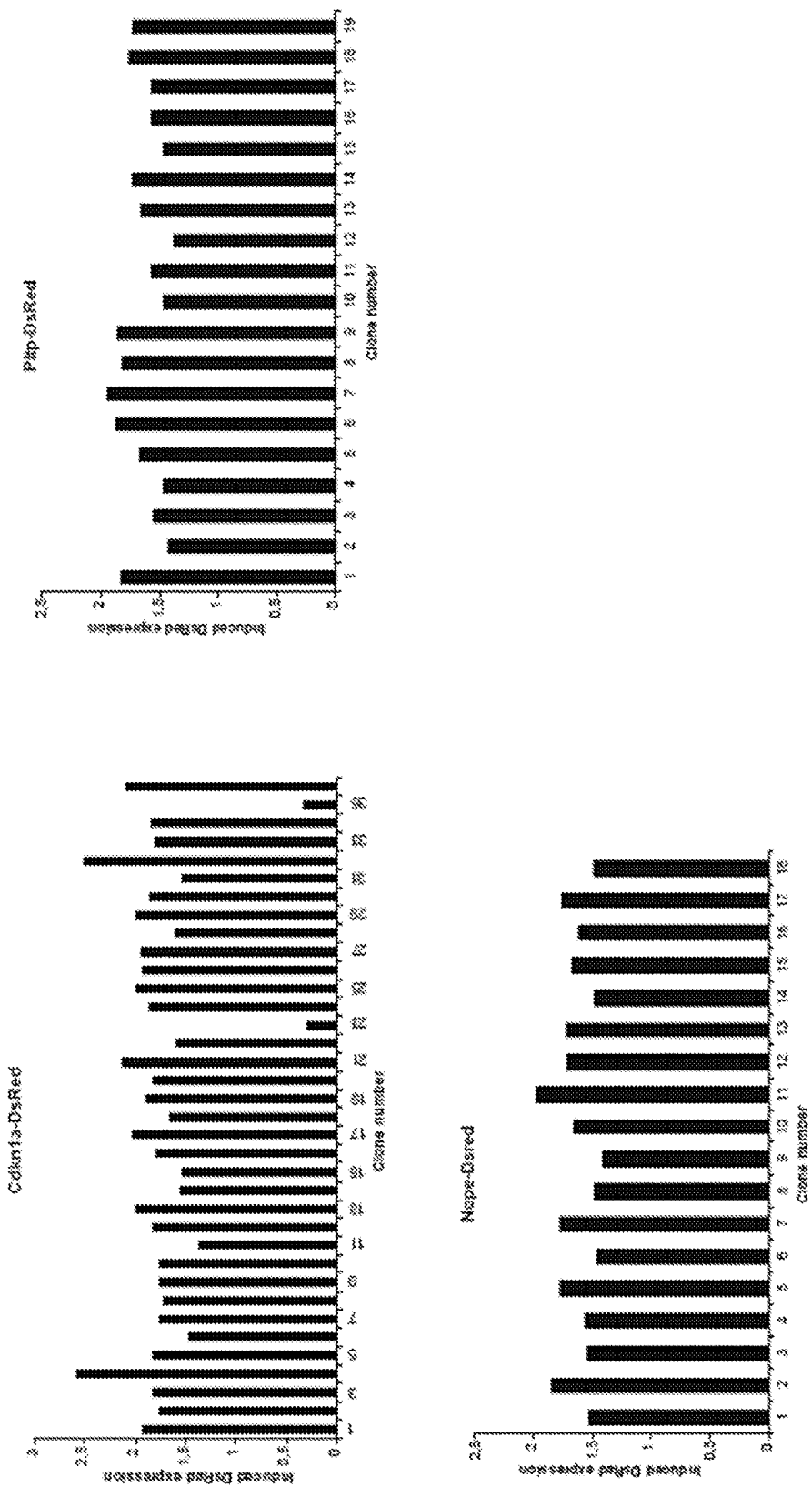
Figure 17:
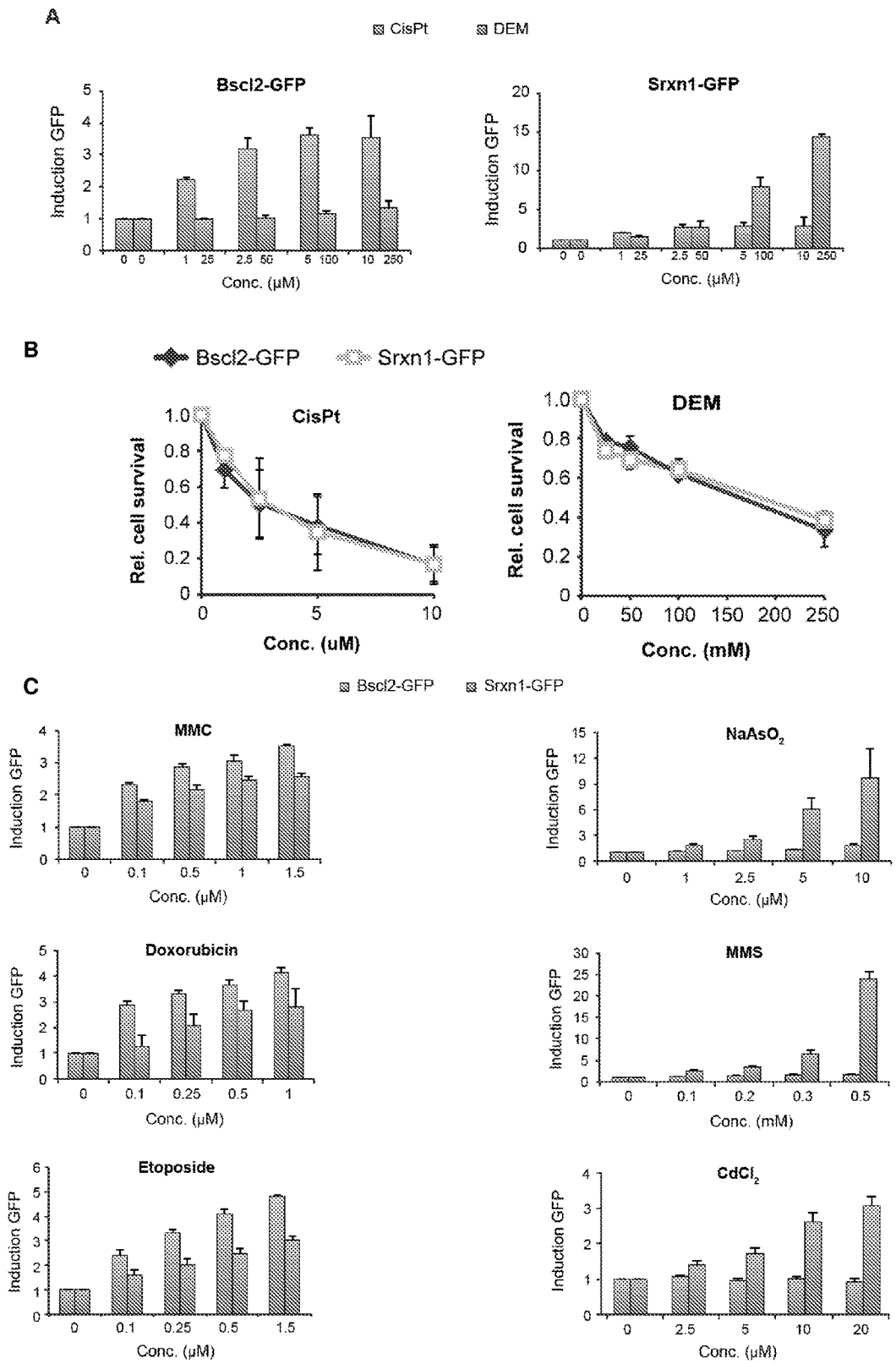
Figure 18:
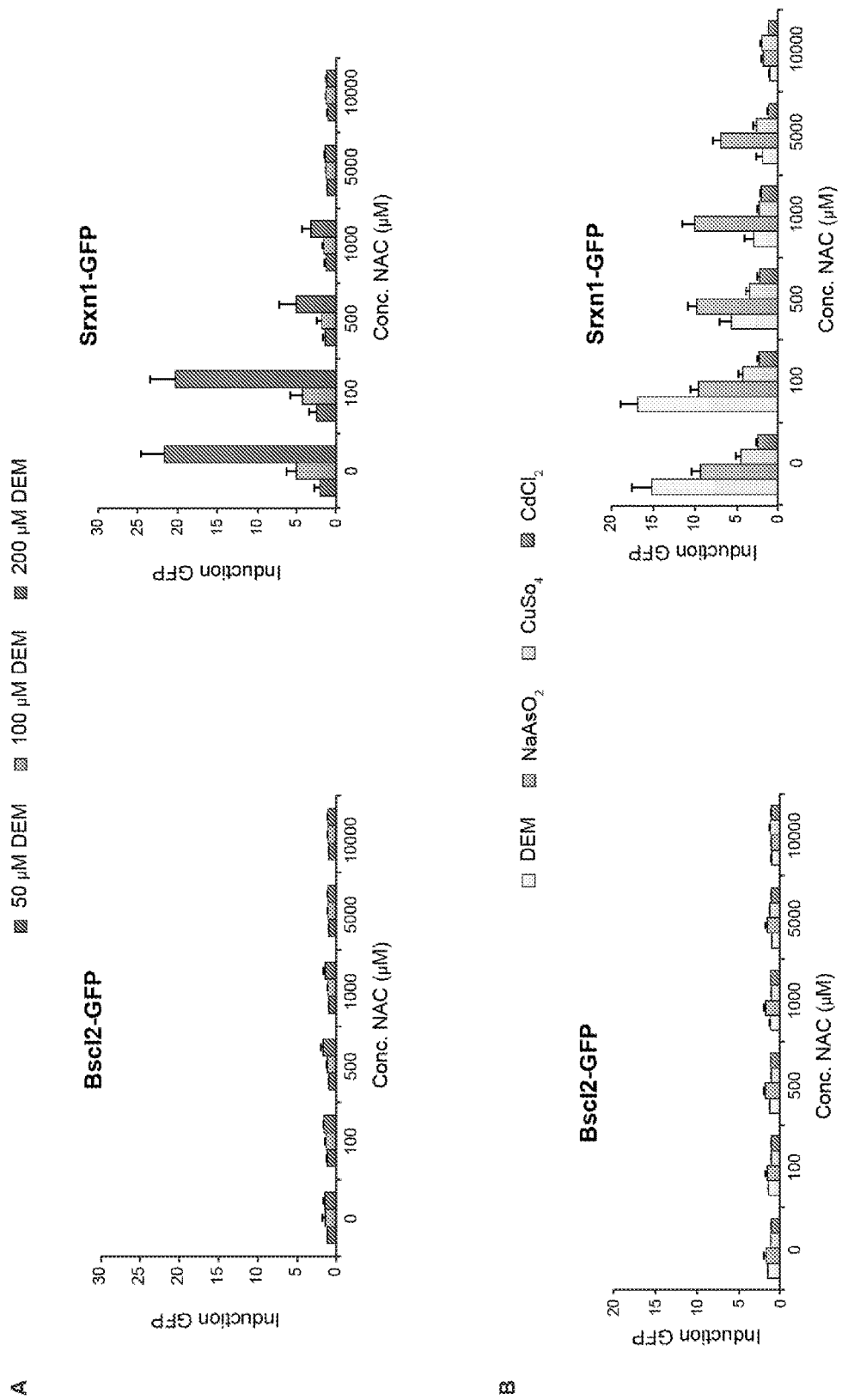
FIG. 18 shows Srxn1-GFP induction in response to ROS production.
Figure 20:
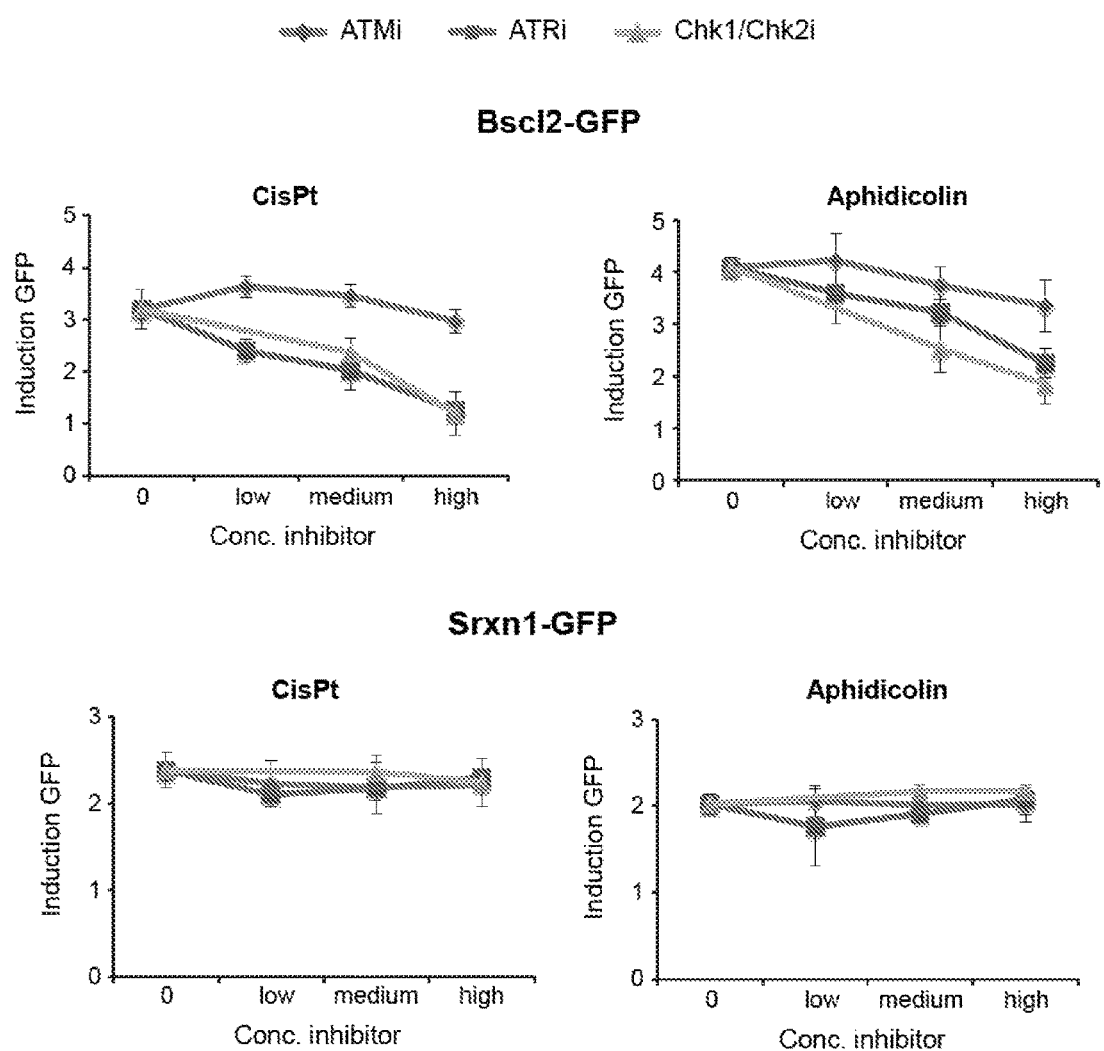
FIG. 20 shows that DNA damage reporter activation depends on ATR signalling.
Figure 28:
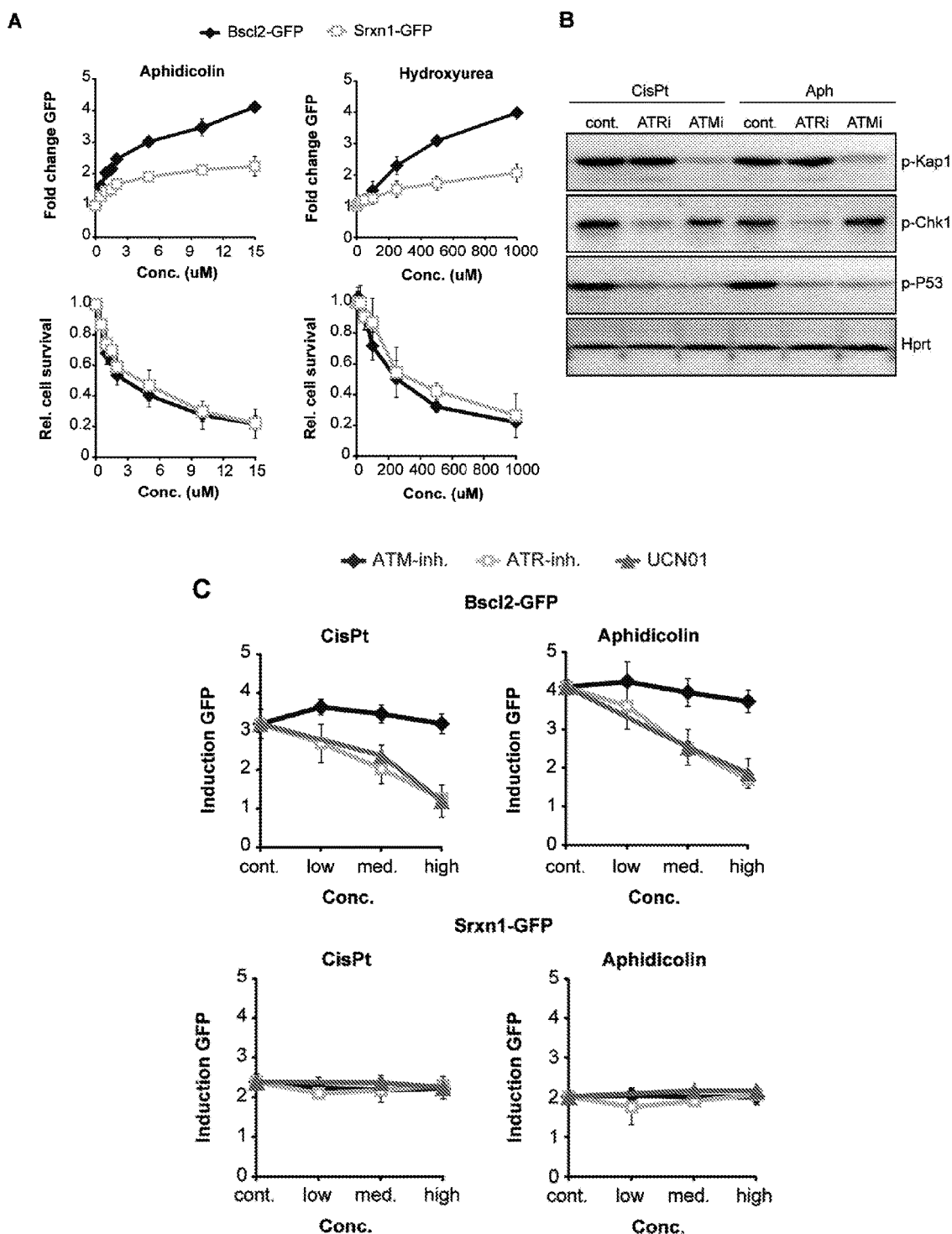

Here we describe the generation of the ToxTracker assay, which consists of different GFP fluorescence mES reporter cell lines that are preferentially responsive to either genotoxic or oxidative stress-inducing compounds. Expression of the Bscl2-GFP reporter is specifically induced when mES cells are exposed to genotoxic compounds but is not elevated by chemicals that induce oxidative stress even though oxygen radicals might also damage DNA (FIG. 17). We provide evidence that Bscl2-GFP reporter activation correlates with inhibition of DNA replication progression (FIG. 28). Most types of oxidative DNA lesions do not provide strong blocks for the DNA replication machinery and are therefore unlikely to induce expression of the Bscl2-GFP reporter (Tolentino et al, 2008). The observation that reporter activation depends on ATR and Chk1 signaling (FIG. 29B) provides further evidence that DNA damage-induced replication blocks induce expression of the Bscl2-GFP reporter. Both kinases are activated upon persistent stalling of DNA replication forks (Paulsen and Cimprich, 2007). Interestingly, Bscl2 expression appears to be independent of p53, although p53 is phosphorylated by Chk1 upon replication stress to halt progression of the cell cycle. Expression of the Srxn1-GFP reporter is induced after exposure of cells to chemicals that result in increased levels of cellular oxidative stress (FIG. 17). Although the extent of activation is much stronger by oxidative stress, the Srxn1-GFP reporter is also somewhat responsive to genotoxic compounds. This suggests that either Srxn1 gene expression is directly induced upon DNA damage, although expression of Srxn1 is independent of the ATR-Chk1 DNA damage signaling (FIG. 28C), or that exposure of cells to genotoxic agents also results in increased ROS levels. Indeed, exposure of cells to the DNA crosslinking agent CisPt was shown to result in increased levels of ROS, caused by impaired mitochondrial function and during apoptosis (Jing et al, 2007). In agreement, exposure of the Srxn1-GFP reporter cells to CisPt in the presence of the ROS scavenger NAC significantly reduced reporter activation (data not shown). Additionally, exposure of cells to genotoxic agents results in activation of p53 that can induce expression of Nrf2. We provide evidence that expression of the Srxn1-GFP reporter is part of the Nrf2 anti-oxidant pathway (FIG. 27) being in line with recent reports that Srxn1 expression is directly controlled by Nrf2 via various ARE elements in the Srxn1 promoter (Singh et al, 2009). Results obtained with the Btg2-GFP reporter were not extensively discussed since its sensitivity and specificity is comparable to the previously described Btg2-DsRed reporter cell line (Hendriks et al, 2011). The Btg2-GFP reporter is activated by p53 upon genotoxic stress and by both p53 and Nrf2 after exposure to oxidative stress-inducing agents. Therefore, activation of the Btg2-GFP reporter displays no selectivity for either genotoxins or pro-oxidants (FIG. 29C).

The Bscl2 gene has originally been identified in patients that suffer from Berardinelli-Seip congenital lipodystrophy, a rare autosomal recessive disease that is characterized by an almost complete absence of adipocytes (Magre et al, 2001). The Bscl2 gene encodes a protein called Seipin that is located to the membrane of the endoplasmic reticulum (Szymanski et al, 2007). In addition, mutations in the Bscl2 gene have also been associated with autosomal-dominant disorders of motoneurons that results in severe atrophy and wasting of distal limb muscles (Agarwal and Garg, 2004). Although Seipin is involved in adipocyte differentiation, it is mainly expressed in the nervous system and testis (Magre et al, 2001). The function of Seipin is largely unknown, although it has been implicated in cytosolic lipid droplet morphology and in intracellular transport of lipids and proteins. So far, there is no implication of Bscl2 in the DNA damage response. Our data show that expression of Bscl2 in mES cells is strongly induced upon exposure to various DNA damaging agents. Basal Bscl2 expression level is low in mES cells. Since Bscl2 expression has been associated with adipocyte differentiation, it is attractive to hypothesize that also in mES cells Bscl2 expression is correlated with the induction of cell differentiation after exposure to genotoxic agents. It is well established that cell differentiation is induced upon DNA damage to maintain genome stability and to prevent malignant transformation of stem cells (Sherman et al, 2011). In agreement, exposure to various genotoxic chemicals did not result in increased expression of the Bscl2 gene in primary liver cells (M. Schaap, personal communication) and only a marginal induction in HepG2 liver carcinoma cells (Magkoufopoulou et al. Submitted). We are currently investigating the role of Bscl2 in the DNA damage response in mES cells.

Various assays are currently used to establish the genotoxic potential of novel chemicals. Although each of these assays has limitations in prediction of genotoxicity, a combination of these tests has proven to reliably predict the genotoxic risk of chemicals (Kirkland et al, 2011). However, many of these genotoxicity tests are based on biological endpoints such as mutations or chromosomal damage and therefore provide limited information on the reactive properties of compounds or the cellular responses activated after exposure. More recently, various genotoxicity assays have been described, including a HepG2 cell luciferase reporter system and the GreenScreen HC assay, that use altered transcriptional activities of specific genes to genotoxic chemicals as basis for their reporter system (Hastwell et al, 2006)(Westerink et al, 2010). Most of the genes selected depend on transcriptional activation by p53. The GreenScreen HC test employs the p53 target gene Gadd45a.

Various validation studies show that the GreenScreen HC assay provides a highly sensitive and selective assay to identify (geno)toxic carcinogens (Knight et al, 2009)(Olaharski et al, 2009). However, the use of p53 target genes does not allow discrimination between different classes of (geno)toxic compounds, as exemplified by our Btg2-GFP reporter cells (FIG. 29C). We previously described four DsRed-based reporters including the p53-dependent Btg2-Dsred, which were all responsive to DNA damaging agents and pro-oxidants (Hendriks et al, 2011). By using combination of different DsRed reporter cell lines, we were able to discriminate between compounds that primarily induce genotoxic or oxidative stress. The novel ToxTracker assay that we describe here has a higher degree of specificity. The Bscl2-GFP reporter is exclusively induced by compounds that affect ongoing DNA replication, while the Srxn1-GFP reporter is preferentially induced by oxidative stress. In conclusion, the ToxTracker assay that consists of three independent GFP-based reporter cell lines is a novel, highly sensitive and specific genotoxicity test that can provide insights in the relative toxicity potential of chemicals.

REFERENCES FOR EXAMPLE 1

1. Riley, T., et al., *Transcriptional control of human p53-regulated genes.* Nat Rev Mol Cell Biol, 2008. 9(5): p. 402-412.
2. Reifferscheid, G., et al., *A microplate version of the SOS/umu-test for rapid detection of genotoxins and genotoxic potentials of environmental samples.* Mutat Res, 1991. 253(3): p. 215-22.
3. van der Lelie, D., et al., *The VITOTOX test, an SOS bioluminescence Salmonella typhimurium test to measure genotoxicity kinetics.* Mutat Res, 1997. 389(2-3): p. 279-90.
4. Aubrecht, J., et al., *Bioluminescent Salmonella reverse mutation assay: a screen for detecting mutagenicity with high throughput attributes.* Mutagenesis, 2007. 22(5): p. 335-42.
5. Schiestl, R. H., et al., *Carcinogens induce intrachromosomal recombination in yeast.* Carcinogenesis, 1989. 10(8): p. 1445-55.
6. Brennan, R. J. and R. H. Schiestl, *Detecting carcinogens with the yeast DEL assay.* Methods Mol Biol, 2004. 262: p. 111-24.
7. Cahill, P. A., et al., *The GreenScreen genotoxicity assay: a screening validation programme.* Mutagenesis, 2004. 19(2): p. 105-19.
8. Knight, A. W., et al., *An analysis of results from 305 compounds tested with the yeast RAD54-GFP genotoxicity assay (GreenScreen GC)-including relative predictivity of regulatory tests and rodent carcinogenesis and performance with autofluorescent and coloured compounds.* Mutagenesis, 2007. 22(6): p. 409-16.
9. Knight, A. W., et al., *Evaluation of high-throughput genotoxicity assays used in profiling the US EPA ToxCast chemicals.* Regul Toxicol Pharmacol, 2009.
10. Ritter, D. and J. Knebel, *Genotoxicity testing in vitro—Development of a higher throughput analysis method based on the comet assay.* Toxicol In Vitro, 2009.
11. Zhou, C., et al., *DNA damage evaluated by gammaH2AX foci formation by a selective group of chemical/physical stressors.* Mutat Res, 2006. 604(1-2): p. 8-18.
12. Watters, G. P., et al., *H2AX phosphorylation as a genotoxicity endpoint.* Mutat Res, 2009.
13. Elkon, R., et al., *Dissection of a DNA-damage-induced transcriptional network using a combination of microarrays, RNA interference and computational promoter analysis.* Genome Biology, 2005. 6(5): p. R43.
14. Corn, P. G. and W. S. El-Deiry, *Microarray analysis of p53-dependent gene expression in response to hypoxia and DNA damage.* Cancer Biol Ther, 2007. 6(12): p. 1858-66.
15. Lu, X., et al., *Early whole-genome transcriptional response induced by benzo[a]pyrene diol epoxide in a normal human cell line.* Genomics, 2009. 93(4): p. 332-342.
16. Hastwell, P. W., et al., *High-specificity and high-sensitivity genotoxicity assessment in a human cell line: validation of the GreenScreen HC GADD45a-GFP genotoxicity assay.* Mutat Res, 2006. 607(2): p. 160-75.
17. Zhan, Q., *Gadd45a, a p53-and BRCA1-regulated stress protein, in cellular response to DNA damage.* Mutat Res, 2005. 569(1-2): p. 133-43.
18. Olaharski, A., et al., *Evaluation of the GreenScreen GADD45[alpha]-GFP indicator assay with non-proprietary and proprietary compounds.* Mutation Research/Genetic Toxicology and Environmental Mutagenesis, 2009. 672(1): p. 10-16.
19. Westerink, W. M., et al., *The development of RAD51C, Cystatin A, p53 and Nrf2 luciferase-reporter assays in metabolically competent HepG2 cells for the assessment of mechanism-based genotoxicity and of oxidative stress in the early research phase of drug development.* Mutat Res, 2009.
20. Sabapathy, K., et al., *Regulation of ES cell differentiation by functional and conformational modulation of p53.* EMBO J, 1997. 16(20): p. 6217-6229.
21. Corbet, S. W., et al., *P53-dependent and-independent links between DNA-damage, apoptosis and mutation frequency in ES cells.* Oncogene, 1999. 18(8): p. 1537-44.
22. de Waard, H., et al., *Cell-type-specific consequences of nucleotide excision repair deficiencies: Embryonic stem cells versus fibroblasts.* DNA Repair, 2008. 7(10): p. 1659-1669.
23. Hendriks, G., et al., *Gene transcription increases DNA damage-induced mutagenesis in mammalian stem cells.* DNA Repair (Amst), 2008. 7(8): p. 1330-9.
24. Kruse, J. J., et al., *A portrait of cisplatin-induced transcriptional changes in mouse embryonic stem cells reveals a dominant p53-like response.* Mutat Res, 2007. 617(1-2): p. 58-70.
25. Lou, Z. and J. Chen, *Mammalian DNA Damage Response Pathway.* 2005. p. 425-455.
26. Cotter, T. G., *Apoptosis and cancer: the genesis of a research field.* Nat Rev Cancer, 2009. 9(7): p. 501-507.
27. Decker, M., M. Arand, and A. Cronin, *Mammalian epoxide hydrolases in xenobiotic metabolism and signalling.* Archives of Toxicology, 2009. 83(4): p. 297-318.
28. Pilka, E. S., et al., *Structural Basis for Substrate Specificity in Human Monomeric Carbonyl Reductases.* PLoS ONE, 2009. 4(10): p. e7113.
29. Rouault, J.-P., et al., *Identification of BTG2, an antiproliferative p53-dependent component of the DNA damage cellular response pathway.* Nat Genet, 1996. 14(4): p. 482-486.
30. Ihrie, R. A., et al., *Perp Is a Mediator of p53-Dependent Apoptosis in Diverse Cell Types.* 2003. 13(22): p. 1985-1990.
31. Rouault, J. P., et al., *Identification of BTG2, an antiproliferative p53-dependent component of the DNA damage cellular response pathway.* Nat Genet, 1996. 14(4): p. 482-6.

32. Attardi, L. D., et al., *PERP, an apoptosis-associated target of p53, is a novel member of the PMP-22/gas3 family*. Genes & Development, 2000. 14(6): p. 704-718.
33. Ihrie, R. A. and L. D. Attardi, *Perpetrating p53-dependent apoptosis*. Cell Cycle, 2004. 3(3): p. 267-9.
34. Strack, R. L., et al., *A noncytotoxic DsRed variant for whole-cell labeling*. Nat Methods, 2008. 5(11): p. 955-7.
35. Francis, M. A. and A. J. Rainbow, *UV-enhanced Expression of a Reporter Gene is Induced at Lower UV Fluences in Transcription-coupled Repair Deficient Compared to Normal Human Fibroblasts, and is Absent in SV40-transformed Counterparts¶*. Photochemistry and Photobiology, 2000. 72(4): p. 554-561.
36. Zacal, N. J., M. A. Francis, and A. J. Rainbow, *Enhanced expression from the human cytomegalovirus immediate-early promoter in a non-replicating adenovirus encoded reporter gene following cellular exposure to chemical DNA damaging agents*. Biochemical and Biophysical Research Communications, 2005. 332(2): p. 441-449.
37. Mizumoto, K., P. A. Glascott Jr, and J. L. Farber, *Roles for oxidative stress and poly(ADP-ribosyl)ation in the killing of cultured hepatocytes by methyl methanesulfonate*. Biochemical Pharmacology, 1993. 46(10): p. 1811-1818.
38. Wilhelm, D., et al., *The level of intracellular glutathione is a key regulator for the induction of stress-activated signal transduction pathways including Jun N-terminal protein kinases and p38 kinase by alkylating agents*. Mol. Cell. Biol., 1997. 17(8): p. 4792-4800.
39. Ashino, T., et al., *Tissue-dependent induction of heme oxygenase-1 and metallothionein-1/2 by methyl methanesulfonate*. The Journal of Toxicological Sciences, 2003. 28(3): p. 181-189.
40. Hernández, L. G., et al., *Mechanisms of non-genotoxic carcinogens and importance of a weight of evidence approach*. Mutation Research/Reviews in Mutation Research. 682(2-3): p. 94-109.
41. Knight, A. W., et al., *Fluorescence polarization discriminates green fluorescent protein from interfering auto fluorescence in a microplate assay for genotoxicity*. Journal of Biochemical and Biophysical Methods, 2002. 51(2): p. 165-177.
42. Westerink, W. M., et al., *Evaluation of the Vitotox and RadarScreen assays for the rapid assessment of genotoxicity in the early research phase of drug development*. Mutat Res, 2009. 676(1-2): p. 113-30.
43. Bevis, B. J. & Glick, B. S. (2002) *Nat. Biotechnol.* 20(1): 83-87.
44. Hendriks, G., Atallah, M., Raamsman, M., Morolli, B., van der Putten, H., Jaadar, H., Tijdens, I., et al. (2011). Sensitive DsRed fluorescence-based reporter cell systems for genotoxicity and oxidative stress assessment Mutation Research. doi:10.1016/j.mrfmmm.2011.02.013.

FURTHER REFERENCES FROM EXAMPLE 6

Agarwal, A. K. and Garg, A. (2004). Seipin: a mysterious protein. *Trends in molecular medicine.* 9, 440-444.
Birrell, L., Cahill, P., Hughes, C., Tate, M., and Walmsley, R. M. (2010). GADD45a-GFP GreenScreen HC assay results for the ECVAM recommended lists of genotoxic and non-genotoxic chemicals for assessment of new genotoxicity tests. *Mutation research.* 1-2, 87-95.
Chang, T.-S., Jeong, W., Woo, H. A., Lee, S. M., Park, S., and Rhee, S. G. (2004). Characterization of mammalian sulfiredoxin and its reactivation of hyperoxidized peroxiredoxin through reduction of cysteine sulfinic acid in the active site to cysteine. *J Biochem.* 49, 50994-51001.
Hayes, J. D. and McLellan, L. I. (1999). Glutathione and glutathione-dependent enzymes represent a coordinately regulated defence against oxidative stress. *Free radical research.* 4, 273-300.
Hendriks, G., Atallah, M., Raamsman, M., Morolli, B., van der Putten, H., Jaadar, H., Tijdens, I., Lange, R. E.-V., Mullenders, L., van de Water, B., and Vrieling, H. (2011). Sensitive DsRed fluorescence-based reporter cell systems for genotoxicity and oxidative stress assessment. *Mutation research.*
Hickson, I., Zhao, Y., Richardson, C. J., Green, S. J., Martin, N. M. B., Orr, A. I., Reaper, P. M., Jackson, S. P., Curtin, N. J., and Smith, G. C. M. (2004). Identification and characterization of a novel and specific inhibitor of the ataxia-telangiectasia mutated kinase ATM. *Cancer Res.* 24, 9152-9159.
Jing, X.-B., Cai, X.-B., Hu, H., Chen, S.-Z., Chen, B.-M., and Cai, J.-Y. (2007). Reactive oxygen species and mitochondrial membrane potential are modulated during CDDP-induced apoptosis in EC-109 cells. *Biochemistry and cell biology=Biochimie et biologie cellulaire.* 2, 265-271.
Kaspar, J. W., Niture, S. K., and Jaiswal, A. K. (2009). Nrf2:INrf2 (Keap1) signaling in oxidative stress. *Free radical biology & medicine.* 9, 1304-1309.
Kirkland, D., Kasper, P., Muller, L., Corvi, R., and Speit, G. (2008). Recommended lists of genotoxic and non-genotoxic chemicals for assessment of the performance of new or improved genotoxicity tests: a follow-up to an ECVAM workshop. *Mutation research.* 1-2, 99-108.
Kirkland, D., Reeve, L., Gatehouse, D., and Vanparys, P. (2011). A core in vitro genotoxicity battery comprising the Ames test plus the in vitro micronucleus test is sufficient to detect rodent carcinogens and in vivo genotoxins. *Mutation research.*
Magre, J., Delépine, M., Khallouf, E., Gedde-Dahl, T., Van Maldergem, L., Sobel, E., Papp, J., Meier, M., Mégarbané, A., Bachy, A., Verloes, A., d'Abronzo, F. H., Seemanova, E., Assan, R., Baudic, N., Bourut, C., Czernichow, P., Huet, F., Grigorescu, F., de Kerdanet, M., Lacombe, D., Labrune, P., Lanza, M., Loret, H., Matsuda, F., Navarro, J., Nivelon-Chevalier, A., Polak, M., Robert, J. J., Tric, P., Tubiana-Rufi, N., Vigouroux, C., Weissenbach, J., Savasta, S., Maassen, J. A., Trygstad, O., Bogalho, P., Freitas, P., Medina, J. L., Bonnicci, F., Joffe, B. I., Loyson, G., Panz, V. R., Raal, F. J., O'Rahilly, S., Stephenson, T., Kahn, C. R., Lathrop, M., Capeau, J., BSCL Working Group (2001). Identification of the gene altered in Berardinelli-Seip congenital lipodystrophy on chromosome 11q13. *Nat Genet.* 4, 365-370.
Meek, D. W. (2009). Tumour suppression by p53: a role for the DNA damage response? *Nat Rev Cancer.* 10, 714-723.
Nishida, H., Tatewaki, N., Nakajima, Y., Magara, T., Ko, K. M., Hamamori, Y., and Konishi, T. (2009). Inhibition of ATR protein kinase activity by schisandrin B in DNA damage response. *Nucleic Acids Res.* 17, 5678-5689.
Niture, S. K., Kaspar, J. W., Shen, J., and Jaiswal, A. K. (2010). Nrf2 signaling and cell survival. *Toxicol Appl Pharmacol.* 1, 37-42.
Paulsen, R. D. and Cimprich, K. A. (2007). The ATR pathway: fine-tuning the fork. *DNA Repair (Amst).* 7, 953-966.
Poser, I., Sarov, M., Hutchins, J., Heriche, J., Toyoda, Y., Pozniakovsky, A., Weigl, D., Nitzsche, A., Hegemann, B., Bird, A., Pelletier, L., Kittler, R., Hua, S., Naumann, R., Augsburg, M., Sykora, M., Hofemeister, H., Zhang, Y., Nasmyth, K., White, K., Dietzel, S., Mechtler, K., Durbin, R., Stewart, A., Peters, J., Buchholz, F., and Hyman, A. (2008). BAC TransgeneOmics: a high-throughput method for exploration of protein function in mammals. *Nat Methods*. 5, 409-415.

Reinhardt, H. C. and Yaffe, M. B. (2009). Kinases that control the cell cycle in response to DNA damage: Chk1, Chk2, and MK2. *Curr Opin Cell Biol*. 2, 245-255.

Sancar, A., Lindsey-Boltz, L., Unsal-Kacmaz, K., and Linn, S. (2004). Molecular mechanisms of mammalian DNA repair and the DNA damage checkpoints. *Annu Rev Biochem*. 39-85.

Sherman, M. H., Bassing, C. H., and Teitell, M. A. (2011). Regulation of cell differentiation by the DNA damage response. *Trends Cell Biol*. 5, 312-319.

Singh, A., Ling, G., Suhasini, A. N., Zhang, P., Yamamoto, M., Navas-Acien, A., Cosgrove, G., Tuder, R. M., Kensler, T. W., Watson, W. H., and Biswal, S. (2009). Nrf2-dependent sulfiredoxin-1 expression protects against cigarette smoke-induced oxidative stress in lungs. *Free radical biology & medicine*. 3, 376-386.

Szymanski, K. M., Binns, D., Bartz, R., Grishin, N. V., Li, W.-P., Agarwal, A. K., Garg, A., Anderson, R. G. W., and Goodman, J. M. (2007). The lipodystrophy protein seipin is found at endoplasmic reticulum lipid droplet junctions and is important for droplet morphology. *Proc Natl Acad Sci USA*. 52, 20890-20895.

Tolentino, J. H., Burke, T. J., Mukhopadhyay, S., McGregor, W. G., and Basu, A. K. (2008). Inhibition of DNA replication fork progression and mutagenic potential of 1, N6-ethenoadenine and 8-oxoguanine in human cell extracts. *Nucleic Acids Res*. 4, 1300-1308.

Wakabayashi, N., Slocum, S. L., Skoko, J. J., Shin, S., and Kensler, T. W. (2010). When NRF2 talks, who's listening? *Antioxidants & redox signaling*. 11, 1649-1663.

Yu, Q., La Rose, J., Zhang, H., Takemura, H., Kohn, K. W., and Pommier, Y. (2002). UCN-01 inhibits p53 up-regulation and abrogates gamma-radiation-induced G(2)-M checkpoint independently of p53 by targeting both of the checkpoint kinases, Chk2 and Chk1. *Cancer Res*. 20, 5743-5748.

The invention claimed is:

1. A polynucleotide comprising a reporter sequence operatively linked to a regulatory element of a gene wherein the gene is Bscl2, wherein the regulatory element stimulates expression of the reporter sequence in response to a genotoxic agent or to an oxidative stress-inducing agent, wherein the polynucleotide does not encode the naturally occurring polypeptide of the gene whose regulatory element the reporter sequence is operatively linked to, and the reporter sequence is not the naturally occurring polynucleotide of the gene whose regulatory element the reporter sequence is operatively linked to.

2. The polynucleotide of claim 1, wherein the reporter sequence comprises a gene encoding DsRed fluorescent protein, horse radish peroxidise (HRP), Green Fluorescent Protein (GFP), luciferase, chloramphenicol acetyl transferase (CAT), or P-galactosidase.

3. The polynucleotide of claim 1, wherein the regulatory element comprises a promoter of the gene.

4. The polynucleotide of claim 1, wherein the regulatory element comprises a transcription start site of the gene.

5. The polynucleotide of claim 1, wherein the regulatory element comprises an at least 400 base pair polynucleotide sequence immediately upstream of the transcription start site of the gene.

6. The polynucleotide of claim 1, wherein the regulatory element comprises a polynucleotide sequence of SEQ ID NO: 1.

7. The polynucleotide of claim 1, wherein the regulatory element stimulates expression of the reporter sequence in response to a genotoxic agent that causes any of base damage, bulky DNA adducts, single-stranded DNA breaks, double-stranded DNA breaks, intra-strand crosslinks, or inter-strand crosslinks.

8. The polynucleotide of claim 7, wherein the regulatory element stimulates expression of the reporter sequence in response to any of an intercalator, a topoisomerase II poison or a methylating agent.

9. The polynucleotide of claim 1, wherein the genotoxic or oxidative stress-inducing agent comprises cisplatin, mitomycin C, doxorubicin, etoposide, methylmethane sulphonate, N-methylnitrosurea, hydrogen peroxide, t-butyl hydroperoxide, menadione, or diethyl maleate.

10. The polynucleotide of claim 1, further defined as comprised in a vector.

11. The polynucleotide of claim 10, wherein the vector is a pDsRed-expression2.1 plasmid.

12. The polynucleotide of claim 1, further defined as comprised in a cell.

13. The polynucleotide of claim 12, wherein the cell is a stem cell, an embryonic stem cell, a mammalian cell, has a functional p53 protein, and/or is a mouse embryonic stem cell.

14. A polynucleotide comprising a reporter sequence operatively linked to a regulatory element of a gene wherein the gene is Bscl2, wherein the regulatory element stimulates expression of the reporter sequence in response to a genotoxic agent or to an oxidative stress-inducing agent wherein the reporter sequence is not the naturally occurring polynucleotide of the gene whose regulatory element the reporter sequence is operatively linked to and wherein the 3' end of the regulatory element is defined as the transcription start site or a region upstream thereof of Bscl2.

15. A polynucleotide comprising a reporter sequence operatively linked to a regulatory element of a gene defined as the upstream or downstream noncoding region of Bscl2, wherein the regulatory element stimulates expression of the reporter sequence in response to a genotoxic agent or to an oxidative stress-inducing agent wherein the reporter sequence is not the naturally occurring polynucleotide of the gene whose regulatory element the reporter sequence is operatively linked to.

16. A polynucleotide comprising a reporter sequence operatively linked to a regulatory element of a gene wherein the gene is Bscl2, wherein the regulatory element stimulates expression of the reporter sequence in response to a genotoxic agent or to an oxidative stress-inducing agent, wherein the polynucleotide does not contain the coding sequence of the gene whose regulatory element the reporter sequence is operatively linked to, and the reporter sequence is not the naturally occurring polynucleotide of the gene whose regulatory element the reporter sequence is operatively linked to.

* * * * *